US011472803B2

(12) United States Patent
Teller et al.

(10) Patent No.: US 11,472,803 B2
(45) Date of Patent: Oct. 18, 2022

(54) 7-SUBSTITUTED 1-ARYL-NAPHTHYRIDINE-3-CARBOXYLIC ACID AMIDES AND USE THEREOF

(71) Applicants: Bayer Aktiengesellschaft, Leverkusen (DE); Bayer Pharma Aktiengesellschaft, Berlin (DE)

(72) Inventors: Henrik Teller, Schwaan (DE); Alexandros Vakalopoulos, Hilden (DE); Melissa Boultadakis Arapinis, Düsseldorf (DE); Alexander Straub, Wuppertal (DE); Hanna Tinel, Wuppertal (DE); Markus Brechmann, San Francisco, CA (US); Matthias Beat Wittwer, Riehen (CH); Maximillian Andreas Kullmann, Leichlingen (DE); Till Freudenberger, Velbert (DE); Thomas Mondritzki, Essen (DE); Tobias Marquardt, Wuppertal (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 17/161,201

(22) Filed: Jan. 28, 2021

(65) Prior Publication Data
US 2021/0261541 A1    Aug. 26, 2021

Related U.S. Application Data

(62) Division of application No. 16/333,079, filed as application No. PCT/EP2017/072339 on Sep. 6, 2017, now Pat. No. 10,927,109.

(30) Foreign Application Priority Data

Sep. 14, 2016  (EP) ................................ 16188728
Dec. 6, 2016   (EP) ................................ 16202509

(51) Int. Cl.
| | | |
|---|---|---|
| *C07D 471/04* | (2006.01) | |
| *A61P 9/06* | (2006.01) | |
| *A61K 31/4375* | (2006.01) | |
| *A61K 31/551* | (2006.01) | |
| *A61K 45/06* | (2006.01) | |
| *C07D 491/107* | (2006.01) | |
| *C07D 519/00* | (2006.01) | |
| *A61P 9/00* | (2006.01) | |
| *A61P 13/00* | (2006.01) | |

(52) U.S. Cl.
CPC ........ *C07D 471/04* (2013.01); *A61K 31/4375* (2013.01); *A61K 31/551* (2013.01); *A61K 45/06* (2013.01); *A61P 9/00* (2018.01); *A61P 9/06* (2018.01); *A61P 13/00* (2018.01); *C07D 491/107* (2013.01); *C07D 519/00* (2013.01)

(58) Field of Classification Search
CPC .................................................. C07D 471/04
USPC ........................................................ 546/123
See application file for complete search history.

(56) References Cited

U.S. PATENT DOCUMENTS

| | | |
|---|---|---|
| 4,990,517 A | 2/1991 | Petersen |
| 5,496,947 A | 3/1996 | Yoon |
| 7,488,739 B2 | 2/2009 | Watanuki |
| 10,435,403 B2 | 10/2019 | Teller |
| 10,519,154 B2 | 12/2019 | Teller |
| 10,927,109 B2 * | 2/2021 | Teller ..................... A61K 45/06 |
| 2009/0291437 A1 | 11/2009 | Obrien et al. |
| 2018/0297994 A1 | 10/2018 | Teller |
| 2019/0241562 A1 | 8/2019 | Teller |
| 2019/0367516 A1 | 12/2019 | Teller |

FOREIGN PATENT DOCUMENTS

| | | |
|---|---|---|
| CA | 3030204 A1 | 1/2018 |
| CL | 200701360 | 11/2007 |
| CL | 201201605 | 6/2012 |
| CL | 201703138 | 6/2018 |
| CL | 201703147 | 6/2018 |
| CN | 102964350 A | 3/2013 |
| CN | 103183676 A | 7/2013 |
| DE | 3514076 A1 | 10/1985 |
| EP | 0350733 A2 | 1/1990 |
| EP | 1650192 A1 | 4/2006 |
| EP | 3312177 A4 | 12/2018 |
| GB | 2158825 A | 11/1985 |
| JP | 2005012561 A | 1/2005 |
| WO | 02085886 A2 | 10/2002 |
| WO | 03050107 A1 | 6/2003 |
| WO | 2005009971 A1 | 2/2005 |

(Continued)

OTHER PUBLICATIONS

Bouzard, D. et al., (1992). "Fluoronaphthyridines as Antibacterial Agents," Med. Chem. 35(3): 518-252.
Chen, P-S. et al. (2014). "Role of the Autonomic Nervous System in Atrial Fibrillation," Circulation Research 114: 1500-1515.
Christopoulos, A. (Nov. 2014). "Advances in G Protein-Coupled Receptor Allostery: From Function to Structure," Mol Pharmacol 86: 436-478.

(Continued)

*Primary Examiner* — Charanjit Aulakh
(74) *Attorney, Agent, or Firm* — Morrison & Foerster LLP

(57) ABSTRACT

The present application relates to novel 7-substituted 1-arylnaphthyridine-3-carboxamides, to processes for their preparation, to their use, alone or in combinations, for the treatment and/or prevention of diseases, and to their use for the production of medicaments for the treatment and/or prevention of diseases, in particular for the treatment and/or prevention of cardiovascular disorders and/or renal disorders.

3 Claims, No Drawings

(56) References Cited

FOREIGN PATENT DOCUMENTS

| | | |
|---|---|---|
| WO | 2005026145 A2 | 3/2005 |
| WO | 2005026165 A1 | 3/2005 |
| WO | 2005028451 A1 | 3/2005 |
| WO | 2005049602 A1 | 6/2005 |
| WO | 2005056552 A1 | 6/2005 |
| WO | 2010093341 A1 | 8/2010 |
| WO | 2011084368 A1 | 7/2011 |
| WO | 2013152704 A1 | 10/2013 |
| WO | 2015189560 A1 | 12/2015 |
| WO | 2016071212 A1 | 5/2016 |
| WO | 2016198342 A1 | 12/2016 |
| WO | 2016200851 A1 | 12/2016 |
| WO | 2018011017 A1 | 1/2018 |
| WO | 2018050510 A1 | 3/2018 |

OTHER PUBLICATIONS

Chu, D.T.W. et al. (1992). "Synthesis and antibacterial activity of novel 6-fluoro-7-(gem-disubstituted piperazin-1-yl)-quinolines," Circ. Res. 114(9), 1500-1515.

Clark, A.L. et al. (1976). "The Inhibitory Effect of Gallamine on Muscarinic Receptors," Br. J. Pharmac. 58: 323-331.

Conn, P.J. et al. (Jan. 2009). "Allosteric modulators of GPCRs: a novel approach for the treatment of CNS disorders," Nat Rev Drug Discov 8(1): 41-54.

Conn, P.J. et al. (Sep. 2014). "Opportunities and challenges in the discovery of allosteric modulators of GPCRs for treating CNS disorders," Nat Rev Drug Discov 13(9): 692-708.

Cooper, C.S. et al. (1992). "Preparation and in Vitro and in Vivo Evaluation of Quinolones with Selective Activity against Gram-Positive Organisms," J. Med. Chem. 35: 1392-1396.

Croy, C.H. et al. (Jul. 2014). "Characterization of the Novel Positive Allosteric Modulator, LY2119620, at the Muscarinic M2 and M4 Receptors," Molecular Pharmacology 86: 106-115.

Davie, B.J. (2013). "Development of M1 mAChR allosteric and Bitopic Ligands: Prospective Therapeutics for the Treatment of Cognitive Deficits," ACS Chem. Neurosci. 4: 1026-1048.

Deferrari, G.M. (2014). "Vagal Stimulation in Heart Failure," J. of Cardiovasc. Trans. Res. 7: 310-320.

Deferrari, G.M. et al. (2011). "Chronic vagus nerve stimulation: a new and promising therapeutic approach for chronic heart failure," European Heart Journal 32: 847-855.

European Search Report dated Oct. 31, 2016 for EP Application No. 16188728.6 filed on Sep. 14, 2016, 1 page. (Not in English).

Gold, M.R. et al. (2016). "Vagus Nerve Stimulation for the Treatment of Heart Failure," Journal of the American College of Cardiology 68(2): 149-158.

Gregory, K.J. et al. (2007). "Allosteric Modulation of Muscarinic Acetylcholine Receptors," current Neuropharmacology 5: 157-167.

Halaris, A. (2013). "Co-Morbidity between Cardiovascular Pathology and Depression: Role of Inflammation," Mod Trends Pharmacopsychiatry 28: 144-161.

Hauptmann, P.J. et al. (2012). "Rationale and study design of the INcrease Of Vagal TonE in Heart Failure study: INOVATE-HF," Am Heart J 163: 954-962.

He, X. et al. (2015). "Novel strategies and underlying protective mechanisms of modulation of vagal activity in cardiovascular diseases," British Journal of Pharmacology DOI: 10.1111/bph.13010.

International Preliminary Report on Patentability dated Jan. 24, 2019, for PCT Application No. PCT/EP2017/066632, filed on Jul. 4, 2017, 21 pages. German with English Translation.

International Search Report and Written Opinion dated Aug. 22, 2016, for PCT Application No. PCT/EP2016/062737, filed on Jun. 6, 2016, 11 pages.

International Search Report and Written Opinion dated Sep. 22, 2017, for PCT Application No. PCT/EP2017/066632, filed on Jul. 4, 2017, 18 pages.

Klopman, G. et al. (Nov. 1996). "N-1-tert-Butyl-Substituted Quinolones: In Vitro Anti-Mycobacterium avium Activities and Structure-Activity Relationship Studies," Antimicrobial Agents and Chemotherapy 40(11): 2637-2643.

Kruse, A. et al. (Dec. 2013). "Activation and allosteric modulation of a muscarinic acetylcholine receptor," Nature 504: 101-106.

Kruse, A. et al. (Oct. 2013). "Muscarinic Receptors as Model Targets and Antitargets for Structure-Based Ligand Discovery," Mol Pharmacol 84: 528-540.

Leong-Sit, P. et al. (2015). "Atrial fibrillation and heart failure: a bad combination," Curr Opin Cardiol 30: 1-7.

Lewalter, T. et al. (2011). "Pathophysiologie, Klinik und Therapieoptionen bei Vorhofflimmern," Fortbildungstelegramm Pharmazie 5(4): 106-127. (English Abstract).

Maisel, W. H. et al. (2003). "Atrial Fibrillation in Heart Failure: Epidemiology, Pathophysiology, and Rationale for Therapy," The American Journal of Cardiology 91(6A): 2d-8d.

Miao, Y. et al. (2016). "Accelerated structure-based design of chemically diverse allosteric modulators of a muscarinic G protein-coupled receptor," PNAS Early Edition, 113(38): E5675-E5684.

Mistry, S.N. (2013). "Synthesis and Pharmacological Profiling of Analogues of Benzyl Quinolone Carboxylic Acid (BQCA) as Allosteric Modulators of the M1 Muscarinic Receptor," J. Med. Chem. 56: 5151-5172.

Neubig, R.R. (2003). "International Union of Pharmacology Committee on Receptor Nomenclature and Drug Classification. XXWIII Update on Terms and Symbols in Quantitative Pharmacology," Pharmacol Rev 55: 597-606.

Olshansky, B. et al. (2008). "Parasympathetic Nervous System and Heart Failure Pathophysiology and Potential Implications for Therapy," Circulation, 118:863-871.

Premchand, R.K. (2014). "Autonomic Regulation Therapy via Left or Right Cervical Vagus Nerve Stimulation in Patients with Chronic Heart Failure: Results of the ANTHEM-HF Trial," Journal of Cardiac Failure 20(11): 808-816.

Ranpuria, R. (Nov. 2007). "Heart rate variability (HRV) in kidney failure: measurement and consequences of reduced HRV," Nephrol Dial Transplant 23: 444-449.

Rash, J.A. (2012). "Attention-deficit hyperactivity disorder and cardiac vagal control: a systematic review," ADHD Atten Def Hyp Disord 4: 167-177.

Rosman, K. et al. (1998). "Isotopic Compositions of the Elements 1997," Pure & Appl. Chem., 70(1):217-235.

Schober, D.A. (Jul. 2014). "Development of a Radioligand, [3H]LY2119620, to Probe the Human M2 and M4 Muscarinic Receptor Allosteric Binding Sites," Mol Pharmacol 86: 116-123.

Schrage, R. (2014). "New insight into active muscarinic receptors with the novel radioagonist [3H]iperoxo," Biochemical Pharmacology 90: 307-319.

Sykora, M. (Dec. 2009). "Baroreflex: A New Therapeutic Target in Human Stroke?" Stroke 40: 678-682.

Wang, L. (2009). "Allosteric Modulators of G Protein-Coupled Receptors: Future Therapeutics for Complex Physiological Disorders," The Journal of Pharmacology and Experimental Therapeutics 331(2): 340-348.

Zannad, F. et al. (Aug. 2014). "Chronic vagal stimulation for the treatment of low ejection fraction heart failure: results of the neural cardiac therapy for heart failure (NECTAR-HF) randomized controlled trial," European Heart Journal 425-433.

Zhang, T. et al. (2015). "Synthesis, antimycobacterial and antibacterial activity of fluroquinolone derivatives containing an 3-alkoxyimino-4-(cyclopropylanimo)methylpyrrolidine moiety," European Journal of Medicinal Chemistry 104: 73-85.

Chu, D.T.W. et al. (1992). "Synthesis and antibacterial activity of novel 6-fluoro-7-(gem-disubstituted piperazin-1-yl)-quinolines," Can. J. Chem., 70:1328-1337.

\* cited by examiner

7-SUBSTITUTED 1-ARYL-NAPHTHYRIDINE-3-CARBOXYLIC ACID AMIDES AND USE THEREOF

CROSS REFERENCE TO RELATED APPLICATIONS

This application is a divisional of U.S. application Ser. No. 16/333,079, which adopts the international filing date of Sep. 6, 2017, which is a national stage application under 35 U.S.C. § 371 of International Application No. PCT/EP2017/072339, filed internationally on Sep. 6, 2017, which claims the benefit of European Application Nos. 16188728.6, filed Sep. 14, 2016, and 16202509.2, filed Dec. 6, 2016.

The present application relates to novel 7-substituted 1-arylnaphthyridine-3-carboxamides, to processes for their preparation, to their use, alone or in combinations, for the treatment and/or prevention of diseases, and to their use for the production of medicaments for the treatment and/or prevention of diseases, in particular for the treatment and/or prevention of cardiovascular disorders and/or renal disorders.

Muscarinergic receptors are receptors which are positioned on the membrane and, as endogenous ligands, can bind the acetylcholine (ACh) neurotransmitter (acetylcholine receptors), but also be activated by muscarine. There are five subtypes of these G protein-coupled receptors (M1-M5) which are expressed in almost all kinds of tissue in the human organism. They are encountered both in the central and in the peripheral nervous system, and in many organs of the vegetative nervous system.

The M2 type (M2R) is expressed predominantly in the heart. At the cellular level, M2R stimulation by the acetylcholine agonist brings about inhibition of adenylcyclase and activation of the inwardly rectifying potassium channel (IKACh channel, GIRK: G protein activated inwardly rectifying K+ channel; also Kir3.x). This increases potassium conductivity, which leads to hyperpolarization of the muscle cells. Accordingly, the cells become more difficult to depolarize, which leads to an adverse chronotropic and dromotropic effect, and so the heart rate drops. M2R is the main mediator of the parasympathetic control of heart function, which is controlled by the vagus nerve. The right vagus nerve reduces the heart rate via the sinus node; the left vagus nerve predominantly increases the atrioventricular conduction time via the atrioventricular node (AV node). Overall, the influence of the vagus nerve on the resting heart rate is predominant compared to the sympathetic nerve. The effects of stimulation of M2R are thus opposed to those of beta-adrenergic stimulation.

The activation of the M2 receptor by the endogenous acetylcholine agonist, but also by synthetic analogues such as carbachol, oxotremorin-M or iperoxo (Schrage et al., *Biochem. Pharmacol.* 2014, 90(3), 307-319), is effected by binding of the agonist to what is called the orthosteric binding site of the receptor and a resultant change in conformation of the receptor or stabilization of the active receptor conformation. The conventional naturally occurring muscarine receptor agonists include, as well as the endogenous acetylcholine (ACh) agonist, various plant alkaloids such as arecoline, muscarine, and also pilocarpine (Neubig et al., *Pharmacol Rev.,* 2003, 55, 597-606). The orthosteric binding site of all muscarinic acetylcholine receptors is highly evolutionarily conserved and has a high sequence and structural homology between the various subtypes. Therefore, many of the known agonists are unselective with respect to the various subtypes of the muscarinic acetylcholine receptors (Kruse et al., *Mol Pharmacol.,* 2013, 84(4), 528-540). M2R has, as well as an orthosteric binding site, an allosteric binding site as well (Gregory et al., *Current Neuropharmacol.,* 2007, 5(3), 157-167). The oldest known allosteric modulator is gallamine (Clark and Mitchelson, *Br. J. Pharmac.,* 1976, 58, 323-331).

Allosteric modulators have distinct differences from conventional orthosteric ligands. The allosteric modulator itself has no direct influence on receptor activation. The allosteric binding instead results in modulation of the binding affinity and/or effectiveness of the orthosteric agonist. The effect of an allosteric modulator can thus be displayed only in the presence of the endogenous ligand. This results in specificity in terms of space and time in the allosteric effect (Conn et al., *Nat. Rev. Drug Disc.,* 2009, 8, 41-54; Conn et al, *Nat. Rev. Drug. Disc.,* 2014, 13, 692-708). Furthermore, the effect of an allosteric modulator is self-limiting when it stabilizes the binding of the agonist in high concentrations. This in turn results, in principle, in a more favourable pharmacological safety profile compared to agonists, since toxic effects caused by receptor overactivation are limited (Christopoulos, *Mol. Pharmacol.,* 2014, 86, 463-478).

The mutual influencing of allosteric and orthosteric ligands in terms of affinity and intrinsic activity, which is referred to as cooperativity, is determined by both ligands. In the case of a positive allosteric modulator of M2R, the effects of ACh (orthosteric ligand) are enhanced (positive cooperativity). Because of their ability to modulate receptor conformations in the presence of an orthosteric ligand, allosteric ligands can bring about fine adjustment of pharmacological effects (Wang et al., *J. Pharmacol. Exp. Therap.,* 2009, 331, 340-348). In the case of the positive allosteric modulator of M2R, this suggests an advantageous effect profile, a reduced risk of side effects and a starting point for the development of more subtype-selective ligands compared to a full agonist.

The crystal structure of the positive allosteric M4R and M2R ligand LY2119620 (3-amino-5-chloro-N-cyclopropyl-4-methyl-6-[2-(4-methylpiperazin-1-yl)-2-oxoethoxy]thieno[2,3-b]pyri-dine-2-carboxamide) in the complex with M2R has been published. The allosteric binding site of M2R is spatially adjacent to but clearly delimited from the orthosteric binding site and, compared to the other muscarinic receptor subtypes, exhibits lower conservation, i.e. has greater differences in sequence (Kruse et al., *Nature,* 2013, 504, 101-106). LY2119620 was described as an unselective M2R/M4R positive allosteric modulator (Cray et al., *Molecular Pharmacology*, July 2014 86, 7, 106-115; Schober et al., *Molecular Pharmacology*, July 2014 86, 7, 116-123).

M2R as a constituent of the autonomic nervous system plays an important role in the pathogenesis and progression of cardiovascular disorders. Autonomic imbalance characterized by vagal (parasympathetic) weakening and dominance of the sympathetic nervous system is closely correlated to increased morbidity and mortality. The clinical and prognostic significance of autonomic imbalance is well documented in various cardiovascular disorders, including heart failure (HF), heart rhythm disorders, ischaemia/reperfusion (I/R), hypertension (He et al., *Br. J. Pharmacol.* 2014, Epub) and chronic kidney disease (Ranpuria et al., *Nephrol Dial Transplant.* 2008, 23(2), 444-4499). Particularly in the case of patients having comorbidities such as diabetes, autonomic imbalance can contribute to increased morbidity and mortality (Vinik et al., *Diabet Med,* 2011, 28(6), 643-651). Baroreceptor reflex dysfunctions, such as hypertensive crises or variability in high blood pressure, as signs of a dysfunctional autonomic nervous system, often accompany the acute phase of ischaemic or haemorrhagic stroke (Sykora et al., *Stroke*, 2009, 40(12), 678-682).

The frequent observation of comorbidity between cardiovascular and psychological disorders, such as between heart failure and depression, is probably based on common pathomechanisms that accompany the autonomic imbalance (Halaris et al., *Mod Trends Pharmacopsychiatri.*, 2013, 28, 144-161). Chronic stress shifts the homeostatic equilibrium of the autonomic nervous system. Reduced vagal tone contributes to pro-inflammatory status, with impairment of neurotransmitter regulation, especially serotonergic transmission. Other psychological disorders have also been connected to autonomic dysregulation, for example attention deficit/hyperactivity disorder (ADHD), which is characterized by loss of inhibition, lack of emotional self-control, inattentive-ness and hyperactivity (Rash and Aguine-Camacho, *Atten Defic Hyperact Disord*, 2012, 4(4), 167-177).

Boosting parasympathetic activity by means of a positive allosteric modulator, including expected anti-inflammatory effects, elevation of nitrogen monoxide (NO), regulation of redox state, improvement of mitochondrial function and of calcium regulation, could therefore constitute a novel therapeutic principle, especially in the case of cardiovascular disorders. There are numerous pointers that the modulation of parasympathetic activity can be considered as a potential therapy target in the event of chronic heart failure. Vagal nerve stimulation in dogs that have recovered from myocardial infarction significantly lowered the incidence of sudden cardiac death, and mortality in rats suffering from chronic heart failure (De Ferrari, *J. Cardiovasc. Transl. Res.*, 2014, 7(3), 310-320). In a dog model with heart failure (LVEF 35%) and an implanted vagal stimulator, it was shown that, in the treatment group compared to the sham group, a significant improvement in the left-ventricular ejection fraction (LVEF) and reduction in the end-systolic and -diastolic volumes (LVESV, LVEDV) occurred, as did a significant reduction in heart rate within 3 months. The described effect of the VNS was additive to beta-blocker administration (De Ferrari, *J. Cardiovasc. Transl. Res.*, 2014, 7(3), 310-320). The plasma level for TNF-α and IL-6 and the myocardial protein expression thereof was lowered by vagal stimulation in this animal model, which suggests that boosting of the parasympathetic nervous system, as well as the effects on LV remodelling, also has positive effects on pro-inflammatory cytokines.

Based on experimental preclinical data, the first clinical studies on vagal stimulation in patients having chronic heart failure have now been done, as already established in the treatment of epilepsy and depression. The effect of boosting the parasympathetic system via direct vagal nerve stimulation (VNS) was assessed in a non-randomized observation study with 32 patients having left-ventricular (LV) systolic dysfunction, and the results suggest that vagal stimulation has a favourable effect on quality of life, stamina and LV remodelling (De Ferrari G M et al., *Eur. Heart J.*, 2011, 32, 847-855). In the multi-centre open-label feasibility study ANTHEN-HF, the safety, compatibility and efficacy of vagal stimulation in patients having chronic stable symptomatic heart failure with reduced ejection fraction (HFrEF) were examined in addition to the standard treatment (Premchand R K et al., *J. Card. Fail.*, 2014, 20(11), 808-816). The continuous vagal nerve stimulation employed in this study led to an improvement in the ejection fraction, variability of heart rate, NYHA class and quality of life. The first placebo-controlled clinical study NECTAR-HF, in contrast, did not show any significant effect of vagal nerve stimulation on the heart function of HF patients after 6 months (Zannad et al., *Eur. Heart J.*, 2015, 36(7), 425-433). The only improvement was in quality of life. The INOVATE-HF study with 650 HF patients was unable to show any effects of this treatment in relation to mortality and hospitalization. (Gold et al., *J Am Coll Cardiol.*, 2016, Mar. 29. pii: S0735-1097(16)32404-4. doi: 10.1016/j.jacc.2016.03.525). Quality of life and walking distance were significantly improved.

As well as the infection risk and the potential risks of a surgical intervention, treatment by means of electrical stimulation of the vagal nerve is limited by side effects such as dysphonia, coughing and oropharyngeal pain (Premchand R K et al., *J. Card Fail.*, 2014, 20(11), 808-816). Medication-assisted boosting of the parasympathetic nervous system by a direct effect on M2R could constitute a novel therapy option.

Atrial fibrillation is the most common persistent heart rhythm disorder, and the prevalence thereof increases with age (Chen et al., *Circ. Res.*, 2014, 114(9), 1500-1515). Atrial fibrillation and heart failure often occur together in a mutually beneficial relationship. Thus, the prevalence of atrial fibrillation increases with the clinical severity of heart failure (Maisel and Stevenson, *Am. J. Cardiol.*, 2003, 91, (suppl) 2D-8D). Clinical data suggest that patients where heart failure is accompanied by atrial fibrillation have a poor prognosis. Both lethality (total lethality, sudden death and pump failure) and morbidity (hospitalization) were found to be significantly increased in this group of patients.

In the treatment of atrial fibrillation, there are two distinct treatment strategies: what is called rate control with adjustment and if at all possible normalization of ventricular frequency, and what is called rhythm control, comprising measures intended to establish or maintain a sinusoidal rhythm. An effective treatment consists of a combination of non-medication-assisted and medication-assisted or intervention measures (Levalter T, *Fortbildungsprogramm Pharmazie*, 2011, 5, 106-127).

For medication-assisted rhythm control after cardioversion, beta-blockers, class I and class m antianhythmics are used according to the underlying cardiac disorder and the extent of left-ventricular pumping function impairment. In patients having permanent atrial fibrillation and in oligosymptomatic (frequently older) patients having persistent or paroxysmal atrial fibrillation, simple rate control with retention and allowance of the atrial fibrillation is often the therapy of choice. Primarily medicaments that affect the refractory period or the conduction capacity of the AV node are used. In principle, this effect can be achieved by stimulation of the M2R, which plays the key physiological role at this point, for example with the aid of a positive allosteric modulator. The drugs available to date are beta-blockers, digitalis, calcium antagonists and, in individual cases, amiodarone, which are used with consideration of the lifestyle, underlying cardiac disorder and any secondary disorders. Especially in patients having reduced left ventricular pumping function and severe heart failure, however, the options for medication-assisted therapy are inadequate. Calcium antagonists are contraindicated in this group of patients. As the most recent studies have shown, treatment with digoxin leads to increased mortality of patients having atrial fibrillation (Leong-Sit and Tang, *Curr. Opin. Cardiol.*, 2015, Epub). For beta-blockers, a lack of effectiveness in patients having atrial fibrillation and heart failure was shown in a meta analysis (Leong-Sit and Tang, *Curr. Opin. Cardiol.*, 2015, Epub). The medical demand for novel efficient and safe treatments for rate control is correspondingly high. This could be achieved by medication-assisted stimulation of M2R.

The problem addressed by the present invention is that of identifying and providing novel substances which constitute potent, positive allosteric modulators of the muscarinic M2 receptor and as such are suitable for treatment and/or prevention particularly of cardiovascular disorders and/or renal disorders.

1-Benzyl-substituted 4-oxo-1,4-dihydroquinoline-3-carboxylic acids have been described as allosteric modulators of the M1 muscarine receptor for treatment of neurodegenerative disorders such as Alzheimer's and schizophrenia (Scammells et al., *ACS Chem. Neurosci.*, 2013, 4 (7), 1026-1048; Mistry et al., *J. Med. Chem.* 2013, 56, 5151-5172). Among other documents, EP 0945435 B1 discloses pyridonecarboxylic acid derivatives having antibacterial activity. WO 2002/085886-A2, WO 2003/050107-A1 and WO 2005/026145-A2 claim 7-piperidino-substituted quinolonecarboxylic acid derivatives, and WO 2005/026165-A1 and WO 2005/049602-A1 various 7-pyrrolidino-substituted quinolonecarboxylic acid derivatives, and EP 1650192-A1 specific 7-azetidinylquinolonecarboxylic acid derivatives having antimicrobial/antibacterial activity. WO 2005/009971-A1 and JP 2005012561 disclose quinolone derivatives which can be used as platelet aggregation inhibitors. WO 2015/189560-A1 discloses 1,4-dihydroquinoline derivatives as NPRC agonists for treatment of cardiovascular disorders. Quinolonecarboxylic acid derivatives as MCT modulators are described in WO 2016/081464-A1, in particular for the treatment of tumour disorders and inflammatory processes.

The present invention relates to compounds of the general formula (I)

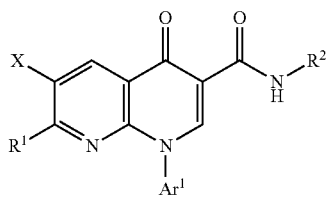

in which
X represents halogen,
$R^1$ represents hydrogen,
or
represents $-NR^4R^5$,
where
$R^4$ represents hydrogen, methyl, $(C_2-C_4)$-alkyl or $(C_3-C_6)$ cycloalkyl,
where $(C_2-C_4)$-alkyl may be substituted by hydroxy or up to trisubstituted by fluorine and
$R^5$ represents $(C_1-C_6)$-alkyl, $(C_3-C_6)$-cycloalkyl, 3- to 6-membered saturated heterocyclyl or $(C_1-C_4)$-alkylsulfonyl,
where $(C_1-C_6)$-alkyl, $(C_3-C_6)$-cycloalkyl and 3- to 6-membered saturated heterocyclyl may be up to trisubstituted by identical of different substituents from the group consisting of methyl, difluoromethyl, trifluoromethyl, hydroxy, hydroxycarbonyl, oxo, methoxy, difluoromethoxy, trifluoromethoxy and cyano and furthermore up to tetrasubstituted by fluorine, or
$R^4$ and $R^5$ together with the nitrogen atom to which they are attached form a saturated or partially unsaturated 3- to 6-membered monocyclic or 6- to 10-membered bicyclic heterocycle which may contain one or two further identical or different heteroatoms from the group consisting of N, O, S, SO and $SO_2$ as ring members,
where the 3- to 6-membered monocyclic and the 6- to 10-membered bicyclic heterocycle may each be substituted by 1 to 5 substituents independently of one another selected from the group consisting of $(C_1-C_4)$-alkyl, difluoromethyl, trifluoromethyl, hydroxy, hydroxycarbonyl, oxo, $(C_1-C_3)$-alkoxy, difluoromethoxy, trifluoromethoxy, cyano, $(C_1-C_3)$-alkoxycarbonyl, aminocarbonyl, mono-$(C_1-C_3)$-alkylaminocarbonyloxy, $-NHC(=O)R^{14A}$, $-CH_2NHC(=O)R^{14B}$ and $-OC(=O)R^{15}$, and additionally up to tetrasubstituted by fluorine,
where $(C_1-C_4)$-alkyl may be mono- or disubstituted by identical or different substituents from the group consisting of hydroxy and $(C_1-C_3)$-alkoxy, and up to tetrasubstituted by fluorine,
$R^{14A}$ and $R^{14B}$ independently of one another represent $(C_1-C_3)$-alkyl or cyclopropyl,
and in which
$R^{15}$ represents $(C_1-C_4)$-alkyl,
$R^2$ represents a group of the formula

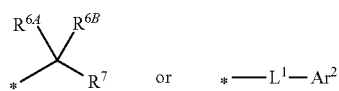

in which
* marks the point of attachment to the nitrogen atom of the amide moiety,
$R^{6A}$ represents hydrogen or $(C_1-C_4)$-alkyl,
$R^{6B}$ represents hydrogen, $(C_1-C_4)$-alkyl, cyclopropyl, monofluoromethyl, difluoromethyl, trifluoromethyl, methoxymethyl or trifluoromethoxymethyl,
$R^7$ represents $(C_1-C_6)$-alkyl or $(C_3-C_5)$-cycloalkyl which is up to tetrasubstituted by fluorine,
where $(C_1-C_6)$-alkyl may be substituted by amino, hydroxy, $(C_1-C_6)$-alkoxy and up to pentasubstituted by fluorine,
where $(C_1-C_6)$-alkoxy may be up to pentasubstituted by fluorine,
$L^1$ represents a bond or a group of the formula $-C(R^{8A}R^{8B})-(C(R^{9A}R^{9B}))_m-$,
in which
m represents 0 or 1,
$R^{8A}$ represents hydrogen or methyl,
$R^{8B}$ represents hydrogen, methyl, trifluoromethyl, pentafluoroethyl or trifluoromethoxymethyl,
$R^{9A}$ and $R^{9B}$ each independently of one another represent hydrogen or methyl,
$Ar^2$ represents phenyl,
where phenyl may be mono- to trisubstituted by identical or different substituents from the group consisting of fluorine, chlorine, $(C_1-C_3)$-alkyl, difluoromethoxymethyl, trifluoromethoxymethyl and trifluoromethyl,
or
represents a 5- to 10-membered monocyclic, bicyclic or tricyclic carbocycle or heterocycle which may contain one or two further identical or different heteroatoms from the group consisting of N and/or O as ring members, where the 5- to 10-membered monocyclic, bicyclic or tricyclic carbocycle or heterocycle may be up to tri-substituted by identical or different substituents from the group consisting of $(C_1-C_3)$-alkyl, trifluoromethyl and $(C_1-C_4)$-alkoxycarbonyl and furthermore up to tetrasubstituted by fluorine, $Ar^1$ represents a group of the formula

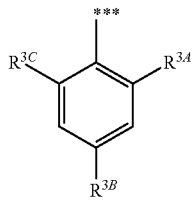

in which

*** marks the point of attachment to the nitrogen atom, $R^{3A}$ represents fluorine, chlorine, trifluoromethyl or methyl, $R^{3B}$ represents hydrogen or fluorine and $R^{3C}$ represents hydrogen, fluorine, chlorine or methyl, or represents a pyridine ring which is attached via a ring carbon atom, where the pyridine ring may be mono- or disubstituted by fluorine, chlorine, cyano, methyl or trifluoromethyl, and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Compounds according to the invention are likewise N-oxides of the compounds of the formula (I) and the salts, solvates and solvates of the salts thereof.

Preferred salts in the context of the present invention are physiologically acceptable salts of the compounds of the invention. Also encompassed are salts which are not themselves suitable for pharmaceutical applications but can be used, for example, for the isolation, purification or storage of the compounds of the invention.

A suitable pharmaceutically acceptable salt of the compounds of the present invention may be, for example, an acid-addition salt of a compound of the present invention bearing a sufficiently basic nitrogen atom in a chain or in a ring, such as an acid-addition salt with an inorganic acid, or "mineral acid", such as hydrochloric acid, hydrobromic acid, hydroiodic acid, sulfuric acid, sulfamic acid, bisulfuric acid, phosphoric acid or nitric acid, for example, or with an organic acid such as formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, 3-phenylpropionic acid, pivalic acid, 2-hydroxyethanesulfonic acid, itaconic acid, trifluoromethanesulfonic acid, dodecylsulfuric acid, ethanesulfonic acid, benzenesulfonic acid, paratoluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid or thiocyanic acid, for example.

Further, another suitable pharmaceutically acceptable salt of a sufficiently acidic compound of the present invention is an alkali metal salt, for example a sodium or potassium salt, an alkaline earth metal salt, for example a calcium, magnesium or strontium salt, or an aluminium or zinc salt, or an ammonium salt derived from ammonia or from an organic primary, secondary or tertiary amine having 1 to 20 carbon atoms, such as ethylamine, diethylamine, triethylamine, ethyl-diisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methylglucamine, N,N-dimethylglucamine, N-ethylglucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognize that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown. Unless specified otherwise, suffixes to chemical names or structural formulae relating to salts, such as "hydrochloride", "trifluoroacetate", "sodium salt", or "xHCl", "xCF$_3$COOH", "xNa$^+$", for example, mean a salt form, the stoichiometry of this salt not being specified. This applies analogously to cases in which synthesis intermediates or example compounds or salts thereof have been obtained as solvates, for example hydrates, by the preparation and/or purification processes described.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner. Preference is given to employing chromatographic methods for this purpose, especially HPLC chromatography on achiral or chiral separation phases. In the case of carboxylic acids as intermediates or end products, separation is alternatively also possible via diastereomeric salts using chiral amine bases.

In the context of the present invention, the term "enantiomerically pure" is understood to the effect that the compound in question with respect to the absolute configuration of the chiral centres is present in an enantiomeric excess of more than 95%, preferably more than 98%. The enantiomeric excess, ee, is calculated here by evaluating an HPLC analysis chromatogram on a chiral phase using the formula below:

$$ee = \left| \frac{\text{Enantiomer 1 (area percent)} - \text{Enantiomer 2 (area percent)}}{\text{Enantiomer 1 (area percent)} + \text{Enantiomer 2 (area percent)}} \right| \times 100\%.$$

If the compounds of the invention can occur in tautomeric forms, the present invention encompasses all the tautomeric forms.

The present invention also encompasses all suitable isotopic variants of the compounds of the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature ("unnatural fraction"). The expression "unnatural fraction" is understood to mean a fraction of such an isotope higher than its natural frequency. The natural frequencies of isotopes to be employed in this connection can be found in "Isotopic Compositions of the Elements 1997", Pure Appl. Chem., 70(1), 217-235, 1998. Examples of isotopes which can be incorporated into a compound of the invention are those of hydrogen, carbon, nitrogen, oxygen, phosphorus, sulfur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. With regard to the treatment and/or prophylaxis of the disorders specified here, the isotopic variants) of the compounds of the general formula (I) preferably contain deuterium ("deuterium-containing compounds of the general formula (I)"). Isotopic variants of the compounds of the general formula (I) into which one or more radioactive isotopes such as $^3H$ or $^{14}C$ have been incorporated are beneficial, for example, in medicament and/or substrate tissue distribution studies. Because of their easy incorporability and detectability, these isotopes are particularly preferred. It is possible to incorporate positron-emitting isotopes such as $^{18}F$ or $^{11}C$ into a compound of the general formula (I). These isotopic variants of the compounds of the general formula (I) are suitable for use in in vivo imaging applications. Deuterium-containing and $^{13}C$-containing compounds of the general formula (I) can be used within the scope of pie-clinical or clinical studies in mass spectrometry analyses (H. J. Leis et al., Curr. Org. Chem, 1998, 2, 131). Isotopic variants of the compounds of the invention can be prepared by commonly used processes known to those skilled in the art, for example by the methods described further down and the procedures described in the working examples, by using corresponding isotopic modifications of the respective reagents and/or starting compounds.

Isotopic variants of the compounds of the general formula (I) can in general be prepared by processes known to those skilled in the art as described in the schemes and/or examples described here, by replacing a reagent with an isotopic variant of the reagent, preferably a deuterium-containing reagent. According to the deuteration sites desired, it is possible in some cases to incorporate deuterium from $D_2O$ either directly into the compounds or into reagents which can be used for the synthesis of such compounds (Esaki et al., Tetrahedron, 2006, 62, 10954; Esaki et al., Chem. Eur. J., 2007, 13, 4052). Another useful reagent for incorporation of deuterium into molecules is deuterium gas. A rapid route for incorporation of deuterium is the catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865). For direct exchange of hydrogen for deuterium in hydrocarbons containing functional groups, it is also possible to use metal catalysts (i.e. Pd, Pt and Rh) in the presence of deuterium gas (J. G. Atkinson et al., U.S. Pat. No. 3,966,781). Various deuterated reagents and synthesis units are commercially available from companies like, for example, C/D/N Isotopes, Quebec, Canada; Cambridge Isotope Laboratories Inc., Andover, Mass., USA; and CombiPhos Catalysts, Inc., Princeton, N.J., USA. Further information relating to the prior art with regard to deuterium-hydrogen exchange can be found, for example, in Hanzlik et al., J. Org. Chem., 1990, 55, 3992-3997; R. P. Hanzlik et al., Biochem. Biophys. Res. Commun., 1989, 160, 844; P. J. Reider et al., J. Org. Chem., 1987, 52, 3326-3334; M. Jar-man et al., Carcinogenesis, 1993, 16(4), 683-688; J. Atzrodt et al., Angew. Chem., Int. Ed 2007, 46, 7744; K. Matoishi et al., 2000, J. Chem. Soc, Chem. Commun., 1519-1520; K. Kassahun et al., WO 2012/112363.

The term "deuterium-containing compound of the general formula (I)" is defined as a compound of the general formula (I) in which one or more hydrogen atoms have been replaced by one or more deuterium atoms and in which the frequency of deuterium in every deuterated position in the compound of the general formula (I) is higher than the natural frequency of deuterium, which is about 0.015%. More particularly, in a deuterium-containing compound of the general formula (I), the frequency of deuterium in every deuterated position in the compound of the general formula (I) is higher than 10%, 20%, 30%, 40%, 50%, 60%, 70% or 80%, preferably higher than 90%, 95%, 96% or 97%, even further preferably higher than 98% or 99%, in this position or these positions. It will be apparent that the frequency of deuterium in every deuterated position is independent of the frequency of deuterium in other deuterated positions.

The selective incorporation of one or more deuterium atoms into a compound of the general formula (I) can alter the physicochemical properties (for example acidity [A. Streitwieser et al., J. Am. Chem. Soc., 1963, 85, 2759; C. L. Perrin et al., J. Am. Chem. Soc., 2007, 129, 4490], basicity [C. L. Perrin, et al., J. Am. Chem. Soc., 2003, 125, 15008; C. L. Perrin in Advances in Physical Organic Chemistry, 44, 144; C. L. Perrin et al., J. Am. Chem. Soc., 2005, 127, 9641], lipophilicity [B. Testa et al., Int. J. Pharm., 1984, 19(3), 271]) and/or the metabolic profile of the molecule, and cause changes in the ratio of parent compound to metabolites or the amounts of metabolites formed. Such changes may lead to particular therapeutic benefits and therefore be preferable under particular circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent compound and metabolites can have important consequences with respect to the pharmacodynamics, tolerability and efficacy of a deuterium-containing compound of the general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, Calif., Oct. 12-16, 2008), ML-337 (C. J. Wenthur et al., J. Med. Chem., 2013, 56, 5208), and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In the context of the present invention, unless specified otherwise, the substituents are defined as follows:

Alkyl per se and "Alk" and "alkyl" in alkoxy, alkylsulfonyl, alkylaminocarbonyloxy and alkoxycarbonyl are a linear or branched alkyl radical having generally 1 to 6 and preferably 1 to 4 or 1 to 3 carbon atoms, by way of example and with preference methyl, ethyl, n-propyl, isopropyl, tert-butyl, isobutyl (2-methylprop-1-yl), n-pentyl and n-hexyl.

Alkoxy is, by way of example and with preference, methoxy, ethoxy, n-propoxy, isopropoxy, tert-butoxy, n-pentoxy and n-hexoxy.

Alkylaminocarbonyloxy is an alkylaminocarbonyloxy radical having one or two (independently chosen) alkyl substituents. $(C_1-C_3)$-Alkylaminocarbonyloxy is, for example, a monoalkylaminocarbonyloxy radical having 1 to 3 carbon atoms or a dialkylaminocarbonyloxy radical having 1 to 3 carbon atoms in each alkyl substituent. Preferred examples include: methylaminocarbonyloxy, ethylaminocarbonyloxy, n-propylaminocarbonyloxy, isopropylaminocarbonyloxy, tert-butylaminocarbonyloxy, n-pentylaminocarbonyloxy, n-hexylaminocarbonyloxy, N,N-dimethylaminocarbonyloxy, N,N-diethylaminocarbonyloxy, N-ethyl-N-methylaminocarbonyloxy, N-methyl-N-n-propylaminocarbonyloxy, N-isopropyl-N-n-propylaminocarbonyloxy, N-tert-butyl-N-methylaminocarbonyl, N-ethyl-N-n-pentylaminocarbonyl and N-n-hexyl-N-methylaminocarbonyloxy.

Alkylsulfonyl in the context of the invention is a straight-chain or branched alkyl radical which has 1 to 4 carbon atoms and is attached via a sulfonyl group. Preferred examples include: methylsulfonyl, ethylsulfonyl, n-propylsulfonyl, isopropylsulfonyl, n-butylsulfonyl and tert-butylsulfonyl.

By way of example and with preference, alkoxycarbonyl is methoxycarbonyl, ethoxycarbonyl, n-propoxycarbonyl, isopropoxycarbonyl and tert-butoxycarbonyl.

Carbocycle in the context of the invention is a mono-, poly- or spirocyclic, preferably mono- or bicyclic, saturated carbocycle having a total of 3 to 6 ring atoms. A monocyclic saturated carbocycle is referred to synonymously as cycloalkyl. Examples include: cyclopropyl, cyclobutyl, cyclopentyl, cyclohexyl, cycloheptyl, cyclopentenyl, cyclohexenyl, cyclohexadienyl, cycloheptenyl, cycloheptadienyl, spiro[2.3]hexyl, spiro[2.4]heptyl, spiro[2.5]octyl, bicyclo[1.1.1]pentyl, bicyclo[2.2.1]heptyl, bicyclo[2.2.2]octyl, tricyclo[3.3.1.13,7]decyl. Monocyclic cycloalkyl having 3 to 5 carbon atoms is preferred. Preferred examples include: cyclopropyl, cyclobutyl, cyclopentyl, bicyclo[2.2.1]heptyl and bicyclo[1.1.1]pent-1-yl.

Heterocyclyl is a mono-, poly- or spirocyclic, preferably mono-, bi- or spirocyclic, nonaromatic heterocyclic radical having generally 3 to 10 ring atoms and up to 3, preferably up to 2, heteroatoms and/or hetero groups from the group consisting of N, O, S, SO and $SO_2$. For the purposes of the present invention, the definition bicyclic heterocycle embraces bicyclic spirocyclic heterocyclyl radicals. The heterocyclyl radicals can be saturated or partially unsaturated. Preference is given to 4- to 6-membered monocyclic saturated heterocyclyl radicals having one nitrogen atom and to those having a further heteroatom from the group consisting of N and O, and also to 6- to 7-membered bi- or spirocyclic saturated heterocyclyl radicals having one nitrogen atom. Preferred examples include: azetidinyl, pyrrolidinyl, piperidinyl, piperazinyl, oxazolidinyl, imidazolidinyl, morpholinyl, tetrahydropyrimidine, azabicyclo[3.1.0]hexyl, azaspiro[2.4]heptyl and 2-oxa-6-azaspiro[3.3]hept-6-yl.

Halogen represents fluorine, chlorine, bromine and iodine, preferably fluorine or chlorine.

In the formula of the group that $R^1$, $R^2$, $Ar^1$ or $L^1$ may represent, the end point of the line marked by the symbol #$^1$; *,  and * does not represent a carbon atom or a CH$_2$ group but is part of the bond to the respective atom to which $R^1$, $R^2$, $Ar^1$ and $L^1$, respectively, is attached.

When radicals in the compounds of the invention are substituted, the radicals may be mono- or polysubstituted, unless specified otherwise. In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the formula (I) in which
in which
X represents fluorine, chlorine or bromine,
$R^1$ represents hydrogen,
or
represents $NR^4R^5$,
in which
$R^4$ represents hydrogen, methyl or ethyl, and
$R^5$ represents $(C_1-C_3)$-alkyl which is up to tetrasubstituted by fluorine,
where $(C_1-C_3)$-alkyl may be substituted by hydroxy,
or
$R^4$ and $R^5$ together with the nitrogen atom to which they are attached form a saturated 4- to 6-membered monocyclic or 6- to 9-membered bicyclic heterocycle which may contain one or two further identical or different heteroatoms from the group consisting of N and O as ring members,
where the 4- to 6-membered monocyclic and the 6- to 9-membered bicyclic heterocycle may each be substituted by 1 to 4 substituents independently of one another selected from the group consisting of $(C_1$-$C_4)$-alkyl, difluoromethyl, trifluoromethyl, hydroxy, oxo, $(C_1$-$C_3)$-alkoxy, difluoromethoxy, trifluoromethoxy, $(C_1$-$C_3)$-alkoxycarbonyl, $(C_1$-$C_3)$-alkylaminocarbonyloxy and —OC(=O)$R^{15}$ and furthermore up to tetrasubstituted by fluorine,
where $(C_1$-$C_4)$-alkyl may be mono- or disubstituted by identical or different substituents from the group consisting of hydroxy and $(C_1$-$C_3)$-alkoxy, and up to tetrasubstituted by fluorine, and where $R^{15}$ represents $(C_1$-$C_4)$-alkyl,
$R^2$ represents a group of the formula

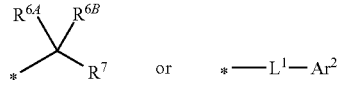

in which
* marks the point of attachment to the nitrogen atom of the amide moiety,
$R^{6A}$ represents hydrogen or $(C_1$-$C_4)$-alkyl,
$R^{6B}$ represents methyl, ethyl, isopropyl, cyclopropyl, monofluoromethyl, difluoromethyl or trifluoromethyl, and
$R^7$ represents $(C_1$-$C_4)$-alkyl which is up to pentasubstituted by fluorine, $(C_3$-$C_5)$-cycloalkyl which is up to tetrasubstituted by fluorine, methoxymethyl or trifluoromethoxy methyl,
$L^1$ represents a bond or a group of the formula —$CR^{8A}R^{8B}$—,
in which
$R^{8A}$ represents hydrogen,
$R^{8B}$ represents hydrogen, methyl, trifluoromethyl, pentafluoroethyl or trifluoromethoxymethyl,
$Ar^2$ represents phenyl,
where phenyl may be mono- to trisubstituted by identical or different substituents from the group consisting of fluorine and chlorine,
or
represents a 5- to 7-membered bicyclic carbocycle or 5- or 6-membered monocyclic heterocycle which contains one nitrogen atom as ring member,
where the 5- to 7-membered bicyclic carbocycle or the 5- or 6-membered monocyclic heterocycle may in each case be substituted by $(C_1$-$C_4)$-alkoxycarbonyl and additionally up to tetrasubstituted by fluorine,
$Ar^1$ represents a group of the formula

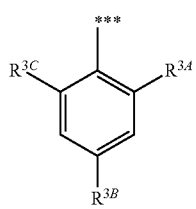

in which
*** marks the point of attachment to the nitrogen atom,
$R^{3A}$ represents fluorine, chlorine, trifluoromethyl or methyl,
$R^{3B}$ represents hydrogen or fluorine
and
$R^{3C}$ represents hydrogen, fluorine, chlorine or methyl,
or
represents a pyridine ring which is attached via a ring carbon atom,
where the pyridine ring may be mono- or disubstituted by fluorine, chlorine or cyano, and the salts, solvates and solvates of the salts thereof.

Particular preference is given in the context of the present invention to compounds of the formula (I)
in which
X represents fluorine, chlorine or bromine,
$R^1$ represents $NR^4R^5$,
in which
$R^4$ represents methyl or ethyl, and
$R^5$ represents methyl, 2-hydroxyethyl or 2-hydroxypropyl,
or
represents a heterocycle, attached via a nitrogen atom, of the formula

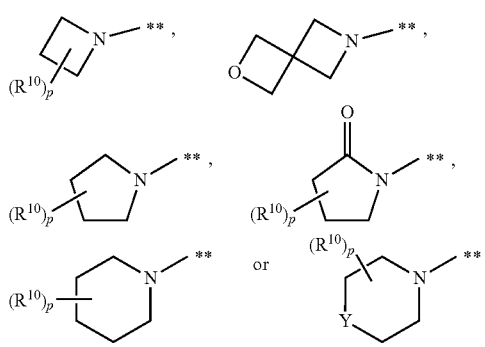

in which
** marks the point of attachment to the remainder of the molecule,
$R^{10}$ represents fluorine, methyl, hydroxy, hydroxymethyl, methoxycarbonyl or acetyloxy,
p represents the number 0, 1 or 2,
where, in the case that the substituents $R^{10}$ occur more than once, their meanings may in each case be identical or different,
$Y^1$ represents —NH—, —N(CH$_3$)— or —O—,
$R^2$ represents a group of the formula

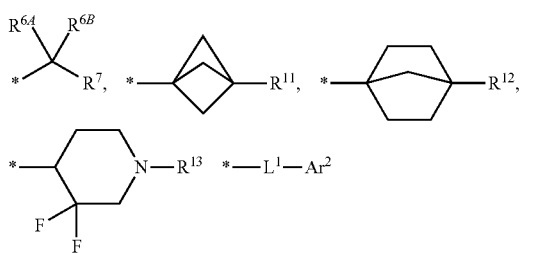

in which
* marks the point of attachment to the nitrogen atom of the amide moiety,
$R^{6A}$ represents hydrogen, methyl or ethyl,
$R^{6B}$ represents methyl, ethyl, trifluoromethyl, isopropyl or cyclopropyl, and
$R^7$ represents methyl, ethyl, difluoromethyl, trifluoromethyl, 2,2,2-trifluoroethyl, pentafluoroethyl, isopropyl, isobutyl, methoxymethyl, trifluoromethoxymethyl or cyclopropyl,
$R^{11}$ represents hydrogen,
$R^{12}$ represents methoxycarbonyl,
$R^{13}$ represents hydrogen or tert-butoxycarbonyl,
$L^1$ represents a bond or a group of the formula —$CR^{8A}R^{8B}$—, in which
$R^{8A}$ represents hydrogen,
$R^{8B}$ represents hydrogen, methyl or trifluoromethyl,
$Ar^2$ represents phenyl,
where phenyl may be mono- to disubstituted by identical or different substituents from the group consisting of fluorine and chlorine,
$Ar^1$ represents a group of the formula

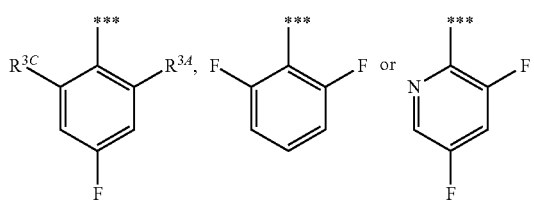

in which
*** marks the point of attachment to the nitrogen atom,
$R^{3A}$ represents fluorine or chlorine,
and
$R^{3C}$ represents hydrogen or fluorine,
and the salts, solvates and solvates of the salts thereof.
Very particular preference is given in the context of the present invention to compounds of the formula (I)
in which
X represents fluorine,
$R^1$ represents a heterocycle, attached via a nitrogen atom, of the formula

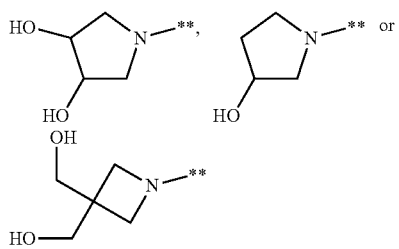

in which
** marks the point of attachment to the remainder of the molecule,
$R^2$ represents a group of the formula

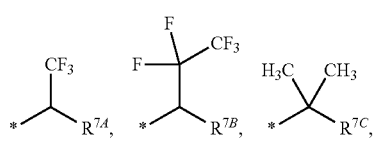

in which
* marks the point of attachment to the nitrogen atom of the amide moiety,
$R^{7A}$ represents trifluoromethyl, ethyl or cyclopropyl,
$R^{7B}$ represents methyl or ethyl,
$R^{7C}$ represents trifluoromethyl or pentafluoroethyl, Ar¹ represents a group of the formula

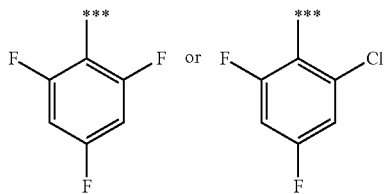

in which
*** marks the point of attachment to the nitrogen atom,
and the salts, solvates and solvates of the salts thereof.

Very particular preference is given in the context of the present invention to compounds of the formula (I)
in which
X represents fluorine,
R¹ represents a heterocycle, attached via a nitrogen atom, of the formula

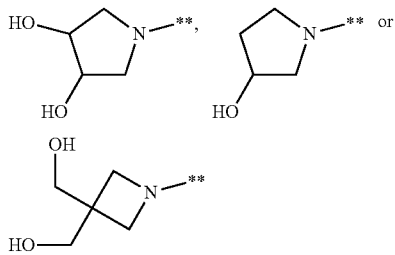

in which
** marks the point of attachment to the remainder of the molecule,
R² represents a group of the formula

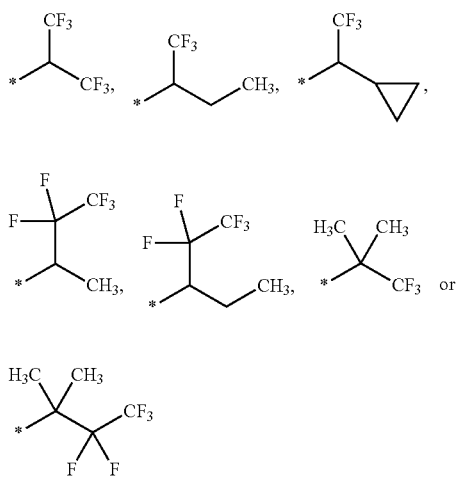

in which
* marks the point of attachment to the nitrogen atom of the amide moiety, Ar¹ represents a group of the formula

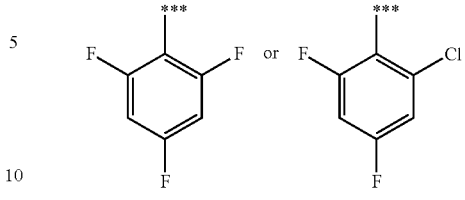

in which
*** marks the point of attachment to the nitrogen atom, and the salts, solvates and solvates of the salts thereof.

A further particular embodiment of the present invention encompasses compounds of the formula (I) in which
X represents fluorine,
R¹ represents a heterocycle, attached by a nitrogen atom, of the formula

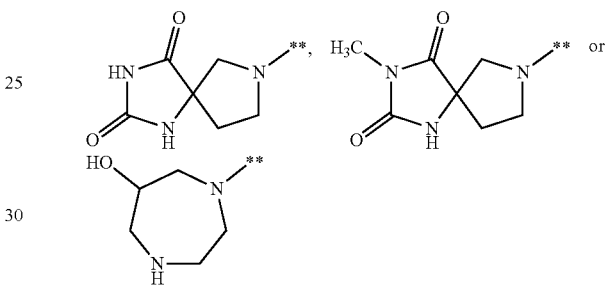

in which
** marks the point of attachment to the remainder of the molecule,
R¹⁰ represents fluorine, methyl, hydroxy, hydroxymethyl, methoxycarbonyl or acetyloxy,
p represents the number 0, 1 or 2,
where, in the case that the substituents R¹⁰ occur more than once, their meanings in each case may be identical or different,
R² represents a group of the formula

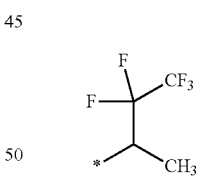

in which
* marks the point of attachment to the nitrogen atom of the amide moiety,
Ar¹ represents a group of the formula

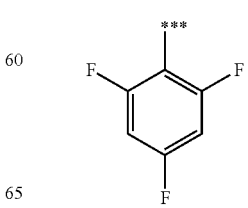

in which
*** marks the point of attachment to the nitrogen atom,
and the salts, solvates and solvates of the salts thereof.

The present invention also provides compounds of the general formula (I)

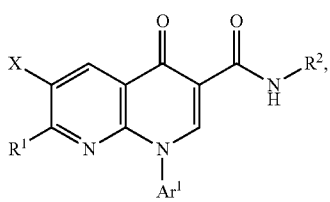

(I)

in which
X represents halogen,
$R^1$ represents hydrogen
or
represents —$NR^4R^5$,
in which
$R^4$ represents hydrogen, methyl, $(C_2-C_4)$-alkyl or $(C_3-C_6)$ cycloalkyl,
where $(C_2-C_4)$-alkyl may be substituted by hydroxy or up to three times by fluorine, and
$R^5$ represents $(C_1-C_6)$-alkyl, $(C_3-C_6)$-cycloalkyl, 3- to 6-membered saturated heterocyclyl or $(C_1-C_4)$-alkylsulfonyl,
where $(C_1-C_6)$-alkyl, $(C_3-C_4)$-cycloalkyl and 3- to 6-membered saturated heterocyclyl may be substituted up to three times by identical or different substituents from the group consisting of methyl, difluoromethyl, trifluoromethyl, hydroxy, hydroxycarbonyl, oxo, methoxy, difluoromethoxy, trifluoromethoxy, cyano and furthermore up to four times by fluorine,
or
$R^4$ and $R^5$ together with the nitrogen atom to which they are attached form a saturated or partially unsaturated 3- to 6-membered monocyclic or 6- to 10-membered bicyclic heterocycle which may contain one or two further identical or different heteroatoms from the group consisting of N, O, S, SO and/or $SO_2$ as ring members,
where the 3- to 6-membered monocyclic and the 6- to 10-membered bicyclic heterocycle may each be substituted by 1 to 5 substituents independently of one another selected from the group consisting of $(C_1-C_4)$-alkyl, difluoromethyl, trifluoromethyl, hydroxy, hydroxycarbonyl, oxo, $(C_1-C_3)$-alkoxy, difluoromethoxy, trifluoromethoxy, cyano, $(C_1-C_3)$-alkoxycarbonyl, aminocarbonyl, mono-$(C_1-C_3)$-alkylaminocarbonyloxy, —NHC(=O)$R^{14A}$, —$CH_2$NHC(=O)$R^{14B}$, —OC(=O)$R^{15}$ and furthermore up to tetrasubstituted by fluorine,
where $(C_1-C_4)$-alkyl may be mono- or disubstituted by identical or different substituents from the group consisting of hydroxy and $(C_1-C_3)$-alkoxy and up to tetrasubstituted by fluorine,
$R^{14A}$ and $R^{14B}$ independently of one another represent $(C_1-C_3)$-alkyl or cyclopropyl,
and where
$R^{15}$ represents $(C_1-C_4)$-alkyl, $R^2$ represents a group of the formula

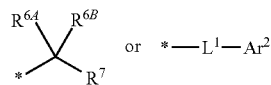

in which
* marks the point of attachment to the nitrogen atom of the amide moiety,
$R^{6A}$ represents hydrogen, methyl, ethyl, n-propyl, isopropyl, tert-butyl, isobutyl, (2-methyl-prop-1-yl) or cyclopropyl,
$R^{6B}$ represents hydrogen, methyl, ethyl, n-propyl, isopropyl, tert-butyl, isobutyl, (2-methyl-prop-1-yl), cyclopropyl, monofluoromethyl, difluoromethyl, trifluoromethyl, methoxymethyl or trifluoromethoxymethyl,
$R^7$ represents $(C_1-C_6)$-alkyl or $(C_3-C_5)$-cycloalkyl which is up to tetrasubstituted by fluorine,
where $(C_1-C_6)$-alkyl may be substituted by amino, hydroxy, $(C_1-C_6)$-alkoxy and up to
pentasubstituted by fluorine,
where $(C_1-C_6)$-alkoxy may be up to pentasubstituted by fluorine
$L^1$ represents a bond or a group of the formula —C($R^{8A}R^{8B}$)—(C($R^{9A}R^{9B}$))$_m$—,
in which
m represents 0 or 1,
$R^{8A}$ represents hydrogen or methyl,
$R^{8B}$ represents hydrogen, methyl, trifluoromethyl, pentafluoroethyl or trifluoromethoxymethyl,
$R^{9A}$ and $R^{9B}$ independently of one another represent hydrogen or methyl,
$Ar^2$ represents phenyl,
where phenyl may be mono- to trisubstituted by identical or different substituents from the group consisting of fluorine, chlorine, $(C_1-C_3)$-alkyl, difluoromethoxymethyl, trifluoromethoxymethyl and/or trifluoromethyl,
or
represents a 5- to 10-membered monocyclic, bicyclic or tricyclic carbocycle or heterocycle which may contain one or two further identical or different heteroatoms from the group consisting of N and/or S as ring members,
where the 5- to 10-membered monocyclic, bicyclic or tricyclic carbocycle or heterocycle may be up to trisubstituted by identical or different substituents from the group consisting of $(C_1-C_3)$-alkyl, trifluoromethyl, $(C_1-C_4)$-alkoxycarbonyl and furthermore up to tetrasubstituted by fluorine,
$Ar^1$ represents a group of the formula

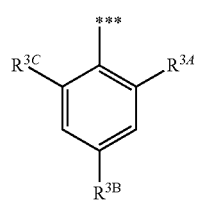

in which

\*\*\* marks the point of attachment to the nitrogen atom, $R^{3A}$ represents fluorine, chlorine, trifluoromethyl or methyl, $R^{3B}$ represents hydrogen or fluorine and $R^{3C}$ represents hydrogen, fluorine, chlorine or methyl, or represents a pyridine ring which is attached via a ring carbon atom, where the pyridine ring may be mono- or disubstituted by fluorine, chlorine, cyano, methyl or trifluoromethyl, and the N-oxides, salts, solvates, salts of the N-oxides and solvates of the N-oxides and salts thereof.

Preference in the context of the present invention is given to compounds of the formula (I), in which X represents fluorine, $R^1$ represents a heterocycle, attached via a nitrogen atom, of the formula

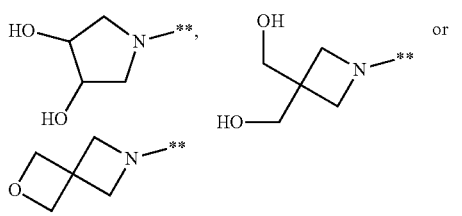

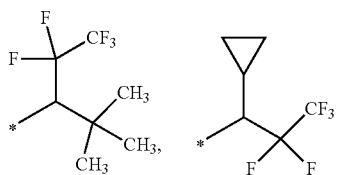

in which

\*\* marks the point of attachment to the remainder of the molecule, $R^2$ represents a group of the formula

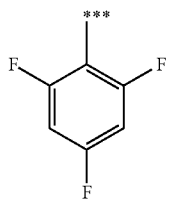

in which

\* marks the point of attachment to the nitrogen atom of the amide moiety, $Ar^1$ represents a group of the formula

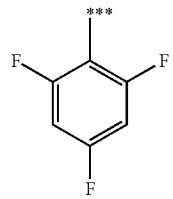

in which

\*\*\* marks the point of attachment to the nitrogen atom, and salts, solvates and solvates of the salts thereof.

Preference in the context of the present invention is given to compounds of the formula (I), in which X represents fluorine, $R^1$ represents a heterocycle, attached via a nitrogen atom, of the formula

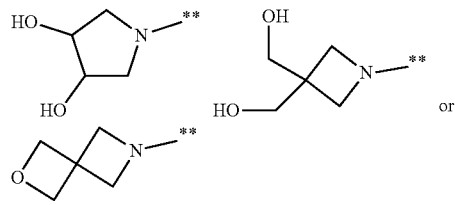

in which

\*\* marks the point of attachment to the remainder of the molecule, $R^2$ represents a group of the formula

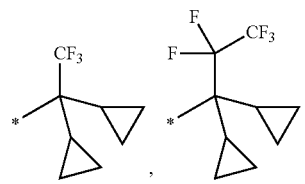

in which

\* marks the point of attachment to the nitrogen atom of the amide moiety, $Ar^1$ represents a group of the formula

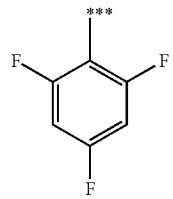

in which

\*\*\* marks the point of attachment to the nitrogen atom, and salts, solvates and solvates of the salts thereof.

A further particular embodiment of the present invention encompasses compounds of the formula (I) in which X represents fluorine or chlorine, A further particular embodiment of the present invention encompasses compounds of the formula (I) in which X represents fluorine, and the N-oxides, salts, solvates, salts of the N-oxides and solvates of the N-oxides or salts thereof.

A further particular embodiment of the present invention encompasses compounds of the formula (I) in which X represents chlorine, and the N-oxides, salts, solvates, salts of the N-oxides and solvates of the N-oxides or salts thereof.

A further particular embodiment of the present invention encompasses compounds of the formula (I) in which X represents bromine, and the N-oxides, salts, solvates, salts of the N-oxides and solvates of the N-oxides or salts thereof.

A further particular embodiment of the present invention encompasses compounds of the formula (I) in which $R^1$ represents $NR^4R^5$, in which $R^4$ represents methyl or ethyl, and $R^5$ represents methyl, 2-hydroxyethyl or 2-hydroxypropyl, and the N-oxides, salts, solvates, salts of the N-oxides and solvates of the N-oxides or salts thereof.

A further particular embodiment of the present invention encompasses compounds of the formula (I) in which $R^1$ represents a heterocycle, attached via a nitrogen atom, of the formula

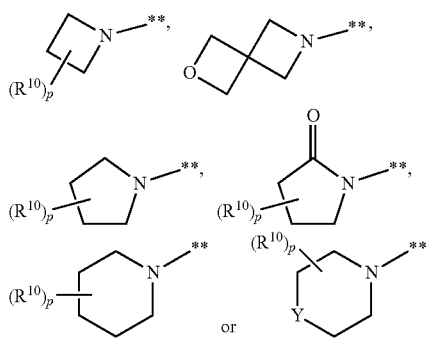

in which

** marks the point of attachment to the remainder of the molecule, $R^{10}$ represents fluorine, methyl, hydroxy, hydroxymethyl, methoxycarbonyl or acetyloxy, p represents the number 0, 1 or 2, where, in the case that the substituents $R^{10}$ occur more than once, their meanings may in each case be identical or different, $Y^1$ represents —NH—, —N(CH$_3$)— or —O—, and the N-oxides, salts, solvates, salts of the N-oxides and solvates of the N-oxides or salts thereof.

A further particular embodiment of the present invention encompasses compounds of the formula (I) in which $R^1$ represents a heterocycle, attached via a nitrogen atom, of the formula

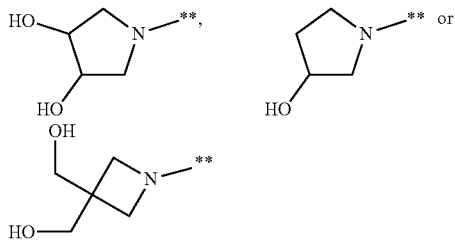

in which

** marks the point of attachment to the remainder of the molecule, and the N-oxides, salts, solvates, salts of the N-oxides and solvates of the N-oxides and salts thereof.

A further particular embodiment of the present invention encompasses compounds of the formula (I) in which $R^1$ represents a heterocycle, attached via a nitrogen atom, of the formula

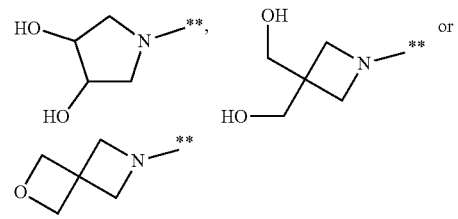

in which

** marks the point of attachment to the remainder of the molecule, and the N-oxides, salts, solvates, salts of the N-oxides and solvates of the N-oxides and salts thereof.

A further particular embodiment of the present invention encompasses compounds of the formula (I) in which $R^1$ represents a heterocycle, attached via a nitrogen atom, of the formula

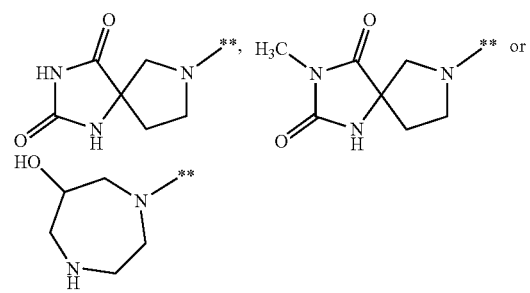

in which

** marks the point of attachment to the remainder of the molecule, and N-oxides, salts, solvates, salts of the N-oxides and solvates of the N-oxides and salts thereof.

A further particular embodiment of the present invention encompasses compounds of the formula (I) in which $R^1$ represents a heterocycle, attached via a nitrogen atom, of the formula

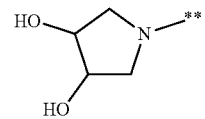

in which

** marks the point of attachment to the remainder of the molecule, and N-oxides, salts, solvates, salts of the N-oxides and solvates of the N-oxides and salts thereof.

A further particular embodiment of the present invention encompasses compounds of the formula (I) in which $R^1$ represents trans-(3R,4R)-3,4-dihydroxypyrrolidin-1-yl of the formula

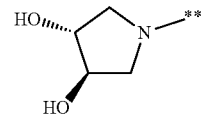

in which
** marks the point of attachment to the remainder of the molecule,
and the salts, solvates and solvates of the salts thereof.

A further particular embodiment of the present invention encompasses compounds of the formula (I) in which
$R^1$ represents cis-(R,S)-3,4-dihydroxypyrrolidin-1-yl of the formula

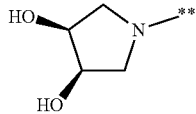

in which
** marks the point of attachment to the remainder of the molecule,
and the salts, solvates and solvates of the salts thereof.

A further particular embodiment of the present invention encompasses compounds of the formula (I) in which
$R^1$ represents a heterocycle, attached via a nitrogen atom, of the formula

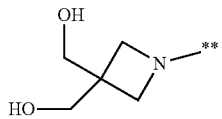

in which
** marks the point of attachment to the remainder of the molecule,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

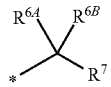

in which
* marks the point of attachment to the nitrogen atom of the amide moiety,
$R^{6A}$ represents hydrogen, methyl or ethyl,
$R^{6B}$ represents methyl, ethyl, trifluoromethyl, isopropyl or cyclopropyl, and
$R^7$ represents methyl, ethyl, difluoromethyl, trifluoromethyl, 2,2,2-trifluoroethyl, pentafluoroethyl, isopropyl, isobutyl, methoxymethyl, trifluoromethoxymethyl or cyclopropyl,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

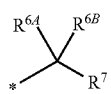

in which
* marks the point of attachment to the nitrogen atom of the amide moiety,
$R^{6A}$ represents hydrogen, methyl or ethyl,
$R^{6B}$ represents methyl, ethyl, trifluoromethyl, isopropyl, tert-butyl or cyclopropyl and
$R^7$ represents methyl, ethyl, difluoromethyl, trifluoromethyl, 2,2,2-trifluoroethyl, pentafluoroethyl, isopropyl, isobutyl, methoxymethyl, trifluoromethoxymethyl or cyclopropyl,
and the N-oxides, salts, solvates, salts of the N-oxides and solvates of the N-oxides and salts thereof.

A further particular embodiment of the present invention encompasses compounds of the formula (I) in which
$R^2$ represents a group of the formula

*-$L^1$-$Ar^2$ in which
* marks the point of attachment to the nitrogen atom of the amide moiety,
$L^1$ represents a bond or a group of the formula —$CR^{8A}R^{8B}$—,
in which
$R^{8A}$ represents hydrogen,
$R^{8B}$ represents hydrogen, methyl or trifluoromethyl,
$Ar^2$ represents a group of the formula

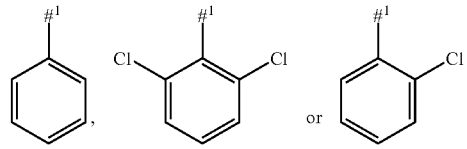

in which
$\#^1$ marks the point of attachment to the remainder of the molecule,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

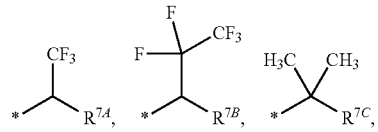

in which
* marks the point of attachment to the nitrogen atom of the amide moiety,
$R^{7A}$ represents trifluoromethyl, ethyl or cyclopropyl,
$R^{7B}$ represents methyl or ethyl,
$R^{7C}$ represents trifluoromethyl or pentafluoroethyl,
and the N-oxides, salts, solvates, salts of the N-oxides and solvates of the N-oxides or salts thereof.

A further particular embodiment of the present invention encompasses compounds of the formula (I) in which
$R^2$ represents a group of the formula

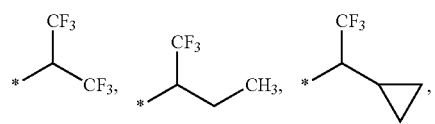

-continued

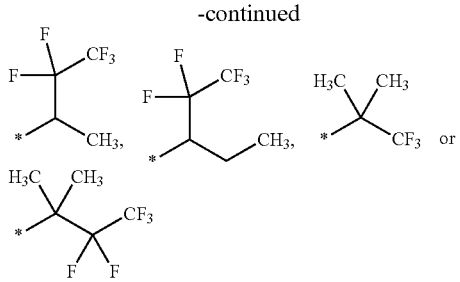

in which
* marks the point of attachment to the nitrogen atom of the amide moiety,
and the N-oxides, salts, solvates, salts of the N-oxides and solvates of the N-oxides or salts thereof.

A further particular embodiment of the present invention encompasses compounds of the formula (I) in which
R² represents a group of the formula

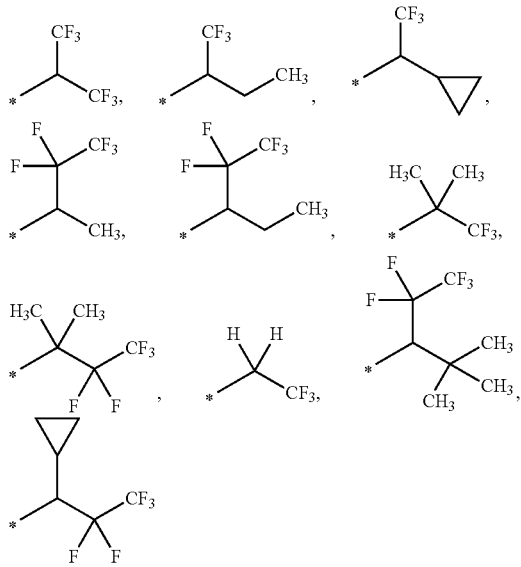

in which
* marks the point of attachment to the nitrogen atom of the amide moiety,
and the N-oxides, salts, solvates, salts of the N-oxides and solvates of the N-oxides and salts thereof.

A further particular embodiment of the present invention encompasses compounds of the formula (I) in which
R² represents a group of the formula

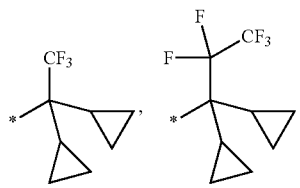

in which
* marks the point of attachment to the nitrogen atom of the amide moiety,
and the N-oxides, salts, solvates, salts of the N-oxides and solvates of the N-oxides and salts thereof.

A further particular embodiment of the present invention encompasses compounds of the formula (I) in which
R² represents a group of the formula

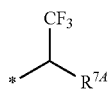

in which
* marks the point of attachment to the nitrogen atom of the amide moiety,
$R^{7A}$ represents trifluoromethyl, ethyl or cyclopropyl,
and the N-oxides, salts, solvates, salts of the N-oxides and solvates of the N-oxides or salts thereof.

A further particular embodiment of the present invention encompasses compounds of the formula (I) in which
R² represents a group of the formula

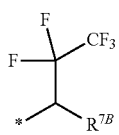

in which
* marks the point of attachment to the nitrogen atom of the amide moiety,
$R^{7B}$ represents methyl or ethyl,
and the N-oxides, salts, solvates, salts of the N-oxides and solvates of the N-oxides or salts thereof.

A further particular embodiment of the present invention encompasses compounds of the formula (I) in which
R² represents a group of the formula

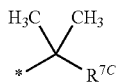

in which
* marks the point of attachment to the nitrogen atom of the amide moiety,
$R^{7C}$ represents trifluoromethyl or pentafluoroethyl,
and the N-oxides, salts, solvates, salts of the N-oxides and solvates of the N-oxides or salts thereof.

A further particular embodiment of the present invention encompasses compounds of the formula (I) in which
R² represents (2S)-1,1,1-trifluorobutan-2-yl of the formula

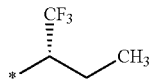

in which
* marks the point of attachment to the nitrogen atom of the amide moiety,
and the salts, solvates and solvates of the salts thereof.

A further particular embodiment of the present invention encompasses compounds of the formula (I) in which R$^2$ represents (1S)-1-cyclopropyl-2,2,2-trifluoroethyl

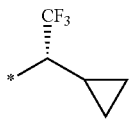

in which
* marks the point of attachment to the nitrogen atom of the amide moiety, and the salts, solvates and solvates of the salts thereof.

A further particular embodiment of the present invention encompasses compounds of the formula (I) in which R$^2$ represents a group of the formula

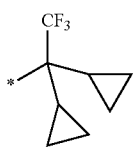 [SMILES: *C(C1CC1)(C1CC1)C(F)(F)F]

in which
* marks the point of attachment to the nitrogen atom of the amide moiety, and the salts, solvates and solvates of the salts thereof.

A further particular embodiment of the present invention encompasses compounds of the formula (I) in which R$^2$ represents a group of the formula

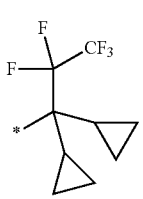

in which
* marks the point of attachment to the nitrogen atom of the amide moiety, and salts, solvates and solvates of the salts thereof.

A further particular embodiment of the present invention encompasses compounds of the formula (I) in which R$^2$ represents a group of the formula

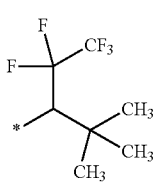

in which
* marks the point of attachment to the nitrogen atom of the amide moiety, and the salts, solvates and solvates of the salts thereof.

A further particular embodiment of the present invention encompasses compounds of the formula (I) in which R$^2$ represents a group of the formula

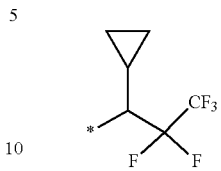

in which
* marks the point of attachment to the nitrogen atom of the amide moiety, and salts, solvates and solvates of the salts thereof.

A further particular embodiment of the present invention encompasses compounds of the formula (I) in which R$^2$ represents 1,1,1,3,3,3-hexafluoropropan-2-yl, and the salts, solvates and solvates of the salts thereof.

A further particular embodiment of the present invention encompasses compounds of the formula (I) in which R$^2$ represents 3,3,4,4,4-pentafluorobutan-2-yl, and the salts, solvates and solvates of the salts thereof.

A further particular embodiment of the present invention encompasses compounds of the formula (I) in which R$^2$ represents 1,1,1,2,2-pentafluoropentan-3-yl, and the salts, solvates and solvates of the salts thereof.

A further particular embodiment of the present invention encompasses compounds of the formula (I) in which R$^2$ represents 1,1,1-trifluoro-2-methylpropan-2-yl, and the salts, solvates and solvates of the salts thereof.

A further particular embodiment of the present invention encompasses compounds of the formula (I) in which Ar$^1$ represents a group of the formula

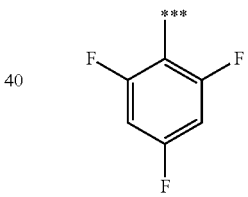

in which
*** marks the point of attachment to the nitrogen atom, and the N-oxides, salts, solvates, salts of the N-oxides and solvates of the N-oxides or salts thereof.

A further particular embodiment of the present invention encompasses compounds of the formula (I) in which Ar$^1$ represents a group of the formula

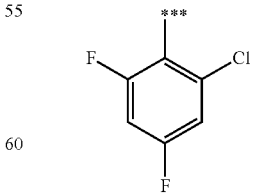

in which
*** marks the point of attachment to the nitrogen atom, and the N-oxides, salts, solvates, salts of the N-oxides and solvates of the N-oxides or salts thereof.

A further particular embodiment of the present invention encompasses compounds of the formula (I) in which
Ar¹ represents a group of the formula

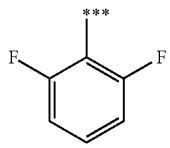

in which
\*\*\* marks the point of attachment to the nitrogen atom,
and the N-oxides, salts, solvates, salts of the N-oxides and solvates of the N-oxides or salts thereof.

A further particular embodiment of the present invention encompasses compounds of the formula (I) in which
Ar¹ represents a group of the formula

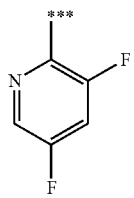

in which
\*\*\* marks the point of attachment to the nitrogen atom,
and the N-oxides, salts, solvates, salts of the N-oxides and solvates of the N-oxides or salts thereof.

The individual radical definitions specified in the respective combinations or preferred combinations of radicals are, independently of the respective combinations of the radicals specified, also replaced as desired by radical definitions of other combinations.

Very particular preference is given to combinations of two or more of the abovementioned preferred ranges and embodiments.

The radical definitions specified as preferred, particularly preferred and very particularly preferred apply both to the compounds of the formula (I) and correspondingly toward all intermediates.

The invention further provides a process for preparing compounds of the formula (I) according to the invention, characterized in that
[A] a compound of the formula (II-A)

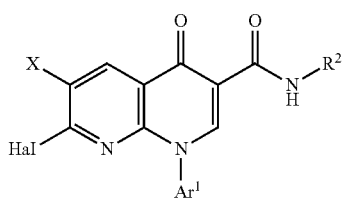

in which X, R² and Ar¹ have the meanings given above, and
Hal represents fluorine, chlorine, bromine or iodine, preferably chlorine,
is reacted with a compound of formula (III)

R¹—H (III)

in which R¹ has the meaning given above and where R¹ does not represent hydrogen, to give the carboxamide of the formula (I-A) according to the invention

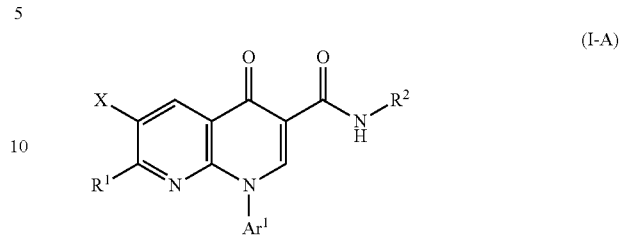

in which X, R¹, R² and Ar¹ have the meanings given above and where R¹ does not represent hydrogen,
or
[B] a compound of the formula (IV)

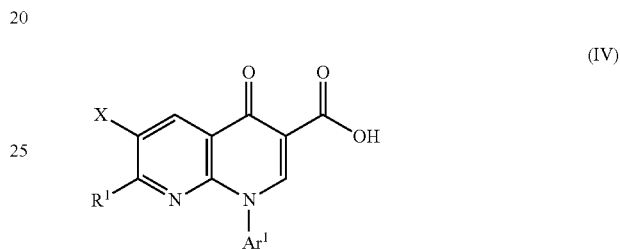

in which X, R¹ and Ar¹ have the meanings given above, is reacted with a compound of the formula (V)

R²—NH₂ (V)

in which R² has the meaning given above,
to give the carboxamide of the formula (I) according to the invention

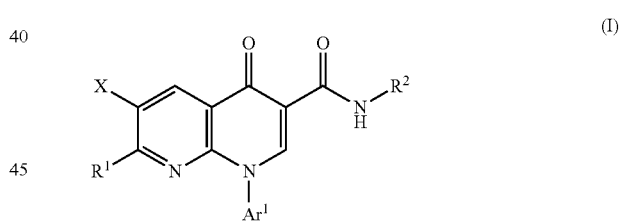

in which X, R¹, R² and Ar¹ have the meanings given above,
and, if appropriate, the compounds of the formula (I) thus obtained are separated into their enantiomers and/or diastereomers and/or converted with the appropriate (i) solvents and/or (ii) bases or acids to their solvates, salts and/or solvates of the salts.

The reaction (II-A)+(III)→(I-A) can be carried out via a nucleophilic substitution reaction or via a transition metal-mediated coupling reaction.

The nucleophilic substitution reaction is preferably carried out in the presence of a base. Suitable bases for the process step (II-A)+(III)→(I-A) are the customary inorganic or organic bases.

These preferably include alkali metal hydroxides, for example lithium hydroxide, sodium hydroxide or potassium hydroxide, alkali metal or alkaline earth metal carbonates such as lithium carbonate, sodium carbonate, potassium carbonate or caesium carbonate, alkali metal alkoxides such as lithium tert-butoxide, sodium tert-butoxide or potassium tert-butoxide, alkali metal hydrides such as sodium hydride or potassium hydride, or organic amines such as N,N-diisopropylethylamine (DIPEA), 1,5-diazabicyclo[4.3.0]non-5-ene (DBN) and 1,8-diazabicyclo[5.4.0]undec-7-ene (DBU). Preference is given to using N,N-diisopropylethylamine (DIPEA), The reaction is carried out generally within a temperature range from 0° C. to +100° C., preferably at +23° C. to +80° C.

Inert solvents for the process step (II-A)+(III)→(I-A) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulfoxide, N,N-dimethylformamide (DMF), N,N'-dimethylpropyleneurea (DMPU) or N-methylpyrrolidone (NMP). It is likewise possible to use mixtures of the solvents mentioned. Preference is given to using dimethylformamide (DMF) or N-methylpyrrolidone (NMP).

In a preferred embodiment, the transition metal-mediated coupling reaction for the process step (II-A)+(III)→(I-A) is carried out in the presence of a palladium catalyst. Suitable palladium catalysts are, for example, palladium(II) acetate, palladium(II) chloride, bis(triphenylphosphine)palladium (II) chloride, bis(acetonitrile)palladium(II) chloride, tetrakis(tri-phenylphosphine)palladium(0), bis(dibenzylideneacetone)palladium(0), tris(dibenzylideneacetone)palladium(0) or [1,1'-bis(diphenylphosphino)ferrocene]palladium(II) chloride, optionally in combination with a suitable phosphine ligand, for example triphenylphosphine, tri-tert-butylphosphine, 2-dicyclohexylphosphino-2',4',6'-triisopropylbiphenyl (X-Phos), 2-dicyclohexylphosphino-2',6'-dimethoxybiphenyl (S-Phos), 1,2,3,4,5-pentaphenyl-1'-(di-tert-butylphosphino)ferrocene (Q-Phos), 4,5-bis(diphenylphosphino)-9,9-dimethylxanthene (Xantphos), 2,2'-bis(diphenylphosphino)-1,1'-binaphthyl (BINAP), 2-dicyclohexylphosphino-2'-(N,N-dimethylamino)biphenyl or 2-di-tert-butylphosphino-2'-(N,N-dimethylamino)biphenyl.

The palladium-catalysed coupling reaction (II-A)+(III)→(I-A) is generally carried out in the presence of a base. Suitable bases are especially alkali metal carbonates such as sodium carbonate, potassium carbonate or caesium carbonate, alkali metal phosphates such as sodium phosphate or potassium phosphate, alkali metal fluorides such as potassium fluoride or caesium fluoride, or alkali metal tert-butoxides such as sodium tert-butoxide or potassium tert-butoxide. The reaction is carried out in an inert solvent, for example toluene, 1,2-dimethoxyethane, tetrahydrofuran, 1,4-dioxane, dimethyl sulfoxide (DMSO), N,N-dimethylformamide (DMF), N,N-dimethylacetamide (DMA) or mixtures thereof, within a temperature range from +80° C. to +200° C., preferably at +80° C. to +150° C., where heating by means of a microwave apparatus may be advantageous.

Preference is given to using, for this coupling reaction, a catalyst/ligand/base system consisting of palladium(II) acetate, 4,5-bis(diphenylphosphino)-9,9-dimethylxanthene (Xantphos) and caesium carbonate or potassium carbonate, and 1,4-dioxane as solvent.

The coupling reaction (II-A)+(III)→(I-A) may, in a further preferred embodiment, also be carried out with the aid of a copper(I) catalyst, such as copper(I) oxide, bromide or iodide, in the presence of a copper ligand such as trans-N,N'-dimethyl-1,2-cyclohexanediamine, 8-hydroxyquinoline or 1,10-phenanthroline, and of an inorganic or organic carbonate base, such as potassium carbonate, caesium carbonate or bis(tetraethylammonium) carbonate. Suitable inert solvents for this reaction are in particular toluene, xylene, 1,4-dioxane, acetonitrile, dimethyl sulfoxide (DMSO), N,N-dimethylformamide (DMF) or mixtures thereof, optionally with addition of water. Preference is given to using a system consisting of copper(I) iodide, trans-N,N'-dimethyl-1,2-cyclohexanediamine and potassium carbonate in dimethylformamide. The reaction is carried out generally within a temperature range from +50° C. to +200° C., preferably at +60° C. to +150° C.

The coupling reaction (IV)+(V)→(I) [amide formation] can be effected either by a direct route with the aid of a condensing or activating agent or via the intermediate stage of a carbonyl chloride, carboxylic ester or carbonyl imidazolide obtainable from (IV).

Suitable for use as condensing agents or activating agents are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), isopropyl chloroformate or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chlorenamines such as 1-chloro-N,N,2-trimethylprop-1-en-1-amine, 1,3,5-tri-azine derivatives such as 4-(4,6-dimethoxy-1,3,5-triazin-2-yl)-4-methylmorpholinium chloride, phosphorus compounds such as n-propanephosphonic anhydride (T3P, PPACA), diethyl cyano-phosphonate, diphenylphosphoryl azide (DPPA), bis(2-oxo-3-oxazolidinyl) phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), O-(1H-6-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine (NMM), N-methylpiperidine (NMP), N,N-diisopropylethylamine (DIPEA), pyridine or 4-N,N-dimethylaminopyridine (DMAP). Condensing or activating agents used with preference are O-(7-azabenzotriazol-1-yl)-N,N,N',N'-tetramethyluronium hexafluorophosphate (HATU) in combination with N,N-diisopropylethylamine (DIPEA), and also n-propanephosphonic anhydride (T3P, PPACA) in combination with N,N-diisopropylethylamine (DIPEA).

The compounds of the formula (II-A) can be prepared by reacting a carboxylic acid compound of the formula (VI-A)

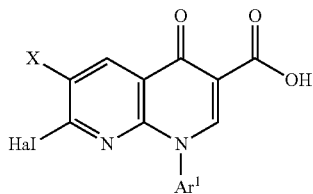
(VI-A)

in which X, Hal and Ar¹ have the meanings given above, with a compound of the formula (V)

R²—NH₂  (V)

in which R² has the meaning given above,
to give the carboxamide of the formula (II-A) according to the invention

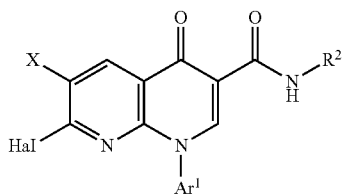
(II-A)

in which X, Hal, R² and Ar¹ have the meanings given above.

Compounds of the formula (I-B) can be prepared analogously to the reaction (VI-A)+(V)→(II-A) by reacting a carboxylic acid compound of the formula (VI-B)

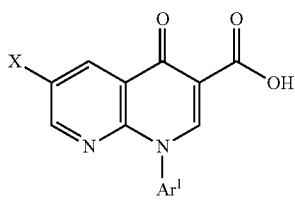
(VI-B)

in which X and Ar¹ have the meanings given above, with a compound of the formula (V)

R²—NH₂  (V)

in which R² has the meaning given above,
to give the carboxamide of the formula (I-B) according to the invention

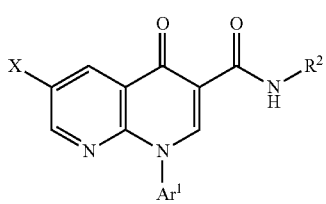
(I-B)

in which X, R² and Ar¹ have the meanings given above.

The coupling reaction (VI-A)+(V)→(II-A) or (VI-B)+(V)→(I-B) [amide formation] can be effected either by a direct route with the aid of a condensing or activating agent or via the intermediate stage of a carbonyl chloride, carboxylic ester or carbonyl imidazolide obtainable from (VI), analogously to the conditions and reagents already described for the reaction (IV)+(V)→(I). If HATU is used as activating agent in the coupling reaction to give (II-A), it is possible that either an individual defined product of the general formula (II-A) is obtained, or else a mixture with a "HATU adduct". A "HATU adduct" in the present context refers to a pseudohalide compound where the Hal substituent in the general formula (II-A) is replaced by the 3H-[1,2,3]triazolo[4,5-b]pyridin-3-ol group, also referred to as 1-hydroxy-7-azabenzotriazole. Such a mixture of a halogen compound of the general formula (II-A) and a "HATU adduct" can also be used, analogously to the reaction described, as reactant for the further reaction (after (I) or (VIII)).

In the case of a two-stage reaction regime via the carbonyl chlorides or carbonyl imidazolides obtainable from (VI), the coupling with the amine component (V) is carried out in the presence of a customary base, for example sodium carbonate or potassium carbonate, triethylamine, DIPEA, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU), 1,5-diazabicyclo[4.3.0]non-5-ene (DBN), sodium methoxide or potassium methoxide, sodium ethoxide or potassium ethoxide, sodium tert-butoxide or potassium tert-butoxide, or sodium hydride or potassium hydride.

The carbonyl imidazolides themselves are obtainable by known methods by reaction of (VI) with N,N'-carbonyldiimidazole (CDI) at elevated temperature (+60° C. to +150° C.) in a correspondingly relatively high-boiling solvent such as N,N-dimethylformamide (DMF). The preparation of the carbonyl chlorides is accomplished in a customary manner by treating (VI) with thionyl chloride or oxalyl chloride in an inert solvent such as dichloromethane or THF.

Insert solvents for the coupling reactions mentioned are—according to the method used—for example ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP). It is also possible to use mixtures of such solvents. Preference is given to using N,N-dimethylformamide (DMF) and dichloromethane (DCM) in combination with triethylamine. The couplings are generally conducted within a temperature range from 0° C. to +130° C., preferably at +20° C. to +30° C.

Depending on their respective substitution pattern, the compounds of the formula (IV-A) can be prepared by reacting either

[C] a compound of the formula (VII-A)

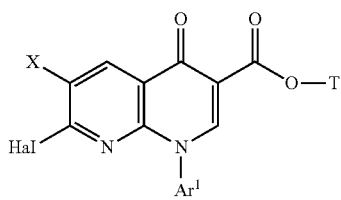
(VII-A)

in which X, Hal and Ar¹ have the meanings given above, and

T represents $(C_1-C_4)$-alkyl or benzyl in a first step with a compound of the formula (III)

R¹—H    (III)

in which R¹ has the meaning given above and where R¹ does not represent hydrogen, to give a compound of the formula (VIII-A)

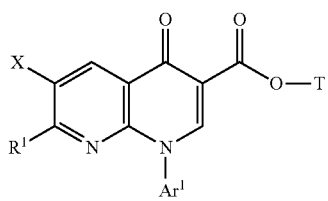
(VIII-A)

in which X, T, R¹ and Ar¹ have the meanings given above and where R¹ does not represent hydrogen, and optionally, in a second step, removing the ester radical T to give the carboxylic acid of the formula (IV-A) according to the invention

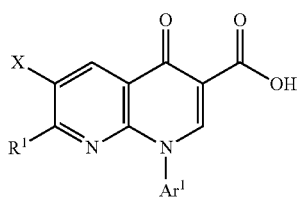
(IV-A)

in which X, R¹ and Ar¹ have the meanings given above and where R¹ does not represent hydrogen, or

[D] a compound of the formula (VI-A)

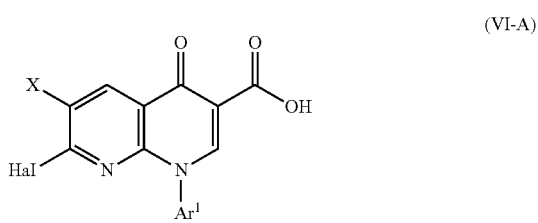
(VI-A)

in which X, Hal and Ar¹ have the meanings given above, with a compound of formula (III)

R¹—H    (III)

in which R¹ has the meaning given above and where R¹ does not represent hydrogen, to give the carboxylic acid of the formula (IV-A) according to the invention (IV-A)

in which X, R¹ and Ar¹ have the meanings given above and where R¹ does not represent hydrogen.

The reaction (VII-A)+(III)→(VIII-A) [route C] or the reaction (VI-A)+(III)→(IV-A) [route D] can be carried out via a nucleophilic substitution reaction or a transition metal-mediated coupling reaction analogously to the conditions and reagents already described for the reaction (II-A)+(III)→(I-A).

In a preferred embodiment, the reaction is conducted according to route C as a nucleophilic substitution reaction in the presence of a base, preference being given to using N,N-diisopropylethylamine (DIPEA). Preference is given to using dimethylformamide (DMF), N-methylpyrrolidone (NMP) or acetonitrile as solvent.

In a preferred embodiment, the reaction is conducted according to route D as a transition metal-mediated coupling reaction in the presence of a suitable palladium catalyst. Preference is given to using a system of palladium(II) acetate in combination with 4,5-bis(diphenylphosphino)-9,9-dimethylxanthene (xantphos), caesium carbonate or potassium carbonate and 1,4-dioxane as solvent.

The removal of the ester group T in process step (VIII-A)→(IV-A) is carried out by customary methods, by treating the ester in an inert solvent with an acid or a base, with conversion of the salt of the carboxylic acid initially formed in the latter variant to the free carboxylic acid by subsequent treatment with acid. In the case of the tert-butyl esters, the ester cleavage is preferably effected with an acid. Benzyl esters can alternatively also be cleaved by hydrogenation (hydrogenolysis) in the presence of a suitable catalyst, for example palladium on activated carbon.

Suitable solvents for these reactions are water and the organic solvents customary for ester cleavage. These include in particular alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulfoxide. It is equally possible to use mixtures of these solvents. In the case of a basic ester hydrolysis, preference is given to using mixtures of water with tetrahydrofuran.

Suitable bases for a hydrolysis reaction are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to using aqueous hydrochloric acid (18 percent) in a water/tetrahydrofuran mixture.

The ester cleavage is generally conducted within a temperature range from −20° C. to +100° C., preferably at 23° C. to +120° C.

Depending on the particular substitution pattern, the compounds of the formula (VI-A) and of the formula (VIII-A) can be prepared by, in analogy to known processes (see, for example, EP 0607825 A1, p. 25-26), reacting a 2,6-dichloronicotinoylacrylate derivative of the formula (IX-A)

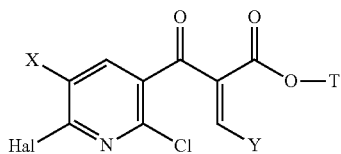
(IX-A)

in which X, Hal and T have the meanings given above
and
Y represents a leaving group such as dimethylamino, methoxy or ethoxy, and in a first stage, preferably in the presence of a suitable base, with an aminopyridine compound of the formula (X)

$Ar^1$—$NH_2$ (X)

in which $Ar^1$ has the meanings given above
and then, in a second step, reacting this in the presence of a suitable base to give the ester compound of the formula (VII-A)

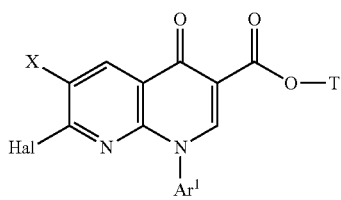
(VII-A)

in which X, Hal, $Ar^1$ and T have the definition given above,
and then optionally converting the ester compound (VII) under hydrolysis conditions in a further step to the carboxylic acid compound (VI-A)

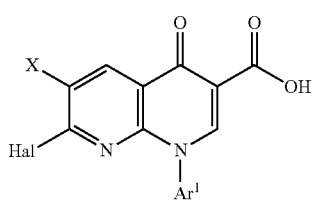
(VI-A)

in which X, Hal and $Ar^1$ have the meanings given above, under the reaction conditions known in the literature.

Compounds of the formula (VI-B) and of the formula (VII-B) can be prepared analogously to the reaction (IX-A)+(X)→(VII-A)→(VI-A) by reacting, analogously to known processes (see, for example, EP 0607825 A1, p. 25-26), a 2,6-dichloronicotinoylacrylate derivative of the formula (IX)

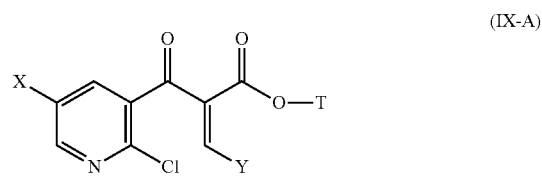
(IX-A)

in which X and T have the definitions given above
and
Y represents a leaving group such as dimethylamino, methoxy or ethoxy, and in a first stage, preferably in the presence of a suitable base, with an aminopyridine compound of the formula (X)

$Ar^1$—$NH_2$ (X)

in which $Ar^1$ has the meanings given above,
and then, in a second step, reacting this in the presence of a suitable base to give the ester compound of the formula (VII-B)

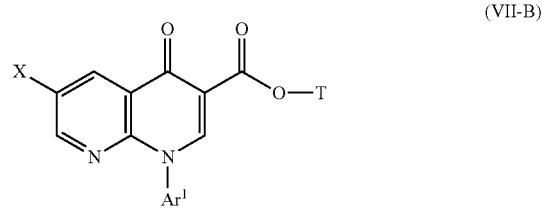
(VII-B)

in which X, $Ar^1$ and T have the meaning given above,
and then optionally converting the ester compound (VII) under hydrolysis conditions in a further step into the carboxylic acid compound (VI-B)

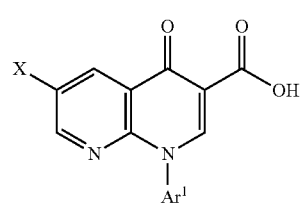
(VI-B)

in which X and $Ar^1$ have the meanings given above, under the reaction conditions known in the literature.

The compounds of the formula (IX) are known from the literature (see, for example, EP 0607825 A1) or can be prepared in analogy to processes known from the literature. The compounds of the formulae (III), (V) and (X) are commercially available or described as such in the literature, or they can be prepared in a way obvious to the person skilled in the art, in analogy to methods published in the literature. Numerous detailed methods and literature data for preparation of the respective starting materials can also be found in the Experimental Part in the section relating to the preparation of the starting compounds and intermediates.

The separation of stereoisomers (enantiomers and/or diastereomers) of the inventive compounds of the formula (I) can be achieved by customary methods familiar to those skilled in the art. Preference is given to employing chromatographic methods on achiral or chiral separation phases for this purpose. Separation of the compounds of the invention into the corresponding enantiomers and/or diastereomers can, if appropriate, also be conducted at the early stage of the intermediates (II), (IV) or (VIII), which are then reacted further in separated form in accordance with the reaction sequence described above. For such a separation of the stereoisomers of intermediates, preference is likewise given to employing chromatographic methods on achiral or chiral separation phases. Alternatively, separation can also be effected via diastereomeric salts of the carboxylic acids of the formula (IV) with chiral amine bases.

The preparation of the compounds of the invention can be illustrated by way of example by the following reaction schemes:

Scheme 1

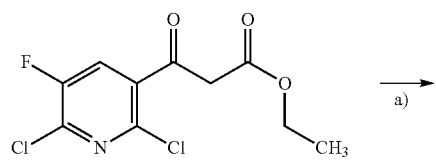

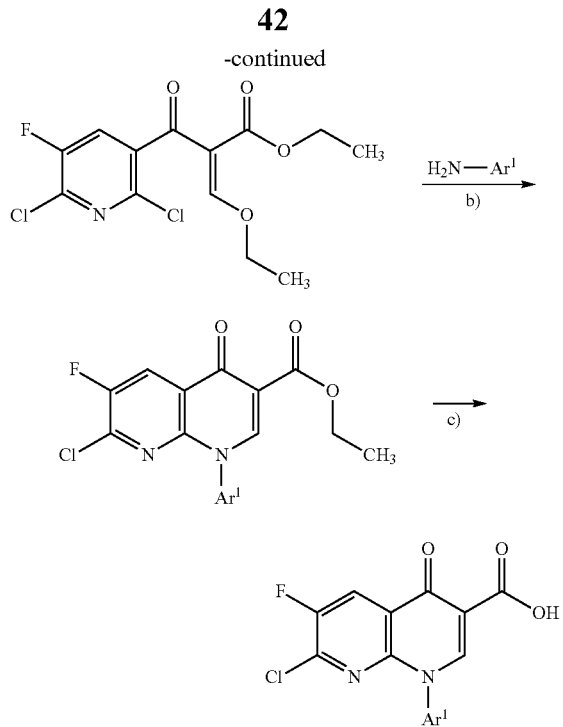

[a]: triethyl orthoformate, acetic anhydride; b): DIPEA, DCM, then K$_2$CO$_3$; c): 18% strength hydrochloric acid, THF, water].

Scheme 2

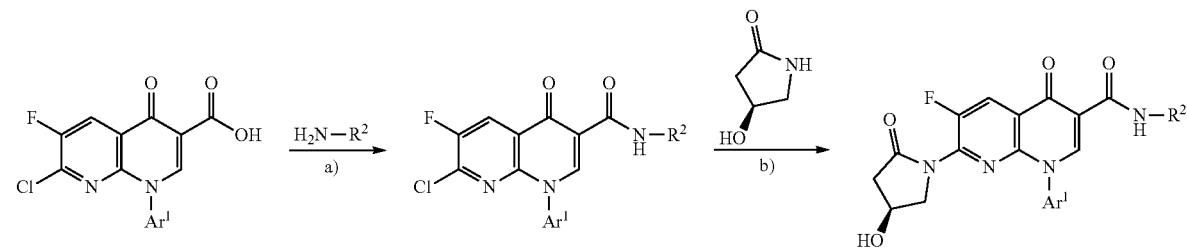

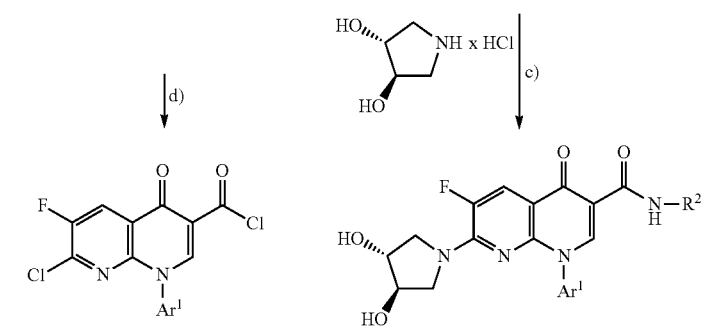

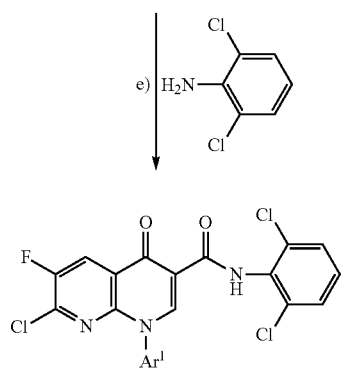
[a]: HATU, DIPEA, DMF or T3P, DIPEA, EtOAc; b): Pd(OAc)$_2$, xantphos, K$_2$CO$_3$, 1,4-dioxane; c): DIPEA, DMF; d): (COCl)$_2$, cat. DMF, THF; e): NaH, DMF or triethylamine, DCM].
Scheme 3
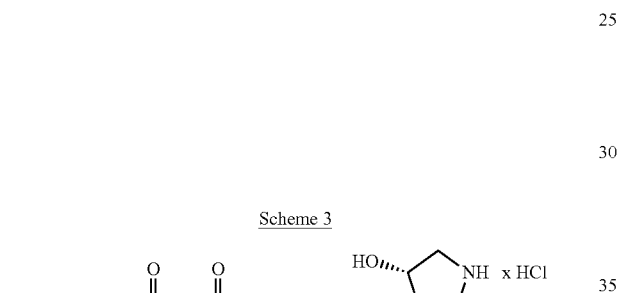
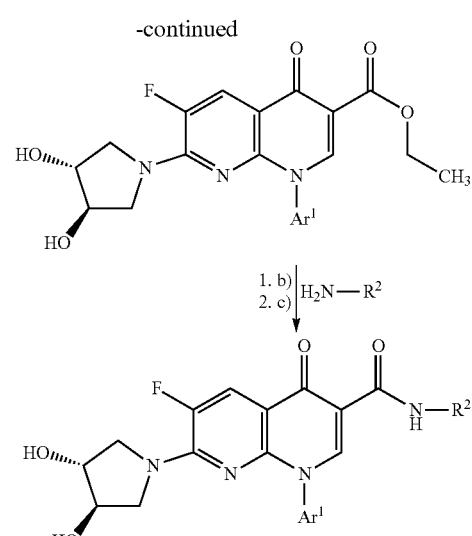
[a]: DIPEA, DMF; b): aq. LiOH, THF or 18% strength hydrochloric acid, THF, water, c): HATU, DIPEA, DMF, RT].
Scheme 4
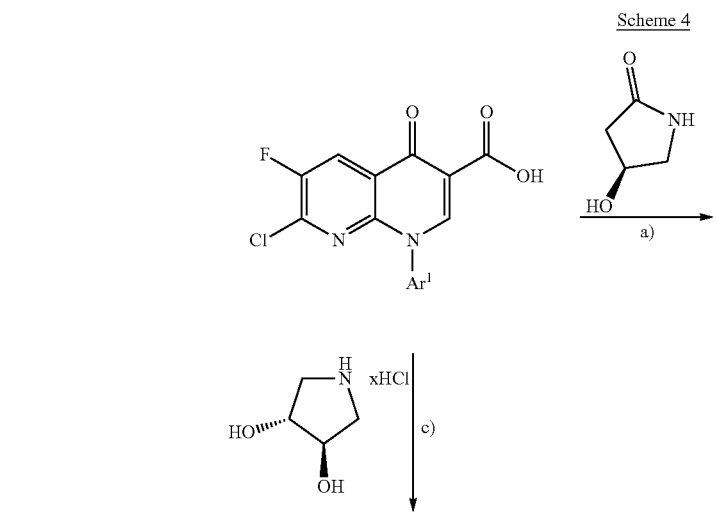

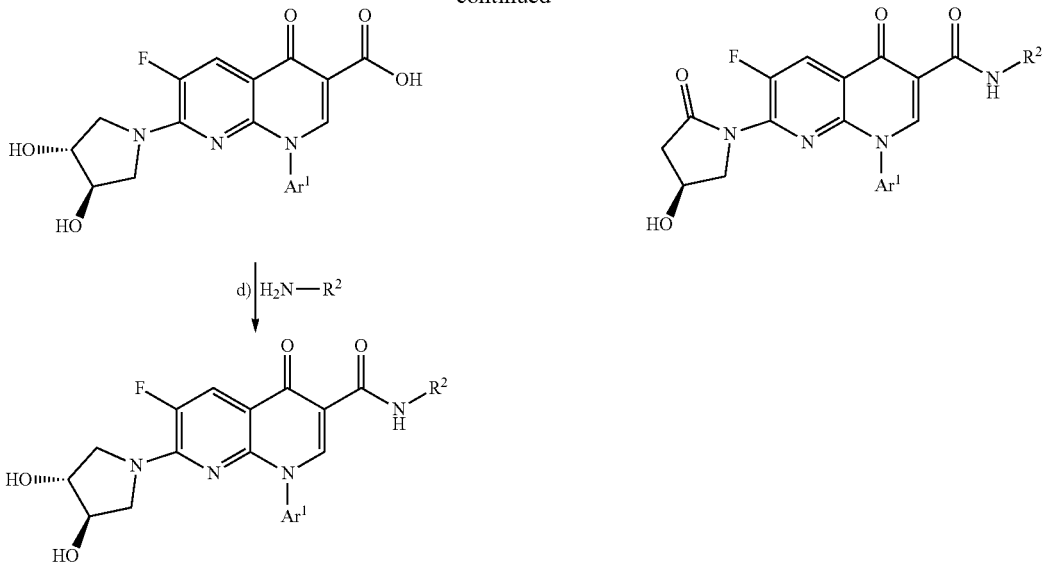

[a): Pd(OAc)$_2$, xantphos, K$_2$CO$_3$, 1,4-dioxane; b) HATU, DIPEA, DMF; c) DIPEA, DMF; d) HATU, DIPEA, DMF].

Scheme 5

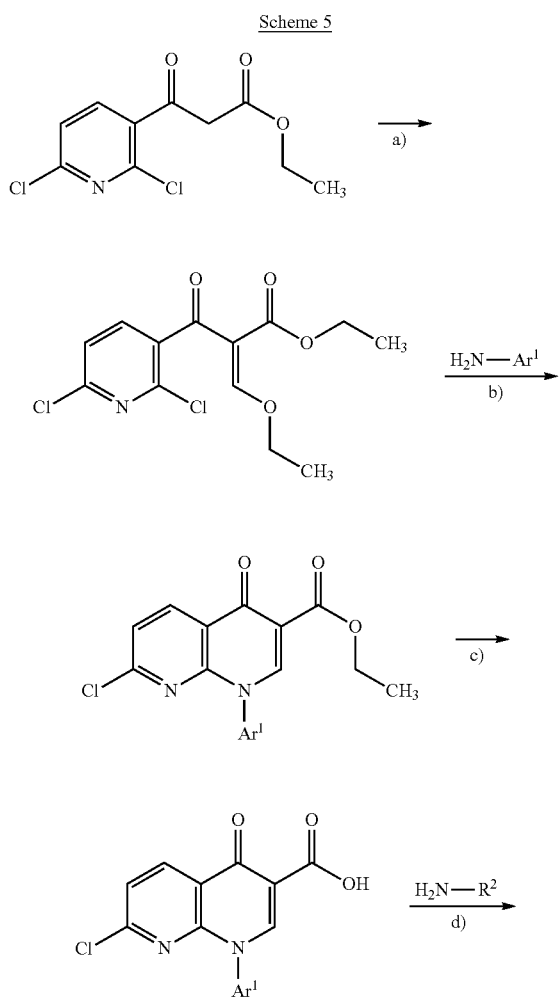

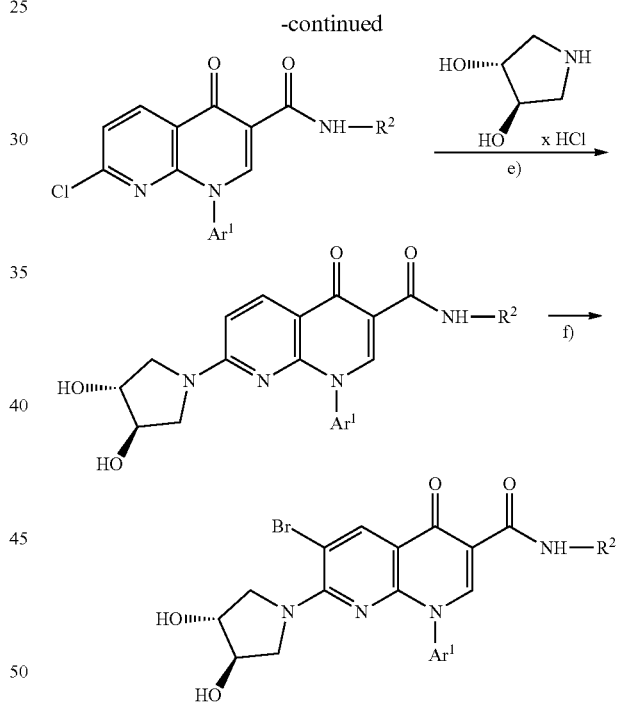

[a): triethyl orthoformate, acetic anhydride; b): DIPEA, DCM, then K$_2$CO$_3$; c): aq. LiOH, THF or 18% strength hydrochloric acid, THF, water, d): HATU, DIPEA, DMF or T3P solution, DIPEA, MeCN; e): DIPEA, DMF; f): NBS, cat. AIBN, MeCN].

Further inventive compounds of the formula (I) can, if appropriate, also be prepared by transformations of functional groups of individual radicals or substituents, especially those listed under R$^1$ and R$^2$, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, (nomination), dehalogenation, amination, alkylation and acylation, the formation of carboxylic esters, carboxamides and sulfonamides, ester cleavage and hydrolysis, and the introduction and removal of temporary protecting groups.

The invention relates, in a further aspect, to intermediates of the general formula (II)

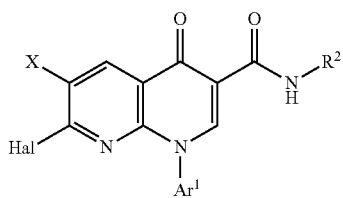

(II)

in which X, $R^2$ and $Ar^1$ have the meanings given above for compounds of the formula (I)

and

Hal represents fluorine, chlorine, bromine or iodine, preferably chlorine.

The invention relates, in a further aspect, to intermediates of the general formula (IV)

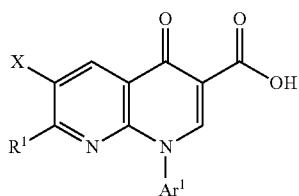

(IV)

in which X, $R^1$ and $Ar^1$ have the meanings given above for compounds of the formula (I).

The invention relates, in a further aspect, to the use of a compound of the general formula (II)

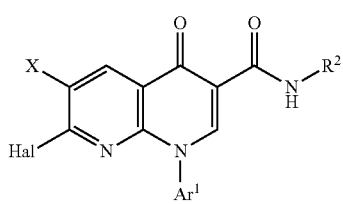

(II)

is in which X, $R^2$ and $Ar^1$ have the meanings given above for compounds of the formula (I)

and

Hal represents fluorine, chlorine, bromine or iodine, preferably chlorine.

or a compound of the general formula (IV)

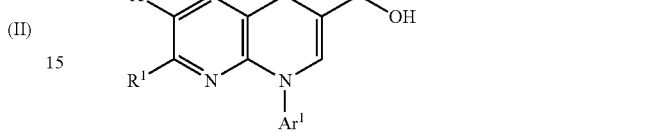

(IV)

in which X, $R^1$ and $Ar^1$ have the meanings given above for compounds of the formula (I), for preparation of a compound of the general formula (I) as defined above.

The compounds according to the invention have an unforeseeable useful spectrum of pharmacological and pharmacokinetic activity.

They are therefore suitable for use as medicaments for treatment and/or prophylaxis of diseases in humans and animals. The compounds of the invention have valuable pharmacological properties and can be used for treatment and/or prophylaxis of disorders in humans and animals.

The compounds according to the invention are positive allosteric modulators of the muscarinic M2 receptor and are therefore suitable for treatment and/or prevention of disorders and pathological processes, especially cardiovascular disorders and/or renal disorders, wherein the M2 receptor is involved in dysregulation of the autonomic nervous system or an imbalance between the activity of the sympathetic and parasympathetic portion of the autonomic nervous system.

The present invention provides positive allosteric modulators of the muscarinic M2 receptor. Allosteric modulators have distinct differences from conventional orthosteric ligands. The effect of an allosteric modulator is self-limiting when it stabilizes the binding of the agonist in high concentrations. Furthermore, the effect of an allosteric modulator can be displayed only in the presence of the endogenous ligand. The allosteric modulator itself has no direct influence on receptor activation. This gives rise to specificity of the allosteric effect in terms of space and time. The mutual influencing of allosteric and orthosteric ligands in terms of affinity and intrinsic activity, which is referred to as cooperativity, is determined by the two ligands. In the case of a positive allosteric modulator, the effects of the orthosteric ligand are enhanced (positive cooperativity). Because of its ability to modulate receptor conformations in the presence of an orthosteric ligand, allosteric ligands can bring about fine adjustment of pharmacological effects.

In the context of the present invention, disorders of the cardiovascular system or cardiovascular disorders are understood to mean, for example, the following disorders: acute and chronic heart failure, arterial hypertension, coronary heart disease, stable and unstable angina pectoris, myocardial ischaemia, myocardial infarction, shock, atherosclerosis, cardiac hypertrophy, cardiac fibrosis, atrial and ventricular arrhythmias, tachycardia, transitory and ischaemic attacks, stroke, pre-eclampsia, inflammatory cardiovascular disorders, peripheral and cardiac vascular disorders, peripheral perfusion disorders, arterial pulmonary hypertension, spasms of the coronary arteries and peripheral arteries, thromboses, thromboembolic disorders, oedema development, for example pulmonary oedema, cerebral oedema, renal oedema or heart failure-related oedema, and restenoses such as after thrombolysis treatments, percutaneous transluminal angioplasty (PTA), translurninal coronary angioplasty (PTCA), heart transplants and bypass operations, and micro- and macrovascular damage (vasculitis), reperfusion damage, arterial and venous thromboses, microalbuminuria, myocardial insufficiency, endothelial dysfunction, peripheral and cardiac vascular disorders, peripheral perfusion disorders, heart failure-related oedema, elevated levels of fibrinogen and of low-density LDL and elevated concentrations of plasminogen activator/inhibitor 1 (PAI 1).

In the context of the present invention, the term "heart failure" also includes more specific or related types of disease, such as acutely decompensated heart failure, right heart failure, left heart failure, global failure, ischaemic cardiomyopathy, dilated cardiomyopathy, congenital heart defects, heart valve defects, heart failure associated with heart valve defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, heart failure with preserved ejection fraction (HFpEF), diastolic heart failure and heart failure with reduced ejection fraction (HfrEF), systolic heart failure.

In the context of the present invention, the term atrial and ventricular arrhythmias also includes more specific or related types of disease, such as: atrial fibrillation, paroxysmal atrial fibrillation, intermittierent atrial fibrillation, permanent atrial fibrillation, atrial flutter, sinusoidal arrhythmia, sinusoidal tachycardia, passive heterotopia, active heterotopia, escape systoles, extrasystoles, impulse conduction disorders, sick sinus syndrome, hypersensitive carotid sinus, tachycardias, AV node reentry tachycardia, atriventricular reentry tachycardia, WPW syndrome (Wolff-Parkinson-White), Mahaim tachycardia, hidden accessory conduction pathway, permanent junctional reentry tachycardia, focal atrial tachycardia, junctional ectopic tachycardia, atrial reentry tachycardia, ventricular tachycardia, ventricular flutter, ventricular fibrillation, sudden cardiac death.

In the context of the present invention, the term coronary heart disease also encompasses more specific or related types of disease, such as: ischaemic heart disease, stable angina pectoris, acute coronary syndrome, unstable angina pectoris, NSTEMI (non-ST elevation myocardial infarction), STEMI (ST elevation myocardial infarction), ischaemic heart muscle damage, heart rhythm dysfunctions and myocardial infarction.

The compounds according to the invention are further suitable for the prophylaxis and/or treatment of polycystic kidney disease (PCKD) and of the syndrome of inappropriate ADH secretion (SIADH).

The compounds of the invention are also suitable for the treatment and/or prophylaxis of kidney disorders, in particular of acute and chronic renal insufficiency and acute and chronic renal failure.

In the context of the present invention, the term "acute renal insufficiency" encompasses acute manifestations of kidney disease, of kidney failure and/or renal insufficiency with and without the need for dialysis, and also underlying or related renal disorders such as renal hypoperfusion, intradialytic hypotension, volume deficiency (e.g. dehydration, blood loss), shock, acute glomerulonephritis, haemolytic-uraemic syndrome (HUS), vascular catastrophe (arterial or venous thrombosis or embolism), cholesterol embolism, acute Bence-Jones kidney in the event of plasmacytoma, acute supravesicular or subvesicular efflux obstructions, immunological renal disorders such as kidney transplant rejection, immune complex-induced renal disorders, tubular dilatation, hyperphosphataemia and/or acute renal disorders which can be characterized by the need for dialysis, including in the case of partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematosus, renal artery thrombosis, renal vein thrombosis, analgesic nephropathy and renal-tubular acidosis, and x-ray contrast agent- and medicament-induced acute interstitial renal disorders.

In the context of the present invention, the term "chronic renal insufficiency" encompasses chronic manifestations of kidney disease, of kidney failure and/or renal insufficiency with and without the need for dialysis, and also underlying or related renal disorders such as renal hypoperfusion, intradialytic hypotension, obstructive uropathy, glomerulopathy, glomerular and tubular proteinuria, renal oedema, haematuria, primary, secondary and chronic glomerulonephritis, membranous and membranoproliferative glomerulonephritis, Alport syndrome, glomerulosclerosis, tubulointerstitial disorders, nephropathic disorders such as primary and congenital kidney disease, renal inflammation, immunological renal disorders such as kidney transplant rejection, immune complex-induced renal disorders, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, glomerular and arteriolar lesions, tubular dilatation, hyperphosphataemia and/or the need for dialysis, and also for renal cell carcinomas, after partial resections of the kidney, dehydration through forced diuresis, uncontrolled blood pressure increase with malignant hypertension, urinary tract obstruction and infection and amyloidosis and systemic disorders with glomerular factors, such as rheumatological-immunological systemic disorders, for example lupus erythematosus, and renal artery stenosis, renal artery thrombosis, renal vein thrombosis, analgesic nephropathy and renal-tubular acidosis. In addition, X-ray contrast agent- and medicament-induced chronic interstitial renal disorders, metabolic syndrome and dyslipidaemia. The present invention also encompasses the use of the compounds according to the invention for treatment and/or prophylaxis of sequelae of renal insufficiency, for example pulmonary oedema, heart failure, uraemia, anaemia, electrolyte disorders (for example hyperkalaemia, hyponatraemia) and disorders in bone and carbohydrate metabolism.

In addition, the compounds according to the invention are also suitable for treatment and/or prophylaxis of pulmonary arterial hypertension (PAH) and other forms of pulmonary hypertension (PH), of chronic obstructive pulmonary disease (COPD), of acute respiratory distress syndrome (ARDS), of acute lung injury (ALI), of alpha-1-antitrypsin deficiency (AATD), of pulmonary fibrosis, of pulmonary emphysema (for example pulmonary emphysema caused by cigarette smoke), of cystic fibrosis (CF), of acute coronary syndrome (ACS), heart muscle inflammations (myocarditis) and other autoimmune cardiac disorders (pericarditis, endocarditis, valvolitis, aortitis, cardiomyopathies), cardiogenic shock, aneurysms, sepsis (SIRS), multiple organ failure (MODS, MOF), inflammatory disorders of the kidney, chronic intestinal disorders (IBD, Crohn's Disease, UC), pancreatitis, peritonitis, rheumatoid disorders, inflammatory skin disorders and inflammatory eye disorders.

The compounds according to the invention can also be used for treatment and/or prophylaxis of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of Bronchiolitis obliterans, bronchiectasis, pneumonia, idiopathic interstitial pneumonia, farmer's lung and related diseases, of coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds described in the present invention are also active compounds for control of central nervous system disorders characterized by disturbances of the NO/cGMP system. In particular, they are suitable for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HTV dementia, schizophrenia with dementia or Korsakoff's psychosis. They are also suitable for treatment and/or prevention of central nervous system disorders such as states of anxiety, tension and depression, bipolar disorder, CNS-related sexual dysfunctions and sleep disturbances, and for controlling pathological disturbances of the intake of food, stimulants and addictive substances.

Furthermore, the compounds according to the invention are also suitable for the treatment and prophylaxis of urological disorders such as: urine incontinence, in particular stress incontinence, urge incontinence, reflex incontinence and overflow incontinence, detrusor hyperactivity, neurogenic detrusor hyperactivity, idiopathic detrusor hyperactivity, benign prostate hyperplasia (BPH syndrome), lower urinary tract symptoms (LUTS).

The compounds according to the invention are furthermore suitable for the treatment and/or prevention of gastroenterological disorders such as oesophagus disorders, emesis, achalasia, gastrooesophageal reflux disease, stomach disorders such as gastritis, disorders of the intestine such as diarrhea, constipation, malassimilation syndrome, bile acid loss syndrome, Crohn's disease, ulcerative colitis, microscopic colitis and irritable bowel syndrome.

The compounds according to the invention are further suitable for the treatment and/or prevention of states of pain such as menstruation disorders, dysmenorrhoea, endometriosis, premature birth, tocolysis.

Because of their profile of biochemical and pharmacological properties, the compounds according to the invention are also especially suitable for treatment and/or prevention of heart failure, coronary heart disease, atrial and ventricular arrhythmia, kidney failure and nephropathy.

The compounds of the invention can additionally be used for the treatment and/or prophylaxis of primary and secondary Raynaud's phenomenon, of microcirculation impairments, claudication, peripheral and autonomic neuropathies, diabetic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds of the invention are additionally suitable for treatment and/or prevention of ophthalmologic disorders, for example glaucoma, age-related macular degeneration (AMD), of dry (non-exudative) AMD, wet (exudative, neovascular) AMD, choroidal neovascularization (CNV), diabetic retinopathy, atrophic changes to the retinal pigment epithelium (RPE), hyper-trophic changes to the retinal pigment epithelium, macular oedema, diabetic macular oedema, retinal vein occlusion, choroidal retinal vein occlusion, macular oedema due to retinal vein occlusion, angiogenesis at the front of the eye, for example corneal angiogenesis, for example following keratitis, cornea transplant or keratoplasty, corneal angiogenesis due to hypoxia (as a result of extensive wearing of contact lenses), pterygium conjunctiva, subietinal oedema and intraretinal oedema. In addition, the compounds of the invention are suitable for treatment and/or prevention of elevated and high intraocular pressure as a result of traumatic hyphaema, periorbital oedema, postoperative viscoelastic retention or intraocular inflammation.

Moreover, the compounds according to the invention are suitable for the treatment and/or prophylaxis of hepatitis, neoplasms, osteoporosis, glaucoma and gastroparesis.

In addition, the compounds of the invention are also suitable for controlling cerebral blood flow and are effective agents for controlling migraine. They are also suitable for the prophylaxis and control of sequelae of cerebral infarct (Apoplexia cerebri) such as stroke, cerebral ischaemias and skull-brain trauma. The compounds of the invention can also be used for controlling pain, neuralgias and tinnitus.

The aforementioned well-characterized diseases in humans can also occur with comparable aetiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The present invention further provides the compounds according to the invention for use in a method of treatment and/or prevention of disorders, especially of the aforementioned disorders.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

hypotensive drugs, by way of example and with preference from the group of calcium antagonists, angiotensin AII antagonists, ACE inhibitors, NEP inhibitors, vasopeptidase inhibitors, endothelin antagonists, renin inhibitors, alpha-receptor blockers, beta-receptor blockers, mineralocorticoid receptor antagonists, and rho kinase inhibitors and the diuretics;

antianhythmics, by way of example and with preference sodium channel blockers, beta receptor blockers, potassium channel blockers, calcium antagonists, If channel blockers, digitalis, parasympatholytics (vagolytics), sympathomimetics and other antianhythmics such as adenosine, adenosine receptor agonists and vernakalant;

compounds having a positive inotropic effect, for example cardiac glycosides (digoxin), beta-adrenergic and dopaminergic agonists such as isoprenaline, adrenaline, noradrenaline, dopamine or dobutamine;

vasopressin receptor antagonists, by way of example and with preference conivaptan, tolvaptan, lixivaptan, mozavaptan, satavaptan, SR-121463, RWJ 676070 or BAY 86-8050, and also the compounds described in WO 2010/105770, WO2011/104322 and WO 2016/071212;

natriuretic peptides, for example atrial natriuretic peptide (ANP), natriuretic peptide type B (BNP, nesiritide) natriuretic peptide type C (CNP) or urodilatin;

activators of cardiac myosins, for example omecamtiv mecarbil (CK-1827452);

calcium sensitizers, for example levosimendan;

compounds which modulate the energy metabolism of the heart, by way of example and with preference etomoxir, dichloroacetate, ranolazine or trimetazidine, full or partial adenosine A1 receptor agonists such as GS-9667 (known beforehand as CVT-3619), capadenoson, neladenoson and BAY 1067197;

compounds which modulate the heart rate, for example ivabradine;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil, udenaftl, desantafil, avanafil, mirodenafil, lodenafil or PF-00489791;

antithrombotics, by way of example and with preference from the group of the platelet aggregation inhibitors, the anticoagulants or the profibrinolytic substances;

bronchodilatory agents, by way of example and with preference from the group of the beta-adreneigic receptor agonists, such as especially albuterol, isoproterenol, metaproterenol, terbutalin, formoterol or salmeterol, or from the group of the anticholinergics, such as especially ipratropium bromide;

anti-inflammatory agents, by way of example and with preference from the group of the glucocorticoids, such as especially prednisone, prednisolone, methylprednisolone, triamcinolone, dexamethasone, beclomethasone, betamethasone, flunisolide, budesonide or fluticasone and also non-steroidal anti-inflammatory drugs (NSAIDs) such as, in particular, acetylsalicylic acid (Aspirin), ibuprofen and naproxen, 5-aminosalicylic acid derivatives, leukotriene antagonists, TNF-alpha inhibitors and chemokine receptor antagonists such as CCR1, 2 and/or 5 inhibitors;

lipid metabolism modifiers, for example and with preference from the group of thyroid receptor agonists, cholesterol synthesis inhibitors, preferred examples being HMG-CoA reductase inhibitors or squalene synthesis inhibitors, of ACAT inhibitors, CETP inhibitors, MTP inhibitors, PPAR-alpha, PPAR-gamma and/or PPAR-5 agonists, cholesterol absorption inhibitors, lipase inhibitors, polymeric bile acid adsorbents, bile acid reabsorption inhibitors and lipoprotein(a) antagonists;

compounds which inhibit the signal transduction cascade, by way of example and with preference from the group of the kinase inhibitors, especially from the group of the tyrosine kinase and/or serine/threonine kinase inhibitors;

compounds which inhibit the degradation and alteration of the extracellular matrix, by way of example and with preference inhibitors of the matrix metalloproteases (MMPs), especially inhibitors of chymase, stromelysin, collagenases, gelatinases and aggrecanases (in this context particularly of MMP-1, MMP-3, MMP-8, MMP-9, MMP-10, MMP-11 and MMP-13) and of metalloelastase (MMP-12) and neutrophile elastase (HNE), such as sivelestat or DX-890;

compounds which block the binding of serotonin to its receptor by way of example and with preference antagonists of the 5-HT$_{2b}$ receptor, organic nitrates and NO donors, for example sodium nitroprusside, nitroglycerin, isosorbide mononitrate, isosorbide dinitrate, molsidomine or SIN-1, and inhaled NO;

NO-independent but haem-dependent stimulators of soluble guanylate cyclase, such as in particular the compounds described in WO 00/06568, WO 00/06569, WO 02/42301, WO 03/095451, WO 2011/147809, WO 2012/004258, WO 2012/028647 and WO 2012/059549;

NO- and haem-independent activators of soluble guanylate cyclase, such as especially the compounds described in WO 01/19355, WO 01/19776, WO 01/19778, WO 01/19780, WO 02/070462 and WO 02/070510;

compounds which increase the synthesis of cGMP, for example sGC modulators such as, by way of example and with preference, riociguat, cinaciguat, vericiguat or BAY 1101042;

prostacyclin analogues, by way of example and with preference iloprost, beraprost, treprostinil or epoprostenol;

compounds which inhibit soluble epoxide hydrolase (sEH), for example N,N'-dicyclohex-ylurea, 12-(3-adamantan-1-ylureido)dodecanoic acid or 1-adamantan-1-yl-3-{5-[2-(2-ethoxyethoxy)ethoxy]pentyl}urea;

active compounds which modulate glucose metabolism, for example insulins, biguanides, thiazolidinediones, sulfonylureas, acarbose, DPP4 inhibitors, GLP-1 analogues or SGLT-1 inhibitors.

In a preferred embodiment of the invention, the compounds according to the invention are used in combination with a kinase inhibitor, by way of example and with preference bortezomib, canertinib, erlotinib, gefitinib, imatinib, lapatinib, lestaurtinib, lonafamib, nintedanib, dasatinib, nilotinib, bosutinib, axitinib, telatinib, imatinib, brivanib, pazopanib, pegaptinib, pelitinib, semaxanib, sorafenib, regorafenib, sunitinib, tandutinib, tipifamib, vatalanib, fasudil, lonidamine, leflunomide, BMS-3354825 or Y-27632.

In a preferred embodiment of the invention, the compounds according to the invention are used in combination with a serotonin receptor antagonist, by way of example and with preference PRX-08066.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference dabigatran, ximelagatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban, edoxaban (DU-176b), apixaban, otamixaban, fidexaban, razaxaban, fondaparinux, idraparinux, PMD-3112, YN-150, KFA-1982, EMD-503982, MCN-17, mLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of calcium antagonists, angiotensin AH antagonists, ACE inhibitors, endothelin antagonists, renin inhibitors, alpha-receptor blockers, beta-receptor blockers, mineralocorticoid receptor antagonists, rho kinase inhibitors, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1 receptor blocker, by way of example and with preference prazosin.

In a preferred embodiment of the invention, the compounds of the invention are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AH antagonist, by way of example and with preference losartan, candesartan, valsartan, telmisartan or embursatan, irbesartan, olmesartan, eprosartan or azilsartan or a dual angiotensin AH antagonist/NEP inhibitor, for example and with preference Entresto (LCZ696, valsartan/sacubitril).

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan, avosentan, macitentan, atrasentan or sitaxsentan.

In a preferred embodiment of the invention, the compounds according to the invention are administered in combination with a TGFbeta antagonist, by way of example and with preference pirfenidone or fresolimumab.

In a preferred embodiment of the invention, the compounds according to the invention are administered in combination with a TNFalpha antagonist, by way of example and with preference adalimumab.

In a preferred embodiment of the invention, the compounds of the invention are administered in combination with a renin inhibitor, by way of example and with preference aliskiren, SPP-600 or SPP-800.

In a preferred embodiment of the invention, the compounds according to the invention are administered in combination with HIF-PH inhibitors, by way of example and with preference molidustat or roxadustat.

In a preferred embodiment of the invention, the compounds of the invention are administered in combination with a mineralocorticoid receptor antagonist, by way of example and with preference spironolactone or eplerenone, finerenone.

In a preferred embodiment of the invention, the compounds according to the invention are administered in combination with a rho kinase inhibitor, by way of example and with preference fasudil, Y-27632, SLx-2119, BF-66851, BF-66852, BF-66853, KI-23095, SB-772077, GSK-269962A or BA-1049.

In a preferred embodiment of the invention, the compounds of the invention are administered in combination with a diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-δ agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), anacetrapib, JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds according to the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

In a preferred embodiment of the invention, the compounds according to the invention are administered in combination with sGC modulators, by way of example and with preference riociguat, cinaciguat, vericiguat or BAY 1101042.

In a preferred embodiment of the invention, the compounds according to the invention are administered in combination with an active ingredient which modulates glucose metabolism, by way of example and with preference insulin, a sulfonylurea, acarbose, DPP4 inhibitors, GLP-1 analogues or SGLT-1 inhibitor.

Particular preference is given to combinations of the compounds according to the invention with one or more further active ingredients selected from the group consisting of active hypotensive ingredients, active antiarrhythmic ingredients, vasopressin receptor antagonists, PDE 5 inhibitors, platelet aggregation inhibitors, sGC activators and sGC stimulators.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral, intravenous and intrapulmonary (inhalative) administration.

The compounds of the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

| Abbreviations and acronyms: | |
|---|---|
| GP | General Procedure |
| abs. | absolute |
| AIBN | azobis(isobutyronitrile) |
| aq. | aqueous, aqueous solution |
| br. | broad (in NMR signal) |
| Ex. | Example |
| Bu | butyl |
| c | concentration |

| Abbreviations and acronyms: | |
|---|---|
| approx. | circa, about |
| cat. | catalytic |
| CDI | carbonyldiimidazole |
| CI | chemical ionization (in MS) |
| d | doublet (in NMR) |
| d | day(s) |
| DCM | dichloromethane |
| dd | doublet of doublets (in NMR) |
| de | diastereomeric excess |
| DEA | diethylamine |
| dist. | distilled |
| DIPEA | N,N-diisopropylethylamine |
| DMAP | 4-N,N-dimethylaminopyridine |
| DMF | N,N-dimethylformamide |
| DMSO | dimethyl sulfoxide |
| dt | doublet of triplets (in NMR) |
| ee | enantiomeric excess |
| EI | electron impact ionization (in MS) |
| ent | enantiomerically pure, enantiomer |
| eq. | equivalent(s) |
| ESI | electrospray ionization (in MS) |
| Et | ethyl |
| GC | gas chromatography |
| GC/MS | gas chromatography-coupled mass spectrometry |
| h | hour(s) |
| HATU | O-(7-azabenzotriazol-1-yl)-N,N,N',N'-tetramethyluronium hexafluorophosphate |
| HPLC | high-pressure, high-performance liquid chromatography |
| conc. | concentrated (in the case of a solution) |
| LC | liquid chromatography |
| LC/MS | liquid chromatography-coupled mass spectrometry |
| lit. | literature (reference) |
| m | multiplet (in NMR) |
| M | molar (in solution) |
| Me | methyl |
| min | minute(s) |
| MS | mass spectrometry |
| NBS | 1-bromopyrrolidine-2,5-dione |
| NMR | nuclear magnetic resonance spectrometry |
| q (or quart) | quartet (in NMR) |
| qd | quartet of doublets (in NMR) |
| quant. | quantitative (in chemical yield) |
| quint | quintet (in NMR) |
| rac | racemic, racemate |
| RP | reverse phase (in HPLC) |
| RT | room temperature |
| Rt | retention time (in HPLC, LC/MS) |
| s | singlet (in NMR) |
| sept | septet (in NMR) |
| SFC | supercritical liquid chromatography |
| t | triplet (in NMR) |
| tBu | tert-butyl |
| td | triplet of doublets (in NMR) |
| TFA | trifluoroacetic acid |
| THF | tetrahydrofuran |
| UV | ultraviolet spectrometry |
| cf. | see |
| v/v | volume to volume ratio (of a solution) |
| Xantphos | 9,9-dimethyl-4,5-bis(diphenylphosphino)xanthene |
| tog. | together |

HPLC and LG/MS Methods:

Method 1:

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2:

MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B:

1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm Method 3:

MS instrument type: Thermo Scientific FT-MS; instrument type UHPLC+: Thermo Scientific UltiMate 3000; column: Waters, HSST3, 2.1×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/Optimum Integration Path 210-300 nm.

Method 4:

Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 5:

Instrument: Agilent MS Quad 6150; HPLC: Agilent 1290; column: Waters Acquity UPLC HSS T3 1.8µ 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.

Method 6:

Instrument: Thermo DFS, Trace GC Ultra; column: Restek RTX-35, 15 m×200 µm×0.33 µm; constant helium flow rate: 1.20 ml/min; oven: 60° C.; inlet: 220° C.; gradient: 60° C., 30° C./min→300° C. (maintain for 3.33 min).

Further Details:

The percentages in the example and test descriptions which follow are, unless indicated otherwise, percentages by weight; parts are parts by weight. Solvent ratios, dilution ratios and concentration data for liquid/liquid solutions are based in each case on volume.

In the case of purifications of compounds of the invention by preparative HPLC by the described methods in which the eluents contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Purity figures are generally based on corresponding peak integrations in the LC/MS chromatogram, but may additionally also have been determined with the aid of the 1H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of 1H NMR signals that follow have in some cases been taken directly from the suggestions of the ACD SpecManager (ACD/Labs Release 12.00, Product version 12.5) and have not necessarily been strictly scrutinized. In addition to these $^1$H NMR data, there may be additional broadened signals—owing to the prevailing molecular dynamics (in particular in the range of 2.50-4.20 ppm)—which are not separately indicated. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the centre of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

The $^1$H NMR data of selected examples are stated in the form of $^1$H NMR peak lists. For each signal peak, first the δ value in ppm and then the signal intensity in round brackets are listed. The δ value/signal intensity number pairs for different signal peaks are listed with separation from one another by commas. The peak list for an example therefore takes the following form: $δ_1$ (intensity$_1$), $δ_2$ (intensity$_2$), . . . , $δ_i$ (intensity$_i$), . . . , $δ_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (Mes-treC, ACD simulation, or using empirically evaluated expected values) can, if required, isolate the peaks of the target compounds, optionally using additional intensity filters. This isolation would be similar to the peak picking in question in conventional $^1$H NMR interpretation. A detailed description of the presentation of NMR data in the form of peak lists can be found in the publication "Citation of NMR Peaklist Data within Patent Applications" (cf. Research Disclosure Database Number 605005, 2014, 1 Aug. 2014 or http://www.researchdisclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analysed, it may be advisable to set the parameters "MinimumHeight" to values of <1%.

Melting points and melting point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

General Procedures

GP1

N,N-Diisopropylethylamine (1.4-1.5 eq., or 2.4-3.0 eq. when the amine was used in hydrochloride form) and HATU (1.0-1.65 eq.) were added to a solution of the corresponding carboxylic acid (1 eq.) in DMF (0.08-0.12M), and the mixture was stirred at RT for 30 min. Subsequently, the appropriate amine (1.04-1.5 eq.) was added and the mixture was stirred at room temperature for a further 0.15-2 h. The reaction was then terminated by the addition of water and 1 M aqueous hydrochloric acid. The precipitate was filtered off, taken up in DCM, dried over magnesium sulfate and filtered, and the solvent was removed under reduced pressure. Alternatively, the acidification was followed by extraction with ethyl acetate, drying of the combined organic phases over magnesium sulfate or sodium sulfate, filtration and removal of the solvent under reduced pressure. The crude product was then purified either by normal phase chromatography (silica gel, mobile phase: cyclohexane/ethyl acetate mixtures or dichloromethane/methanol mixtures) or by preparative RP-HPLC (water/acetonitrile gradient). Alternatively, the reaction mixture was diluted with a little acetonitrile, water and formic acid and the crude solution obtained was purified by RP-HPLC (water/acetonitrile gradient). Further alternatives for work-up, if carried out, are described with the respective experiment.

GP2

Potassium carbonate or caesium carbonate (1.5-2.5 eq.) was baked in a reaction vessel under reduced pressure. The vessel was cooled to RT and flooded with argon. Palladium acetate (0.1-0.36 eq.), 9,9-dimethyl-4,5-bis(diphenylphosphino)xanthene (Xantphos, 0.18-0.36 eq.) and dioxane (0.04-0.12M) were added, and the suspension was degassed in an argon stream at room temperature for 10 min. Subsequently, the appropriate amide (1.0-10 eq.) and the appropriate 7-chloro-4-oxo-1,4-dihydro-1,8-naphthyridine (1.0 eq.) were added. The mixture was stirred at 80-110° C. for 1 h (or until conversion was complete by analytical HPLC or thin-layer chromatography with appropriate mobile phase mixtures). The mixture was then cooled to RT and all volatile components were removed under reduced pressure, or alternatively the reaction mixture was poured into water, the pH was adjusted to pH 1 with 1M aqueous hydrochloric acid, the mixture was extracted with ethyl acetate, the combined organic phases were washed with saturated aqueous sodium chloride solution, dried over magnesium sulfate and filtered, and the solvent was removed under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient). Alternatively, the reaction mixture was diluted with a little acetonitrile, water and formic acid or TFA and the crude solution obtained was purified by RP-HPLC (water/acetonitrile gradient). Further alternatives for work-up, if carried out differently, are described with the respective experiment.

GP3

The appropriate amine (1.2 eq.) and DIPEA (1.5-3.5 eq.) were added to a solution of the appropriate 7-chloro-4-oxo-1,4-dihydro-1,8-naphthyridine in DMF (0.10-0.22 M). The reaction solution was stirred at RT overnight. The crude product was subsequently, after aqueous work-up and extraction with the appropriate organic solvent, purified either by normal-phase chromatography (mobile phase: cyclohexane/ethyl acetate mixtures or dichloromethane/methanol mixtures) or by preparative RP-HPLC (water/acetonitrile gradient). Alternatively, the reaction mixture was diluted with a little acetonitrile, water and formic acid and the crude solution obtained was purified by RP-HPLC (water/acetonitrile gradient). Further alternatives for work-up, if carried out, are described with the respective experiment.

Starting Compounds and Intermediates

Example 1A

Ethyl 7-chloro-1-(2,6-difluorophenyl)-6-fluoro-4-oxo-1,4-dihydro-1,8-naphthyridine-3-carboxylate

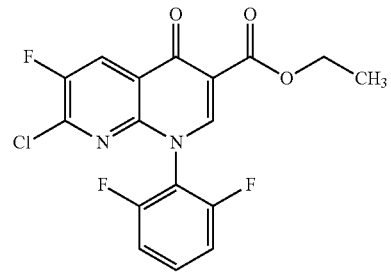 [SMILES: CCOC(=O)c1cn(-c2c(F)cccc2F)c2nc(Cl)c(F)cc2c1=O]

21.8 ml (125 mmol) of DIPEA were added to a solution of 6.00 g (17.8 mmol) of ethyl 2-[(2,6-dichloro-5-fluoropyridin-3-yl)carbonyl]-3-ethoxyacrylate (preparation described in U.S. Pat. No. 4,840,954 A, Example G, step 1, page 7) and 3.23 g (24.9 mmol) of 2,6-difluoroaniline in 30 ml of dichloromethane, and the mixture was stirred at RT for 4 h. 2.47 g (17.8 mmol) of potassium carbonate were then added, and the mixture was heated under reflux overnight. The mixture was diluted with 200 ml of dichloromethane and washed twice with 150 ml of 1 M aqueous hydrochloric acid. The organic phase was dried over sodium sulfate and filtered, and the solvent was removed under reduced pressure. The mixture was diluted with 80 ml of tert-butyl methyl ether and the precipitate was filtered off with suction and washed with 10 ml of tert-butyl methyl ether. This gave 3.22 g (45% of theory, 95.7% pure) of the title compound.

LC-MS (Method 1): $R_t$=0.96 min; MS (ESIpos): m/z=383 [M+H]+.

$^1$H NMR (400 MHz, DMSO-d6): δ [ppm]=8.95 (s, 1H), 8.57 (d, 1H), 7.80-7.71 (m, 1H), 7.50-7.43 (m, 2H), 4.25 (q, 2H), 1.26 (t, 3H).

Example 2A

7-Chloro-1-(2,6-difluorophenyl)-6-fluoro-4-oxo-1,4-dihydro-1,8-naphthyridine-3-carboxylic Acid

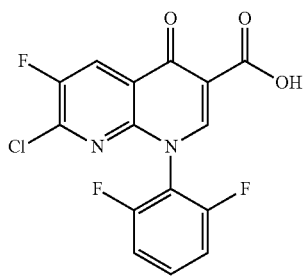 [SMILES: O=C(O)c1cn(-c2c(F)cccc2F)c2nc(Cl)c(F)cc2c1=O]

3.22 g (8.41 mmol) of ethyl 7-chloro-1-(2,6-difluorophenyl)-6-fluoro-4-oxo-1,4-dihydro-1,8-naphthyridine-3-carboxylate were initially charged in 25.2 ml of water, 25.2 ml of 36 percent strength aqueous hydrochloric acid and 25.2 ml of THF were added and the mixture was stirred at 110° C. for 4 h. The reaction mixture was cooled to RT and the precipitate was Altered off with suction, washed twice with 30 ml of water and dried under high vacuum. This gave 4.1 g (quantitative, 96.8% pure) of the title compound.

LC-MS (Method 1): $R_t$=0.96 min; MS (ESIpos): m/z=355 [M+H]$^+$.

$^1$H NMR (400 MHz, DMSO-d6): δ [ppm]=13.70 (s, 1H), 9.25 (s, 1H), 8.76 (d, 1H), 7.80-7.72 (m, 1H), 7.51-7.43 (m, 2H).

Example 3A

7-Chloro-1-(2,6-difluorophenyl)-6-fluoro-4-oxo-N-[(2S)-1,1,1-trifluorobutan-2-yl]-1,4-dihydro-1,8-naphthyridine-3-carboxamide

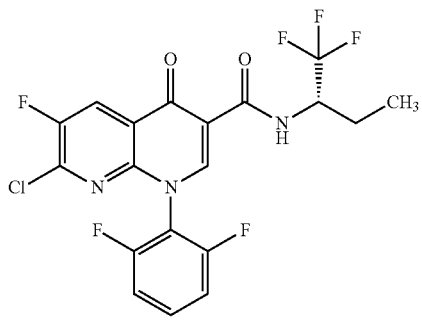 [SMILES: CC[C@H](NC(=O)c1cn(-c2c(F)cccc2F)c2nc(Cl)c(F)cc2c1=O)C(F)(F)F]

According to GP1, 1.00 g (2.82 mmol) of 7-chloro-1-(2,6-difluorophenyl)-6-fluoro-4-oxo-1,4-dihydro-1,8-naphthyridine-3-carboxylic acid was reacted with 553 mg (3.38 mmol) of (2S)-1,1,1-trifluorobutan-2-amine hydrochloride in the presence of 1.29 g (3.38 mmol) of HATU and 1.96 ml (11.3 mmol) of DIPEA in 20 ml of DMF. The reaction solution was stirred for 1 min and added to a mixture of water, 1M aqueous hydrochloric acid and ethyl acetate. The phases were separated and the aqueous phase was extracted four times with 50 ml of ethyl acetate. The combined organic phases were washed with saturated aqueous sodium chloride solution, dried over sodium sulfate and filtered, and the solvent was removed under reduced pressure. The crude product was dissolved in a little ethyl acetate and purified by normal phase chromatography (cyclohexane/ethyl acetate, 5:1). The fractions were combined and concentrated under reduced pressure and the residue was lyophilized from acetonitrile overnight. This gave 331 mg (25% of theory, 100% pure) of the title compound.

LC-MS (Method 3): $R_t$=2.32 min; MS (ESIpos): m/z=464 [M+H]

$^1$H NMR (400 MHz, DMSO-d6): δ [ppm]=9.84 (d, 1H), 9.12 (s, 1H), 8.72 (d, 1H), 7.80-7.72 (m, 1H), 7.51-7.44 (m, 2H), 4.85-4.71 (m, 1H), 1.96-1.83 (m, 1H), 1.75-1.61 (m, 1H), 0.98 (t, 3H).

Example 4A

Ethyl 7-chloro-1-(2,4,6-trifluorophenyl)-6-fluoro-4-oxo-1,4-dihydro-1,8-naphthyridine-3-carboxylate

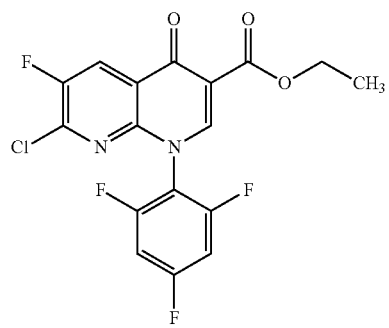 [SMILES: CCOC(=O)c1cn(-c2c(F)cc(F)cc2F)c2nc(Cl)c(F)cc2c1=O]

43.5 ml (250 mmol) of DIPEA were added to a solution of 12.0 g (35.7 mmol) of ethyl 2-[(2,6-dichloro-5-fluoropyridin-3-yl)carbonyl]-3-ethoxyacrylate (U.S. Pat. No. 4,840,954 A, Example G, step 1, page 7) and 7.35 g (49.9 mmol) of 2,4,6-trifluoroaniline in 60 ml of dichloromethane, and the mixture was stirred at RT for 4 h. Subsequently, 4.93 g (35.7 mmol) of potassium carbonate were added and the mixture was heated under reflux overnight. The mixture was then diluted with 200 ml of dichloromethane and washed three times with 150 ml of 1 M aqueous hydrochloric acid. The organic phase was dried over sodium sulfate and filtered, and the solvent was removed under reduced pressure. The mixture was diluted with 100 ml of tert-butyl methyl ether and the precipitate was filtered off with suction and washed three times with 20 ml of tert-butyl methyl ether and dried under high vacuum. This gave 8.80 g (58% of theory, 94.6% pure) of the title compound.

LC-MS (Method 1): $R_t$=1.01 min; MS (ESIpos): m/z=401 [M+H]+.

$^1$H NMR (400 MHz, DMSO-d6): δ [ppm]=8.97 (s, 1H), 8.56 (d, 1H), 7.67-7.56 (m, 2H), 4.26 (q, 2H), 1.28 (t, 3H).

Example 5A

7-Chloro-6-fluoro-4-oxo-1-(2,4,6-trifluorophenyl)-1,4-dihydro-1,8-naphthyridine-3-carboxylic Acid

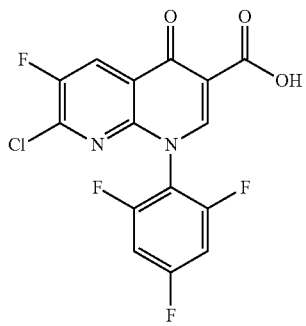 [SMILES: O=C(O)c1cn(-c2c(F)cc(F)cc2F)c2nc(Cl)c(F)cc2c1=O]

8.80 g (21.9 mmol) of ethyl 7-chloro-1-(2,4,6-trifluorophenyl)-6-fluoro-4-oxo-1,4-dihydro-1,8-naphthyridine-3-carboxylate were initially charged in 66.2 ml of water, 66.2 ml of 36 percent strength aqueous hydrochloric acid and 66.2 ml of THF were added and the mixture was stirred at 110° C. for 4 h. The reaction mixture was cooled to RT and the precipitate was filtered off with suction, washed four times with 40 ml of water and dried under high vacuum. This gave 7.37 g (89% of theory, 99% pure) of the title compound.

LC-MS (Method 3): $R_t$=1.84 min; MS (ESIpos): m/z=373 [M+H]$^+$.

$^1$H NMR (400 MHz, DMSO-d6): δ [ppm]=13.67 (s, 1H), 9.28 (s, 1H), 8.76 (d, 1H), 7.68-7.59 (m, 2H).

Example 6A

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic Acid

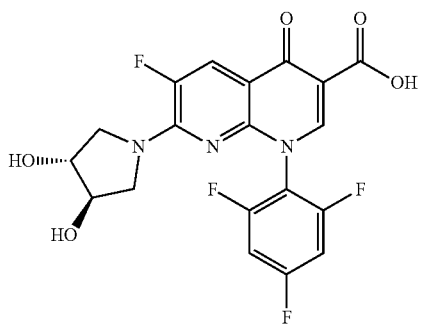 [SMILES: O=C(O)c1cn(-c2c(F)cc(F)cc2F)c2nc(N3C[C@@H](O)[C@H](O)C3)c(F)cc2c1=O]

At RT, 5.89 ml (33.8 mmol) of DIPEA were added to a solution of 3.60 g (9.66 mmol) of 7-chloro-1-(2,4,6-trifluorophenyl)-6-fluoro-4-oxo-1,4-dihydro-1,8-naphthyridine-3-carboxylic acid and 1.48 g (10.6 mmol) of (3R,4R)-pyrrolidine-3,4-diol hydrochloride in 50 ml of DMF. The mixture was stirred at RT for a further 1 h. 150 ml of water and 100 ml of aqueous 1M hydrochloric acid were then added and the precipitate formed was filtered off with suction. The precipitate was washed with water and dried under high vacuum. This gave 3.96 g (93% of theory, 100% pure) of the title compound.

LC-MS (Method 3): $R_t$=1.23 min; MS (ESIpos): m/z=440 [M+H]+.

$^1$H NMR (500 MHz, DMSO-d6): δ [ppm]=15.01 (s, 1H), 9.05 (s, 1H), 8.07 (d, 1H), 7.64-7.54 (m, 2H), 5.30-5.14 (m, 2H), 4.09-3.64 (m, 4H), 3.28-3.21 (m, 0.6H, partly under the water resonance), 3.15-3.01 (m, 1H).

Example 7A

6-Fluoro-7-[(4S)-4-hydroxy-2-oxopyrrolidin-1-yl]-4-oxo-1-(2,4,6-trifluorophenyl)-1,4-dihydro-1,8-naphthyridine-3-carboxylic Acid

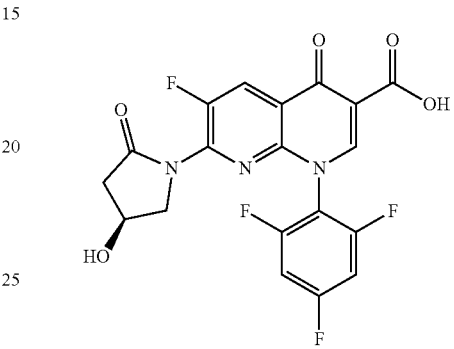

According to GP2,100 mg (268 μmol) of 7-chloro-1-(2,4,6-trifluorophenyl)-6-fluoro-4-oxo-1,4-dihydro-1,8-naphthyridine-3-carboxylic acid were reacted with 32.6 mg (322 μmol) of (4S)-4-hydroxypyrrolidin-2-one in the presence of 92.7 mg (671 μmol) of potassium carbonate, 6.0 mg (27 μmol) of palladium acetate and 33 mg (54 μmol) of Xantphos in 2.4 ml of dioxane at 90° C. for 1 h. The reaction mixture was diluted with 1 ml of aqueous 1M hydrochloric acid and 1 ml of DMSO and purified directly by prep. HPLC (acetonitrile/water with formic acid, C18 RP-HPLC). This gave 61.7 mg (42% of theory, 80% pure) of the title compound.

LC-MS (Method 3): $R_t$=1.19 min; MS (ESIpos): m/z=438 [M+H]$^+$.

Example 8A

7-[(3S,4S)-3,4-Dihydroxypyrrolidin-1-yl]-6-fluoro-4-oxo-1-(2,4,6-trifluorophenyl)-1,4-dihydro-1,8-naphthyridine-3-carboxylic Acid

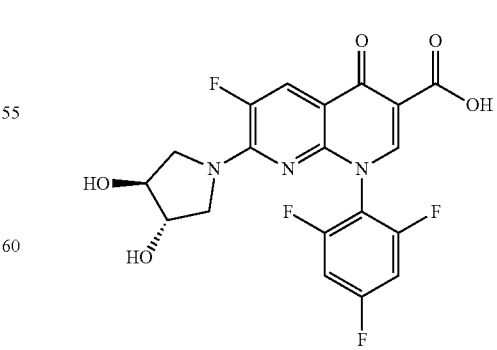

At RT, 280 μl (1.61 mmol) of DIPEA were added to a solution of 240 mg (644 μmol) of 7-chloro-1-(2,4,6-trifluorophenyl)-6-fluoro-4-oxo-1,4-dihydro-1,8-naphthyridine-3-carboxylic acid and 73.0 mg (708 µmol) of (3R,4R)-pyrrolidine-3,4-diol in 3.3 ml of DMF. The mixture was stirred at RT for a further 1 h. The reaction mixture was diluted with 0.4 ml of aqueous 1M hydrochloric acid and 1 ml of acetonitrile and purified directly by prep. HPLC (acetonitrile/water with formic acid, C18 RP-HPLC). This gave 232 mg (74% of theory, 94.4% pure) of the title compound.

LC-MS (Method 1): R$_t$=0.69 min; MS (ESIpos): m/z=440 [M+H]+.

$^1$H NMR (500 MHz, DMSO-d6): δ [ppm]=15.01 (s, 1H), 9.05 (s, 1H), 8.07 (d, 1H), 7.64-7.55 (m, 2H), 5.33-5.10 (m, 2H), 4.10-3.63 (m, 4H), 3.29-3.20 (m, 0.8H, partly under the water resonance), 3.15-3.00 (m, 1H).

Example 9A

7-[(3R,4S)-3,4-Dihydroxypyrrolidin-1-yl]-6-fluoro-4-oxo-1-(2,4,6-trifluorophenyl)-1,4-dihydro-1,8-naphthyridine-3-carboxylic Acid

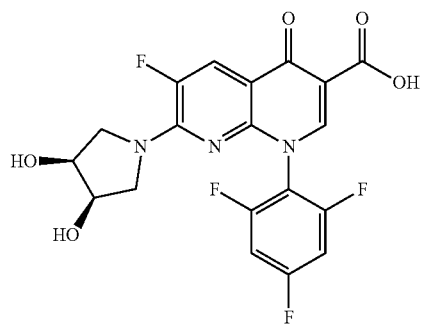 [SMILES: O=C(O)c1cn(-c2c(F)cc(F)cc2F)c2nc(N3C[C@@H](O)[C@@H](O)C3)c(F)cc2c1=O]

At RT, 409 µl (2.35 mmol) of DIPEA were added to a solution of 250 mg (671 µmol) of 7-chloro-1-(2,4,6-trifluorophenyl)-6-fluoro-4-oxo-1,4-dihydro-1,8-naphthyridine-3-carboxylic acid and 103 mg (738 µmol) of cis-pyrrolidine-3,4-diol hydrochloride in 3.5 ml of DMF. The mixture was stirred at RT for a further 1 h. The reaction mixture was acidified with 7 ml of aqueous 1 M hydrochloric acid, 15 ml of water were added and the precipitate was filtered off with suction. The residue was washed with water and lyophilized. This gave 256 mg (86% of theory, 99% pure) of the title compound.

LC-MS (Method 1): R$_t$=0.71 min; MS (ESIpos): m/z=440 [M+H]+.

$^1$H NMR (500 MHz, DMSO-d6): δ [ppm]=15.0 (s, 1H), 9.05 (s, 1H), 8.05 (d, 1H), 7.63-7.54 (m, 2H), 5.15-4.89 (m, 2H), 4.13-3.86 (m, 3H), 3.61 (br. s, 1H), 3.21 (br. s, 1H), 3.04 (br. s, 1H).

Example 10A

6-Fluoro-7-[(3S)-3-hydroxypyrrolidin-1-yl]-4-oxo-1-(2,4,6-trifluorophenyl)-1,4-dihydro-1,8-naphthyridine-3-carboxylic Acid

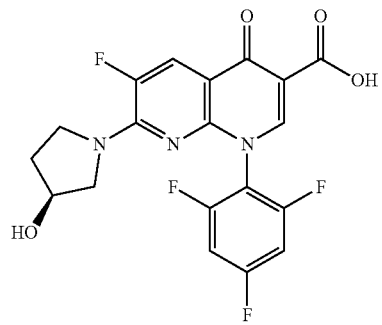 [SMILES: O=C(O)c1cn(-c2c(F)cc(F)cc2F)c2nc(N3CC[C@H](O)C3)c(F)cc2c1=O]

7-Chloro-6-fluoro-4-oxo-1-(2,4,6-trifluorophenyl)-1,4-dihydro-1,8-naphthyridine-3-carboxylic acid (800 mg, 2.15 mmol) was initially charged in 8 ml of DMF, (3S)-pyrrolidin-3-ol (206 mg, 2.36 mmol) and N,N-diisopropylethylamine (1.3 ml, 7.5 mmol) were added and the mixture was stirred at RT for 2 h. The reaction mixture was added to water, and 1M hydrochloric acid and ethyl acetate were added. The organic phase was removed and the aqueous phase was extracted three times with ethyl acetate. The combined organic phases were washed once with sat. sodium chloride solution, dried over sodium sulfate and concentrated. The product was stirred with acetonitrile, filtered off, washed with a little cold acetonitrile and dried. This gave 770 mg (85% of theory, 100% pure) of the title compound.

LC-MS (Method 1): R$_t$=0.82 min; MS (ESIpos): m/z=424 [M+H]$^+$ $^1$H NMR (400 MHz, DMSO-d6) δ[ppm]: −0.008 (2.22), 0.008 (2.03), 1.909 (0.87), 2.074 (16.00), 3.222 (0.71), 3.875 (0.53), 4.309 (0.50), 5.024 (1.35), 7.565 (2.70), 7.586 (4.97), 7.608 (2.81), 8.037 (5.77), 8.068 (5.70), 9.043 (10.89), 15.025 (9.55).

Example 11A

N-[(1S)-1-Cyclopropyl-2,2,2-trifluoroethyl]-6-fluoro-4-oxo-7-(3H-[1,2,3]triazolo[4,5-b]pyridin-3-yloxy)-1-(2,4,6-trifluorophenyl)-1,4-dihydro-1,8-naphthyridine-3-carboxamide

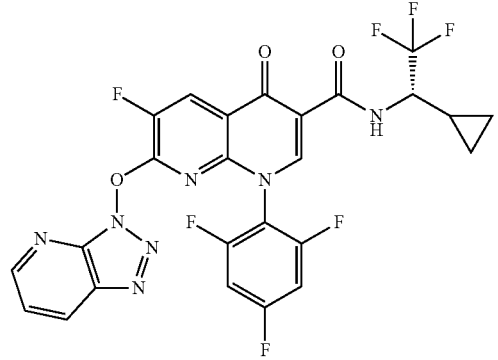 [SMILES: O=C(N[C@@H](C1CC1)C(F)(F)F)c1cn(-c2c(F)cc(F)cc2F)c2nc(On3nnc4cccnc43)c(F)cc2c1=O]

According to GP1,500 mg (1.34 mmol) of 7-chloro-1-(2,6-difluorophenyl)-6-fluoro-4-oxo-1,4-dihydro-1,8-naphthyridine-3-carboxylic acid were reacted with 283 mg (1.61 mmol) of (1S)-1-cyclopropyl-2,2,2-trifluoroethanamine hydrochloride in the presence of 612 mg (1.61 mmol) of HATU and 935 µl (5.37 mmol) of DIPEA in 10 ml of DMF. The reaction solution was stirred at RT for 1 h and added to a mixture of water and ethyl acetate. The phases were separated and the aqueous phase was extracted four times with 50 ml of ethyl acetate. The organic phases were combined, washed with 50 ml of buffer pH 7 and twice with 50 ml of saturated aqueous sodium chloride solution, dried over sodium sulfate, filtered and concentrated. The substance was dissolved in ethyl acetate and applied to silica gel and purified by normal phase chromatography (cyclohexane-ethyl acetate gradient). The fractions were combined and concentrated under reduced pressure and the residue was lyophilized from acetonitrile overnight. This gave 534 mg (66% of theory, 99% pure) of the title compound.

LC-MS (Method 3): $R_t$=2.21 min; MS (ESIpos): m/z=594 [M+H]

$^1$H NMR (400 MHz, DMSO-d6): δ [ppm]=10.01 (d, 1H), 8.96 (s, 1H), 8.88 (d, 1H), 8.74 (dd, 1H), 8.63 (dd, 1H), 7.65 (dd, 1H), 7.05-6.97 (m, 2H), 4.42-4.37 (m, 1H), 1.28-1.17 (m, 1H), 0.71-0.51 (m, 3H), 0.36-0.28 (m, 1H).

Example 12A

6-Fluoro-4-oxo-7-(3H-[1,2,3]triazolo[4,5-b]pyridin-3-yloxy)-N-[(2S)-1,1,1-trifluorobutan-2-yl]-1-(2,4,6-trifluorophenyl)-1,4-dihydro-1,8-naphthyridine-3-carboxamide

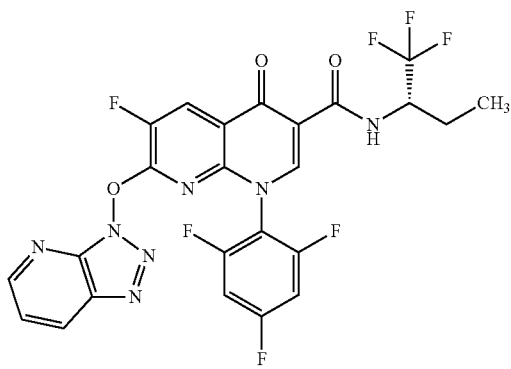 [SMILES: CC[C@H](NC(=O)c1cn(-c2c(F)cc(F)cc2F)c2nc(On3nnc4cccnc43)c(F)cc2c1=O)C(F)(F)F]

According to GP1,500 mg (1.34 mmol) of 7-chloro-1-(2,6-difluorophenyl)-6-fluoro-4-oxo-1,4-dihydro-1,8-naphthyridine-3-carboxylic acid were reacted with 263 mg (1.61 mmol) of (S)-1,1,1-trifluorobutan-2-amine hydrochloride in the presence of 612 mg (1.61 mmol) of HATU and 935 µl (5.37 mmol) of DIPEA in 9.5 ml of DMF. The reaction solution was stirred at RT for 1 h and added to a mixture of water and ethyl acetate. The phases were separated and the aqueous phase was extracted four times with 50 ml of ethyl acetate. The organic phases were combined, washed with 50 ml of buffer pH 7 and twice with 50 ml of saturated aqueous sodium chloride solution, dried over sodium sulfate, filtered and concentrated. The substance was dissolved in ethyl acetate and applied to silica gel and purified by normal phase chromatography (cyclohexane-ethyl acetate gradient). The fractions were combined and concentrated under reduced pressure and the residue was lyophilized from acetonitrile overnight. This gave 522 mg (66% of theory, 99% pure) of the title compound.

LC-MS (Method 3): $R_t$=2.19 min; MS (ESIpos): m/z=582 [M+H]$^+$.

$^1$H NMR (400 MHz, DMSO-d6): δ [ppm]=9.85 (d, 1H), 8.97 (s, 1H), 8.87 (d, 1H), 8.74 (dd, 1H), 8.63 (dd, 1H), 7.65 (dd, 1H), 7.06-6.96 (m, 2H), 4.81-4.66 (m, 1H), 1.94-1.81 (m, 1H), 1.73-1.59 (m, 1H), 0.96 (t, 3H).

Example 13A tert-Butyl 4-[6-{[(1S)-1-cyclopropyl-2,2,2-trifluoroethyl]carbamoyl}-3-fluoro-5-oxo-8-(2,4,6-trifluorophenyl)-5,8-dihydro-1,8-naphthyridin-2-yl]piperazine-1-carboxylate

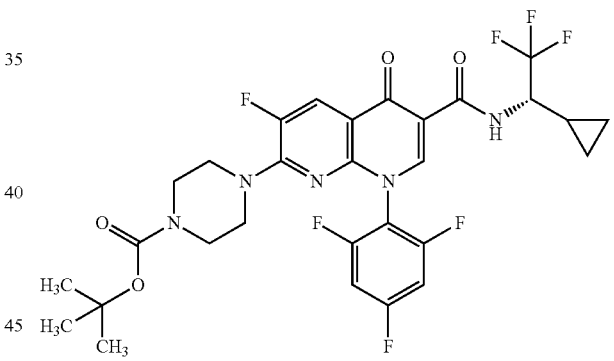

7-Chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide (60.0 mg, 122 µmol) was initially charged in 1.2 ml of acetonitrile, tert-butyl piperazine-1-carboxylate (45.3 mg, 243 µmol) and N,N-diisopropylethylamine (74 µl, 430 µmol) were added and the mixture was stirred at room temperature for 2 h. The reaction solution was concentrated under reduced pressure and used without further purification for the next step. This gave 113 mg of the target compound (quantitative yield, purity about 69%).

LC-MS (Method 3): $R_t$=2.61 min; MS (ESIpos): m/z=644 [M+H]$^+$

Example 14A tert-Butyl (2S)-4-[6-{[(1S)-1-cyclopropyl-2,2,2-trifluoroethyl]carbamoyl}-3-fluoro-5-oxo-8-(2,4,6-trifluorophenyl)-5,8-dihydro-1,8-naphthyridin-2-yl]-2-methylpiperazine-1-carboxylate

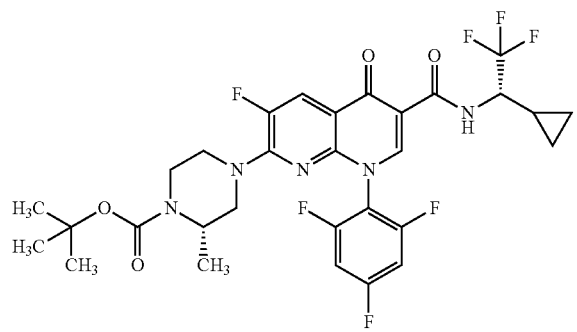 [SMILES: C[C@H]1CN(c2nc3c(cc2F)c(=O)c(C(=O)N[C@@H](C2CC2)C(F)(F)F)cn3-c2c(F)cc(F)cc2F)CCN1C(=O)OC(C)(C)C]

7-Chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide (60.0 mg, 122 µmol) was initially charged in 1.2 ml of DMF, tert-butyl (2S)-2-methylpiperazine-1-carboxylate (34.1 mg, 170 µmol) and N,N-diisopropylethylamine (74 µl, 430 µmol) were added and the mixture was stirred at room temperature for 1 h. The reaction solution was taken up in ethyl acetate and extracted three times with a semisaturated ammonium chloride solution. The combined aqueous phases were re-extracted once with ethyl acetate. The combined organic phases were dried over sodium sulfate, filtered and concentrated under reduced pressure. This gave 82 mg of the target compound (91% of theory, purity 90%).

LC-MS (Method 3): $R_t$=2.64 min; MS (ESIpos): m/z=658 $[M+H]^+$

Example 15A

Ethyl 7-chloro-1-(3,5-difluoropyridin-2-yl)-6-fluoro-4-oxo-1,4-dihydro-1,8-naphthyridine-3-carboxylate

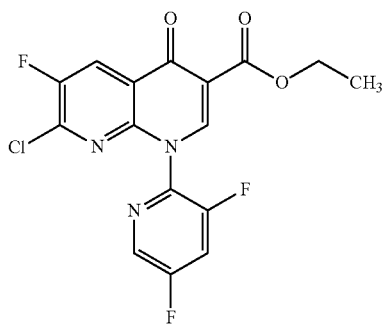 [SMILES: CCOC(=O)c1cn(-c2ncc(F)cc2F)c2nc(Cl)c(F)cc2c1=O]

21.8 ml (125 mmol) of DIPEA were added to a solution of 6.00 g (17.8 mmol) of ethyl 2-[(2,6-dichloro-5-fluoropyridin-3-yl)carbonyl]-3-ethoxyacrylate (U.S. Pat. No. 4,840,954, 1989, Example G, step 1, page 7) and 3.25 g (25.0 mmol) of 2-amino-3,5-difluoropyridine in 30 ml of dichloromethane, and the mixture stirred at RT for 4 h. 2.47 g (17.8 mmol, 1 eq.) of potassium carbonate were then added, and the mixture was heated under reflux overnight. A further equivalent of potassium carbonate was then added, and the mixture was again heated under reflux overnight. A further equivalent of potassium carbonate was then added, and stirring of the mixture under reflux was continued for a further 3 d. The mixture was diluted with 200 ml of dichloromethane and washed twice with 200 ml of 1 M aqueous hydrochloric acid. The organic phase was dried over sodium sulfate and filtered, and the solvent was removed under reduced pressure. The mixture was diluted with 80 ml of tert-butyl methyl ether and the precipitate was filtered off with suction, washed with 10 ml of tert-butyl methyl ether and dried under high vacuum. This gave 3.73 g (54% of theory, 99% pure) of the title compound.

LC-MS (Method 1): $R_t$=0.93 min; MS (ESIpos): m/z=384 [M+H]+.

$^1$H NMR (400 MHz, DMSO-d6): δ [ppm]=8.92 (s, 1H), 8.66 (d, 1H), 8.56 (d, 1H), 8.44-8.37 (m, 1H), 4.26 (q, 2H), 1.28 (t, 3H).

Example 16A

7-Chloro-1-(3,5-difluoropyridin-2-yl)-6-fluoro-4-oxo-1,4-dihydro-1,8-naphthyridine-3-carboxylic Acid

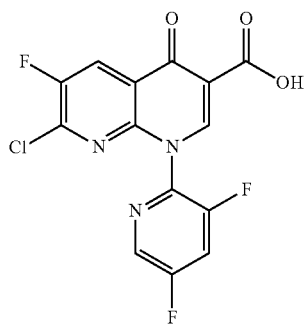 [SMILES: O=C(O)c1cn(-c2ncc(F)cc2F)c2nc(Cl)c(F)cc2c1=O]

3.60 g (9.38 mmol) of ethyl 7-chloro-1-(3,5-difluoropyridin-2-yl)-6-fluoro-4-oxo-1,4-dihydro-1,8-naphthyridine-3-carboxylate were initially charged in 28.3 ml of water, 28.3 ml of 36 percent strength aqueous hydrochloric acid and 28.3 ml of THF were added and the mixture was stirred at 110° C. for 4 h. Subsequently, twice in each case 28.3 ml of 36 percent strength aqueous hydrochloric acid were added in succession, and the mixture was stirred at 110° C. for 2 d. The reaction mixture was cooled to RT and the precipitate was filtered off with suction, washed with water and dried under high vacuum. This gave 3.25 g (96% of theory, 99% pure) of the title compound.

LC-MS (Method 1): $R_t$=0.90 min; MS (ESIpos): m/z=356 $[M+H]^+$.

$^1$H NMR (400 MHz, DMSO-d6): δ [ppm]=13.71 (s, 1H), 9.18 (s, 1H), 8.76 (d, 1H), 8.68 (dd, 1H), 8.46-8.39 (m, 1H).

Example 17A 1-(3,5-Difluoropyridin-2-yl)-7-[(3R,4R)-3,4-dihydroxypyrrolidin-1-yl]-6-fluoro-4-oxo-1,4-dihydro-1,8-naphthyridine-3-carboxylic Acid

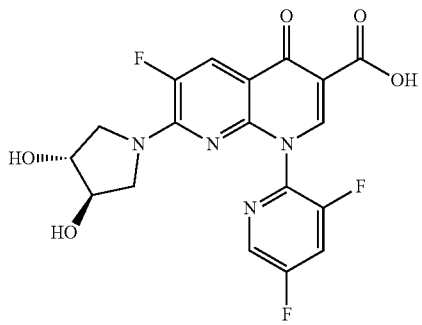 [SMILES: O=C(O)c1cn(-c2ncc(F)cc2F)c2nc(N3C[C@@H](O)[C@H](O)C3)c(F)cc2c1=O]

At RT, 2.57 ml (14.8 mmol) of DIPEA were added to a solution of 1.50 g (4.22 mmol) of 7-chloro-1-(3,5-difluoropyridin-2-yl)-6-fluoro-4-oxo-1,4-dihydro-1,8-naphthyridine-3-carboxylic acid and 648 mg (4.64 mmol) of (3R,4R)-pyrrolidine-3,4-diol hydrochloride in 21 ml of DMF. The mixture was stirred at RT for a further 2 h. The mixture was acidified with aqueous 1M hydrochloric acid and then diluted with 100 ml of water and 50 ml of ethyl acetate. The phases were separated and the aqueous phase was extracted twice with 50 ml of ethyl acetate. The combined organic phases were washed twice with 50 ml of a pH 7 buffer solution and once with 50 ml of saturated aqueous sodium chloride solution, dried over sodium sulfate, filtered and concentrated under reduced pressure. The residue was stirred with 20 ml of tert-butyl methyl ether and decanted off, and the precipitate was dried under high vacuum. This gave 1.41 g (78% of theory, 99% pure) of the title compound.

LC-MS (Method 3): $R_t$=1.07 min; MS (ESIpos): m/z=423 [M+H]+.

$^1$H NMR (500 MHz, DMSO-d6): δ [ppm]=15.02 (s, 1H), 8.96 (s, 1H), 8.66-8.61 (m, 1H), 8.41-8.34 (m, 1H), 8.07 (d, 1H), 5.34-5.06 (m, 2H), 4.14-3.59 (m, 4H), 3.44-3.20 (m, 1H, partly under the water resonance), 3.19-3.01 (m, 1H).

Example 18A 1-(3,5-Difluoropyridin-2-yl)-6-fluoro-7-[(3S)-3-hydroxypyrrolidin-1-yl]-4-oxo-1,4-dihydro-1,8-naphthyridine-3-carboxylic Acid

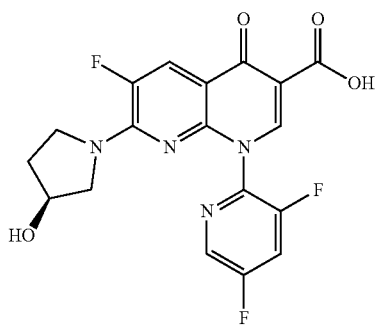 [SMILES: O=C(O)c1cn(-c2ncc(F)cc2F)c2nc(N3CC[C@H](O)C3)c(F)cc2c1=O]

According to GP3, 81 mg (928 μmol) of (S)-3-pyrrolidinol and 0.514 ml (2.95 mmol) of DIPEA were added to 300 mg (843 μmol) of 7-chloro-1-(3,5-difluoropyridin-2-yl)-6-fluoro-4-oxo-1,4-dihydro-1,8-naphthyridine-3-carboxylic acid in 3.1 ml of DMF, and the mixture was stirred at RT for 1 h. Another 20 mg (232 μmol) of (S)-3-pyrrolidinol were then added, and the mixture was stirred at RT for 1 h. The reaction mixture was diluted with water and purified directly by preparative HPLC (acetonitrile/water with formic acid, C18 RP-HPLC). This gave 244 mg (72% of theory, 100% pure) of the title compound.

LC-MS (Method 3): $R_t$=1.36 min; MS (ESIpos): m/z=407 [M+H]+.

Example 19A 1-(3,5-Difluoropyridin-2-yl)-6-fluoro-7-(3-hydroxyazetidin-1-yl)-4-oxo-1,4-dihydro-1,8-naphthyridine-3-carboxylic Acid

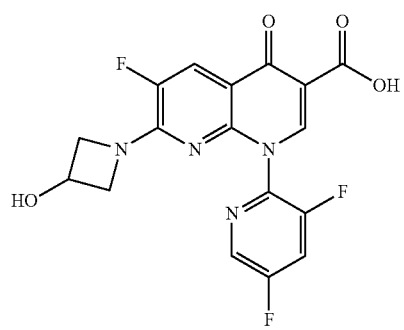 [SMILES: O=C(O)c1cn(-c2ncc(F)cc2F)c2nc(N3CC(O)C3)c(F)cc2c1=O]

At RT, 857 μl (4.92 mmol) of DIPEA were added to a solution of 500 mg (1.41 mmol) of 7-chloro-1-(3,5-difluoropyridin-2-yl)-6-fluoro-4-oxo-1,4-dihydro-1,8-naphthyridine-3-carboxylic acid and 169 mg (1.55 mmol) of 3-hydroxyazetidine hydrochloride in 7 ml of DMF. The mixture was stirred at RT for a further 2.5 h. The mixture was acidified with aqueous 1M hydrochloric acid and diluted with 30 ml of water and 30 ml of ethyl acetate. The precipitate was filtered off with suction (first product fraction). The phases were separated and the aqueous phase was ex-traded twice with 15 ml of ethyl acetate. The combined organic phases were washed twice with 15 ml of buffer pH 7 and once with 15 ml of saturated aqueous sodium chloride solution, dried over sodium sulfate, filtered and concentrated under reduced pressure. The residue was stirred with 10 ml of tert-butyl methyl ether and decanted off, and the precipitate was dried under high vacuum (second product fraction). This gave 476 mg (86% of theory, 99% pure) of the title compound in total.

LC-MS (Method 3): $R_t$=1.35 min; MS (ESIpos): m/z=393 [M+H]+.

$^1$H NMR (500 MHz, DMSO-d6): δ [ppm]=14.98 (s, 1H), 8.95 (s, 1H), 8.62 (d, 1H), 8.39-8.31 (m, 1H), 8.05 (d, 1H), 5.80 (d, 1H), 4.81-3.50 (m, 5H).

Example 20A 1-(3,5-Difluoropyridin-2-yl)-6-fluoro-7-(3-hydroxy-3-methylazetidin-1-yl)-4-oxo-1,4-dihydro-1,8-naphthyridine-3-carboxylic Acid

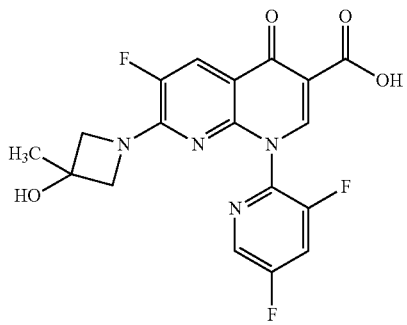 [SMILES: CC1(O)CN(c2nc3c(cc2F)c(=O)c(C(=O)O)cn3-c2ncc(F)cc2F)C1]

At RT, 857 μl (4.92 mmol) of DIPEA were added to a solution of 500 mg (1.41 mmol) of 7-chloro-1-(3,5-difluoropyridin-2-yl)-6-fluoro-4-oxo-1,4-dihydro-1,8-naphthyridine-3-carboxylic acid and 191 mg (1.55 mmol) of 3-methylazetidin-3-ol hydrochloride in 7 ml of DMF. The mixture was stirred at RT for a further 2 h. The mixture was acidified with aqueous 1 M hydrochloric acid and diluted with 40 ml of water, and the precipitate was filtered off with suction. The precipitate was washed with 5 ml of water three times and dried under high vacuum. This gave 534 mg (93% of theory, 99% pure) of the title compound.

LC-MS (Method 3): $R_t$=1.43 min; MS (ESIpos): m/z=407 $[M+H]^+$.

$^1$H NMR (500 MHz, DMSO-d6): δ [ppm]=14.98 (s, 1H), 8.95 (s, 1H), 8.62 (d, 1H), 8.39-8.32 (m, 1H), 8.06 (d, 1H), 5.72 (s, 1H), 4.48-3.49 (m, 4H), 1.38 (s, 3H).

Example 21A

Ethyl (2Z)-2-[(2,6-dichloro-5-fluoropyridin-3-yl)carbonyl]-3-ethoxyacrylate

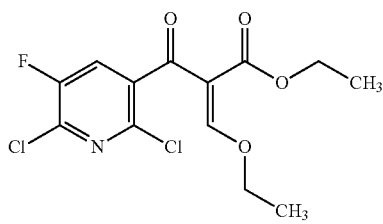

Ethyl 3-(2,6-dichloro-5-fluoropyridin-3-yl)-3-oxopropanoate (19.5 g, 69.6 mmol) and triethyl orthoformate (23.1 ml, 140 mmol) were initially charged in acetic anhydride (46 ml, 490 mmol) and the mixture was stirred at 140° C. overnight. The reaction mixture was then concentrated under reduced pressure and reacted further in the subsequent steps without further work-up. Quantitative conversion was assumed.

LC-MS (Method 1): $R_t$=1.00 min; MS (ESIpos): m/z=336 $[M+H]^+$

Example 22A

Ethyl 7-chloro-1-(2-chloro-4,6-difluorophenyl)-6-fluoro-4-oxo-1,4-dihydro-1,8-naphthyridine-3-carboxylate (Atropisomer Mixture)

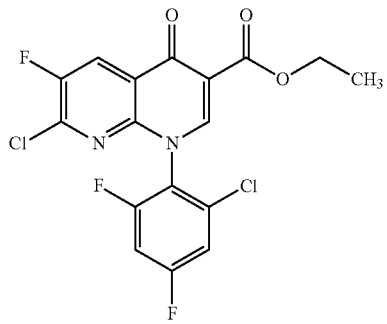 [SMILES: CCOC(=O)c1cn(-c2c(F)cc(F)cc2Cl)c2nc(Cl)c(F)cc2c1=O]

Under argon, ethyl (2Z)-2-[(2,6-dichloro-5-fluoropyridin-3-yl)carbonyl]-3-ethoxyacrylate (24.0 g, 71.4 mmol) and 2-chloro-4,6-difluoroaniline (16.3 g, 100 mmol) were initially charged in 120 ml of dichloromethane, and N,N-diisopropylethylamine (87 ml, 500 mmol) was added at room temperature. The reaction solution was stirred at room temperature for 4 h. Potassium carbonate (9.87 g, 71.4 mmol) was then added and the mixture was stirred under reflux overnight. The reaction mixture was cooled, diluted with 300 ml of dichloromethane and washed three times with in each case 180 ml of 1 M hydrochloric acid. The organic phase was dried over sodium sulfate, filtered and concentrated under reduced pressure. The suspension thus obtained was stirred in 150 ml of tert-butyl methyl ether. The solution was concentrated under reduced pressure. The resulting crude product was purified by silica gel chromatography (mobile phase: cyclohexane/ethyl acetate 10/1 then 5/1 then 2/1). This gave 13.75 g of the target compound (46% of theory, purity 99%).

LC-MS (Method 3): $R_t$=1.98 min; MS (ESIpos): m/z=417 $[M+H]^+$

Example 23A

7-Chloro-1-(2-chloro-4,6-difluorophenyl)-6-fluoro-4-oxo-1,4-dihydro-1,8-naphthyridine-3-carboxylic Acid (Atropisomer Mixture)

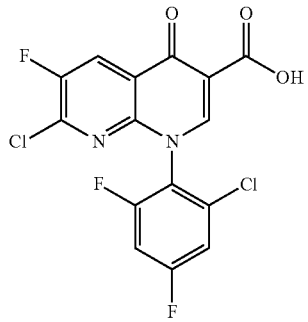 [SMILES: O=C(O)c1cn(-c2c(F)cc(F)cc2Cl)c2nc(Cl)c(F)cc2c1=O]

Ethyl 7-chloro-1-(2-chloro-4,6-difluorophenyl)-6-fluoro-4-oxo-1,4-dihydro-1,8-naphthyridine-3-carboxylate (6.00 g, 99% pure, 14.2 mmol) was suspended in 43 ml of THF. Water (43 ml) and conc. hydrochloric acid (43 ml) were added and the mixture was left to stir at a bath temperature of 110° C. for 4 h. Most of the organic solvent was removed under reduced pressure. 20 ml of water were added to the suspension and the precipitate formed was filtered off. This gave 5.12 g of the target compound (92% of theory, purity 99%).

LC-MS (Method 3): $R_t$=1.93 min; MS (ESIpos): m/z=389 [M+H]$^+$ $^1$H NMR (400 MHz, DMSO-d6) δ[ppm]: −0.008 (3.01), 0.008 (2.85), 2.327 (0.79), 2.671 (0.75), 7.752 (1.44), 7.758 (2.19), 7.774 (2.10), 7.782 (6.12), 7.794 (2.31), 7.805 (5.86), 7.816 (1.78), 8.760 (8.43), 8.778 (8.40), 9.250 (16.00), 13.654 (2.73).

Example 24A

7-Chloro-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (Atropisomer Mixture)

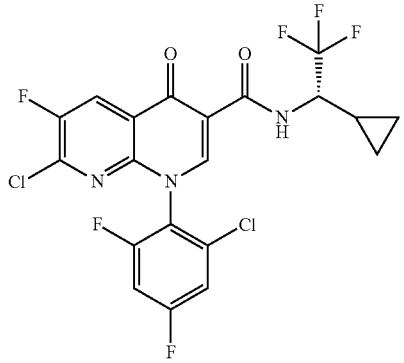 [SMILES: O=C(N[C@@H](C1CC1)C(F)(F)F)c1cn(-c2c(F)cc(F)cc2Cl)c2nc(Cl)c(F)cc2c1=O]

7-Chloro-1-(2-chloro-4,6-difluorophenyl)-6-fluoro-4-oxo-1,4-dihydro-1,8-naphthyridine-3-carboxylic acid (atropisomer mixture, 1.50 g, 3.85 mmol) was initially charged in 34 ml of DMF. HATU (1.47 g, 3.85 mmol) and N,N-diisopropylethylamine (1.6 ml, 9.3 mmol) were added and the mixture was pre-stirred at room temperature for 30 min. (1S)-1-Cyclopropyl-2,2,2-trifluoroethanamine hydrochloride (745 mg, 4.24 mmol) was then added and the mixture was left to stir at room temperature for 2 min. The reaction was worked up directly, without reaction monitoring. The mixture was added to 340 ml of water. The solids that precipitated out were filtered off and dried under high vacuum. This gave 2.13 g of the target compound (62% of theory, purity 57%).

LC-MS (Method 3): $R_t$=2.46 min; MS (ESIpos): m/z=510 [M+H]$^+$

Example 25A 1-(2-Chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic Acid (Atropisomer Mixture)

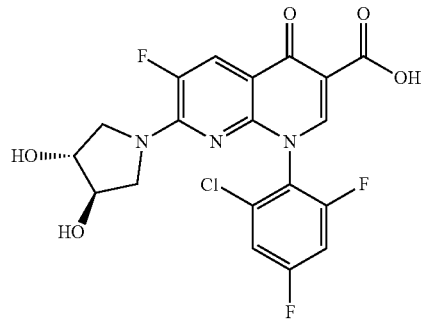 [SMILES: O=C(O)c1cn(-c2c(F)cc(F)cc2Cl)c2nc(N3C[C@@H](O)[C@H](O)C3)c(F)cc2c1=O]

At RT, 2.57 ml (14.8 mmol) of DIPEA were added to a solution of 500 mg (1.29 mmol) of 7-chloro-1-(2-chloro-4,6-difluorophenyl)-6-fluoro-4-oxo-1,4-dihydro-1,8-naphthyridine-3-carboxylic acid (atropisomer mixture) and 648 mg (4.64 mmol) of (3R,4R)-pyrrolidine-3,4-diol hydrochloride in 21 ml of DMF. The mixture was stirred at RT for a further 12 h. The mixture was stirred into 100 ml of water and the precipitate was filtered off with suction. The precipitate was washed with water and dried under high vacuum. This gave 463 mg (78% of theory, 99% pure) of the title compound.

LC-MS (Method 3): $R_t$=1.30 min; MS (ESIpos): m/z=456 [M+H]+.

$^1$H NMR (400 MHz, DMSO-d6): δ [ppm]=15.04 (s, 1H), 9.01 (s, 1H), 8.07 (d, 1H), 7.80-7.69 (m, 1H)), 5.22 (br. s, 2H), 4.09-3.64 (m, 4H), 3.28-3.17 (m, 1H), 3.11-2.94 (m, 1H).

Example 26A 1-(2,6-Difluorophenyl)-7-[(3R,4R)-3,4-dihydroxypyrrolidin-1-yl]-6-fluoro-4-oxo-1,4-dihydro-1,8-naphthyridine-3-carboxylic Acid

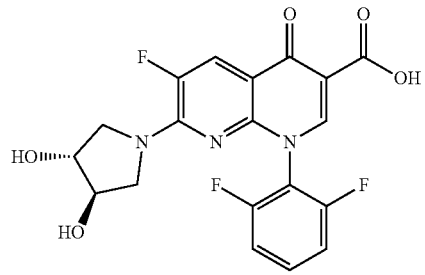 [SMILES: O=C(O)c1cn(-c2c(F)cccc2F)c2nc(N3C[C@@H](O)[C@H](O)C3)c(F)cc2c1=O]

At RT, 1.72 ml (9.87 mmol) of DIPEA were added to a solution of 1.00 g (2.82 mmol) of 7-chloro-1-(2,6-difluorophenyl)-6-fluoro-4-oxo-1,4-dihydro-1,8-naphthyridine-3-carboxylic acid and 433 g (3.10 mmol) of (3R,4R)-pyrrolidine-3,4-diol hydrochloride in 15.4 ml of DMF. The mixture was stirred at RT for a further 2 h. The mixture was then acidified with aqueous 1M hydrochloric acid and diluted with 200 ml of water and 100 ml of ethyl acetate. The phases were separated and the aqueous phase was extracted twice with 50 ml of ethyl acetate. The combined organic phases were washed twice with 25 ml of buffer pH 7 and once with 50 ml of saturated aqueous sodium chloride solution, dried over magnesium sulfate, filtered and concentrated under reduced pressure. This gave 1.03 g (87% of theory, 100% pure) of the title compound.

LC-MS (Method 3): $R_t$=1.19 min; MS (ESIpos): m/z=422 [M+H]$^+$.

$^1$H NMR (400 MHz, DMSO-d6): δ [ppm]=15.04 (s, 1H), 9.01 (s, 1H), 8.08 (d, 1H), 7.78-7.68 (m, 1H)), 7.47-7.39 (m, 2H), 5.28-5.14 (m, 2H), 4.09-3.62 (m, 4H), 3.26-3.15 (m, 1H), 3.08-2.96 (m, 1H).

Example 27A

Ethyl (2Z)-3-ethoxy-2-[(2,5,6-trichloropyridin-3-yl)carbonyl]acrylate

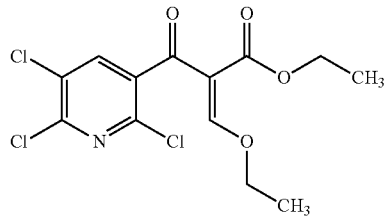 [SMILES: CCO/C=C(\C(=O)OCC)C(=O)c1cc(Cl)c(Cl)nc1Cl]

Ethyl 3-oxo-3-(2,5,6-trichloropyridin-3-yl)propanoate (1.6 g, 5.40 mmol) and (diethoxymethoxy)ethane (1.80 ml, 1.3 mmol) were initially charged, and acetic anhydride (3.31 ml, 35.1 mmol) was added. The mixture was stirred at 140° C. overnight. The mixture was concentrated and reacted further without any further purification (100% conversion assumed).

Example 28A

Ethyl 6,7-dichloro-4-oxo-1-(2,4,6-trifluorophenyl)-1,4-dihydro-1,8-naphthyridine-3-carboxylate

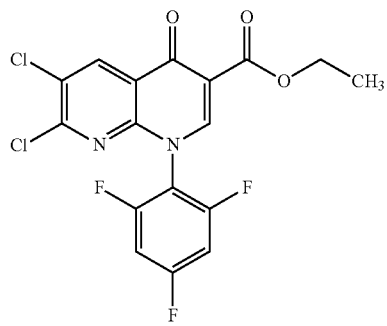 [SMILES: CCOC(=O)c1cn(-c2c(F)cc(F)cc2F)c2nc(Cl)c(Cl)cc2c1=O]

Under argon, ethyl (2Z)-3-ethoxy-2-[(2,5,6-trichloropyridin-3-yl)carbonyl]acrylate (assumed: 1.90 g, 5.39 mmol) from the precursor and 2,4,6-trifluoroaniline (1.11 g, 7.54 mmol) were initially charged in 50 ml of dichloromethane. N,N-Diisopropylethylamine (6.6 ml, 38 mmol) was added and the mixture was stirred again at RT for 4 h. Potassium carbonate (745 mg, 5.39 mmol) was then added and the mixture was stirred at reflux overnight. The reaction mixture was diluted with 120 ml of dichloromethane and washed twice with 40 ml of 1M hydrochloric acid, dried and concentrated. The residue was purified on silica gel (mobile phase cyclohexane/ethyl acetate=4:1). The product-containing fractions were concentrated. This gave 0.298 g (13% of theory, 100% pure) of the title compound.

LC-MS (Method 1): $R_t$=1.08 min; MS (ESIpos): m/z=417 [M+H]$^+$.

Example 29A 6,7-Dichloro-4-oxo-1-(2,4,6-trifluorophenyl)-1,4-dihydro-1,8-naphthyridine-3-carboxylic Acid

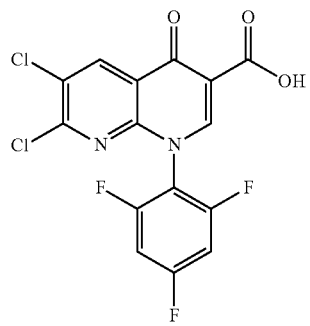 [SMILES: O=C(O)c1cn(-c2c(F)cc(F)cc2F)c2nc(Cl)c(Cl)cc2c1=O]

292 mg of ethyl 6,7-dichloro-4-oxo-1-(2,4,6-trifluorophenyl)-1,4-dihydro-1,8-naphthyridine-3-carboxylate (700 μmol) were initially charged in THF (4.0 ml, 49 mmol), ethanol (2.0 ml, 34 mmol) and water (1.0 ml) and, at RT, acidified with conc. hydrochloric acid (about 2 ml) and then stirred at 110° C. for 4 d. The precipitate was filtered off, washed with water and dried under high vacuum overnight. This gave 253 mg (90% of theory, 97% pure) of the title compound.

LC-MS (Method 3): $R_t$=1.99 min; MS (ESIpos): m/z=389 [M+H]$^+$.

Example 30A

6-Chloro-7-[(3R,4R)-3,4-dihydroxypyrrolidin-1-yl]-4-oxo-1-(2,4,6-trifluorophenyl)-1,4-dihydro-1,8-naphthyridine-3-carboxylic Acid

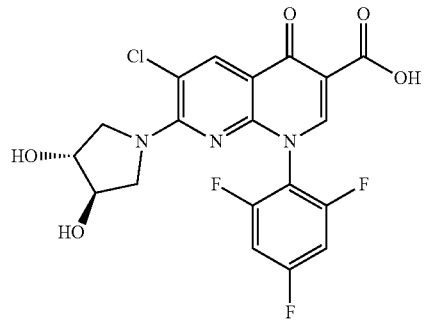 [SMILES: O=C(O)c1cn(-c2c(F)cc(F)cc2F)c2nc(N3C[C@@H](O)[C@H](O)C3)c(Cl)cc2c1=O]

253 mg of 6,7-dichloro-4-oxo-1-(2,4,6-trifluorophenyl)-1,4-dihydro-1,8-naphthyridine-3-carboxylic acid (97% pure, 631 μmol) were dissolved in DMF (6.0 ml, 78 mmol). (3R,4R)-Pyrrolidine-3,4-diol hydrochloride (99.8 mg, 97% pure, 694 µmol) and N,N-diisopropylethylamine (384 µl, 2.2 mmol) were added and the mixture was stirred at RT for 1 h. The mixture was diluted with 20 ml of water, 5 ml of 1N hydrochloric acid and 20 ml of ethyl acetate. The organic phases were separated, and the aqueous phase was extracted three times with 20 ml of ethyl acetate. The combined org. phases were washed twice with 20 ml of buffer (pH 7) and 20 ml of sat. aqueous sodium chloride solution, dried over magnesium sulfate, filtered and concentrated. This gave 172 mg (57% of theory, 95% pure) of the title compound.

LC-MS (Method 3): $R_t$=1.33 min; MS (ESIpos): m/z=456 [M+H]$^+$ $^1$H NMR (400 MHz, DMSO-d6) δ[ppm]: −0.150 (0.50), 0.008 (4.41), 0.146 (0.53), 1.157 (0.75), 1.175 (1.58), 1.193 (1.14), 1.211 (0.80), 1.229 (0.63), 1.263 (0.54), 1.988 (2.86), 2.327 (0.86), 2.366 (0.56), 2.670 (1.04), 2.710 (0.65), 2.731 (7.25), 2.891 (9.16), 3.940 (5.63), 4.003 (0.85), 4.021 (1.18), 4.038 (1.09), 4.056 (0.63), 4.176 (0.54), 4.194 (0.51), 5.210 (10.86), 5.216 (10.51), 5.754 (0.55), 7.582 (5.35), 7.604 (9.75), 7.626 (5.44), 7.952 (1.08), 8.314 (15.84), 9.065 (16.00), 14.776 (6.50).

Example 31A

7-Chloro-6-fluoro-4-oxo-1-(2,4,6-trifluorophenyl)-1,4-dihydro-1,8-naphthyridine-3-carbonyl chloride

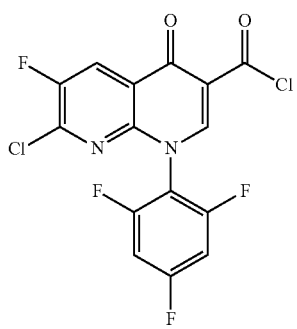 [SMILES: O=C(Cl)c1cn(-c2c(F)cc(F)cc2F)c2nc(Cl)c(F)cc2c1=O]

To a solution of 300 mg (805 µmol) of 7-chloro-6-fluoro-4-oxo-1-(2,4,6-trifluorophenyl)-1,4-dihydro-1,8-naphthyridine-3-carboxylic acid in 6 ml of THF were added 180 µl (2.40 mmol) of thionyl chloride and the mixture was stirred under reflux for a further 3 h, and then all the volatile components were removed under reduced pressure. The crude product was used in the next step without further workup (conversion was assumed to be quantitative).

Example 32A

7-Chloro-N-(2,6-dichlorophenyl)-6-fluoro-4-oxo-1-(2,4,6-trifluorophenyl)-1,4-dihydro-1,8-naphthyridine-3-carboxamide

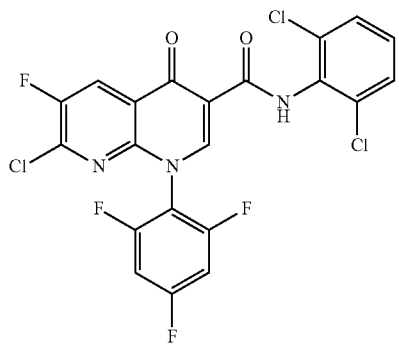 [SMILES: O=C(Nc1c(Cl)cccc1Cl)c1cn(-c2c(F)cc(F)cc2F)c2nc(Cl)c(F)cc2c1=O]

At RT, 340 µl (2.40 mmol) of triethylamine and 156 mg (963 µmol) of 2,6-dichloroaniline were added to a solution of 314 mg (803 µmol) of 7-chloro-6-fluoro-4-oxo-1-(2,4,6-trifluorophenyl)-1,4-dihydro-1,8-naphthyridine-3-carbonyl chloride in 20 ml of dichloromethane. The mixture was stirred at RT for 30 min and at 50° C. overnight. The reaction mixture was concentrated and taken up in dichloromethane, washed twice with 1 M aqueous hydrochloric acid, dried over magnesium sulfate and filtered, and the solvent was removed under reduced pressure. The crude product was purified by preparative HPLC (column: acetonitrile/water/ 0.1% of formic acid). This gave 255 mg (61% of theory, 100% pure) of the title compound.

LC-MS (Method 1): $R_t$=1.28 min; MS (ESIpos): m/z=516 [M+H]$^+$ $^1$H NMR (400 MHz, DMSO-d6) δ[ppm]: −0.149 (0.50), −0.008 (5.02), 0.008 (4.03), 0.146 (0.49), 1.245 (0.63), 1.260 (0.75), 1.275 (0.44), 2.073 (11.19), 2.328 (0.67), 2.367 (0.63), 2.524 (2.42), 2.670 (0.76), 2.710 (0.70), 2.891 (0.41), 7.381 (3.22), 7.402 (6.06), 7.422 (4.60), 7.596 (16.00), 7.608 (4.71), 7.616 (13.09), 7.629 (7.60), 7.652 (4.03), 8.767 (6.42), 8.786 (6.40), 9.250 (10.90), 11.287 (9.23).

Example 33A

Ethyl 2-[(2,5-dichloropyridin-3-yl)carbonyl]-3-(dimethylamino)acrylate

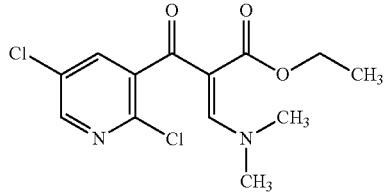 [SMILES: CCOC(=O)/C(=C\N(C)C)C(=O)c1cc(Cl)cnc1Cl]

At RT, 1.34 ml (15.39 mmol) of oxalyl chloride and 4 drops of DMF were added to 2.0 g (10.42 mmol) of 2,5-dichloronicotinic acid in 27 ml of dichloromethane, and the mixture was stirred at RT for 1.5 h. The clear solution was then concentrated, toluene was added and the mixture was concentrated again (twice). The intermediate obtained was dissolved in 67 ml of toluene, and 2.17 ml (15.60 mmol) of triethylamine and 1.94 g (13.54 mmol) of ethyl (2E)-3-(dimethylamino)acrylate were added. The mixture was stirred at 90° C. for 2.5 h, filtered and evaporated to dryness. The crude product was purified by silica gel chromatography (solvent: cyclohexane/ethyl acetate=1:1). This gave 4.10 g (quantitative yield, about 95% pure) of the title compound.

LC-MS (Method 1): $R_t$=0.76 min; MS (ESIpos): m/z=317 [M+H]$^+$

Example 34A

Ethyl 6-chloro-1-(2,4-difluorophenyl)-4-oxo-1,4-dihydro-1,8-naphthyridine-3-carboxylate

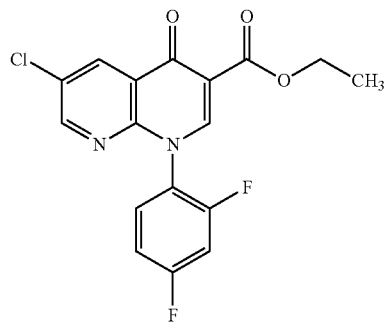 [SMILES: CCOC(=O)c1cn(-c2ccc(F)cc2F)c2ncc(Cl)cc2c1=O]

770 µl (7.60 mmol) of 2,4-difluoroaniline in 3.8 ml of THF were added to a solution of 2.00 g (6.31 mmol) of ethyl 2-[(2,5-dichloropyridin-3-yl)carbonyl]-3-(dimethylamino)acrylate in 15 ml of ethanol, and the reaction mixture was stirred at RT overnight. Subsequently, the solvent was removed under reduced pressure, the residue was taken up in 20 ml of DMF, and 1.31 g (9.48 mmol) of potassium carbonate were added. The suspension was then stirred at 100° C. for 1 h, subsequently cooled to RT and added to 50 ml of water. The precipitate was filtered off and washed three times with water. This gave 1.06 g (46% of theory, 91% pure) of the title compound which was used without further purification for the next step.

LC-MS (Method 1): $R_t$=0.99 min; MS (ESIpos): m/z=365 [M+H]$^+$ $^1$H NMR (400 MHz, DMSO-d$_6$): δ ppm=8.80 (d, 1H), 8.78 (s, 1H), 8.59 (d, 1H), 7.80-7.88 (m, 1H), 7.57-7.65 (m, 1H), 7.31-7.39 (m, 1H), 4.24 (q, 2H), 1.28 (t, 3H).

Example 35A

6-Chloro-1-(2,4-difluorophenyl)-4-oxo-1,4-dihydro-1,8-naphthyridine-3-carboxylic Acid

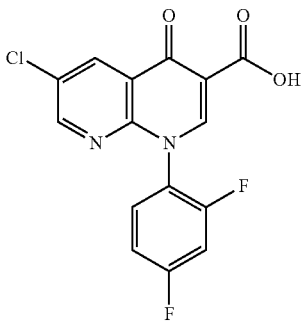 [SMILES: O=C(O)c1cn(-c2ccc(F)cc2F)c2ncc(Cl)cc2c1=O]

127 mg (3.02 mmol) of lithium hydroxide monohydrate were added to a suspension of 1.10 g (3.02 mmol) of ethyl 6-chloro-1-(2,4-difluorophenyl)-4-oxo-1,4-dihydro-1,8-naphthyridine-3-carboxylate in 10 ml of THF and 3.6 ml of water, and the reaction mixture was stirred at room temperature for 1 h. The mixture was then diluted with 20 ml of THF and 20 ml of water and the pH was adjusted to pH 1 with 1M aqueous hydrochloric acid. Ethyl acetate was added and the aqueous phase was extracted three times with ethyl acetate. The organic phase was dried over sodium sulfate, filtered and the solvent was removed under reduced pressure. This gave 0.90 g (86% of theory, 97% pure) of the title compound.

LC-MS (Method 1): $R_t$=0.96 min; MS (ESIpos): m/z=337 [M+H]$^+$ $^1$H NMR (400 MHz, DMSO-d$_6$): δ ppm=13.98 (br s, 1H), 9.10 (s, 1H), 8.95 (d, 1H), 8.80 (d, 1H), 7.80-7.89 (m, 1H), 7.58-7.67 (m, 1H), 7.26-7.47 (m, 1H).

Example 36A

6-Chloro-1-(2,4-difluorophenyl)-4-oxo-1,4-dihydro-1,8-naphthyridine-3-carbonyl chloride

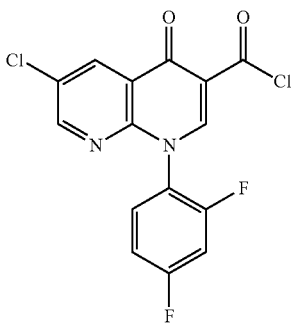 [SMILES: O=C(Cl)c1cn(-c2ccc(F)cc2F)c2ncc(Cl)cc2c1=O]

58 µl (670 µmol) of oxalyl chloride and DMF (catalytic amounts) were added to a solution of 150 mg (446 µmol) of 6-chloro-1-(2,4-difluorophenyl)-4-oxo-1,4-dihydro-1,8-naphthyridine-3-carboxylic acid in 3 ml of THF. The reaction mixture was stirred at room temperature for 1 h and under reflux for a further hour. Subsequently, all volatile components were removed under reduced pressure. The crude product was used in the next step without further workup (conversion was assumed to be quantitative).

Example 37A

7-Chloro-N-[(1S)-1-cyclopropyl-2,2,2-trifluoro-ethyl]-6-fluoro-4-oxo-1-(2,4,6-trifluorophenyl)-1,4-dihydro-1,8-naphthyridine-3-carboxamide

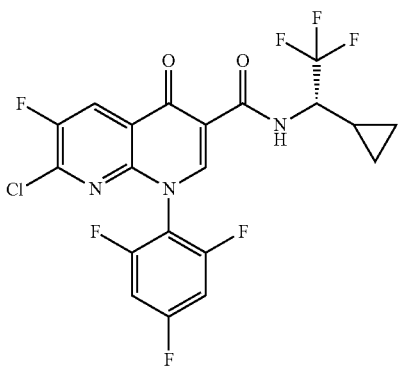 [SMILES: O=C(N[C@@H](C1CC1)C(F)(F)F)c1cn(-c2c(F)cc(F)cc2F)c2nc(Cl)c(F)cc2c1=O]

7-Chloro-6-fluoro-4-oxo-1-(2,4,6-trifluorophenyl)-1,4-dihydro-1,8-naphthyridine-3-carboxylic acid (100 mg, 268 µmol) was initially charged in 2.5 ml of acetonitrile, and (1S)-1-cyclopropyl-2,2,2-trifluoroethanamine hydrochloride (51.8 mg, 295 µmol) and N,N-diisopropylethylamine (190 µl, 1.1 mmol) were added. T3P solution (propylphosphonic acid cyclic anhydride, 50% in ethyl acetate, 190 µl, 320 µmol) was then added. The reaction solution was stirred at room temperature overnight. Water was then added to the reaction mixture and the precipitated solid was filtered off and dried under high vacuum. This gave 145 mg of the target compound (quantitative yield).

LC-MS (Method 3): R$_t$=2.42 min; MS (ESIpos): m/z=494 [M+H]$^+$ $^1$H NMR (400 MHz, DMSO-d6) δ[ppm]: −0.150 (0.74), 0.146 (0.69), 0.335 (4.38), 0.348 (3.99), 0.359 (2.50), 0.567 (5.66), 0.579 (6.91), 0.590 (7.00), 0.624 (1.67), 0.651 (2.50), 0.670 (4.11), 0.687 (2.47), 1.224 (2.32), 1.237 (3.75), 1.245 (3.07), 1.257 (3.55), 1.268 (2.06), 2.328 (1.49), 2.366 (1.19), 2.669 (1.43), 2.710 (1.01), 4.370 (2.03), 4.391 (3.66), 4.411 (3.61), 4.433 (1.94), 5.754 (2.89), 7.602 (6.41), 7.624 (12.45), 7.647 (6.50), 8.709 (9.33), 8.728 (9.33), 9.157 (16.00), 9.972 (6.97), 9.996 (6.88).

Example 38A

N-Benzyl-1,1,1,2,2-pentafluorobutan-3-amine (Racemate)

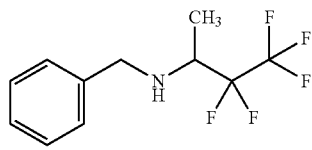 [SMILES: CC(NCc1ccccc1)C(F)(F)C(F)(F)F]

To a solution of 2.00 g (12.2 mmol) of 3,3,4,4,4-pentafluorobutan-2-one in 10 ml of dichloromethane were added, at 0° C., 5.40 ml (18.3 mmol) of titanium tetraisopropoxide and 2.66 ml (24.4 mmol) of benzylamine. The mixture was stirred at RT for a further 90 min before being cooled down again to 0° C. Subsequently, 2.14 g (34.1 mmol) of sodium cyanoborohydride, 36 ml of methanol and 3 Å molecular sieve were added. The mixture was warmed to RT and stirred for a further 2 d. A little water and ethyl acetate were then added and the reaction solution was filtered. The filtrate was washed twice with saturated aqueous sodium bicarbonate solution and once with saturated aqueous sodium chloride solution. The organic phase was dried over sodium sulfate and filtered, and the solvent was removed under reduced pressure. The residue was purified twice by means of normal phase chromatography (ethyl acetate/cyclohexane 1/20), and 1.65 g (48% of theory; 91% purity) of the title compound were obtained.

LC-MS (Method 6): R$_t$=2.17 min; MS (ESIpos): m/z=254 [M+H]$^+$.

$^1$H NMR (500 MHz, DMSO-d6): δ [ppm]=7.28-7.36 (m, 4H), 7.20-7.27 (m, 1H), 3.83 (dd, 1H), 3.72 (dd, 1H), 3.22-3.30 (m, 1H), 2.43-2.48 (m, 1H), 1.20 (d, 3H).

Example 39A 1,1,1,2,2-Pentafluorobutan-3-amine hydrochloride (Racemate)

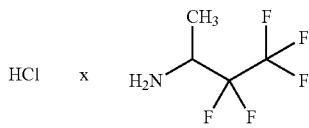

To a solution of 1.50 g (5.92 mmol) of N-benzyl-1,1,1,2,2-pentafluoropentan-3-amine in 27.4 ml of methanol were added 150 mg of palladium on charcoal (10%), and hydrogenation was effected at standard pressure and room temperature for 6 h. The reaction mixture was then filtered through a Millipore filter and the solvent was removed under reduced pressure. The receiver containing the solvent distilled off was then transferred to a flask and admixed with 4 N aqueous hydrochloric acid in dioxane and concentrated again. The residue was stirred with diethyl ether and the precipitate was filtered off with suction and dried under high vacuum. This gave 456 mg (39% of theory, 100% pure) of the title compound.

$^1$H NMR (500 MHz, DMSO-d6): δ [ppm]=9.21 (br. s, 3H), 4.40-4.29 (m, 1H), 1.41 (d, 3H).

Example 40A

N-Benzyl-1,1,1,2,2-pentafluoropentan-3-amine (Racemate)

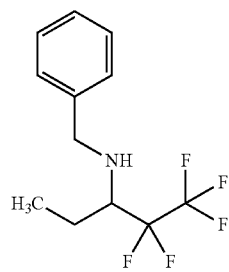 [SMILES: CCC(NCc1ccccc1)C(F)(F)C(F)(F)F]

To a solution of 2.00 g (11.4 mmol) of 1,1,1,2,2-pentafluoropentan-3-one in 10 ml of dichloromethane were added, at 0° C., 5.03 ml (17.0 mmol) of titanium tetraisopropoxide and 2.48 ml (22.7 mmol) of benzylamine. The mixture was stirred at RT for a further 90 min before being cooled down again to 0° C. Subsequently, 2.00 g (31.8 mmol) of sodium cyanoborohydride, 36 ml of methanol and 3 Å molecular sieve were added. The mixture was warmed to RT and stirred for a further 2 d. The reaction solution was then admixed with a little water and ethyl acetate and filtered. The filtrate was washed twice with saturated aqueous sodium bicarbonate solution and once with saturated aqueous sodium chloride solution. The organic phase was dried over sodium sulfate and filtered, and the solvent was removed under reduced pressure. The residue was purified by means of normal phase chromatography (ethyl acetate/cyclohexane 1/20), and 989 mg (25% of theory; 76% purity) of the title compound were obtained.

LC-MS (Method 1): $R_t$=1.27 min; MS (ESIpos): m/z=268 $[M+H]^+$ $^1$H NMR (400 MHz, DMSO-d6): δ [ppm]=7.21-7.36 (m, 5H), 3.73-3.85 (m, 2H), 3.05-3.20 (m, 1H), 1.63-1.75 (m, 1H), 1.49-1.61 (m, 1H), 1.15-1.20 (m, 1H), 0.96 (t, 3H).

Example 41A 1,1,1,2,2-Pentafluoropentan-3-amine hydrochloride (Racemate)

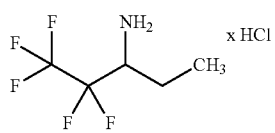

75 mg of palladium on charcoal (10%) were added to a solution of 980 mg (2.75 mmol, 75% pure) of the compound from Example 40A in 11.3 ml of methanol, and the mixture was hydrogenated at atmospheric pressure and room temperature for 6 h. The reaction mixture was then filtered through a Millipore filter and the solvent was removed under reduced pressure. The receiver containing the solvent distilled off was then transferred to a flask, 4 M aqueous hydrochloric acid in dioxane was added and the mixture was concentrated again. The residue was stirred with diethyl ether and the precipitate was filtered off with suction and dried under high vacuum. This gave 379 mg (65% of theory, 100% pure) of the title compound.

$^1$H NMR (400 MHz, DMSO-d6): δ [ppm]=8.97 (br. s, 3H), 4.16-4.28 (m, 1H), 1.67-1.94 (m, 2H), 1.05 (t, 3H).

Example 41B

Ethyl 7-chloro-4-oxo-1-(2,4,6-trifluorophenyl)-1,4-dihydro-1,8-naphthyridine-3-carboxylate

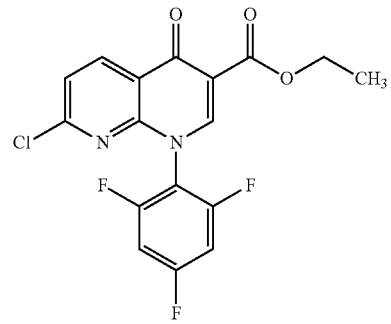 [SMILES: CCOC(=O)c1cn(-c2c(F)cc(F)cc2F)c2nc(Cl)ccc2c1=O]

To a solution of 12.1 g (38.0 mmol) of ethyl 2-[(2,6-dichloropyridin-3-yl)carbonyl]-3-ethoxyacrylate (CAS 157373-27-8) and 7.83 g (53.2 mmol) of 2,4,6-trifluoroaniline in 60.5 ml of DCM were added 46.4 ml (266 mmol) of DIPEA, and the mixture was stirred at RT for 4 h. Subsequently, 5.26 g (38.0 mmol) of potassium carbonate were added and the mixture was heated under reflux overnight. The mixture was diluted with 200 ml of DCM and washed twice with 150 ml of 1 M aqueous hydrochloric acid. The organic phase was dried over sodium sulfate and filtered, and the solvent was removed under reduced pressure. The suspension obtained was stirred with 80 ml of tert-butyl methyl ether, and the precipitate was filtered off with suction, washed with 10 ml of tert-butyl methyl ether and dried under high vacuum. This gave 8.60 g (58% of theory, 99% pure) of the title compound.

LC-MS (Method 1): $R_t$=0.97 min; 383 $[M+H]^+$.

Example 41C 7-chloro-4-oxo-1-(2,4,6-trifluorophenyl)-1,4-dihydro-1,8-naphthyridine-3-carboxylic Acid

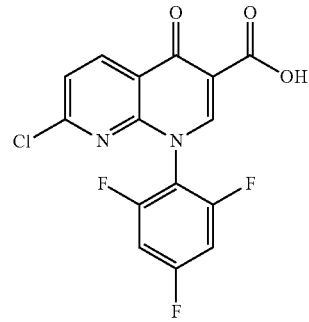 [SMILES: O=C(O)c1cn(-c2c(F)cc(F)cc2F)c2nc(Cl)ccc2c1=O]

8.60 g (22.5 mmol) of ethyl 7-chloro-4-oxo-1-(2,4,6-trifluorophenyl)-1,4-dihydro-1,8-naphthyridine-3-carboxylate (Example 100A) were initially charged in 67.7 ml of water, 67.7 ml of 36% strength aqueous hydrochloric acid and 67.7 ml of THF were added and the mixture was stirred at 110° C. for 4.5 h. The reaction mixture was cooled to RT. The precipitate was filtered off with suction, washed with water and dried under high vacuum. This gave 7.87 g (98% of theory, 99% pure) of the title compound.

LC-MS (Method 1): $R_t$=0.95 min; MS (ESIpos): m/z=355 [M+H]$^+$.

$^1$H NMR (400 MHz, DMSO-d6): δ [ppm]=13.83 (s, 1H), 9.27 (s, 1H), 8.78 (d, 1H), 7.82 (d, 1H), 7.67-7.59 (m, 2H).

Example 42A

6-Fluoro-7-(morpholin-4-yl)-4-oxo-1-(2,4,6-trifluorophenyl)-1,4-dihydro-1,8-naphthyridine-3-carboxylic Acid

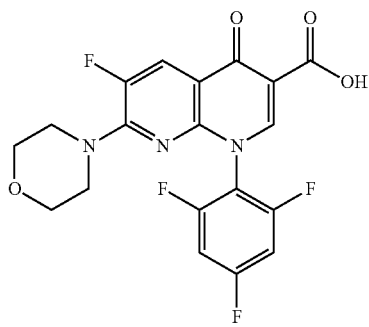 [SMILES: O=C(O)c1cn(-c2c(F)cc(F)cc2F)c2nc(N3CCOCC3)c(F)cc2c1=O]

At RT, 840 μl (4.80 mmol) of DIPEA were added to a solution of 600 mg (1.61 mmol) of 7-chloro-6-fluoro-4-oxo-1-(2,4,6-trifluorophenyl)-1,4-dihydro-1,8-naphthyridine-3-carboxylic acid and 200 μl (2.30 mmol) of morpholine in 8.0 ml DMF. The mixture was stirred at RT overnight. The reaction mixture was diluted with acetonitrile, a little water and formic acid and the crude product was purified by preparative HPLC (column: acetonitrile/water/0.1% of formic acid). This gave 658 mg (97% of theory, 100% pure) of the title compound.

LC-MS (Method 3): $R_t$=1.76 min; MS (ESIpos): m/z=424 [M+H]$^+$ $^1$H-NMR (400 MHz, DMSO-d6) δ[ppm]: −0.149 (0.48), 0.146 (0.51), 2.328 (0.72), 2.367 (0.64), 2.671 (0.77), 2.711 (0.64), 3.558 (12.72), 3.570 (14.98), 3.602 (16.00), 3.615 (13.62), 5.754 (1.56), 7.568 (4.70), 7.591 (8.79), 7.613 (4.66), 8.159 (7.09), 8.192 (7.01), 9.099 (13.11), 14.766 (1.97).

Example 43A

7-Chloro-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide

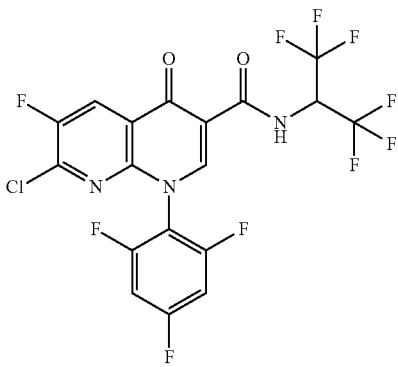 [SMILES: O=C(NC(C(F)(F)F)C(F)(F)F)c1cn(-c2c(F)cc(F)cc2F)c2nc(Cl)c(F)cc2c1=O]

3.8 ml (6.40 mmol) of 2,4,6-tripropyl-1,3,5,2,4,6-trioxatriphosphorinane 2,4,6-trioxide (T3P, 50% in DMF) were added dropwise to a solution of 600 mg (1.61 mmol) of 7-chloro-6-fluoro-4-oxo-1-(2,4,6-trifluorophenyl)-1,4-dihydro-1,8-naphthyridine-3-carboxylic acid, 296 mg (1.77 mmol) of 1,1,1,3,3,3-hexafluoropropan-2-amine and 840 μl (4.80 mmol) of DIPEA in 14 ml of ethyl acetate. The mixture was stirred at 80° C. overnight. The reaction mixture was poured into water and ethyl acetate, and the phases were separated. The organic phase was washed with water, dried over sodium sulfate and filtered, and the solvent was removed under reduced pressure. The residue was dissolved in a little acetonitrile, filtered over a Millipore filter and purified in three runs by preparative HPLC (column: acetonitrile/water/0.1% of formic acid). This gave 414 mg (49% of theory, 100% pure) of the title compound.

LC-MS (Method 3): $R_t$=2.47 min; MS (ESIpos): m/z=522 [M+H]$^+$ $^1$H-NMR (400 MHz, DMSO-d6) δ[ppm]: −0.149 (0.77), −0.008 (7.00), 0.146 (0.77), 2.073 (0.49), 2.328 (0.60), 2.367 (0.60), 2.671 (0.69), 2.711 (0.60), 6.375 (0.60), 6.394 (1.45), 6.412 (2.11), 6.418 (2.09), 6.437 (2.25), 6.454 (1.48), 6.472 (0.55), 7.616 (5.90), 7.638 (11.25), 7.660 (5.93), 8.756 (9.74), 8.774 (9.85), 9.288 (16.00), 10.694 (6.45), 10.720 (6.28).

Example 44A

7-Chloro-1-(3,5-difluoropyridin-2-yl)-6-fluoro-N-(1,1,1,3,3,3-hexafluoropropan-2-yl)-4-oxo-1,4-dihydro-1,8-naphthyridine-3-carboxamide

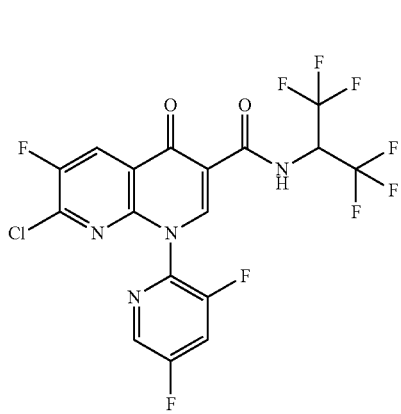 [SMILES: O=C(NC(C(F)(F)F)C(F)(F)F)c1cn(-c2ncc(F)cc2F)c2nc(Cl)c(F)cc2c1=O]

1.7 ml (2.80 mmol) of 2,4,6-tripropyl-1,3,5,2,4,6-trioxatriphosphorinane 2,4,6-trioxide (T3P, 50% in ethyl acetate) were added dropwise to a solution of 250 mg (703 µmol) of 7-chloro-1-(3,5-difluoropyridin-2-yl)-6-fluoro-4-oxo-1,4-dihydro-1,8-naphthyridine-3-carboxylic acid, 129 mg (773 µmol) of 1,1,1,3,3,3-hexafluoropropan-2-amine and 370 µl (2.10 mmol) of DIPEA in 10 ml of ethyl acetate. The mixture was stirred at 80° C. overnight. 50 ml of water were added to the reaction mixture. The precipitate was filtered off with suction, washed with water and dried under high vacuum. This gave 259 mg (69% of theory, 94% pure) of the title compound.

LC-MS (Method 3): $R_t$=2.34 min; MS (ESIpos): m/z=505 [M+H]$^+$ $^1$H-NMR (400 MHz, DMSO-d6) δ[ppm]: −0.149 (1.14), 0.146 (1.21), 0.931 (1.84), 0.949 (3.59), 0.967 (1.98), 1.175 (0.70), 1.243 (2.59), 1.260 (2.64), 1.273 (1.61), 1.298 (0.51), 1.487 (1.14), 1.496 (1.19), 1.668 (0.58), 1.988 (0.51), 2.328 (1.28), 2.366 (0.93), 2.670 (1.21), 2.710 (0.89), 6.406 (1.45), 6.424 (2.05), 6.448 (2.17), 6.467 (1.38), 8.399 (2.33), 8.405 (2.89), 8.426 (4.48), 8.443 (2.54), 8.449 (2.66), 8.615 (0.49), 8.682 (10.68), 8.688 (9.63), 8.753 (9.52), 8.772 (9.52), 8.922 (0.42), 9.184 (1.75), 9.217 (16.00), 9.284 (0.44), 10.705 (5.78), 10.731 (5.69).

Example 45A

7-Chloro-4-oxo-N-[1,1,1,2,2-pentafluoropentan-3-yl]-1-(2,4,6-trifluorophenyl)-1,4-dihydro-1,8-naphthyridine-3-carboxamide (Racemate)

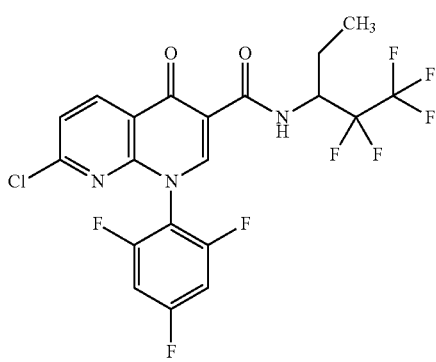 [SMILES: CCC(NC(=O)c1cn(-c2c(F)cc(F)cc2F)c2nc(Cl)ccc2c1=O)C(F)(F)C(F)(F)F]

1.6 ml (2.80 mmol) of 2,4,6-tripropyl-1,3,5,2,4,6-trioxatriphosphorinane 2,4,6-trioxide (T3P, 50% in ethyl acetate) were added dropwise to a solution of 250 mg (705 µmol) of 7-chloro-4-oxo-1-(2,4,6-trifluorophenyl)-1,4-dihydro-1,8-naphthyridine-3-carboxylic acid, 166 mg (775 µmol) of 1,1,1,2,2-pentafluoropentan-3-amine hydrochloride (racemate) and 490 µl (2.80 mmol) of DIPEA in 7.0 ml of ethyl acetate. The mixture was stirred at 80° C. overnight. 50 ml of water were added to the reaction mixture. The aqueous phase was extracted twice with ethyl acetate. All organic phases were dried over sodium sulfate and filtered, and the solvent was removed under reduced pressure. This gave 360 mg (89% of theory, 90% pure) of the title compound.

LC-MS (Method 3): $R_t$=2.45 min; MS (ESIpos): m/z=514 [M+H]$^+$ $^1$H-NMR (400 MHz, DMSO-d6) δ[ppm]: −0.149 (0.93), −0.008 (7.96), 0.008 (8.00), 0.146 (0.79), 0.834 (0.71), 0.852 (1.07), 0.950 (1.23), 0.968 (0.79), 1.180 (0.89), 1.234 (2.12), 1.266 (0.69), 1.285 (0.99), 1.302 (0.54), 1.410 (15.56), 1.427 (15.60), 1.497 (0.62), 2.328 (1.15), 2.367 (0.93), 2.671 (1.07), 2.711 (0.83), 4.998 (0.77), 5.020 (1.35), 5.044 (1.59), 5.062 (1.61), 5.086 (1.31), 5.107 (0.69), 7.596 (6.17), 7.618 (11.61), 7.640 (6.35), 7.648 (2.20), 7.754 (0.50), 7.773 (12.55), 7.794 (13.00), 7.811 (1.47), 7.832 (1.53), 8.741 (12.74), 8.762 (12.37), 8.772 (1.71), 8.793 (1.37), 9.057 (0.40), 9.143 (16.00), 9.273 (1.69), 9.986 (6.15), 10.010 (5.94).

Example 46A

7-[(3R,4R)-3,4-Dihydroxypyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (Diastereomer Mixture)

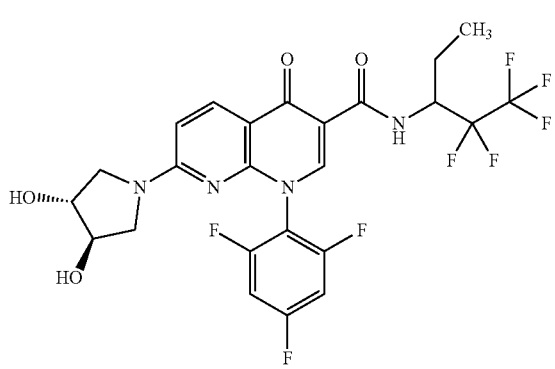 [SMILES: CCC(NC(=O)c1cn(-c2c(F)cc(F)cc2F)c2nc(N3C[C@@H](O)[C@H](O)C3)ccc2c1=O)C(F)(F)C(F)(F)F]

According to GP3, 360 mg (700 μmol) of 7-chloro-4-oxo-N-[1,1,1,2,2-pentafluoropentan-3-yl]-1-(2,4,6-trifluorophenyl)-1,4-dihydro-1,8-naphthyridine-3-carboxamide were reacted with 81.9 mg (586 μmol) of (3R,4R)-pyrrolidine-3,4-diol hydrochloride and 430 μl (2.50 mmol) of DIPEA in 4 ml of DMF. Aqueous 1N hydrochloric acid was added and the reaction mixture was extracted with ethyl acetate. The organic phase was dried over sodium sulfate and filtered, and the solvent was removed under reduced pressure. The crude product was purified by preparative HPLC (column: acetonitrile/water/0.1% of formic acid). This gave 242 mg (60% of theory, 100% pure) of the title compound.

LC-MS (Method 3): $R_t$=1.86 min; MS (ESIpos): m/z=581 [M+H]$^+$ $^1$H-NMR (400 MHz, DMSO-d6) δ[ppm]: 0.008 (2.01), 0.946 (7.17), 0.965 (16.00), 0.983 (7.77), 1.618 (0.90), 1.636 (1.25), 1.644 (1.05), 1.652 (1.50), 1.662 (1.35), 1.671 (1.20), 1.679 (1.40), 1.697 (1.00), 1.920 (1.30), 2.073 (0.80), 2.329 (0.80), 2.368 (0.70), 2.524 (2.46), 2.671 (0.85), 2.711 (0.75), 3.055 (2.76), 3.087 (3.71), 3.239 (2.36), 3.262 (1.76), 3.353 (3.76), 3.606 (2.06), 3.627 (1.71), 3.929 (3.46), 4.050 (3.46), 4.826 (0.80), 4.850 (1.15), 4.876 (1.10), 4.902 (0.85), 5.144 (4.97), 5.152 (4.97), 5.235 (5.02), 5.244 (4.87), 6.770 (7.32), 6.792 (7.52), 7.544 (2.71), 7.566 (4.82), 7.584 (2.76), 8.268 (8.58), 8.290 (8.13), 8.815 (14.50), 10.470 (4.97), 10.495 (4.76).

Example 47A

7-Chloro-4-oxo-N-[3,3,4,4,4-pentafluorobutan-2-yl]-1-(2,4,6-trifluorophenyl)-1,4-dihydro-1,8-naphthyridine-3-carboxamide (Racemate)

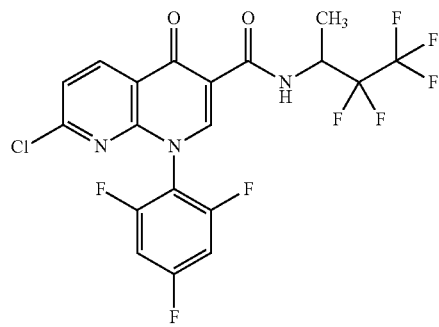 [SMILES: CC(NC(=O)c1cn(-c2c(F)cc(F)cc2F)c2nc(Cl)ccc2c1=O)C(F)(F)C(F)(F)F]

1.6 ml (2.80 mmol) of 2,4,6-tripropyl-1,3,5,2,4,6-trioxatriphosphorinane 2,4,6-trioxide (T3P, 50% in ethyl acetate) were added dropwise to a solution of 250 mg (705 μmol) of 7-chloro-4-oxo-1-(2,4,6-trifluorophenyl)-1,4-dihydro-1,8-naphthyridine-3-carboxy lie acid, 155 mg (775 μmol) of 3,3,4,4,4-pentafluorobutan-2-amine hydrochloride (racemate) and 490 μl (2.80 mmol) of DIPEA in 7.0 ml of ethyl acetate. Stirring was continued at 80° C. for 30 minutes. The solvent was removed under reduced pressure and the crude product was purified by preparative HPLC (column: acetonitrile/water/0.1% of formic acid). This gave 325 mg (83% of theory, 90% pure) of the title compound.

LC-MS (Method 3): $R_t$=2.37 min; MS (ESIpos): m/z=500 [M+H]$^+$ $^1$H-NMR (400 MHz, DMSO-d6) δ[ppm]: −0.149 (1.17), −0.008 (16.00), 0.008 (8.86), 0.146 (1.23), 0.849 (0.84), 0.942 (1.10), 0.959 (0.65), 1.233 (1.59), 1.283 (0.62), 1.409 (11.07), 1.426 (10.77), 1.487 (0.55), 2.327 (1.53), 2.366 (1.43), 2.524 (9.70), 2.670 (1.62), 2.710 (1.46), 5.020 (0.94), 5.042 (1.20), 5.060 (1.20), 5.086 (1.01), 7.595 (4.38), 7.617 (8.11), 7.639 (4.35), 7.772 (8.18), 7.793 (8.31), 7.811 (0.97), 7.832 (1.04), 8.741 (8.18), 8.761 (7.89), 8.772 (1.07), 8.793 (0.88), 9.142 (10.90), 9.272 (1.14), 9.985 (4.28), 10.009 (4.19).

Example 48A

7-[(3R,4R)-3,4-Dihydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

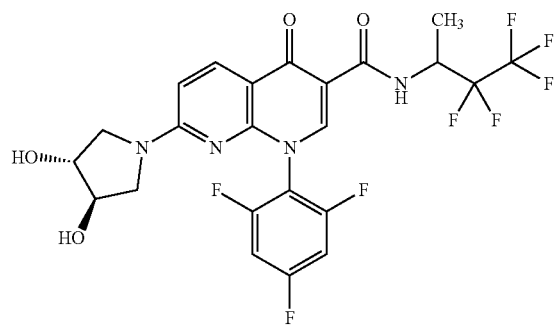 [SMILES: CC(NC(=O)c1cn(-c2c(F)cc(F)cc2F)c2nc(N3C[C@@H](O)[C@H](O)C3)ccc2c1=O)C(F)(F)C(F)(F)F]

According to GP3, 325 mg (650 µmol) of 7-chloro-4-oxo-N-[3,3,4,4,4-pentafluorobutan-2-yl]-1-(2,4,6-trifluorophenyl)-1,4-dihydro-1,8-naphthyridine-3-carboxamide (racemate) were reacted with 76.1 mg (545 µmol) of (3R,4R)-pyrrolidine-3,4-diol hydrochloride and 400 µl (2.30 mmol) of DIPEA in 3.7 ml of DMF. Aqueous 1N hydrochloric acid was added and the reaction mixture was extracted with ethyl acetate. The organic phase was dried over sodium sulfate and filtered, and the solvent was removed under reduced pressure. The crude product was purified by preparative HPLC (column: acetonitrile/water/ 0.1% of formic acid). This gave 239 mg (65% of theory, 100% pure) of the title compound.

LC-MS (Method 3): $R_t$=1.76 min; MS (ESIpos): m/z=567 [M+H]$^+$ $^1$H-NMR (400 MHz, DMSO-d6) δ[ppm]: 1.388 (15.08), 1.401 (16.00), 2.672 (0.88), 3.053 (3.67), 3.086 (4.68), 3.601 (3.82), 3.929 (6.14), 4.052 (6.04), 5.005 (2.33), 5.146 (6.42), 5.237 (6.35), 6.768 (5.34), 6.790 (5.44), 7.564 (8.09), 8.261 (5.29), 8.283 (5.16), 8.808 (8.64), 10.549 (4.91), 10.573 (4.81).

Example 49A

7-Chloro-4-oxo-N-(1,1,1-trifluoro-2-methylpropan-2-yl)-1-(2,4,6-trifluorophenyl)-1,4-dihydro-1,8-naphthyridine-3-carboxamide

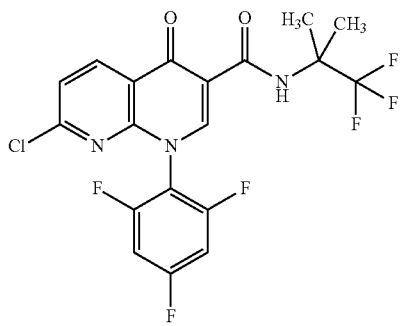 [SMILES: CC(C)(NC(=O)c1cn(-c2c(F)cc(F)cc2F)c2nc(Cl)ccc2c1=O)C(F)(F)F]

1.6 ml (2.80 mmol) of 2,4,6-tripropyl-1,3,5,2,4,6-trioxatriphosphorinane 2,4,6-trioxide (T3P, 50% in ethyl acetate) were added dropwise to a solution of 250 mg (705 µmol) of 7-chloro-4-oxo-1-(2,4,6-trifluorophenyl)-1,4-dihydro-1,8-naphthyridine-3-carboxy lie acid, 127 mg (775 µmol) of 1,1,1-trifluoro-2-methylpropan-2-amine hydrochloride and 490 µl (2.80 mmol) of DIPEA in 7.0 ml of ethyl acetate. The mixture was stirred at 80° C. for 30 minutes. The solvent was removed under reduced pressure and the reaction mixture was diluted with 50 ml of water. The precipitate formed was filtered off, washed with water and dried. This gave 297 mg (88% of theory, 97% pure) of the title compound.

LC-MS (Method 3): $R_t$=2.34 min; MS (ESIpos): m/z=464 [M+H]$^+$ $^1$H-NMR (400 MHz, DMSO-d6) δ[ppm]: –0.062 (0.91), –0.008 (0.99), 0.008 (1.16), 1.653 (16.00), 7.597 (1.19), 7.618 (2.22), 7.641 (1.22), 7.767 (2.50), 7.788 (2.63), 8.746 (2.59), 8.767 (2.51), 9.080 (3.17), 10.101 (2.55).

Example 50A

7-[(3R,4R)-3,4-Dihydroxypyrrolidin-1-yl]-4-oxo-N-(1,1,1-trifluoro-2-methylpropan-2-yl)-1-(2,4,6-trifluorophenyl)-1,4-dihydro-1,8-naphthyridine-3-carboxamide

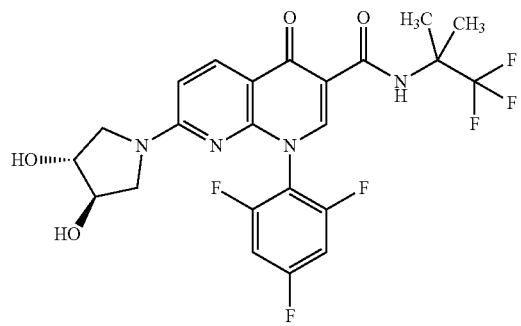 [SMILES: CC(C)(NC(=O)c1cn(-c2c(F)cc(F)cc2F)c2nc(N3C[C@@H](O)[C@H](O)C3)ccc2c1=O)C(F)(F)F]

According to GP3, 297 mg (666 µmol) of 7-chloro-4-oxo-N-(1,1,1-trifluoro-2-methylpropan-2-yl)-1-(2,4,6-trifluorophenyl)-1,4-dihydro-1,8-naphthyridine-3-carboxamide were reacted with 102 mg (733 nmol) of (3R,4R)-pyrrolidine-3,4-diol hydrochloride and 410 µl (2.30 mmol) of DIPEA in 6.0 ml of DMF. 20 ml of water and aqueous 1N hydrochloric acid were added to the reaction mixture. The precipitate formed was filtered off, washed with water and dried. This gave 272 mg (77% of theory, 100% pure) of the title compound.

LC-MS (Method 3): $R_t$=1.73 min; MS (ESIpos): m/z=531 [M+H]$^+$ $^1$H-NMR (400 MHz, DMSO-d6) δ[ppm]: –0.008 (1.79), 0.008 (1.49), 1.634 (16.00), 2.073 (5.68), 3.052 (0.77), 3.083 (1.03), 3.226 (0.66), 3.235 (0.76), 3.257 (0.63), 3.268 (0.68), 3.348 (1.35), 3.593 (0.56), 3.603 (0.65), 3.621 (0.52), 3.630 (0.49), 3.923 (0.97), 4.046 (0.97), 6.759 (1.98), 6.782 (2.03), 7.545 (0.73), 7.567 (1.31), 7.585 (0.74), 8.266 (2.23), 8.289 (2.10), 8.739 (3.50), 10.653 (2.89).

Example 51A

7-Chloro-N-[(1S)-1-cyclopropyl-2,2,2-trifluoroethyl]-4-oxo-1-(2,4,6-trifluorophenyl)-1,4-dihydro-1,8-naphthyridine-3-carboxamide

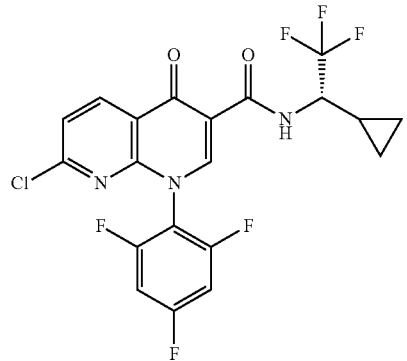 [SMILES: O=C(N[C@@H](C1CC1)C(F)(F)F)c1cn(-c2c(F)cc(F)cc2F)c2nc(Cl)ccc2c1=O]

26 ml (45.0 mmol) of 2,4,6-tripropyl-1,3,5,2,4,6-trioxatriphosphorinane 2,4,6-trioxide (T3P, 50% in ethyl acetate) were added dropwise to a solution of 4.00 g (11.3 mmol) of 7-chloro-4-oxo-1-(2,4,6-trifluorophenyl)-1,4-dihydro-1,8-naphthyridine-3-carboxylic acid, 2.18 g (12.4 mmol) of (1S)-1-cyclopropyl-2,2,2-trifluoroethanamine hydrochloride and 7.9 ml (45.0 mmol) of DIPEA in 110 ml of ethyl acetate. Stirring was continued at 80° C. for 30 minutes. The solvent was removed under reduced pressure and the reaction mixture was diluted with 150 ml of water. The precipitate was filtered off, washed with water and dried. This gave 5.30 g (95% of theory, 96% pure) of the title compound.

LC-MS (Method 3): $R_t$=2.33 min; MS (ESIpos): m/z=476 [M+H]$^+$ $^1$H-NMR (400 MHz, DMSO-d6) δ[ppm]: −0.149 (0.55), −0.062 (4.39), 0.008 (4.02), 0.146 (0.52), 0.322 (1.81), 0.335 (3.73), 0.348 (3.42), 0.361 (1.95), 0.370 (1.38), 0.566 (5.17), 0.580 (6.61), 0.589 (5.43), 0.609 (2.33), 0.623 (1.38), 0.645 (1.67), 0.652 (2.21), 0.666 (3.50), 0.679 (1.90), 0.688 (2.13), 0.694 (2.24), 0.716 (0.40), 0.850 (0.43), 0.934 (1.01), 1.157 (1.38), 1.175 (2.70), 1.193 (1.52), 1.202 (0.83), 1.215 (1.55), 1.223 (2.13), 1.235 (3.76), 1.244 (3.07), 1.256 (3.56), 1.265 (2.10), 1.275 (1.49), 1.282 (1.41), 1.300 (0.57), 1.486 (0.80), 1.989 (4.83), 2.329 (1.01), 2.367 (0.89), 2.524 (4.77), 2.671 (1.03), 2.711 (0.83), 4.003 (0.43), 4.021 (1.18), 4.039 (1.15), 4.056 (0.40), 4.243 (0.49), 4.261 (0.40), 4.341 (0.60), 4.361 (1.87), 4.382 (3.22), 4.403 (3.04), 4.424 (1.61), 4.444 (0.43), 7.594 (6.32), 7.617 (11.78), 7.639 (6.18), 7.699 (0.43), 7.776 (11.69), 7.797 (12.21), 8.748 (12.18), 8.769 (11.75), 8.940 (0.46), 9.126 (16.00), 10.025 (6.55), 10.049 (6.26).

Example 52A

N-[(1S)-1-Cyclopropyl-2,2,2-trifluoroethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide

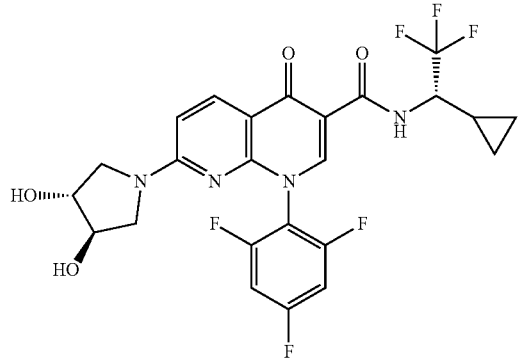 [SMILES: O=C(N[C@@H](C1CC1)C(F)(F)F)c1cn(-c2c(F)cc(F)cc2F)c2nc(N3C[C@@H](O)[C@H](O)C3)ccc2c1=O]

According to GP3, 5.30 g (11.1 mmol) of 7-chloro-N-[(1S)-1-cyclopropyl-2,2,2-trifluoroethyl]-4-oxo-1-(2,4,6-trifluorophenyl)-1,4-dihydro-1,8-naphthyridine-3-carboxamide were reacted with 1.87 g (13.4 mmol) of (3R,4R)-pyrrolidine-3,4-diol hydrochloride and 6.8 ml (39.0 mmol) of DIPEA in 50 ml of DMF. 400 ml of water and aqueous 1N hydrochloric acid were added to the reaction mixture. The precipitate was filtered off, washed with water and dried. This gave 5.47 g (91% of theory, 100% pure) of the title compound.

LC-MS (Method 3): $R_t$=1.71 min; MS (ESIpos): m/z=543 [M+H]$^+$ $^1$H-NMR (400 MHz, DMSO-d6) δ[ppm]: −0.149 (0.74), −0.061 (4.97), −0.008 (6.91), 0.008 (5.18), 0.146 (0.66), 0.324 (1.75), 0.334 (2.68), 0.346 (2.68), 0.358 (2.07), 0.370 (1.01), 0.510 (1.88), 0.522 (2.81), 0.535 (2.49), 0.547 (2.58), 0.556 (2.24), 0.567 (2.75), 0.578 (2.32), 0.588 (2.16), 0.598 (1.73), 0.612 (1.10), 0.626 (1.37), 0.636 (1.52), 0.647 (2.47), 0.657 (2.16), 0.662 (2.11), 0.670 (2.03), 0.682 (1.01), 0.691 (0.72), 0.944 (1.48), 1.165 (0.82), 1.177 (1.44), 1.186 (1.99), 1.198 (3.15), 1.206 (2.49), 1.218 (3.32), 1.231 (2.32), 1.238 (1.99), 1.263 (1.33), 1.398 (0.59), 2.328 (0.85), 2.367 (0.78), 2.524 (2.62), 2.670 (0.80), 2.711 (0.68), 2.731 (3.21), 2.891 (3.89), 3.056 (3.25), 3.088 (4.25), 3.230 (2.62), 3.239 (2.98), 3.261 (2.35), 3.272 (2.32), 3.353 (4.10), 3.600 (2.37), 3.609 (2.71), 3.627 (2.20), 3.637 (1.99), 3.927 (3.89), 4.050 (3.89), 4.356 (1.39), 4.377 (2.41), 4.398 (2.39), 4.418 (1.25), 5.145 (3.74), 5.233 (3.53), 6.772 (8.20), 6.794 (8.43), 7.543 (3.17), 7.566 (5.60), 7.583 (3.19), 7.953 (0.51), 8.271 (9.72), 8.293 (9.13), 8.798 (16.00), 10.558 (5.71), 10.582 (5.45).

Example 53A 1,1,1,2,2-Pentafluoro-N-[(1S)-1-phenylethyl]pentan-3-imine

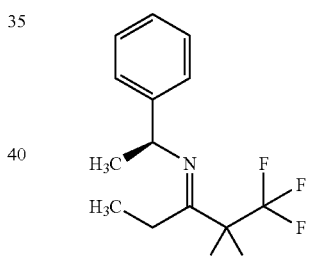

1,1,1,2,2-Pentafluoropentan-3-one (50.0 g, 284 mmol) was initially charged in 2 l of diethyl ether and cooled to 0° C. (1S)-1-Phenylethanamine (34.4 g, 284 mmol) and triethylamine (79 ml, 570 mmol) were then added rapidly, and at an internal temperature of 0° C. titanium(IV) chloride (1 M in toluene, 140 ml, 140 mmol) was subsequently slowly added dropwise. The ice bath was then removed and the mixture was warmed to RT. The reaction mixture was subsequently heated under reflux for 1 h and then stirred at RT overnight. Kieselguhr was added to the reaction mixture, the mixture was stirred for 1 h and then filtered through kieselguhr and the kieselguhr was washed thoroughly with diethyl ether. The filtrate was concentrated at water bath temperature of 20° C. The crude product was used for the next step without further purification. This gave 79 g (quantitative yield) of the title compound.

Example 54A 1,1,1,2,2-Pentafluoro-N-[(1S)-1-phenylethyl]pentan-3-amine hydrochloride (Enantiomerically Pure)

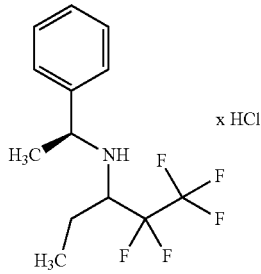 [SMILES: CCC(N[C@@H](C)c1ccccc1)C(F)(F)C(F)(F)F]

1,1,1,2,2-Pentafluoro-N-[(1S)-1-phenylethyl]pentan-3-imine (79 g, 283 mmol) was initially charged in 640 ml of dichloromethane, 130 ml of DMF and molecular sieve 3 Å were then added and the mixture was stirred at RT for 1 h. The reaction mixture was cooled to −50° C., and trichlorosilane (86 ml, 850 mmol) was slowly added dropwise. After 30 min and at an internal temperature of −70° C. to −50° C., the mixture was quenched first with saturated sodium bicarbonate solution and then with solid sodium bicarbonate until a pH of 7 had been reached. Dichloromethane was added and the phases were separated. The organic phase was dried over sodium sulfate, 200 ml of hydrogen chloride in diethyl ether (2 M solution) were then added and the crude product was concentrated under reduced pressure. This gave 48.6 g (54% of theory) of the title compound.

$^1$H NMR (400 MHz, DMSO-d6): δ [ppm]=7.82 (br. s, 1H), 7.26-7.60 (m, 5H), 4.13 (br. s, 1H), 3.20 (br. s, 1H), 1.40-1.77 (m, 5H), 0.80 (t, 3H).

Example 55A 1,1,1,2,2-Pentafluoropentan-3-amine hydrochloride (Enantiomerically Pure)

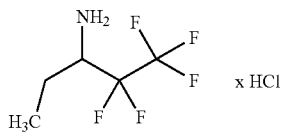

48.6 g (153 mmol) of 1,1,1,2,2-pentafluoro-N-[(1S)-1-phenylethyl]pentan-3-amine hydrochloride (enantiomerically pure, from Example 54A) were dissolved in 250 ml of ethanol, 4.86 g of palladium(II) hydroxide (20% on carbon) were added and the mixture was then hydrogenated at RT and standard pressure overnight. The precipitate was filtered off and washed thoroughly, and the filtrate was concentrated carefully. This gave 31.7 g (97% of theory) of the title compound.

$^1$H NMR (400 MHz, DMSO-d6): δ [ppm]=9.16 (br. s, 3H), 4.12-4.28 (m, 1H), 3.47 (br. s, 1H), 1.69-1.96 (m, 2H), 1.06 (t, 3H).

Example 56A 3,3,4,4,4-Pentafluoro-N-[(1S)-1-phenylethyl]butan-2-imine

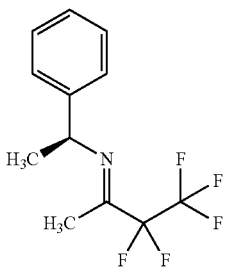 [SMILES: C/C(=N\[C@@H](C)c1ccccc1)C(F)(F)C(F)(F)F]

3,3,4,4,4-Pentafluorobutan-2-one (200 g, 1.23 mol) was initially charged in 6.4l of diethyl ether and cooled to −40° C. (1S)-1-Phenylethanamine (160 ml 1.2 mol) and triethylamine (340 ml, 2.5 mol) were then added rapidly, and at an internal temperature of 0° C. titanium(IV) chloride (1 M in toluene, 620 ml, 620 mmol) was subsequently slowly added dropwise. The ice bath was then removed and the mixture was warmed to RT. The reaction mixture was subsequently heated under reflux for 1 h and then stirred at RT overnight. Celite was added to the reaction mixture, the mixture was stirred for 1 h and then filtered through Celite and the Celite was washed thoroughly with diethyl ether. The filtrate was concentrated at water bath temperature of 25° C. Cyclohexane was added to the residue and the residue was once more filtered off through Celite and washed with cyclohexane. The filtrate was concentrated at water bath temperature of 25° C. The crude product was used for the next step without further purification. This gave 289 g (88% of theory) of the title compound.

Example 57A 3,3,4,4,4-Pentafluoro-N-[(1S)-1-phenylethyl]butan-2-amine hydrochloride (Enantiomerically Pure)

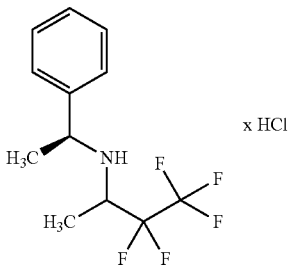 [SMILES: CC(N[C@@H](C)c1ccccc1)C(F)(F)C(F)(F)F]

3,3,4,4,4-Pentafluoro-N-[(1S)-1-phenylethyl]butan-2-imine (239 g, 901 mmol) was initially charged in 1.9l of dichloromethane, 420 ml of DMF and molecular sieve 3 Å were then added and the mixture was stirred at RT for 1 h. The reaction mixture was then cooled to −50° C., and trichlorosilane (270 ml, 2.7 mol) was slowly added dropwise. After 30 min and at an internal temperature of −70° C. to −50° C., the mixture was carefully quenched with semi-concentrated sodium hydroxide solution until a pH of 7 had been reached. Dichloromethane was added and the phases were separated. The organic phase was dried over sodium sulfate, 2.21 of hydrogen chloride in diethyl ether (2 M solution) were then added and the crude product was concentrated under reduced pressure. This gave 192 g (70% of theory) of the title compound.

LC-MS (Method 1): $R_t$=1.22 min; MS (ESIpos): m/z=268 [M–HCl+H]$^+$

Example 58A 3,3,4,4,4-Pentafluorobutan-2-amine hydrochloride (Enantiomerically Pure)

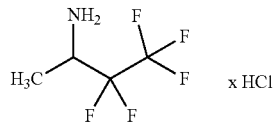

192 g (632 mmol) of 3,3,4,4,4-pentafluoro-N-[(1S)-1-phenylethyl]butan-2-amine hydrochloride (enantiomerically pure, from Example 57A) were dissolved in 1.2 l of ethanol, 19.2 g of palladium(II) hydroxide (20% on carbon) were added and the mixture was then hydrogenated at RT and standard pressure overnight. The precipitate was filtered off and washed thoroughly, and the filtrate was concentrated carefully. This gave 117 g (93% of theory) of the title compound.

$^1$H NMR (400 MHz, DMSO-d6): δ [ppm]=9.29 (br. s, 3H), 4.22-4.44 (m, 1H), 1.42 (d, H).

Example 59A

7-Chloro-6-fluoro-4-oxo-N-[1,1,1,2,2-pentafluoro-pentan-3-yl]-1-(2,4,6-trifluorophenyl)-1,4-dihydro-1,8-naphthyridine-3-carboxamide (Racemate)

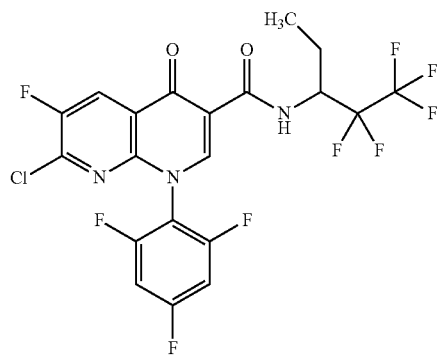 [SMILES: CCC(NC(=O)c1cn(-c2c(F)cc(F)cc2F)c2nc(Cl)c(F)cc2c1=O)C(F)(F)C(F)(F)F]

7-Chloro-6-fluoro-4-oxo-1-(2,4,6-trifluorophenyl)-1,4-dihydro-1,8-naphthyridine-3-carboxylic acid (200 mg, 537 μmol) was initially charged in 1.3 ml of acetonitrile, and 1,1,1,2,2-pentafluoro-pentan-3-amine hydrochloride (racemate, 138 mg, 644 μmol) and N,N-diisopropylethylamine (370 μl, 2.1 mmol) were added, followed by 380 μl (50% pure, 640 μmol) of T3P solution (propanephosphonic acid cyclic anhydride, 50% in ethyl acetate). The reaction solution was stirred overnight and then added to water. The mixture was freed from acetonitrile and extracted three times with dichloromethane. The combined organic phases were dried over sodium sulfate, filtered and concentrated under reduced pressure. This gave 282 mg of the target compound (97% of theory, purity 98%).

LC-MS (Method 3): $R_t$=2.53 min; MS (ESIpos): m/z=532 [M+H]$^+$

Example 60A

7-Chloro-6-fluoro-4-oxo-N-[1,1,1,2,2-pentafluoro-pentan-3-yl]-1-(2,4,6-trifluorophenyl)-1,4-dihydro-1,8-naphthyridine-3-carboxamide (Enantiomerically Pure)

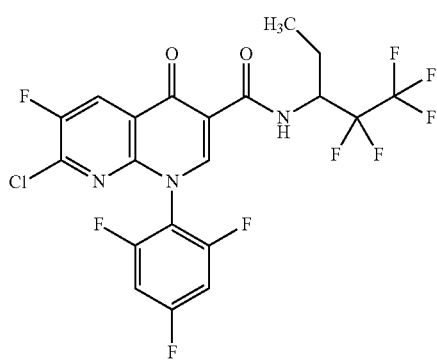 [SMILES: CCC(NC(=O)c1cn(-c2c(F)cc(F)cc2F)c2nc(Cl)c(F)cc2c1=O)C(F)(F)C(F)(F)F]

7-Chloro-6-fluoro-4-oxo-1-(2,4,6-trifluorophenyl)-1,4-dihydro-1,8-naphthyridine-3-carboxylic acid (5.00 g, 13.4 mmol) was initially charged in 33 ml of acetonitrile. 3.44 g, (16.1 mmol) of 1,1,1,2,2-pentafluoropentan-3-amine hydrochloride (enantiomerically pure, from Example 55A) and N,N-diisopropylethylamine (9.3 ml, 54 mmol) were added. T3P solution (propanephosphonic acid cyclic anhydride, 50% in ethyl acetate, 9.5 ml, 50% pure, 16 mmol) was then added and the mixture was stirred at room temperature overnight. Water was added to the reaction solution. A viscous suspension was formed. This was acidified with dilute hydrochloric acid and stirred at room temperature for 1 h. The solid was filtered off, then washed with water and dried under high vacuum. This gave 6.69 g of the compound (84% of theory, purity 90%).

LC-MS (Method 5): $R_t$=1.67 min; MS (ESIpos): m/z=532 [M+H]$^+$

Example 61A tert-Butyl 4-[3-fluoro-5-oxo-6-{[1,1,1,2,2-pentafluoropentan-3-yl]carbamoyl}-8-(2,4,6-trifluorophenyl)-5,8-dihydro-1,8-naphthyridin-2-yl]-2-(hydroxymethyl)piperazine-1-carboxylate (Diastereomer Mixture)

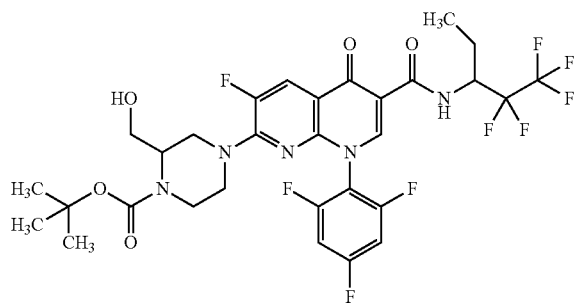 [SMILES: CCC(NC(=O)c1cn(-c2c(F)cc(F)cc2F)c2nc(N3CCN(C(=O)OC(C)(C)C)C(CO)C3)c(F)cc2c1=O)C(F)(F)C(F)(F)F]

7-Chloro-6-fluoro-4-oxo-N-[1,1,1,2,2-pentafluoropentan-3-yl]-1-(2,4,6-trifluorophenyl)-1,4-di-hydro-1,8-naphthyridine-3-carboxamide (enantiomerically pure from Example 60A, 200 mg, 90% pure, 338 µmol) was initially charged in 1.7 ml of DMF, and N,N-diisopropylethylamine (590 µl, 3.4 mmol) and tert-butyl (2-(hydroxymethyl)piperazine-1-carboxylate (80.5 mg, 372 µmol) were added at room temperature. The reaction solution was stirred at room temperature for 1 h. The reaction solution was admixed with water and extracted three times with ethyl acetate. The combined organic phases were twice washed with water, dried over sodium sulfate, filtered and concentrated. The crude product was purified by silica gel chromatography (mobile phase: cyclohexane/ethyl acetate=2/1). This gave 204 mg of the target compound (85% of theory, purity 100%) as a diastereomer mixture of two diastereomers.

LC-MS (Method 5): $R_t$=1.62 min; MS (ESIpos): m/z=712 [M+H]$^+$

Example 62A

7-Chloro-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Racemate)

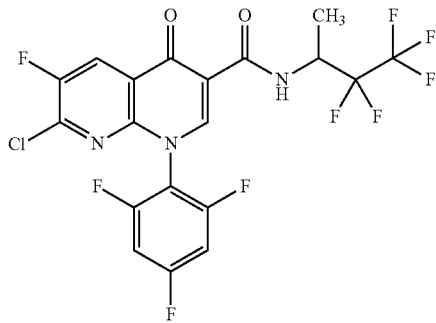 [SMILES: CC(NC(=O)c1cn(-c2c(F)cc(F)cc2F)c2nc(Cl)c(F)cc2c1=O)C(F)(F)C(F)(F)F]

7-Chloro-6-fluoro-4-oxo-1-(2,4,6-trifluorophenyl)-1,4-dihydro-1,8-naphthyridine-3-carboxylic acid (200 mg, 537 µmol) was initially charged in 1.3 ml of acetonitrile. 1,1,1,2,2-Pentafluorobutan-3-amine hydrochloride (racemate, 129 mg, 644 µmol) and N,N-diisopropylethylamine (370 µl, 2.1 mmol) were added, followed by 380 µl (50% pure, 640 µmol) of T3P solution (propanephosphonic acid cyclic anhydride, 50% in ethyl acetate). The reaction solution was stirred overnight. The reaction solution was added to water and precipitated. The solid was filtered off and dried under high vacuum overnight. This gave 250 mg of the compound (76% of theory, purity 84%).

LC-MS (Method 3): $R_t$=2.45 min; MS (ESIpos): m/z=518 [M+H]$^+$

Example 63A

7-Chloro-6-fluoro-4-oxo-N-(3,3,4,4,4-pentafluoro-2-methylbutan-2-yl)-1-(2,4,6-trifluorophenyl)-1,4-dihydro-1,8-naphthyridine-3-carboxamide

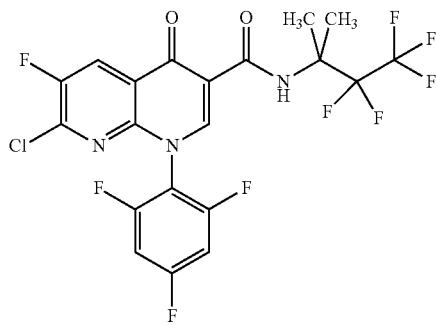 [SMILES: CC(C)(NC(=O)c1cn(-c2c(F)cc(F)cc2F)c2nc(Cl)c(F)cc2c1=O)C(F)(F)C(F)(F)F]

7-Chloro-6-fluoro-4-oxo-1-(2,4,6-trifluorophenyl)-1,4-dihydro-1,8-naphthyridine-3-carboxylic acid (1.50 g, 4.03 mmol) was initially charged in 38 ml of acetonitrile. 3,3,4,4-Pentafluoro-2-methylbutan-2-amine hydrochloride (1.12 g, 5.23 mmol) and N,N-diisopropylethylamine (3.5 ml, 20 mmol) were added, followed by 3.6 ml (50% pure, 6.0 mmol) T3P solution (propanephosphonic acid cyclic anhydride, 50% in ethyl acetate). The reaction solution was stirred at room temperature overnight. Water was then added to the reaction solution. Under reduced pressure, the solution was freed almost completely from acetonitrile, and gradually a solid precipitated on evaporation. The solid obtained was washed with water. The solid was dried under high vacuum. This gave 1.96 g of the target compound (91% of theory, 99% pure).

LC-MS (Method 3): $R_t$=2.50 min; MS (ESIpos): m/z=532 [M+H]$^+$

Example 64A

Ethyl (2Z)-2-[(2,6-dichloro-5-fluoropyridin-3-yl)carbonyl]-3-ethoxyacrylate

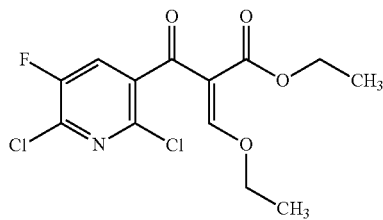 [SMILES: CCO/C=C(\C(=O)OCC)C(=O)c1cc(F)c(Cl)nc1Cl]

Ethyl 3-(2,6-dichloro-5-fluoropyridin-3-yl)-3-oxopropanoate (500 mg, 1.79 mmol) and (diethoxymethoxy)ethane (590 μl, 3.6 mmol) were initially charged in acetic anhydride (1.2 ml, 12 mmol) and stirred at 140° C. overnight. The reaction solution was concentrated and, without further purification, reacted further in the next step.

LC-MS (Method 1): R$_t$=1.01 min; MS (ESIpos): m/z=336 [M+H]$^+$

Example 65A

Ethyl 7-chloro-6-fluoro-1-(4-fluoro-2,6-dimethylphenyl)-4-oxo-1,4-dihydro-1,8-naphthyridine-3-carboxylate

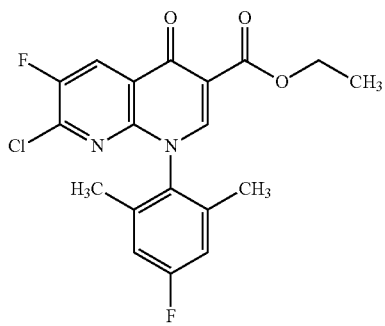 [SMILES: CCOC(=O)c1cn(-c2c(C)cc(F)cc2C)c2nc(Cl)c(F)cc2c1=O]

Ethyl (2Z)-2-[(2,6-dichloro-5-fluoropyridin-3-yl)carbonyl]-3-ethoxyacrylate (9.36 g, 27.8 mmol) and 4-fluoro-2,6-dimethylaniline (4.65 g, 33.4 mmol) were initially charged in 47 ml of dichloromethane, and N,N-diisopropylethylamine (34 ml, 194.9 mmol) was added at room temperature (exothermic). The reaction solution was stirred at room temperature for 4 h. Subsequently, potassium carbonate (3.85 g, 27.84 mmol) was added and the mixture was stirred under reflux overnight. The reaction mixture was then cooled, diluted with dichloromethane and washed with 1M hydrochloric acid until the colour changed. The organic phase was dried over sodium sulfate, filtered, concentrated and dried under high vacuum. The crude product was purified by silica gel chromatography (mobile phase: cyclohexane/ethyl acetate: 5/1 to cyclohexane/ethyl acetate: 3/1). This gave 6.47 g of the target compound (58% of theory, purity 99%).

LC-MS (Method 3): R$_t$=2.00 min; MS (ESIpos): m/z=393 [M+H]$^+$ $^1$H-NMR (400 MHz, DMSO-d6) δ[ppm]: −0.008 (0.95), 0.008 (0.78), 1.254 (2.75), 1.271 (5.79), 1.289 (2.77), 1.975 (16.00), 2.523 (0.61), 4.205 (0.87), 4.222 (2.65), 4.240 (2.61), 4.258 (0.82), 5.754 (3.81), 7.188 (2.22), 7.211 (2.23), 8.543 (1.72), 8.561 (5.10).

Example 66A

7-Chloro-6-fluoro-1-(4-fluoro-2,6-dimethylphenyl)-4-oxo-1,4-dihydro-1,8-naphthyridine-3-carboxylic Acid

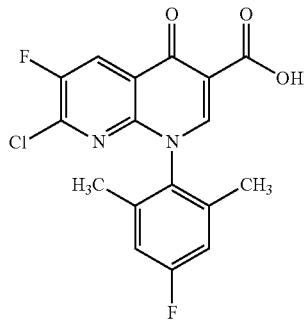 [SMILES: Cc1cc(F)cc(C)c1-n1cc(C(=O)O)c(=O)c2cc(F)c(Cl)nc21]

Ethyl 7-chloro-6-fluoro-1-(4-fluoro-2,6-dimethylphenyl)-4-oxo-1,4-dihydro-1,8-naphthyridine-3-carboxylate (6.47 g, 99% pure, 16.3 mmol) was suspended in 49 ml of THF. 49 ml of water and 49 ml of conc. hydrochloric acid were added and the mixture was left to stir at a bath temperature of 110° C. for 4 h. Most of the THF was removed under reduced pressure. With ice cooling, 100 ml of water were added to the aqueous phase. A solid precipitated out. This was filtered off and rinsed three times with water. This gave 5.35 g of the target compound (89% of theory, purity 99%).

LC-MS (Method 1): R$_t$=1.03 min; MS (ESIpos): m/z=365 [M+H]$^+$ $^1$H-NMR (400 MHz, DMSO-d6) δ[ppm]: 1.957 (16.00), 1.975 (0.43), 7.195 (2.23), 7.218 (2.20), 8.775 (1.30), 8.794 (1.29), 8.871 (2.87).

Example 67A

7-Chloro-N-[(1S)-1-cyclopropyl-2,2,2-trifluoroethyl]-6-fluoro-1-(4-fluoro-2,6-dimethylphenyl)-4-oxo-1,4-dihydro-1,8-naphthyridine-3-carboxamide

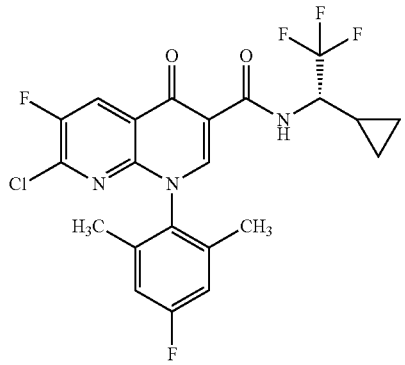 [SMILES: Cc1cc(F)cc(C)c1-n1cc(C(=O)N[C@@H](C2CC2)C(F)(F)F)c(=O)c2cc(F)c(Cl)nc21]

7-Chloro-6-fluoro-1-(4-fluoro-2,6-dimethylphenyl)-4-oxo-1,4-dihydro-1,8-naphthyridine-3-carboxylic acid (1.00 g, 2.74 mmol) was initially charged in 25.5 ml of acetonitrile, and (1S)-1-cyclopropyl-2,2,2-trifluoroethanamine hydrochloride (530 mg, 3.02 mmol) and N,N-diisopropylethylamine (1.9 ml, 11 mmol) were added, followed by 1.9 ml (3.29 mmol) of T3P solution (propanephosphonic acid cyclic anhydride, 50% in ethyl acetate). The reaction solution was stirred at room temperature overnight. More (1S)-1-cyclopropyl-2,2,2-trifluoroethanamine hydrochloride (144 mg, 823 µmol), 0.32 ml (1.1 mmol) T3P solution (propanephosphonic acid cyclic anhydride, 50% in ethyl acetate) and N,N-diisopropylethylamine (0.48 ml, 2.74 mmol) were added. Stirring of the reaction solution was continued at room temperature over the weekend. The mixture was subsequently freed from acetonitrile and extracted twice with dichloromethane. The combined organic phases were dried over sodium sulphate, filtered and dried under high vacuum. The residue was purified by column chromatography (silica gel, mobile phase: dichloromethane/cyclohexane=7.5/1). This gave 1.05 g (99% pure, 78% of theory) of the target compound.

LC-MS (Method 1): $R_t$=1.28 min; MS (ESIpos): m/z=486 $[M+H]^+$ $^1$H-NMR (400 MHz, DMSO-d6) δ[ppm]: 0.008 (1.25), 0.339 (0.87), 0.353 (0.89), 0.364 (0.51), 0.554 (0.81), 0.567 (1.37), 0.582 (1.20), 0.601 (0.63), 0.610 (0.52), 0.651 (0.46), 0.666 (0.81), 0.671 (0.70), 0.684 (0.55), 1.219 (0.47), 1.231 (0.87), 1.240 (0.65), 1.251 (0.75), 1.264 (0.44), 1.957 (16.00), 4.361 (0.43), 4.382 (0.73), 4.402 (0.73), 4.422 (0.40), 5.754 (3.95), 7.193 (3.42), 7.216 (3.43), 8.709 (7.53), 8.726 (2.88), 10.138 (1.51), 10.162 (1.49).

Example 68A

7-Chloro-6-fluoro-4-oxo-N-(3,3,4,4,4-pentafluorobutan-2-yl)-1-(2,4,6-trifluorophenyl)-1,4-dihydro-1,8-naphthyridine-3-carboxamide (Enantiomerically Pure)

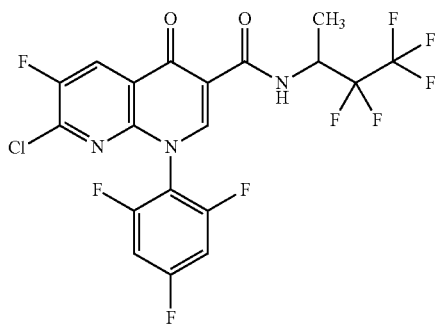 [SMILES: CC(NC(=O)c1cn(-c2c(F)cc(F)cc2F)c2nc(Cl)c(F)cc2c1=O)C(F)(F)C(F)(F)F]

7-Chloro-6-fluoro-4-oxo-1-(2,4,6-trifluorophenyl)-1,4-dihydro-1,8-naphthyridine-3-carboxylic acid (500 mg, 1.34 mmol) was initially charged in 5 ml of acetonitrile. 3,3,4,4,4-Pentafluorobutan-2-amine hydrochloride (enantiomerically pure) (321 mg, 1.61 mmol) and N,N-diisopropylethylamine (930 µl, 5.4 mmol) were added. T3P solution (propanephosphonic anhydride solution 50% in ethyl acetate) (950 µl, 50% pure, 1.6 mmol) was then added and the mixture was stirred at room temperature overnight. The reaction solution was added to water. The acetonitrile was evaporated and the residue was extracted with dichloromethane three times. The combined organic phases were dried over sodium sulphate, filtered and concentrated by evaporation. This gave 785 mg (99% of theory, 88% pure) of the title compound.

LC-MS (Method 5): $R_t$=1.60 min; MS (ESIpos): m/z=518 $[M+H]^+$ $^1$H NMR (400 MHz, DMSO-d6) δ[ppm]: −0.149 (1.04), −0.008 (8.48), 0.008 (8.27), 0.146 (1.00), 0.891 (0.71), 0.910 (0.58), 1.157 (2.01), 1.175 (4.01), 1.193 (2.59), 1.244 (2.51), 1.259 (2.92), 1.356 (0.67), 1.411 (14.66), 1.429 (14.62), 1.455 (0.92), 1.473 (0.84), 1.511 (2.26), 1.528 (2.21), 1.864 (0.50), 1.988 (6.56), 2.328 (1.46), 2.367 (1.80), 2.671 (1.50), 2.711 (1.75), 4.003 (0.58), 4.021 (1.50), 4.039 (1.55), 4.057 (0.54), 5.000 (0.71), 5.022 (1.34), 5.045 (1.59), 5.065 (1.55), 5.088 (1.25), 5.109 (0.67), 7.270 (0.58), 7.337 (0.71), 7.347 (0.71), 7.367 (1.21), 7.385 (1.13), 7.401 (1.50), 7.418 (0.84), 7.467 (0.75), 7.490 (0.58), 7.604 (6.02), 7.626 (11.07), 7.648 (5.81), 8.412 (0.50), 8.574 (0.46), 8.687 (0.92), 8.702 (10.11), 8.721 (9.78), 8.750 (0.50), 9.055 (1.21), 9.173 (16.00), 9.877 (0.46), 9.896 (0.50), 9.938 (5.89), 9.961 (5.68).

Example 69A 1-tert-butyl 2-ethyl (2R,3S)-3-hydroxypyrrolidine-1,2-dicarboxylate

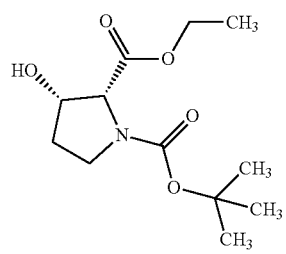

Ethyl (3S)-3-hydroxy-D-prolinate (1.13 g, 7.08 mmol) was initially charged in 50 ml of dichloro-methane. Triethylamine (3.0 ml, 21 mmol) and di-tert-butyl dicarbonate (1.8 ml, 7.8 mmol) were added and the mixture was stirred at room temperature overnight. The reaction mixture was washed with saturated aqueous sodium bicarbonate solution. The organic phase was dried over sodium sulphate, filtered and concentrated by evaporation. The residue was taken up in ethyl acetate and washed twice with 1M hydrochloric acid. The organic phase was dried over sodium sulphate, filtered and concentrated by evaporation. This gave 1.3 g (57% of theory, 80% pure) of the title compound.

$^1$H NMR (400 MHz, DMSO-d6) δ[ppm]: 1.152 (0.77), 1.170 (1.65), 1.178 (1.69), 1.188 (0.96), 1.195 (3.23), 1.213 (1.56), 1.321 (16.00), 1.383 (8.03), 1.988 (0.75), 3.266 (0.62), 3.294 (0.42), 3.404 (0.44), 3.409 (0.43), 3.423 (0.42), 4.019 (0.41), 4.037 (0.44), 4.046 (0.70), 4.064 (0.85), 4.082 (0.46), 4.111 (0.57), 4.129 (0.54), 4.150 (1.28), 4.156 (0.42), 4.167 (1.45), 4.433 (0.46), 4.449 (0.53), 5.398 (1.16), 5.410 (1.11).

Example 70A tert-butyl (2S,3S)-3-hydroxy-2-(hydroxymethyl)pyrrolidine-1-carboxylate

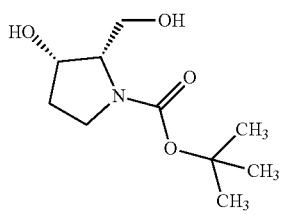

Under argon, 1-tert-butyl 2-ethyl (2R,3S)-3-hydroxypyrrolidine-1,2-dicarboxylate (1.30 g, 5.01 mmol) was initially charged in 20 ml of THF and cooled to 0° C. Lithium borohydride (10 ml, 2.0 M, 20 mmol) was added at 0° C. and the mixture was stirred at room temperature overnight. The reaction mixture was cooled to 0° C. and saturated aqueous ammonium chloride solution was added carefully. Dichloromethane was added and the mixture was separated on an Extrelut cartridge. The organic phase was concentrated by evaporation and the residue was dried under high vacuum. This gave 506 mg (37% of theory, 80% pure) of the title compound.

$^1$H NMR (400 MHz, DMSO-d6) δ[ppm]: 1.391 (16.00), 1.409 (2.86), 1.860 (0.40), 3.601 (0.62), 3.608 (0.58), 3.615 (0.78), 3.629 (0.46), 3.633 (0.42).

Example 71A (2S,3S)-2-(hydroxymethyl)pyrrolidin-3-ol hydrochloride

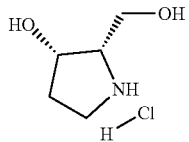

1-tert-butyl 2-ethyl (2R,3S)-3-hydroxypyrrolidine-1,2-dicarboxylate (506 mg, 1.95 mmol) was initially charged in 20 ml of 4N aqueous hydrochloric acid in dioxane and stirred at room temperature overnight. The reaction mixture was concentrated by evaporation and the residue was dried under high vacuum. This gave 380 mg (127% of theory, 80% pure) of the title compound.

$^1$H NMR (400 MHz, DMSO-d6) δ[ppm]: −0.149 (1.17), −0.008 (10.39), 0.008 (8.46), 0.146 (1.12), 0.912 (0.42), 1.130 (0.62), 1.180 (0.99), 1.235 (1.17), 1.259 (1.59), 1.276 (1.51), 1.292 (1.07), 1.308 (0.84), 1.356 (3.67), 1.596 (1.31), 1.847 (3.37), 1.857 (3.45), 1.862 (3.72), 1.872 (5.90), 1.876 (5.04), 1.881 (5.11), 1.884 (4.79), 1.891 (4.81), 1.895 (5.01), 1.900 (4.59), 1.954 (1.36), 1.974 (3.15), 1.985 (4.12), 1.998 (5.48), 2.008 (7.59), 2.032 (4.96), 2.042 (3.97), 2.055 (1.89), 2.067 (1.84), 2.073 (2.08), 2.090 (0.97), 2.104 (1.54), 2.115 (2.06), 2.139 (1.81), 2.148 (1.44), 2.182 (0.84), 2.328 (1.96), 2.367 (1.04), 2.524 (1.24), 2.666 (1.02), 2.670 (1.44), 2.675 (0.99), 2.711 (0.45), 3.150 (3.84), 3.161 (5.23), 3.174 (6.15), 3.187 (6.55), 3.201 (5.83), 3.212 (6.23), 3.236 (5.95), 3.241 (5.93), 3.260 (3.82), 3.306 (6.40), 3.322 (7.64), 3.343 (6.05), 3.364 (2.90), 3.450 (8.83), 3.462 (8.88), 3.474 (8.33), 3.490 (7.32), 3.502 (6.38), 3.609 (10.64), 3.631 (10.54), 3.638 (14.78), 3.660 (13.59), 3.680 (3.32), 3.699 (3.27), 3.708 (2.68), 3.712 (3.00), 3.733 (11.88), 3.746 (12.38), 3.762 (9.30), 3.774 (9.13), 4.073 (4.22), 4.106 (5.66), 4.266 (4.34), 4.274 (4.49), 4.300 (16.00), 4.669 (2.95), 4.678 (4.94), 5.329 (0.72), 7.112 (1.49), 7.240 (1.56), 7.368 (1.41), 8.748 (2.90), 9.193 (1.39), 9.383 (1.81), 10.016 (0.45).

Example 72A

Ethyl 3-(2,6-dichloropyridin-3-yl)-3-oxopropanoate

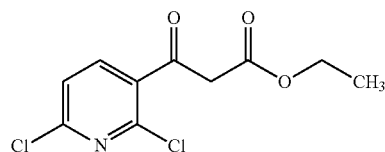 [SMILES: CCOC(=O)CC(=O)c1ccc(Cl)nc1Cl]

Under argon, 1500 ml of THF were initially charged and 2,6-dichloronicotinic acid (200 g, 1.04 mol) was added. 4-Dimethylaminopyridine (63.6 g, 521 mmol) and 1,1'-carbonyldiimidazole (253 g, 1.56 mol) were added a little at a time (evolution of gas). The mixture was stirred at room temperature for 24 h. A precipitate formed (suspension 1). In another flask, potassium 3-ethoxy-3-oxopropanoate (266 g, 1.56 mol) was initially charged in 1000 ml of THF, and magnesium chloride (179 g, 1.87 mol) was added. The suspension was stirred at 50° C. for 24 h (suspension 2). Suspension 2 was subsequently added to suspension 1 and stirred at room temperature for 24 h. The mixture was then stirred into 5 l of ice and about 20 l of water and adjusted to pH 4 using about 500 ml of hydrochloric acid/water (1:1). The mixture was subsequently extracted twice with ethyl acetate. The org. phase was washed with 10% strength NaCl solution.

The phases were separated, dried over magnesium sulphate, concentrated by evaporation and dried under high vacuum. This gave 255 g of the target compound (93.5% of theory).

LC-MS (Method 1): $R_t$=0.89 min; MS (ESIpos): m/z=261 [M+H]$^+$

Example 73A

Ethyl (2Z)-2-[(2,6-dichloropyridin-3-yl)carbonyl]-3-ethoxyacrylate

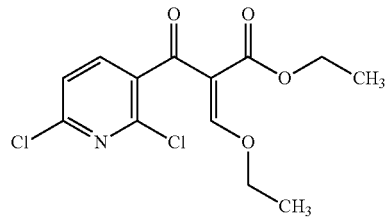

Ethyl 3-(2,6-dichloropyridin-3-yl)-3-oxopropanoate (4 g, 15 mmol) and (diethoxymethoxy)ethane (5 ml, 30 mmol) were initially charged and acetic anhydride (11.7 ml, 99 mmol) was added. The reaction mixture was stirred at 140°

Example 74A

N-benzyl-1,1-dicyclopropylmethanimine

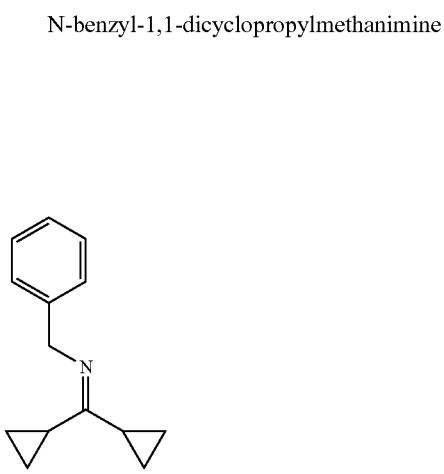

Dicyclopropylmethanone (13 ml, 110 mmol) was initially charged in 430 ml of diethyl ether and cooled to −40° C. 1-Phenylmethanamine (12 ml, 110 mmol) and triethylamine (32 ml, 230 mmol) were then added quickly, and titanium (IV) chloride (57 ml, 57 mmol, 1M in toluene) was slowly added dropwise at an internal temperature of 0° C. The ice bath was then removed and the mixture was allowed to warm to RT. The mixture was then stirred under reflux for 1 h. The mixture was stirred at room temperature for another 3 h. Celite was then added, and the mixture was stirred for 1 h. The mixture was then filtered off through celite, washing repeatedly with diethyl ether. At a bath temperature of 30° C., the filtrate was carefully concentrated by evaporation. This gave 18.86 g of the target compound (73% of theory, purity 88%).

$^1$H NMR (400 MHz, DMSO-d6) δ[ppm]: 0.542 (1.44), 0.550 (3.04), 0.558 (4.43), 0.562 (2.41), 0.565 (2.73), 0.571 (3.30), 0.578 (5.02), 0.585 (2.16), 0.664 (2.05), 0.671 (4.51), 0.678 (3.98), 0.683 (5.39), 0.690 (3.22), 0.700 (1.42), 0.830 (0.46), 0.839 (1.51), 0.843 (2.02), 0.851 (8.62), 0.855 (8.05), 0.863 (8.85), 0.868 (9.08), 0.877 (5.06), 0.881 (2.92), 0.887 (7.68), 0.894 (1.79), 0.901 (0.41), 0.907 (0.50), 0.922 (0.49), 0.956 (1.93), 0.966 (4.42), 0.971 (4.39), 0.979 (4.47), 0.984 (4.15), 0.996 (1.28), 1.186 (0.70), 1.198 (1.38), 1.206 (1.44), 1.218 (2.55), 1.230 (1.31), 1.238 (1.20), 1.250 (0.55), 1.929 (0.78), 1.942 (1.59), 1.949 (1.59), 1.954 (0.98), 1.963 (3.02), 1.971 (0.92), 1.975 (1.51), 1.984 (1.44), 1.997 (0.66), 2.104 (0.65), 2.115 (1.21), 2.122 (1.09), 2.128 (0.77), 2.134 (2.24), 2.142 (0.78), 2.147 (1.20), 2.153 (1.01), 2.166 (0.60), 2.299 (7.88), 3.217 (0.51), 3.313 (4.75), 4.582 (16.00), 7.142 (0.84), 7.162 (1.77), 7.174 (1.38), 7.180 (2.56), 7.191 (2.64), 7.202 (1.07), 7.208 (1.78), 7.212 (1.21), 7.230 (1.81), 7.235 (0.73), 7.249 (2.09), 7.255 (1.43), 7.260 (2.42), 7.268 (1.78), 7.276 (10.04), 7.282 (12.94), 7.289 (1.48), 7.299 (6.19), 7.303 (2.61), 7.315 (0.93), 7.318 (1.58).

Example 75A

N-benzyl-1,1-dicyclopropyl-2,2,2-trifluoroethanamine hydrochloride

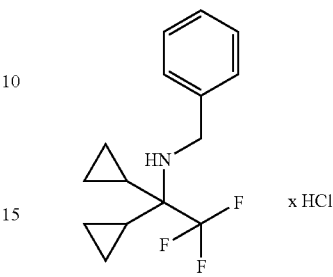

N-benzyl-1,1-dicyclopropylmethanimine (35.4 g, 89% purity, 158 mmol) was initially charged in a mixture of 320 ml of acetonitrile and 70 ml of DMF and cooled to 0° C. Potassium hydrogen difluoride (39.5 g, 506 mmol) was added at 0° C., and TFA (22 ml, 280 mmol) was added to the mixture at 0° C. Trimethyl(trifluoromethyl)silane (82 ml, 550 mmol) was then added dropwise. The reaction mixture was stirred at room temperature for 4 h. The reaction solution was cooled to 0° C., and potassium hydrogen difluoride (9.26 g, 119 mmol) and trimethyl(trifluoromethyl)silane (18 ml, 120 mmol) were added. The reaction solution was stirred further at room temperature overnight. Potassium hydrogen difluoride (9.26 g, 119 mmol), trifluoroacetic acid (4.9 ml, 63 mmol) and trimethyl(trifluoromethyl)silane (12 ml, 79 mmol) were added and stirring was continued at room temperature for 3.5 h. Trimethyl(trifluoromethyl)silane (23 ml, 160 mmol) was then added and the mixture was stirred at 60° C. for 2.5 h. Saturated aqueous sodium carbonate solution was added and the mixture was extracted twice with ethyl acetate. The combined organic phases were washed once with saturated aqueous sodium chloride solution, dried over sodium sulphate and filtered. 4 M HCl in dioxane (400 ml, 1.6 mol) was then added to the filtrate and the mixture was concentrated on a rotary evaporator at a water bath temperature of 30° C. The residue was purified by flash chromatography (cyclohexane/dichloromethane 20/1 to cyclohexane/dichloromethane 10/1). This gave 10.64 g of the target compound (22% of theory, purity 99%).

LC-MS (Method 1): $R_t$=1.31 min; MS (ESIpos): m/z=270 [M−HCl+H]$^−$

1H NMR (400 MHz, DMSO-d6) delta [ppm]: −0.008 (1.25), 0.008 (1.56), 0.591 (10.11), 0.750 (13.34), 0.876 (1.90), 0.952 (1.06), 1.091 (6.01), 1.236 (1.18), 1.906 (0.42), 2.329 (0.82), 2.367 (0.46), 2.571 (0.49), 2.589 (0.63), 2.671 (0.80), 2.711 (0.55), 3.615 (0.68), 4.212 (4.68), 5.107 (0.66), 7.358 (13.21), 7.375 (16.00), 7.502 (7.66).

Example 76A

1,1-Dicyclopropyl-2,2,2-trifluoroethanamine hydrochloride

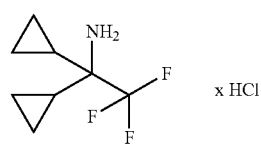 [SMILES: NC(C1CC1)(C1CC1)C(F)(F)F]

Under argon, N-benzyl-1,1-dicyclopropyl-2,2,2-trifluoro-ethanamine hydrochloride (10.6 g, 34.8 mmol) was initially charged in 200 ml of ethanol, and 1 M hydrochloric acid in ethanol (170 ml) and palladium on activated carbon (3.70 g, 10% pure) were added. The mixture was hydrogenated at atmospheric pressure and room temperature for 60 min. The mixture was filtered through celite, 4 M hydrochloric acid in dioxane (87 ml, 350 mmol) was added and the mixture was concentrated by evaporation at a water bath temperature of 30° C. Diethyl ether was added to the residue, the mixture was stirred for 10 min and the solid obtained was filtered off. This gave 6.39 g of the target compound (84% of theory) which were reacted further without further purification.

LC-MS (Method 1): $R_t$=0.49 min; MS (ESIpos): m/z=180 [M−HCl+H]$^+$ $^1$H NMR (400 MHz, DMSO-d6) δ[ppm]: 0.489 (2.34), 0.502 (4.38), 0.512 (7.72), 0.524 (12.33), 0.535 (11.32), 0.546 (9.58), 0.557 (10.43), 0.569 (9.17), 0.581 (11.40), 0.591 (13.47), 0.603 (8.94), 0.614 (4.93), 0.626 (3.21), 0.778 (2.86), 0.791 (6.70), 0.803 (9.45), 0.815 (13.47), 0.827 (13.55), 0.838 (11.65), 0.850 (13.01), 0.862 (13.43), 0.874 (9.35), 0.886 (6.06), 0.899 (2.37), 1.056 (4.75), 1.070 (9.13), 1.078 (10.15), 1.091 (16.00), 1.099 (6.84), 1.105 (8.35), 1.113 (7.66), 1.126 (3.14), 8.942 (2.96).

Example 77A

N-benzyl-1,1-dicyclopropyl-2,2,3,3,3-pentafluoro-propan-1-amine hydrochloride

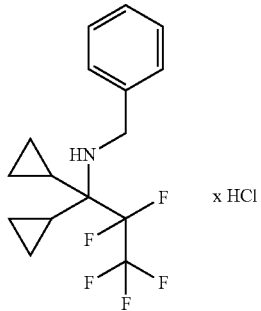 [SMILES: FC(F)(F)C(F)(F)C(NCc1ccccc1)(C1CC1)C1CC1]

Under argon, N-benzyl-1,1-dicyclopropylmethanimine (4.00 g, 20.1 mmol) was initially charged in a mixture of 40 ml of acetonitrile and 8.9 ml of DMF and cooled to 0° C. Potassium hydrogen difluoride (5.02 g, 64.2 mmol) was added at 0° C. and TFA (2.8 ml, 36 mmol) was added to the mixture at 0° C. Trimethyl(pentafluoroethyl)silane (12 ml, 70 mmol) was then added dropwise. The reaction mixture was stirred at room temperature for 3 days. The mixture was stirred at 60° C. for 7.5 h. 20 ml of acetonitrile and 4.5 ml of DMF were added and the mixture was cooled to 0° C. At 0° C., potassium hydrogen difluoride (1.88 g, 24.1 mmol), TFA (770 µl, 10 mmol) and trimethyl(pentafluoroethyl) silane (5.3 ml, 30 mmol) were added and stirring was continued at room temperature overnight. Saturated aqueous sodium carbonate solution was added and the mixture was extracted twice with ethyl acetate. The combined organic phases were washed with saturated aqueous sodium chloride solution, dried over sodium sulphate and filtered. 4 M HCl in dioxane (50 ml, 200 mmol) was then added to the filtrate and the mixture was concentrated by evaporation. The residue was purified by silica gel chromatography (mobile phase: cyclohexane/dichloromethane: 20/1). The production fractions were combined, 4 M HCl in dioxane (50 ml, 200 mmol) was added and the mixture was concentrated by evaporation at a water bath temperature of 30° C. This gave 2.14 g of the target compound (30% of theory, purity 99%).

LC-MS (Method 1): $R_t$=1.39 min; MS (ESIpos): m/z=320 [M−HCl+H]$^+$

1H NMR (400 MHz, DMSO-d6) delta [ppm]: 0.008 (1.21), 0.331 (1.50), 0.354 (4.75), 0.365 (5.92), 0.376 (5.94), 0.385 (4.06), 0.397 (2.65), 0.450 (2.43), 0.461 (3.95), 0.470 (6.34), 0.482 (6.37), 0.491 (5.64), 0.502 (3.07), 0.515 (2.14), 0.648 (6.10), 0.659 (6.45), 0.668 (6.49), 0.680 (7.00), 0.690 (6.84), 0.703 (4.80), 0.909 (2.14), 0.930 (4.98), 0.944 (7.05), 0.957 (4.27), 0.978 (1.50), 2.329 (0.40), 3.568 (11.42), 4.046 (14.52), 7.064 (0.43), 7.098 (0.47), 7.128 (0.48), 7.194 (2.29), 7.212 (5.53), 7.229 (4.28), 7.279 (6.89), 7.298 (16.00), 7.316 (12.69), 7.331 (13.22), 7.349 (5.73).

Example 78A 1,1-Dicyclopropyl-2,2,3,3,3-pentafluoropropan-1-amine hydrochloride

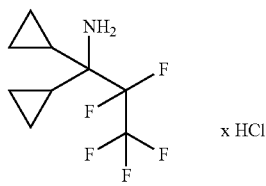 [SMILES: NC(C1CC1)(C1CC1)C(F)(F)C(F)(F)F]

Under argon, 90 ml of ethanol, 45 ml of 1M hydrochloric acid in ethanol and 964 mg (10%) of palladium on activated carbon were added to N-benzyl-1,1-dicyclopropyl-2,2,3,3,3-pentafluoropropan-1-amine hydrochloride (3.22 g, 9.06 mmol). The mixture was hydrogenated at atmospheric pressure and room temperature for 45 min. The mixture was filtered through celite, washing well with ethanol, 23 ml of 4M hydrochloric acid in dioxane were added and the mixture was concentrated by evaporation at a water bath temperature of 30° C. Diethyl ether was added to the residue, the mixture was stirred for 10 min and the solid obtained was filtered off. The product was reacted further without purification. This gave 1.64 g of the target compound (68% of theory).

$^1$H NMR (400 MHz, DMSO-d6) δ [ppm]: −0.150 (1.30), −0.008 (13.14), 0.008 (11.58), 0.146 (1.12), 0.540 (12.55), 0.550 (12.29), 0.572 (11.02), 0.605 (12.52), 0.791 (12.35), 0.875 (10.67), 1.060 (4.89), 1.080 (11.64), 1.094 (16.00), 1.128 (3.30), 2.328 (2.12), 2.366 (0.80), 2.670 (2.12), 2.710 (0.65), 8.767 (1.97).

Example 79A

N-[(E)-cyclopropylmethylene]-2-methylpropane-2-sulfinamide (Enantiomer 1)

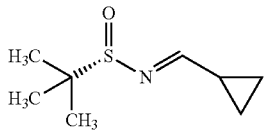

Under argon, (S)-2-methylpropane-2-sulfinamide (8.65 g, 71.3 mmol) was initially charged in 430 ml of dichloromethane and cyclopropanecarbaldehyde (11 ml, 140 mmol) and anhydrous copper(II) sulphate (34.2 g, 214 mmol) were added at room temperature. The mixture was stirred at room temperature overnight. The reaction mixture was filtered through celite, washing with diethyl ether, and the filtrate was concentrated by evaporation and dried under high vacuum. This gave 15.3 g of the target compound (99% of theory, purity about 80%).

LC-MS (Method 1): $R_t$=0.73 min; MS (ESIpos): m/z=174 [M+H]$^+$ $^1$H NMR (400 MHz, DMSO-d6) δ[ppm]: 0.952 (0.47), 0.958 (0.76), 0.964 (0.55), 0.967 (0.45), 0.970 (0.53), 1.041 (0.67), 1.055 (1.45), 1.061 (0.80), 1.068 (0.56), 1.070 (0.52), 1.082 (1.02), 1.092 (16.00), 5.751 (1.54), 7.389 (0.82), 7.409 (0.82).

Example 80A

N-[1-cyclopropyl-2,2,3,3,3-pentafluoropropyl]-2-methylpropane-2-sulfinamide (Diastereomer 1)

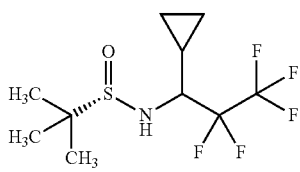 [SMILES: CC(C)(C)[S@](=O)NC(C1CC1)C(F)(F)C(F)(F)F]

In a glovebox, N-[(E)-cyclopropylmethylene]-2-methylpropane-2-sulfinamide (Enantiomer 1) (5.00 g, 28.9 mmol) was, together with tetramethylammonium fluoride (6.45 g, 69.3 mmol), initially charged under argon. After 14 h, the reaction vessel was removed from the glovebox, 110 ml of THF were added and, at −55° C., a solution of trimethyl(pentafluoroethyl)silane (13 ml, 72 mmol), dissolved in 170 ml of THF, was added slowly to the mixture. After the addition had ended, the mixture was stirred for 30 min, and 50 ml of saturated aqueous ammonium chloride solution and 165 ml of water were then added carefully at −30° C. The aqueous phase was extracted twice with tert-butyl methyl ether. The combined organic phases were washed in each case once with water and saturated aqueous sodium chloride solution. The organic phase was dried over sodium sulphate, filtered and concentrated by evaporation. The crude product was purified on silica gel (mobile phase: cyclohexane 100% to cyclohexane/ethyl acetate 2/1). This gave 4.9 g of the target compound (58% of theory, >95%).

LC-MS (Method 1): $R_t$=0.92 min; MS (ESIpos): m/z=294 [M+H]$^+$

Example 81A

1-Cyclopropyl-2,2,3,3,3-pentafluoropropan-1-amine hydrochloride (Enantiomer 1)

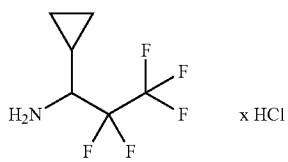 [SMILES: NC(C1CC1)C(F)(F)C(F)(F)F]

N-[1-cyclopropyl-2,2,3,3,3-pentafluoropropyl]-2-methylpropane-2-sulfinamide (Diastereomer 1) (4.10 g, 14.0 mmol) was initially charged in 130 ml of diethyl ether and 25 ml of methanol. 2 N hydrochloric acid in diethyl ether (130 ml, 250 mmol) was then added dropwise at room temperature, and the mixture was stirred at room temperature for 2.5 h. At a water bath temperature of 30° C., the reaction mixture was substantially concentrated by evaporation. The residue was stirred with 10 ml of acetonitrile, filtered off and washed with a few drops of acetonitrile. This gave 2.1 g of the target compound (65% of theory, purity 98%).

LC-MS (Method 1): $R_t$=0.31 min; MS (ESIpos): m/z=190 [M−HCl+H]$^+$ $^1$H NMR (400 MHz, DMSO-d6) δ[ppm]: 0.543 (2.57), 0.556 (4.32), 0.569 (5.47), 0.584 (3.62), 0.604 (0.54), 0.669 (0.44), 0.685 (1.59), 0.699 (3.25), 0.718 (8.78), 0.733 (16.00), 0.748 (15.55), 0.759 (5.58), 0.767 (3.55), 1.019 (0.99), 1.038 (2.50), 1.045 (5.40), 1.050 (3.89), 1.064 (3.94), 1.077 (3.57), 1.103 (14.10), 1.270 (0.53), 2.330 (0.40), 2.363 (0.83), 3.167 (10.46), 3.671 (6.50), 3.685 (5.12), 3.697 (4.27), 3.712 (3.56), 3.723 (7.42), 3.739 (2.98), 3.751 (2.86), 3.765 (2.47), 4.059 (0.82), 9.207 (10.25).

Example 82A

N-[(E)-cyclopropylmethylene]-2-methylpropane-2-sulfinamide (Enantiomer 2)

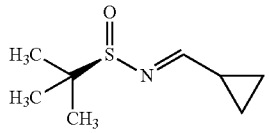

Under argon, (R)-2-methylpropane-2-sulfinamide (13.0 g, 107 mmol) was initially charged in 640 ml of dichloromethane, and cyclopropanecarbaldehyde (15.0 g, 214 mmol) and anhydrous copper(II) sulphate (51.2 g, 321 mmol) were added at room temperature. The mixture was stirred at room temperature overnight. The reaction mixture was filtered through celite, washing with diethyl ether, and the filtrate was concentrated by evaporation and dried under high vacuum. This gave 18.9 g of the target compound (100% of theory, purity about 98%).

LC-MS (Method 1): $R_t$=0.72 min; MS (ESIpos): m/z=174 [M+H]$^+$ $^1$H NMR (400 MHz, DMSO-d6) δ[ppm]: 0.952 (0.48), 0.958 (0.77), 0.964 (0.57), 0.967 (0.47), 0.969 (0.54), 1.055 (0.76), 1.061 (0.80), 1.068 (0.57), 1.070 (0.53), 1.081 (1.07), 1.092 (16.00), 7.389 (0.83), 7.409 (0.82).

Example 83A

N-[1-cyclopropyl-2,2,3,3,3-pentafluoropropyl]-2-methylpropane-2-sulfinamide (Diastereomer 2)

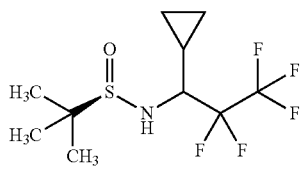 [SMILES: CC(C)(C)[S@@](=O)NC(C1CC1)C(F)(F)C(F)(F)F]

In a glovebox, N-[(E)-cyclopropylmethylene]-2-methylpropane-2-sulfinamide (Enantiomer 2) (5.10 g, 98% purity, 28.8 mmol) was, together with tetramethylammonium fluoride (6.45 g, 69.2 mmol), initially charged under argon. After 14 h, the reaction vessel was removed from the glovebox, 110 ml of THF were added and, at −55° C., a solution of trimethyl(pentafluoroethyl)silane (13 ml, 72 mmol), dissolved in 170 ml of THF, was added slowly to the mixture. After the addition had ended, the mixture was stirred for 30 min, and 50 ml of saturated aqueous ammonium chloride solution and 165 ml of water were then added carefully at −30° C. The aqueous phase was extracted twice with tert-butyl methyl ether. The combined organic phases were washed in each case once with water and saturated aqueous sodium chloride solution. The organic phase was dried over sodium sulphate, filtered and concentrated by evaporation. The crude product was purified on silica gel (mobile phase: cyclohexane 100% to cyclohexane/ethyl acetate 2/1). This gave 5.8 g of the target compound (69% of theory, >95%).

LC-MS (Method 1): $R_t$=0.92 min; MS (ESIpos): m/z=294 [M+H]$^+$

Example 84A

1-Cyclopropyl-2,2,3,3,3-pentafluoropropan-1-amine hydrochloride (Enantiomer 2)

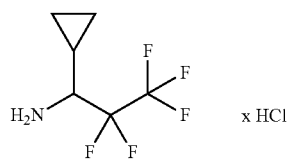 [SMILES: NC(C1CC1)C(F)(F)C(F)(F)F]

N-[1-cyclopropyl-2,2,3,3,3-pentafluoropropyl]-2-methylpropane-2-sulfinamide (Diastereomer 2) (5.00 g, 17.0 mmol) was initially charged in 150 ml of diethyl ether and 31 ml of methanol. 2 N hydrochloric acid in diethyl ether (150 ml, 2.0 M, 300 mmol) was then added dropwise at room temperature, and the mixture was stirred at room temperature for 2.5 h. At a water bath temperature of 30° C., the reaction solution was substantially concentrated by evaporation. The residue was stirred with 10 ml of acetonitrile, filtered off and washed with a few drops of acetonitrile. This gave 2.5 g of the target compound (64% of theory, purity 98%).

LC-MS (Method 1): $R_t$=0.33 min; MS (ESIpos): m/z=190 [M−HCl+H]$^+$ $^1$H NMR (400 MHz, DMSO-d6) δ[ppm]: −0.008 (1.70), 0.008 (1.55), 0.549 (4.38), 0.565 (4.26), 0.574 (3.54), 0.586 (2.02), 0.688 (2.56), 0.706 (9.75), 0.723 (16.00), 0.743 (10.93), 0.765 (2.53), 0.783 (0.70), 1.014 (0.92), 1.029 (1.97), 1.046 (3.89), 1.058 (3.39), 1.072 (2.94), 1.086 (1.64), 1.103 (0.66), 2.329 (0.53), 2.671 (0.54), 3.669 (2.36), 3.683 (2.43), 3.695 (2.47), 3.710 (2.40), 3.722 (2.51), 3.737 (2.41), 3.748 (2.39), 3.763 (2.17), 9.063 (5.76).

Example 85A

N-[(1E)-2,2-dimethylpropylidene]-2-methylpropane-2-sulfinamide (Enantiomer 1)

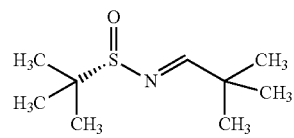

Under argon, (S)-2-methylpropane-2-sulfinamide (15.0 g, 124 mmol) was initially charged in 650 ml of dichloromethane, and pivalaldehyde (27 ml, 250 mmol) and anhydrous copper(II) sulphate (59.3 g, 371 mmol) were added at room temperature. The mixture was stirred at room temperature for 4 days. The reaction mixture was filtered through celite, washing with diethyl ether, and the filtrate was concentrated by evaporation and dried under high vacuum. This gave 22.7 g of the target compound (97% of theory).

LC-MS (Method 1): $R_t$=0.93 min; MS (ESIpos): m/z=190 [M+H]$^+$ $^1$H NMR (400 MHz, DMSO-d6) δ[ppm]: 1.013 (0.56), 1.079 (2.03), 1.102 (15.53), 1.113 (1.97), 1.120 (16.00), 1.271 (1.00), 7.814 (1.55).

Example 86A

2-Methyl-N-[1,1,1,2,2-pentafluoro-4,4-dimethylpentan-3-yl]propane-2-sulfinamide (Diastereomer 1)

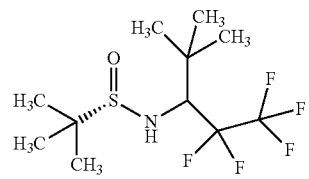 [SMILES: CC(C)(C)C(N[S@@](=O)C(C)(C)C)C(F)(F)C(F)(F)F]

In a glovebox, N-[(1E)-2,2-dimethylpropylidene]-2-methylpropane-2-sulfinamide (Enantiomer 1) (3.50 g, 18.5 mmol) was, together with tetramethylammonium fluoride (4.13 g, 44.4 mmol), initially charged under argon. After 14 h, the reaction vessel was removed from the glovebox, 56 ml of THF were added and, at −78° C., a solution of trimethyl (pentafluoroethyl)silane (8.1 ml, 46 mmol), dissolved in 82 ml of THF, was added slowly to the mixture. The reaction mixture was stirred at −78° C. for 3.5 h. At about −50° C., saturated aqueous ammonium chloride solution and water were added to the reaction solution. The aqueous phase was extracted twice with ethyl acetate. The combined organic phases were washed in each case once with water and saturated aqueous sodium chloride solution. The organic phase was dried over sodium sulphate, filtered and concentrated by evaporation. The residue was purified by silica gel (mobile phase: cyclohexane, then cyclohexane/ethylacetate: 5/1). This gave 4.25 g of the target compound (73% of theory, purity 98%, >95%).

LC-MS (Method 4): $R_t$=3.30 min; MS (ESIpos): m/z=310 [M+H]$^+$ $^1$H NMR (400 MHz, DMSO-d6) δ[ppm]: −0.008 (1.33), 0.008 (0.58), 1.054 (0.45), 1.058 (0.43), 1.104 (7.77), 1.106

(7.67), 1.178 (16.00), 1.201 (1.02), 2.519 (0.54), 2.524 (0.57), 5.114 (0.43), 5.137 (0.41).

Example 87A 1,1,1,2,2-Pentafluoro-4,4-dimethylpentan-3-amine hydrochloride (Enantiomer 1)

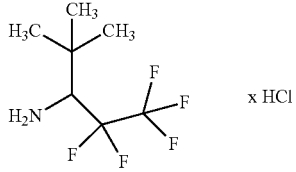

2-Methyl-N-[1,1,1,2,2-pentafluoro-4,4-dimethylpentan-3-yl]propane-2-sulfinamide (Diastereomer 1) (4.14 g, 98% purity, 13.1 mmol) was initially charged in 240 ml of diethyl ether and 48 ml of methanol. 2 N hydrochloric acid in diethyl ether (240 ml, 480 mmol) was then added, and the mixture was stirred at room temperature for 2.5 h. At a water bath temperature of 35° C., the reaction solution was substantially concentrated by evaporation. The residue was stirred with about 5 ml of diethyl ether and filtered off and the residue was dried. 20 ml of 20% strength potassium hydroxide solution was added and the mixture was extracted three times with dichloromethane. 2 N hydrochloric acid in diethyl ether was added to the combined organic phases and the mixture was concentrated by evaporation at a bath temperature of 35° C. and dried under high vacuum. This gave 2.94 g of the target compound (89% of theory), which were used without further purification for the next step.

LC-MS (Method 1): $R_t$=0.81 min; MS (ESIpos): m/z=206 [M−HCl+H]$^+$

Example 88A

N-[(1E)-2,2-dimethylpropylidene]-2-methylpropane-2-sulfinamide (Enantiomer 2)

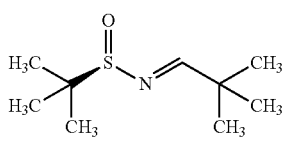

Under argon, (R)-2-methylpropane-2-sulfinamide (15.0 g, 124 mmol) was initially charged in 650 ml of dichloromethane, and pivalaldehyde (27 ml, 250 mmol) and anhydrous copper(II) sulphate (59.3 g, 371 mmol) were added at room temperature. The mixture was stirred at room temperature for 4 days. More copper sulphate (24.7 g, 155 mmol) was added and stirring was continued at room temperature overnight. The reaction mixture was filtered through celite, washing with diethyl ether, and the filtrate was concentrated by evaporation and dried under high vacuum. This gave 20.15 g of the target compound (86% of theory).

LC-MS (Method 1): $R_t$=0.94 min; MS (ESIpos): m/z=190 [M+H]$^+$ $^1$H NMR (400 MHz, DMSO-d6) δ[ppm]: 1.078 (14.51), 1.102 (16.00), 1.113 (1.88), 1.120 (15.93), 1.270 (1.08), 5.290 (0.56), 7.814 (1.44).

Example 89A

2-Methyl-N-[1,1,1,2,2-pentafluoro-4,4-dimethylpentan-3-yl]propane-2-sulfinamide (Diastereomer 2)

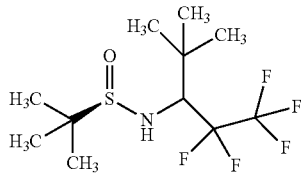

Under argon! for drying, the flask and the tetramethylammonium fluoride were placed in a glovebox overnight! N-[(1E)-2,2-dimethylpropylidene]-2-methylpropane-2-sulfinamide (Enantiomer 2) (4.38 g, 80% purity, 18.5 mmol), together with tetramethylammonium fluoride (4.13 g, 44.4 mmol), was initially charged under argon in a glovebox. After 14 h, the reaction vessel was removed from the glovebox, 56 ml of THF were added and, at −78° C., a solution of trimethyl(pentafluoroethyl)silane (8.1 ml, 46 mmol), dissolved in 82 ml of THF, was added slowly to the mixture. The reaction mixture was stirred at −70° C. for 3 h and then, slowly thawing, stirred at room temperature overnight. Saturated aqueous ammonium chloride solution and water were added carefully to the reaction solution. The aqueous phase was extracted twice with ethyl acetate. The combined organic phases were washed in each case once with water and saturated aqueous sodium chloride solution. The organic phase was dried over sodium sulphate, filtered and concentrated by evaporation. The residue was purified on silica gel (mobile phase: 100% cyclohexane, then cyclohexane/ethyl acetate: 2/1). This gave 3.81 g of the target compound (65% of theory, purity 98%, >90%).

LC-MS (Method 4): $R_t$=3.30 min; MS (ESIpos): m/z=310 [M+H]$^+$ $^1$H NMR (400 MHz, DMSO-d6) δ[ppm]: 1.054 (0.40), 1.059 (0.42), 1.104 (7.59), 1.106 (7.75), 1.178 (16.00), 1.201 (1.05), 5.113 (0.42).

Example 90A 1,1,1,2,2-Pentafluoro-4,4-dimethylpentan-3-amine hydrochloride (Enantiomer 2)

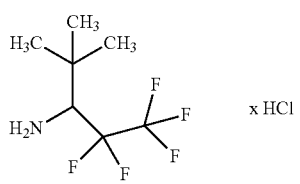

2-Methyl-N-[1,1,1,2,2-pentafluoro-4,4-dimethylpentan-3-yl]propane-2-sulfinamide (Diastereomer 2) (3.73 g, 12.0 mmol) was initially charged in 220 ml of diethyl ether and 44 ml of methanol. 2 N hydrochloric acid in diethyl ether (220 ml, 440 mmol) was then added and the mixture was stirred at room temperature for 2.5 h. At a water bath temperature of 35° C., the reaction solution was substantially concentrated by evaporation. The residue was stirred

Example 91A

7-Chloro-N-[1-cyclopropyl-2,2,3,3,3-pentafluoro-propyl]-6-fluoro-4-oxo-1-(2,4,6-trifluoro-phenyl)-1,4-dihydro-1,8-naphthyridine-3-carboxamide (Enantiomer 1)

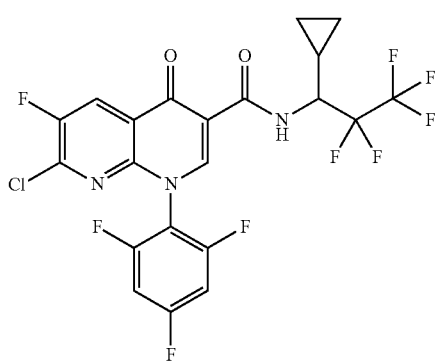 [SMILES: O=C(NC(C1CC1)C(F)(F)C(F)(F)F)c1cn(-c2c(F)cc(F)cc2F)c2nc(Cl)c(F)cc2c1=O]

7-Chloro-6-fluoro-4-oxo-1-(2,4,6-trifluorophenyl)-1,4-dihydro-1,8-naphthyridine-3-carboxylic acid (300 mg, 805 µmol) was initially charged in 7.5 ml of acetonitrile. 1-Cyclopropyl-2,2,3,3,3-pentafluoropropan-1-amine hydrochloride (Enantiomer 1) (204 mg, 98% purity, 886 µmol) and N,N-diisopropylethylamine (560 µl, 3.2 mmol) were added. T3P solution (propanephosphonic acid cyclic anhydride, 50% in ethyl acetate; 570 µl, 970 µmol) was then added to the mixture. The reaction solution was stirred at room temperature overnight. Water was added to the mixture and the precipitated solid was filtered off, washed with water and dried under high vacuum. This gave 439 mg of the target compound (99% of theory, purity 99%).

LC-MS (Method 3): $R_t$=2.53 min; MS (ESIpos): m/z=544 [M+H]$^+$ $^1$H NMR (400 MHz, DMSO-d6) δ[ppm]: −0.149 (1.22), −0.008 (9.36), 0.008 (8.14), 0.146 (0.95), 0.328 (1.83), 0.338 (2.78), 0.350 (2.78), 0.363 (2.07), 0.373 (1.05), 0.542 (2.14), 0.554 (3.12), 0.566 (2.71), 0.580 (2.58), 0.589 (2.34), 0.600 (2.68), 0.612 (2.54), 0.622 (2.10), 0.668 (1.29), 0.688 (2.51), 0.699 (2.31), 0.712 (2.14), 0.734 (0.81), 1.243 (0.85), 1.264 (1.76), 1.276 (2.64), 1.285 (2.07), 1.297 (2.58), 2.073 (0.58), 2.328 (1.53), 2.367 (1.05), 2.670 (1.56), 2.711 (0.88), 4.442 (0.68), 4.466 (1.63), 4.488 (2.00), 4.507 (2.03), 4.530 (1.63), 4.554 (0.64), 7.602 (5.39), 7.624 (10.27), 7.646 (5.42), 8.719 (9.63), 8.738 (9.63), 9.167 (16.00), 10.048 (5.32), 10.072 (5.32).

Example 92A

7-Chloro-N-[1-cyclopropyl-2,2,3,3,3-pentafluoro-propyl]-6-fluoro-4-oxo-1-(2,4,6-trifluoro-phenyl)-1,4-dihydro-1,8-naphthyridine-3-carboxamide (Enantiomer 2)

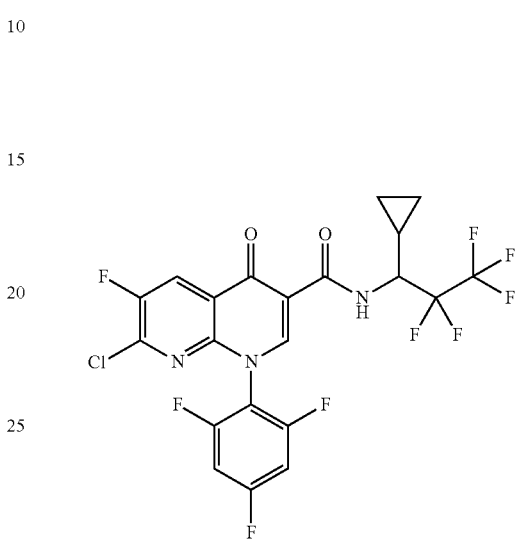

7-Chloro-6-fluoro-4-oxo-1-(2,4,6-trifluorophenyl)-1,4-dihydro-1,8-naphthyridine-3-carboxylic acid (300 mg, 805 µmol) was initially charged in 7.5 ml of acetonitrile. 1-Cyclopropyl-2,2,3,3,3-pentafluoropropan-1-amine hydrochloride (Enantiomer 2) (204 mg, 98% purity, 886 µmol) and N,N-diisopropylethylamine (560 µl, 3.2 mmol) were added. T3P solution (propanephosphonic acid cyclic anhydride, 50% in ethyl acetate; 570 µl, 970 µmol) was then added to the mixture. The reaction solution was stirred at room temperature overnight. Water was added to the mixture and the precipitated solid was filtered off, washed with water and dried under high vacuum. This gave 422 mg of the target compound (96% of theory, purity 100%).

LC-MS (Method 3): $R_t$=2.52 min; MS (ESIpos): m/z=544 [M+H]$^+$ $^1$H NMR (400 MHz, DMSO-d6) δ[ppm]: −0.149 (0.93), −0.008 (7.99), 0.008 (6.97), 0.146 (0.89), 0.316 (0.84), 0.328 (2.12), 0.338 (3.25), 0.351 (3.23), 0.363 (2.48), 0.374 (1.19), 0.530 (0.88), 0.542 (2.44), 0.553 (3.54), 0.566 (3.10), 0.579 (2.86), 0.589 (2.57), 0.600 (3.16), 0.611 (2.79), 0.622 (2.43), 0.633 (2.04), 0.646 (1.15), 0.667 (1.46), 0.678 (1.71), 0.688 (2.81), 0.700 (2.63), 0.713 (2.41), 0.721 (1.24), 0.734 (0.78), 1.243 (0.60), 1.256 (1.20), 1.264 (1.77), 1.276 (2.90), 1.285 (2.34), 1.296 (2.85), 1.308 (1.57), 1.317 (1.00), 1.329 (0.42), 2.074 (2.03), 2.328 (0.75), 2.367 (0.58), 2.671 (0.77), 2.711 (0.55), 4.442 (0.77), 4.466 (1.97), 4.488 (2.26), 4.508 (2.30), 4.530 (1.93), 4.554 (0.71), 7.601 (5.75), 7.623 (11.11), 7.646 (5.82), 8.719 (9.38), 8.738 (9.40), 9.167 (16.00), 10.048 (6.22), 10.072 (6.09).

---

with diethyl ether and dried under high vacuum. This gave 2.48 g of the target compound (81% of theory, purity 95%).

LC-MS (Method 1): $R_t$=0.80 min; MS (ESIpos): m/z=206 [M−HCl+H]$^+$

Example 93A

7-Chloro-N-(1,1-dicyclopropyl-2,2,2-trifluoroethyl)-6-fluoro-4-oxo-1-(2,4,6-trifluoro-phenyl)-1,4-dihydro-1,8-naphthyridine-3-carboxamide

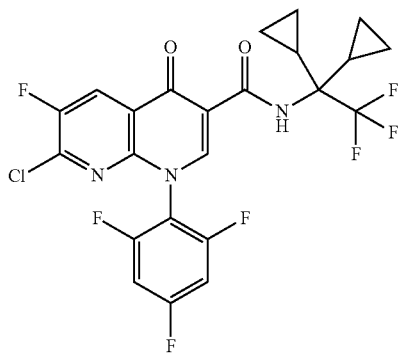 [SMILES: O=C(NC(C1CC1)(C1CC1)C(F)(F)F)c1cn(-c2c(F)cc(F)cc2F)c2nc(Cl)c(F)cc2c1=O]

7-Chloro-6-fluoro-4-oxo-1-(2,4,6-trifluorophenyl)-1,4-dihydro-1,8-naphthyridine-3-carboxylic acid (100 mg, 268 μmol), 1,1-dicyclopropyl-2,2,2-trifluoroethanamine hydrochloride (63.7 mg, 295 μmol) and N,N-diisopropylethylamine (160 μl, 940 μmol) were initially charged in 2.4 ml of ethyl acetate. T3P solution (propanephosphonic acid cyclic anhydride, 50% in ethyl acetate; 630 μl, 1.1 mmol) was added and the mixture was stirred at 80° C. for 2 h. Water was added and the mixture was extracted twice with ethyl acetate. The combined organic phases were washed with saturated aqueous sodium chloride solution, dried over sodium sulphate, filtered and concentrated by evaporation. The residue was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined organic phases were reextracted twice with dichloromethane. The combined organic phases were dried over sodium sulphate, filtered and concentrated by evaporation. This gave 101 mg of the target compound (70% of theory, purity 99%).

LC-MS (Method 1): $R_t$=1.33 min; MS (ESIpos): m/z=534 [M+H]$^+$ $^1$H NMR (400 MHz, DMSO-d6) δ[ppm]: −0.149 (1.44), −0.008 (11.48), 0.008 (10.40), 0.146 (1.35), 0.486 (1.29), 0.499 (2.28), 0.509 (4.55), 0.521 (5.24), 0.532 (5.99), 0.544 (3.36), 0.554 (2.88), 0.578 (1.80), 0.589 (3.87), 0.603 (4.52), 0.610 (5.81), 0.625 (7.01), 0.636 (5.63), 0.646 (6.26), 0.658 (7.40), 0.671 (6.17), 0.683 (5.48), 0.697 (5.66), 0.707 (5.99), 0.720 (4.25), 0.730 (2.79), 0.744 (1.02), 1.234 (1.17), 1.527 (1.98), 1.541 (4.13), 1.548 (4.34), 1.563 (7.58), 1.577 (4.04), 1.584 (3.72), 1.597 (1.59), 2.323 (1.65), 2.328 (2.22), 2.366 (1.05), 2.523 (5.48), 2.665 (1.77), 2.670 (2.40), 2.710 (1.17), 5.754 (0.48), 7.599 (5.66), 7.621 (10.64), 7.643 (5.84), 8.754 (10.37), 8.773 (10.40), 9.117 (16.00), 9.409 (12.46).

Example 94A

7-Chloro-N-(1,1-dicyclopropyl-2,2,3,3,3-pentafluoropropyl)-6-fluoro-4-oxo-1-(2,4,6-trifluorophenyl)-1,4-dihydro-1,8-naphthyridine-3-carboxamide

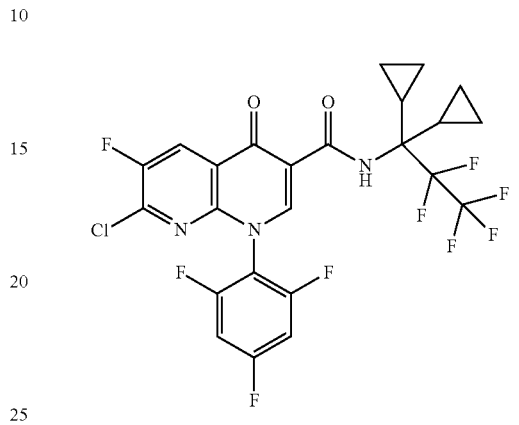

7-Chloro-6-fluoro-4-oxo-1-(2,4,6-trifluorophenyl)-1,4-dihydro-1,8-naphthyridine-3-carboxylic acid (140 mg, 376 μmol), 1,1-dicyclopropyl-2,2,3,3,3-pentafluoropropan-1-amine hydrochloride (110 mg, 413 μmol) and N,N-diisopropylethylamine (230 μl, 1.3 mmol) were initially charged in ethyl acetate. T3P solution (propanephosphonic acid cyclic anhydride, 50% in ethyl acetate; 890 μl, 1.5 mmol) was added and the mixture was stirred at 80° C. for 2 h. Water was added and the mixture was extracted twice with ethyl acetate. The combined organic phases were washed with saturated aqueous sodium chloride solution, dried over sodium sulphate, filtered and concentrated by evaporation. The residue was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined organic phases were reextracted twice with dichloromethane. The combined aqueous phases were dried over sodium sulphate, filtered and concentrated by evaporation. This gave 88 mg of the target compound (40% of theory, purity 99%).

LC-MS (Method 1): $R_t$=1.44 min; MS (ESIpos): m/z=584 [M+H]$^+$ $^1$H NMR (400 MHz, DMSO-d6) δ[ppm]: −0.149 (0.61), −0.008 (4.76), 0.008 (4.40), 0.146 (0.56), 0.489 (1.21), 0.501 (2.46), 0.511 (3.85), 0.524 (5.52), 0.537 (5.23), 0.546 (3.52), 0.559 (2.46), 0.597 (1.64), 0.609 (3.74), 0.624 (4.52), 0.631 (6.04), 0.645 (6.88), 0.657 (5.30), 0.668 (6.10), 0.681 (6.68), 0.695 (5.21), 0.708 (1.89), 0.737 (2.53), 0.751 (5.27), 0.763 (5.87), 0.774 (4.85), 0.786 (3.29), 0.800 (1.19), 1.233 (0.96), 1.589 (1.67), 1.604 (3.78), 1.611 (4.10), 1.625 (6.63), 1.639 (3.88), 1.660 (1.40), 2.328 (0.83), 2.367 (0.48), 2.671 (0.90), 2.710 (0.50), 5.755 (0.47), 7.597 (5.68), 7.619 (10.97), 7.641 (5.82), 8.759 (9.67), 8.778 (9.61), 9.126 (16.00), 9.386 (11.83).

Example 95A

7-Chloro-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 1)

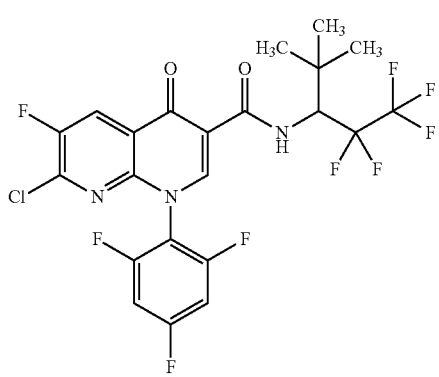 [SMILES: CC(C)(C)C(NC(=O)c1cn(-c2c(F)cc(F)cc2F)c2nc(Cl)c(F)cc2c1=O)C(F)(F)C(F)(F)F]

7-Chloro-6-fluoro-4-oxo-1-(2,4,6-trifluorophenyl)-1,4-dihydro-1,8-naphthyridine-3-carboxylic acid (300 mg, 805 µmol) was initially charged in 7.5 ml of acetonitrile. 1,1,1,2,2-Pentafluoro-4,4-dimethylpentan-3-amine hydrochloride (Enantiomer 1) (214 mg, 100% purity, 886 µmol) and N,N-diisopropylethylamine (560 µl, 3.2 mmol) were added. A T3P solution (propanephosphonic acid cyclic anhydride, 50% in ethyl acetate; 570 µl, 970 µmol) was added. The reaction solution was stirred at room temperature overnight. More 1,1,1,2,2-pentafluoro-4,4-dimethylpentan-3-amine hydrochloride (Enantiomer 1) (97 mg, 403 µmol) was added to the reaction solution and the mixture was stirred at room temperature for 2 days. More 1,1,1,2,2-pentafluoro-4,4-dimethylpentan-3-amine hydrochloride (Enantiomer 1) (97 mg, 403 µmol), N,N-diisopropylethylamine (280 µl, 1.6 mmol) and a T3P solution (propanephosphonic acid cyclic anhydride, 50% in ethyl acetate; 285 µl, 480 µmol) were added to the reaction solution and the mixture was stirred at room temperature for 2 days. The reaction solution was diluted with dichloromethane and washed twice with water. The combined aqueous phases were reextracted with dichloromethane. The combined organic phases were dried over sodium sulphate, filtered and concentrated by evaporation. The residue was purified by silica gel (mobile phase: cyclohexane/ethyl acetate gradient: ethyl acetate 4% to 32%). This gave 318 mg of the target compound (71% of theory, purity 100%).

LC-MS (Method 5): $R_t$=1.72 min; MS (ESIpos): m/z=560 [M+H]$^+$

Example 96A

7-Chloro-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 2)

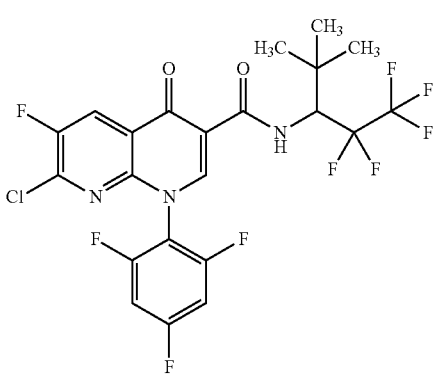 [SMILES: CC(C)(C)C(NC(=O)c1cn(-c2c(F)cc(F)cc2F)c2nc(Cl)c(F)cc2c1=O)C(F)(F)C(F)(F)F]

7-Chloro-6-fluoro-4-oxo-1-(2,4,6-trifluorophenyl)-1,4-dihydro-1,8-naphthyridine-3-carboxylic acid (300 mg, 805 µmol) was initially charged in 7.5 ml of acetonitrile. 1,1,1,2,2-Pentafluoro-4,4-dimethylpentan-3-amine hydrochloride (Enantiomer 2) (214 mg, 100% purity, 886 µmol) and N,N-diisopropylethylamine (560 µl, 3.2 mmol) were added. A T3P solution (propanephosphonic acid cyclic anhydride, 50% in ethyl acetate; 570 µl, 970 µmol) was added. The reaction solution was stirred at room temperature overnight. More 1,1,1,2,2-pentafluoro-4,4-dimethylpentan-3-amine hydrochloride (Enantiomer 2) (97 mg, 403 µmol) was added to the reaction solution and the mixture was stirred at room temperature for 2 days. More 1,1,1,2,2-pentafluoro-4,4-dimethylpentan-3-amine hydrochloride (Enantiomer 2) (97 mg, 403 µmol), N,N-diisopropylethylamine (280 µl, 1.6 mmol) and a T3P solution (propanephosphonic acid cyclic anhydride, 50% in ethyl acetate; 285 µl, 480 µmol) were added to the reaction solution and the mixture was stirred at room temperature for 2 days. The reaction solution was diluted with dichloromethane and washed twice with water. The combined aqueous phases were reextracted with dichloromethane. The combined organic phases were dried over sodium sulphate, filtered and concentrated by evaporation. The residue was purified by silica gel (mobile phase: cyclohexane/ethyl acetate gradient: ethyl acetate 4% to 32%). This gave 373 mg of the target compound (82% of theory, purity 99%).

LC-MS (Method 5): $R_t$=1.73 min; MS (ESIpos): m/z=560 [M+H]$^+$

Example 97A

7-Chloro-4-oxo-N-[3,3,4,4,4-pentafluorobutan-2-yl]-1-(2,4,6-trifluorophenyl)-1,4-dihydro-1,8-naphthyridine-3-carboxamide (Enantiomerically Pure)

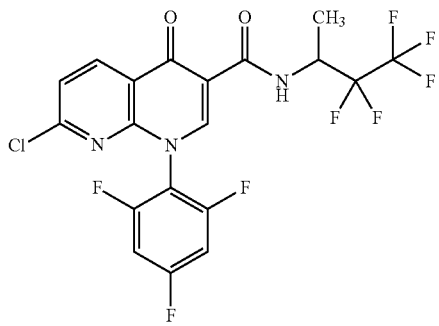 [SMILES: CC(NC(=O)c1cn(-c2c(F)cc(F)cc2F)c2nc(Cl)ccc2c1=O)C(F)(F)C(F)(F)F]

16.5 ml (28.2 mmol) of 2,4,6-tripropyl-1,3,5,2,4,6-trioxatriphosphorinane 2,4,6-trioxide (T3P, 50% in ethyl acetate) were added dropwise to a solution of 2.50 g (7.05 mmol) of 7-chloro-4-oxo-1-(2,4,6-trifluorophenyl)-1,4-dihydro-1,8-naphthyridine-3-carboxylic acid, 1.55 g (7.75 mmol) of 3,3,4,4,4-pentafluorobutan-2-amine hydrochloride (enantiomerically pure) and 3.7 ml (21.1 mmol) of DIPEA in 70 ml of ethyl acetate. The mixture was stirred at 80° C. overnight. The reaction mixture was concentrated by evaporation and poured onto water. The precipitate was filtered off, dissolved in DCM, dried over sodium sulphate and filtered and the solvent was removed under reduced pressure. The crude product was used for the next step without further purification. This gave 3.35 g (95% of theory, 100% pure) of the title compound.

LC-MS (Method 3): $R_t$=2.34 min; MS (ESIpos): m/z=500 [M+H]$^+$ $^1$H NMR (400 MHz, DMSO-d6) δ[ppm]: −0.149 (0.92), 0.146 (0.85), 0.928 (1.24), 0.943 (1.22), 1.175 (0.71), 1.244 (1.98), 1.259 (2.16), 1.274 (1.27), 1.409 (15.77), 1.426 (16.00), 1.488 (0.94), 1.988 (1.17), 2.328 (1.68), 2.367 (1.01), 2.670 (1.82), 2.711 (1.04), 4.998 (0.81), 5.020 (1.36), 5.043 (1.68), 5.062 (1.73), 5.086 (1.43), 5.107 (0.78), 7.595 (5.78), 7.618 (11.30), 7.640 (5.82), 7.773 (10.54), 7.794 (11.10), 8.741 (11.23), 8.761 (10.77), 9.142 (15.95), 9.986 (6.05), 10.010 (5.92).

Example 98A

7-[(3S)-3-hydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Enantiomerically Pure)

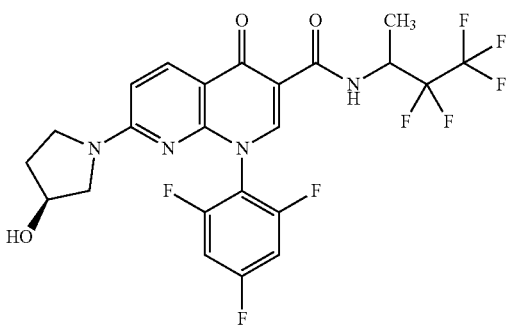 [SMILES: CC(NC(=O)c1cn(-c2c(F)cc(F)cc2F)c2nc(N3CC[C@H](O)C3)ccc2c1=O)C(F)(F)C(F)(F)F]

According to GP3, 5.00 g (10.0 mmol) of 7-chloro-4-oxo-N-[3,3,4,4,4-pentafluorobutan-2-yl]-1-(2,4,6-trifluorophenyl)-1,4-dihydro-1,8-naphthyridine-3-carboxamide (enantiomerically pure) were reacted with 1.36 g (11.0 mmol) of (3S)-pyrrolidin-3-ol hydrochloride and 7.0 ml (40.0 mmol) of N,N-diisopropylethylamine in 37 ml of dimethylformamide. The reaction mixture was poured onto water and extracted three times with ethyl acetate. The combined organic phases were washed once with sat. sodium chloride solution, dried over sodium sulphate and concentrated by evaporation. The crude product was purified by normal-phase chromatography (cyclohexane/ethyl acetate gradient). This gave 4.99 g (88% of theory, 97% pure) of the title compound.

LC-MS (Method 1): $R_t$=1.04 min; MS (ESIpos): m/z=551 [M+H]$^+$ $^1$H NMR (400 MHz, DMSO-d6) δ[ppm]: −0.149 (0.51), 0.147 (0.51), 1.157 (0.52), 1.175 (1.05), 1.193 (0.49), 1.385 (14.87), 1.402 (14.89), 1.788 (0.91), 1.921 (1.77), 1.989 (2.75), 2.329 (0.83), 2.367 (0.42), 2.671 (0.79), 2.711 (0.44), 3.051 (1.08), 3.083 (1.84), 3.163 (2.28), 3.185 (2.68), 3.518 (2.49), 3.534 (2.97), 4.021 (0.47), 4.039 (0.47), 4.270 (1.69), 4.387 (1.43), 4.961 (2.74), 4.984 (1.50), 5.007 (1.64), 5.052 (3.17), 6.744 (1.70), 6.773 (2.76), 6.798 (2.07), 7.530 (3.28), 7.553 (6.61), 7.575 (3.83), 8.265 (3.13), 8.286 (2.86), 8.805 (16.00), 10.551 (6.33), 10.575 (6.15).

WORKING EXAMPLES

Example 1

1-(2,6-Difluorophenyl)-7-[(3R,4R)-3,4-dihydroxy-pyrrolidin-1-yl]-6-fluoro-4-oxo-N-(4,4,4-tri-fluoro-2-methylbutan-2-yl)-1,4-dihydro-1,8-naphthyridine-3-carboxamide

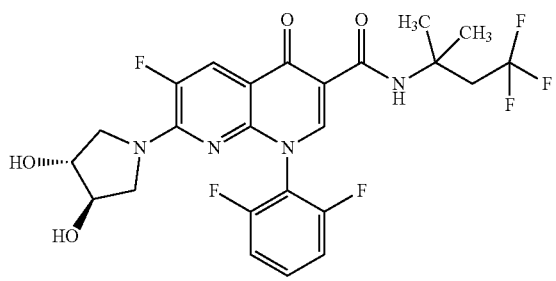 [SMILES: CC(C)(CC(F)(F)F)NC(=O)c1cn(-c2c(F)cccc2F)c2nc(N3C[C@@H](O)[C@H](O)C3)c(F)cc2c1=O]

According to GP1, 99.9 mg (237 μmol) of 1-(2,6-difluorophenyl)-7-[(3R,4R)-3,4-dihydroxypyrrolidin-1-yl]-6-fluoro-4-oxo-1,4-dihydro-1,8-naphthyridine-3-carboxylic acid were reacted with 40.1 mg (284 μmol) of 4,4,4-trifluoro-2-methylbutan-2-amine in the presence of 108 mg (284 μmol) of HATU and 103 μl (593 μmol) of DIPEA in 2.4 ml of DMF. The reaction mixture was purified directly by preparative HPLC [at UV max: 265 nm, column: Chromatorex C18, 10 μm, 125×30 mm, solvent: acetonitrile/0.05% formic acid gradient (0 to 3 min 10% acetonitrile, to 15 min 90% acetonitrile and a further 3 min 90% acetonitrile)]. The product fractions were combined, freed from the solvent and lyophilized. This gave 107 mg (82% of theory, 99% pure) of the title compound.

LC-MS (Method 3): $R_t$=1.76 min; MS (ESIpos): m/z=545 [M+H]

$^1$H NMR (400 MHz, DMSO-d6): δ [ppm]=10.10 (s, 1H), 8.67 (s, 1H), 8.00 (d, 1H), 7.77-7.66 (m, 1H), 7.47-7.36 (m, 2H), 5.18 (br. s, 2H), 4.09-3.51 (br. m, 4H), 3.27-2.86 (m, 4H).

Example 2

N-[(1S)-1-Cyclopropyl-2,2,2-trifluoroethyl]-1-(2,6-difluorophenyl)-7-[(3R,4R)-3,4-dihydroxypyrrolidin-1-yl]-6-fluoro-4-oxo-1,4-dihydro-1,8-naphthyridine-3-carboxamide

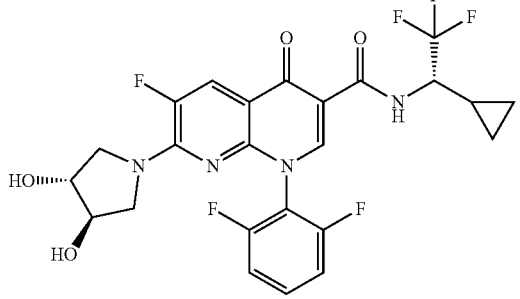

According to GP1, 99.9 mg (237 μmol) of 1-(2,6-difluorophenyl)-7-[(3R,4R)-3,4-dihydroxypyrrolidin-1-yl]-6-fluoro-4-oxo-1,4-dihydro-1,8-naphthyridine-3-carboxylic acid were reacted with 49.9 mg (284 μmol) of (1S)-1-cyclopropyl-2,2,2-trifluoroethanamine hydrochloride in the presence of 108 mg (284 μmol) of HATU and 103 μl (593 μmol) of DIPEA in 2.4 ml of DMF. The reaction mixture was then purified directly by preparative HPLC [at UV max: 265 nm, column: Chromatorex C18, 10 μm, 125×30 mm, solvent: acetonitrile/0.05% formic acid gradient (0 to 3 min 10% acetonitrile, to 15 min 90% acetonitrile and a further 3 min 90% acetonitrile)]. The product fractions were combined, freed from the solvent and lyophilized. This gave 100 mg (77% of theory, 99% pure) of the title compound.

LC-MS (Method 3): $R_t$=1.77 min; MS (ESIpos): m/z=543 [M+H]$^+$.

$^1$H NMR (400 MHz, DMSO-d6): δ [ppm]=10.49 (d, 1H), 8.78 (s, 1H), 8.02 (d, 1H), 7.76-7.67 (m, 1H), 7.46-7.38 (m, 2H), 5.19 (br. s, 2H), 4.45-4.32 (m, 1H), 4.11-3.53 (br. m, 4H), 3.27-2.89 (m, 2H), 1.27-1.16 (m, 1H), 0.70-0.49 (m, 3H), 0.38-0.28 (m, 1H).

Example 3

1-(2,6-Difluorophenyl)-7-[(3R,4R)-3,4-dihydroxy-pyrrolidin-1-yl]-6-fluoro-4-oxo-N-[(2S)-1,1,1-trifluorobutan-2-yl]-1,4-dihydro-1,8-naphthyridine-3-carboxamide

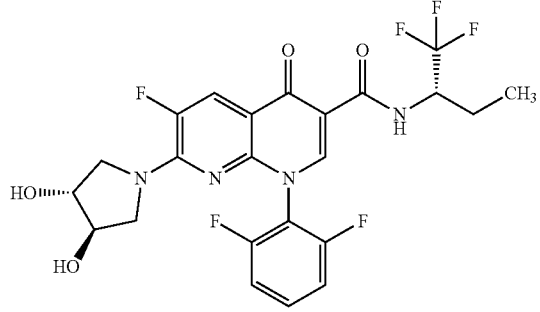 [SMILES: CC[C@H](NC(=O)c1cn(-c2c(F)cccc2F)c2nc(N3C[C@@H](O)[C@H](O)C3)c(F)cc2c1=O)C(F)(F)F]

According to GP1, 100 mg (237 μmol) of 1-(2,6-difluorophenyl)-7-[(3R,4R)-3,4-dihydroxypyrrolidin-1-yl]-6-fluoro-4-oxo-1,4-dihydro-1,8-naphthyridine-3-carboxylic acid were reacted with 46.6 mg (285 μmol) of (2S)-1,1,1-trifluorobutan-2-amine hydrochloride in the presence of 108 mg (285 μmol) of HATU and 103 μl (593 μmol) of DIPEA in 2.4 ml of DMF. The reaction mixture was then diluted with 2 ml of aqueous hydrochloric acid and purified by preparative HPLC [at UV max: 265 nm, column: Chromatorex C18, 10 μm, 125×30 mm, solvent: acetonitrile/0.05% formic acid gradient (0 to 3 min 10% acetonitrile, to 15 min 90% acetonitrile and a further 3 min 90% acetonitrile)]. The product fractions were combined, freed from the solvent and lyophilized. This gave 32.7 mg (26% of theory, 100% pure) of the title compound.

LC-MS (Method 1): $R_t$=0.92 min; MS (ESIpos): m/z=531 [M+H]$^+$.

$^1$H NMR (400 MHz, DMSO-d6): δ [ppm]=10.36 (d, 1H), 8.79 (s, 1H), 8.02 (d, 1H), 7.77-7.67 (m, 1H), 7.47-7.38 (m, 2H), 5.19 (br. s, 2H), 4.81-4.67 (m, 1H), 4.10-3.56 (br. m, 4H), 3.27-2.90 (m, 2H), 1.94-1.82 (m, 1H), 1.71-1.58 (m, 1H), 0.97 (t, 1H).

Example 4

1-(2,6-Difluorophenyl)-6-fluoro-7-[(2-hydroxyethyl)(methyl)amino]-4-oxo-N-[(2S)-1,1,1-trifluorobutan-2-yl]-1,4-dihydro-1,8-naphthyridine-3-carboxamide

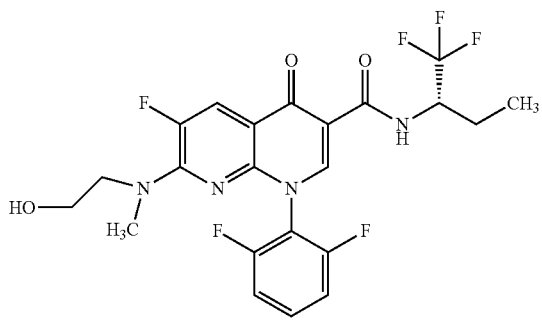 [SMILES: CC[C@H](NC(=O)c1cn(-c2c(F)cccc2F)c2nc(N(C)CCO)c(F)cc2c1=O)C(F)(F)F]

According to GP3, 50.0 mg (108 μmol) of 7-chloro-1-(2,6-difluorophenyl)-6-fluoro-4-oxo-N-[(2S)-1,1,1-trifluorobutan-2-yl]-1,4-dihydro-1,8-naphthyridine-3-carboxamide were reacted with 8.91 mg (119 μmol) of 2-(methylamino)ethanol in the presence of 66 μl (0.38 mmol) of DIPEA in 0.5 ml of DMF. The mixture was then diluted with acetonitrile, water and 0.2 ml of aqueous hydrochloric acid and the crude solution was purified by preparative HPLC (acetonitrile/water with formic acid, C18 RP-HPLC). The product fractions were combined, concentrated under reduced pressure and lyophilized from acetonitrile/water overnight. This gave 37.9 mg (70% of theory, 100% pure) of the title compound.

LC-MS (Method 3): $R_t$=1.97 min; MS (ESIpos): m/z=503 [M+H]$^+$.

$^1$H NMR (400 MHz, DMSO-d6): δ [ppm]=10.33 (d, 1H), 8.81 (s, 1H), 8.01 (d, 1H), 7.75-7.65 (m, 1H), 7.45-7.37 (m, 2H), 4.80-4.67 (m, 2H), 3.51-3.35 (m, 4H), 3.05 (s, 3H), 1.94-1.82 (m, 1H), 1.71-1.58 (m, 1H), 0.97 (t, 3H).

Example 5

N-(Bicyclo[1.1.1]pent-1-yl)-1-(2,6-difluorophenyl)-7-[(3R,4R)-3,4-dihydroxypyrrolidin-1-yl]-6-fluoro-4-oxo-1,4-dihydro-1,8-naphthyridine-3-carboxamide

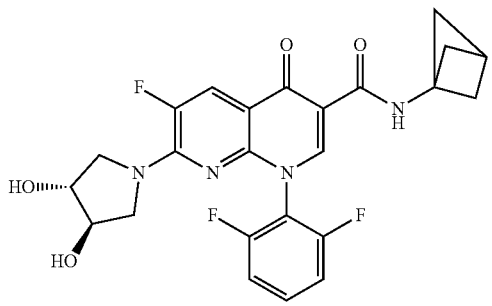 [SMILES: O=C(NC12CC(C1)C2)c1cn(-c2c(F)cccc2F)c2nc(N3C[C@@H](O)[C@H](O)C3)c(F)cc2c1=O]

According to GP1, 100 mg (237 μmol) of 1-(2,6-difluorophenyl)-7-[(3R,4R)-3,4-dihydroxypyrrolidin-1-yl]-6-fluoro-4-oxo-1,4-dihydro-1,8-naphthyridine-3-carboxylic acid were reacted with 34.1 mg (285 μmol) of bicyclo[1.1.1]pentan-1-amine hydrochloride in the presence of 108 mg (285 μmol) of HATU and 103 μl (593 μmol) of DIPEA in 2.4 ml of DMF. The reaction mixture was then diluted with 2 ml of aqueous hydrochloric acid and purified twice by preparative HPLC [at UV max: 265 nm, column: Chromatorex C18, 10 μm, 125×30 mm, solvent: acetonitrile/0.05% formic acid gradient (0 to 3 min 10% acetonitrile, to 15 min 90% acetonitrile and a further 3 min 90% acetonitrile)]. The product fractions were combined, freed from the solvent and lyophilized. This gave 3 mg (2% of theory, 100% pure) of the title compound.

LC-MS (Method 3): $R_t$=1.65 min; MS (ESIpos): m/z=487 [M+H]$^+$.

Example 6

7-[(3R,4R)-3,4-Dihydroxypyrrolidin-1-yl]-6-fluoro-4-oxo-N-[(2S)-1,1,1-trifluorobutan-2-yl]-1-(2,4,6-trifluorophenyl)-1,4-dihydro-1,8-naphthyridine-3-carboxamide

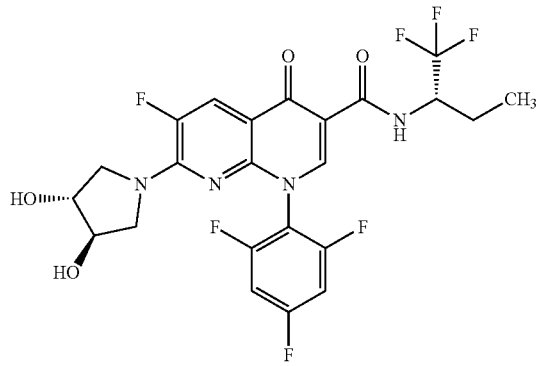 [SMILES: CC[C@H](NC(=O)c1cn(-c2c(F)cc(F)cc2F)c2nc(N3C[C@@H](O)[C@H](O)C3)c(F)cc2c1=O)C(F)(F)F]

According to GP3, 417 mg (717 μmol) of 6-fluoro-4-oxo-7-(1-[1,2,3]triazol[4,5-h]pyridin-1-yloxy)-N-[(2S)-1,1,1-trifluorobutan-2-yl]-1-(2,4,6-trifluorophenyl)-1,4-dihydro-1,8-naphthyridine-3-carboxamide were reacted with 120 mg (861 μmol) of (3R,4R)-pyrrolidine-3,4-diol hydrochloride in the presence of 437 μl (2.51 mmol) of DIPEA in 7.25 ml of DMF. The reaction solution was then added to 80 ml of water and acidified with 2 ml of aqueous 1M hydrochloric acid and the precipitate was filtered off with suction and washed with water. The residue was taken up in 6 ml of acetonitrile and purified by preparative HPLC (acetonitrile/water with formic acid, C18 RP-HPLC). The product fractions were combined and concentrated under reduced pressure and the residue was lyophilized from acetonitrile/water overnight. This gave 296 mg (74% of theory, 99% pure) of the title compound.

LC-MS (Method 3): $R_t$=1.78 min; MS (ESIpos): m/z=549 [M+H]$^+$.

$^1$H NMR (400 MHz, DMSO-d6): δ [ppm]=10.34 (d, 1H), 8.84 (s, 1H), 8.02 (d, 1H), 7.62-7.53 (m, 2H), 5.20 (br. s, 2H), 4.82-4.67 (m, 1H), 4.13-3.54 (br. m, 4H), 3.28-2.95 (m, 2H), 1.94-1.81 (m, 1H), 1.72-1.57 (m, 1H), 0.97 (t, 1H).

Example 7

N-[(1S)-1-Cyclopropyl-2,2,2-trifluoroethyl]-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide

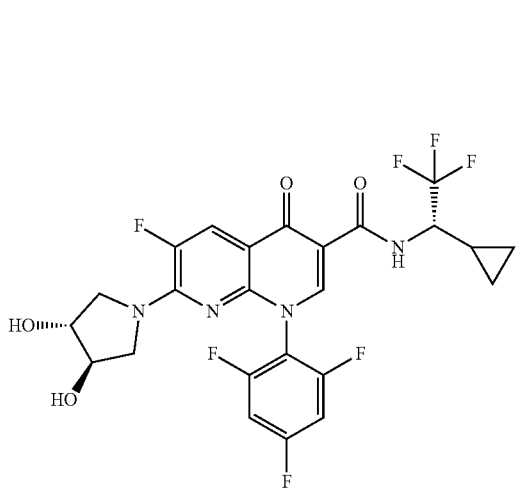 [SMILES: O=C(N[C@@H](C1CC1)C(F)(F)F)c1cn(-c2c(F)cc(F)cc2F)c2nc(N3C[C@@H](O)[C@H](O)C3)c(F)cc2c1=O]

According to GP1, 1.00 g (2.28 mmol) of 7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 480 mg (2.73 mmol) of (1S)-1-cyclopropyl-2,2,2-trifluoroethanamine hydrochloride in the presence of 1.04 g (2.73 mmol) of HATU and 991 µl (5.69 mmol) of DIPEA in 23 ml of DMF. The mixture was then acidified with aqueous 1M hydrochloric acid and diluted with 200 ml of water and 100 ml of ethyl acetate. The phases were separated and the aqueous phase was extracted twice with 60 ml of ethyl acetate. The combined organic phases were washed with 50 ml of buffer pH 7 and with 50 ml of saturated aqueous sodium chloride solution, dried over magnesium sulfate, filtered and concentrated under reduced pressure. The residue was purified by normal phase chromatography (cyclohexane/ethyl acetate) and the fractions was combined, concentrated under reduced pressure and lyophilized from acetonitrile/water overnight. This gave 1.05 g (83% of theory, 100% pure) of the title compound.

LC-MS (Method 3): $R_t$=1.81 min; MS (ESIpos): m/z=561 [M+H]$^+$.

$^1$H NMR (400 MHz, DMSO-d6): δ [ppm]=10.48 (d, 1H), 8.83 (s, 1H), 8.02 (d, 1H), 7.62-7.52 (m, 2H), 5.20 (br. s, 2H), 4.45-4.31 (m, 1H), 4.11-3.55 (br. m, 4H), 3.29-2.95 (m, 2H), 1.26-1.14 (m, 1H), 0.70-0.48 (m, 3H), 0.38-0.28 (m, 1H).

Example 8

7-[(3R,4R)-3,4-Dihydroxypyrrolidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

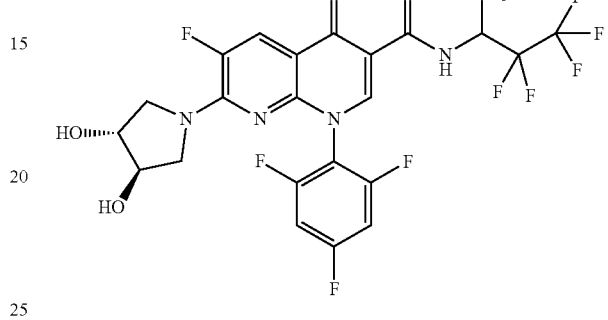

According to GP1, 2.77 g (6.31 mmol) of 7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 1.51 g (7.57 mmol) of 3,3,4,4,4-pentafluorobutan-2-amine hydrochloride (racemate) in the presence of 2.88 g (7.57 mmol) of HATU and 3.84 ml (22.1 mmol) of DIPEA in 30 ml of DMF. The reaction solution was subsequently added dropwise to a mixture of 3 ml of aqueous 1M hydrochloric acid and 300 ml of ice-water. The precipitate formed was filtered off, dried and purified by normal phase chromatography (cyclohexane/ethyl acetate). This gave 2.40 g (65% of theory, 100% pure) of the title compound.

LC-MS (Method 3): $R_t$=1.84 min; MS (ESIpos): m/z=585 [M+H]$^+$.

2.40 g of the title compound (diastereomer mixture) were separated by chiral SFC into the diastereomers (preparative SFC: column Daicel Chiralpak AD, 5 µm, 250×30 mm; mobile phase: 85% carbon dioxide, 15% isopropanol; temperature: 38° C.; flow rate: 130 ml/min; pressure: 140 bar; UV detection: 210 nm.)

This gave (in the sequence of elution from the column) 1.15 g of diastereomer 1 from Example 9 (99% de) $R_t$=3.23 min, 1.09 g of diastereomer 2 from Example 10 (94% de) $R_t$=4.79 min. [Analytical SFC: column Daicel Chiralpak AD-3.3 µm, 100×4.6 mm; mobile phase: 90% carbon dioxide, 10% isopropanol; temperature: 60° C.; flow rate: 3.0 ml/min; pressure: 130 bar, UV detection: 220 nm].

Diastereomer 1 was re-purified by normal phase chromatography (cyclohexane/ethyl acetate). This gave 903 mg (24% of theory, 99% purity) of the compound from Example 9.

Diastereomer 2 was re-purified by normal phase chromatography (cyclohexane/ethyl acetate). This gave 912 mg (25% of theory, 99% purity) of the compound from Example 10.

Example 9

7-[(3R,4R)-3,4-Dihydroxypyrrolidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Diastereomer 1)

LC-MS (Method 3): $R_t$=1.84 min; MS (ESIpos): m/z=585 [M+H]$^+$.

$^1$H NMR (400 MHz, DMSO-d6): δ [ppm]=10.46 (d, 1H), 8.84 (s, 1H), 8.01 (d, 1H), 7.62-7.53 (m, 2H), 5.20 (br. s, 2H), 5.10-4.93 (m, 1H), 4.11-3.55 (br. m, 4H), 3.29-2.95 (m, 2H), 1.39 (d, 3H).

Example 10

7-[(3R,4R)-3,4-Dihydroxypyrrolidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Diastereomer 2)

LC-MS (Method 3): $R_t$=1.84 min; MS (ESIpos): m/z=585 [M+H]$^+$.

$^1$H NMR (400 MHz, DMSO-d6): δ [ppm]=10.47 (d, 1H), 8.84 (s, 1H), 8.01 (d, 1H), 7.62-7.54 (m, 2H), 5.20 (br. s, 2H), 5.10-4.93 (m, 1H), 4.11-3.57 (br. m, 4H), 3.29-2.96 (m, 2H), 1.39 (d, 3H).

The following working examples were prepared analogously to Example 8 according to GP1:

| Example | IUPAC name<br>Structure<br>LC-MS (method): retention time; detected mass<br>$^1$H NMR<br>amine used<br>(yield, purity) |
|---|---|
| 11 | 7-[(3R,4S)-3,4-dihydroxypyrrolidin-1-yl]-6-fluoro-4-oxo-N-[(2S)-1,1,1-trifluoro-4-methylpentan-2-yl]-1-(2,4,6-trifluorophenyl)-1,4-dihydro-1,8-naphthyridine-3-carboxamide<br>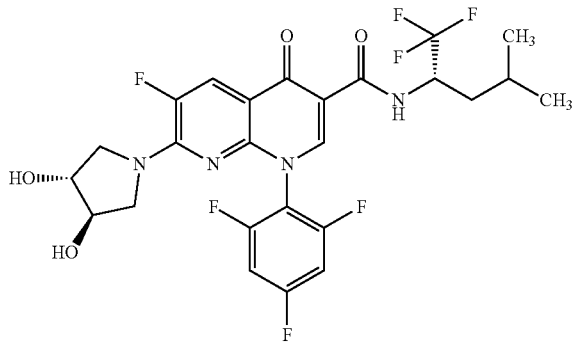 [SMILES: CC(C)C[C@H](NC(=O)c1cn(-c2c(F)cc(F)cc2F)c2nc(N3C[C@@H](O)[C@H](O)C3)c(F)cc2c1=O)C(F)(F)F]<br>LC-MS (Method 1): $R_t$ = 1.07 min; MS (ESIpos): m/z = 577 [M + H]$^+$<br>$^1$H NMR (400 MHz, DMSO-d6) δ [ppm]: 0.008 (1.63), 0.882 (15.82), 0.898 (15.97), 0.940 (15.69), 0.956 (16.00), 1.527 (0.65), 1.562 (2.61), 1.590 (2.10), 1.640 (2.07), 1.650 (3.07), 1.676 (3.98), 1.703 (1.66), 2.328 (0.72), 2.366 (0.49), 2.524 (2.17), 2.670 (0.75), 2.710 (0.47), 3.070 (0.79), 3.696 (0.83), 3.904 (1.68), 4.017 (1.18), 4.815 (1.32), 4.838 (1.35), 4.857 (0.78), 5.201 (2.98), 7.554 (2.23), 7.558 (2.44), 7.575 (4.26), 7.580 (4.31), 7.597 (2.46), 7.993 (6.91), 8.025 (6.83), 8.847 (12.23), 10.316 (4.89), 10.340 (4.71).<br>(2S)-1,1,1-trifluoro-4-methylpentan-2-amine hydrochloride<br>(75% of theory, 99% pure) |
| 12 | N-(bicyclo[1.1.1]pent-1-yl)-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide<br>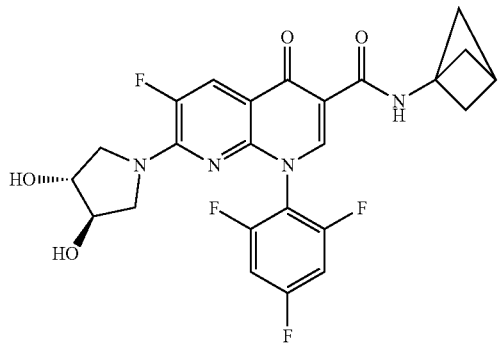 [SMILES: O=C(NC12CC(C1)C2)c1cn(-c2c(F)cc(F)cc2F)c2nc(N3C[C@@H](O)[C@H](O)C3)c(F)cc2c1=O]<br>LC-MS (Method 1): $R_t$ = 0.91 min; MS (ESIpos): m/z = 505 [M + H]$^+$<br>$^1$H NMR (400 MHz, DMSO-d6) δ [ppm]: 2.074 (0.98), 2.094 (16.00), 2.477 (2.52), 2.519 (0.42), 5.188 (0.90), 7.557 (0.60), 7.579 (1.03), 7.599 (0.60), 7.949 (1.39), 7.981 (1.36), 8.696 (2.25), 10.195 (1.71). |

| Example | IUPAC name<br>Structure<br>LC-MS (method): retention time; detected mass<br>¹H NMR<br>amine used<br>(yield, purity) |
|---|---|
| | bicyclo[1.1.1]pentan-1-amine hydrochloride<br>(69% of theory, 100% pure) |
| 13 | 7-[(3R,4R)-3,4-dihydroxypyrrolidin-1-yl]-6-fluoro-4-oxo-N-(4,4,4-trifluoro-2-methyl-butan-2-yl)-1-(2,4,6-trifluorophenyl)-1,4-dihydro-1,8-naphthyridine-3-carboxamide |

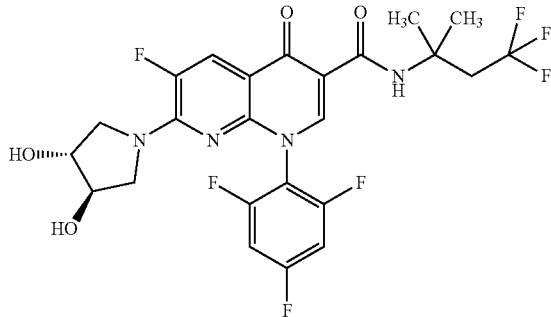 [SMILES: CC(C)(CC(F)(F)F)NC(=O)c1cn(-c2c(F)cc(F)cc2F)c2nc(N3C[C@@H](O)[C@H](O)C3)c(F)cc2c1=O]

LC-MS (Method 3): $R_t$ = 1.8 min; MS (ESIpos): m/z = 563 [M + H]⁺

¹H NMR (400 MHz, DMSO-d6) δ [ppm]: 1.480 (16.00), 2.902 (0.72), 2.932 (2.07), 2.963 (2.01), 2.992 (0.69), 3.908 (0.59), 5.192 (1.67), 7.552 (1.20), 7.573 (2.17), 7.595 (1.21), 7.980 (2.69), 8.012 (2.63), 8.724 (4.96), 10.086 (3.27).

4,4,4-trifluoro-2-methylbutan-2-amine hydrochloride (92% of theory, 100% pure)

| 14 | 7-[(3R,4S)-3,4-dihydroxypyrrolidin-1-yl]-6-fluoro-4-oxo-N-[(2R)-1,1,1-trifluoro-4-methylpentan-2-yl]-1-(2,4,6-trifluorophenyl)-1,4-dihydro-1,8-naphthyridine-3-carboxamide |
|---|---|

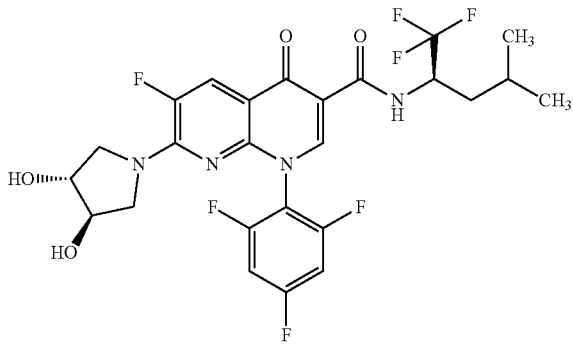 [SMILES: CC(C)C[C@@H](NC(=O)c1cn(-c2c(F)cc(F)cc2F)c2nc(N3C[C@@H](O)[C@H](O)C3)c(F)cc2c1=O)C(F)(F)F]

LC-MS (Method 1): $R_t$ = 1.07 min; MS (ESIpos): m/z = 577 [M + H]⁺

¹H NMR (400 MHz, DMSO-d6) δ [ppm]: −0.008 (2.52), 0.008 (2.37), 0.882 (15.72), 0.898 (15.79), 0.940 (15.66), 0.956 (16.00), 1.528 (0.63), 1.534 (0.59), 1.555 (1.28), 1.563 (2.58), 1.571 (1.29), 1.591 (2.06), 1.640 (1.99), 1.650 (2.98), 1.676 (3.84), 1.704 (1.62), 1.713 (1.08), 2.329 (0.42), 2.524 (1.33), 2.671 (0.45), 3.070 (0.76), 3.694 (0.77), 3.912 (1.65), 4.018 (1.13), 4.816 (1.26), 4.839 (1.29), 4.858 (0.73), 5.201 (4.77), 7.556 (3.83), 7.578 (6.91), 7.599 (3.80), 7.994 (7.11), 8.026 (6.94), 8.848 (12.19), 10.318 (4.80), 10.342 (4.57).

(2R)-1,1,1-trifluoro-4-methylpentan-2-amine hydrochloride (73% of theory, 97% pure)

| Example | IUPAC name<br>Structure<br>LC-MS (method): retention time; detected mass<br>¹H NMR<br>amine used<br>(yield, purity) |
|---|---|
| 15 | 7-[(3R,4R)-3,4-dihydroxypyrrolidin-1-yl]-6-fluoro-N-[(2R)-3-methylbutan-2-yl]-4-oxo-1-(2,4,6-trifluorophenyl)-1,4-dihydro-1,8-naphthyridine-3-carboxamide<br>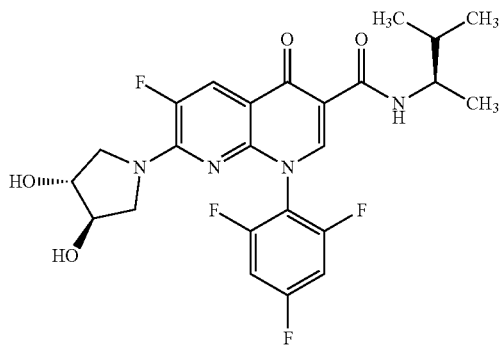 [SMILES: CC(C)[C@@H](C)NC(=O)c1cn(-c2c(F)cc(F)cc2F)c2nc(N3C[C@@H](O)[C@H](O)C3)c(F)cc2c1=O]<br>LC-MS (Method 3): $R_t$ = 1.67 min; MS (ESIpos): m/z = 509 [M + H]⁺<br>¹H NMR (400 MHz, DMSO-d6) δ [ppm]: −0.008 (2.45), 0.008 (1.92), 0.900 (14.25), 0.918 (16.00), 0.924 (14.85), 0.941 (14.39), 1.098 (14.84), 1.115 (14.90), 1.731 (0.46), 1.747 (1.23), 1.764 (1.75), 1.778 (1.69), 1.795 (1.13), 1.811 (0.41), 2.328 (0.43), 2.519 (1.74), 2.524 (1.27), 2.671 (0.43), 3.070 (0.46), 3.269 (0.67), 3.276 (0.53), 3.680 (0.48), 3.887 (2.02), 3.903 (2.66), 3.908 (2.44), 3.921 (2.64), 3.938 (2.04), 3.954 (1.12), 5.191 (3.01), 7.550 (2.38), 7.571 (4.17), 7.592 (2.37), 7.992 (5.69), 8.024 (5.64), 8.711 (9.43), 9.868 (3.38), 9.890 (3.30).<br>(2R)-3-methylbutan-2-amine<br>(75% of theory, 99% pure) |
| 16 | 7-[(3R,4R)-3,4-dihydroxypyrrolidin-1-yl]-6-fluoro-N-[(2S)-3-methylbutan-2-yl]-4-oxo-1-(2,4,6-trifluorophenyl)-1,4-dihydro-1,8-naphthyridine-3-carboxamide<br>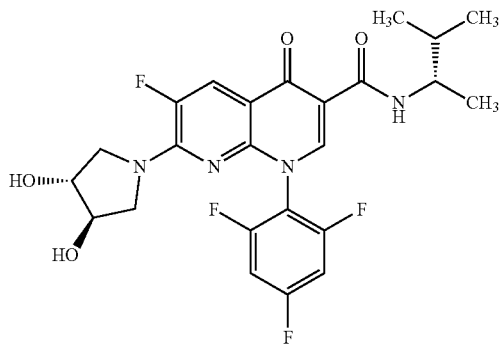 [SMILES: CC(C)[C@H](C)NC(=O)c1cn(-c2c(F)cc(F)cc2F)c2nc(N3C[C@@H](O)[C@H](O)C3)c(F)cc2c1=O]<br>LC-MS (Method 3): $R_t$ = 1.67 min; MS (ESIpos): m/z = 509 [M + H]⁺<br>¹H NMR (400 MHz, DMSO-d6) δ [ppm]: 0.008 (1.40), 0.901 (14.31), 0.918 (16.00), 0.925 (14.98), 0.942 (14.43), 1.099 (14.84), 1.116 (14.86), 1.731 (0.49), 1.748 (1.30), 1.765 (1.85), 1.778 (1.73), 1.795 (1.14), 3.063 (0.51), 3.680 (0.53), 3.888 (2.11), 3.904 (2.84), 3.922 (2.79), 3.939 (2.15), 5.194 (4.39), 7.550 (2.81), 7.572 (4.99), 7.593 (2.71), 7.994 (6.12), 8.026 (6.00), 8.713 (11.30), 9.870 (3.57), 9.892 (3.45).<br>(2S)-3-methylbutan-2-amine<br>(77% of theory, 100% pure) |

| Example | IUPAC name<br>Structure<br>LC-MS (method): retention time; detected mass<br>¹H NMR<br>amine used<br>(yield, purity) |
|---|---|
| 17 | 7-[(3R,4R)-3,4-dihydroxypyrrolidin-1-yl]-6-fluoro-N-[(2S)-1-methoxy-3-methylbutan-2-yl]-4-oxo-1-(2,4,6-trifluorophenyl)-1,4-dihydro-1,8-naphthyridine-carboxamide 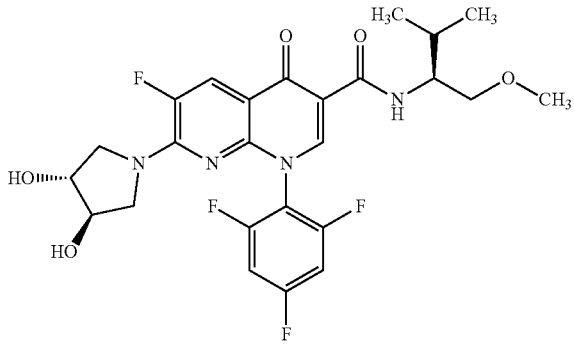 [SMILES: COC[C@@H](NC(=O)c1cn(-c2c(F)cc(F)cc2F)c2nc(N3C[C@@H](O)[C@H](O)C3)c(F)cc2c1=O)C(C)C] LC-MS (Method 3): $R_t$ = 1.58 mm; MS (ESIpos): m/z = 539 [M + H]⁺<br>¹H NMR (400 MHz, DMSO-d6) δ [ppm]: −0.008 (1.71), 0.008 (1.47), 0.912 (10.53), 0.929 (10.84), 1.903 (0.49), 1.920 (0.75), 1.936 (0.74), 1.953 (0.46), 3.269 (16.00), 3.352 (0.72), 3.365 (0.83), 3.377 (1.17), 3.390 (1.12), 3.439 (1.10), 3.453 (1.22), 3.464 (0.76), 3.477 (0.70), 3.919 (0.46), 3.965 (0.52), 3.980 (0.91), 3.994 (0.99), 4.002 (1.00), 4.017 (0.87), 5.192 (1.07), 7.553 (0.86), 7.573 (1.56), 7.594 (0.86), 8.000 (2.37), 8.031 (2.31), 8.723 (4.24), 9.926 (1.34), 9.949 (1.29).<br>(2S)-1-methoxy-3-methylbutan-2-amine hydrochloride<br>(87% of theory, 99% pure) |
| 18 | 7-[(3R,4R)-3,4-dihydroxypyrrolidin-1-yl]-6-fluoro-4-oxo-1-(2,4,6-trifluorophenyl)-N-[(2S)-1,1,1-trifluoropropan-2-yl]-1,4-dihydro-1,8-naphthyridine-3-carboxamide 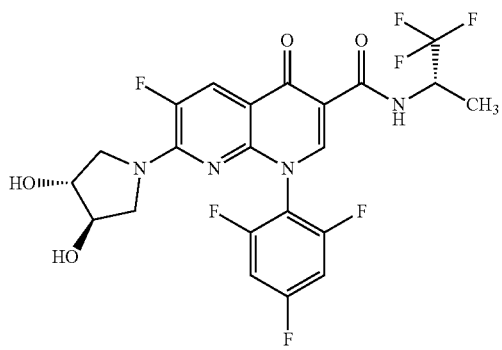 [SMILES: C[C@H](NC(=O)c1cn(-c2c(F)cc(F)cc2F)c2nc(N3C[C@@H](O)[C@H](O)C3)c(F)cc2c1=O)C(F)(F)F] LC-MS (Method 1): $R_t$ = 0.89 min; MS (ESIpos): m/z = 535 [M + H]⁺<br>¹H NMR (400 MHz, DMSO-d6) δ [ppm]: −0.008 (3.40), 1.366 (15.93), 1.383 (16.00), 2.328 (0.75), 2.367 (0.46), 2.670 (0.72), 2.710 (0.46), 3.065 (0.82), 3.692 (0.82), 3.906 (1.71), 4.011 (1.21), 4.842 (0.45), 4.861 (1.18), 4.882 (1.82), 4.902 (1.87), 4.920 (1.20), 5.199 (4.80), 7.555 (2.86), 7.577 (5.42), 7.598 (2.83), 7.990 (8.04), 8.022 (7.89), 8.837 (14.74), 10.383 (5.19), 10.406 (4.90).<br>(2S)-1,1,1-trifluoropropan-2-amine<br>(77% of theory, 99% pure) |

| Example | IUPAC name<br>Structure<br>LC-MS (method): retention time; detected mass<br>¹H NMR<br>amine used<br>(yield, purity) |
|---|---|
| 19 | N-[(1R)-1-cyclopropylethyl]-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide<br>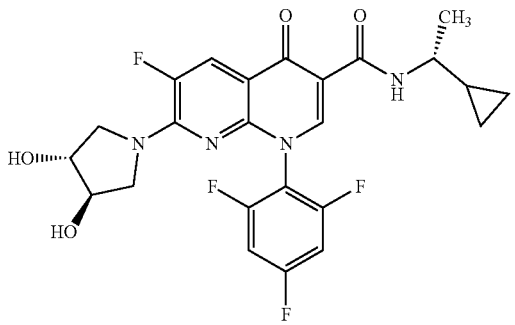 [SMILES: C[C@@H](NC(=O)c1cn(-c2c(F)cc(F)cc2F)c2nc(N3C[C@@H](O)[C@H](O)C3)c(F)cc2c1=O)C1CC1]<br>LC-MS (Method 3): $R_t$ = 1.63 min; MS (ESIpos): m/z = 507 [M + H]⁺<br>¹H NMR (400 MHz, DMSO-d6) δ [ppm]: −0.150 (0.68), −0.008 (6.67), 0.008 (5.02), 0.146 (0.68), 0.218 (1.10), 0.229 (1.68), 0.241 (2.46), 0.249 (2.36), 0.261 (1.43), 0.266 (1.39), 0.278 (2.30), 0.287 (2.75), 0.299 (1.94), 0.310 (1.26), 0.322 (0.55), 0.394 (0.65), 0.402 (0.65), 0.414 (1.85), 0.425 (2.27), 0.435 (2.59), 0.447 (3.11), 0.461 (2.75), 0.469 (2.01), 0.482 (1.59), 0.491 (0.62), 0.940 (0.45), 0.952 (0.87), 0.960 (1.30), 0.972 (2.27), 0.980 (1.46), 0.992 (2.14), 1.004 (1.10), 1.012 (0.74), 1.215 (15.87), 1.231 (16.00), 2.327 (1.13), 2.366 (1.00), 2.523 (3.85), 2.670 (1.23), 2.710 (1.10), 3.064 (0.55), 3.482 (0.42), 3.498 (1.39), 3.518 (2.56), 3.535 (2.49), 3.553 (1.33), 3.571 (0.49), 3.679 (0.62), 3.917 (1.39), 5.189 (4.15), 7.546 (3.17), 7.568 (5.73), 7.589 (3.21), 7.975 (6.25), 8.007 (6.19), 8.708 (10.85), 9.864 (4.05), 9.884 (3.92).<br>(1R)-1-cyclopropylethanamine<br>(76% of theory, 100% pure) |
| 20 | N-[(1S)-1-cyclopropylethyl]-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide<br>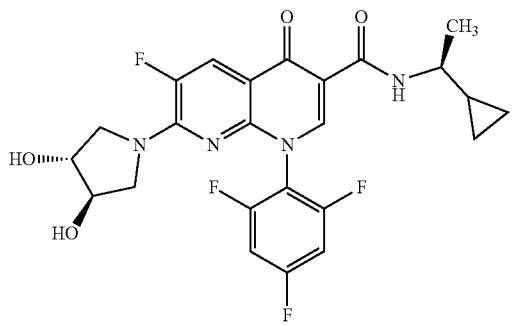 [SMILES: C[C@H](NC(=O)c1cn(-c2c(F)cc(F)cc2F)c2nc(N3C[C@@H](O)[C@H](O)C3)c(F)cc2c1=O)C1CC1]<br>LC-MS (Method 3): $R_t$ = 1.62 min; MS (ESIpos): m/z = 507 [M + H]⁺<br>¹H NMR (400 MHz, DMSO-d6) δ [ppm]: −0.149 (0.42), −0.008 (4.00), 0.008 (2.96), 0.146 (0.42), 0.207 (0.46), 0.218 (1.12), 0.229 (1.67), 0.241 (2.46), 0.249 (2.39), 0.261 (1.42), 0.266 (1.39), 0.278 (2.32), 0.287 (2.75), 0.299 (1.93), 0.310 (1.19), 0.321 (0.56), 0.394 (0.60), 0.402 (0.67), 0.414 (1.84), 0.425 (2.23), 0.435 (2.56), 0.448 (3.05), 0.456 (1.96), 0.461 (2.72), 0.470 (1.98), 0.482 (1.60), 0.491 (0.60), 0.502 (0.44), 0.940 (0.44), 0.952 (0.88), 0.960 (1.26), 0.972 (2.25), 0.980 (1.44), 0.984 (1.40), 0.992 (2.16), 1.005 (1.09), 1.012 (0.74), 1.215 (15.91), 1.232 (16.00), 2.328 (0.61), 2.367 (0.60), 2.524 (2.23), 2.670 (0.65), 2.710 (0.58), 3.073 (0.54), 3.484 (0.40), 3.501 (1.35), 3.520 (2.49), 3.537 (2.46), 3.556 (1.30), 3.573 (0.44), 3.673 (0.56), 3.909 (1.32), 5.190 (4.47), 7.547 (2.51), 7.568 (4.49), 7.589 (2.51), 7.976 (6.25), 8.008 (6.18), 8.709 (10.70), 9.864 (4.05), 9.884 (3.89).<br>(1S)-1-cyclopropylethanamine<br>(77% of theory, 100% pure) |

| Example | IUPAC name<br>Structure<br>LC-MS (method): retention time; detected mass<br>¹H NMR<br>amine used<br>(yield, purity) |
|---|---|
| 21 | N-(dicyclopropylmethyl)-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide<br>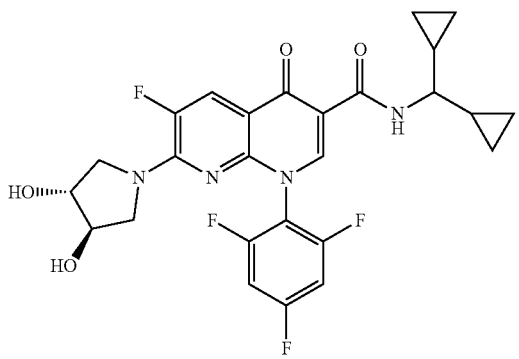 [SMILES: O=C(NC(C1CC1)C1CC1)c1cn(-c2c(F)cc(F)cc2F)c2nc(N3C[C@@H](O)[C@H](O)C3)c(F)cc2c1=O]<br>LC-MS (Method 1): $R_t$ = 0.94 min; MS (ESIpos): m/z = 533 [M + H]⁺<br>¹H NMR (400 MHz, DMSO-d6) δ [ppm]: −0.149 (1.11), −0.008 (9.56), 0.008 (7.59), 0.146 (1.11), 0.299 (15.57), 0.311 (15.27), 0.322 (4.14), 0.370 (2.56), 0.393 (6.91), 0.415 (5.85), 0.452 (4.99), 0.472 (6.31), 0.498 (1.92), 1.016 (2.82), 1.029 (5.25), 1.036 (3.41), 1.049 (4.99), 1.061 (2.60), 2.328 (2.22), 2.367 (1.11), 2.670 (2.13), 2.710 (1.07), 3.221 (2.22), 3.239 (4.44), 3.261 (4.74), 3.280 (2.86), 3.903 (1.79), 5.189 (5.16), 7.545 (3.50), 7.568 (6.27), 7.588 (3.58), 7.988 (9.09), 8.020 (8.75), 8.709 (16.00), 9.892 (5.03), 9.914 (4.82).<br>1,1-dicyclopropylmethanamine<br>(61% of theory, 99% pure) |
| 22 | N-(1,1-difluoro-2-methylpropan-2-yl)-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide<br>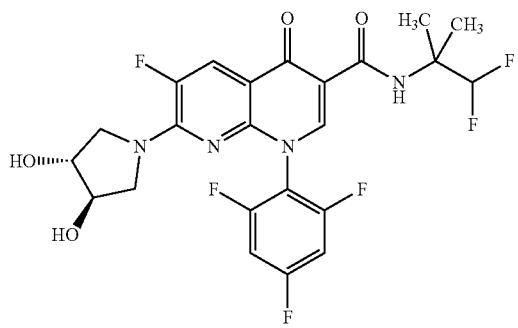 [SMILES: CC(C)(NC(=O)c1cn(-c2c(F)cc(F)cc2F)c2nc(N3C[C@@H](O)[C@H](O)C3)c(F)cc2c1=O)C(F)F]<br>LC-MS (Method 1): $R_t$ = 0.93 min; MS (ESIpos): m/z = 531 [M + H]⁺<br>¹H NMR (400 MHz, DMSO-d6) δ [ppm]: −0.008 (1.57), 0.008 (1.50), 1.434 (16.00), 2.073 (0.74), 2.328 (0.48), 2.670 (0.52), 3.910 (0.55), 5.192 (1.49), 6.277 (0.88), 6.420 (1.62), 6.562 (0.73), 7.554 (1.10), 7.577 (1.94), 7.597 (1.10), 7.987 (2.44), 8.019 (2.41), 8.750 (4.28), 10.232 (3.14).<br>1,1-difluoro-2-methylpropan-2-amine hydrochloride<br>(57% of theory, 100% pure) |

| Example | IUPAC name<br>Structure<br>LC-MS (method): retention time; detected mass<br>¹H NMR<br>amine used<br>(yield, purity) |
|---|---|
| 23 | 7-[(3R,4R)-3,4-dihydroxypyrrolidin-1-yl]-6-fluoro-4-oxo-N-(1,1,1-trifluoro-2-methylpropan-2-yl)-1-(2,4,6-trifluorophenyl)-1,4-dihydro-1,8-naphthyridine-3-carboxamide<br>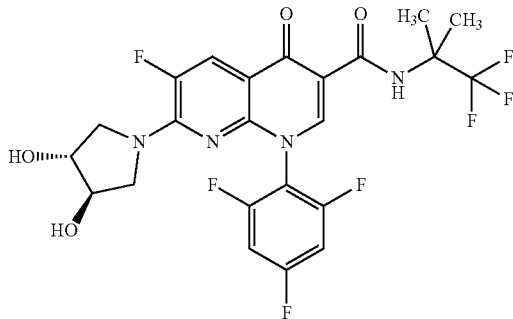 [SMILES: CC(C)(NC(=O)c1cn(-c2c(F)cc(F)cc2F)c2nc(N3C[C@@H](O)[C@H](O)C3)c(F)cc2c1=O)C(F)(F)F]<br>LC-MS (Method 3): $R_t$ = 1.77 min; MS (ESIpos): m/z = 549 [M + H]⁺<br>¹H NMR (400 MHz, DMSO-d6) δ [ppm]: -0.008 (0.89), 0.008 (0.56), 1.633 (16.00), 2.520 (0.82), 2.524 (0.74), 3.908 (0.50), 5.194 (1.18), 7.557 (0.97), 7.579 (1.58), 7.600 (0.89), 8.008 (2.21), 8.040 (2.14), 8.775 (3.54), 10.561 (2.95).<br>1,1,1-trifluoro-2-methylpropan-2-amine hydrochloride<br>(63% of theory, 100% pure) |
| 24 | 7-[(3R,4R)-3,4-dihydroxypyrrolidin-1-yl]-N-(2,4-dimethylpentan-3-yl)-6-fluoro-4-oxo-1-(2,4,6-trifluorophenyl)-1,4-dihydro-1,8-naphthyridine-3-carboxamide<br>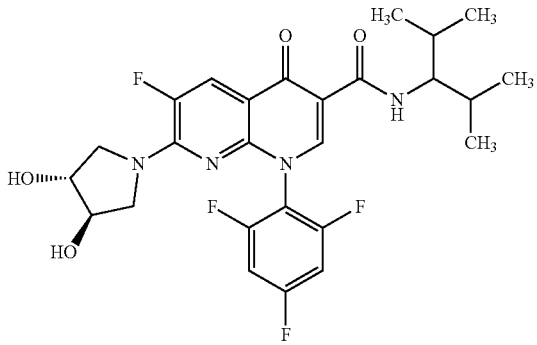 [SMILES: CC(C)C(NC(=O)c1cn(-c2c(F)cc(F)cc2F)c2nc(N3C[C@@H](O)[C@H](O)C3)c(F)cc2c1=O)C(C)C]<br>LC-MS (Method 3): $R_t$ = 1.87 min; MS (ESIpos): m/z = 537 [M + H]⁺<br>¹H NMR (400 MHz, DMSO-d6) δ [ppm]: -0.008 (0.92), 0.008 (0.71), 0.865 (13.39), 0.877 (15.46), 0.881 (16.00), 0.893 (13.11), 1.810 (0.43), 1.827 (15.26), 1.844 (2.06), 1.860 (2.00), 1.877 (1.16), 2.524 (0.55), 3.640 (0.71), 3.656 (1.27), 3.666 (0.90), 3.672 (0.89), 3.681 (1.31), 3.697 (0.75), 3.911 (0.57), 5.198 (1.63), 7.550 (1.24), 7.572 (2.16), 7.592 (1.23), 8.013 (3.06), 8.045 (2.98), 8.727 (5.38), 9.761 (1.66), 9.786 (1.59).<br>2,4-dimethylpentan-3-amine<br>(57% of theory, 100% pure) |
| 25 | N-(2-cyclopropylpropan-2-yl)-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide<br>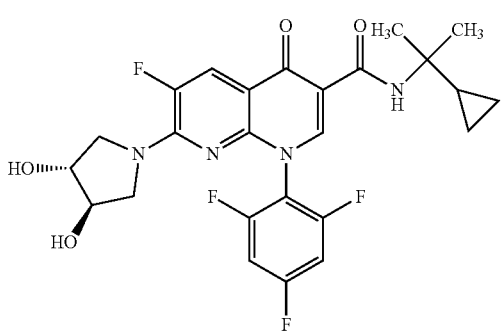 [SMILES: CC(C)(NC(=O)c1cn(-c2c(F)cc(F)cc2F)c2nc(N3C[C@@H](O)[C@H](O)C3)c(F)cc2c1=O)C1CC1] |

| Example | IUPAC name<br>Structure<br>LC-MS (method): retention time; detected mass<br>¹H NMR<br>amine used<br>(yield, purity) |
|---|---|

LC-MS (Method 3): R_t = 1.79 min; MS (ESIpos): m/z = 521 [M + H]⁺
¹H NMR (400 MHz, DMSO-d6) δ [ppm]: 0.397 (5.62), 0.414 (4.00), 1.290 (0.69), 1.311 (16.00), 1.325 (0.79), 5.187 (1.10), 7.550 (0.76), 7.572 (1.33), 7.593 (0.73), 7.993 (1.77), 8.024 (1.73), 8.680 (3.16), 9.863 (2.07).
2-cyclopropylpropan-2-amine
(95% of theory, 100% pure)

26   7-[(3R,4R)-3,4-dihydroxypyrrolidin-1-yl]-6-fluoro-4-oxo-N-[(2)-1-(trifluoromethoxy)butan-2-yl]-1-(2,4,6-trifluorophenyl)-1,4-dihydro-1,8-naphthyridine-3-carboxamide (diastereomer mixture)

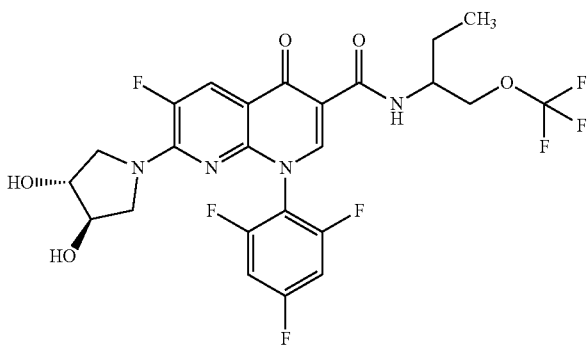 [SMILES: CCC(COC(F)(F)F)NC(=O)c1cn(-c2c(F)cc(F)cc2F)c2nc(N3C[C@@H](O)[C@H](O)C3)c(F)cc2c1=O]

LC-MS (Method 3): R_t = 1.78 min; MS (ESIpos): m/z = 579 [M + H]⁺
¹H NMR (400 MHz, DMSO-d6) δ [ppm]: −0.008 (2.02), 0.008 (1.73), 0.922 (6.79), 0.941 (16.00), 0.959 (7.44), 1.550 (0.56), 1.568 (0.97), 1.585 (1.26), 1.603 (1.40), 1.622 (0.89), 1.633 (0.55), 1.651 (1.04), 1.663 (1.19), 1.669 (1.15), 1.682 (1.27), 1.698 (0.74), 1.716 (0.46), 2.074 (1.63), 2.328 (0.45), 2.524 (1.32), 2.671 (0.43), 3.069 (0.51), 3.685 (0.52), 3.911 (1.21), 4.148 (2.09), 4.162 (2.31), 4.176 (3.98), 4.183 (4.11), 4.194 (4.10), 4.211 (2.53), 5.193 (3.51), 7.552 (2.57), 7.574 (4.50), 7.595 (2.53), 7.995 (6.24), 8.026 (6.06), 8.762 (10.71), 9.985 (2.62), 10.005 (2.44).
1-(trifluoromethoxy)butan-2-amine hydrochloride (racemate)
(54% of theory, 100% pure)

27   7-[(3R,4R)-3,4-dihydroxypyrrolidin-1-yl]-6-fluoro-4-oxo-N-[(3)-1,1,1,2,2-pentafluoropentan-3-yl]-1-(2,4,6-trifluorophenyl)-1,4-dihydro-1,8-naphthyridine-3-carboxamide (diastereomer mixture)

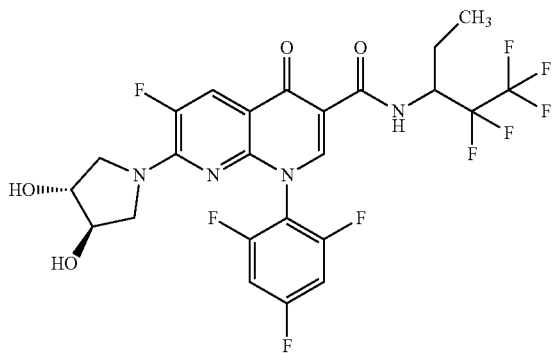 [SMILES: CCC(NC(=O)c1cn(-c2c(F)cc(F)cc2F)c2nc(N3C[C@@H](O)[C@H](O)C3)c(F)cc2c1=O)C(F)(F)C(F)(F)F]

LC-MS (Method 3): R_t = 1.93 min; MS (ESIpos): m/z = 599 [M + H]⁺
¹H NMR (400 MHz, DMSO-d6) δ [ppm]: 0.944 (7.18), 0.962 (16.00), 0.981 (7.74), 1.619 (0.90), 1.638 (1.31), 1.654 (1.50), 1.663 (1.39), 1.673 (1.34), 1.681 (1.41), 1.699 (1.00), 1.922 (1.31), 2.329 (0.58), 2.672 (0.66), 3.079 (0.81), 3.693 (0.86), 3.905 (1.75), 4.012 (1.22), 4.852 (1.12), 4.879 (1.06), 5.208 (3.80), 7.557 (3.27), 7.579 (5.89), 7.599 (3.25), 8.005 (7.21), 8.037 (7.04), 8.850 (14.56), 10.377 (4.69), 10.402 (4.39).
1,1,1,2,2-pentafluoropentan-3-amine hydrochloride (racemate)
(85% of theory, 99% pure)

| Example | IUPAC name<br>Structure<br>LC-MS (method): retention time; detected mass<br>¹H NMR<br>amine used<br>(yield, purity) |
|---|---|
| 28 | 7-[(3R,4R)-3,4-Dihydroxypyrrolidin-1-yl]-6-fluoro-N-(2-methylpentan-3-yl)-4-oxo-1-(2,4,6-trifluorophenyl)-1,4-dihydro-1,8-naphthyridine-3-carboxamide (diastereomer mixture)<br><br>LC-MS (Method 3): $R_t$ = 1.80 min; MS (ESIpos): m/z = 523 [M + H]⁺<br>¹H NMR (400 MHz, DMSO-d6) δ [ppm]: 0.008 (1.53), 0.851 (4.76), 0.869 (11.65), 0.878 (11.15), 0.888 (7.46), 0.896 (16.00), 0.915 (10.32), 1.380 (0.55), 1.397 (0.79), 1.414 (1.00), 1.436 (1.06), 1.454 (0.71), 1.538 (0.78), 1.550 (0.92), 1.568 (1.02), 1.584 (0.72), 1.602 (0.49), 1.794 (0.89), 1.810 (1.24), 1.824 (1.23), 1.840 (0.80), 2.328 (0.45), 3.680 (0.42), 3.764 (0.53), 3.777 (0.93), 3.788 (1.29), 3.799 (1.63), 3.811 (1.29), 3.822 (0.87), 3.834 (0.59), 3.907 (0.94), 5.199 (2.67), 7.551 (2.01), 7.573 (3.53), 7.594 (1.96), 7.999 (4.29), 8.031 (4.21), 8.716 (8.19), 9.768 (2.51), 9.792 (2.39).<br>2-methylpentan-3-amine hydrochloride (racemate)<br>(31% of theory, 100% pure) |

Example 29

7-[(3R,4R)-3,4-Dihydroxypyrrolidin-1-yl]-6-fluoro-N-(2-methylpentan-3-yl)-4-oxo-1-(2,4,6-trifluorophenyl)-1,4-dihydro-1,8-naphthyridine-3-carboxamide (Diastereomer 1)

37 mg of 7-[(3R,4R)-3,4-dihydroxypyrrolidin-1-yl]-6-fluoro-4-oxo-N-(2-methylpentan-3-yl)-4-oxo-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak OX-H, 5 μm, 250×20 mm; mobile phase: 80% n-heptane/20% isopropanol; flow rate 15 ml/min; temperature: 35° C., detection: 265 nm).

Diastereomer 1: 13 mg (>99% de)
$R_t$=6.27 min [analytical HPLC: column Daicel® Chiralpak OX-H, 1 ml/min; 5 μm, 250×4.6 mm; mobile phase: 75% isohexane/25% isopropanol+0.2% DEA; detection: 265 nm].
LC-MS (Method 3): $R_t$=1.80 min; MS (ESIpos): m/z=523 [M+H]⁺

Example 30

7-[(3R,4R)-3,4-Dihydroxypyrrolidin-1-yl]-6-fluoro-N-(2-methylpentan-3-yl)-4-oxo-1-(2,4,6-trifluorophenyl)-1,4-dihydro-1,8-naphthyridine-3-carboxamide (Diastereomer 2)

37 mg of 7-[(3R,4R)-3,4-dihydroxypyrrolidin-1-yl]-6-fluoro-4-oxo-N-(2-methylpentan-3-yl)-4-oxo-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak OX-H, 5 μm, 250×20 mm; mobile phase: 80% n-heptane/20% isopropanol; flow rate 15 ml/min; temperature: 35° C., detection: 265 nm).

Diastereomer 2: 13 mg (>99% de)
$R_t$=7.35 min [analytical HPLC: column Daicel® Chiralpak OX-H, 1 ml/min; 5 μm, 250×4.6 mm; mobile phase: 75% isohexane/25% isopropanol+0.2% DEA; detection: 265 nm].
LC-MS (Method 3): $R_t$=1.80 min; MS (ESIpos): m/z=523 [M+H]⁺

Example 31

7-[(3R,4R)-3,4-Dihydroxypyrrolidin-1-yl]-6-fluoro-4-oxo-N-[(2)-1-(trifluoromethoxy)butan-2-yl]-1-(2,4,6-trifluorophenyl)-1,4-dihydro-1,8-naphthyridine-3-carboxamide (Diastereomer 1)

218 mg of 7-[(3R,4R)-3,4-dihydroxypyrrolidin-1-yl]-6-fluoro-4-oxo-N-[(2)-1-(trifluoromethoxy)butan-2-yl]-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak ID, 5 μm, 250×20 mm; mobile phase: 85% n-heptane/15% isopropanol; flow rate 15 ml/min; temperature: 30° C., detection: 220 nm).

Diastereomer 1: 63.7 mg (99% de)
$R_t$=5.50 min [analytical HPLC: column Daicel® Chiralpak ID, 1 ml/min; 5 μm, 250×4.6 mm; mobile phase: 80% isohexane/20% propanol; detection: 220 nm].
LC-MS (Method 3): $R_t$=1.78 min; MS (ESIpos): m/z=579 [M+H]⁺

Example 32

7-[(3R,4R)-3,4-Dihydroxypyrrolidin-1-yl]-6-fluoro-4-oxo-N-[(2)-1-(trifluoromethoxy)butan-2-yl]-1-(2,4,6-trifluorophenyl)-1,4-dihydro-1,8-naphthyridine-3-carboxamide (Diastereomer 2)

218 mg of 7-[(3R,4R)-3,4-dihydroxypyrrolidin-1-yl]-6-fluoro-4-oxo-N-[(2)-1-(trifluoromethoxy)butan-2-yl]-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak ID, 5 μm, 250×20 mm; mobile phase: 85% n-heptane/15% isopropanol; flow rate 15 ml/min; temperature: 30° C., detection: 220 nm).

Diastereomer 2: 64.2 mg (97.6% de)

$R_t$=6.23 min [analytical HPLC: column Daicel® Chiralpak ID, 1 ml/min; 5 μm, 250×4.6 mm; mobile phase: 80% isohexane/20% propanol; detection: 220 nm].

LC-MS (Method 3): $R_t$=1.78 min; MS (ESIpos): m/z=579 $[M+H]^+$

Example 33

7-[(3R,4R)-3,4-Dihydroxypyrrolidin-1-yl]-6-fluoro-4-oxo-N-[(3)-1,1,1,2,2-pentafluoropentan-3-yl]-1-(2,4,6-trifluorophenyl)-1,4-dihydro-1,8-naphthyridine-3-carboxamide (Diastereomer 1)

292 mg of 7-[(3R,4R)-3,4-dihydroxypyrrolidin-1-yl]-6-fluoro-4-oxo-N-[(3)-1,1,1,2,2-pentafluoropentan-3-yl]-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak IA, 5 μm, 250×20 mm; mobile phase: 85% n-heptane/15% isopropanol; flow rate 15 ml/min; temperature: 30° C., detection: 220 nm).

Diastereomer 1: 111.6 mg (>99% de)

$R_t$=6.10 min [analytical HPLC: column Daicel® Chiralpak IA, 1 ml/min; 5 μm, 250×4.6 mm; mobile phase: 80% isohexane/20% propanol; detection: 265 nm].

LC-MS (Method 3): $R_t$=1.93 min; MS (ESIpos): m/z=599 $[M+H]^+$

Example 34

7-[(3R,4R)-3,4-Dihydroxypyrrolidin-1-yl]-6-fluoro-4-oxo-N-[(3)-1,1,1,2,2-pentafluoropentan-3-yl]-1-(2,4,6-trifluorophenyl)-1,4-dihydro-1,8-naphthyridine-3-carboxamide (Diastereomer 2)

292 mg of 7-[(3R,4R)-3,4-dihydroxypyrrolidin-1-yl]-6-fluoro-4-oxo-N-[(3)-1,1,1,2,2-pentafluoropentan-3-yl]-1-(2,4,6-trifluorophenyl)-1,4-dihydro-1,8-naphthyridine-3-carboxamide (diastereomer mixture)

were separated into the diastereomers by chiral HPLC (preparative HPLC: column Daicel® Chiralpak IA, 5 μm, 250×20 mm; mobile phase: 85% n-heptane/15% isopropanol; flow rate 15 ml/min; temperature: 30° C., detection: 220 nm).

Diastereomer 2: 110.1 mg 99.5% de)

$R_t$=6.76 min [analytical HPLC: column Daicel® Chiralpak IA, 1 ml/min; 5 μm, 250×4.6 mm; mobile phase: 80% isohexane/20% propanol; detection: 265 nm], LC-MS (Method 3): $R_t$=1.93 min; MS (ESIpos): m/z=599 $[M+H]^+$

Example 35

(3R,4R)-1-[3-Fluoro-5-oxo-6-{[(2S)-1,1,1-trifluorobutan-2-yl]carbamoyl}-8-(2,4,6-trifluoro-phenyl)-5,8-dihydro-1,8-naphthyridin-2-yl]-4-hydroxypyrrolidin-3-yl acetate

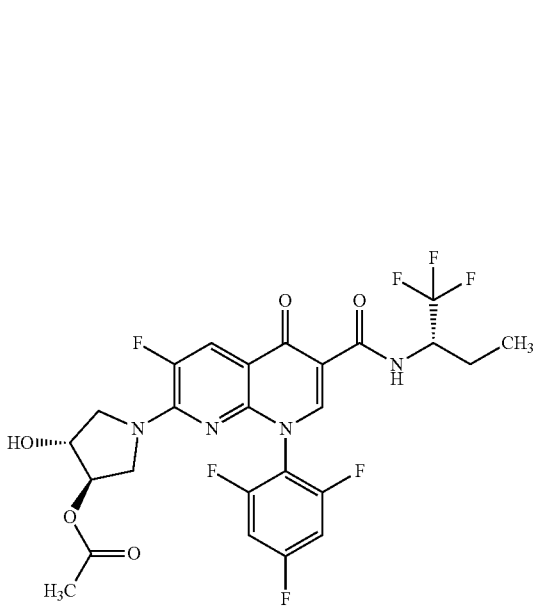 [SMILES: CC[C@H](NC(=O)c1cn(-c2c(F)cc(F)cc2F)c2nc(N3C[C@@H](O)[C@H](OC(C)=O)C3)c(F)cc2c1=O)C(F)(F)F]

(7-[(3R,4R)-3,4-Dihydroxypyrrolidin-1-yl]-6-fluoro-4-oxo-N-[(2S)-1,1,1-trifluorobutan-2-yl]-1-(2,4,6-trifluorophenyl)-1,4-dihydro-1,8-naphthyridine-3-carboxamide (60.0 mg, 109 μmol) was dissolved in dichloromethane (1.0 ml), and dimethylaminopyridine (1.34 mg, 10.9 μmol) was added. At 0° C., acetyl chloride (5.4 μl, 77 μmol) was added dropwise, and the mixture was stirred at RT for 3 h. The reaction mixture was concentrated and the residue was taken up in acetonitrile and purified by preparative HPLC (acetonitrile/water with formic acid, C18 RP-HPLC). The product fractions were combined, concentrated and lyophilized from acetonitrile/water overnight. This gave 25.9 mg (39% of theory, 99% pure) of the title compound.

LC-MS (Method 3): $R_t$=2.07 min; MS (ESIpos): m/z=591 $[M+H]^+$ $^1$H-NMR (400 MHz, DMSO-d6) δ[ppm]: −0.149 (0.90), −0.008 (7.72), 0.008 (6.90), 0.146 (0.88), 0.952 (2.34), 0.971 (5.26), 0.989 (2.57), 1.625 (0.47), 1.642 (0.53), 1.651 (0.53), 1.661 (0.51), 1.668 (0.53), 1.685 (0.41), 1.852 (0.41), 1.871 (0.49), 1.881 (0.58), 1.897 (0.45), 1.990 (16.00), 2.328 (0.68), 2.523 (1.81), 2.670 (0.68), 2.710 (0.41), 4.139 (0.45), 4.738 (0.51), 4.951 (0.41), 5.607 (0.94), 7.555 (1.38), 7.577 (2.51), 7.599 (1.40), 8.036 (2.20), 8.067 (2.20), 8.858 (5.18), 10.300 (1.75), 10.324 (1.68).

The following reactions were prepared analogously to Example 1 according to GP1:

| Example | IUPAC name<br>Structure<br>LC-MS (method): retention time; detected mass<br>¹H NMR<br>amine used<br>(yield, purity) |
|---|---|
| 36 | 7-[(3R,4R)-3,4-dihydroxypyrrolidin-1-yl]-6-fluoro-4-oxo-N-[(2R)-1,1,1-trifluoro-butan-2-yl]-1-(2,4,6-trifluorophenyl)-1,4-dihydro-1,8-naphthyridine-3-carboxamide<br><br>LC-MS (Method 3): $R_t$ = 1.78 min; MS (ESIpos): m/z = 549 [M + H]⁺<br>¹H NMR (400 MHz, DMSO-d6) δ [ppm]: −0.149 (0.60), −0.008 (5.32), 0.008 (4.91), 0.147 (0.57), 0.950 (7.28), 0.969 (16.00), 0.987 (7.85), 1.604 (1.06), 1.622 (1.40), 1.629 (1.28), 1.639 (1.74), 1.647 (1.55), 1.657 (1.47), 1.664 (1.70), 1.682 (1.28), 1.851 (1.32), 1.860 (1.51), 1.868 (1.47), 1.879 (1.74), 1.885 (1.51), 1.895 (1.32), 1.904 (1.13), 1.914 (0.98), 2.328 (1.36), 2.366 (0.94), 2.524 (4.68), 2.670 (1.43), 2.710 (0.98), 3.067 (0.79), 3.691 (0.87), 3.906 (1.81), 4.012 (1.25), 4.735 (1.43), 4.754 (1.36), 5.200 (4.83), 7.558 (3.89), 7.580 (6.87), 7.601 (3.89), 7.999 (7.58), 8.030 (7.51), 8.840 (13.17), 10.329 (5.21), 10.353 (5.02).<br>(2R)-1,1,1-trifluorobutan-2-amine hydrochloride<br>(69% of theory, 99% pure) |
| 37 | 6-chloro-N-[(1S)-1-cyclopropyl-2,2,2-trifluoroethyl]-7-[(3R,4R)-3,4-dihydroxy-pyrrolidin-1-yl]-4-oxo-1-(2,4,6-trifluorophenyl)-1,4-dihydro-1,8-naphthyridine-3-carboxamide<br>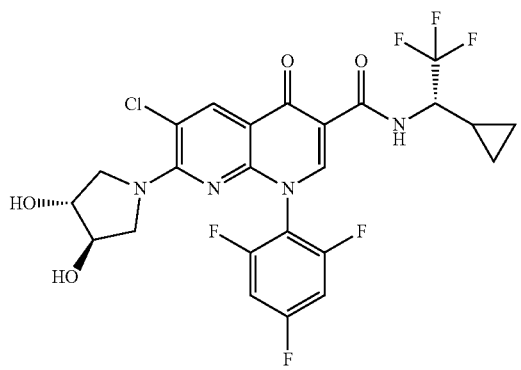 [SMILES: O=C(N[C@@H](C1CC1)C(F)(F)F)c1cn(-c2c(F)cc(F)cc2F)c2nc(N3C[C@@H](O)[C@H](O)C3)c(Cl)cc2c1=O]<br>LC-MS (Method 3): $R_t$ = 1.89 min; MS (ESIpos): m/z = 577.11 [M + H]⁺<br>¹H NMR (400 MHz, DMSO-d6) δ [ppm]: −0.008 (1.73), 0.008 (1.41), 0.320 (1.55), 0.330 (2.59), 0.342 (2.48), 0.353 (1.79), 0.365 (1.00), 0.522 (1.67), 0.534 (2.52), 0.547 (2.55), 0.553 (2.84), 0.571 (2.95), 0.580 (2.20), 0.591 (1.98), 0.601 (1.63), 0.615 (0.97), 0.630 (1.27), 0.639 (1.31), 0.650 (2.61), 0.660 (2.01), 0.667 (1.80), 0.685 (0.98), 0.693 (0.58), 1.170 (0.48), 1.182 (1.01), 1.190 (1.45), 1.203 (2.41), 1.212 (1.79), 1.223 (2.40), 1.235 (1.31), 1.244 (0.87), 2.329 (0.60), 2.367 (0.41), 2.524 (2.02), 2.671 (0.70), 2.711 (0.47), 3.683 (0.57), 3.930 (5.71), 4.342 (1.32), 4.363 (2.25), 4.384 (2.19), 4.405 (1.19), 5.188 (9.80), 5.196 (9.81), 7.564 (3.82), 7.585 (6.78), 7.607 (3.80), 8.284 (16.00), 8.856 (13.94), 10.356 (5.25), 10.379 (5.07).<br>(1S)-1-cyclopropyl-2,2,2-trifluoroethanamine hydrochloride<br>(81% of theory, 99% pure) |

| Example | IUPAC name<br>Structure<br>LC-MS (method): retention time; detected mass<br>¹H NMR<br>amine used<br>(yield, purity) |
|---|---|
| 38 | 6-chloro-7-[(3R,4R)-3,4-dihydroxypyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide 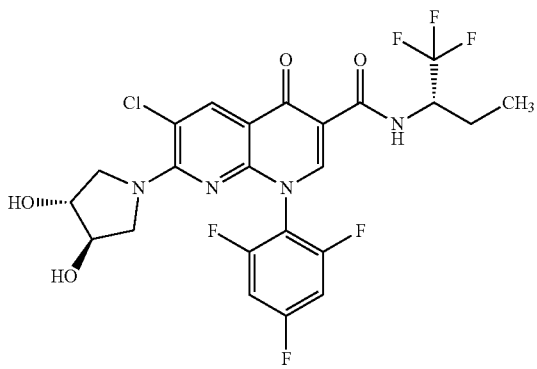 [SMILES: CC[C@H](NC(=O)c1cn(-c2c(F)cc(F)cc2F)c2nc(N3C[C@@H](O)[C@H](O)C3)c(Cl)cc2c1=O)C(F)(F)F] LC-MS (Method 3): $R_t$ = 1.86 min; MS (ESIpos): m/z = 565 [M + H]⁺<br>¹H NMR (400 MHz, DMSO-d6) δ [ppm]: −0.008 (1.70), 0.008 (1.59), 0.951 (7.25), 0.970 (16.00), 0.988 (7.86), 1.609 (1.08), 1.626 (1.45), 1.633 (1.27), 1.644 (1.73), 1.652 (1.56), 1.662 (1.48), 1.669 (1.66), 1.687 (1.24), 1.832 (0.43), 1.850 (1.31), 1.860 (1.52), 1.869 (1.52), 1.879 (1.75), 1.885 (1.54), 1.895 (1.33), 1.904 (1.13), 1.913 (0.96), 2.328 (0.61), 2.367 (0.50), 2.524 (1.95), 2.671 (0.63), 2.711 (0.53), 3.671 (0.56), 3.930 (5.75), 4.735 (1.45), 4.750 (1.34), 5.185 (13.17), 5.192 (13.00), 7.566 (4.26), 7.588 (7.94), 7.610 (4.20), 8.279 (13.40), 8.865 (12.98), 10.212 (5.29), 10.236 (4.98).<br>(2S)-1,1,1-trifluorobutan-2-amine hydrochloride<br>(72% of theory, 99% pure) |
| 39 | 1-(3,5-difluoropyridin-2-yl)-7-[(3R,4R)-3,4-dihydroxypyrrolidin-1-yl]-6-fluoro-4-oxo-N-[(2)-3,3,4,4,4-pentafluorobutan-2-yl]-1,4-dihydro-1,8-naphthyridine-3-carboxamide (diastereomer mixture) 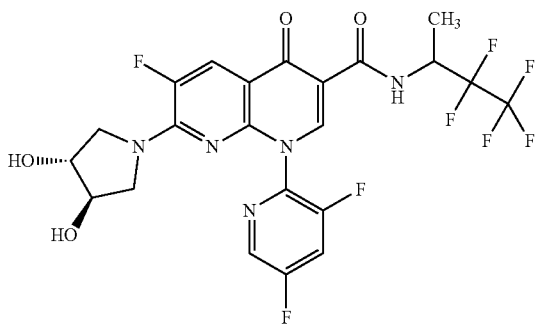 [SMILES: CC(NC(=O)c1cn(-c2ncc(F)cc2F)c2nc(N3C[C@@H](O)[C@H](O)C3)c(F)cc2c1=O)C(F)(F)C(F)(F)F] LC-MS (Method 3): $R_t$ = 1.71 min; MS (ESIpos): m/z = 568 [M + H]⁺<br>¹H NMR (400 MHz, DMSO-d6) δ [ppm]: −0.149 (0.43), −0.008 (4.17), 0.008 (3.72), 0.146 (0.45), 1.389 (16.00), 1.405 (15.88), 2.328 (0.93), 2.367 (0.71), 2.524 (2.99), 2.670 (0.91), 2.711 (0.68), 3.067 (0.88), 3.691 (1.06), 3.918 (3.12), 4.976 (1.14), 4.997 (1.93), 5.018 (2.30), 5.041 (2.36), 5.063 (2.17), 5.084 (1.55), 5.102 (1.09), 5.200 (5.07), 7.997 (7.54), 8.028 (7.69), 8.329 (2.76), 8.351 (5.01), 8.373 (2.71), 8.616 (11.67), 8.622 (10.91), 8.837 (7.39), 8.844 (8.07), 10.451 (7.34), 10.475 (7.07).<br>3,3,4,4,4-pentafluorobutan-2-amine hydrochloride (racemate)<br>(78% of theory, 99% pure) |

| Example | IUPAC name<br>Structure<br>LC-MS (method): retention time; detected mass<br>¹H NMR<br>amine used<br>(yield, purity) |
|---|---|
| 40 | 1-(2-chloro-4,6-difluorophenyl)-7-[(3R,4R)-3,4-dihydroxypyrrolidin-1-yl]-6-fluoro-4-oxo-N-[(2S)-1,1,1-trifluorobutan-2-yl]-1,4-dihydro-1,8-naphthyridine-3-carboxamide (atropisomer mixture)<br>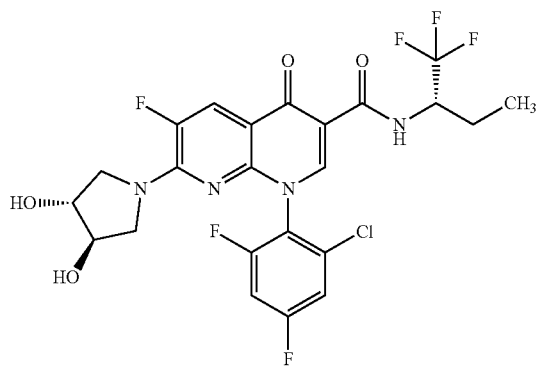 [SMILES: CC[C@H](NC(=O)c1cn(-c2c(F)cc(F)cc2Cl)c2nc(N3C[C@@H](O)[C@H](O)C3)c(F)cc2c1=O)C(F)(F)F]<br>LC-MS (Method 3): $R_t$ = 1.83 min; MS (ESIpos): m/z = 565 [M + H]⁺<br>¹H NMR (400 MHz, DMSO-d6) δ [ppm]: 0.008 (1.02), 0.949 (4.31), 0.958 (5.08), 0.967 (9.96), 0.977 (9.85), 0.985 (5.50), 0.995 (4.62), 1.603 (0.66), 1.614 (0.80), 1.621 (1.07), 1.638 (1.64), 1.648 (1.55), 1.657 (1.71), 1.664 (1.33), 1.674 (1.24), 1.681 (0.93), 1.692 (0.76), 1.852 (1.27), 1.862 (1.49), 1.870 (1.55), 1.880 (1.71), 1.898 (1.31), 1.905 (1.13), 1.915 (0.91), 2.328 (0.73), 2.366 (0.58), 2.524 (2.35), 2.670 (0.78), 2.710 (0.62), 3.018 (0.87), 3.220 (0.93), 3.693 (0.95), 3.891 (1.82), 4.013 (1.37), 4.734 (1.57), 4.750 (1.47), 5.202 (4.19), 7.686 (0.84), 7.693 (1.27), 7.709 (1.69), 7.717 (2.44), 7.728 (3.11), 7.732 (3.15), 7.740 (3.53), 7.751 (3.53), 7.763 (2.35), 8.004 (7.55), 8.035 (7.54), 8.794 (16.00), 10.347 (3.64), 10.351 (3.73), 10.371 (3.57), 10.375 (3.55).<br>(2S)-1,1,1-trifluorobutan-2-amine hydrochloride<br>(83% of theory, 100% pure) |
| 41 | 1-(2-chloro-4,6-difluorophenyl)-7-[(3R,4R)-3,4-dihydroxypyrrolidin-1-yl]-6-fluoro-4-oxo-N-(1,1,1-trifluoro-2-methylpropan-2-yl)-1,4-dihydro-1,8-naphthyridine-3-carboxamide (atropisomer mixture)<br>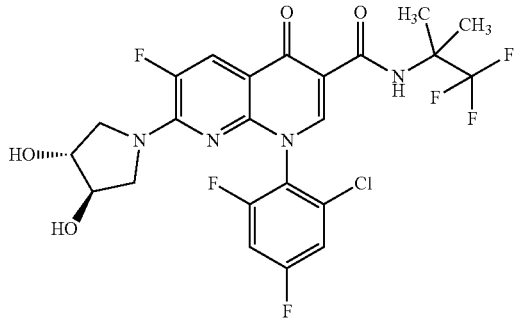 [SMILES: CC(C)(NC(=O)c1cn(-c2c(F)cc(F)cc2Cl)c2nc(N3C[C@@H](O)[C@H](O)C3)c(F)cc2c1=O)C(F)(F)F]<br>LC-MS (Method 3): $R_t$ = 1.85 min; MS (ESIpos): m/z = 565 [M + H]⁺<br>¹H NMR (400 MHz, DMSO-d6) δ [ppm]: −0.008 (1.27), 0.008 (0.95), 1.634 (16.00), 2.524 (0.91), 3.894 (0.45), 5.193 (1.23), 7.709 (0.41), 7.717 (0.65), 7.726 (0.67), 7.732 (0.70), 7.739 (0.91), 7.749 (0.72), 7.764 (0.59), 8.012 (1.99), 8.044 (1.97), 8.723 (3.93), 10.582 (2.93).<br>1,1,1-trifluoro-2-methylpropan-2-amine<br>(96% of theory, 99% pure) |

| Example | IUPAC name<br>Structure<br>LC-MS (method): retention time; detected mass<br>¹H NMR<br>amine used<br>(yield, purity) |
|---|---|
| 42 | 1-(2-chloro-4,6-difluorophenyl)-N-[(1S)-1-cyclopropyl-2,2,2-trifluoroethyl]-7-[(3R,4R)-3,4-dihydroxypyrrolidin-1-yl]-6-fluoro-4-oxo-1,4-dihydro-1,8-naphthyridine-3-carboxamide (atropisomer mixture) |

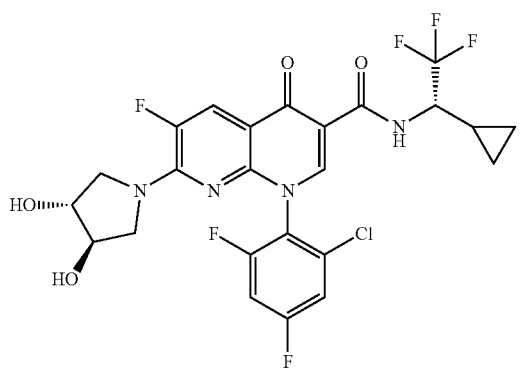 [SMILES: O=C(N[C@@H](C1CC1)C(F)(F)F)c1cn(-c2c(F)cc(F)cc2Cl)c2nc(N3C[C@@H](O)[C@H](O)C3)c(F)cc2c1=O]

LC-MS (Method 3): $R_t$ = 1.86 min; MS (ESIpos): m/z = 577 [M + H]⁺
¹H NMR (400 MHz, DMSO-d6) δ [ppm]: −0.149 (0.75), −0.008 (7.24), 0.008 (5.85), 0.146 (0.80), 0.317 (1.19), 0.328 (2.21), 0.340 (2.61), 0.351 (2.36), 0.363 (1.54), 0.374 (0.62), 0.526 (2.24), 0.543 (2.26), 0.555 (2.21), 0.565 (2.36), 0.575 (2.54), 0.586 (2.24), 0.596 (1.92), 0.610 (1.29), 0.624 (1.02), 0.634 (1.34), 0.644 (1.92), 0.655 (2.24), 0.668 (1.99), 0.677 (1.49), 1.167 (0.47), 1.179 (1.00), 1.187 (1.42), 1.199 (2.44), 1.209 (1.87), 1.220 (2.44), 1.232 (1.34), 1.241 (0.85), 1.253 (0.42), 2.327 (1.12), 2.366 (0.77), 2.523 (3.66), 2.665 (0.95), 2.670 (1.24), 2.710 (0.82), 3.015 (0.85), 3.221 (0.90), 3.687 (0.95), 3.894 (1.79), 4.013 (1.37), 4.340 (0.80), 4.359 (1.64), 4.378 (2.12), 4.399 (1.64), 4.418 (0.75), 5.199 (4.33), 7.684 (0.85), 7.691 (1.39), 7.701 (1.37), 7.707 (1.59), 7.715 (2.76), 7.724 (2.84), 7.730 (2.86), 7.737 (3.66), 7.747 (3.09), 7.761 (2.36), 8.008 (7.12), 8.039 (7.07), 8.785 (16.00), 10.486 (4.95), 10.510 (4.70).
(1S)-1-cyclopropyl-2,2,2-trifluoroethanamine hydrochloride
(81% of theory, 99% pure)

| 43 | 1-(2-chloro-4,6-difluorophenyl)-N-[(1S)-1-cyclopropylethyl]-7-[(3R,4R)-3,4-dihydroxypyrrolidin-1-yl]-6-fluoro-4-oxo-1,4-dihydro-1,8-naphthyridine-3-carboxamide (atropisomer mixture) |
|---|---|

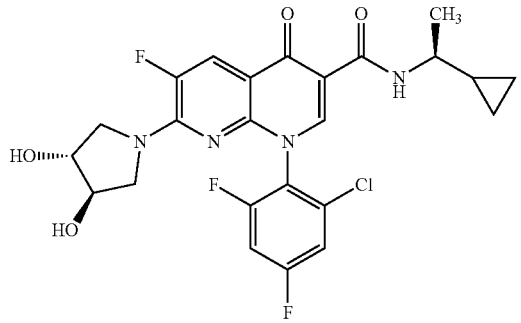 [SMILES: C[C@H](NC(=O)c1cn(-c2c(F)cc(F)cc2Cl)c2nc(N3C[C@@H](O)[C@H](O)C3)c(F)cc2c1=O)C1CC1]

LC-MS (Method 3): $R_t$ = 1.67 min; MS (ESIpos): m/z = 523 [M + H]⁺
¹H NMR (400 MHz, DMSO-d6) δ [ppm]: −0.008 (6.44), 0.008 (2.37), 0.217 (1.40), 0.228 (2.02), 0.240 (2.94), 0.251 (2.63), 0.264 (1.75), 0.277 (2.10), 0.285 (2.72), 0.292 (2.28), 0.305 (1.58), 0.401 (0.92), 0.412 (1.75), 0.422 (2.76), 0.433 (3.20), 0.443 (3.59), 0.453 (3.51), 0.459 (2.85), 0.467 (3.11), 0.479 (1.88), 0.487 (1.23), 0.959 (1.27), 0.964 (1.45), 0.971 (2.02), 0.977 (2.10), 0.984 (1.93), 0.991 (1.93), 0.996 (1.71), 1.004 (1.14), 1.213 (12.01), 1.220 (11.79), 1.230 (11.88), 1.236 (10.48), 2.328 (1.01), 2.366 (0.75), 2.519 (5.57), 2.670 (1.01), 2.710 (0.70), 3.008 (0.70), 3.488 (1.14), 3.507 (2.24), 3.524 (2.98), 3.540 (2.10), 3.560 (1.05), 3.669 (0.75), 3.894 (1.75), 5.186 (5.92), 7.676 (1.01), 7.682 (1.40), 7.693 (1.71), 7.698 (1.84), 7.706 (2.54), 7.717 (3.07), 7.722 (3.07), 7.729 (3.42), 7.739 (2.98), 7.751 (2.15), 7.980 (7.80), 8.011 (7.63), 8.653 (16.00), 9.881 (3.29), 9.887 (3.20), 9.902 (3.16), 9.906 (2.94).
(S)-1-cyclopropylethanamine
(84% of theory, 99% pure)

| Example | IUPAC name<br>Structure<br>LC-MS (method): retention time; detected mass<br>¹H NMR<br>amine used<br>(yield, purity) |
|---|---|
| 44 | 1-(2-chloro-4,6-difluorophenyl)-N-[(1R)-1-cyclopropylethyl]-7-[(3R,4R)-3,4-dihydroxypyrrolidin-1-yl]-6-fluoro-4-oxo-1,4-dihydro-1,8-naphthyridine-3-carboxamide (atropisomer mixture)<br><br>LC-MS (Method 3): $R_t$ = 1.67 min; MS (ESIpos): m/z = 523 [M + H]⁺<br>¹H NMR (400 MHz, DMSO-d6) δ [ppm]: −0.008 (1.78), 0.008 (1.48), 0.218 (1.23), 0.229 (2.01), 0.240 (2.94), 0.252 (2.71), 0.265 (1.58), 0.279 (2.08), 0.286 (2.81), 0.294 (2.36), 0.307 (1.73), 0.328 (0.45), 0.392 (0.43), 0.402 (0.78), 0.413 (1.63), 0.423 (2.69), 0.434 (3.19), 0.445 (3.77), 0.454 (3.59), 0.459 (2.86), 0.467 (3.19), 0.480 (2.03), 0.487 (1.31), 0.501 (0.65), 0.959 (1.18), 0.964 (1.36), 0.972 (1.93), 0.977 (2.11), 0.984 (1.88), 0.992 (2.01), 0.997 (1.81), 1.004 (1.23), 1.010 (1.05), 1.213 (11.53), 1.220 (12.21), 1.229 (12.16), 1.236 (11.68), 2.328 (0.53), 2.367 (0.48), 2.524 (1.93), 2.671 (0.60), 2.711 (0.50), 3.006 (0.70), 3.227 (0.78), 3.486 (1.16), 3.505 (2.36), 3.522 (3.27), 3.539 (2.36), 3.558 (1.18), 3.575 (0.40), 3.677 (0.78), 3.898 (1.76), 5.188 (5.70), 7.676 (0.85), 7.684 (1.66), 7.692 (1.36), 7.700 (1.63), 7.707 (3.09), 7.715 (2.56), 7.730 (3.99), 7.738 (2.84), 7.749 (2.66), 7.754 (2.44), 7.979 (8.26), 8.011 (8.16), 8.653 (16.00), 9.886 (3.74), 9.904 (3.77).<br>(R)-1-cyclopropylethanamine<br>(91% of theory, 99% pure) |

Example 45

1-(3,5-Difluoropyridin-2-yl)-7-[(3R,4R)-3,4-dihydroxypyrrolidin-1-yl]-6-fluoro-4-oxo-N-[(2)-3,3,4,4,4-pentafluorobutan-2-yl]-1,4-dihydro-1,8-naphthyridine-3-carboxamide (Diastereomer 1)

486 mg of 1-(3,5-difluoropyridin-2-yl)-7-[(3R,4R)-3,4-dihydroxypyrrolidin-1-yl]-6-fluoro-4-oxo-N-[(2)-3,3,4,4,4-pentafluorobutan-2-yl]-1,4-dihydro-1,8-naphthyridine-3-carboxamide (diastereomer mixture) were separated into the diastereomers by chiral HPLC (preparative HPLC: column Daicel® Chiralpak IE, 5 μm, 250×20 mm; mobile phase: 70% n-heptane/30% isopropanol+0.2% diethylamine; flow rate 15 ml/min; temperature: 25° C., detection: 270 nm).

Diastereomer 1: 172.5 mg (>99% de)

$R_t$=4.82 min [analytical HPLC: column Daicel® Chiralpak IE, 1 ml/min; 3 μm, 50×4.6 mm; mobile phase: 80% isohexane/20% isopropanol+0.2% diethylamine; detection: 220 nm].

Example 46

1-(3,5-Difluoropyridin-2-yl)-7-[(3R,4R)-3,4-dihydroxypyrrolidin-1-yl]-6-fluoro-4-oxo-N-[(2)-3,3,4,4,4-pentafluorobutan-2-yl]-1,4-dihydro-1,8-naphthyridine-3-carboxamide (Diastereomer 2)

486 mg of 1-(3,5-difluoropyridin-2-yl)-7-[(3R,4R)-3,4-dihydroxypyrrolidin-1-yl]-6-fluoro-4-oxo-N-[(2)-3,3,4,4,4-pentafluorobutan-2-yl]-1,4-dihydro-1,8-naphthyridine-3-carboxamide (diastereomer mixture) were separated into the diastereomers by chiral HPLC (preparative HPLC: column Daicel® Chiralpak IE, 5 μm, 250×20 mm; mobile phase: 70% n-heptane/30% isopropanol+diethylamine; flow rate 15 ml/min; temperature: 25° C., detection: 270 nm).

Diastereomer 2: 160.3 mg (>99% de)

$R_t$=7.11 min [analytical HPLC: column Daicel® Chiralpak IE, 1 ml/min; 3 μm, 50×4.6 mm; mobile phase: 80% isohexane/20% isopropanol+0.2% diethylamine; detection: 220 nm].

Example 47

1-(2-Chloro-4,6-difluorophenyl)-7-[(3R,4R)-3,4-dihydroxypyrrolidin-1-yl]-6-fluoro-4-oxo-N-[(2S)-1,1,1-trifluorobutan-2-yl]-1,4-dihydro-1,8-naphthyridine-3-carboxamide (Atropisomer 1)

103 mg of 1-(2-chloro-4,6-difluorophenyl)-7-[(3R,4R)-3,4-dihydroxypyrrolidin-1-yl]-6-fluoro-4-oxo-N-[(2S)-1,1,1-trifluorobutan-2-yl]-1,4-dihydro-1,8-naphthyridine-3-carboxamide (atropisomer mixture) were separated into the atropisomers by chiral HPLC (preparative HPLC: column Daicel® Chiralpak IG, 5 μm, 250×20 mm; mobile phase:

75% n-heptane/25% isopropanol+0.2% diethylamine; flow rate 15 ml/min; temperature: 30° C., detection: 265 nm).

Atropisomer 1: 38 mg (>99% de)

$R_t$=4.71 min [analytical HPLC: column Daicel® Chiralpak IG, 1 ml/min; 5 μm, 250×4.6 mm; mobile phase: 70% isohexane/30% isopropanol+0.2% diethylamine; detection: 265 nm].

Example 48

1-(2-Chloro-4,6-difluorophenyl)-7-[(3R,4R)-3,4-dihydroxypyrrolidin-1-yl]-6-fluoro-4-oxo-N-[(2S)-1,1,1-trifluorobutan-2-yl]-1,4-dihydro-1,8-naphthyridine-3-carboxamide (atropisomer 2)

103 mg of 1-(2-chloro-4,6-difluorophenyl)-7-[(3R,4R)-3,4-dihydroxypyrrolidin-1-yl]-6-fluoro-4-oxo-N-[(2S)-1,1,1-trifluorobutan-2-yl]-1,4-dihydro-1,8-naphthyridine-3-carboxamide (atropisomer mixture) were separated into the atropisomers by chiral HPLC (preparative HPLC: column Daicel® Chiralpak IG, 5 μm, 250×20 mm; mobile phase: 75% n-heptane/25% isopropanol+0.2% diethylamine; flow rate 15 ml/min; temperature: 30° C., detection: 265 nm).

Atropisomer 2: 40 mg (>99% de)

$R_t$=5.95 min [analytical HPLC: column Daicel® Chiralpak IG, 1 ml/min; 5 μm, 250×4.6 mm; mobile phase: 70% isohexane/30% isopropanol+0.2% diethylamine; detection: 265 nm].

Example 49

1-(2-Chloro-4,6-difluorophenyl)-7-[(3R,4R)-3,4-dihydroxypyrrolidin-1-yl]-6-fluoro-4-oxo-N-(1,1,1-trifluoro-2-methylpropan-2-yl)-1,4-dihydro-1,8-naphthyridine-3-carboxamide (Atropisomer 1)

119 mg of 1-(2-chloro-4,6-difluorophenyl)-7-[(3R,4R)-3,4-dihydroxypyrrolidin-1-yl]-6-fluoro-4-oxo-N-(1,1,1-trifluoro-2-methylpropan-2-yl)-1,4-dihydro-1,8-naphthyridine-3-carboxamide (atropisomer mixture) were separated into the atropisomers by chiral HPLC (preparative HPLC: column YMC Chiral art Amylose SA, 5 μm, 250×30 mm; mobile phase: 80% n-heptane/20% isopropanol+0.2% diethylamine; flow rate 30 ml/min; temperature: 30° C., detection: 265 nm).

Atropisomer 1: 26 mg (>99% de)

$R_t$=4.86 min [analytical HPLC: column YMC Chiralart Amylose SA, 1 ml/min; 5 μm, 250×4.6 mm; mobile phase: 70% n-heptane/30% isopropanol+0.2% diethylamine; detection: 265 nm].

Example 50

1-(2-Chloro-4,6-difluorophenyl)-7-[(3R,4R)-3,4-dihydroxypyrrolidin-1-yl]-6-fluoro-4-oxo-N-(1,1,1-trifluoro-2-methylpropan-2-yl)-1,4-dihydro-1,8-naphthyridine-3-carboxamide (Atropisomer 2)

119 mg of 1-(2-chloro-4,6-difluorophenyl)-7-[(3R,4R)-3,4-dihydroxypyrrolidin-1-yl]-6-fluoro-4-oxo-N-(1,1,1-trifluoro-2-methylpropan-2-yl)-1,4-dihydro-1,8-naphthyridine-3-carboxamide (atropisomer mixture) were separated into the atropisomers by chiral HPLC (preparative HPLC: column YMC Chiral art Amylose SA, 5 μm, 250×30 mm; mobile phase: 80% n-heptane/20% isopropanol+0.2% diethylamine; flow rate 30 ml/min; temperature: 30° C., detection: 265 nm).

Atropisomer 2: 25 mg (99% de)

$R_t$=5.42 min [analytical HPLC: column YMC Chiralart Amylose SA, 1 ml/min; 5 μm, 250×4.6 mm; mobile phase: 70% n-heptane/30% isopropanol+0.2% diethylamine; detection: 265 nm].

Example 51

1-(2-Chloro-4,6-difluorophenyl)-N-[(1S)-1-cyclopropyl-2,2,2-trifluoroethyl]-7-[(3R,4R)-3,4-dihydroxypyrrolidin-1-yl]-6-fluoro-4-oxo-1,4-dihydro-1,8-naphthyridine-3-carboxamide (Atropisomer 1)

103 mg of 1-(2-chloro-4,6-difluorophenyl)-N-[(1S)-1-cyclopropyl-2,2,2-trifluoroethyl]-7-[(3R,4R)-3,4-dihydroxypyrrolidin-1-yl]-6-fluoro-4-oxo-1,4-dihydro-1,8-naphthyridine-3-carboxamide (atropisomer mixture) were separated into the atropisomers by chiral HPLC (preparative HPLC: column Daicel® Chiralpak AD-H, 5 μm, 250×20 mm; mobile phase: 80% n-heptane/20% ethanol; flow rate 25 ml/min; temperature: 40° C., detection: 210 nm).

Atropisomer 1: 30 mg (99% de)

$R_t$=6.04 min [analytical HPLC: column Daicel® Chiralpak AI, 1 ml/min; 5 μm, 250×4.6 mm; mobile phase: 80% isohexane/20% ethanol; detection: 235 nm].

Example 52

1-(2-Chloro-4,6-difluorophenyl)-N-[(1S)-1-cyclopropyl-2,2,2-trifluoroethyl]-7-[(3R,4R)-3,4-dihydroxypyrrolidin-1-yl]-6-fluoro-4-oxo-1,4-dihydro-1,8-naphthyridine-3-carboxamide (Atropisomer 2)

103 mg of 1-(2-chloro-4,6-difluorophenyl)-N-[(1S)-1-cyclopropyl-2,2,2-trifluoroethyl]-7-[(3R,4R)-3,4-dihydroxypyrrolidin-1-yl]-6-fluoro-4-oxo-1,4-dihydro-1,8-naphthyridine-3-carboxamide (atropisomer mixture) were separated into the atropisomers by chiral HPLC (preparative HPLC: column Daicel® Chiralpak AD-H, 5 μm, 250×20 mm; mobile phase: 80% n-heptane/20% ethanol; flow rate 25 ml/min; temperature: 40° C., detection: 210 nm).

Atropisomer 2: 30 mg (89% de)

$R_t$=7.33 min [analytical HPLC: column Daicel® Chiralpak AI, 1 ml/min; 5 μm, 250×4.6 mm; mobile phase: 80% isohexane/20% ethanol; detection: 235 nm].

Example 53

N-[(1S)-1-Cyclopropyl-2,2,2-trifluoroethyl]-6-fluoro-7-(3-hydroxy-3-methylazetidin-1-yl)-4-oxo-1-(2,4,6-trifluorophenyl)-1,4-dihydro-1,8-naphthyridine-3-carboxamide

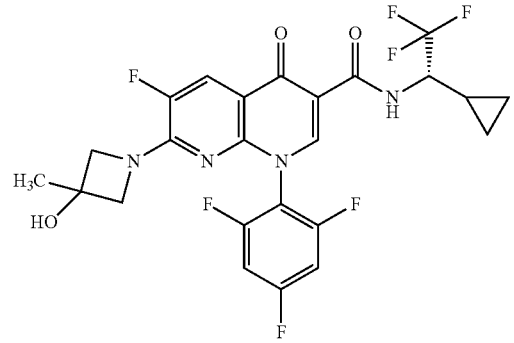 [SMILES: CC1(O)CN(c2nc3c(cc2F)c(=O)c(C(=O)N[C@@H](C2CC2)C(F)(F)F)cn3-c2c(F)cc(F)cc2F)C1]

50 mg of N-[(1S)-1-cyclopropyl-2,2,2-trifluoroethyl]-6-fluoro-4-oxo-7-(3H-[1,2,3]triazolo[4,5-b]pyridin-3-yloxy)-1-(2,4,6-trifluorophenyl)-1,4-dihydro-1,8-naphthyridine-3-carboxamide (84.3 µmol) were dissolved in DMF (980 µl). 3-Methylazetidin-3-ol hydrochloride (20.8 mg, 169 µmol) and N,N-diisopropylethylamine (51 µl, 290 µmol) were added and the mixture was stirred at RT for 2 h. 0.3 ml of 1 N hydrochloric acid and 1 ml of acetonitrile were then added, and the reaction mixture was purified by preparative HPLC (acetonitrile/water with formic acid, C18 RP-HPLC). The product fractions were combined, concentrated and lyophilized from acetonitrile/water overnight. This gave 36.2 mg (78% of theory, 99% pure) of the title compound.

LC-MS (Method 1): $R_t$=1.13 min; MS (ESIpos): m/z=545 [M+H]$^+$ $^1$H-NMR (400 MHz, DMSO-d6) δ[ppm]: −0.008 (2.92), 0.008 (2.80), 0.314 (0.84), 0.325 (1.33), 0.337 (1.27), 0.349 (1.02), 0.360 (0.50), 0.512 (0.90), 0.522 (1.35), 0.535 (1.27), 0.545 (1.38), 0.564 (1.40), 0.574 (1.14), 0.585 (1.02), 0.594 (0.87), 0.608 (0.52), 0.625 (0.77), 0.634 (0.73), 0.645 (1.26), 0.656 (1.01), 0.667 (0.95), 1.177 (0.55), 1.185 (0.79), 1.198 (1.31), 1.206 (0.92), 1.218 (1.38), 1.230 (0.71), 1.382 (16.00), 2.328 (0.67), 2.367 (0.45), 2.670 (0.60), 2.711 (0.41), 3.896 (0.45), 4.350 (0.73), 4.372 (1.28), 4.394 (1.17), 4.413 (0.68), 5.673 (9.48), 7.535 (2.55), 7.557 (4.79), 7.579 (2.54), 8.000 (4.69), 8.028 (4.62), 8.835 (8.40), 10.440 (2.87), 10.464 (2.65).

Example 54

N-[(1S)-1-Cyclopropyl-2,2,2-trifluoroethyl]-6-fluoro-7-(3-hydroxyazetidin-1-yl)-4-oxo-1-(2,4,6-trifluorophenyl)-1,4-dihydro-1,8-naphthyridine-3-carboxamide

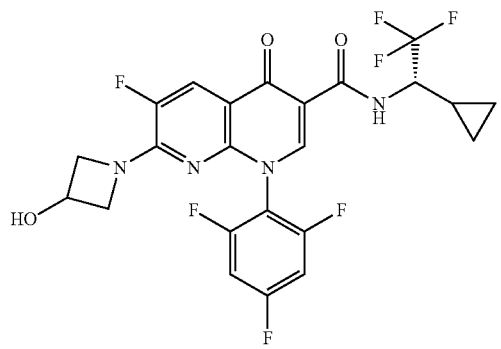 [SMILES: O=C(N[C@@H](C1CC1)C(F)(F)F)c1cn(-c2c(F)cc(F)cc2F)c2nc(N3CC(O)C3)c(F)cc2c1=O]

50 mg of N-[(1S)-1-cyclopropyl-2,2,2-trifluoroethyl]-6-fluoro-4-oxo-7-(3H-[1,2,3]triazolo[4,5-b]pyridin-3-yloxy)-1-(2,4,6-trifluorophenyl)-1,4-dihydro-1,8-naphthyridine-3-carboxamide (84.3 µmol) were dissolved in DMF (980 µl). Azetidin-3-ol hydrochloride (18.5 mg, 169 µmol) and N,N-diisopropylethylamine (51 µl, 290 µmol) were added and the mixture was stirred at RT for 2 h. 0.3 ml of 1 N hydrochloric acid and 1 ml of acetonitrile were then added, and the reaction mixture was purified by preparative HPLC (acetonitrile/water with formic acid, C18 RP-HPLC). The product fractions were combined, concentrated and lyophilized from acetonitrile/water overnight. This gave 32.2 mg (71% of theory, 99% pure) of the title compound.

LC-MS (Method 1): $R_t$=1.08 min; MS (ESIpos): m/z=531 [M+H]$^+$ $^1$H-NMR (400 MHz, DMSO-d6) δ[ppm]: −0.149 (0.55), −0.008 (6.99), 0.008 (4.19), 0.146 (0.49), 0.314 (2.27), 0.324 (3.51), 0.337 (3.32), 0.348 (2.57), 0.360 (1.23), 0.511 (2.49), 0.522 (3.55), 0.534 (3.29), 0.545 (3.63), 0.563 (3.70), 0.573 (2.93), 0.584 (2.64), 0.594 (2.21), 0.608 (1.40), 0.624 (1.96), 0.634 (1.95), 0.644 (3.27), 0.655 (2.74), 0.660 (2.57), 0.667 (2.47), 0.676 (1.25), 0.689 (0.81), 1.164 (0.76), 1.176 (1.47), 1.185 (2.06), 1.197 (3.32), 1.205 (2.49), 1.217 (3.15), 1.229 (1.72), 1.238 (1.19), 1.250 (0.49), 2.328 (0.85), 2.366 (0.70), 2.524 (4.17), 2.670 (0.85), 2.710 (0.57), 3.821 (1.08), 4.330 (1.23), 4.350 (2.42), 4.371 (3.53), 4.392 (3.34), 4.412 (1.87), 4.501 (0.94), 4.517 (2.23), 4.528 (3.61), 4.544 (3.31), 4.555 (1.74), 4.571 (0.57), 5.741 (9.80), 5.757 (9.35), 7.532 (5.86), 7.555 (10.75), 7.577 (5.65), 7.992 (9.11), 8.020 (8.88), 8.832 (16.00), 10.439 (6.76), 10.462 (6.37).

Example 55

N-[(1S)-1-Cyclopropyl-2,2,2-trifluoroethyl]-6-fluoro-7-[(2-hydroxyethyl)(methyl)amino]-4-oxo-1-(2,4,6-trifluorophenyl)-1,4-dihydro-1,8-naphthyridine-3-carboxamide

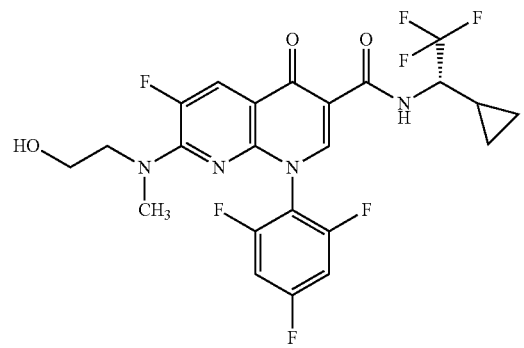 [SMILES: CN(CCO)c1nc2c(cc1F)c(=O)c(C(=O)N[C@@H](C1CC1)C(F)(F)F)cn2-c1c(F)cc(F)cc1F]

80 mg of N-[(1S)-1-cyclopropyl-2,2,2-trifluoroethyl]-6-fluoro-4-oxo-7-(3H-[1,2,3]triazolo[4,5-b]pyridin-3-yloxy)-1-(2,4,6-trifluorophenyl)-1,4-dihydro-1,8-naphthyridine-3-carboxamide (135 µmol) were dissolved in DMF (980 µl). 2-(Methylamino)ethanol (20.3 mg, 270 µmol) and N, N-diisopropylethylamine (82 µl, 470 µmol) were added and the mixture was stirred at RT for 2 h. 0.2 ml of 1 N hydrochloric acid and 2 ml of acetonitrile were added, and the reaction mixture was purified by preparative HPLC (acetonitrile/water with formic acid, C18 RP-HPLC). The product fractions were combined, concentrated and lyophilized from acetonitrile/water overnight. This gave 45.1 mg (62% of theory, 99% pure) of the title compound.

LC-MS (Method 1): $R_t$=1.09 min; MS (ESIpos): m/z=533 [M+H]$^+$ $^1$H-NMR (400 MHz, DMSO-d6) δ[ppm]: −0.149 (0.80), −0.008 (7.20), 0.146 (0.77), 0.319 (1.97), 0.329 (3.20), 0.341 (3.09), 0.353 (2.45), 0.365 (1.17), 0.513 (2.13), 0.525 (3.31), 0.538 (2.91), 0.548 (3.25), 0.567 (3.33), 0.577 (2.75), 0.588 (2.40), 0.598 (2.05), 0.612 (1.25), 0.626 (1.68), 0.636 (1.63), 0.647 (2.93), 0.657 (2.53), 0.663 (2.40), 0.670 (2.37), 0.679 (1.15), 0.691 (0.80), 1.166 (0.59), 1.178 (1.23), 1.187 (1.81), 1.199 (3.04), 1.208 (2.21), 1.219 (2.99), 1.231 (1.63), 1.240 (1.12), 1.252 (0.48), 2.327 (1.49), 2.366 (1.23), 2.523 (5.39), 2.669 (1.60), 2.710 (1.20), 3.076 (9.76), 3.442 (6.83), 3.470 (5.87), 4.331 (0.40), 4.351 (1.63), 4.373 (2.85), 4.393 (2.80), 4.414 (1.49), 4.713 (2.96), 4.725 (6.51), 4.738 (3.01), 7.539 (5.52), 7.561 (10.56), 7.583 (5.60), 7.994 (9.63), 8.028 (9.44), 8.849 (16.00), 10.436 (6.37), 10.459 (6.16).

Example 56

N-(Dicyclopropylmethyl)-1-(3,5-difluoropyridin-2-yl)-6-fluoro-7-(3-hydroxy-3-methylazetidin-1-yl)-4-oxo-1,4-dihydro-1,8-naphthyridine-3-carboxamide

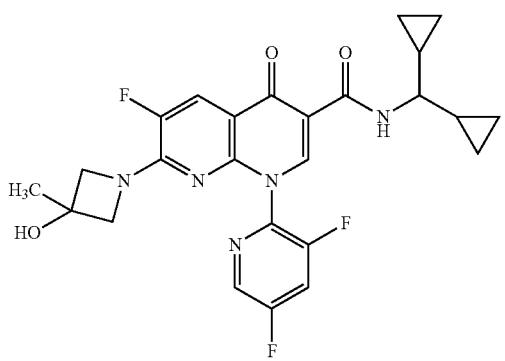 [SMILES: CC1(O)CN(c2nc3c(cc2F)c(=O)c(C(=O)NC(C2CC2)C2CC2)cn3-c2ncc(F)cc2F)C1]

50 mg of 1-(3,5-difluoropyridin-2-yl)-6-fluoro-7-(3-hydroxy-3-methylazetidin-1-yl)-4-oxo-1,4-dihydro-1,8-naphthyridine-3-carboxylic acid (123 µmol) were dissolved in DMF (980 µl). HATU (56.2 mg, 148 µmol), N,N-diisopropylethylamine (54 µl, 308 µmol) and 1,1-dicyclopropylmethanamine (15.1 mg, 135 µmol) were added and the mixture was stirred at RT for 2 h. 0.1 ml of 1 M hydrochloric acid and 1 ml of acetonitrile were added, and the reaction mixture was purified by preparative HPLC (acetonitrile/water with formic acid, C18 RP-HPLC). The product fractions were combined, concentrated and lyophilized from acetonitrile/water overnight. This gave 48.7 mg (78% of theory, 99% pure) of the title compound.

LC-MS (Method 1): $R_t$=1.04 min; MS (ESIpos): m/z=500 [M+H]$^+$ $^1$H-NMR (400 MHz, DMSO-d6) δ[ppm]: −0.008 (3.14), 0.008 (2.56), 0.300 (6.52), 0.387 (1.96), 0.397 (2.30), 0.416 (1.48), 0.455 (1.94), 0.475 (2.68), 1.031 (2.06), 1.044 (2.01), 1.382 (16.00), 2.323 (0.44), 2.328 (0.58), 2.524 (1.88), 2.670 (0.60), 3.235 (1.02), 3.254 (2.27), 3.276 (2.41), 3.928 (0.72), 5.676 (6.09), 7.985 (4.45), 8.014 (4.40), 8.292 (1.04), 8.298 (1.18), 8.316 (1.67), 8.319 (1.81), 8.337 (1.07), 8.343 (1.16), 8.591 (5.22), 8.597 (4.96), 8.753 (9.26), 9.856 (2.93), 9.878 (2.87).

Example 57

6-Fluoro-7-[(2S)-2-(hydroxymethyl)piperidin-1-yl]-4-oxo-N-[(2S)-1,1,1-trifluorobutan-2-yl]-1-(2,4,6-trifluorophenyl)-1,4-dihydro-1,8-naphthyridine-3-carboxamide

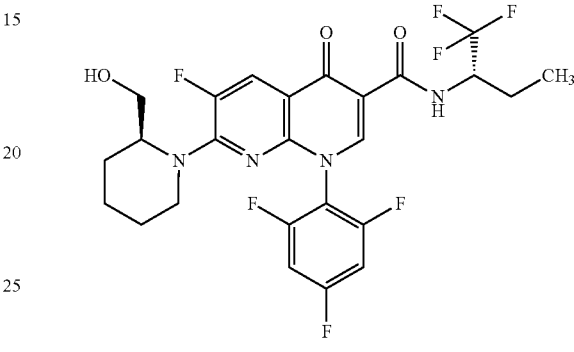

50 mg of 6-fluoro-4-oxo-7-(3H-[1,2,3]triazolo[4,5-b]pyridin-3-yloxy)-N-[(2S)-1,1,1-trifluoro-butan-2-yl]-1-(2,4,6-trifluorophenyl)-1,4-dihydro-1,8-naphthyridine-3-carboxamide (86.0 µmol) were dissolved in DMF (980 µl). (2S)-Piperidin-2-ylmethanol (19.8 mg, 172 µmol) and N,N-diisopropylethylamine (52 µl, 300 µmol) were added and the mixture was stirred at RT for 2 h. 0.3 ml of 1 M hydrochloric acid and 1 ml of acetonitrile were then added to the reaction mixture, and the product was purified by preparative HPLC (acetonitrile/water with formic acid, C18 RP-HPLC). The product fractions were combined, concentrated and lyophilized from acetonitrile/water overnight. This gave 37.3 mg (77% of theory, 99% pure) of the title compound.

LC-MS (Method 3): $R_t$=2.25 min; MS (ESIpos): m/z=561 [M+H]$^+$ $^1$H-NMR (400 MHz, DMSO-d6) δ[ppm]: −0.149 (0.55), −0.008 (4.87), 0.008 (4.03), 0.146 (0.52), 0.948 (7.19), 0.967 (16.00), 0.985 (7.82), 1.344 (1.09), 1.376 (1.34), 1.471 (1.90), 1.530 (3.44), 1.549 (5.64), 1.577 (2.47), 1.606 (1.34), 1.624 (1.56), 1.631 (1.36), 1.641 (1.83), 1.649 (1.65), 1.659 (1.59), 1.666 (1.77), 1.684 (1.47), 1.703 (0.91), 1.723 (1.95), 1.740 (1.83), 1.832 (0.43), 1.851 (1.31), 1.861 (1.54), 1.869 (1.56), 1.879 (1.74), 1.886 (1.54), 1.896 (1.34), 1.905 (1.15), 1.914 (0.98), 2.367 (0.70), 2.519 (3.11), 2.524 (2.47), 2.711 (0.66), 2.925 (1.07), 2.955 (1.99), 2.988 (1.07), 3.479 (1.00), 3.495 (1.47), 3.506 (2.47), 3.520 (2.63), 3.536 (1.90), 3.559 (1.20), 3.574 (2.02), 3.588 (1.77), 3.616 (0.68), 3.855 (1.79), 3.888 (1.68), 4.288 (2.04), 4.662 (3.01), 4.676 (6.53), 4.689 (2.97), 4.737 (1.41), 4.758 (1.32), 7.531 (1.43), 7.535 (1.41), 7.550 (3.99), 7.555 (4.15), 7.573 (4.28), 7.578 (3.88), 7.597 (1.36), 8.001 (8.41), 8.036 (8.14), 8.869 (13.96), 10.274 (5.15), 10.298 (4.94).

Example 58

N-[(1S)-1-Cyclopropyl-2,2,2-trifluoroethyl]-6-fluoro-7-[(2S)-2-(hydroxymethyl)piperidin-1-yl]-4-oxo-1-(2,4,6-trifluorophenyl)-1,4-dihydro-1,8-naphthyridine-3-carboxamide

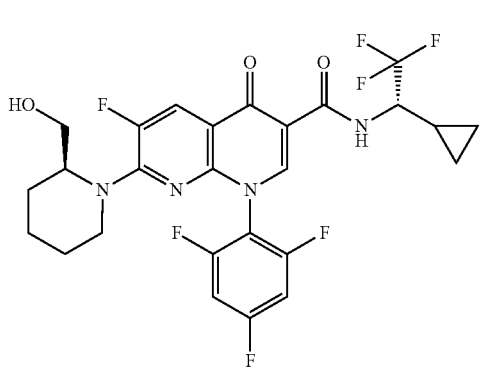 [SMILES: O=C(N[C@@H](C1CC1)C(F)(F)F)c1cn(-c2c(F)cc(F)cc2F)c2nc(N3CCCC[C@H]3CO)c(F)cc2c1=O]

50 mg of N-[(1S)-1-cyclopropyl-2,2,2-trifluoroethyl]-6-fluoro-4-oxo-7-(1H-[1,2,3]triazolo[4,5-b]pyridin-1-yloxy)-1-(2,4,6-trifluorophenyl)-1,4-dihydro-1,8-naphthyridine-3-carboxamide 50 mg of N-[(1S)-1-cyclopropyl-2,2,2-trifluoroethyl]-6-fluoro-4-oxo-7-(3H-[1,2,3]triazolo[4,5-b]pyridin-3-yloxy)-1-(2,4,6-trifluorophenyl)-1,4-dihydro-1,8-naphthyridine-3-carboxamide (84.3 µmol) were dissolved in DMF (980 µl). (2S)-Piperidin-2-ylmethanol (19.4 mg, 169 µmol) and N,N-diisopropylethylamine (51 µl, 290 µmol) were added and the mixture was stirred at RT for 2 h. 0.3 ml of 1 N hydrochloric acid and 1 ml of acetonitrile were added to the reaction mixture, and the product was purified by preparative HPLC (acetonitrile/water with formic acid, C18 RP-HPLC). The product fractions were combined, concentrated and lyophilized from acetonitrile/water overnight. This gave 36.5 mg (75% of theory, 99% pure) of the title compound.

LC-MS (Method 1): $R_t$=1.21 min; MS (ESIpos): m/z=573 [M+H]$^+$ $^1$H-NMR (400 MHz, DMSO-d6) δ[ppm]: −0.149 (0.72), −0.008 (6.54), 0.008 (5.08), 0.147 (0.62), 0.318 (1.64), 0.330 (2.51), 0.342 (2.47), 0.353 (1.96), 0.516 (1.76), 0.528 (2.59), 0.539 (2.36), 0.550 (2.63), 0.568 (2.76), 0.579 (2.15), 0.589 (2.00), 0.599 (1.66), 0.613 (1.02), 0.628 (1.49), 0.637 (1.40), 0.648 (2.51), 0.659 (2.08), 0.664 (1.98), 0.670 (1.96), 1.189 (1.51), 1.201 (2.61), 1.209 (1.87), 1.221 (2.57), 1.233 (1.44), 1.377 (1.34), 1.472 (2.00), 1.532 (3.55), 1.551 (5.84), 1.577 (2.55), 1.723 (1.98), 1.740 (1.87), 2.328 (1.13), 2.367 (0.70), 2.524 (3.19), 2.670 (1.08), 2.711 (0.70), 2.924 (1.10), 2.954 (2.10), 2.987 (1.15), 3.479 (1.00), 3.495 (1.47), 3.506 (2.59), 3.520 (2.74), 3.536 (1.95), 3.574 (2.08), 3.587 (1.85), 3.859 (1.95), 3.892 (1.79), 4.286 (2.17), 4.352 (1.30), 4.373 (2.30), 4.394 (2.32), 4.414 (1.25), 4.662 (2.95), 4.675 (6.42), 4.688 (2.87), 7.533 (1.59), 7.547 (3.89), 7.553 (4.38), 7.569 (4.48), 7.576 (3.85), 7.590 (1.53), 8.006 (8.95), 8.041 (8.61), 8.860 (16.00), 10.414 (5.44), 10.437 (5.10).

Example 59

N-[(1S)-1-Cyclopropyl-2,2,2-trifluoroethyl]-6-fluoro-7-[(4S)-4-hydroxy-2-oxopyrrolidin-1-yl]-4-oxo-1-(2,4,6-trifluorophenyl)-1,4-dihydro-1,8-naphthyridine-3-carboxamide

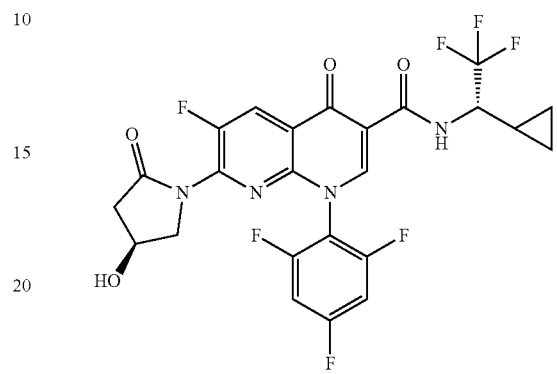

According to GP1, 61.7 mg (80% pure, 113 µmol) of 6-fluoro-7-[(4S)-4-hydroxy-2-oxopyrrolidin-1-yl]-4-oxo-1-(2,4,6-trifluorophenyl)-1,4-dihydro-1,8-naphthyridine-3-carboxylic acid were reacted with 29.7 mg of (1S)-1-cyclopropyl-2,2,2-trifluoroethanamine hydrochloride (169 µmol) in the presence of 64.4 mg (169 µmol) of HATU and 98 µl (560 µmol) of DIPEA in 3.0 ml of DMF. The reaction mixture was diluted with 0.5 ml of aqueous hydrochloric acid and purified by preparative HPLC [at UV max: 265 nm, column: Chromatorex C18, 10 µm, 125×30 mm, solvent: acetonitrile/0.05% formic acid gradient (0 to 3 min 10% acetonitrile, to 15 min 90% acetonitrile and a further 3 min 90% acetonitrile)]. The product fractions were combined, freed from the solvent and lyophilized. This gave 27.2 mg (43% of theory, 100% pure) of the title compound.

LC-MS (Method 3): $R_t$=1.80 min; MS (ESIpos): m/z=559 [M+H]$^+$

Example 60

N-tert-Butyl-7-(dimethylamino)-6-fluoro-4-oxo-1-(2,4,6-trifluorophenyl)-1,4-dihydro-1,8-naphthyridine-3-carboxamide

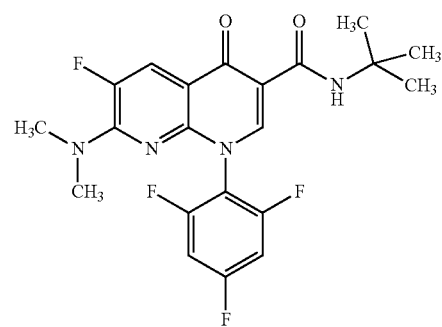 [SMILES: CN(C)c1nc2c(cc1F)c(=O)c(C(=O)NC(C)(C)C)cn2-c1c(F)cc(F)cc1F]

7-Chloro-6-fluoro-4-oxo-1-(2,4,6-trifluorophenyl)-1,4-dihydro-1,8-naphthyridine-3-carboxylic acid (120 mg, 322 µmol) was initially charged in 2.4 ml of DMF, HATU (147 mg, 386 µmol) and N,N-diisopropylethylamine (200 µl, 1.1 mmol) were added and the mixture was stirred at room temperature for 30 min. 2-Methylpropan-2-amine (41 µl, 390 µmol) was added and the mixture was stirred at room temperature for 5 min. After 5 min, water was added to the reaction mixture. The resulting suspension was allowed to stand overnight. The next morning, a solid that could be removed by filtration with suction had formed. This residue was purified by column chromatography (silica gel; mobile phase: dichloromethane/methanol gradient: 100/0 to 100/1). This gave 23 mg (16% of theory) of the target compound.

LC-MS (Method 3): $R_t$=2.32 min; MS (ESIpos): m/z=437 [M+H]$^+$

Example 61

7-(Dimethylamino)-6-fluoro-N-(2-methylbutan-2-yl)-4-oxo-1-(2,4,6-trifluorophenyl)-1,4-dihydro-1,8-naphthyridine-3-carboxamide

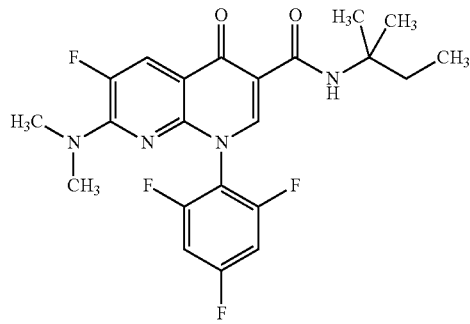 [SMILES: CCC(C)(C)NC(=O)c1cn(-c2c(F)cc(F)cc2F)c2nc(N(C)C)c(F)cc2c1=O]

7-Chloro-6-fluoro-4-oxo-1-(2,4,6-trifluorophenyl)-1,4-dihydro-1,8-naphthyridine-3-carboxylic acid (120 mg, 322 µmol) was initially charged in 2.4 ml of DMF, HATU (147 mg, 386 µmol) and N,N-diisopropylethylamine (200 µl, 1.1 mmol) were added and the mixture was stirred at room temperature for 30 min. 2-Methylbutan-2-amine (45 µl, 390 µmol) was added and the mixture was stirred at room temperature for 5 min. After 5 min, water was added to the reaction mixture. The resulting suspension was allowed to stand overnight. The next morning, a solid that could be removed by filtration with suction had formed. This residue was purified by column chromatography (silica gel; mobile phase: dichloromethane/methanol gradient: 100/0 to 100/1). This gave 19 mg (13% of theory) of the target compound.

LC-MS (Method 3): $R_t$=2.42 min; MS (ESIpos): m/z=451 [M+H]$^+$

Example 62

7-(Dimethylamino)-6-fluoro-4-oxo-N-(1,1,1-trifluoro-2-methylpropan-2-yl)-1-(2,4,6-trifluoro-phenyl)-1,4-dihydro-1,8-naphthyridine-3-carboxamide

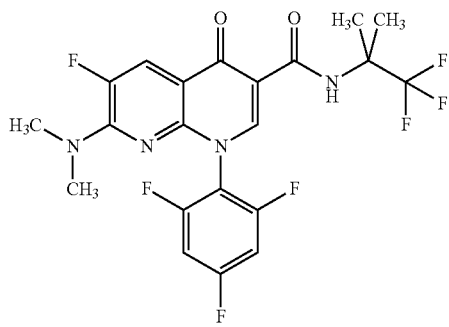 [SMILES: CN(C)c1nc2c(cc1F)c(=O)c(C(=O)NC(C)(C)C(F)(F)F)cn2-c1c(F)cc(F)cc1F]

7-Chloro-6-fluoro-4-oxo-1-(2,4,6-trifluorophenyl)-1,4-dihydro-1,8-naphthyridine-3-carboxylic acid (120 mg, 322 µmol) was initially charged in 2.4 ml of DMF, HATU (147 mg, 386 µmol) and N,N-diisopropylethylamine (200 µl, 1.1 mmol) were added and the mixture was stirred at room temperature for 30 min. 1,1,1-Trifluoro-2-methylpropan-2-amine (49.1 mg, 386 µmol) was added and the mixture was stirred at room temperature for 5 min. After 5 min, water was added to the reaction mixture. The resulting suspension was allowed to stand overnight. The next morning, a solid that could be removed by filtration with suction had formed. This residue was purified by column chromatography (silica gel; mobile phase: dichloromethane/methanol gradient: 100/0 to 100/1). This gave 30 mg (19% of theory) of the target compound.

LC-MS (Method 3): $R_t$=2.42 min; MS (ESIpos): m/z=491 [M+H]$^+$

Example 63

7-(Dimethylamino)-6-fluoro-4-oxo-N-(4,4,4-trifluoro-2-methylbutan-2-yl)-1-(2,4,6-trifluoro-phenyl)-1,4-dihydro-1,8-naphthyridine-3-carboxamide

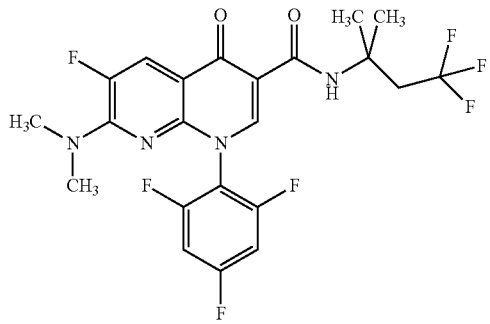 [SMILES: CN(C)c1nc2c(cc1F)c(=O)c(C(=O)NC(C)(C)CC(F)(F)F)cn2-c1c(F)cc(F)cc1F]

7-Chloro-6-fluoro-4-oxo-1-(2,4,6-trifluorophenyl)-1,4-dihydro-1,8-naphthyridine-3-carboxylic acid (120 mg, 322 µmol) was initially charged in 2.4 ml of DMF, HATU (147 mg, 386 µmol) and N,N-diisopropylethylamine (200 µl, 1.1 mmol) were added and the mixture was stirred at room temperature for 30 min. 4,4,4-Trifluoro-2-methylbutan-2- amine hydrochloride (68.6 mg, 386 μmol) was added and the mixture was stirred at room temperature for 5 min. After 5 min, water was added to the reaction mixture. The resulting suspension was allowed to stand overnight. The next morning, a solid that could be removed by filtration with suction had formed. This residue was purified by column chromatography (silica gel; mobile phase: dichloromethane/methanol gradient: 100/0 to 100/1). This gave 24 mg (15% of theory) of the target compound.

LC-MS (Method 3): $R_t$=2.42 min; MS (ESIpos): m/z=505 [M+H]$^+$

Example 64

N-[(1S)-1-Cyclopropyl-2,2,2-trifluoroethyl]-6-fluoro-7-{[(2S)-2-hydroxypropyl](methyl)amino}-4-oxo-1-(2,4,6-trifluorophenyl)-1,4-dihydro-1,8-naphthyridine-3-carboxamide

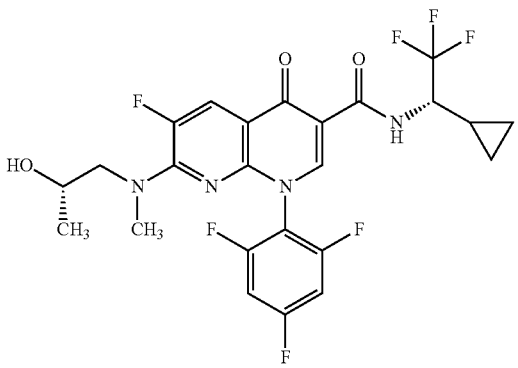 [SMILES: C[C@H](O)CN(C)c1nc2c(cc1F)c(=O)c(C(=O)N[C@@H](C1CC1)C(F)(F)F)cn2-c1c(F)cc(F)cc1F]

7-Chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide (60.0 mg, 122 μmol) was initially charged in 1.2 ml of DMF, (2S)-1-(methylamino) propan-2-ol (21.7 mg, 243 μmol) and N,N-diisopropylethylamine (74 μl, 430 μmol) were added and the mixture was stirred at room temperature for 2 h. Acetonitrile/water was added and the reaction solution was purified by preparative HPLC (RP18 column, mobile phase: acetonitrile/water gradient with addition of 0.1% TFA). The product fractions were combined and concentrated to dryness under reduced pressure. The residue was taken up in dichloromethane and extracted twice with saturated aqueous sodium bicarbonate solution. The combined aqueous phases were re-extracted once with dichloromethane. The combined organic phases were dried over sodium sulfate, filtered and concentrated under reduced pressure. This gave 47 mg of the target compound (70% of theory).

LC-MS (Method 3): $R_t$=2.15 min; MS (ESIpos): m/z=547 [M+H]$^+$ $^1$H NMR (400 MHz, DMSO-d$_6$) δ [ppm]: −0.149 (0.68), −0.059 (5.17), −0.008 (4.04), 0.008 (3.41), 0.146 (0.41), 0.318 (1.61), 0.328 (2.49), 0.340 (2.44), 0.352 (1.95), 0.364 (0.96), 0.512 (1.71), 0.523 (2.54), 0.535 (2.29), 0.547 (2.57), 0.555 (1.96), 0.566 (2.64), 0.576 (2.19), 0.586 (1.99), 0.597 (1.62), 0.611 (1.01), 0.625 (1.41), 0.636 (1.41), 0.646 (2.39), 0.656 (2.07), 0.662 (2.01), 0.670 (2.00), 0.678 (1.03), 0.690 (0.76), 0.834 (7.90), 0.849 (7.89), 1.166 (0.69), 1.178 (1.23), 1.186 (1.66), 1.198 (2.72), 1.207 (1.98), 1.219 (2.71), 1.231 (1.99), 1.251 (0.59), 2.074 (0.65), 2.329 (0.46), 2.671 (0.42), 3.160 (4.79), 3.460 (2.29), 3.490 (1.88), 3.705 (1.53), 4.354 (1.31), 4.375 (2.27), 4.396 (2.20), 4.417 (1.17), 4.738 (5.75), 4.750 (5.64), 5.755 (2.37), 7.561 (3.16), 7.582 (5.63), 7.603 (3.10), 7.989 (8.41), 8.023 (8.17), 8.841 (16.00), 10.441 (5.22), 10.464 (5.04).

Example 65

N-[(1S)-1-Cyclopropyl-2,2,2-trifluoroethyl]-7-[ethyl (2-hydroxypropyl)amino]-6-fluoro-4-oxo-1-(2,4,6-trifluorophenyl)-1,4-dihydro-1,8-naphthyridine-3-carboxamide (Diastereomer Mixture)

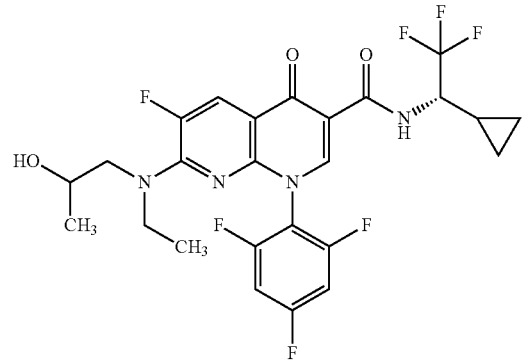 [SMILES: CCN(CC(C)O)c1nc2c(cc1F)c(=O)c(C(=O)N[C@@H](C1CC1)C(F)(F)F)cn2-c1c(F)cc(F)cc1F]

7-Chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide (80.0 mg, 162 μmol) was initially charged in 1.6 ml of acetonitrile, 1-(ethylamino) propan-2-ol (33.4 mg, 324 μmol; racemate) and N,N-diisopropylethylamine (99 μl, 570 μmol) were added and the mixture was stirred at room temperature for 2 h. The reaction solution was then concentrated under reduced pressure. The residue was taken up in ethyl acetate, and water was added. The aqueous phase was acidified with 1 M hydrochloric acid and extracted twice. The organic phase was extracted once with saturated aqueous sodium bicarbonate solution and once with saturated aqueous sodium chloride solution, dried over sodium sulfate, filtered and concentrated under reduced pressure. This gave 76 mg of the target compound (82% of theory).

LC-MS (Method 3): $R_t$=2.23 min; MS (ESIpos): m/z=561 [M+H]$^+$ $^1$H NMR (400 MHz, DMSO-d$_6$) δ [ppm]: −0.149 (0.87), −0.008 (7.43), 0.008 (7.19), 0.146 (0.84), 0.329 (2.28), 0.342 (2.25), 0.514 (1.80), 0.525 (2.61), 0.549 (2.52), 0.568 (2.61), 0.577 (2.19), 0.588 (2.07), 0.626 (1.32), 0.647 (2.43), 0.851 (6.17), 1.013 (5.51), 1.157 (1.05), 1.175 (2.52), 1.185 (1.74), 1.197 (2.94), 1.206 (2.22), 1.217 (2.82), 1.238 (1.89), 1.988 (3.09), 2.328 (1.86), 2.367 (0.93), 2.670 (1.86), 2.711 (1.05), 3.061 (0.93), 3.418 (2.19), 3.455 (2.55), 3.575 (1.14), 3.710 (1.59), 4.021 (0.84), 4.039 (0.81), 4.350 (1.20), 4.370 (2.22), 4.391 (2.22), 4.412 (1.17), 4.736 (4.04), 4.748 (3.96), 7.566 (3.06), 7.588 (5.51), 7.607 (3.12), 7.996 (8.21), 8.031 (8.03), 8.843 (16.00), 10.439 (5.21), 10.463 (5.00).

Example 66

N-[(1S)-1-Cyclopropyl-2,2,2-trifluoroethyl]-7-[ethyl (2-hydroxypropyl)amino]-6-fluoro-4-oxo-1-(2,4,6-trifluorophenyl)-1,4-dihydro-1,8-naphthyridine-3-carboxamide (Diastereomer 1)

69 mg of N-[(1S)-1-cyclopropyl-2,2,2-trifluoroethyl]-7-[ethyl(2-hydroxypropyl)amino]-6-fluoro-4-oxo-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak AD-H, 5 μm, 250×20 mm; mobile phase: 80% n-heptane/20% isopropanol; flow rate 15 ml/min; temperature: 25° C., detection: 210 nm).

Diastereomer 1: 30 mg (>99% de)

$R_t$=1.37 min [analytical HPLC: column Daicel® Chiralpak AD, 1 ml/min; 3 μm, 50×4.6 mm; mobile phase: 80% isohexane/20% isopropanol; detection: 220 nm].

LC-MS (Method 3): $R_t$=2.25 min; MS (ESIpos): m/z=561 [M+H]$^+$ $^1$H NMR (400 MHz, DMSO-d$_6$) δ [ppm]: −0.008 (1.84), 0.008 (1.52), 0.321 (1.83), 0.331 (2.88), 0.343 (2.85), 0.355 (2.22), 0.367 (1.10), 0.503 (0.76), 0.515 (1.97), 0.526 (2.98), 0.539 (2.67), 0.550 (2.97), 0.557 (2.12), 0.568 (3.14), 0.578 (2.48), 0.589 (2.26), 0.599 (1.84), 0.613 (1.18), 0.627 (1.69), 0.637 (1.61), 0.648 (2.73), 0.659 (2.37), 0.664 (2.19), 0.670 (2.15), 0.680 (1.11), 0.684 (1.10), 0.692 (0.80), 0.852 (6.50), 0.863 (6.50), 1.012 (5.79), 1.165 (0.66), 1.177 (1.26), 1.185 (1.75), 1.198 (2.95), 1.206 (2.09), 1.218 (2.89), 1.230 (1.55), 1.238 (1.05), 1.250 (0.45), 2.328 (0.82), 2.333 (0.60), 2.367 (0.56), 2.519 (3.02), 2.524 (2.34), 2.666 (0.58), 2.670 (0.80), 2.675 (0.58), 2.710 (0.51), 3.075 (0.94), 3.419 (2.44), 3.454 (2.73), 3.578 (1.05), 3.708 (1.64), 4.347 (1.48), 4.368 (2.54), 4.389 (2.50), 4.410 (1.34), 4.735 (4.60), 4.747 (4.46), 7.566 (3.23), 7.587 (5.73), 7.606 (3.23), 7.996 (9.12), 8.031 (8.91), 8.843 (16.00), 10.440 (6.11), 10.463 (5.86).

Example 67

N-[(1S)-1-Cyclopropyl-2,2,2-trifluoroethyl]-7-[ethyl (2-hydroxypropyl)amino]-6-fluoro-4-oxo-1-(2,4,6-trifluorophenyl)-1,4-dihydro-1,8-naphthyridine-3-carboxamide (diastereomer 2)

69 mg of N-[(1S)-1-cyclopropyl-2,2,2-trifluoroethyl]-7-[ethyl(2-hydroxypropyl)amino]-6-fluoro-4-oxo-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak AD-H, 5 μm, 250×20 mm; mobile phase: 80% n-heptane/20% isopropanol; flow rate 15 ml/min; temperature: 25° C., detection: 210 nm).

Diastereomer 2: 30 mg (>99% de)

$R_t$=2.31 min [analytical HPLC: column Daicel® Chiralpak AD, 1 ml/min; 3 μm, 50×4.6 mm; mobile phase: 80% isohexane/20% isopropanol; detection: 220 nm].

LC-MS (Method 3): $R_t$=2.25 min; MS (ESIpos): m/z=561 [M+H]$^+$ $^1$H NMR (400 MHz, DMSO-d$_6$) δ [ppm]: 0.318 (1.80), 0.328 (2.83), 0.340 (2.58), 0.514 (1.98), 0.525 (3.01), 0.537 (2.55), 0.548 (2.78), 0.567 (2.79), 0.576 (2.35), 0.588 (2.12), 0.626 (1.52), 0.647 (2.48), 0.657 (2.17), 0.851 (6.26), 1.013 (5.57), 1.177 (1.33), 1.185 (1.71), 1.198 (2.72), 1.218 (2.67), 1.230 (1.43), 2.328 (1.15), 2.671 (1.04), 3.063 (1.04), 3.420 (2.39), 3.453 (2.67), 3.585 (1.11), 3.711 (1.63), 4.350 (1.49), 4.371 (2.39), 4.393 (2.19), 4.413 (1.31), 4.737 (4.38), 4.749 (4.05), 7.567 (3.32), 7.588 (5.50), 7.607 (2.95), 7.997 (7.99), 8.032 (7.81), 8.844 (16.00), 10.440 (5.11), 10.463 (5.00).

Example 68

1-(2-Chloro-4,6-difluorophenyl)-N-[(1S)-1-cyclopropyl-2,2,2-trifluoroethyl]-6-fluoro-7-(2-oxa-6-azaspiro[3.3]hept-6-yl)-4-oxo-1,4-dihydro-1,8-naphthyridine-3-carboxamide trifluoroacetate (Atropisomer Mixture)

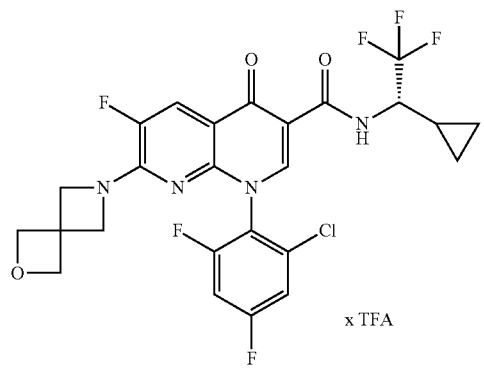 [SMILES: O=C(N[C@@H](C1CC1)C(F)(F)F)c1cn(-c2c(F)cc(F)cc2Cl)c2nc(N3CC4(COC4)C3)c(F)cc2c1=O]

7-Chloro-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (atropisomer mixture, purity 57%, 90.0 mg, 176 μmol) was initially charged in 1.7 ml of DMF, ethanedioic acid 2-oxa-6-azaspiro[3.3]heptane (1:1) (46.7 mg, 247 μmol) and N,N-diisopropylethylamine (150 μl, 880 μmol) were added and the mixture was stirred at room temperature overnight. Acetonitrile/water was added and the reaction solution was purified by preparative HPLC (RP18 column, mobile phase: acetonitrile/water gradient with addition of 0.1% TFA). (Fraction 1). The product fractions were combined and concentrated to dryness under reduced pressure. The residue was taken up in dichloromethane and extracted twice with saturated aqueous sodium bicarbonate solution. The combined aqueous phases were re-extracted once with dichloromethane. The combined organic phases were dried over sodium sulfate, filtered and concentrated under reduced pressure. This gave 74 mg of the target compound (60% of theory, purity 98%).

LC-MS (Method 3): $R_t$=2.28 min; MS (ESIpos): m/z=573 [M−TFA+H]$^+$ $^1$H NMR (500 MHz, DMSO-d$_6$) δ [ppm]: 0.006 (0.44), 0.313 (0.41), 0.322 (0.73), 0.331 (0.87), 0.341 (0.77), 0.350 (0.49), 0.524 (0.72), 0.536 (0.69), 0.544 (0.68), 0.552 (0.50), 0.561 (0.59), 0.571 (0.77), 0.580 (0.71), 0.587 (0.60), 0.597 (0.45), 0.635 (0.46), 0.644 (0.64), 0.652 (0.79), 0.663 (0.77), 0.672 (0.54), 1.188 (0.50), 1.197 (0.83), 1.205 (0.69), 1.213 (0.78), 1.222 (0.48), 2.073 (6.12), 2.519 (0.49), 4.339 (0.49), 4.355 (0.83), 4.372 (0.98), 4.388 (0.77), 4.649 (16.00), 7.680 (0.58), 7.686 (0.77), 7.699 (1.02), 7.704 (1.35), 7.718 (0.63), 7.724 (1.34), 7.745 (1.11), 7.999 (2.73), 8.022 (2.68), 8.777 (6.49), 10.453 (1.61), 10.471 (1.53).

Example 69

7-[3,3-Bis(hydroxymethyl)azetidin-1-yl]-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (Atropisomer Mixture)

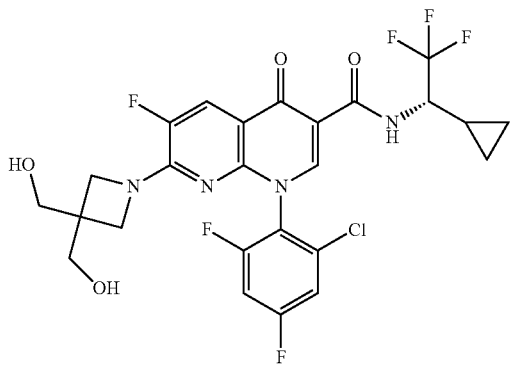 [SMILES: O=C(N[C@@H](C1CC1)C(F)(F)F)c1cn(-c2c(F)cc(F)cc2Cl)c2nc(N3CC(CO)(CO)C3)c(F)cc2c1=O]

1-(2-Chloro-4,6-difluorophenyl)-N-[(1S)-1-cyclopropyl-2,2,2-trifluoroethyl]-6-fluoro-7-(2-oxa-6-azaspiro[3.3]hept-6-yl)-4-oxo-1,4-dihydro-1,8-naphthyridine-3-carboxamide trifluoroacetate (atropisomer mixture, 70.0 mg, 102 μmol) was initially charged in trifluoroacetic acid (640 μl, 8.3 mmol), 640 μl of water and 0.2 ml of acetonitrile were added and the mixture was stirred at room temperature for 4 days. The reaction solution was purified by preparative HPLC (RP18 column, mobile phase: acetonitrile/water gradient with addition of 0.1% TFA). The product fractions were concentrated under reduced pressure and the residue was taken up in dichloromethane and washed twice with saturated aqueous sodium bicarbonate solution. The combined aqueous phases were re-extracted once with dichloro me thane. The combined organic phases were dried over sodium sulfate, filtered and concentrated under reduced pressure. This gave 60 mg of the target compound (98% of theory, purity 98%).

LC-MS (Method 3): $R_t$=1.91 min; MS (ESIpos): m/z=591 [M+H]$^+$ $^1$H NMR (400 MHz, DMSO-d$_6$) δ [ppm]: −0.149 (0.88), −0.008 (7.82), 0.008 (6.52), 0.146 (0.86), 0.312 (0.99), 0.323 (1.77), 0.334 (2.13), 0.346 (1.93), 0.358 (1.22), 0.523 (1.69), 0.538 (1.80), 0.561 (1.93), 0.572 (2.02), 0.583 (1.74), 0.593 (1.49), 0.606 (1.08), 0.621 (0.83), 0.631 (1.13), 0.641 (1.55), 0.652 (1.82), 0.667 (1.60), 0.675 (1.19), 0.687 (0.69), 1.162 (0.44), 1.175 (0.80), 1.183 (1.16), 1.195 (1.99), 1.205 (1.55), 1.215 (1.96), 1.227 (1.22), 1.235 (1.13), 2.073 (0.77), 2.328 (1.16), 2.366 (0.80), 2.523 (4.37), 2.670 (1.30), 2.710 (0.94), 3.465 (15.72), 3.479 (16.00), 4.118 (0.91), 4.333 (0.66), 4.353 (1.33), 4.373 (1.77), 4.392 (1.35), 4.411 (0.64), 4.831 (5.11), 4.844 (12.10), 4.858 (5.06), 7.667 (1.27), 7.673 (1.82), 7.690 (2.10), 7.697 (3.45), 7.713 (3.43), 7.720 (3.87), 7.731 (2.57), 7.742 (1.71), 7.967 (6.38), 7.996 (6.33), 8.758 (14.51), 10.481 (4.03), 10.505 (3.90).

Example 70

7-[3,3-Bis(hydroxymethyl)azetidin-1-yl]-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (Atropisomer 1)

55 mg of 7-[3,3-bis(hydroxymethyl)azetidin-1-yl]-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (atropisomer mixture) were separated into the atropisomers by chiral HPLC (preparative HPLC: column Daicel® Chiralpak OX-H, 5 μm, 250×20 mm; mobile phase: 80% n-heptane/20% ethanol+0.2% diethylamine; flow rate 20 ml/min; temperature: 23° C., detection: 220 nm). The product fractions were concentrated at 30° C.

Atropisomer 1: 22 mg (>99% stereochemically pure)

$R_t$=4.16 min [analytical HPLC: column Daicel® Chiralpak OX, 1 ml/min; 3 μm, 50×4.6 mm; mobile phase: 90% n-hexane/20% ethanol+0.2% diethylamine; detection: 220 nm].

LC-MS (Method 3): $R_t$=1.90 min; MS (ESIpos): m/z=591 [M+H]$^+$ $^1$H NMR (400 MHz, DMSO-d$_6$) δ [ppm]: −0.149 (0.82), −0.008 (7.57), 0.008 (6.50), 0.146 (0.85), 0.312 (1.26), 0.322 (2.17), 0.335 (2.11), 0.346 (1.65), 0.358 (0.85), 0.508 (1.45), 0.519 (2.22), 0.531 (1.98), 0.543 (2.14), 0.561 (2.22), 0.571 (1.81), 0.582 (1.59), 0.593 (1.32), 0.606 (0.80), 0.621 (1.15), 0.631 (1.15), 0.642 (1.95), 0.652 (1.73), 0.664 (1.54), 1.099 (0.82), 1.118 (1.51), 1.135 (0.71), 1.182 (1.26), 1.194 (2.14), 1.202 (1.56), 1.214 (2.14), 1.226 (1.21), 1.234 (1.13), 2.327 (1.56), 2.366 (0.91), 2.523 (4.89), 2.670 (1.54), 2.710 (0.91), 2.820 (0.41), 3.465 (15.78), 3.479 (16.00), 4.131 (0.93), 4.348 (1.13), 4.370 (1.92), 4.392 (1.84), 4.411 (0.99), 4.831 (5.19), 4.844 (12.24), 4.857 (5.10), 7.666 (1.29), 7.673 (1.92), 7.690 (2.17), 7.697 (3.49), 7.713 (3.60), 7.720 (3.95), 7.731 (2.66), 7.967 (7.27), 7.996 (7.03), 8.758 (15.86), 10.482 (4.56), 10.506 (4.42).

Example 71

7-[3,3-Bis(hydroxymethyl)azetidin-1-yl]-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (Atropisomer 2)

55 mg of 7-[3,3-bis(hydroxymethyl)azetidin-1-yl]-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (atropisomer mixture) were separated into the atropisomers by chiral HPLC (preparative HPLC: column Daicel® Chiralpak OX-H, 5 μm, 250×20 mm; mobile phase: 80% n-heptane/20% ethanol+0.2% diethylamine; flow rate 20 ml/min; temperature: 23° C., detection: 220 nm). The product fractions were concentrated at 30° C.

Atropisomer 2: 22 mg (>98.5% stereochemically pure)

$R_t$=6.25 min [analytical HPLC: column Daicel® Chiralpak OX, 1 ml/min; 3 μm, 50×4.6 mm; mobile phase: 90% n-hexane/20% ethanol+0.2% diethylamine; detection: 220 nm].

LC-MS (Method 3): $R_t$=1.90 min; MS (ESIpos): m/z=591 [M+H]$^+$ $^1$H NMR (400 MHz, DMSO-d$_6$) δ [ppm]: −0.149 (0.93), −0.008 (8.98), 0.008 (6.74), 0.146 (0.86), 0.323 (1.38), 0.333 (2.14), 0.346 (2.11), 0.359 (1.59), 0.370 (0.79), 0.513 (1.52), 0.525 (2.14), 0.538 (1.90), 0.552 (1.76), 0.560 (1.66), 0.572 (2.11), 0.582 (1.80), 0.593 (1.66), 0.604 (1.35), 0.616 (0.90), 0.630 (1.00), 0.640 (1.17), 0.651 (1.83), 0.661 (1.73), 0.675 (1.62), 0.696 (0.55), 1.101 (1.42), 1.119 (2.80), 1.137 (1.35), 1.175 (0.90), 1.183 (1.31), 1.196 (2.18), 1.205 (1.56), 1.216 (2.11), 1.228 (1.24), 2.323 (1.42), 2.327 (1.83), 2.366 (1.52), 2.523 (5.46), 2.670 (1.73), 2.710 (1.35), 2.825 (0.59), 2.843 (0.59), 3.465 (15.86), 3.479 (16.00), 4.127 (0.90), 4.333 (1.14), 4.354 (1.90), 4.374 (1.87), 4.395 (1.00), 4.830 (5.36), 4.844 (12.75), 4.857 (5.22), 7.667 (1.24), 7.673

(1.90), 7.690 (2.14), 7.697 (3.46), 7.713 (3.52), 7.720 (3.84), 7.732 (2.63), 7.967 (7.02), 7.995 (6.88), 8.758 (15.14), 10.480 (4.53), 10.503 (4.32).

Example 72

1-(2-Chloro-4,6-difluorophenyl)-N-[(1S)-1-cyclopropyl-2,2,2-trifluoroethyl]-6-fluoro-7-{[(2S)-2-hydroxypropyl](methyl)amino}-4-oxo-1,4-dihydro-1,8-naphthyridine-3-carboxamide (Atropisomer Mixture)

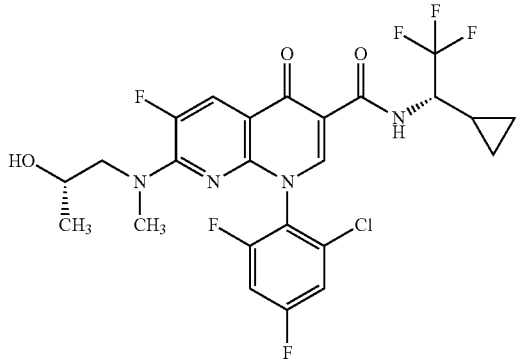 [SMILES: C[C@H](O)CN(C)c1nc2c(cc1F)c(=O)c(C(=O)N[C@@H](C1CC1)C(F)(F)F)cn2-c1c(F)cc(F)cc1Cl]

7-Chloro-1-(2-chloro-4,6-difluorophenyl)-N-[(1S)-1-cyclopropyl-2,2,2-trifluoroethyl]-6-fluoro-4-oxo-1,4-dihydro-1,8-naphthyridine-3-carboxamide (atropisomer mixture, purity 57%, 90.0 mg, 176 µmol) was initially charged in 1.8 ml of DMF, (2S)-1-(methylamino)propan-2-ol (31.4 mg, 353 µmol) and N,N-diisopropylethylamine (110 µl, 620 µmol) were added and the mixture was stirred at room temperature overnight. The reaction solution was added to water and the resulting solid was stirred for about 30 min and then filtered off, washed with water and dried under high vacuum. The residue was purified by thick-layer chromatography (mobile phase: cyclohexane/ethyl acetate=2/1). This gave 31 mg of the target compound (31% of theory, purity 98%).

LC-MS (Method 3): $R_t$=2.20 min; MS (ESIpos): m/z=563 [M+H]$^+$ $^1$H NMR (400 MHz, DMSO-d$_6$) δ [ppm]: −0.149 (0.69), −0.008 (7.05), 0.008 (5.36), 0.146 (0.72), 0.314 (1.84), 0.325 (3.49), 0.336 (4.05), 0.348 (3.84), 0.360 (2.56), 0.525 (3.62), 0.545 (3.56), 0.552 (3.49), 0.563 (3.49), 0.573 (4.02), 0.584 (3.59), 0.593 (3.12), 0.607 (2.03), 0.623 (1.53), 0.632 (2.09), 0.642 (2.90), 0.653 (3.59), 0.667 (3.34), 0.676 (2.68), 0.807 (11.54), 0.822 (7.64), 1.165 (0.78), 1.178 (1.59), 1.185 (2.34), 1.198 (4.02), 1.207 (2.99), 1.218 (3.84), 1.230 (2.12), 1.238 (1.43), 1.250 (0.65), 2.073 (0.53), 2.328 (1.72), 2.366 (1.03), 2.524 (4.96), 2.670 (1.81), 2.710 (1.06), 3.011 (1.40), 3.175 (6.49), 3.422 (2.50), 3.447 (2.50), 3.470 (1.72), 3.681 (2.50), 4.339 (1.31), 4.359 (2.68), 4.378 (3.27), 4.397 (2.46), 4.418 (1.09), 4.723 (5.02), 4.730 (6.80), 4.735 (5.99), 4.743 (5.68), 7.690 (1.28), 7.697 (2.00), 7.708 (2.56), 7.713 (2.50), 7.721 (4.05), 7.736 (6.83), 7.743 (5.74), 7.757 (6.11), 7.995 (13.35), 8.029 (13.13), 8.791 (14.07), 8.795 (16.00), 10.460 (7.42), 10.484 (7.14).

Example 73

1-(2-Chloro-4,6-difluorophenyl)-7-[(3R,4R)-3,4-dihydroxypyrrolidin-1-yl]-6-fluoro-N-(2-methylbutan-2-yl)-4-oxo-1,4-dihydro-1,8-naphthyridine-3-carboxamide (Atropisomer Mixture)

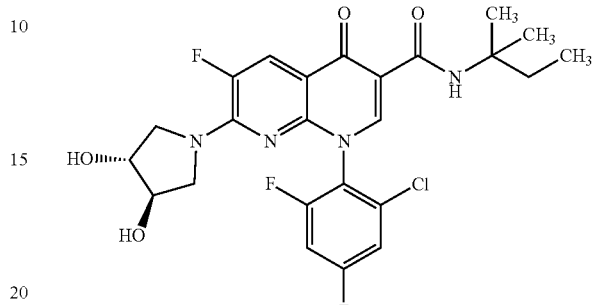

1-(2-Chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic acid (80.0 mg, 176 µmol) was initially charged in 1.2 ml of DMF, HATU (80.1 mg, 211 µmol) and N,N-diisopropylethylamine (110 µl, 610 µmol) were added and the mixture was stirred at room temperature for 30 min. 2-Methylbutan-2-amine (18.4 mg, 211 µmol) was added and the mixture was stirred at room temperature overnight. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with dichloromethane. The combined organic phases were washed twice with saturated aqueous sodium bicarbonate solution. The combined aqueous phases were re-extracted with dichloromethane. The combined organic phases were dried over sodium sulfate, filtered and concentrated under reduced pressure. This gave 58 mg of the target compound (62% of theory, purity 99%).

LC-MS (Method 3): $R_t$=1.82 min; MS (ESIpos): m/z=525 [M+H]$^+$

Example 74

N-tert-Butyl-1-(2-chloro-4,6-difluorophenyl)-7-[(3R,4R)-3,4-dihydroxypyrrolidin-1-yl]-6-fluoro-4-oxo-1,4-dihydro-1,8-naphthyridine-3-carboxamide (Atropisomer Mixture)

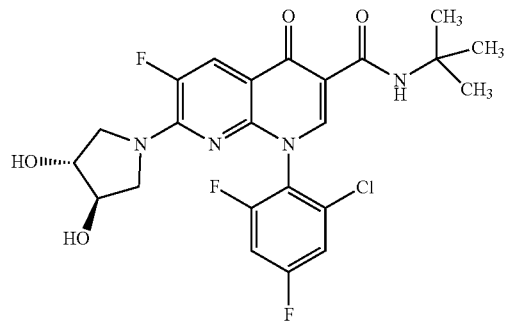 [SMILES: CC(C)(C)NC(=O)c1cn(-c2c(F)cc(F)cc2Cl)c2nc(N3C[C@@H](O)[C@H](O)C3)c(F)cc2c1=O]

1-(2-Chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic acid (100 mg, 219 µmol) was initially charged in 3.1 ml of DMF, HATU (100 mg, 263 µmol) and N,N-diisopropylethylamine (130 µl, 770 µmol) were added and the mixture was stirred at room temperature for 30 min. 2-Methylpropan-2-amine (19.3 mg, 263 µmol) was added and the mixture was stirred at room temperature overnight. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with dichloromethane. The combined organic phases were washed twice with saturated aqueous sodium bicarbonate solution. The combined aqueous phases were re-extracted with dichloromethane. The combined organic phases were dried over sodium sulfate, filtered and concentrated under reduced pressure. This gave 86 mg of the target compound (76% of theory, purity 99%).

LC-MS (Method 3): $R_t$=1.71 min; MS (ESIpos): m/z=511 [M+H]$^+$

Example 75

1-(3,5-Difluoropyridin-2-yl)-7-[(3R,4R)-3,4-dihydroxypyrrolidin-1-yl]-6-fluoro-N-(2-methyl-butan-2-yl)-4-oxo-1,4-dihydro-1,8-naphthyridine-3-carboxamide

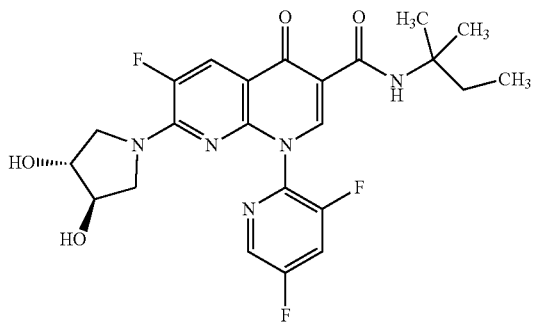 [SMILES: CCC(C)(C)NC(=O)c1cn(-c2ncc(F)cc2F)c2nc(N3C[C@@H](O)[C@H](O)C3)c(F)cc2c1=O]

1-(3,5-Difluoropyridin-2-yl)-7-[(3R,4R)-3,4-dihydroxypyrrolidin-1-yl]-6-fluoro-4-oxo-1,4-di-hydro-1,8-naphthyridine-3-carboxylic acid (57.0 mg, 135 µmol) was initially charged in 1.4 ml of DMF, HATU (61.6 mg, 162 µmol) and N,N-diisopropylethylamine (94 µl, 540 µmol) were added and the mixture was stirred at room temperature for 10 min. 2-Methylbutan-2-amine (24 µl, 200 µmol) was added and the reaction mixture was stirred at room temperature for 2 h. Acetonitrile/water/TFA were added and the reaction solution was purified by preparative HPLC (RP18 column, mobile phase: acetonitrile/water gradient with addition of 0.1% TFA). The product fractions were substantially concentrated under reduced pressure and the residue was made basic with saturated aqueous sodium bicarbonate solution and extracted twice with dichloromethane. The combined organic phases were dried over sodium sulfate, filtered and concentrated under reduced pressure. This gave 55 mg of the target compound (82% of theory, purity 98%).

LC-MS (Method 3): $R_t$=1.63 min; MS (ESIpos): m/z=492 [M+H]$^+$

Example 76

1-(3,5-Difluoropyridin-2-yl)-7-[(3R,4R)-3,4-dihydroxypyrrolidin-1-yl]-6-fluoro-N-(3-methylpentan-3-yl)-4-oxo-1,4-dihydro-1,8-naphthyridine-3-carboxamide

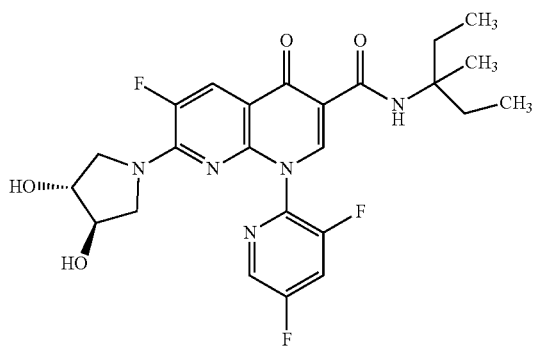 [SMILES: CCC(C)(CC)NC(=O)c1cn(-c2ncc(F)cc2F)c2nc(N3C[C@@H](O)[C@H](O)C3)c(F)cc2c1=O]

1-(3,5-Difluoropyridin-2-yl)-7-[(3R,4R)-3,4-dihydroxypyrrolidin-1-yl]-6-fluoro-4-oxo-1,4-di-hydro-1,8-naphthyridine-3-carboxylic acid (57.0 mg, 135 µmol) was initially charged in 1.4 ml of DMF, HATU (61.6 mg, 162 µmol) and N,N-diisopropylethylamine (140 µl, 810 µmol) were added and the mixture was stirred at room temperature for 10 min. 3-Methylpentan-3-amine hydrochloride (27.9 mg, 202 µmol) was added and the reaction mixture was stirred at room temperature for 2 h. Acetonitrile/water/TFA was added and the reaction solution was purified by preparative HPLC (RP18 column, mobile phase: acetonitrile/water gradient with addition of 0.1% TFA). The product fractions were substantially concentrated under reduced pressure and the residue was made basic with saturated aqueous sodium bicarbonate solution and extracted twice with dichloromethane. The combined organic phases were dried over sodium sulfate, filtered and concentrated under reduced pressure. This gave 51 mg of the target compound (74% of theory, purity 98%).

LC-MS (Method 3): $R_t$=1.74 min; MS (ESIpos): m/z=506 [M+H]$^+$

Example 77

7-[(3R,4S)-3,4-Dihydroxypyrrolidin-1-yl]-N-(3-ethylpentan-3-yl)-6-fluoro-4-oxo-1-(2,4,6-tri-fluorophenyl)-1,4-dihydro-1,8-naphthyridine-3-carboxamide

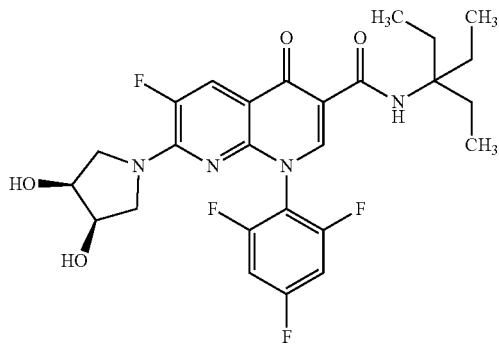 [SMILES: CCC(CC)(CC)NC(=O)c1cn(-c2c(F)cc(F)cc2F)c2nc(N3C[C@@H](O)[C@@H](O)C3)c(F)cc2c1=O]

7-[(3R,4S)-3,4-Dihydroxypyrrolidin-1-yl]-6-fluoro-4-oxo-1-(2,4,6-trifluorophenyl)-1,4-dihydro-1,8-naphthyridine-3-carboxylic acid (75.0 mg, 81% pure, 138 μmol) was initially charged in 1.9 ml of DMF, 3-ethylpentan-3-amine (19.1 mg, 166 μmol), N,N-diisopropylethylamine (84 μl, 480 μmol) and HATU (63.1 mg, 166 μmol) were added and the mixture was stirred at room temperature for 4 h. Acetonitrile/water/TFA was added and the reaction solution was purified by preparative HPLC (RP18 column, mobile phase: acetonitrile/water gradient with addition of 0.1% TFA). The product fractions were substantially concentrated under reduced pressure and the aqueous residue was made basic with saturated aqueous sodium bicarbonate solution and extracted twice with dichloromethane. The combined organic phases were dried over sodium sulfate, filtered and concentrated under reduced pressure. This gave 59 mg of the target compound (78% of theory, purity 98%).

LC-MS (Method 5): $R_t$=1.41 min; MS (ESIpos): m/z=537 [M+H]$^+$ $^1$H NMR (400 MHz, DMSO-d$_6$) δ [ppm]: −0.008 (1.80), 0.008 (1.47), 0.768 (6.83), 0.786 (16.00), 0.805 (7.41), 1.699 (1.98), 1.718 (6.06), 1.736 (5.80), 1.755 (1.82), 2.328 (0.52), 2.366 (0.40), 2.670 (0.59), 4.030 (0.92), 4.991 (0.91), 7.545 (1.37), 7.567 (2.66), 7.589 (1.38), 7.979 (2.75), 8.011 (2.73), 8.667 (4.92), 9.612 (2.83).

Example 78

7-[(3R,4S)-3,4-Dihydroxypyrrolidin-1-yl]-6-fluoro-N-(3-methylpentan-3-yl)-4-oxo-1-(2,4,6-trifluorophenyl)-1,4-dihydro-1,8-naphthyridine-3-carboxamide

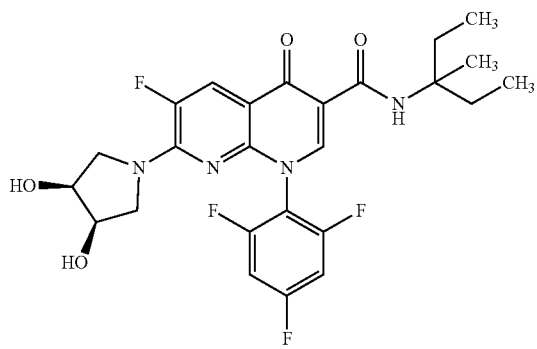 [SMILES: CCC(C)(CC)NC(=O)c1cn(-c2c(F)cc(F)cc2F)c2nc(N3C[C@@H](O)[C@@H](O)C3)c(F)cc2c1=O]

7-[(3R,4S)-3,4-Dihydroxypyrrolidin-1-yl]-6-fluoro-4-oxo-1-(2,4,6-trifluorophenyl)-1,4-dihydro-1,8-naphthyridine-3-carboxylic acid (75.0 mg, 81% pure, 138 μmol) was initially charged in 1.9 ml of DMF, 3-methylpentan-3-amine hydrochloride (22.8 mg, 166 μmol), N,N-diisopropylethylamine (84 μl, 480 μmol) and HATU (63.1 mg, 166 μmol) were added and the mixture was stirred at room temperature for 4 h. Acetonitrile/water/TFA was added and the reaction solution was purified by preparative HPLC (RP18 column, mobile phase: acetonitrile/water gradient with addition of 0.1% TFA). The product fractions were substantially concentrated under reduced pressure and the aqueous residue was made basic with saturated aqueous sodium bicarbonate solution and extracted twice with dichloromethane. The combined organic phases were dried over sodium sulfate, filtered and concentrated under reduced pressure. This gave 63 mg of the target compound (85% of theory, purity 98%).

LC-MS (Method 5): $R_t$=1.35 min; MS (ESIpos): m/z=523 [M+H]$^+$ $^1$H NMR (400 MHz, DMSO-d$_6$) δ [ppm]: −0.008 (1.46), 0.008 (1.29), 0.814 (6.64), 0.833 (15.52), 0.851 (7.27), 1.234 (0.50), 1.279 (16.00), 1.613 (0.42), 1.631 (1.48), 1.649 (1.89), 1.665 (2.44), 1.684 (1.96), 1.703 (0.49), 1.769 (0.57), 1.787 (2.03), 1.806 (2.32), 1.822 (1.86), 1.841 (1.35), 2.073 (8.37), 2.328 (0.49), 2.523 (1.67), 2.670 (0.52), 4.031 (1.20), 4.989 (1.19), 7.546 (1.83), 7.568 (3.46), 7.590 (1.84), 7.977 (3.61), 8.008 (3.53), 8.669 (6.19), 9.728 (3.98).

Example 79

7-[(3R,4S)-3,4-Dihydroxypyrrolidin-1-yl]-6-fluoro-N-(2-methylbutan-2-yl)-4-oxo-1-(2,4,6-tri-fluorophenyl)-1,4-dihydro-1,8-naphthyridine-3-carboxamide

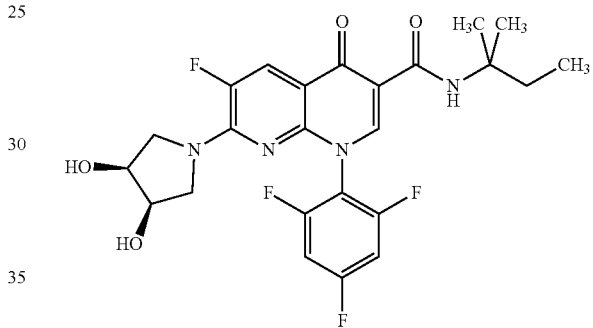

7-[(3R,4S)-3,4-Dihydroxypyrrolidin-1-yl]-6-fluoro-4-oxo-1-(2,4,6-trifluorophenyl)-1,4-dihydro-1,8-naphthyridine-3-carboxylic acid (75.0 mg, 81% pure, 138 μmol) was initially charged in 1.9 ml of DMF, 2-methylbutan-2-amine (19 μl, 170 μmol), N,N-diisopropylethylamine (84 μl, 480 μmol) and HATU (63.1 mg, 166 μmol) were added and the mixture was stirred at room temperature for 4 h. Acetonitrile/water/TFA was added and the reaction solution was purified by preparative HPLC (RP18 column, mobile phase: acetonitrile/water gradient with addition of 0.1% TFA). The product fractions were substantially concentrated under reduced pressure and the aqueous residue was made basic with saturated aqueous sodium bicarbonate solution and extracted twice with dichloromethane. The combined organic phases were dried over sodium sulfate, filtered and concentrated under reduced pressure. This gave 63 mg of the target compound (88% of theory, purity 98%).

LC-MS (Method 5): $R_t$=1.29 min; MS (ESIpos): m/z=509 [M+H]$^+$ $^1$H NMR (400 MHz, DMSO-d$_6$) δ [ppm]: −0.008 (0.76), 0.008 (0.52), 0.848 (1.75), 0.867 (4.17), 0.885 (1.87), 1.341 (16.00), 1.703 (0.53), 1.722 (1.62), 1.740 (1.54), 1.759 (0.45), 2.073 (3.41), 2.518 (0.96), 2.523 (0.79), 4.032 (0.61), 4.989 (0.60), 5.754 (0.54), 7.547 (0.88), 7.569 (1.67), 7.591 (0.89), 7.970 (1.66), 8.001 (1.63), 8.673 (2.83), 9.810 (2.01).

Example 80

N-tert-Butyl-7-[(3R,4S)-3,4-dihydroxypyrrolidin-1-yl]-6-fluoro-4-oxo-1-(2,4,6-trifluoro-phenyl)-1,4-dihydro-1,8-naphthyridine-3-carboxamide

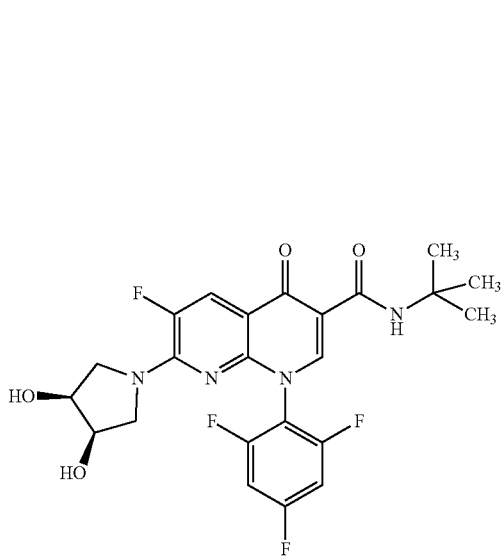 [SMILES: CC(C)(C)NC(=O)c1cn(-c2c(F)cc(F)cc2F)c2nc(N3C[C@@H](O)[C@@H](O)C3)c(F)cc2c1=O]

7-[(3R,4S)-3,4-Dihydroxypyrrolidin-1-yl]-6-fluoro-4-oxo-1-(2,4,6-trifluorophenyl)-1,4-dihydro-1,8-naphthyridine-3-carboxylic acid (75.0 mg, 81% pure, 138 μmol) was initially charged in 1.9 ml of DMF, 2-methylpropan-2-amine (17 μl, 170 μmol), N,N-diisopropylethylamine (84 μl, 480 μmol) and HATU (63.1 mg, 166 μmol) were added and the mixture was stirred at room temperature over the weekend. Acetonitrile/water/TFA was added and the reaction solution was purified by preparative HPLC (RP18 column, mobile phase: acetonitrile/water gradient with addition of 0.1% TFA). The product fractions were concentrated under reduced pressure and the residue was dissolved in dichloromethane/a little methanol. The organic phase was washed twice with saturated aqueous sodium bicarbonate solution. The combined aqueous phases were re-extracted once with dichloromethane. The combined organic phases were dried over sodium sulfate, filtered and concentrated under reduced pressure. This gave 42 mg of the target compound (60% of theory, purity 98%).

LC-MS (Method 3): $R_t$=1.72 min; MS (ESIpos): m/z=495 [M+H]$^+$ $^1$H NMR (400 MHz, DMSO-d$_6$) δ [ppm]: 0.008 (1.47), 1.388 (16.00), 2.073 (1.33), 4.028 (0.44), 4.989 (0.44), 7.547 (0.61), 7.569 (1.21), 7.591 (0.63), 7.957 (1.13), 7.989 (1.12), 8.679 (2.13), 9.865 (1.33).

Example 81

N-[(1S)-1-Cyclopropyl-2,2,2-trifluoroethyl]-6-fluoro-4-oxo-7-(piperazin-1-yl)-1-(2,4,6-trifluorophenyl)-1,4-dihydro-1,8-naphthyridine-3-carboxamide

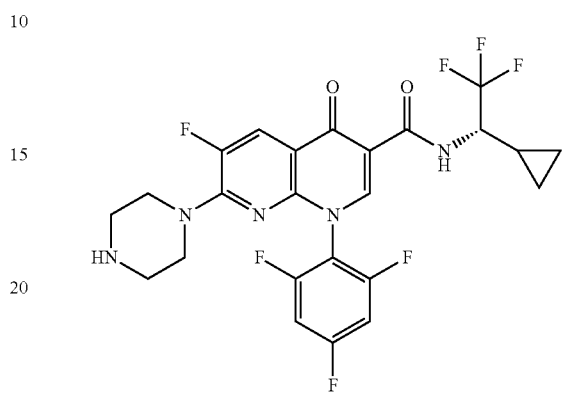

tert-Butyl 4-[6-{[(1S)-1-cyclopropyl-2,2,2-trifluoroethyl]carbamoyl}-3-fluoro-5-oxo-8-(2,4,6-trifluorophenyl)-5,8-dihydro-1,8-naphthyridin-2-yl]piperazine-1-carboxylate (113 mg, 69% pure, 121 μmol) was initially charged in 0.72 ml of dichloromethane, trifluoroacetic acid (360 μl, 4.7 mmol) was added and the mixture was stirred at room temperature for 1 h. The reaction solution was concentrated under reduced pressure, acetonitrile/water/TFA was added and the product was purified by preparative HPLC (RP18 column, mobile phase: methanol/water gradient with addition of 0.1% TFA). The product fractions were substantially concentrated. The residue was taken up in ethyl acetate and the aqueous phase was made basic using saturated aqueous sodium bicarbonate solution. The aqueous phase was extracted three times with ethyl acetate. The combined organic phases were dried over sodium sulfate, filtered and concentrated under reduced pressure. The crude product was purified further by thick-layer chromatography (mobile phase: dichloromethane/2M ammonia in methanol=20/1). This gave 43 mg of the target compound (65% of theory, purity 99%).

LC-MS (Method 3): $R_t$=1.36 min; MS (ESIpos): m/z=544 [M+H]$^+$ $^1$H NMR (400 MHz, DMSO-d$_6$) δ [ppm]: −0.149 (0.64), −0.008 (6.43), 0.008 (5.61), 0.146 (0.68), 0.319 (2.04), 0.329 (3.29), 0.342 (3.21), 0.353 (2.50), 0.365 (1.25), 0.504 (0.82), 0.516 (2.18), 0.528 (3.29), 0.541 (3.07), 0.550 (3.43), 0.568 (3.57), 0.578 (2.79), 0.589 (2.54), 0.599 (2.07), 0.613 (1.29), 0.628 (1.86), 0.638 (1.71), 0.648 (3.14), 0.659 (2.61), 0.665 (2.43), 0.671 (2.39), 0.680 (1.18), 0.693 (0.79), 1.170 (0.64), 1.182 (1.32), 1.190 (1.89), 1.202 (3.18), 1.211 (2.32), 1.223 (3.18), 1.235 (2.07), 1.243 (1.29), 1.256 (0.57), 2.073 (0.96), 2.328 (1.21), 2.367 (1.04), 2.524 (4.82), 2.663 (12.39), 2.675 (16.00), 2.687 (12.50), 2.710 (1.39), 3.440 (12.39), 3.452 (15.11), 3.464 (11.71), 4.333 (0.43), 4.353 (1.64), 4.374 (2.89), 4.395 (2.86), 4.415 (1.54), 5.754 (0.43), 7.555 (5.61), 7.577 (10.82), 7.599 (5.71), 8.060 (9.39), 8.094 (9.29), 8.876 (15.57), 10.387 (6.43), 10.411 (6.29).

Example 82

N-[(1S)-1-Cyclopropyl-2,2,2-trifluoroethyl]-6-fluoro-7-[(3S)-3-methylpiperazin-1-yl]-4-oxo-1-(2,4,6-trifluorophenyl)-1,4-dihydro-1,8-naphthyridine-3-carboxamide

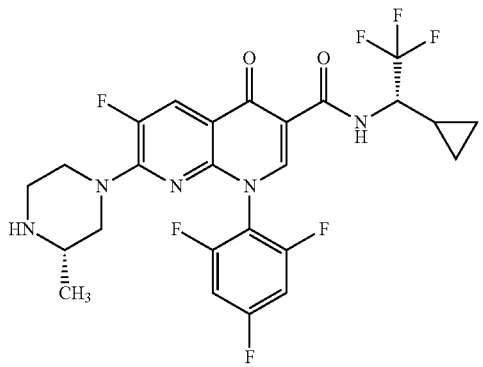 [SMILES: C[C@H]1CN(c2nc3c(cc2F)c(=O)c(C(=O)N[C@@H](C2CC2)C(F)(F)F)cn3-c2c(F)cc(F)cc2F)CCN1]

tert-Butyl (2S)-4-[6-{[(1S)-1-cyclopropyl-2,2,2-trifluoroethyl]carbamoyl}-3-fluoro-5-oxo-8-(2,4,6-trifluorophenyl)-5,8-dihydro-1,8-naphthyridin-2-yl]-2-methylpiperazine-1-carboxylate (81.5 mg, 90% pure, 112 μmol) was initially charged in 0.66 ml of dichloromethane, trifluoroacetic acid (330 μl, 4.3 mmol) was added and the mixture was stirred at room temperature for 1 h. The reaction solution was diluted with dichloromethane and washed three times with saturated aqueous sodium chloride solution. The combined aqueous phases were re-extracted with dichloromethane. The combined organic phases were dried over sodium sulfate, filtered and concentrated under reduced pressure. Acetonitrile/water/TFA was added and the reaction solution was purified by preparative HPLC (RP18 column, mobile phase: acetonitrile/water gradient with addition of 0.1% TFA). The product fractions were substantially concentrated. The residue was taken up in ethyl acetate and the aqueous phase was made basic using saturated aqueous sodium bicarbonate solution. The aqueous phase was extracted three times with ethyl acetate. The combined organic phases were dried over sodium sulfate, filtered and concentrated under reduced pressure. The crude product was purified further by thick-layer chromatography (mobile phase: dichloromethane/2 N ammonia solution in methanol=20/1). This gave 26.3 mg of the target compound (40% of theory, purity 95%).

LC-MS (Method 3): $R_t$=1.40 min; MS (ESIpos): m/z=558 [M+H]$^+$ $^1$H NMR (400 MHz, DMSO-d$_6$) δ [ppm]: −0.149 (0.92), −0.008 (8.28), 0.008 (6.83), 0.146 (0.92), 0.320 (1.78), 0.330 (2.85), 0.342 (2.76), 0.354 (2.17), 0.365 (1.07), 0.516 (1.90), 0.527 (2.85), 0.540 (2.64), 0.549 (2.97), 0.568 (3.09), 0.578 (2.40), 0.588 (2.20), 0.599 (1.81), 0.613 (1.10), 0.628 (1.60), 0.638 (1.54), 0.648 (2.73), 0.659 (2.29), 0.664 (2.11), 0.670 (2.11), 0.680 (1.10), 0.693 (0.80), 0.837 (15.47), 0.852 (16.00), 0.919 (0.53), 1.169 (0.62), 1.182 (1.22), 1.190 (1.75), 1.202 (2.82), 1.210 (2.08), 1.222 (2.82), 1.234 (1.99), 1.242 (1.16), 1.255 (0.53), 2.119 (0.42), 2.302 (2.94), 2.323 (1.22), 2.328 (1.34), 2.366 (0.74), 2.524 (4.36), 2.573 (3.06), 2.605 (1.51), 2.666 (0.95), 2.670 (1.28), 2.675 (0.92), 2.711 (0.74), 2.805 (2.64), 2.834 (2.05), 2.965 (1.40), 2.972 (1.57), 2.998 (2.52), 3.027 (1.57), 3.869 (3.06), 3.896 (3.06), 3.972 (2.43), 4.004 (2.29), 4.355 (1.45), 4.375 (2.52), 4.397 (2.49), 4.417 (1.37), 7.577 (4.93), 7.599 (9.26), 7.622 (4.96), 7.630 (1.75), 8.053 (8.55), 8.088 (8.37), 8.890 (14.58), 8.913 (0.50), 10.390 (5.67), 10.414 (5.34).

Example 83

N-[(1S)-1-Cyclopropyl-2,2,2-trifluoroethyl]-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide

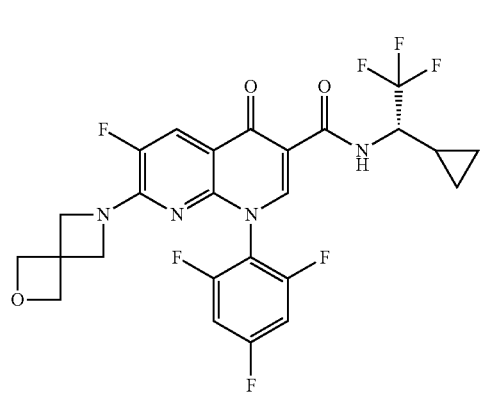 [SMILES: O=C(N[C@@H](C1CC1)C(F)(F)F)c1cn(-c2c(F)cc(F)cc2F)c2nc(N3CC4(COC4)C3)c(F)cc2c1=O]

7-Chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide (1.20 g, 2.43 mmol) was initially charged in 23 ml of DMF, ethanedioic acid 2-oxa-6-azaspiro[3.3]heptane (1:1) (644 mg, 3.40 mmol) and N,N-diisopropylethylamine (2.1 ml, 12 mmol) were added and the mixture was stirred at room temperature overnight. Water was added to the reaction solution and the resulting precipitated solid was filtered off and dried under high vacuum. The crude product was purified by silica gel chromatography (mobile phase: 100% dichloromethane to dichloromethane/methanol=100/1). This gave 1.0 g of the target compound (73% of theory, purity 99%).

LC-MS (Method 3): $R_t$=2.20 min; MS (ESIpos): m/z=557 [M+H]$^+$

Example 84

7-[3,3-Bis(hydroxymethyl)azetidin-1-yl]-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide

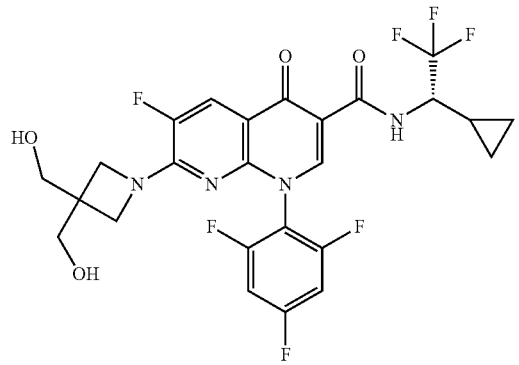 [SMILES: O=C(N[C@@H](C1CC1)C(F)(F)F)c1cn(-c2c(F)cc(F)cc2F)c2nc(N3CC(CO)(CO)C3)c(F)cc2c1=O]

N-[(1S)-1-Cyclopropyl-2,2,2-trifluoroethyl]-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide (65.0 mg, 117 µmol) was initially charged in trifluoroacetic acid (730 µl, 9.5 mmol), 730 µl of water and 730 µl of acetonitrile were added and the mixture was stirred at room temperature for two days. The reaction solution was purified by preparative HPLC (RP18 column, mobile phase: acetonitrile/water gradient with addition of 0.1% TFA). The product fractions were concentrated under reduced pressure and the residue was taken up in dichloromethane and washed twice with saturated aqueous sodium bicarbonate solution. The combined aqueous phases were re-extracted with dichloromethane. The combined organic phases were dried over sodium sulfate, filtered and concentrated under reduced pressure. This gave 45 mg of the target compound (66% of theory, purity 99%).

LC-MS (Method 3): $R_t$=1.86 min; MS (ESIpos): m/z=575 [M+H]$^+$ $^1$H NMR (400 MHz, DMSO-d$_6$) δ [ppm]: −0.149 (0.42), −0.008 (3.70), 0.008 (3.30), 0.146 (0.41), 0.316 (1.31), 0.326 (2.15), 0.338 (2.07), 0.350 (1.69), 0.362 (0.80), 0.510 (1.45), 0.521 (2.09), 0.534 (1.89), 0.545 (2.18), 0.553 (1.61), 0.564 (2.23), 0.575 (1.72), 0.585 (1.64), 0.595 (1.33), 0.609 (0.83), 0.624 (1.13), 0.634 (1.13), 0.645 (1.97), 0.655 (1.70), 0.668 (1.59), 1.163 (0.46), 1.175 (0.92), 1.183 (1.27), 1.195 (2.15), 1.204 (1.50), 1.215 (2.10), 1.228 (1.24), 1.236 (1.21), 2.074 (10.78), 2.328 (0.75), 2.366 (0.47), 2.670 (0.66), 2.710 (0.41), 3.475 (15.83), 3.488 (16.00), 4.130 (0.94), 4.349 (1.22), 4.369 (1.91), 4.390 (1.84), 4.410 (0.97), 4.835 (5.32), 4.848 (12.45), 4.861 (5.07), 5.754 (4.77), 7.532 (3.99), 7.554 (7.54), 7.576 (3.92), 7.963 (6.93), 7.992 (6.79), 8.808 (12.92), 10.463 (4.45), 10.487 (4.20).

Example 85 tert-Butyl 4-[({7-[(3R,4R)-3,4-dihydroxypyrrolidin-1-yl]-6-fluoro-4-oxo-1-(2,4,6-trifluoro-phenyl)-1,4-dihydro-1,8-naphthyridin-3-yl}carbonyl)amino]-3,3-difluoropiperidine-1-carboxylate

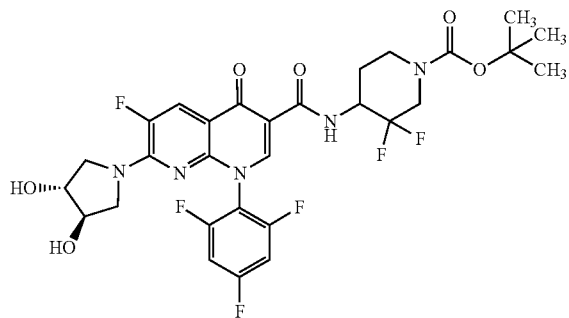 [SMILES: CC(C)(C)OC(=O)N1CCC(NC(=O)c2cn(-c3c(F)cc(F)cc3F)c3nc(N4C[C@@H](O)[C@H](O)C4)c(F)cc3c2=O)C(F)(F)C1]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (50.0 mg, 73% pure, 83.1 µmol) was initially charged in 1.2 ml of DMF, HATU (37.9 mg, 99.7 µmol) and N,N-diisopropylethylamine (36 µl, 210 µmol) were added and the mixture was stirred at room temperature for 30 min. tert-Butyl 4-amino-3,3-difluoropiperidine-1-carboxylate (23.6 mg, 99.7 µmol) was added and the mixture was left to stir at room temperature for 2 h. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with dichloromethane. The combined organic phases were washed twice with saturated aqueous sodium bicarbonate solution. The combined aqueous phases were re-extracted with dichloromethane. The combined organic phases were dried over sodium sulfate, filtered and concentrated under reduced pressure. This gave 48 mg of the target compound (87% of theory, purity 99%).

LC-MS (Method 3): $R_t$=1.81 min; MS (ESIpos): m/z=658 [M+H]$^+$ $^1$H NMR (400 MHz, DMSO-d$_6$) δ [ppm]: −0.008 (0.48), 1.157 (0.55), 1.175 (1.10), 1.193 (0.55), 1.427 (16.00), 1.988 (2.06), 4.021 (0.59), 4.038 (0.53), 5.192 (0.56), 7.572 (0.73), 7.995 (0.80), 8.026 (0.78), 8.807 (1.58), 10.314 (0.54), 10.337 (0.51).

Example 86

Methyl 4-[({7-[(3R,4R)-3,4-dihydroxypyrrolidin-1-yl]-6-fluoro-4-oxo-1-(2,4,6-trifluoro-phenyl)-1,4-dihydro-1,8-naphthyridin-3-yl}carbonyl)amino]bicyclo[2.2.1]heptane-1-carboxylate

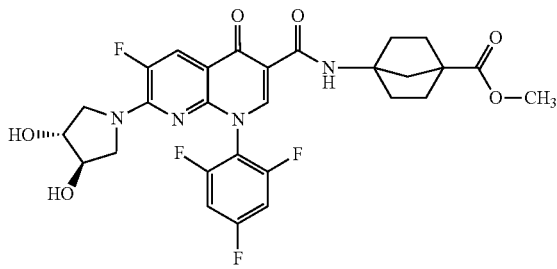 [SMILES: COC(=O)C12CCC(NC(=O)c3cn(-c4c(F)cc(F)cc4F)c4nc(N5C[C@@H](O)[C@H](O)C5)c(F)cc4c3=O)(CC1)C2]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (50.0 mg, 98% pure, 112 µmol) was initially charged in 1.6 ml of DMF, HATU (50.9 mg, 134 µmol) and N,N-diisopropylethylamine (49 µl, 280 µmol) were added and the mixture was stirred at room temperature for 30 min. Methyl 4-aminobicyclo[2.2.1]heptane-1-carboxylate (22.6 mg, 134 µmol) was added and the mixture was left to stir at room temperature for 2 h. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with dichloromethane. The combined organic phases were washed twice with saturated aqueous sodium bicarbonate solution. The combined aqueous phases were re-extracted with dichloromethane. The combined organic phases were dried over sodium sulfate, filtered and concentrated under reduced pressure. This gave 52 mg of the target compound (78% of theory, purity 99%).

LC-MS (Method 3): $R_t$=1.68 min; MS (ESIpos): m/z=591 [M+H]$^+$ $^1$H NMR (400 MHz, CHLOROFORM-d) δ [ppm]: −0.008 (0.56), 0.008 (0.54), 1.584 (6.18), 1.725 (0.82), 1.751 (1.60), 1.765 (1.06), 1.903 (0.99), 1.917 (1.54), 1.943 (0.96), 2.006 (0.84), 2.083 (0.44), 2.124 (3.16), 2.138 (3.63), 2.155 (4.94), 2.279 (1.00), 3.693 (16.00), 4.255 (2.00), 6.860 (1.01), 6.880 (1.82), 6.899 (1.04), 7.997 (1.62), 8.029 (1.61), 8.522 (3.08), 10.228 (2.05).

Example 87

7-[(3R,4R)-3,4-Dihydroxypyrrolidin-1-yl]-N-(3-ethylpentan-3-yl)-6-fluoro-4-oxo-1-(2,4,6-tri-fluorophenyl)-1,4-dihydro-1,8-naphthyridine-3-carboxamide

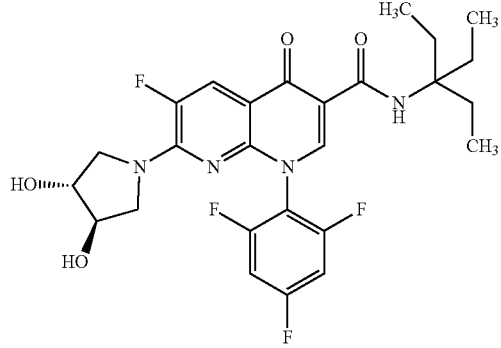 [SMILES: CCC(CC)(CC)NC(=O)c1cn(-c2c(F)cc(F)cc2F)c2nc(N3C[C@@H](O)[C@H](O)C3)c(F)cc2c1=O]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (50.0 mg, 73% pure, 83.1 µmol) was initially charged in 1.2 ml of DMF, HATU (37.9 mg, 99.7 µmol) and N,N-diisopropylethylamine (36 µl, 210 µmol) were added and the mixture was stirred at room temperature for 30 min. 3-Ethylpentan-3-amine (11.5 mg, 99.7 µmol) was added and the mixture was stirred at room temperature overnight. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with ethyl acetate. The combined organic phases were washed twice with saturated aqueous sodium bicarbonate solution. The combined aqueous phases were re-extracted with ethyl acetate. The combined organic phases were dried over sodium sulfate, filtered and concentrated under reduced pressure. This gave 36 mg of the target compound (80% of theory, purity 99%).

LC-MS (Method 3): $R_t$=1.99 min; MS (ESIpos): m/z=537 [M+H]$^+$ $^1$H NMR (400 MHz, DMSO-d6) δ[ppm]: −0.008 (0.97), 0.008 (0.75), 0.770 (6.80), 0.789 (16.00), 0.807 (7.33), 1.702 (1.95), 1.720 (6.78), 1.739 (5.74), 1.757 (1.74), 2.524 (0.69), 3.918 (0.49), 5.191 (1.51), 7.549 (1.11), 7.571 (1.93), 7.592 (1.09), 7.991 (2.75), 8.023 (2.69), 8.671 (4.76), 9.621 (2.85).

Example 88

7-[(3R,4R)-3,4-Dihydroxypyrrolidin-1-yl]-6-fluoro-N-(3-methylpentan-3-yl)-4-oxo-1-(2,4,6-trifluorophenyl)-1,4-dihydro-1,8-naphthyridine-3-carboxamide

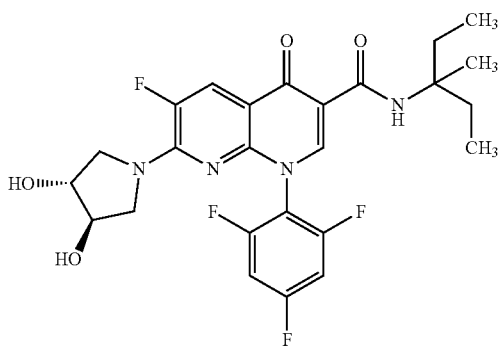 [SMILES: CCC(C)(CC)NC(=O)c1cn(-c2c(F)cc(F)cc2F)c2nc(N3C[C@@H](O)[C@H](O)C3)c(F)cc2c1=O]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (40.0 mg, 73% pure, 66.5 µmol) was initially charged in 0.93 of DMF, HATU (30.3 mg, 79.8 µmol) and N,N-diisopropylethylamine (29 µl, 170 µmol) were added and the mixture was stirred at room temperature for 30 min. 3-Methylpentan-3-amine hydrochloride (11.0 mg, 79.8 µmol) was added and the mixture was stirred at room temperature for 2 h. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with dichloromethane. The combined organic phases were washed twice with saturated aqueous sodium bicarbonate solution. The combined aqueous phases were re-extracted with dichloromethane. The combined organic phases were dried over sodium sulfate, filtered and concentrated under reduced pressure. This gave 29 mg of the target compound (83% of theory, purity 99%).

LC-MS (Method 3): $R_t$=1.88 min; MS (ESIpos): m/z=523 [M+H]$^+$ $^1$H NMR (400 MHz, DMSO-d6) δ[ppm]: 0.008 (2.16), 0.817 (6.77), 0.835 (15.54), 0.854 (7.44), 1.282 (16.00), 1.616 (0.41), 1.634 (1.39), 1.652 (1.86), 1.668 (2.36), 1.687 (1.89), 1.705 (0.53), 1.773 (0.62), 1.791 (2.07), 1.809 (2.44), 1.826 (1.91), 1.844 (1.39), 3.908 (0.77), 5.190 (2.41), 7.550 (1.66), 7.572 (3.01), 7.593 (1.62), 7.990 (3.59), 8.022 (3.54), 8.673 (6.67), 9.737 (4.26).

Example 89

7-[(3R,4R)-3,4-dihydroxypyrrolidin-1-yl]-6-fluoro-N-(2-methylbutan-2-yl)-4-oxo-1-(2,4,6-tri-fluoro-phenyl)-1,4-dihydro-1,8-naphthyridine-3-carboxamide

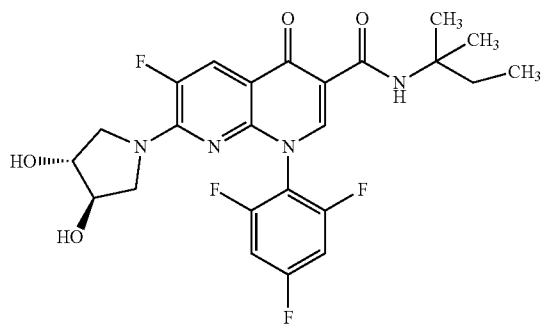 [SMILES: CCC(C)(C)NC(=O)c1cn(-c2c(F)cc(F)cc2F)c2nc(N3C[C@@H](O)[C@H](O)C3)c(F)cc2c1=O]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (50.0 mg, 73% pure, 83.1 µmol) was initially charged in 1.2 ml of DMF, HATU (37.9 mg, 99.7 µmol) and N,N-diisopropylethylamine (36 µl, 210 µmol) were added and the mixture was stirred at room temperature for 30 min. 2-Methylbutan-2-amine (12 µl, 100 µmol) was added and the mixture was stirred at room temperature for 2 h. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with ethyl acetate. The combined organic phases were washed twice with saturated aqueous sodium bicarbonate solution. The combined aqueous phases were re-extracted with ethyl acetate. The combined organic phases were dried over sodium sulfate, filtered and concentrated under reduced pressure. This gave 34 mg of the target compound (80% of theory, purity 99%).

LC-MS (Method 3): $R_t$=1.76 min; MS (ESIpos): m/z=509 [M+H]$^+$ $^1$H NMR (400 MHz, DMSO-d6) δ[ppm]: 0.008 (1.67), 0.851 (1.89), 0.869 (4.29), 0.888 (1.90), 1.343 (16.00), 1.706 (0.62), 1.724 (1.70), 1.743 (1.61), 1.761 (0.47), 3.909 (0.41), 5.186 (1.22), 7.551 (0.86), 7.573 (1.45), 7.593 (0.83), 7.982 (1.87), 8.014 (1.83), 8.676 (3.26), 9.818 (2.08).

Example 90

N-tert-Butyl-7-[(3R,4R)-3,4-dihydroxypyrrolidin-1-yl]-6-fluoro-4-oxo-1-(2,4,6-trifluoro-phenyl)-1,4-dihydro-1,8-naphthyridine-3-carboxamide

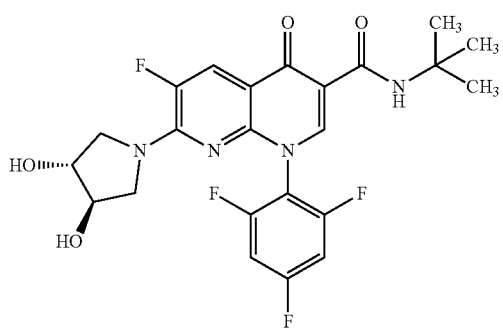 [SMILES: CC(C)(C)NC(=O)c1cn(-c2c(F)cc(F)cc2F)c2nc(N3C[C@@H](O)[C@H](O)C3)c(F)cc2c1=O]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (60.0 mg, 73% pure, 99.7 µmol) was initially charged in 1.4 ml of DMF, HATU (45.5 mg, 120 µmol) and N,N-diisopropylethylamine (43 µl, 250 µmol) were added and the mixture was stirred at room temperature for 30 min. 2-Methylpropan-2-amine (8.75 mg, 120 µmol) was added and the mixture was stirred at room temperature for 2 h. Acetonitrile/water/TFA was added and the reaction solution was purified by preparative HPLC (RP18 column, mobile phase: acetonitrile/water gradient with addition of 0.1% TFA). The product fractions were very substantially concentrated under reduced pressure and the residue was extracted twice with dichloromethane. The combined organic phases were washed twice with saturated aqueous sodium bicarbonate solution. The combined aqueous phases were re-extracted with dichloromethane. The combined organic phases were dried over sodium sulfate, filtered and concentrated under reduced pressure. This gave 26 mg of the target compound (52% of theory, purity 99%).

LC-MS (Method 3): $R_t$=1.66 min; MS (ESIpos): m/z=495 [M+H]$^+$ $^1$H NMR (400 MHz, DMSO-d6) δ[ppm]: 0.008 (1.87), 1.245 (0.76), 1.260 (0.86), 1.275 (0.48), 1.390 (16.00), 5.185 (0.79), 7.551 (0.52), 7.573 (0.92), 7.594 (0.53), 7.970 (1.13), 8.002 (1.11), 8.682 (2.04), 9.872 (1.36).

Example 91

7-[(3R,4S)-3,4-Dihydroxypyrrolidin-1-yl]-6-fluoro-4-oxo-N-(4,4,4-trifluoro-2-methylbutan-2-yl)-1-(2,4,6-trifluorophenyl)-1,4-dihydro-1,8-naphthyridine-3-carboxamide

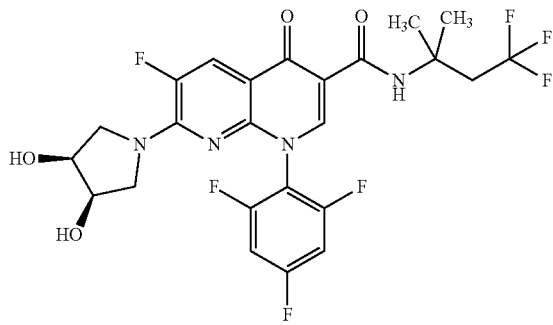 [SMILES: CC(C)(CC(F)(F)F)NC(=O)c1cn(-c2c(F)cc(F)cc2F)c2nc(N3C[C@@H](O)[C@@H](O)C3)c(F)cc2c1=O]

According to GP1, 80.0 mg (182 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 45.3 mg (255 µmol) of 4,4,4-trifluoro-2-methylbutan-2-amine hydrochloride in the presence of 83.1 mg (219 µmol) of HATU and 95 µl (550 µmol) of DIPEA in 730 µl of DMF. The crude product was purified by preparative HPLC (column: acetonitrile/water/0.1% of formic acid). This gave 88.9 mg (87% of theory, 100% pure) of the title compound.

LC-MS (Method 3): $R_t$=1.84 min; MS (ESIpos): m/z=563 [M+H]$^+$ $^1$H NMR (400 MHz, DMSO-d6): δ [ppm]=10.08 (s, 1H), 8.72 (s, 1H), 7.98 (d, 1H), 7.53-7.61 (m, 2H), 4.87-5.10 (m, 2H), 3.83-4.11 (m, 3H), 3.48-3.69 (m, 1H), 3.12-3.27 (m, 1H), 2.87-3.09 (m, 3H), 1.48 (s, 6H).

Example 92

7-[(3R,4S)-3,4-Dihydroxypyrrolidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

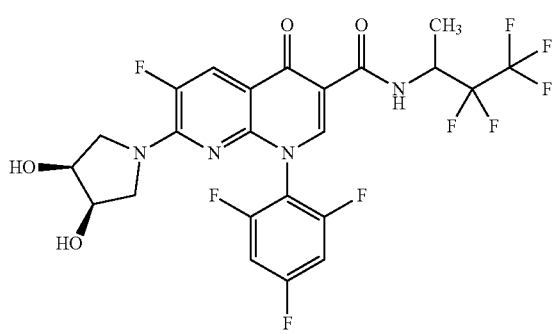 [SMILES: CC(NC(=O)c1cn(-c2c(F)cc(F)cc2F)c2nc(N3C[C@@H](O)[C@@H](O)C3)c(F)cc2c1=O)C(F)(F)C(F)(F)F]

According to GP1, 150 mg (341 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 95.4 mg (478 µmol) of 3,3,4,4,4-pentafluorobutan-2-amine hydrochloride (racemate) in the presence of 156 mg (410 µmol) of HATU and 180 µl (1.00 mmol) of DIPEA in 1.4 ml of DMF. The crude product was purified by preparative HPLC (column: acetonitrile/water/0.1% of formic acid). This gave 149 mg (75% of theory, 100% pure) of the title compound.

LC-MS (Method 3): $R_t$=1.87 min; MS (ESIpos): m/z=585 [M+H]$^+$ $^1$H-NMR (400 MHz, DMSO-d6): δ [ppm]=10.46 (d, 1H), 8.84 (s, 1H), 8.00 (d, 1H), 7.53-7.61 (m, 2H), 4.89-5.12 (m, 3H), 3.85-4.12 (m, 3H), 3.47-3.70 (m, 1H), 2.91-3.28 (m, 2H), 1.39 (d, 3H).

146 mg of the title compound (diastereomer mixture) were separated by chiral HPLC into the diastereomers (preparative HPLC: column Daicel Chiralcel OX-H, 5 µm, 250×30 mm; mobile phase: 80% n-heptane, 20% ethanol; temperature: 25° C.; flow rate: 40 ml/min; UV detection: 265 nm.)

This gave (in the sequence of elution from the column) 56.0 mg of diastereomer 1 (99% de) $R_t$=6.40 min and 55.8 mg of diastereomer 2 (98% de) $R_t$=8.57 min.

[Analytical HPLC: column Daicel OX-3.3 µm, 50×4.6 mm; mobile phase: 80% isohexane, 20% ethanol; UV detection: 220 nm].

Diastereomer 1 was additionally purified by preparative HPLC (column: acetonitrile/water/0.1% formic acid, giving 41.0 mg (21% of theory, 100% pure) of the title compound from Example 93.

Diastereomer 2 was additionally purified by preparative HPLC (column: acetonitrile/water/0.1% formic acid, giving 42.0 mg (21% of theory, 100% pure) of the title compound from Example 94.

Example 93

7-[(3R,4S)-3,4-Dihydroxypyrrolidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Diastereomer 1)

LC-MS (Method 3): $R_t$=1.89 min; MS (ESIpos): m/z=585 [M+H]$^+$ $^1$H-NMR (400 MHz, DMSO-d6): δ [ppm]=10.46 (d, 1H), 8.84 (s, 1H), 8.00 (d, 1H), 7.54-7.61 (m, 2H), 4.91-5.10 (m, 3H), 3.84-4.12 (m, 3H), 3.43-3.67 (m, 1H), 3.12-3.28 (m, 1H), 2.88-3.11 (m, 1H), 1.39 (d, 3H).

Example 94

7-[(3R,4S)-3,4-Dihydroxypyrrolidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Diastereomer 2)

LC-MS (Method 3): $R_t$=1.89 min; MS (ESIpos): m/z=585 [M+H]$^+$ $^1$H-NMR (400 MHz, DMSO-d6): δ [ppm]=10.46 (d, 1H), 8.84 (s, 1H), 8.00 (d, 1H), 7.54-7.61 (m, 2H), 4.92-5.09 (m, 3H), 3.85-4.11 (m, 3H), 3.42-3.68 (m, 1H), 3.12-3.28 (m, 1H), 2.92-3.11 (m, 1H), 1.39 (d, 3H).

Example 95

7-[(3R,4S)-3,4-Dihydroxypyrrolidin-1-yl]-6-fluoro-4-oxo-N-[1-(trifluoromethoxy)butan-2-yl]-1-(2,4,6-trifluorophenyl)-1,4-dihydro-1,8-naphthyridine-3-carboxamide (Diastereomer Mixture)

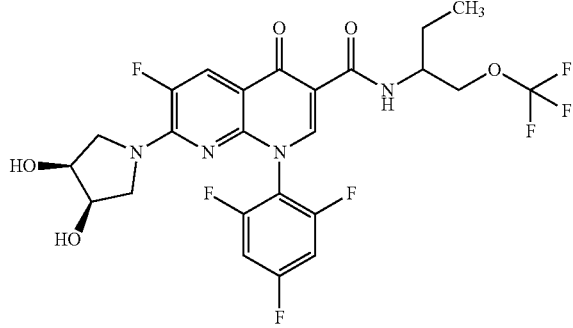 [SMILES: CCC(COC(F)(F)F)NC(=O)c1cn(-c2c(F)cc(F)cc2F)c2nc(N3C[C@@H](O)[C@@H](O)C3)c(F)cc2c1=O]

According to GP1, 120 mg (273 μmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 74.0 mg (382 μmol) of 1-(trifluoromethoxy)butan-2-amine hydrochloride (racemate) in the presence of 125 mg (328 μmol) of HATU and 140 μl (820 μmol) of DIPEA in 1.1 ml of DMF. The crude product was purified by preparative HPLC (column: acetonitrile/water/0.1% of formic acid). This gave 103 mg (65% of theory, 100% pure) of the title compound.

LC-MS (Method 1): $R_t$=0.99 min; MS (ESIpos): m/z=579 [M+H]$^+$ $^1$H-NMR (400 MHz, DMSO-d6): δ [ppm]=9.99 (br d, 1H), 8.76 (s, 1H), 8.00 (d, 1H), 7.53-7.61 (m, 2H), 4.79-5.20 (m, 2H), 4.11-4.23 (m, 3H), 3.77-4.10 (m, 3H), 3.43-3.74 (m, 1H), 2.85-3.26 (m, 2H), 1.52-1.73 (m, 2H), 0.94 (t, 3H).

100 mg of the title compound (diastereomer mixture) were separated by chiral HPLC into the diastereomers (preparative HPLC: column Chiralpak AD-H, 5 μm, 250×30 mm; mobile phase: 80% n-heptane, 20% ethanol; temperature: 25° C.; flow rate: 40 ml/min; UV detection: 265 nm.)

This gave (in the sequence of elution from the column) 23.6 mg of diastereomer 1 (99% de) Rt=10.77 min and 13.5 mg (9% of theory, 100% pure) of diastereomer 2 (98% de) Rt=12.40 min.

[Analytical HPLC: column Chiraltek AD-3, 3 μm; mobile phase: 80% isohexane, 20% ethanol; UV detection: 220 nm], Diastereomer 1 was additionally purified by preparative HPLC (column: acetonitrile/water/0.1% formic acid, giving 4.30 mg (3% of theory, 100% pure) of the title compound from Example 96.

Example 96

7-[(3R,4S)-3,4-Dihydroxypyrrolidin-1-yl]-6-fluoro-4-oxo-N-[1-(trifluoromethoxy)butan-2-yl]-1-(2,4,6-trifluorophenyl)-1,4-dihydro-1,8-naphthyridine-3-carboxamide (Diastereomer 1)

LC-MS (Method 3): $R_t$=1.87 min; MS (ESIpos): m/z=579 [M+H]$^+$ $^1$H-NMR (500 MHz, DMSO-d6): δ [ppm]=9.98 (br d, 1H), 8.76 (s, 1H), 8.00 (d, 1H), 7.54-7.60 (m, 2H), 4.91-5.07 (m, 2H), 4.13-4.22 (m, 3H), 3.82-4.10 (m, 3H), 3.44-3.66 (m, 1H), 3.12-3.29 (m, 1H), 2.93-3.11 (m, 1H), 1.63-1.72 (m, 1H), 1.53-1.63 (m, 1H), 0.94 (t, 3H).

Example 97

7-[(3R,4S)-3,4-Dihydroxypyrrolidin-1-yl]-6-fluoro-4-oxo-N-[1-(trifluoromethoxy)butan-2-yl]-1-(2,4,6-trifluorophenyl)-1,4-dihydro-1,8-naphthyridine-3-carboxamide (Diastereomer 2)

LC-MS (Method 3): $R_t$=1.87 min; MS (ESIpos): m/z=579 [M+H]$^+$ $^1$H-NMR (400 MHz, DMSO-d6): δ [ppm]=9.99 (brd, 1H), 8.76 (s, 1H), 8.00 (d, 1H), 7.53-7.61 (m, 2H), 4.90-5.08 (m, 2H), 4.13-4.23 (m, 3H), 3.79-4.10 (m, 3H), 3.45-3.69 (m, 1H), 3.11-3.27 (m, 1H), 2.86-3.11 (m, 1H), 1.53-1.72 (m, 2H), 0.94 (t, 3H).

Example 98

7-[(3R,4S)-3,4-Dihydroxypyrrolidin-1-yl]-6-fluoro-4-oxo-N-[(2S)-1,1,1-trifluorobutan-2-yl]-1-(2,4,6-trifluorophenyl)-1,4-dihydro-1,8-naphthyridine-3-carboxamide

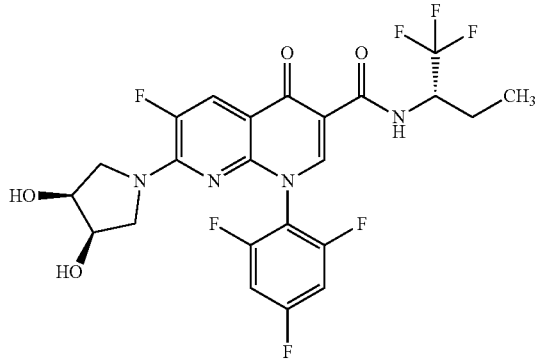 [SMILES: CC[C@H](NC(=O)c1cn(-c2c(F)cc(F)cc2F)c2nc(N3C[C@@H](O)[C@@H](O)C3)c(F)cc2c1=O)C(F)(F)F]

According to GP1, 50.0 mg (114 μmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 26.1 mg (159 μmol) of (2S)-1,1,1-trifluorobutan-2-amine hydrochloride in the presence of 51.9 mg (137 μmol) of HATU and 59 μl (340 μmol) of DIPEA in 460 μl of DMF. The crude product was purified by preparative HPLC (column: acetonitrile/water/0.1% of formic acid). This gave 47.2 mg (76% of theory, 100% pure) of the title compound.

LC-MS (Method 1): $R_t$=0.98 min; MS (ESIpos): m/z=549 [M+H]$^+$ $^1$H-NMR (400 MHz, DMSO-d6): δ [ppm]=10.33 (d, 1H), 8.84 (s, 1H), 8.00 (d, 1H), 7.54-7.61 (m, 2H), 4.84-5.23 (m, 2H), 4.67-4.83 (m, 1H), 3.81-4.16 (m, 3H), 3.42-3.70 (m, 2H), 2.95-3.14 (m, 1H), 1.83-1.93 (m, 1H), 1.58-1.70 (m, 1H), 0.97 (t, 3H).

Example 99

7-[(3R,4S)-3,4-Dihydroxypyrrolidin-1-yl]-6-fluoro-N-[(2R)-3-methylbutan-2-yl]-4-oxo-1-(2,4,6-trifluorophenyl)-1,4-dihydro-1,8-naphthyridine-3-carboxamide

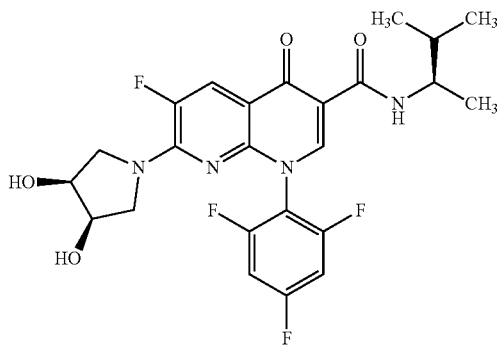 [SMILES: CC(C)[C@@H](C)NC(=O)c1cn(-c2c(F)cc(F)cc2F)c2nc(N3C[C@@H](O)[C@@H](O)C3)c(F)cc2c1=O]

According to GP1, 50.0 mg (114 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 13.9 mg (159 µmol) of (2R)-3-methylbutan-2-amine in the presence of 51.9 mg (137 µmol) of HATU and 59 µl (340 µmol) of DIPEA in 460 µl of DMF. The crude product was purified by preparative HPLC (column: acetonitrile/water/0.1% of formic acid). This gave 21.6 mg (37% of theory, 100% pure) of the title compound.

LC-MS (Method 3): $R_t$=1.74 min; MS (ESIpos): m/z=509 [M+H]$^+$ $^1$H-NMR (400 MHz, DMSO-d6): δ [ppm]=9.87 (d, 1H), 8.71 (s, 1H), 8.00 (d, 1H), 7.53-7.60 (m, 2H), 4.88-5.10 (m, 2H), 3.80-4.16 (m, 4H), 3.47-3.72 (m, 1H), 3.12-3.27 (m, 1H), 2.88-3.11 (m, 1H), 1.72-1.81 (m, 1H), 1.10 (d, 3H), 0.93 (d, 3H), 0.91 (d, 3H).

Example 100

7-[(3R,4S)-3,4-Dihydroxypyrrolidin-1-yl]-6-fluoro-N-[(2S)-3-methylbutan-2-yl]-4-oxo-1-(2,4,6-trifluorophenyl)-1,4-dihydro-1,8-naphthyridine-3-carboxamide

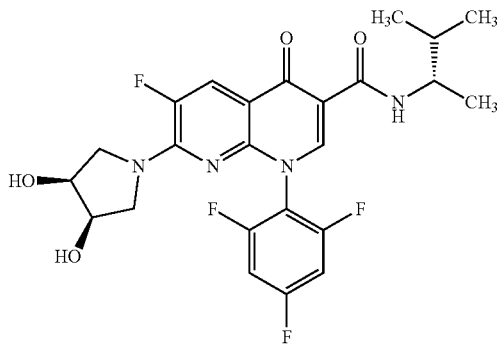 [SMILES: CC(C)[C@H](C)NC(=O)c1cn(-c2c(F)cc(F)cc2F)c2nc(N3C[C@@H](O)[C@@H](O)C3)c(F)cc2c1=O]

According to GP1, 50.0 mg (114 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 13.9 mg (159 µmol) of (2S)-3-methylbutan-2-amine in the presence of 51.9 mg (137 µmol) of HATU and 59 µl (340 µmol) of DIPEA in 460 µl of DMF. The crude product was purified by preparative HPLC (column: acetonitrile/water/0.1% of formic acid). This gave 52.0 mg (90% of theory, 100% pure) of the title compound.

LC-MS (Method 3): $R_t$=1.74 min; MS (ESIpos): m/z=509 [M+H]$^+$ $^1$H-NMR (400 MHz, DMSO-d6): δ [ppm]=9.87 (d, 1H), 8.71 (s, 1H), 7.99 (d, 1H), 7.53-7.60 (m, 2H), 4.79-5.23 (m, 2H), 3.81-4.10 (m, 4H), 3.44-3.71 (m, 1H), 2.86-3.23 (m, 2H), 1.72-1.81 (m, 1H), 1.10 (d, 3H), 0.93 (br d, 3H), 0.91 (br d, 3H).

Example 101

N-[(1S)-1-Cyclopropyl-2,2,2-trifluoroethyl]-7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxamide

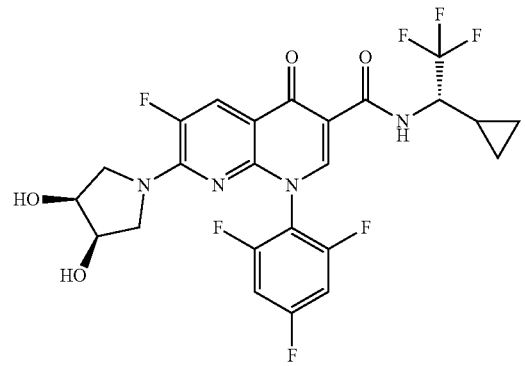 [SMILES: O=C(N[C@@H](C1CC1)C(F)(F)F)c1cn(-c2c(F)cc(F)cc2F)c2nc(N3C[C@@H](O)[C@@H](O)C3)c(F)cc2c1=O]

According to GP1, 50.0 mg (114 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 28.0 mg (159 µmol) of (1S)-1-cyclopropyl-2,2,2-trifluoroethanamine hydrochloride in the presence of 51.9 mg (137 µmol) of HATU and 59 µl (340 µmol) of DIPEA in 460 µl of DMF. The crude product was purified by preparative HPLC (column: acetonitrile/water/0.1% of formic acid). This gave 36.9 mg (58% of theory, 100% pure) of the title compound.

LC-MS (Method 3): $R_t$=1.85 min; MS (ESIpos): m/z=561 [M+H]$^+$ $^1$H-NMR (400 MHz, DMSO-d6): δ [ppm]=10.47 (d, 1H), 8.83 (s, 1H), 8.01 (d, 1H), 7.53-7.61 (m, 2H), 4.91-5.09 (m, 2H), 4.33-4.43 (m, 1H), 3.86-4.14 (m, 3H), 3.39-3.67 (m, 1H), 3.13-3.27 (m, 1H), 2.92-3.12 (m, 1H), 1.16-1.25 (m, 1H), 0.50-0.69 (m, 3H), 0.29-0.37 (m, 1H).

Example 102

7-[(3R,4S)-3,4-Dihydroxypyrrolidin-1-yl]-6-fluoro-N-[(2S)-1-methoxy-3-methylbutan-2-yl]-4-oxo-1-(2,4,6-trifluorophenyl)-1,4-dihydro-1,8-naphthyridine-3-carboxamide

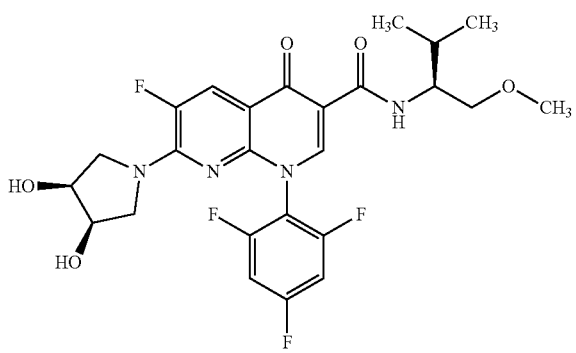 [SMILES: COC[C@@H](NC(=O)c1cn(-c2c(F)cc(F)cc2F)c2nc(N3C[C@@H](O)[C@@H](O)C3)c(F)cc2c1=O)C(C)C]

According to GP1, 30.0 mg (68.3 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 11.2 mg (95.6 µmol) of (2S)-1-methoxy-3-methylbutan-2-amine in the presence of 31.2 mg (81.9 µmol) of HATU and 36 µl (200 µmol) of DIPEA in 270 µl of DMF. The crude product was purified by preparative HPLC (column: acetonitrile/water/0.1% of formic acid). This gave 32.1 mg (87% of theory, 100% pure) of the title compound.

LC-MS (Method 3): $R_t$=1.64 min; MS (ESIpos): m/z=539 [M+H]$^+$ $^1$H-NMR (400 MHz, DMSO-d6): δ [ppm]=9.93 (d, 1H), 8.72 (s, 1H), 8.00 (d, 1H), 7.53-7.61 (m, 2H), 4.82-5.15 (m, 2H), 3.81-4.14 (m, 4H), 3.50-3.73 (m, 1H), 3.34-3.49 (m, 3H), 3.13-3.24 (m, 1H), 2.88-3.10 (m, 1H), 1.87-1.97 (m, 1H), 0.92 (d, 6H).

Example 103

7-[(3R,4S)-3,4-Dihydroxypyrrolidin-1-yl]-N-(2,4-dimethylpentan-3-yl)-6-fluoro-4-oxo-1-(2,4,6-trifluorophenyl)-1,4-dihydro-1,8-naphthyridine-3-carboxamide

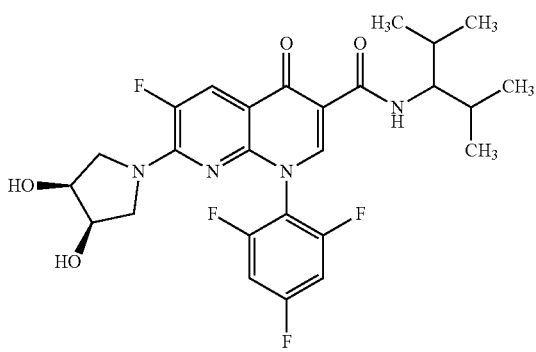 [SMILES: CC(C)C(NC(=O)c1cn(-c2c(F)cc(F)cc2F)c2nc(N3C[C@@H](O)[C@@H](O)C3)c(F)cc2c1=O)C(C)C]

According to GP1, 30.0 mg (68.3 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 11.0 mg (95.6 µmol) of 2,4-dimethylpentan-3-amine in the presence of 31.2 mg (81.9 µmol) of HATU and 36 µl (200 µmol) of DIPEA in 270 µl of DMF. The crude product was purified by preparative HPLC (column: acetonitrile/water/0.1% of formic acid). This gave 29.1 mg (79% of theory, 100% pure) of the title compound.

LC-MS (Method 3): $R_t$=1.94 min; MS (ESIpos): m/z=537 [M+H]$^+$ $^1$H-NMR (400 MHz, DMSO-d6): δ [ppm]=9.76 (d, 1H), 8.72 (s, 1H), 8.02 (d, 1H), 7.53-7.60 (m, 2H), 4.91-5.07 (m, 2H), 3.80-4.15 (m, 3H), 3.48-3.74 (m, 2H), 2.89-3.28 (m, 2H), 1.80-1.90 (m, 2H), 0.88 (dd, 12H).

Example 104

7-[(3R,4S)-3,4-Dihydroxypyrrolidin-1-yl]-6-fluoro-N-[2-methylpentan-3-yl]-6-fluoro-4-oxo-1-(2,4,6-trifluorophenyl)-1,4-dihydro-1,8-naphthyridine-3-carboxamide (Diastereomer Mixture)

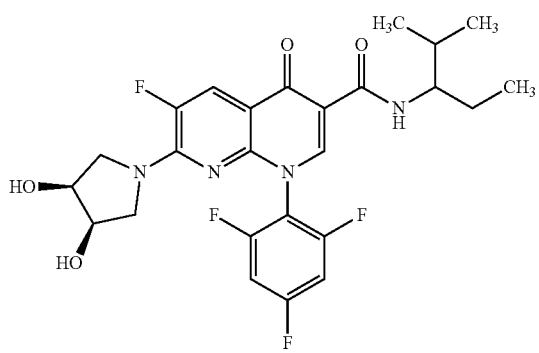 [SMILES: CCC(NC(=O)c1cn(-c2c(F)cc(F)cc2F)c2nc(N3C[C@@H](O)[C@@H](O)C3)c(F)cc2c1=O)C(C)C]

According to GP1, 100 mg (228 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 32.2 mg (319 µmol) of 2-methylpentan-3-amine in the presence of 104 mg (273 µmol) of HATU and 120 µl (680 µmol) of DIPEA in 920 µl of DMF. The crude product was purified by preparative HPLC (column: acetonitrile/water/0.1% of formic acid). This gave 68.5 mg (58% of theory, 100% pure) of the title compound.

LC-MS (Method 3): $R_t$=1.85 min; MS (ESIpos): m/z=523 [M+H]$^+$ $^1$H-NMR (400 MHz, DMSO-d6): δ [ppm]=9.77 (d, 1H), 8.71 (s, 1H), 8.00 (d, 1H), 7.53-7.61 (m, 2H), 4.90-5.09 (m, 2H), 3.86-4.16 (m, 3H), 3.72-3.85 (m, 1H), 3.41-3.69 (m, 1H), 3.13-3.28 (m, 1H), 2.90-3.12 (m, 1H), 1.77-1.87 (m, 1H), 1.51-1.62 (m, 1H), 1.35-1.47 (m, 1H), 0.84-0.92 (m, 9H).

65.0 mg of the title compound (diastereomer mixture) were separated by chiral HPLC into the diastereomers (preparative HPLC: column Daicel Chiralcel OX-H, 5 µm, 250×20 mm; mobile phase: 80% n-heptane, 20% ethanol; temperature: 23° C.; flow rate: 20 ml/min; UV detection: 220 nm.)

This gave (in the sequence of elution from the column) 26.1 mg (22% of theory, 100% purity) of diastereomer 1 from Example 105 (99% de) Rt=11.82 min and 32.0 mg (27% of theory, 100% purity) of diastereomer 2 from Example 106 (99% de) Rt=15.94 min.

Example 105

7-[(3R,4S)-3,4-Dihydroxypyrrolidin-1-yl]-6-fluoro-V-[2-methylpentan-3-yl]-6-fluoro-4-oxo-1-(2,4,6-trifluorophenyl)-1,4-dihydro-1,8-naphthyridine-3-carboxamide (Diastereomer 1)

LC-MS (Method 3): $R_t$=1.89 min; MS (ESIpos): m/z=523 [M+H]$^+$
$^1$H-NMR (400 MHz, DMSO-d6): δ [ppm]=9.77 (d, 1H), 8.71 (s, 1H), 8.00 (d, 1H), 7.53-7.60 (m, 2H), 4.91-5.07 (m, 2H), 3.85-4.15 (m, 3H), 3.76-3.83 (m, 1H), 3.43-3.64 (m, 1H), 3.11-3.28 (m, 1H), 2.92-3.10 (m, 1H), 1.77-1.86 (m, 1H), 1.51-1.61 (m, 1H), 1.36-1.47 (m, 1H), 0.84-0.92 (m, 9H).

Example 106

7-[(3R,4S)-3,4-Dihydroxypyrrolidin-1-yl]-6-fluoro-V-[2-methylpentan-3-yl]-6-fluoro-4-oxo-1-(2,4,6-trifluorophenyl)-1,4-dihydro-1,8-naphthyridine-3-carboxamide (Diastereomer 2)

LC-MS (Method 3): $R_t$=1.89 min; MS (ESIpos): m/z=523 [M+H]$^+$
$^1$H-NMR (400 MHz, DMSO-d6): δ [ppm]=9.77 (d, 1H), 8.71 (s, 1H), 8.00 (d, 1H), 7.48-7.66 (m, 2H), 4.88-5.11 (m, 2H), 3.86-4.15 (m, 3H), 3.76-3.83 (m, 1H), 3.44-3.69 (m, 1H), 3.13-3.29 (m, 1H), 2.87-3.11 (m, 1H), 1.76-1.86 (m, 1H), 1.51-1.62 (m, 1H), 1.29-1.47 (m, 1H), 0.84-0.93 (m, 9H).

Example 107

6-Fluoro-7-[(3S)-3-hydroxypyrrolidin-1-yl]-4-oxo-N-(4,4,4-trifluoro-2-methylbutan-2-yl)-1-(2,4,6-trifluorophenyl)-1,4-dihydro-1,8-naphthyridine-3-carboxamide

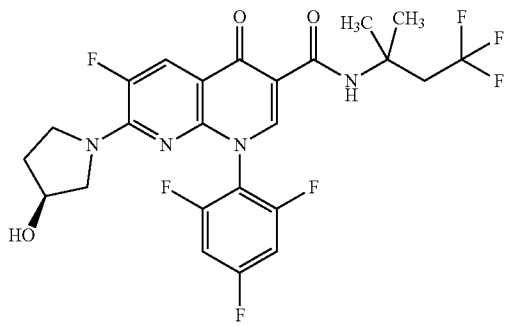 [SMILES: CC(C)(CC(F)(F)F)NC(=O)c1cn(-c2c(F)cc(F)cc2F)c2nc(N3CC[C@H](O)C3)c(F)cc2c1=O]

According to GP1, 50.0 mg (118 nmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 23.1 mg (130 nmol) of 4,4,4-trifluoro-2-methylbutan-2-amine hydrochloride in the presence of 53.9 mg (142 nmol) of HATU and 82 μl (470 μmol) of DIPEA in 750 μl of DMF. The crude product was purified by preparative HPLC (column: acetonitrile/water/0.1% of formic acid). This gave 51.0 mg (79% of theory, 100% pure) of the title compound.

LC-MS (Method 3): $R_t$=2.06 min; MS (ESIpos): m/z=547 [M+H]$^+$
$^1$H-NMR (400 MHz, DMSO-d$_6$): δ [ppm]=10.09 (s, 1H), 8.72 (s, 1H), 7.98 (d, 1H), 7.56 (t, 2H), 4.95-5.04 (m, 1H), 4.18-4.37 (m, 1H), 3.34-4.01 (m, 3H), 3.06-3.27 (m, 1H), 2.95 (q, 2H), 1.72-1.98 (m, 2H), 1.48 (s, 6H).

Example 108

N-[(1S)-1-Cyclopropyl-2,2,2-trifluoroethyl]-6-fluoro-7-[(3S)-3-hydroxypyrrolidin-1-yl]-4-oxo-1-(2,4,6-trifluorophenyl)-1,4-dihydro-1,8-naphthyridine-3-carboxamide

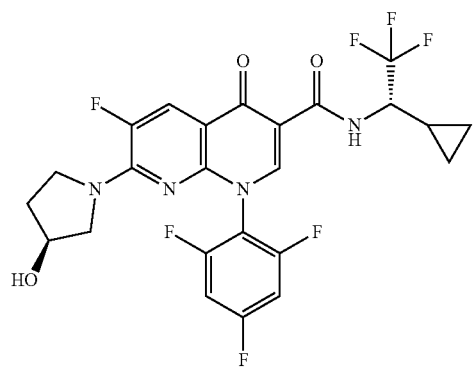 [SMILES: O=C(N[C@@H](C1CC1)C(F)(F)F)c1cn(-c2c(F)cc(F)cc2F)c2nc(N3CC[C@H](O)C3)c(F)cc2c1=O]

According to GP1, 50.0 mg (118 μmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 22.8 mg (130 μmol) of (1S)-1-cyclopropyl-2,2,2-trifluoroethanamine hydrochloride in the presence of 53.9 mg (142 μmol) of HATU and 82 μl (470 μmol) of DIPEA in 750 μl of DMF. The crude product was purified by preparative HPLC (column: acetonitrile/water/0.1% of formic acid). This gave 50.3 mg (78% of theory, 100% pure) of the title compound.

LC-MS (Method 3): $R_t$=2.07 min; MS (ESIpos): m/z=545 [M+H]$^+$
$^1$H-NMR (400 MHz, DMSO-d6): δ [ppm]=10.48 (d, 1H), 8.83 (s, 1H), 8.01 (d, 1H), 7.53-7.60 (m, 2H), 4.97-5.04 (m, 1H), 4.21-4.43 (m, 2H), 3.34-4.03 (m, 3H), 3.01-3.29 (m, 1H), 1.74-1.98 (m, 2H), 1.16-1.25 (m, 1H), 0.50-0.69 (m, 3H), 0.30-0.37 (m, 1H).

Example 109

6-Fluoro-7-[(3S)-3-hydroxypyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (Diastereomer Mixture)

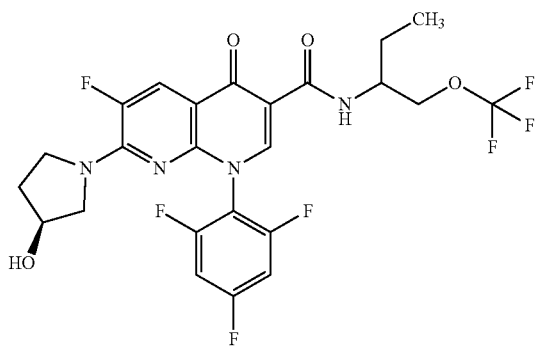 [SMILES: CCC(COC(F)(F)F)NC(=O)c1cn(-c2c(F)cc(F)cc2F)c2nc(N3CC[C@H](O)C3)c(F)cc2c1=O]

According to GP1, 100 mg (236 μmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 50.3 mg (260 μmol) of 1-(trifluoromethoxy)butan-2-amine hydrochloride (racemate) in the presence of 108 mg (283 μmol) of HATU and 160 μl (940 μmol) of DIPEA in 1.5 ml of DMF. The crude product was purified by preparative HPLC (column: acetonitrile/water/0.1% of formic acid). This gave 89.3 mg (67% of theory, 100% pure) of the title compound.

LC-MS (Method 3): $R_t$=2.08 min; MS (ESIpos): m/z=563 [M+H]$^+$ $^1$H-NMR (400 MHz, DMSO-d6): δ [ppm]=10.00 (br d, 1H), 8.75 (s, 1H), 8.00 (d, 1H), 7.56 (br t, 2H), 4.95-5.04 (m, 1H), 4.24-4.35 (m, 1H), 4.12-4.24 (m, 3H), 3.33-4.07 (m, 3H), 3.02-3.29 (m, 1H), 1.74-2.00 (m, 2H), 1.55-1.73 (m, 2H), 0.94 (t, 3H).

88.0 mg of the title compound (diastereomer mixture) were separated by chiral HPLC into the diastereomers (preparative HPLC: column Daicel Chiralpak IE 5 μm 250×20 mm; mobile phase: 85% n-heptane, 15% ethanol+0.2% DEA; temperature: 23° C.; flow rate: 20 ml/min; UV detection: 220 nm.)

This gave (in the sequence of elution from the column) 22.6 mg (17% of theory, 95% purity) of diastereomer 1 from Example 110 (99% de) Rt=11.90 min and 24.7 mg (19% of theory, 95% purity) of diastereomer 2 from Example 111 (93% de) Rt=13.32 min.

[Analytical HPLC: column Daicel Chiralpak IE-3, 3 μm, 50×4.6 mm; mobile phase: 90% n-heptane, 10% ethanol+0.2% DEA; flow rate: 1.0 ml/min; UV detection: 220 nm].

Example 110

6-Fluoro-7-[(3S)-3-hydroxypyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (Diastereomer 1)

LC-MS (Method 3): $R_t$=2.08 min; MS (ESIpos): m/z=563 [M+H]$^+$ $^1$H-NMR (500 MHz, DMSO-d6): δ [ppm]=10.00 (d, 1H), 8.75 (s, 1H), 8.00 (d, 1H), 7.56 (br t, 2H), 4.96-5.03 (m, 1H), 4.23-4.36 (m, 1H), 4.13-4.22 (m, 3H), 3.36-4.04 (m, 2H), 2.96-3.29 (m, 1H), 1.74-2.00 (m, 2H), 1.54-1.73 (m, 2H), 0.94 (t, 3H).

Example 111

6-Fluoro-7-[(3S)-3-hydroxypyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (Diastereomer 2)

LC-MS (Method 3): $R_t$=2.08 min; MS (ESIpos): m/z=563 [M+H]$^+$ $^1$H-NMR (500 MHz, DMSO-d6): δ [ppm]=10.00 (d, 1H), 8.75 (s, 1H), 8.00 (d, 1H), 7.53-7.59 (m, 2H), 4.96-5.03 (m, 1H), 4.23-4.35 (m, 1H), 4.13-4.22 (m, 3H), 3.33-4.01 (m, 3H), 3.05-3.29 (m, 1H), 1.73-1.99 (m, 2H), 1.54-1.72 (m, 2H), 0.94 (t, 3H).

Example 112

6-Fluoro-7-[(3S)-3-hydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

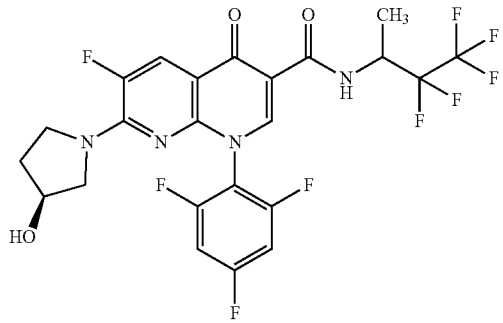 [SMILES: CC(NC(=O)c1cn(-c2c(F)cc(F)cc2F)c2nc(N3CC[C@H](O)C3)c(F)cc2c1=O)C(F)(F)C(F)(F)F]

According to GP1, 100 mg (236 μmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 51.9 mg (260 nmol) of 3,3,4,4,4-pentafluorobutan-2-amine hydrochloride (racemate) in the presence of 108 mg (283 μmol) of HATU and 160 μl (940 μmol) of DIPEA in 1.5 ml of DMF. The crude product was purified by preparative HPLC (column: acetonitrile/water/0.1% of formic acid). This gave 107 mg (80% of theory, 100% pure) of the title compound.

LC-MS (Method 3): $R_t$=2.10 min; MS (ESIpos): m/z=569 [M+H]$^+$ $^1$H-NMR (400 MHz, DMSO-d6): δ [ppm]=10.47 (d, 1H), 8.84 (s, 1H), 8.00 (d, 1H), 7.56 (t, 2H), 4.95-5.08 (m, 2H), 4.19-4.37 (m, 1H), 3.34-4.06 (m, 3H), 3.01-3.28 (m, 1H), 1.73-1.98 (m, 2H), 1.39 (d, 3H).

105 mg of the title compound (diastereomer mixture) were separated by chiral SFC into the diastereomers (preparative SFC: column Chiralpak AD, 250×20 mm; mobile phase: 80% carbon dioxide, 20% isopropanol; temperature: 40° C.; flow rate: 60 ml/min; UV detection: 210 nm.)

This gave (in the sequence of elution from the column) 39.2 mg (29% of theory, 100% purity) of diastereomer 1 from Example 113 (99% de) Rt=2.07 min and 32.8 mg (25% of theory, 100% purity) of diastereomer 2 from Example 114 (99% de) Rt=2.59 min.

[Analytical SFC: column AD; mobile phase: 80% carbon dioxide, 20% isopropanol; flow rate: 3.0 ml/min; UV detection: 210 nm].

Example 113

6-Fluoro-7-[(3S)-3-hydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Diastereomer 1)

LC-MS (Method 3): $R_t$=2.11 min; MS (ESIpos): m/z=569 [M+H]$^+$
$^1$H-NMR (400 MHz, DMSO-d6): δ [ppm]=10.47 (d, 1H), 8.84 (s, 1H), 8.00 (d, 1H), 7.57 (br t, 2H), 4.95-5.08 (m, 2H), 4.21-4.37 (m, 1H), 3.36-4.05 (m, 3H), 3.01-3.27 (m, 1H), 1.72-1.98 (m, 2H), 1.39 (d, 3H).

Example 114

6-Fluoro-7-[(3S)-3-hydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Diastereomer 2)

LC-MS (Method 3): $R_t$=2.11 min; MS (ESIpos): m/z=569 [M+H]$^+$
$^1$H-NMR (400 MHz, DMSO-d6): δ [ppm]=10.47 (d, 1H), 8.84 (s, 1H), 8.00 (d, 1H), 7.53-7.60 (m, 2H), 4.96-5.07 (m, 2H), 4.26-4.34 (m, 1H), 3.34-3.98 (m, 3H), 3.00-3.26 (m, 1H), 1.70-2.01 (m, 2H), 1.39 (d, 3H).

Example 115

6-Fluoro-7-[(3S)-3-hydroxypyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide

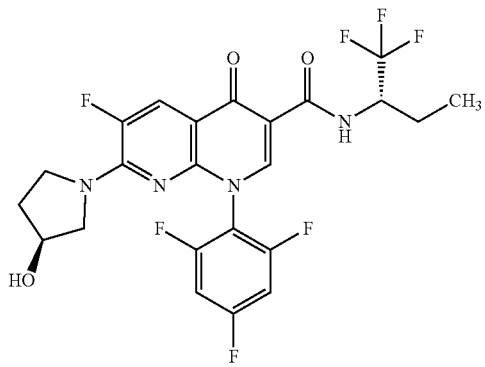 [SMILES: CC[C@H](NC(=O)c1cn(-c2c(F)cc(F)cc2F)c2nc(N3CC[C@H](O)C3)c(F)cc2c1=O)C(F)(F)F]

According to GP1, 50.0 mg (118 µmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 21.3 mg (130 µmol) of (2S)-1,1,1-trifluorobutan-2-amine hydrochloride in the presence of 53.9 mg (142 µmol) of HATU and 82 µl (470 µmol) of DIPEA in 750 µl of DMF. The crude product was purified by preparative HPLC (column: acetonitrile/water/0.1% of formic acid). This gave 46.8 mg (74% of theory, 100% pure) of the title compound.

LC-MS (Method 3): $R_t$=2.05 min; MS (ESIpos): m/z=533 [M+H]$^+$
$^1$H-NMR (400 MHz, DMSO-d6): δ [ppm]=10.34 (d, 1H), 8.83 (s, 1H), 8.00 (d, 1H), 7.53-7.61 (m, 2H), 4.96-5.05 (m, 1H), 4.68-4.79 (m, 1H), 4.19-4.39 (m, 1H), 3.33-4.04 (m, 3H), 3.02-3.28 (m, 1H), 1.72-1.97 (m, 3H), 1.58-1.70 (m, 1H), 0.97 (t, 3H).

Example 116

6-Fluoro-7-[(3S)-3-hydroxypyrrolidin-1-yl]-N-[2-methylpentan-3-yl]-4-oxo-1-(2,4,6-trifluoro-phenyl)-1,4-dihydro-1,8-naphthyridine-3-carboxamide (Diastereomer Mixture)

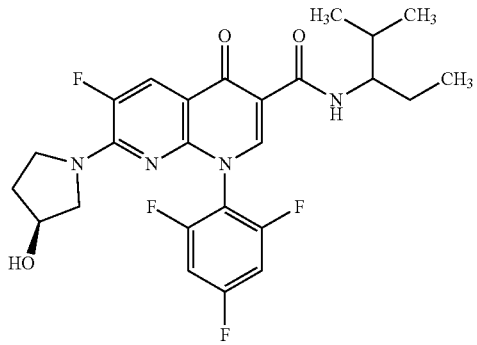 [SMILES: CCC(NC(=O)c1cn(-c2c(F)cc(F)cc2F)c2nc(N3CC[C@H](O)C3)c(F)cc2c1=O)C(C)C]

According to GP1, 100 mg (236 µmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 35.8 mg (260 µmol) of 2-methylpentan-3-amine hydrochloride (racemate) in the presence of 108 mg (283 µmol) of HATU and 160 µl (940 µmol) of DIPEA in 1.5 ml of DMF. The crude product was purified by preparative HPLC (column: acetonitrile/water/0.1% of formic acid). This gave 90.1 mg (75% of theory, 100% pure) of the title compound.

LC-MS (Method 3): $R_t$=2.10 min; MS (ESIpos): m/z=507 [M+H]$^+$
$^1$H-NMR (400 MHz, DMSO-d6): δ [ppm]=9.78 (d, 1H), 8.71 (s, 1H), 8.00 (d, 1H), 7.56 (br t, 2H), 4.96-5.03 (m, 1H), 4.20-4.38 (m, 1H), 3.35-4.05 (m, 4H), 3.01-3.30 (m, 1H), 1.73-1.98 (m, 3H), 1.51-1.62 (m, 1H), 1.36-1.47 (m, 1H), 0.84-0.92 (m, 9H).

99 mg of the title compound (diastereomer mixture) were separated by chiral HPLC into the diastereomers (preparative HPLC: column Daicel Chiralpak AY-H 5 µm 250×20 mm; mobile phase: 70% n-heptane, 30% ethanol+0.2% DEA; temperature: 60° C.; flow rate: 15 ml/min; UV detection: 260 nm.)

This gave (in the sequence of elution from the column) 21.0 mg (17% of theory, 100% purity) of diastereomer 1 from Example 117 (97% de) Rt=4.45 min and 23.0 mg (19% of theory, 100% purity) of diastereomer 2 from Example 118 (76% de) Rt=7.56 min.

[Analytical HPLC: column Daicel Chiralpak AY-H 5 µm 250×4.6 mm; mobile phase: 70% isohexane, 30% ethanol+0.2% DEA; temperature: 60° C.; flow rate: 1.0 ml/min; UV detection: 260 nm].

Example 117

6-Fluoro-7-[(3S)-3-hydroxypyrrolidin-1-yl]-N-[2-methylpentan-3-yl]-4-oxo-1-(2,4,6-trifluoro-phenyl)-1,4-dihydro-1,8-naphthyridine-3-carboxamide (Diastereomer 1)

LC-MS (Method 3): $R_t$=2.10 min; MS (ESIpos): m/z=507 [M+H]$^+$
$^1$H-NMR (400 MHz, DMSO-d6): δ [ppm]=9.78 (d, 1H), 8.71 (s, 1H), 8.00 (d, 1H), 7.53-7.59 (m, 2H), 4.98-5.01 (m, 1H), 4.26-4.32 (m, 1H), 3.36-4.10 (m, 4H), 2.99-3.27 (m, 1H), 1.76-1.94 (m, 3H), 1.52-1.60 (m, 1H), 1.37-1.45 (m, 1H), 0.84-0.92 (m, 9H).

Example 118

6-Fluoro-7-[(3S)-3-hydroxypyrrolidin-1-yl]-N-[2-methylpentan-3-yl]-4-oxo-1-(2,4,6-trifluoro-phenyl)-1,4-dihydro-1,8-naphthyridine-3-carboxamide (Diastereomer 2)

LC-MS (Method 3): $R_t$=2.11 min; MS (ESIpos): m/z=507 [M+H]$^+$
$^1$H-NMR (400 MHz, DMSO-d6): δ [ppm]=9.78 (d, 1H), 8.71 (s, 1H), 8.00 (d, 1H), 7.53-7.60 (m, 2H), 4.96-5.02 (m, 1H), 4.24-4.34 (m, 1H), 3.33-4.08 (m, 3H), 3.07-3.29 (m, 1H), 1.75-1.96 (m, 3H), 1.51-1.63 (m, 1H), 1.36-1.47 (m, 1H), 0.83-0.92 (m, 9H).

Example 119

6-Fluoro-7-[(3S)-3-hydroxypyrrolidin-1-yl]-N-[(2S)-3-methylbutan-2-yl]-4-oxo-1-(2,4,6-tri-fluorophenyl)-1,4-dihydro-1,8-naphthyridine-3-carboxamide

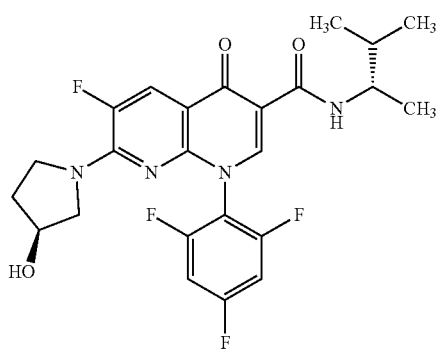 [SMILES: CC(C)[C@H](C)NC(=O)c1cn(-c2c(F)cc(F)cc2F)c2nc(N3CC[C@H](O)C3)c(F)cc2c1=O]

According to GP1, 50.0 mg (118 μmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 11.3 mg (130 μmol) of (2S)-3-methylbutan-2-amine in the presence of 53.9 mg (142 μmol) of HATU and 62 μl (350 μmol) of DIPEA in 750 μl of DMF. The crude product was purified by preparative HPLC (column: acetonitrile/water/0.1% of formic acid). This gave 45.2 mg (78% of theory, 100% pure) of the title compound.
LC-MS (Method 3): $R_t$=1.99 min; MS (ESIpos): m/z=493 [M+H]$^+$
$^1$H-NMR (400 MHz, DMSO-d6): δ [ppm]=9.88 (d, 1H), 8.70 (s, 1H), 7.99 (d, 1H), 7.56 (br t, 2H), 4.95-5.03 (m, 1H), 4.19-4.37 (m, 1H), 3.33-4.10 (m, 4H), 3.01-3.26 (m, 1H), 1.70-1.96 (m, 3H), 1.10 (d, 3H), 0.88-0.95 (m, 6H).

Example 120

6-Fluoro-7-[(3S)-3-hydroxypyrrolidin-1-yl]-N-[(2R)-3-methylbutan-2-yl]-4-oxo-1-(2,4,6-tri-fluoro-phenyl)-1,4-dihydro-1,8-naphthyridine-3-carboxamide

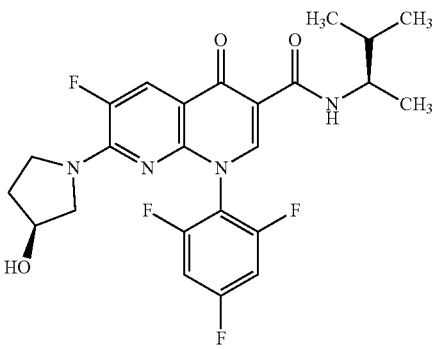 [SMILES: CC(C)[C@@H](C)NC(=O)c1cn(-c2c(F)cc(F)cc2F)c2nc(N3CC[C@H](O)C3)c(F)cc2c1=O]

According to GP1, 50.0 mg (118 μmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 11.3 mg (130 μmol) of (2R)-3-methylbutan-2-amine in the presence of 53.9 mg (142 μmol) of HATU and 62 μl (350 μmol) of DIPEA in 750 μl of DMF. The crude product was purified by preparative HPLC (column: acetonitrile/water/0.1% of formic acid). This gave 45.8 mg (79% of theory, 100% pure) of the title compound.
LC-MS (Method 3): $R_t$=1.99 min; MS (ESIpos): m/z=493 [M+H]$^+$
$^1$H-NMR (400 MHz, DMSO-d6): δ [ppm]=9.88 (d, 1H), 8.70 (s, 1H), 7.99 (d, 1H), 7.56 (br t, 2H), 4.96-5.03 (m, 1H), 4.21-4.37 (m, 1H), 3.36-4.11 (m, 4H), 3.02-3.28 (m, 1H), 1.71-1.97 (m, 3H), 1.10 (d, 3H), 0.88-0.96 (m, 6H).

Example 121

6-Fluoro-7-[(3S)-3-hydroxypyrrolidin-1-yl]-N-[(2R)-1-methoxy-3-methylbutan-2-yl]-4-oxo-1-(2,4,6-trifluorophenyl)-1,4-dihydro-1,8-naphthyridine-3-carboxamide

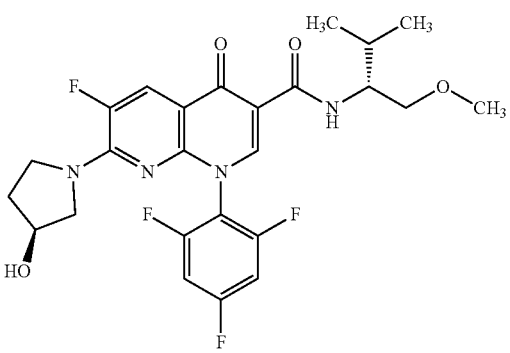 [SMILES: COC[C@H](NC(=O)c1cn(-c2c(F)cc(F)cc2F)c2nc(N3CC[C@H](O)C3)c(F)cc2c1=O)C(C)C]

According to GP1, 50.0 mg (118 μmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 20.0 mg (130 μmol) of (2R)-1-methoxy- 3-methylbutan-2-amine hydrochloride in the presence of 53.9 mg (142 µmol) of HATU and 62 µl (350 µmol) of DIPEA in 750 µl of DMF. The crude product was purified by preparative HPLC (column: acetonitrile/water/0.1% of formic acid). This gave 45.5 mg (74% of theory, 100% pure) of the title compound.

LC-MS (Method 3): $R_t$=1.88 min; MS (ESIpos): m/z=523 [M+H]$^+$ $^1$H-NMR (400 MHz, DMSO-d6): δ [ppm]=9.94 (d, 1H), 8.72 (s, 1H), 8.00 (d, 1H), 7.52-7.60 (m, 2H), 4.94-5.05 (m, 1H), 4.29 (br s, 1H), 3.96-4.03 (m, 1H), 3.50-3.94 (m, 2H), 3.34-3.49 (m, 3H), 3.27 (s, 3H), 2.90-3.24 (m, 1H), 1.74-1.99 (m, 3H), 0.92 (d, 6H).

Example 122

N-(2,4-Dimethylpentan-3-yl)-6-fluoro-7-[(3S)-3-hydroxypyrrolidin-1-yl]-4-oxo-1-(2,4,6-tri-fluorophenyl)-1,4-dihydro-1,8-naphthyridine-3-carboxamide

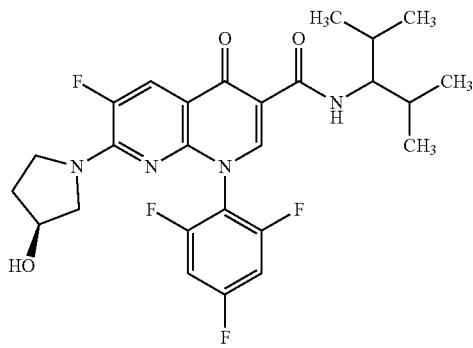 [SMILES: CC(C)C(NC(=O)c1cn(-c2c(F)cc(F)cc2F)c2nc(N3CC[C@H](O)C3)c(F)cc2c1=O)C(C)C]

According to GP1, 50.0 mg (118 µmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 15.0 mg (130 µmol) of 2,4-dimethylpentan-3-amine in the presence of 53.9 mg (142 µmol) of HATU and 62 µl (350 µmol) of DIPEA in 750 µl of DMF. The crude product was purified by preparative HPLC (column: acetonitrile/water/0.1% of formic acid). This gave 50.7 mg (82% of theory, 100% pure) of the title compound.

LC-MS (Method 3): $R_t$=2.19 min; MS (ESIpos): m/z=521 [M+H]$^+$ $^1$H-NMR (400 MHz, DMSO-d6): δ [ppm]=9.77 (d, 1H), 8.72 (s, 1H), 8.01 (d, 1H), 7.56 (br t, 2H), 4.96-5.03 (m, 1H), 4.21-4.36 (m, 1H), 3.37-3.98 (m, 4H), 3.01-3.27 (m, 1H), 1.74-1.96 (m, 4H), 0.88 (dd, 12H).

Example 123

7-[(3R,4S)-3,4-Dihydroxypyrrolidin-1-yl]-6-fluoro-4-oxo-N-[1,1,1-trifluoro-3-methylbutan-2-yl]-1-(2,4,6-trifluorophenyl)-1,4-dihydro-1,8-naphthyridine-3-carboxamide (Diastereomer Mixture)

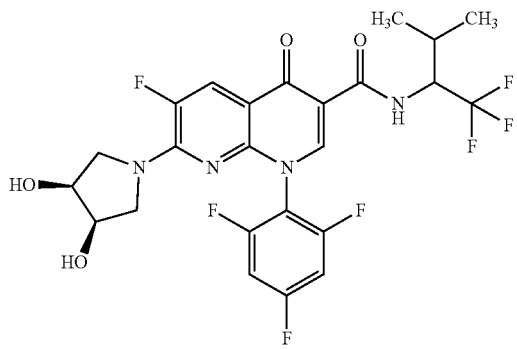 [SMILES: CC(C)C(NC(=O)c1cn(-c2c(F)cc(F)cc2F)c2nc(N3C[C@@H](O)[C@@H](O)C3)c(F)cc2c1=O)C(F)(F)F]

According to GP1, 100 mg (228 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 36.4 mg (250 µmol, 97% pure) of 1,1,1-trifluoro-3-methylbutan-2-amine (racemate) in the presence of 104 mg (273 µmol) of HATU and 160 µl (910 µmol) of DIPEA in 2.0 ml of DMF. The crude product was purified by preparative HPLC (column: acetonitrile/water/0.1% of formic acid). This gave 52.0 mg (41% of theory, 100% pure) of the title compound.

LC-MS (Method 3): $R_t$=1.94 min; MS (ESIpos): m/z=563 [M+H]$^+$ $^1$H-NMR (400 MHz, DMSO-d6): δ [ppm]=10.53 (d, 1H), 8.84 (s, 1H), 8.04 (d, 1H), 7.58 (br t, 2H), 4.92-5.08 (m, 2H), 4.71-4.81 (m, 1H), 3.86-4.12 (m, 3H), 3.47-3.68 (m, 1H), 2.88-3.25 (m, 2H), 2.18-2.30 (m, 1H), 1.02 (d, 3H), 0.96 (d, 3H).

Example 124

7-[(3R,4S)-3,4-Dihydroxypyrrolidin-1-yl]-6-fluoro-4-oxo-N-(1,1,1-trifluoro-2-methylpropan-2-yl)-1-(2,4,6-trifluorophenyl)-1,4-dihydro-1,8-naphthyridine-3-carboxamide

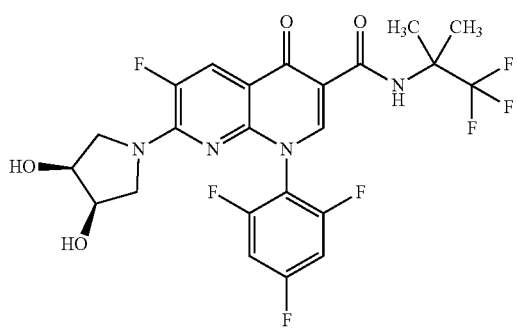 [SMILES: CC(C)(NC(=O)c1cn(-c2c(F)cc(F)cc2F)c2nc(N3C[C@@H](O)[C@@H](O)C3)c(F)cc2c1=O)C(F)(F)F]

According to GP1, 50.0 mg (114 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 15.9 mg (125 µmol) of 1,1,1-trifluoro-2-methylpropan-2-amine in the presence of 51.9 mg (137 µmol) of HATU and 59 µl (340 µmol) of DIPEA in 1.0 ml of DMF. The crude product was purified by preparative HPLC (column: acetonitrile/water/0.1% of formic acid). This gave 45.0 mg (72% of theory, 100% pure) of the title compound.

LC-MS (Method 3): $R_t$=1.87 min; MS (ESIpos): m/z=549 [M+H]$^+$ $^1$H-NMR (400 MHz, DMSO-d6): δ [ppm]=10.55 (s, 1H), 8.77 (s, 1H), 8.01 (d, 1H), 7.54-7.61 (m, 2H), 4.89-5.10 (m, 2H), 3.79-4.14 (m, 3H), 3.44-3.67 (m, 1H), 3.12-3.28 (m, 1H), 2.87-3.12 (m, 1H), 1.63 (s, 6H).

Example 125

6-Fluoro-7-[(3S)-3-hydroxypyrrolidin-1-yl]-4-oxo-N-(1,1,1-trifluoro-2-methylpropan-2-yl)-1-(2,4,6-trifluorophenyl)-1,4-dihydro-1,8-naphthyridine-3-carboxamide

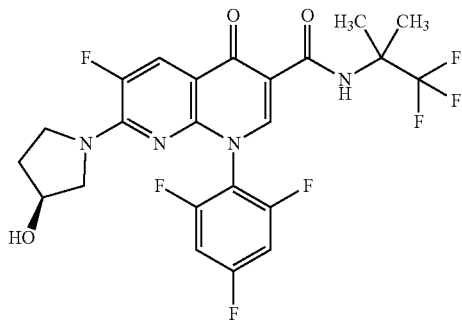

According to GP1, 20.0 mg (47.2 nmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 6.60 mg (52.0 nmol) of 1,1,1-trifluoro-2-methylpropan-2-amine in the presence of 21.6 mg (56.7 nmol) of HATU and 25 µl (140 nmol) of DIPEA in 420 µl of DMF. The crude product was purified by preparative HPLC (column: acetonitrile/water/0.1% of formic acid). This gave 18.0 mg (72% of theory, 100% pure) of the title compound.

LC-MS (Method 1): $R_t$=1.10 min; MS (ESIpos): m/z=533 [M+H]$^+$ $^1$H-NMR (400 MHz, DMSO-d6): δ [ppm]=10.56 (s, 1H), 8.77 (s, 1H), 8.01 (d, 1H), 7.53-7.61 (m, 2H), 4.96-5.03 (m, 1H), 4.20-4.35 (m, 1H), 3.37-4.07 (m, 3H), 2.98-3.26 (m, 1H), 1.74-2.00 (m, 2H), 1.63 (s, 6H).

Example 126

6-Fluoro-7-[(3S)-3-hydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (Diastereomer Mixture)

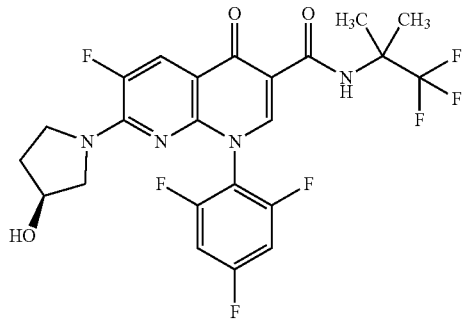 [SMILES: CC(C)(NC(=O)c1cn(-c2c(F)cc(F)cc2F)c2nc(N3CC[C@H](O)C3)c(F)cc2c1=O)C(F)(F)F]

According to GP1, 65.0 mg (154 µmol) of 6-fluoro-7-[(3S)-3-hydroxypyrrolidin-1-yl]-4-oxo-1-(2,4,6-trifluorophenyl)-1,4-dihydro-1,8-naphthyridine-3-carboxylic acid were reacted with 24.6 mg (169 µmol, 97% pure) of 1,1,1-trifluoro-3-methylbutan-2-amine (racemate) in the presence of 70.1 mg (184 µmol) of HATU and 80 µl (460 nmol) of DIPEA in 1.3 ml of DMF. The crude product was purified by preparative HPLC (column: acetonitrile/water/0.1% of formic acid). This gave 54.0 mg (64% of theory, 99% pure) of the title compound.

LC-MS (Method 3): $R_t$=2.16 min; MS (ESIpos): m/z=547 [M+H]$^+$ $^1$H-NMR (400 MHz, DMSO-d6): δ [ppm]=10.54 (d, 1H), 8.84 (s, 1H), 8.04 (d, 1H), 7.54-7.60 (m, 2H), 4.97-5.04 (m, 1H), 4.71-4.82 (m, 1H), 4.24-4.36 (m, 1H), 3.33-4.10 (m, 3H), 2.97-3.27 (m, 1H), 2.20-2.28 (m, 1H), 1.71-2.00 (m, 2H), 1.03 (d, 3H), 0.96 (d, 3H).

Example 127

1-(3,5-Difluoropyridin-2-yl)-6-fluoro-7-[(3S)-3-hydroxypyrrolidin-1-yl]-4-oxo-N-[3,3,4,4,4-pentafluorobutan-2-yl]-1,4-dihydro-1,8-naphthyridine-3-carboxamide (Diastereomer Mixture)

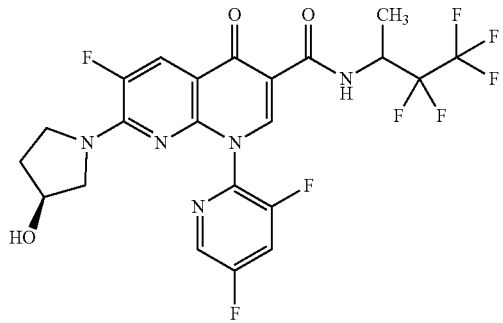 [SMILES: CC(NC(=O)c1cn(-c2ncc(F)cc2F)c2nc(N3CC[C@H](O)C3)c(F)cc2c1=O)C(F)(F)C(F)(F)F]

According to GP1, 100 mg (246 µmol) of 1-(3,5-difluoropyridin-2-yl)-6-fluoro-7-[(3S)-3-hydroxypyrrolidin-1-yl]-4-oxo-1,4-dihydro-1,8-naphthyridine-3-carboxylic acid were reacted with 54.0 mg (271 µmol) of 3,3,4,4,4-pentafluorobutan-2-amine hydrochloride (racemate) in the presence of 112 mg (295 µmol) of HATU and 170 µl (980 µmol) of DIPEA in 2.2 ml of DMF. The crude product was purified by preparative HPLC (column: acetonitrile/water/0.1% of formic acid). This gave 100 mg (74% of theory, 100% pure) of the title compound.

LC-MS (Method 3): $R_t$=1.98 min; MS (ESIpos): m/z=552 [M+H]$^+$ $^1$H-NMR (400 MHz, DMSO-d6): δ [ppm]=10.46 (d, 1H), 8.83 (d, 1H), 8.61 (d, 1H), 8.30-8.37 (m, 1H), 8.00 (d, 1H), 4.93-5.09 (m, 2H), 4.20-4.39 (m, 1H), 3.35-4.06 (m, 3H), 3.01-3.28 (m, 1H), 1.73-1.98 (m, 2H), 1.39 (br d, 3H).

98.0 mg of the title compound (diastereomer mixture) were separated by chiral HPLC into the diastereomers (preparative HPLC: column Daicel Chiralpak IE 5 µm 250×20 mm; mobile phase: 70% n-heptane, 30% ethanol+ 0.2% DEA; temperature: 35° C.; flow rate: 15 ml/min; UV detection: 265 nm.)

This gave (in the sequence of elution from the column) 46.0 mg of diastereomer 1 (99% de) $R_t$=8.64 min and 47.0 mg of diastereomer 2 (99% de) $R_t$=12.08 min.

[Analytical HPLC: column Daicel Chiralpak IE, 5 µm, 250×4.6 mm; mobile phase: 70% n-heptane, 30% ethanol+ 0.2% DEA; temperature: 35° C.; flow rate: 1.0 ml/min; UV detection: 265 nm].

Diastereomer 1 was additionally purified by preparative HPLC (column: acetonitrile/water/0.1% formic acid, giving 40.0 mg (30% of theory, 100% pure) of the title compound from Example 128.

Diastereomer 2 was additionally purified by preparative HPLC (column: acetonitrile/water/0.1% formic acid, giving 42.0 mg (31% of theory, 100% pure) of the title compound from Example 129.

Example 128

1-(3,5-Difluoropyridin-2-yl)-6-fluoro-7-[(3S)-3-hydroxypyrrolidin-1-yl]-4-oxo-N-[3,3,4,4,4-pentafluorobutan-2-yl]-1,4-dihydro-L8-naphthyridine-3-carboxamide (Diastereomer 1)

LC-MS (Method 3): $R_t$=1.97 min; MS (ESIpos): m/z=552 [M+H]$^+$ $^1$H-NMR (400 MHz, DMSO-d6): δ [ppm]=10.46 (d, 1H), 8.83 (d, 1H), 8.60-8.63 (m, 1H), 8.31-8.37 (m, 1H), 8.00 (d, 1H), 4.95-5.08 (m, 2H), 4.22-4.36 (m, 1H), 3.36-4.04 (m, 3H), 2.95-3.27 (m, 1H), 1.73-1.96 (m, 2H), 1.39 (br d, 3H).

Example 129

1-(3,5-Difluoropyridin-2-yl)-6-fluoro-7-[(3S)-3-hydroxypyrrolidin-1-yl]-4-oxo-N-[3,3,4,4,4-pentafluorobutan-2-yl]-1,4-dihydro-L8-naphthyridine-3-carboxamide (diastereomer 2)

LC-MS (Method 3): $R_t$=1.97 min; MS (ESIpos): m/z=552 [M+H]$^+$ $^1$H-NMR (400 MHz, DMSO-d6): δ [ppm]=10.46 (br d, 1H), 8.83 (d, 1H), 8.61 (d, 1H), 8.30-8.38 (m, 1H), 8.00 (d, 1H), 4.93-5.10 (m, 2H), 4.22-4.37 (m, 1H), 3.36-4.07 (m, 3H), 2.96-3.29 (m, 1H), 1.73-1.98 (m, 2H), 1.39 (brd, 3H).

Example 130

N-(2,6-Dichlorophenyl)-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide

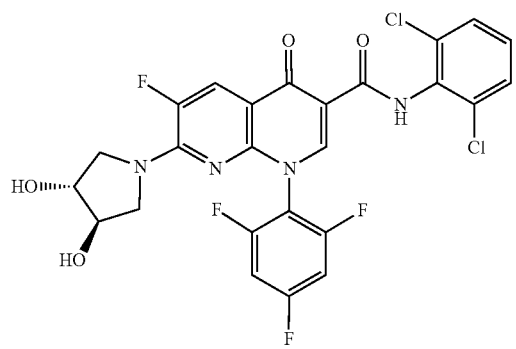 [SMILES: O=C(Nc1c(Cl)cccc1Cl)c1cn(-c2c(F)cc(F)cc2F)c2nc(N3C[C@@H](O)[C@H](O)C3)c(F)cc2c1=O]

According to GP3, 255 mg (494 µmol) of 7-chloro-N-(2,6-dichlorophenyl)-6-fluoro-4-oxo-1-(2,4,6-trifluorophenyl)-1,4-dihydro-1,8-naphthyridine-3-carboxamide were reacted with 75.8 mg (543 µmol) of (3R,4R)-pyrrolidine-3,4-diol hydrochloride and 300 µl (1.70 mmol) of N,N-diisopropylethylamine in 5 ml of dimethylformamide. The crude product was diluted with a little acetonitrile and purified by preparative HPLC (column: acetonitrile/water/ 0.1% of formic acid). This gave 216 mg (75% of theory, 100% pure) of the title compound.

LC-MS (Method 3): $R_t$=1.82 min; MS (ESIpos): m/z=583 [M+H]$^+$ $^1$H-NMR (400 MHz, DMSO-d6) δ[ppm]: 0.947 (0.79), 1.257 (3.15), 2.328 (0.67), 2.366 (0.53), 2.671 (0.73), 2.710 (0.55), 2.731 (4.61), 2.890 (5.57), 3.054 (1.06), 3.705 (0.95), 3.912 (1.83), 4.029 (1.36), 5.216 (3.69), 7.360 (2.39), 7.380 (4.91), 7.400 (3.33), 7.562 (3.25), 7.581 (16.00), 7.601 (11.10), 7.952 (0.78), 8.062 (4.69), 8.093 (4.59), 8.929 (8.31), 11.845 (8.05).

Example 131

N-[1-(2-Chlorophenyl)-2,2,2-trifluoroethyl]-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide (Diastereomer Mixture)

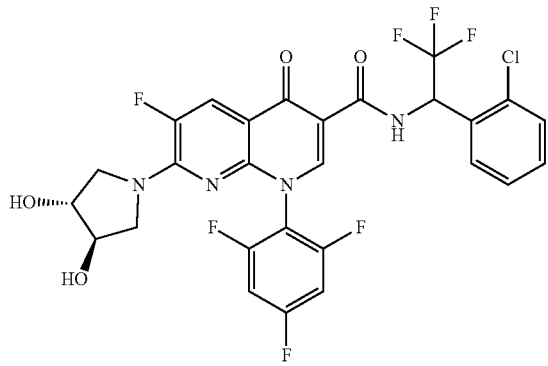 [SMILES: O=C(NC(c1ccccc1Cl)C(F)(F)F)c1cn(-c2c(F)cc(F)cc2F)c2nc(N3C[C@@H](O)[C@H](O)C3)c(F)cc2c1=O]

According to GP1, 100 mg (228 µmol) of 7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 52.5 mg (250 µmol) of 1-(2-chlorophenyl)-2,2,2-trifluoroethanamine (racemate) in the presence of 104 mg (273 µmol) of HATU and 120 µl (680 µmol) of DIPEA in 1.4 ml of DMF. The crude product was purified by preparative HPLC (column: acetonitrile/water/0.1% of formic acid). This gave 104 mg (71% of theory, 98% pure) of the title compound.

LC-MS (Method 1): $R_t$=1.09 min; MS (ESIpos): m/z=631 [M+H]$^+$ $^1$H-NMR (400 MHz, DMSO-d6) δ[ppm]: −0.149 (0.55), −0.008 (5.54), 0.146 (0.64), 2.074 (0.71), 2.329 (1.11), 2.367 (0.95), 2.671 (1.20), 2.711 (0.93), 3.064 (1.11), 3.696 (1.09), 3.897 (2.04), 4.021 (1.60), 5.203 (4.37), 6.404 (0.75), 6.423 (2.53), 6.445 (3.43), 6.465 (2.39), 7.484 (1.62), 7.499 (4.37), 7.503 (4.83), 7.517 (4.54), 7.522 (4.79), 7.533 (3.68), 7.551 (7.45), 7.566 (7.05), 7.589 (4.65), 7.607 (12.96), 7.627 (7.80), 8.050 (8.75), 8.082 (8.62), 8.861 (16.00), 11.447 (5.70), 11.470 (5.39).

Example 132

N-(2,6-Dichlorobenzyl)-7-[(3R,4R)-3,4-dihydroxypyrrolidin-1-yl]-6-fluoro-4-oxo-1-(2,4,6-tri-fluorophenyl)-1,4-dihydro-1,8-naphthyridine-3-carboxamide

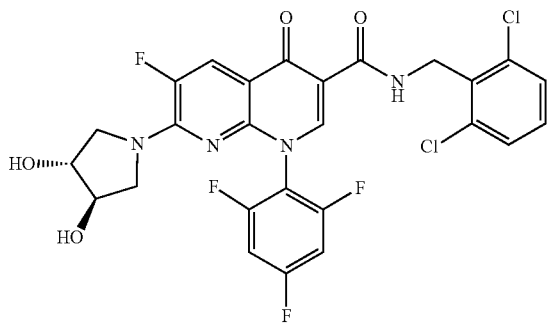 [SMILES: O=C(NCc1c(Cl)cccc1Cl)c1cn(-c2c(F)cc(F)cc2F)c2nc(N3C[C@@H](O)[C@H](O)C3)c(F)cc2c1=O]

According to GP1, 100 mg (228 µmol) of 7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 44.1 mg (250 µmol) of 1-(2,6-dichlorophenyl)methanamine in the presence of 104 mg (273 µmol) of HATU and 120 µl (680 µmol) of DIPEA in 1.4 ml of DMF. The crude product was purified by preparative HPLC (column: acetonitrile/water/0.1% of formic acid). This gave 121 mg (89% of theory, 100% pure) of the title compound.

LC-MS (Method 1): $R_t$=1.00 min; MS (ESIpos): m/z=597 [M+H]$^+$ $^1$H-NMR (400 MHz, DMSO-d6) δ[ppm]: −0.149 (0.53), −0.008 (5.53), 0.008 (3.79), 0.146 (0.53), 2.367 (0.81), 2.519 (3.30), 2.524 (2.91), 2.711 (0.74), 3.046 (0.63), 3.671 (0.60), 3.903 (1.44), 4.809 (10.37), 4.823 (10.16), 5.181 (4.47), 7.379 (3.42), 7.398 (5.05), 7.401 (5.23), 7.420 (5.84), 7.525 (16.00), 7.545 (12.28), 7.569 (5.33), 7.591 (3.09), 7.953 (7.16), 7.985 (6.98), 8.782 (12.02), 10.219 (2.47), 10.232 (4.91), 10.245 (2.14).

Example 133

6-Chloro-N-(2,6-dichlorophenyl)-1-(2,4-difluorophenyl)-4-oxo-1,4-dihydro-1,8-naphthyridine-3-carboxamide

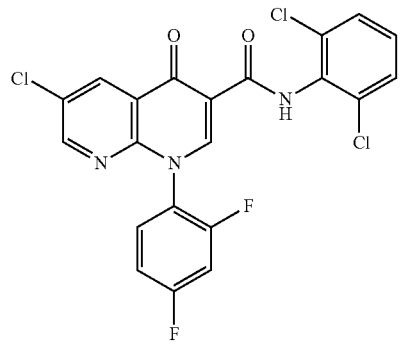 [SMILES: O=C(Nc1c(Cl)cccc1Cl)c1cn(-c2ccc(F)cc2F)c2ncc(Cl)cc2c1=O]

A solution of 79.4 mg (490 µmol) of 2,6-dichloroaniline in 1.0 ml of DMF was added to a solution of 158 mg (446 µmol) of 6-chloro-1-(2,4-difluorophenyl)-4-oxo-1,4-dihydro-1,8-naphthyridine-3-carbonyl chloride in 1.0 ml of DMF, and 19.6 mg (490 µmol) of sodium hydride (60% in mineral oil) were then added. The mixture was then stirred at RT for 2 h. The reaction was terminated by addition of water, acetonitrile and formic acid and the crude product was purified by preparative HPLC (column: acetonitrile/water/0.1% of formic acid). This gave 36.0 mg (16% of theory, 93% pure) of the title compound.

LC-MS (Method 1): $R_t$=1.24 min; MS (ESIpos): m/z=480 [M+H]$^+$ $^1$H-NMR (400 MHz, DMSO-d6): δ [ppm]=11.41 (s, 1H), 9.02 (s, 1H), 8.92 (d, 1H), 8.81 (d, 1H), 7.85-7.94 (m, 1H), 7.57-7.67 (m, 3H), 7.32-7.44 (m, 2H).

Example 134

6-Chloro-N-[1-(2-chlorophenyl)-2,2,2-trifluoroethyl]-1-(2,4-difluorophenyl)-4-oxo-1,4-dihydro-1,8-naphthyridine-3-carboxamide (Racemate)

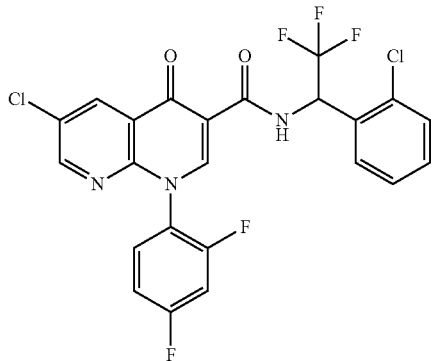 [SMILES: O=C(NC(c1ccccc1Cl)C(F)(F)F)c1cn(-c2ccc(F)cc2F)c2ncc(Cl)cc2c1=O]

According to GP1, 150 mg (446 µmol) of 6-chloro-1-(2,4-difluorophenyl)-4-oxo-1,4-dihydro-1,8-naphthyridine-3-carboxylic acid were reacted with 140 mg (668 µmol) of 1-(2-chloro-phenyl)-2,2,2-trifluoroethanamine (racemate) in the presence of 203 mg (535 µmol) of HATU and 230 µl (1.30 mmol) of DIPEA in 1.5 ml of DMF. The crude product was purified by preparative HPLC (column: acetonitrile/water/0.1% of formic acid). This gave 197 mg (83% of theory, 99% pure) of the title compound.

LC-MS (Method 1): $R_t$=1.37 min; MS (ESIpos): m/z=528 [M+H]$^+$ $^1$H-NMR (400 MHz, DMSO-d6): δ [ppm]=11.03 (d, 1H), 8.96 (s, 1H), 8.90 (d, 1H), 8.80 (d, 1H), 7.74-7.91 (m, 1H), 7.48-7.67 (m, 5H), 7.31-7.41 (m, 1H), 6.43-6.53 (m, 1H).

Example 135

6-Chloro-1-(2,4-difluorophenyl)-4-oxo-N-[1-(trifluoromethoxy)propan-2-yl]-1,4-dihydro-1,8-naphthyridine-3-carboxamide (Racemate)

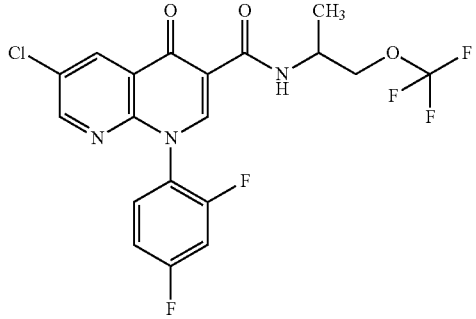 [SMILES: CC(COC(F)(F)F)NC(=O)c1cn(-c2ccc(F)cc2F)c2ncc(Cl)cc2c1=O]

According to GP1, 150 mg (446 µmol) of 6-chloro-1-(2,4-difluorophenyl)-4-oxo-1,4-dihydro-1,8-naphthyridine-3-carboxylic acid were reacted with 120 mg (668 nmol) of 1-(trifluoromethoxy)propan-2-amine hydrochloride (racemate) in the presence of 203 mg (535 µmol) of HATU and 310 µl (1.80 mmol) of DIPEA in 1.5 ml of DMF. The crude product was purified by preparative HPLC (column: acetonitrile/water/0.1% of formic acid). This gave 159 mg (77% of theory, 100% pure) of the title compound.

LC-MS (Method 1): $R_t$=1.21 min; MS (ESIpos): m/z=462 [M+H]$^+$ $^1$H-NMR (400 MHz, DMSO-d6): δ [ppm]=9.69 (d, 1H), 8.86-8.89 (m, 2H), 8.73 (d, 1H), 7.81-7.89 (m, 1H), 7.62 (ddd, 1H), 7.33-7.39 (m, 1H), 4.33-4.42 (m, 1H), 4.16-4.23 (m, 2H), 1.27 (d, 3H).

Example 136

1-(2-Chloro-4,6-difluorophenyl)-7-[(3R,4R)-3,4-dihydroxypyrrolidin-1-yl]-6-fluoro-4-oxo-N-[1,1,1-trifluoro-3-methylbutan-2-yl]-1,4-dihydro-1,8-naphthyridine-3-carboxamide (Diastereomer Mixture)

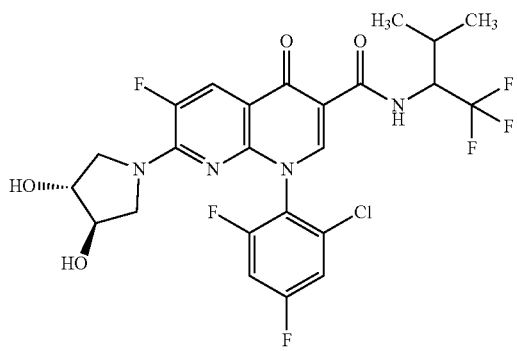 [SMILES: CC(C)C(NC(=O)c1cn(-c2c(F)cc(F)cc2Cl)c2nc(N3C[C@@H](O)[C@H](O)C3)c(F)cc2c1=O)C(F)(F)F]

According to GP1, 200 mg (83% pure, 364 µmol) of 1-(2-chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic acid were reacted with 58.3 mg (97%, 401 µmol) of 1,1,1-trifluoro-3-methylbutan-2-amine in the presence of 166 mg (437 µmol) of HATU and 190 µl (1.10 mmol) of DIPEA in 3.2 ml of DMF. The crude product was purified by preparative HPLC (column: acetonitrile/water/0.1% of formic acid). This gave 210 mg (100% of theory, 100% pure) of the title compound.

LC-MS (Method 3): $R_t$=1.95 min; MS (ESIpos): m/z=579 [M+H]$^+$ $^1$H-NMR (400 MHz, DMSO-d6) δ[ppm]: −0.149 (0.42), 0.008 (3.45), 0.146 (0.45), 0.953 (9.63), 0.962 (10.81), 0.969 (10.83), 0.979 (9.65), 1.019 (9.50), 1.025 (9.91), 1.036 (10.14), 1.042 (9.33), 2.224 (1.64), 2.234 (1.74), 2.241 (2.15), 2.251 (2.15), 2.267 (1.51), 2.285 (0.59), 2.328 (0.63), 2.367 (0.54), 2.524 (2.19), 2.670 (0.65), 2.711 (0.54), 2.732 (2.24), 2.891 (2.92), 3.015 (0.96), 3.225 (0.99), 3.687 (1.01), 3.893 (1.99), 4.013 (1.51), 4.747 (1.32), 4.769 (1.91), 4.789 (1.28), 5.201 (5.09), 5.754 (5.44), 7.688 (0.85), 7.695 (1.33), 7.710 (1.74), 7.719 (2.68), 7.728 (2.97), 7.734 (3.17), 7.742 (3.82), 7.751 (3.28), 7.765 (2.51), 8.041 (7.79), 8.073 (7.68), 8.802 (16.00), 10.536 (3.12), 10.545 (3.29), 10.561 (3.10), 10.569 (3.09).

Example 137

7-[(3R,4S)-3,4-Dihydroxypyrrolidin-1-yl]-6-fluoro-4-oxo-N-[1,1,1-trifluoro-3-methylbutan-2-yl]-1-(2,4,6-trifluorophenyl)-1,4-dihydro-1,8-naphthyridine-3-carboxamide (Diastereomer 1)

52.0 mg of 7-[(3R,4S)-3,4-dihydroxypyrrolidin-1-yl]-6-fluoro-4-oxo-N-[1,1,1-trifluoro-3-methylbutan-2-yl]-1-(2,4, 6-trifluorophenyl)-1,4-dihydro-1,8-naphthyridine-3-carboxamide (diasteieomer mixture) were separated into the diastereomers by chiral HPLC (preparative HPLC: column Daicel Chiralcel OX-H, 5 µm, 250×20 mm; mobile phase: 80% n-heptane/20% ethanol; flow rate 15 ml/min; temperature: 25° C., detection: 210 nm).

Diasteieomer 1: 19.5 mg (>99% ee)

$R_t$=1.30 min [HPLC: column Daicel OX-3; 3 µm, 50×4.6 mm; mobile phase: 80% isohexane/20% ethanol; detection: 220 nm].

Diasteieomer 1 was additionally purified by preparative HPLC (column: acetonitrile/water/0.1% formic acid, giving 14.0 mg (100% pure) of the title compound.

LC-MS (Method 3): $R_t$=1.96 min; MS (ESIpos): m/z=563 [M+H]$^+$ $^1$H-NMR (400 MHz, DMSO-d6) δ[ppm]: −0.149 (0.79), −0.008 (7.62), 0.008 (5.42), 0.146 (0.71), 0.953 (15.75), 0.970 (16.00), 1.017 (13.54), 1.034 (13.74), 2.203 (0.62), 2.221 (1.58), 2.230 (1.66), 2.237 (2.09), 2.247 (2.12), 2.254 (1.55), 2.264 (1.47), 2.328 (1.13), 2.366 (1.21), 2.523 (4.06), 2.670 (1.19), 2.710 (1.24), 3.036 (0.62), 3.406 (0.90), 3.583 (0.68), 3.803 (0.45), 3.821 (0.45), 4.034 (2.34), 4.738 (1.24), 4.747 (1.35), 4.761 (1.83), 4.770 (1.89), 4.783 (1.30), 4.793 (1.19), 5.004 (2.00), 7.556 (3.89), 7.577 (7.37), 7.600 (3.87), 8.025 (7.37), 8.057 (7.37), 8.845 (13.43), 10.514 (4.94), 10.540 (4.77).

Example 138

7-[(3R,4S)-3,4-Dihydroxypyrrolidin-1-yl]-6-fluoro-4-oxo-N-[1,1,1-trifluoro-3-methylbutan-2-yl]-1-(2,4,6-trifluorophenyl)-1,4-dihydro-1,8-naphthyridine-3-carboxamide (Diastereomer 2)

52.0 mg of 7-[(3R,4S)-3,4-dihydroxypyrrolidin-1-yl]-6-fluoro-4-oxo-N-[1,1,1-trifluoro-3-methylbutan-2-yl]-1-(2,4,6-trifluorophenyl)-1,4-dihydro-1,8-naphthyridine-3-carboxamide (diastereomer mixture) were separated into the diastereomers by chiral HPLC (preparative HPLC: column Daicel Chiralcel OX-H, 5 µm, 250×20 mm; mobile phase: 80% n-heptane/20% ethanol; flow rate 15 ml/min; temperature: 25° C., detection: 210 nm).

Diastereomer 2: 21.5 mg (90.4% ee)

$R_t$=1.77 min [HPLC: column Daicel OX-3; 3 µm, 50×4.6 mm; mobile phase: 80% isohexane/20% ethanol; detection: 220 nm].

Diastereomer 2 was additionally purified by preparative HPLC (column: acetonitrile/water/0.1% formic acid), giving 15.0 mg (100% pure) of the title compound.

LC-MS (Method 3): $R_t$=1.97 min; MS (ESIpos): m/z=563 [M+H]$^+$ $^1$H-NMR (400 MHz, DMSO-d6) δ[ppm]: −0.149 (0.48), −0.008 (4.54), 0.008 (3.45), 0.146 (0.46), 0.930 (3.74), 0.949 (12.03), 0.953 (15.89), 0.970 (16.00), 1.017 (13.01), 1.034 (13.22), 2.204 (0.59), 2.221 (1.53), 2.231 (1.58), 2.238 (2.01), 2.248 (2.01), 2.255 (1.48), 2.264 (1.41), 2.281 (0.53), 2.328 (0.69), 2.367 (0.75), 2.451 (0.77), 2.468 (2.26), 2.524 (2.47), 2.671 (0.75), 2.711 (0.78), 3.023 (0.62), 3.594 (0.64), 3.951 (0.80), 4.039 (2.22), 4.738 (1.17), 4.747 (1.32), 4.761 (1.74), 4.771 (1.76), 4.784 (1.25), 4.793 (1.16), 5.006 (1.69), 7.556 (3.68), 7.578 (6.92), 7.600 (3.70), 8.026 (7.19), 8.057 (7.07), 8.266 (0.77), 8.846 (12.46), 10.515 (4.82), 10.540 (4.65).

Example 139

6-Fluoro-7-[(3S)-3-hydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (Diastereomer 1)

54.0 mg of 6-fluoro-7-[(3S)-3-hydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer mixture) were separated into the diastereomers by chiral HPLC (preparative HPLC: column Daicel Chiralpak IE, 5 µm, 250×20 mm; mobile phase: 70% n-heptane/30% isopropanol; flow rate 15 ml/min; temperature: 25° C., detection: 270 nm).

Diastereomer 1: 21.5 mg (>99% ee)

$R_t$=2.20 min [HPLC: column Daicel IE-3; 3 µm, 50×4.6 mm; mobile phase: 80% isohexane/20% isopropanol; detection: 220 nm].

LC-MS (Method 1): $R_t$=1.13 min; MS (ESIpos): m/z=547 [M+H]$^+$ $^1$H-NMR (400 MHz, DMSO-d6) δ[ppm]: −0.149 (0.42), −0.008 (3.86), 0.008 (3.14), 0.955 (15.68), 0.971 (16.00), 1.018 (13.42), 1.036 (13.72), 1.234 (0.52), 1.814 (0.98), 2.205 (0.64), 2.222 (1.58), 2.231 (1.64), 2.239 (2.10), 2.248 (2.10), 2.255 (1.60), 2.265 (1.50), 2.282 (0.54), 2.328 (0.88), 2.366 (0.72), 2.524 (2.80), 2.670 (0.94), 2.710 (0.76), 3.841 (0.46), 4.299 (1.22), 4.739 (1.24), 4.748 (1.36), 4.762 (1.78), 4.771 (1.82), 4.785 (1.30), 4.794 (1.20), 5.015 (1.18), 7.549 (2.90), 7.570 (5.35), 7.591 (3.08), 8.024 (7.85), 8.056 (7.69), 8.843 (13.18), 10.526 (4.95), 10.551 (4.79).

Example 140

6-Fluoro-7-[(3S)-3-hydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (Diastereomer 2)

54.0 mg of 6-fluoro-7-[(3S)-3-hydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer mixture) were separated into the diastereomers by chiral HPLC (preparative HPLC: column Daicel Chiralpak IE, 5 µm, 250×20 mm; mobile phase: 70% n-heptane/30% isopropanol; flow rate 15 ml/min; temperature: 25° C., detection: 270 nm).

Diastereomer 2: 19.5 mg (96.8% ee)

$R_t$=3.41 min [HPLC: column Daicel IE-3; 3 µm, 50×4.6 mm; mobile phase: 80% isohexane/20% isopropanol; detection: 220 nm], LC-MS (Method 1): $R_t$=1.14 min; MS (ESIpos): m/z=547 [M+H]$^+$ $^1$H-NMR (400 MHz, DMSO-d6) δ[ppm]: 0.008 (2.57), 0.858 (0.51), 0.954 (15.74), 0.971 (16.00), 1.018 (13.62), 1.035 (13.86), 1.233 (0.75), 1.827 (1.03), 2.204 (0.66), 2.222 (1.61), 2.232 (1.70), 2.239 (2.10), 2.248 (2.14), 2.255 (1.59), 2.265 (1.52), 2.282 (0.58), 2.329 (0.88), 2.367 (0.58), 2.670 (0.86), 2.711 (0.56), 3.814 (0.49), 4.294 (1.27), 4.739 (1.29), 4.748 (1.37), 4.763 (1.82), 4.771 (1.85), 4.786 (1.26), 4.794 (1.24), 5.008 (2.70), 7.549 (4.18), 7.571 (7.89), 7.593 (4.22), 8.025 (7.63), 8.057 (7.57), 8.843 (13.71), 10.527 (4.93), 10.552 (4.78).

Example 141

1-(2-Chloro-4,6-difluorophenyl)-N-(1,1-difluoro-2-methylpropan-2-yl)-7-[(3R,4R)-3,4-dihydroxypyrrolidin-1-yl]-6-fluoro-4-oxo-1,4-dihydro-1,8-naphthyridine-3-carboxamide (Atropisomer Mixture)

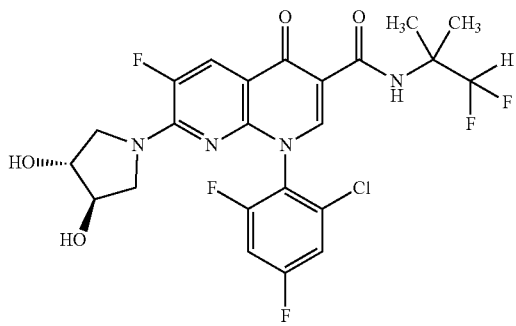 [SMILES: CC(C)(NC(=O)c1cn(-c2c(F)cc(F)cc2Cl)c2nc(N3C[C@@H](O)[C@H](O)C3)c(F)cc2c1=O)C(F)F]

According to GP1, 100 mg (83% pure, 182 μmol) of 1-(2-chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic acid were reacted with 30.1 mg (97% pure, 200 μmol) of 1,1-difluoro-2-methylpropan-2-amine hydrochloride in the presence of 83.1 mg (219 μmol) of HATU and 130 μl (730 μmol) of DIPEA in 1.6 ml of DMF. The crude product was purified by preparative HPLC (column: acetonitrile/water/0.1% of formic acid). This gave 97.0 mg (97% of theory, 100% pure) of the title compound.

LC-MS (Method 3): $R_t$=1.80 min; MS (ESIpos): m/z=547 [M+H]$^+$ $^1$H-NMR (400 MHz, DMSO-d6) δ[ppm]: 10.25 (s, 1H), 8.70 (s, 1H), 8.01 (d, 1H), 7.68-7.79 (m, 2H), 6.25-6.58 (m, 1H), 5.19 (br s, 2H), 3.79-4.06 (m, 3H), 3.56-3.78 (m, 1H), 3.12-3.28 (m, 1H), 2.93-3.11 (m, 1H), 1.43 (s, 6H).

Example 142

1-(2-Chloro-4,6-difluorophenyl)-N-(1,1-difluoro-2-methylpropan-2-yl)-7-[(3R,4R)-3,4-dihydroxypyrrolidin-1-yl]-6-fluoro-4-oxo-1,4-dihydro-1,8-naphthyridine-3-carboxamide (Atropisomer 1)

97.0 mg of 1-(2-chloro-4,6-difluorophenyl)-N-(1,1-difluoro-2-methylpropan-2-yl)-7-[(3R,4R)-3,4-dihydroxypyrrolidin-1-yl]-6-fluoro-4-oxo-1,4-dihydro-1,8-naphthyridine-3-carboxamide (atropisomer mixture) were separated into the atropisomers by chiral HPLC (preparative HPLC: column Daicel Chiralpak IA, 5 μm, 250×20 mm; mobile phase: 75% n-heptane/25% isopropanol+0.2% DEA; flow rate 15 ml/min; temperature: 35° C., detection: 220 nm).

Atropisomer 1: 34.4 mg (>99% ee)

$R_t$=9.05 min [HPLC: column Daicel Chiralpak IA, 1 ml/min; 5 μm, 250×4.6 mm; mobile phase: 80% n-hexane/20% isopropanol+0.2% DEA; detection: 235 nm].

LC-MS (Method 3): $R_t$=1.76 min; MS (ESIpos): m/z=547 [M+H]$^+$ $^1$H NMR (400 MHz, DMSO-d$_6$) δ ppm 10.25 (s, 1H), 8.70 (s, 1H), 8.01 (d, 1H), 7.68-7.77 (m, 2H), 6.22-6.58 (m, 1H), 5.19 (br s, 2H), 3.79-4.08 (m, 3H), 3.59-3.78 (m, 1H), 3.15-3.28 (m, 1H), 2.89-3.10 (m, 1H), 1.44 (s, 6H).

Example 143

1-(2-Chloro-4,6-difluorophenyl)-N-(1,1-difluoro-2-methylpropan-2-yl)-7-[(3R,4R)-3,4-dihydroxypyrrolidin-1-yl]-6-fluoro-4-oxo-1,4-dihydro-1,8-naphthyridine-3-carboxamide (Atropisomer 2)

97.0 mg of 1-(2-chloro-4,6-difluorophenyl)-N-(1,1-difluoro-2-methylpropan-2-yl)-7-[(3R,4R)-3,4-dihydroxypyrrolidin-1-yl]-6-fluoro-4-oxo-1,4-dihydro-1,8-naphthyridine-3-carboxamide (atropisomer mixture) were separated into the atropisomers by chiral HPLC (preparative HPLC: column Daicel Chiralpak IA, 5 μm, 250×20 mm; mobile phase: 75% n-heptane/25% isopropanol+0.2% DEA; flow rate 15 ml/min; temperature: 35° C., detection: 220 nm).

Atropisomer 2: 5.50 mg (>99% ee)

$R_t$=13.64 min [HPLC: column Daicel Chiralpak IA, 1 ml/min; 5 μm, 250×4.6 mm; mobile phase: 80% n-hexane/20% isopropanol+0.2% DEA; detection: 235 nm], LC-MS (Method 3): $R_t$=1.76 min; MS (ESIpos): m/z=547 [M+H]$^+$ $^1$H NMR (400 MHz, DMSO-d6) δ[ppm]: 10.25 (s, 1H), 8.70 (s, 1H), 8.01 (d, 1H), 7.67-7.77 (m, 2H), 6.25-6.58 (m, 1H), 5.14-5.24 (m, 2H), 3.78-4.08 (m, 3H), 3.57-3.77 (m, 1H), 3.12-3.27 (m, 1H), 2.92-3.11 (m, 1H), 1.43 (s, 6H).

Example 144

7-[(3R,4R)-3,4-Dihydroxypyrrolidin-1-yl]-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide

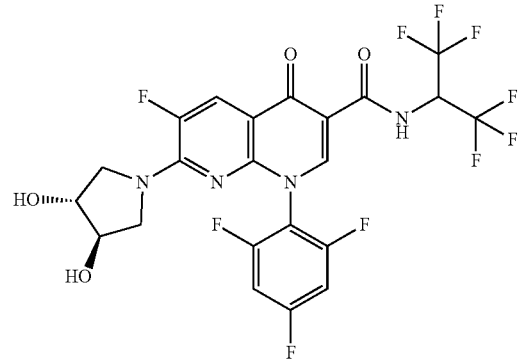 [SMILES: O=C(NC(C(F)(F)F)C(F)(F)F)c1cn(-c2c(F)cc(F)cc2F)c2nc(N3C[C@@H](O)[C@H](O)C3)c(F)cc2c1=O]

According to GP3, 80.0 mg (153 μmol) of 7-chloro-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide were reacted with 23.5 mg (169 μmol) of (3R,4R)-pyrrolidine-3,4-diol hydrochloride and 93 μl (540 μmol) of DIPEA in 1.5 ml of DMF. The crude product was purified by preparative HPLC (column: acetonitrile/water/0.1% of formic acid). This gave 88.0 mg (98% of theory, 100% pure) of the title compound.

LC-MS (Method 3): $R_t$=1.91 min; MS (ESIpos): m/z=589 [M+H]$^+$ $^1$H-NMR (400 MHz, DMSO-d6) δ[ppm]: −0.149 (0.63), −0.008 (5.64), 0.008 (4.87), 0.146 (0.63), 2.073 (0.88), 2.328 (0.91), 2.367 (0.67), 2.670 (0.95), 2.711 (0.67), 3.081 (1.16), 3.708 (1.16), 3.903 (2.10), 4.025 (1.68), 5.208 (3.85), 6.280 (0.49), 6.297 (1.23), 6.316 (1.75), 6.340 (1.86), 6.358

(1.23), 7.569 (3.78), 7.590 (6.79), 7.611 (3.78), 8.033 (8.96), 8.065 (8.79), 8.969 (16.00), 11.296 (5.95), 11.321 (5.67).

Example 145

1-(3,5-Difluoropyridin-2-yl)-7-[(3R,4R)-3,4-dihydroxypyrrolidin-1-yl]-6-fluoro-N-(1,1,1,3,3,3-hexafluoropropan-2-yl)-4-oxo-1,4-dihydro-1,8-naphthyridine-3-carboxamide

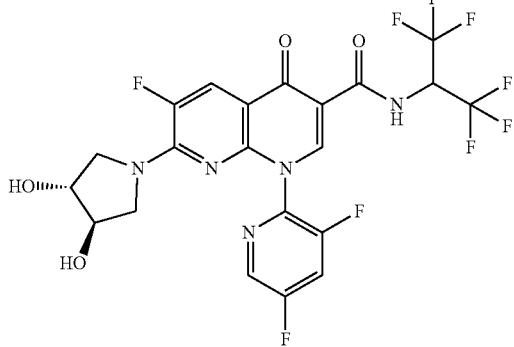

According to GP3, 249 mg (493 µmol) of 7-chloro-1-(3,5-difluoropyridin-2-yl)-6-fluoro-N-(1,1,1,3,3,3-hexafluoropropan-2-yl)-4-oxo-1,4-dihydro-1,8-naphthyridine-3-carboxamide were reacted with 75.8 mg (543 µmol) of (3R,4R)-pyrrolidine-3,4-diol hydrochloride and 300 µl (1.70 mmol) of DIPEA in 5 ml of DMF. The crude product was purified by preparative HPLC (column: acetonitrile/water/0.1% of formic acid). This gave 197 mg (70% of theory, 100% pure) of the title compound.

LC-MS (Method 3): $R_t$=1.79 min; MS (ESIpos): m/z=572 [M+H]$^+$ $^1$H-NMR (400 MHz, DMSO-d6) δ[ppm]: −0.150 (0.81), 0.146 (0.81), 0.950 (1.31), 0.966 (1.16), 2.327 (1.26), 2.367 (1.26), 2.670 (1.46), 2.710 (1.26), 3.060 (0.86), 3.717 (0.96), 3.905 (2.68), 4.017 (1.92), 5.118 (0.91), 5.207 (3.43), 6.309 (1.56), 6.328 (2.32), 6.351 (2.37), 6.369 (1.56), 8.034 (6.06), 8.066 (6.21), 8.340 (2.37), 8.346 (2.78), 8.367 (4.74), 8.384 (2.47), 8.390 (2.68), 8.633 (8.98), 8.933 (16.00), 11.291 (7.32), 11.317 (7.07).

Example 146

6-Fluoro-7-(morpholin-4-yl)-4-oxo-N-[3,3,4,4,4-pentafluorobutan-2-yl]-1-(2,4,6-trifluoro-phenyl)-1,4-dihydro-1,8-naphthyridine-3-carboxamide (Racemate)

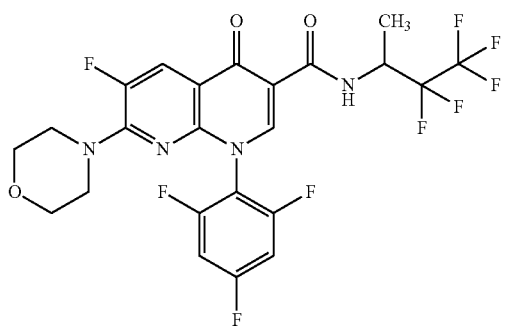 [SMILES: CC(NC(=O)c1cn(-c2c(F)cc(F)cc2F)c2nc(N3CCOCC3)c(F)cc2c1=O)C(F)(F)C(F)(F)F]

According to GP1, 100 mg (236 µmol) of 6-fluoro-7-(morpholin-4-yl)-4-oxo-1-(2,4,6-trifluoro-phenyl)-1,4-dihydro-1,8-naphthyridine-3-carboxylic acid were reacted with 51.9 mg (260 µmol) of 3,3,4,4,4-pentafluorobutan-2-amine hydrochloride (racemate) in the presence of 108 mg (283 µmol) of HATU and 120 µl (710 µmol) of DIPEA in 2.3 ml of DMF. The crude product was purified by preparative HPLC (column: acetonitrile/water/0.1% of formic acid). This gave 86.0 mg (64% of theory, 100% pure) of the title compound.

LC-MS (Method 3): $R_t$=2.33 min; MS (ESIpos): m/z=569 [M+H]$^+$ $^1$H-NMR (400 MHz, DMSO-d6) δ[ppm]: −0.149 (1.35), −0.008 (14.16), 0.008 (14.02), 0.146 (1.44), 1.389 (12.85), 1.407 (12.72), 1.988 (0.85), 2.327 (2.07), 2.366 (1.84), 2.523 (7.64), 2.670 (2.20), 2.710 (1.84), 3.506 (8.45), 3.517 (14.92), 3.529 (14.38), 3.596 (15.28), 3.608 (16.00), 3.619 (9.17), 3.741 (0.58), 4.038 (0.40), 5.015 (1.39), 5.034 (1.35), 7.550 (5.12), 7.572 (9.75), 7.594 (5.12), 8.103 (8.94), 8.137 (8.76), 8.711 (0.49), 8.907 (15.60), 10.344 (5.26), 10.368 (5.17).

Example 147

N-[(1S)-Cyclopropyl-2,2,2-trifluoroethyl]-6-fluoro-7-(morpholin-4-yl)-4-oxo-1-(2,4,6-trifluorophenyl)-1,4-dihydro-1,8-naphthyridine-3-carboxamide

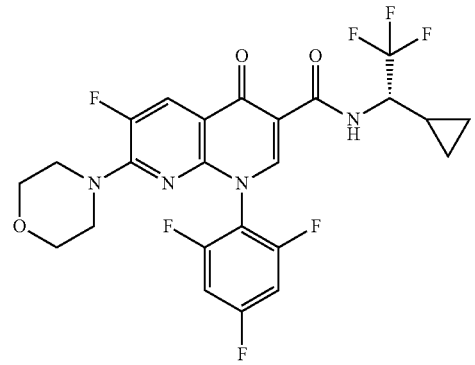 [SMILES: O=C(N[C@@H](C1CC1)C(F)(F)F)c1cn(-c2c(F)cc(F)cc2F)c2nc(N3CCOCC3)c(F)cc2c1=O]

According to GP1, 80.0 mg (189 nmol) of 6-fluoro-7-(morpholin-4-yl)-4-oxo-1-(2,4,6-trifluorophenyl)-1,4-dihydro-1,8-naphthyridine-3-carboxylic acid were reacted with 36.5 mg (208 nmol) of (1S)-cyclopropyl-2,2,2-trifluoroethanamine hydrochloride in the presence of 86.2 mg (227 µmol) of HATU and 99 µl (570 nmol) of DIPEA in 1.8 ml of DMF. The crude product was purified by preparative HPLC (column: acetonitrile/water/0.1% of formic acid). This gave 91.9 mg (89% of theory, 100% pure) of the title compound.

LC-MS (Method 3): $R_t$=2.33 min; MS (ESIpos): m/z=545 [M+H]$^+$ $^1$H-NMR (400 MHz, DMSO-d6) δ[ppm]: −0.149 (0.68), −0.008 (8.06), 0.008 (4.92), 0.146 (0.68), 0.320 (1.83), 0.330 (2.93), 0.343 (2.81), 0.354 (2.06), 0.366 (1.15), 0.508 (0.77), 0.521 (1.90), 0.532 (2.93), 0.545 (2.88), 0.551 (3.23), 0.570 (3.35), 0.579 (2.48), 0.590 (2.25), 0.600 (1.83), 0.614 (1.12), 0.630 (1.52), 0.640 (1.50), 0.650 (3.00), 0.660 (2.32), 0.667 (2.08), 0.672 (2.01), 0.686 (1.10), 0.694 (0.68), 1.172 (0.59), 1.185 (1.19), 1.193 (1.64), 1.205 (2.76), 1.214 (2.11), 1.225 (2.69), 1.237 (1.52), 1.246 (1.01), 1.258 (0.45), 2.073 (1.10), 2.328 (0.82), 2.367 (0.94), 2.524 (3.40), 2.670 (0.91), 2.710 (1.01), 3.509 (8.88), 3.520 (15.46), 3.532 (14.62), 3.549 (1.52), 3.600 (15.77), 3.612 (16.00), 3.622 (9.04), 4.353 (1.50), 4.374 (2.60), 4.396 (2.48), 4.415 (1.36), 7.550 (5.06), 7.573 (9.77), 7.595 (5.15), 7.603 (1.62), 8.112 (8.78), 8.146 (8.62), 8.896 (14.52), 10.361 (5.67), 10.384 (5.51).

Example 148

6-Fluoro-7-(morpholin-4-yl)-4-oxo-N-[1,1,1,2,2-pentafluoropentan-3-yl]-1-(2,4,6-trifluoro-phenyl)-1,4-dihydro-1,8-naphthyridine-3-carboxamide (Racemate)

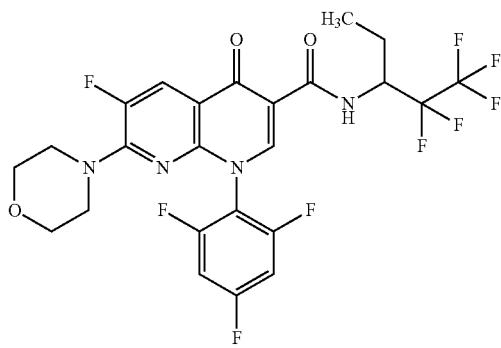 [SMILES: CCC(NC(=O)c1cn(-c2c(F)cc(F)cc2F)c2nc(N3CCOCC3)c(F)cc2c1=O)C(F)(F)C(F)(F)F]

According to GP1, 100 mg (236 μmol) of 6-fluoro-7-(morpholin-4-yl)-4-oxo-1-(2,4,6-trifluoro-phenyl)-1,4-dihydro-1,8-naphthyridine-3-carboxylic acid were reacted with 55.5 mg (260 μmol) of 1,1,1,2,2-pentafluoropentan-3-amine hydrochloride (racemate) in the presence of 108 mg (283 μmol) of HATU and 120 μl (710 μmol) of DIPEA in 2.3 ml of DMF. The crude product was purified by preparative HPLC (column: acetonitrile/water/0.1% of formic acid). This gave 108 mg (78% of theory, 100% pure) of the title compound.

LC-MS (Method 3): $R_t$=2.42 min; MS (ESIpos): m/z=583 [M+H]$^+$ $^1$H-NMR (400 MHz, DMSO-d6) δ[ppm]: −0.149 (1.17), −0.008 (10.68), 0.008 (8.97), 0.146 (1.22), 0.943 (7.08), 0.962 (16.00), 0.980 (7.66), 1.157 (0.90), 1.175 (1.80), 1.193 (0.95), 1.234 (0.41), 1.624 (0.86), 1.642 (1.22), 1.650 (1.13), 1.659 (1.44), 1.669 (1.31), 1.677 (1.26), 1.685 (1.44), 1.703 (0.99), 1.907 (1.44), 1.988 (3.20), 2.328 (1.35), 2.366 (1.89), 2.523 (5.00), 2.670 (1.58), 2.710 (1.94), 3.508 (6.76), 3.519 (12.21), 3.531 (11.85), 3.547 (1.58), 3.597 (12.57), 3.610 (12.94), 3.620 (7.35), 4.021 (0.81), 4.038 (0.72), 4.831 (0.86), 4.857 (1.08), 4.883 (1.08), 4.907 (0.86), 7.551 (4.01), 7.573 (7.80), 7.595 (4.10), 8.113 (6.94), 8.147 (6.85), 8.914 (11.67), 10.266 (4.42), 10.291 (4.28).

Example 149

6-Fluoro-7-(morpholin-4-yl)-4-oxo-N-(1,1,1-trifluoro-2-methylpropan-2-yl)-1-(2,4,6-trifluorophenyl)-1,4-dihydro-1,8-naphthyridine-3-carboxamide

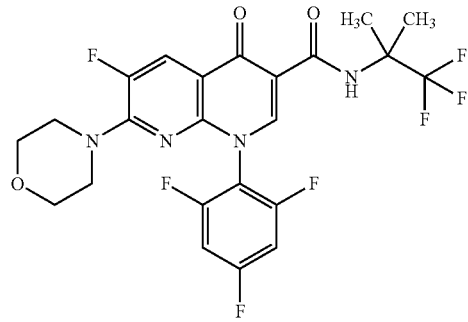 [SMILES: CC(C)(NC(=O)c1cn(-c2c(F)cc(F)cc2F)c2nc(N3CCOCC3)c(F)cc2c1=O)C(F)(F)F]

According to GP1, 80.0 mg (189 μmol) of 6-fluoro-7-(morpholin-4-yl)-4-oxo-1-(2,4,6-trifluorophenyl)-1,4-dihydro-1,8-naphthyridine-3-carboxylic acid were reacted with 34.0 mg (208 μmol) of 1,1,1-trifluoro-2-methylpropan-2-amine hydrochloride in the presence of 86.2 mg (227 μmol) of HATU and 99 μl (570 μmol) of DIPEA in 1.8 ml of DMF. The crude product was purified by preparative HPLC (column: acetonitrile/water/0.1% of formic acid). This gave 87.6 mg (87% of theory, 100% pure) of the title compound.

LC-MS (Method 3): $R_t$=2.34 min; MS (ESIpos): m/z=533 [M+H]$^+$ $^1$H-NMR (400 MHz, DMSO-d6) δ[ppm]: −0.008 (2.83), 0.008 (2.66), 1.636 (16.00), 2.073 (1.35), 2.670 (0.47), 2.710 (0.42), 3.504 (2.00), 3.514 (3.57), 3.526 (3.45), 3.596 (3.60), 3.609 (3.83), 3.619 (2.21), 7.552 (1.12), 7.574 (2.09), 7.596 (1.15), 8.115 (1.92), 8.149 (1.92), 8.840 (3.18), 10.452 (2.69).

Example 150

N-(1,1-Difluoro-2-methylpropan-2-yl)-6-fluoro-7-(morpholin-4-yl)-4-oxo-1-(2,4,6-trifluoro-phenyl)-1,4-dihydro-1,8-naphthyridine-3-carboxamide

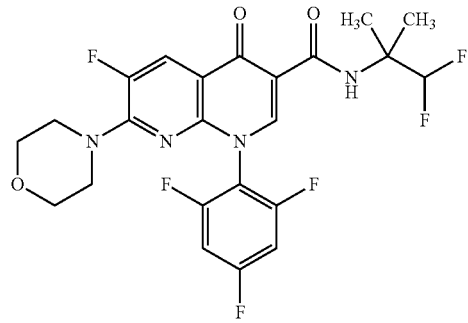 [SMILES: CC(C)(NC(=O)c1cn(-c2c(F)cc(F)cc2F)c2nc(N3CCOCC3)c(F)cc2c1=O)C(F)F]

According to GP1, 80.0 mg (189 μmol) of 6-fluoro-7-(morpholin-4-yl)-4-oxo-1-(2,4,6-trifluorophenyl)-1,4-dihydro-1,8-naphthyridine-3-carboxylic acid were reacted with 30.3 mg (208 μmol) of 1,1-difluoro-2-methylpropan-2-amine hydrochloride in the presence of 86.2 mg (227

µmol) of HATU and 99 µl (570 µmol) of DIPEA in 1.8 ml of DMF. The crude product was purified by preparative HPLC (column: acetonitrile/water/0.1% of formic acid). This gave 128 mg (quantitative, 100% pure) of the title compound.

LC-MS (Method 1): $R_t$=1.17 min; MS (ESIpos): m/z=515 [M+H]$^+$ $^1$H-NMR (400 MHz, DMSO-d6) δ[ppm]: 0.008 (2.62), 1.439 (16.00), 2.073 (1.40), 2.328 (0.43), 2.670 (0.45), 3.500 (2.43), 3.510 (4.30), 3.522 (4.05), 3.595 (4.20), 3.607 (4.50), 3.618 (2.59), 6.277 (0.88), 6.419 (1.63), 6.562 (0.74), 7.550 (1.32), 7.572 (2.49), 7.594 (1.34), 8.095 (2.20), 8.129 (2.19), 8.817 (3.74), 10.135 (2.90).

Example 151

6-Fluoro-7-(morpholin-4-yl)-4-oxo-N-[(2S)-1,1,1-trifluorobutan-2-yl]-1-(2,4,6-trifluoro-phenyl)-1,4-dihydro-1,8-naphthyridine-3-carboxamide

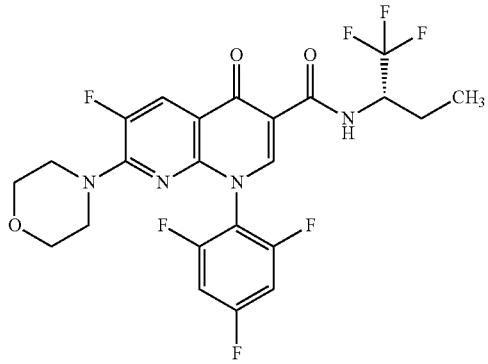 [SMILES: CC[C@H](NC(=O)c1cn(-c2c(F)cc(F)cc2F)c2nc(N3CCOCC3)c(F)cc2c1=O)C(F)(F)F]

According to GP1, 80.0 mg (189 µmol) of 6-fluoro-7-(morpholin-4-yl)-4-oxo-1-(2,4,6-trifluorophenyl)-1,4-dihydro-1,8-naphthyridine-3-carboxylic acid were reacted with 34.0 mg (208 µmol) of (2S)-1,1,1-trifluorobutan-2-amine hydrochloride in the presence of 86.2 mg (227 µmol) of HATU and 99 µl (570 µmol) of DIPEA in 1.8 ml of DMF. The crude product was purified by preparative HPLC (column: acetonitrile/water/0.1% of formic acid). This gave 83.0 mg (82% of theory, 100% pure) of the title compound.

LC-MS (Method 1): $R_t$=1.20 min; MS (ESIpos): m/z=533 [M+H]$^+$ $^1$H-NMR (400 MHz, DMSO-d6) δ[ppm]: 0.951 (7.27), 0.969 (16.00), 0.988 (7.90), 1.611 (1.05), 1.629 (1.46), 1.635 (1.29), 1.646 (1.77), 1.654 (1.58), 1.664 (1.52), 1.671 (1.69), 1.689 (1.27), 1.835 (0.42), 1.854 (1.32), 1.864 (1.52), 1.872 (1.57), 1.882 (1.75), 1.889 (1.54), 1.899 (1.38), 1.907 (1.15), 1.917 (0.96), 2.074 (0.67), 3.510 (8.13), 3.520 (14.34), 3.532 (13.50), 3.549 (1.33), 3.600 (14.03), 3.612 (14.78), 3.622 (8.39), 4.742 (1.52), 4.762 (1.43), 7.554 (4.14), 7.576 (8.01), 7.598 (4.19), 8.107 (6.29), 8.141 (6.26), 8.906 (11.53), 10.220 (4.83), 10.244 (4.71).

Example 152

1-(3,5-Difluoropyridin-2-yl)-6-fluoro-7-[(3S)-3-hydroxypyrrolidin-1-yl]-4-oxo-N-[(2S)-1,1,1-trifluorobutan-2-yl]-1,4-dihydro-1,8-naphthyridine-3-carboxamide

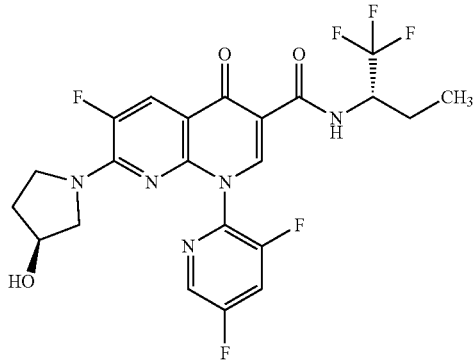 [SMILES: CC[C@H](NC(=O)c1cn(-c2ncc(F)cc2F)c2nc(N3CC[C@H](O)C3)c(F)cc2c1=O)C(F)(F)F]

According to GP1, 45.0 mg (111 µmol) of 1-(3,5-difluoropyridin-2-yl)-6-fluoro-7-[(3S)-3-hydroxypyrrolidin-1-yl]-4-oxo-1,4-dihydro-1,8-naphthyridine-3-carboxylic acid were reacted with 19.9 mg (122 µmol) of (2S)-1,1,1-trifluorobutan-2-amine hydrochloride in the presence of 50.5 mg (133 µmol) of HATU and 77 µl (440 µmol) of DIPEA in 1.0 ml of DMF. The crude product was purified by preparative HPLC (column: acetonitrile/water/0.1% of formic acid). This gave 42.0 mg (74% of theory, 100% pure) of the title compound.

LC-MS (Method 3): $R_t$=1.95 min; MS (ESIpos): m/z=516 [M+H]$^+$ $^1$H-NMR (400 MHz, DMSO-d6) δ[ppm]: −0.149 (1.48), −0.008 (16.00), 0.008 (9.38), 0.146 (1.14), 0.959 (6.81), 0.975 (6.86), 0.992 (2.91), 1.637 (1.30), 1.883 (2.23), 2.328 (1.72), 2.523 (6.83), 2.670 (1.32), 3.342 (1.11), 4.303 (1.46), 4.741 (1.40), 4.995 (2.89), 5.004 (2.91), 7.988 (5.03), 8.020 (5.01), 8.315 (1.59), 8.321 (1.72), 8.342 (2.65), 8.365 (1.51), 8.617 (5.62), 8.837 (15.23), 10.328 (3.10), 10.353 (2.89).

Example 153

N-[(1S)-1-Cyclopropyl-2,2,2-trifluoroethyl]-1-(3,5-difluoropyridin-2-yl)-6-fluoro-7-[(3S)-3-hydroxypyrrolidin-1-yl]-4-oxo-1,4-dihydro-1,8-naphthyridine-3-carboxamide

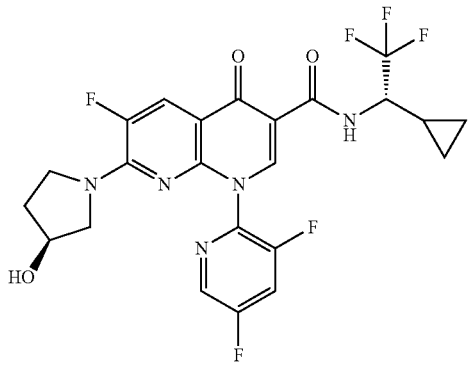 [SMILES: O=C(N[C@@H](C1CC1)C(F)(F)F)c1cn(-c2ncc(F)cc2F)c2nc(N3CC[C@H](O)C3)c(F)cc2c1=O]

235

According to GP1, 45.0 mg (111 µmol) of 1-(3,5-difluoropyridin-2-yl)-6-fluoro-7-[(3S)-3-hydroxypyrrolidin-1-yl]-4-oxo-1,4-dihydro-1,8-naphthyridine-3-carboxylic acid were reacted with 21.4 mg (122 µmol) of (1S)-1-cyclopropyl-2,2,2-trifluoroethanamine hydrochloride in the presence of 50.5 mg (133 µmol) of HATU and 77 µl (440 µmol) of DIPEA in 1.0 ml of DMF. The crude product was purified by preparative HPLC (column: acetonitrile/water/0.1% of formic acid). This gave 45.0 mg (77% of theory, 100% pure) of the title compound.

LC-MS (Method 3): $R_t$=1.97 min; MS (ESIpos): m/z=528 $[M+H]^+$ $^1$H-NMR (400 MHz, DMSO-d6) δ[ppm]: −0.149 (1.00), 0.008 (9.61), 0.147 (1.11), 0.339 (2.15), 0.537 (2.19), 1.200 (2.37), 1.220 (2.40), 1.894 (1.33), 2.073 (6.17), 2.328 (2.12), 2.523 (6.89), 2.670 (2.26), 2.710 (1.15), 4.295 (1.69), 4.394 (2.30), 4.412 (2.37), 4.994 (3.62), 7.994 (6.31), 8.026 (6.39), 8.318 (2.08), 8.339 (3.55), 8.356 (1.79), 8.611 (6.67), 8.828 (16.00), 10.464 (2.69), 10.481 (2.76).

Example 154

1-(3,5-Difluoropyridin-2-yl)-6-fluoro-7-[(3S)-3-hydroxypyrrolidin-1-yl]-4-oxo-N-(1,1,1-tri-fluoro-2-methylpropan-2-yl)-1,4-dihydro-1,8-naphthyridine-3-carboxamide

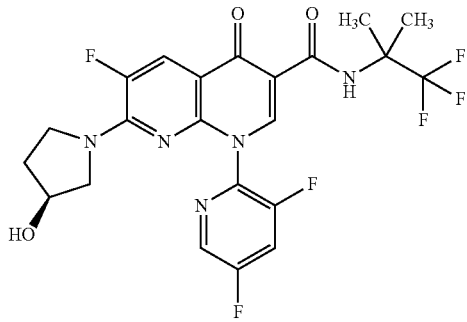 [SMILES: CC(C)(NC(=O)c1cn(-c2ncc(F)cc2F)c2nc(N3CC[C@H](O)C3)c(F)cc2c1=O)C(F)(F)F]

According to GP1, 45.0 mg (111 µmol) of 1-(3,5-difluoropyridin-2-yl)-6-fluoro-7-[(3S)-3-hydroxypyrrolidin-1-yl]-4-oxo-1,4-dihydro-1,8-naphthyridine-3-carboxylic acid were reacted with 15.5 mg (122 µmol) of 1,1,1-trifluoro-2-methylpropan-2-amine in the presence of 50.5 mg (133 µmol) of HATU and 58 µl (330 µmol) of DIPEA in 1.0 ml of DMF. The crude product was purified by preparative HPLC (column: acetonitrile/water/0.1% of formic acid). This gave 42.0 mg (74% of theory, 100% pure) of the title compound.

LC-MS (Method 3): $R_t$=1.94 min; MS (ESIpos): m/z=516 $[M+H]^+$ $^1$H NMR (400 MHz, DMSO-$d_6$) δ ppm: 10.56 (s, 1H), 8.78 (s, 1H), 8.61 (d, 1H), 8.30-8.37 (m, 1H), 8.01 (d, 1H), 4.99 (br d, 1H), 4.20-4.38 (m, 1H), 3.35-4.05 (m, 1H), 3.00-3.28 (m, 1H), 1.72-1.97 (m, 2H), 1.63 (s, 6H).

236

Example 155

7-[(3R,4S)-3,4-Dihydroxypyrrolidin-1-yl]-6-fluoro-4-oxo-N-[(2R)-1,1,1-trifluorobutan-2-yl]-1-(2,4,6-trifluorophenyl)-1,4-dihydro-1,8-naphthyridine-3-carboxamide

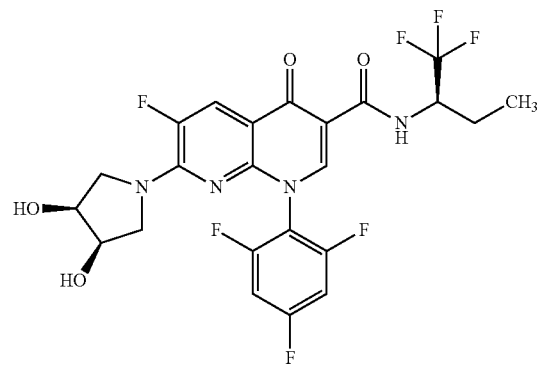 [SMILES: CC[C@@H](NC(=O)c1cn(-c2c(F)cc(F)cc2F)c2nc(N3C[C@@H](O)[C@@H](O)C3)c(F)cc2c1=O)C(F)(F)F]

According to GP1, 30.0 mg (68.3 µmol) of 7-[(3R,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 13.4 mg (81.9 µmol) of (2R)-1,1,1-trifluorobutan-2-amine hydrochloride in the presence of 31.2 mg (81.9 µmol) of HATU and 42 µl (240 µmol) of DIPEA in 1.0 ml of DMF. Aqueous 1N hydrochloric acid and acetonitrile were added to the crude product, which was then purified by preparative HPLC (column: acetonitrile/water/0.1% of formic acid). This gave 29.5 mg (78% of theory, 99% pure) of the title compound.

LC-MS (Method 3): $R_t$=1.84 min; MS (ESIpos): m/z=549 $[M+H]^+$ $^1$H-NMR (400 MHz, DMSO-d6) δ[ppm]: −0.008 (1.76), 0.008 (1.54), 0.949 (7.24), 0.967 (16.00), 0.985 (7.83), 1.603 (1.05), 1.621 (1.44), 1.628 (1.26), 1.638 (1.72), 1.646 (1.56), 1.656 (1.48), 1.663 (1.68), 1.681 (1.24), 1.831 (0.43), 1.850 (1.28), 1.859 (1.50), 1.868 (1.50), 1.878 (1.72), 1.884 (1.52), 1.894 (1.32), 1.903 (1.14), 1.913 (0.97), 2.328 (0.55), 2.367 (0.41), 2.524 (1.78), 2.671 (0.57), 2.711 (0.41), 3.027 (0.59), 3.212 (0.67), 3.589 (0.59), 4.036 (2.41), 4.733 (1.44), 4.753 (1.34), 5.003 (2.13), 7.555 (3.93), 7.577 (7.42), 7.599 (3.91), 7.988 (7.40), 8.019 (7.36), 8.838 (12.76), 10.322 (5.21), 10.346 (4.97).

Example 156

7-[(3S,4S)-3,4-Dihydroxypyrrolidin-1-yl]-6-fluoro-4-oxo-N-[(2R)-1,1,1-trifluorobutan-2-yl]-1-(2,4,6-trifluorophenyl)-1,4-dihydro-1,8-naphthyridine-3-carboxamide

Example 157

6-Bromo-7-[(3R,4R)-3,4-dihydroxypyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (Diastereomer Mixture)

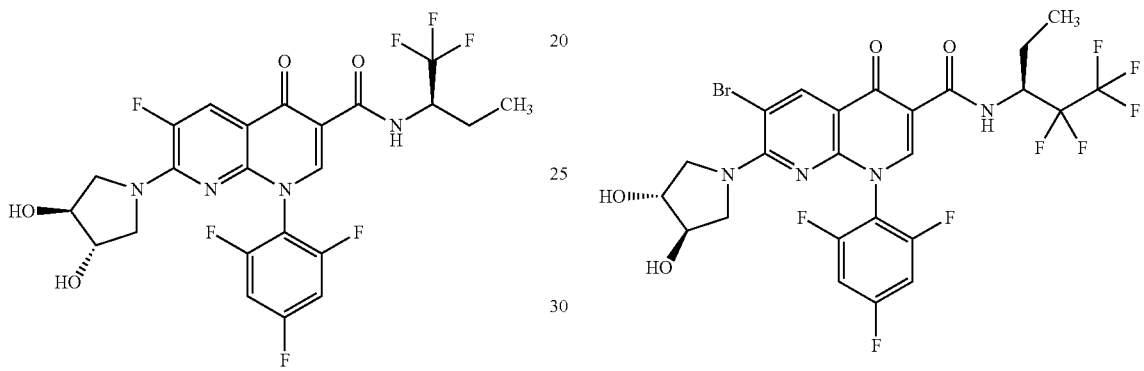

According to GP1, 30.0 mg (68.3 µmol) of 7-[(3S,4S)-3,4-dihydroxypyrrolidin-1-yl]-6-fluoro-4-oxo-1-(2,4,6-trifluorophenyl)-1,4-dihydro-1,8-naphthyridine-3-carboxylic acid were reacted with 13.4 mg (81.9 µmol) of (2R)-1,1,1-trifluorobutan-2-amine hydrochloride in the presence of 31.2 mg (81.9 µmol) of HATU and 42 µl (240 µmol) of DIPEA in 690 µl of DMF. Aqueous 1N hydrochloric acid and acetonitrile were added to the crude product, which was then purified by preparative HPLC (column: acetonitrile/water/0.1% of formic acid). This gave 30.6 mg (81% of theory, 99% pure) of the title compound.

LC-MS (Method 3): $R_t$=1.78 min; MS (ESIpos): m/z=549 [M+H]$^+$ $^1$H-NMR (400 MHz, DMSO-d6) δ[ppm]: −0.149 (0.47), 0.146 (0.47), 0.951 (7.20), 0.969 (16.00), 0.987 (7.86), 1.604 (1.09), 1.622 (1.40), 1.639 (1.71), 1.647 (1.56), 1.664 (1.67), 1.683 (1.25), 1.851 (1.21), 1.860 (1.56), 1.868 (1.48), 1.879 (1.67), 1.896 (1.36), 1.913 (0.93), 2.328 (1.48), 2.366 (1.21), 2.523 (4.71), 2.669 (1.44), 2.710 (1.13), 3.070 (0.86), 3.698 (0.86), 3.906 (1.75), 4.735 (1.52), 5.203 (3.70), 7.559 (3.04), 7.579 (5.37), 7.599 (2.92), 7.999 (8.02), 8.031 (7.82), 8.840 (14.75), 10.329 (5.14), 10.353 (4.87).

At RT, 160 mg (896 µmol) of 1-bromopyrrolidine-2,5-dione (NBS) and 10.0 mg (60.9 µmol) of 2,2'-(E)-diazene-1,2-diylbis(2-methylpropanenitrile) (AIBN) were added to a solution of 242 mg (417 µmol) of 7-[(3R,4R)-3,4-dihydroxypyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide in 5.0 ml of acetonitrile. The mixture was stirred at 60° C. for 1 h. The reaction mixture was cooled, concentrated to half of its volume (under reduced pressure) and purified by preparative HPLC (column: acetonitrile/water/0.1% of formic acid). This gave 103 mg (37% of theory, 100% pure) of the title compound.

LC-MS (Method 3): $R_t$=2.08 min; MS (ESIpos): m/z=659 [M+H]$^+$ $^1$H-NMR (400 MHz, DMSO-d6) δ[ppm]: −0.149 (0.81), −0.008 (6.76), 0.008 (6.78), 0.146 (0.81), 0.943 (7.54), 0.961 (16.00), 0.979 (8.14), 1.620 (1.01), 1.656 (1.75), 1.664 (1.68), 1.682 (1.66), 1.699 (1.15), 1.920 (1.87), 2.111 (0.55), 2.328 (1.01), 2.367 (0.85), 2.524 (3.23), 2.671 (1.01), 2.711 (0.76), 3.733 (1.22), 3.929 (8.99), 4.826 (1.18), 4.851 (1.54), 4.877 (1.54), 4.901 (1.13), 5.188 (2.81), 7.567 (3.67), 7.588 (6.46), 7.608 (3.46), 8.473 (13.99), 8.881 (15.40), 10.242 (5.19), 10.266 (5.10).

Example 158

6-Bromo-7-[(3R,4R)-3,4-dihydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

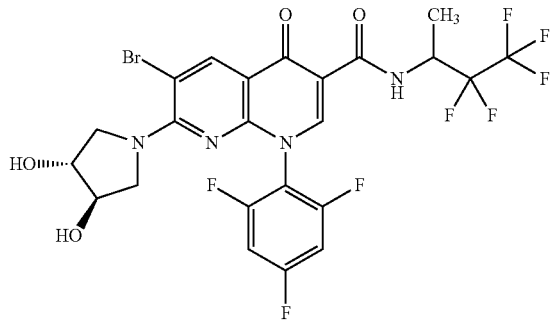 [SMILES: CC(NC(=O)c1cn(-c2c(F)cc(F)cc2F)c2nc(N3C[C@@H](O)[C@H](O)C3)c(Br)cc2c1=O)C(F)(F)C(F)(F)F]

At RT, 161 mg (907 µmol) of 1-bromopyrrolidine-2,5-dione (NBS) and 10.0 mg (60.9 µmol) of AIBN were added to a solution of 239 mg (422 µmol) of 7-[(3R,4R)-3,4-dihydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide in 7.1 ml of acetonitrile. The mixture was stirred at 60° C. for 1 h. The reaction mixture was cooled, concentrated to half of its volume (under reduced pressure) and purified by preparative HPLC (column: acetonitrile/water/0.1% of formic acid). This gave 175 mg (64% of theory, 100% pure) of the title compound.

LC-MS (Method 3): $R_t$=1.98 min; MS (ESIpos): m/z=645 [M+H]$^+$ $^1$H-NMR (400 MHz, DMSO-d6) δ[ppm]: −0.149 (0.50), −0.008 (4.75), 0.146 (0.50), 1.386 (15.73), 1.404 (16.00), 2.074 (4.75), 2.329 (0.69), 2.367 (0.52), 2.671 (0.69), 2.711 (0.53), 3.421 (1.36), 3.734 (1.34), 3.930 (9.47), 4.966 (0.78), 4.986 (1.47), 5.008 (1.78), 5.028 (1.79), 5.052 (1.47), 5.073 (0.82), 5.185 (9.07), 7.565 (3.88), 7.586 (6.91), 7.607 (3.78), 8.453 (1.24), 8.462 (11.09), 8.466 (10.96), 8.876 (15.27), 9.513 (0.44), 9.518 (0.44), 10.318 (5.44), 10.342 (5.29).

Example 159

6-Bromo-7-[(3R,4R)-3,4-dihydroxypyrrolidin-1-yl]-4-oxo-N-(1,1,1-trifluoro-2-methylpropan-2-yl)-1-(2,4,6-trifluorophenyl)-1,4-dihydro-1,8-naphthyridine-3-carboxamide

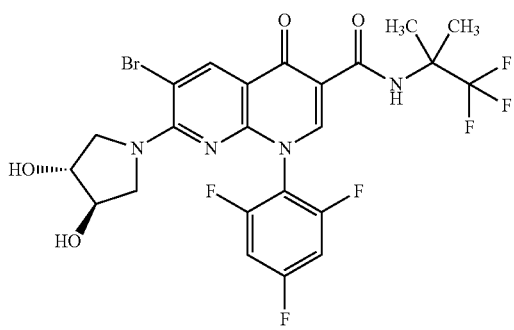 [SMILES: CC(C)(NC(=O)c1cn(-c2c(F)cc(F)cc2F)c2nc(N3C[C@@H](O)[C@H](O)C3)c(Br)cc2c1=O)C(F)(F)F]

At RT, 196 mg (1.10 mmol) of 1-bromopyrrolidine-2,5-dione (NBS) and 10.0 mg (60.9 µmol) of AIBN were added to a solution of 272 mg (513 µmol) of 7-[(3R,4R)-3,4-dihydroxypyrrolidin-1-yl]-4-oxo-N-(1,1,1-trifluoro-2-methylpropan-2-yl)-1-(2,4,6-trifluorophenyl)-1,4-dihydro-1,8-naphthyridine-3-carboxamide in 8.0 ml of acetonitrile. The mixture was stirred at 60° C. for 1 h. The reaction mixture was cooled, concentrated to half of its volume (under reduced pressure) and purified by preparative HPLC (column: acetonitrile/water/0.1% of formic acid). This gave 128 mg (41% of theory, 100% pure) of the title compound.

LC-MS (Method 3): $R_t$=1.95 min; MS (ESIpos): m/z=609 [M+H]$^+$ $^1$H-NMR (400 MHz, DMSO-d6) δ[ppm]: −0.008 (2.95), 0.008 (2.81), 1.632 (16.00), 2.523 (1.40), 3.928 (1.71), 5.176 (2.24), 5.184 (2.24), 7.567 (0.69), 7.587 (1.17), 7.607 (0.66), 8.463 (0.44), 8.473 (4.19), 8.807 (3.19), 10.425 (2.53).

Example 160

6-Bromo-N-[(1S)-1-cyclopropyl-2,2,2-trifluoroethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide

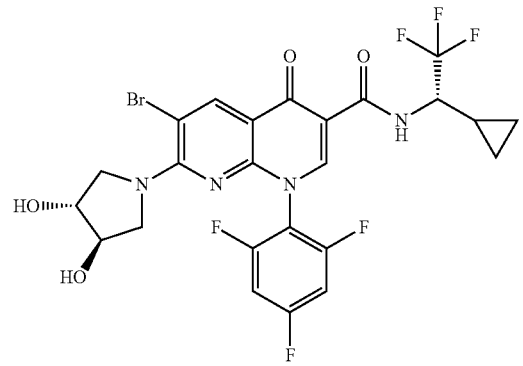 [SMILES: O=C(N[C@@H](C1CC1)C(F)(F)F)c1cn(-c2c(F)cc(F)cc2F)c2nc(N3C[C@@H](O)[C@H](O)C3)c(Br)cc2c1=O]

At RT, 39 mg (219 µmol) of 1-bromopyrrolidine-2,5-dione (NBS) and 3.00 mg (18.4 µmol) of AIBN were added to a solution of 100 mg (184 µmol) of N-[(1S)-1-cyclopropyl-2,2,2-trifluoroethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide in 6.7 ml of acetonitrile. The mixture was stirred at 60° C. for 4 h, a further 15 mg (84.3 µmol) of NBS were then added and the solution was stirred at 60° C. overnight. The reaction mixture was cooled, concentrated to half of its volume (under reduced pressure) and purified by preparative HPLC (column: acetonitrile/water/0.1% of formic acid). This gave 90.0 mg (79% of theory, 100% pure) of the title compound.

LC-MS (Method 3): $R_t$=1.02 min; MS (ESIpos): m/z=621 [M+H]$^+$ $^1$H-NMR (400 MHz, DMSO-d6) δ[ppm]: 0.342 (4.23), 0.556 (5.62), 0.660 (4.02), 1.219 (3.63), 3.424 (2.52), 3.736 (2.56), 3.933 (12.28), 4.382 (3.45), 5.188 (16.00), 7.587 (8.46), 8.473 (9.13), 8.863 (9.13), 10.338 (4.81), 10.361 (5.05).

Example 161

6-Fluoro-7-(2-oxa-6-azaspiro[3.3]hept-6-yl)-4-oxo-N-[1,1,1,2,2-pentafluoropentan-3-yl]-1-(2,4,6-trifluorophenyl)-1,4-dihydro-1,8-naphthyridine-3-carboxamide (Racemate)

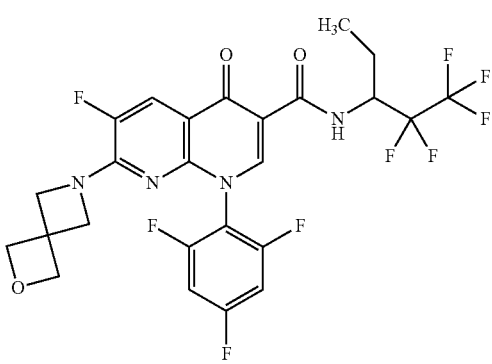 [SMILES: CCC(NC(=O)c1cn(-c2c(F)cc(F)cc2F)c2nc(N3CC4(COC4)C3)c(F)cc2c1=O)C(F)(F)C(F)(F)F]

7-Chloro-6-fluoro-4-oxo-N-[1,1,1,2,2-pentafluoropentan-3-yl]-1-(2,4,6-trifluorophenyl)-1,4-di-hydro-1,8-naphthyridine-3-carboxamide (racemate, 282 mg, 531 µmol) was initially charged in 3.6 ml of DMF, ethanedioic acid 2-oxa-6-azaspiro[3.3]heptane (1:1) (141 mg, 743 µmol) and N,N-diisopropylethylamine (560 µl, 3.2 mmol) were added and the mixture was stirred at room temperature for 2 h. More ethanedioic acid 2-oxa-6-azaspiro[3.3]heptane (1:1) (30.1 mg, 159 µmol) and N,N-diisopropylethylamine (93 µl, 530 µmol) were added, and the mixture was stirred at room temperature overnight. Water was added to the mixture and the precipitated solid was filtered off and then purified on a silica gel column (mobile phase: cyclohexane/ethyl acetate=2/1). This gave 199 mg of the target compound (62% of theory, purity 98%).

LC-MS (Method 3): $R_t$=2.35 min; MS (ESIpos): m/z=595 [M+H]$^+$ $^1$H-NMR (400 MHz, DMSO-d6) δ[ppm]: −0.149 (0.56), 0.146 (0.63), 0.935 (3.05), 0.953 (6.63), 0.971 (3.23), 1.235 (0.77), 1.630 (0.56), 1.647 (0.70), 1.656 (0.65), 1.673 (0.63), 1.692 (0.45), 1.915 (0.59), 2.085 (0.97), 2.327 (0.90), 2.366 (1.04), 2.670 (0.99), 2.710 (1.06), 4.209 (0.47), 4.656 (16.00), 4.843 (0.56), 4.870 (0.50), 7.542 (1.67), 7.565 (3.27), 7.587 (1.69), 7.991 (2.57), 8.020 (2.57), 8.844 (4.63), 10.339 (1.90), 10.364 (1.85).

Example 162

6-Fluoro-7-(2-oxa-6-azaspiro[3.3]hept-6-yl)-4-oxo-N-[3,3,4,4,4-pentafluorobutan-2-yl]-1-(2,4,6-trifluorophenyl)-1,4-dihydro-1,8-naphthyridine-3-carboxamide (Racemate)

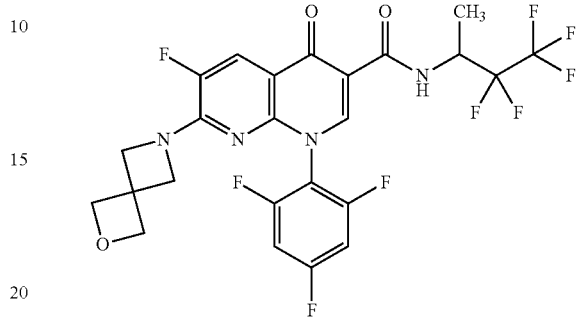

7-Chloro-6-fluoro-4-oxo-N-[3,3,4,4,4-pentafluorobutan-2-yl]-1-(2,4,6-trifluorophenyl)-1,4-di-hydro-1,8-naphthyridine-3-carboxamide (racemate, 250 mg, 482 µmol) was initially charged in 3.3 ml of DMF, ethanedioic acid 2-oxa-6-azaspiro[3.3]heptane (1:1) (128 mg, 675 µmol) and N,N-diisopropylethylamine (500 µl, 2.9 mmol) were added and the mixture was stirred at room temperature for 2 h. More ethanedioic acid 2-oxa-6-azaspiro[3.3]heptane (1:1) (27.4 mg, 145 µmol) and N,N-diisopropylethylamine (84 µl, 480 µmol) were added, and the mixture was stirred at room temperature overnight. Water was added to the reaction mixture and the precipitated solid was filtered off. The solid was purified on a silica gel column (mobile phase: cyclohexane/ethyl acetate=2/1). This gave 165 mg of the target compound (58% of theory, purity 99%).

LC-MS (Method 3): $R_t$=2.26 min; MS (ESIpos): m/z=581 [M+H]$^+$ $^1$H-NMR (400 MHz, DMSO-d6) δ[ppm]: −0.008 (2.46), 0.008 (2.00), 1.379 (4.40), 1.397 (4.88), 2.524 (1.24), 2.670 (0.42), 4.654 (16.00), 5.001 (0.45), 5.022 (0.45), 7.541 (1.69), 7.563 (3.22), 7.586 (1.72), 7.982 (2.85), 8.011 (2.85), 8.838 (4.94), 10.417 (1.91), 10.441 (1.84).

Example 163

6-Fluoro-7-(2-oxa-6-azaspiro[3.3]hept-6-yl)-4-oxo-N-(3,3,4,4,4-pentafluoro-2-methylbutan-2-yl)-1-(2,4,6-trifluorophenyl)-1,4-dihydro-1,8-naphthyridine-3-carboxamide (Racemate)

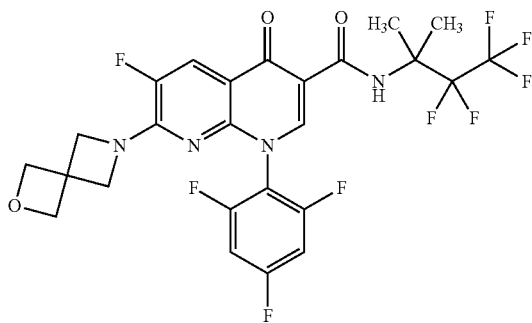 [SMILES: CC(C)(NC(=O)c1cn(-c2c(F)cc(F)cc2F)c2nc(N3CC4(COC4)C3)c(F)cc2c1=O)C(F)(F)C(F)(F)F]

7-Chloro-6-fluoro-4-oxo-N-(3,3,4,4,4-pentafluoro-2-methylbutan-2-yl)-1-(2,4,6-trifluoro-phenyl)-1,4-dihydro-1,8-naphthyridine-3-carboxamide (300 mg, 564 µmol) was initially charged in 5.4 ml of DMF, ethanedioic acid 2-oxa-6-azaspiro[3.3]heptane (1:2) (97.6 mg, 338 µmol) and N,N-diisopropylethylamine (490 µl, 2.8 mmol) were added and the mixture was then stirred at room temperature for 3 h. The reaction solution was added to water, resulting in the formation of a fine precipitate. The aqueous suspension was then acidified with 1 N hydrochloric acid. The precipitate was washed thoroughly with water and dried under high vacuum. This gave 340 mg of the target compound (94% of theory, purity 93%).

LC-MS (Method 3): $R_t$=2.32 min; MS (ESIpos): m/z=595 [M+H]$^+$ $^1$H NMR (400 MHz, DMSO-d6) δ[ppm]: −0.008 (2.38), 0.008 (2.11), 1.674 (15.31), 2.328 (0.46), 2.524 (1.28), 2.670 (0.46), 4.653 (16.00), 7.541 (1.72), 7.563 (3.03), 7.585 (1.72), 8.001 (3.03), 8.030 (3.00), 8.774 (5.32), 10.529 (3.97).

Example 164

7-[(3R,4R)-3,4-Dihydroxypyrrolidin-1-yl]-6-fluoro-4-oxo-N-(3,3,4,4,4-pentafluoro-2-methyl-butan-2-yl)-1-(2,4,6-trifluorophenyl)-1,4-dihydro-1,8-naphthyridine-3-carboxamide

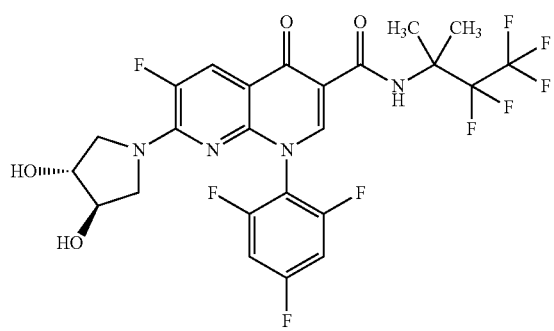 [SMILES: CC(C)(NC(=O)c1cn(-c2c(F)cc(F)cc2F)c2nc(N3C[C@@H](O)[C@H](O)C3)c(F)cc2c1=O)C(F)(F)C(F)(F)F]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (30.0 mg, 68.3 µmol) was initially charged in 0.47 ml of DMF. HATU (31.2 mg, 81.9 µmol), N,N-diisopropylethylamine (59 µl, 340 µmol) and 3,3,4,4,4-pentafluoro-2-methylbutan-2-amine hydrochloride (1:1) (19.0 mg, 88.8 µmol) were added to the solution and the mixture was stirred at room temperature overnight. Water was then added and the mixture was adjusted to about pH neutral with 1 M hydrochloric acid. The precipitated solid was filtered off, taken up in acetonitrile/water/TFA and purified by preparative HPLC (RP18 column, mobile phase: acetonitrile/water gradient with addition of 0.1% TFA). The product fractions were concentrated under reduced pressure and the residue was taken up in dichloromethane and washed twice with saturated aqueous sodium bicarbonate solution. The combined aqueous phases were re-extracted with dichloromethane. The combined organic phases were dried over sodium sulfate, filtered and concentrated under reduced pressure. This gave 31 mg of the target compound (75% of theory, purity 99%).

LC-MS (Method 1): $R_t$=1.04 min; MS (ESIpos): m/z=599 [M+H]$^+$ $^1$H NMR (400 MHz, DMSO-d6) δ[ppm]: 1.680 (16.00), 3.903 (0.72), 4.012 (0.50), 5.198 (1.65), 7.555 (1.28), 7.576 (2.37), 7.597 (1.30), 8.014 (2.65), 8.045 (2.62), 8.778 (4.80), 10.565 (4.02).

Example 165

7-[(3R,4R)-3,4-Dihydroxypyrrolidin-1-yl]-6-fluoro-4-oxo-1-(2,4,6-trifluorophenyl)-N-(2,3,3-trimethylbutan-2-yl)-1,4-dihydro-1,8-naphthyridine-3-carboxamide

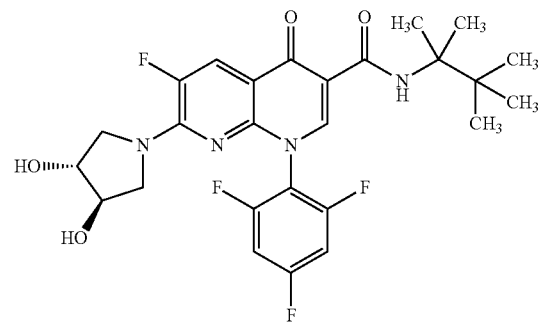 [SMILES: CC(C)(C)C(C)(C)NC(=O)c1cn(-c2c(F)cc(F)cc2F)c2nc(N3C[C@@H](O)[C@H](O)C3)c(F)cc2c1=O]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (60.0 mg, 137 µmol) was initially charged in 0.93 ml of DMF. HATU (62.3 mg, 164 µmol), N,N-diisopropylethylamine (71 µl, 410 µmol) and 2,3,3-trimethylbutan-2-amine (20.5 mg, 178 µmol) were added to the solution and the mixture was stirred at room temperature for 2.5 h. Acetonitrile/water/TFA was then added and the reaction mixture was purified by preparative HPLC (RP18 column, mobile phase: acetonitrile/water gradient with addition of 0.1% TFA). The product fractions were concentrated under reduced pressure and the residue was taken up in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 34 mg of the target compound (47% of theory, purity 95%).

LC-MS (Method 1): $R_t$=1.04 min; MS (ESIpos): m/z=537 [M+H]$^+$ $^1$H NMR (400 MHz, DMSO-d6) δ[ppm]: −0.008 (0.57), 1.039 (16.00), 1.411 (11.99), 7.551 (0.52), 7.573 (0.93), 7.594 (0.52), 8.034 (1.09), 8.066 (1.08), 8.678 (1.90), 10.097 (1.36).

Example 166

7-[3,3-Bis(hydroxymethyl)azetidin-1-yl]-6-fluoro-4-oxo-N-(3,3,4,4,4-pentafluoro-2-methyl-butan-2-yl)-1-(2,4,6-trifluorophenyl)-1,4-dihydro-1,8-naphthyridine-3-carboxamide

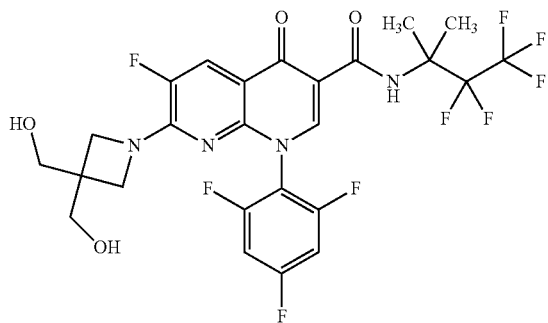 [SMILES: CC(C)(NC(=O)c1cn(-c2c(F)cc(F)cc2F)c2nc(N3CC(CO)(CO)C3)c(F)cc2c1=O)C(F)(F)C(F)(F)F]

6-Fluoro-7-(2-oxa-6-azaspiro[3.3]hept-6-yl)-4-oxo-N-(3,3,4,4,4-pentafluoro-2-methylbutan-2-yl)-1-(2,4,6-trifluorophenyl)-1,4-dihydro-1,8-naphthyridine-3-carboxamide (100 mg, 93% pure, 156 μmol) was initially charged in 1 ml of acetonitrile, 1 ml of water and 1 ml of trifluoroacetic acid were added and the mixture was stirred at room temperature for 2 days. The mixture was purified by preparative HPLC (RP18 column, mobile phase: acetonitrile/water gradient with addition of 0.1% TFA). The product fractions were concentrated under reduced pressure and the residue was dissolved in dichloromethane/a little methanol and washed twice with saturated aqueous sodium bicarbonate solution. The combined aqueous phases were reextracted twice with dichloromethane. The combined organic phases were dried over sodium sulfate, filtered and concentrated under reduced pressure. This gave 66 mg of the target compound (68% of theory, purity 98%).

LC-MS (Method 3): $R_t$=1.98 min; MS (ESIpos): m/z=613 [M+H]$^+$ $^1$H NMR (400 MHz, DMSO-d6) δ[ppm]: 1.676 (16.00), 3.471 (7.03), 3.484 (7.17), 4.127 (0.45), 4.834 (2.20), 4.847 (5.01), 4.861 (2.14), 7.532 (1.56), 7.553 (2.96), 7.575 (1.60), 7.973 (2.48), 8.001 (2.43), 8.754 (4.63), 10.561 (3.80).

Example 167

7-[(3R,4R)-3,4-Dihydroxypyrrolidin-1-yl]-6-fluoro-4-oxo-N-[(1S)-1-phenylethyl]-1-(2,4,6-tri-fluorophenyl)-1,4-dihydro-1,8-naphthyridine-3-carboxamide

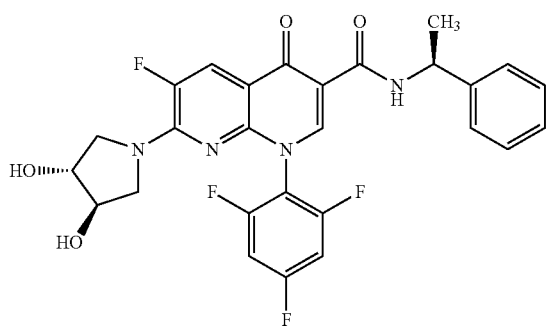 [SMILES: C[C@H](NC(=O)c1cn(-c2c(F)cc(F)cc2F)c2nc(N3C[C@@H](O)[C@H](O)C3)c(F)cc2c1=O)c1ccccc1]

7-[(3R,4R)-3,4-Dihydroxypyrrolidin-1-yl]-6-fluoro-4-oxo-1-(2,4,6-trifluorophenyl)-1,4-dihydro-1,8-naphthyridine-3-carboxylic acid (150 mg, 341 μmol) was initially charged in 3.0 ml of DMF. HATU (156 mg, 410 μmol), N,N-diisopropylethylamine (300 μl, 1.7 mmol) and (1S)-1-phenylethanamine (53 μl, 410 μmol) were added to the solution and the mixture was stirred at room temperature for 2 d. Acetonitrile/water/TFA was added and the reaction solution was purified by preparative HPLC (RP18 column, mobile phase: acetonitrile/water gradient with addition of 0.1% TFA). The product fractions were combined and freed from acetonitrile and the residue was made basic with saturated aqueous sodium bicarbonate solution and extracted three times with dichloromethane. The combined organic phases were washed with saturated aqueous sodium bicarbonate solution. The combined organic phases were dried over sodium sulfate, filtered and concentrated under reduced pressure. This gave 159 mg of the target compound (84% of theory, purity 98%).

LC-MS (Method 3): $R_t$=1.74 min; MS (ESIpos): m/z=543 [M+H]$^+$ $^1$H NMR (400 MHz, DMSO-d6) δ[ppm]: –0.008 (1.38), 0.008 (1.36), 1.486 (14.29), 1.503 (14.41), 2.328 (0.50), 2.671 (0.55), 3.058 (0.57), 3.675 (0.57), 3.908 (1.33), 5.126 (0.59), 5.143 (2.31), 5.162 (3.54), 5.180 (4.40), 5.195 (4.16), 7.244 (1.38), 7.261 (3.28), 7.273 (1.45), 7.278 (2.64), 7.282 (1.66), 7.341 (3.02), 7.361 (8.77), 7.379 (16.00), 7.384 (11.89), 7.401 (3.16), 7.405 (1.95), 7.545 (3.57), 7.567 (6.49), 7.588 (3.54), 7.992 (6.78), 8.023 (6.63), 8.726 (12.10), 10.325 (4.28), 10.345 (4.11).

Example 168

7-[3,3-Bis(hydroxymethyl)azetidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Racemate)

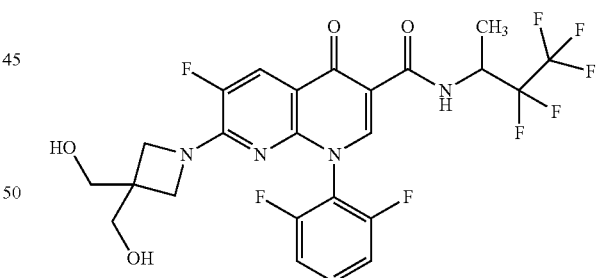

6-Fluoro-7-(2-oxa-6-azaspiro[3.3]hept-6-yl)-4-oxo-N-[3,3,4,4,4-pentafluorobutan-2-yl]-1-(2,4,6-trifluorophenyl)-1,4-dihydro-1,8-naphthyridine-3-carboxamide (racemate, 165 mg, 284 μmol) was initially charged in 1.8 ml of trifluoroacetic acid, 1.8 ml of water and 1.8 ml of acetonitrile were added and the mixture was stirred at room temperature for 2 days. The reaction solution was purified by preparative HPLC (RP18 column, mobile phase: acetonitrile/water gradient with addition of 0.1% TFA). The product fractions were concentrated under reduced pressure and the residue was taken up in dichloromethane and washed twice with saturated aqueous sodium bicarbonate solution. The combined aqueous phases were re-extracted with dichloromethane. The combined organic phases were dried over sodium sulfate, filtered and concentrated under reduced pressure. This gave in 140 mg of the target compound (82% of theory, purity 99%).

LC-MS (Method 3): $R_t$=1.91 min; MS (ESIpos): m/z=599 [M+H]$^+$ $^1$H NMR (400 MHz, DMSO-d6) δ[ppm]: −0.149 (0.50), −0.008 (4.12), 0.008 (3.62), 0.146 (0.50), 1.177 (0.47), 1.234 (1.73), 1.381 (9.75), 1.398 (9.79), 2.328 (0.67), 2.367 (0.63), 2.524 (2.11), 2.670 (0.78), 2.711 (0.73), 3.472 (15.61), 3.485 (16.00), 4.124 (0.93), 4.835 (4.98), 4.848 (11.73), 4.862 (4.96), 4.958 (0.48), 4.981 (0.84), 5.004 (0.99), 5.023 (1.01), 5.047 (0.86), 5.067 (0.48), 5.754 (2.05), 7.532 (3.90), 7.554 (7.40), 7.576 (3.99), 7.954 (6.69), 7.983 (6.62), 8.819 (12.01), 10.450 (4.38), 10.474 (4.27).

Example 169

7-[3,3-Bis(hydroxymethyl)azetidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Enantiomer A)

69 mg of 7-[3,3-bis(hydroxymethyl)azetidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (racemate) were separated into the enantiomers by chiral HPLC (preparative HPLC: column Daicel® Chiralpak AD-H, 5 μm, 250×20 mm; mobile phase: 70% n-heptane/30% isopropanol; flow rate: 19 ml/min; temperature: 25° C., detection: 240 nm).

Enantiomer A: 66 mg (>99% ee)

$R_t$=4.45 min [HPLC: column Daicel® Chiralcel OD-H, 1 ml/min; 5 μm, 250×4.6 mm; mobile phase: 70% n-heptane/30% isopropanol; detection: 240 nm].

Example 170

7-[3,3-Bis(hydroxymethyl)azetidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Enantiomer B)

69 mg of 7-[3,3-bis(hydroxymethyl)azetidin-1-yl]-6-fluoro-4-oxo-N-[3,3,4,4,4-pentafluorobutan-2-yl]-1-(2,4,6-trifluorophenyl)-1,4-dihydro-1,8-naphthyridine-3-carboxamide (racemate) were separated into the enantiomers by chiral HPLC (preparative HPLC: column Daicel® Chiralpak AD-H, 5 μm, 250×20 mm; mobile phase: 70% n-heptane/30% isopropanol; flow rate: 19 ml/min; temperature: 25° C., detection: 240 nm).

Enantiomer B: 68 mg (>99% ee)

$R_t$=5.99 min [HPLC: column Daicel® Chiralcel OD-H, 1 ml/min; 5 μm, 250×4.6 mm; mobile phase: 70% n-heptane/30% isopropanol; detection: 240 nm].

Example 171

7-[3,3-Bis(hydroxymethyl)azetidin-1-yl]-6-fluoro-4-oxo-N-[1,1,1,2,2-pentafluoropentan-3-yl]-1-(2,4,6-trifluorophenyl)-1,4-dihydro-1,8-naphthyridine-3-carboxamide (Racemate)

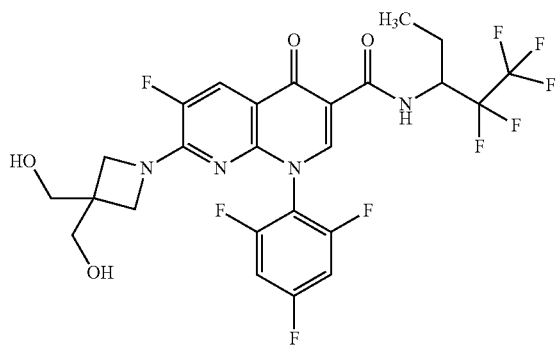 [SMILES: CCC(NC(=O)c1cn(-c2c(F)cc(F)cc2F)c2nc(N3CC(CO)(CO)C3)c(F)cc2c1=O)C(F)(F)C(F)(F)F]

6-Fluoro-7-(2-oxa-6-azaspiro[3.3]hept-6-yl)-4-oxo-N-[1,1,1,2,2-pentafluoropentan-3-yl]-1-(2,4,6-trifluorophenyl)-1,4-dihydro-1,8-naphthyridine-3-carboxamide (racemate, 199 mg, 335 μmol) was initially charged in 2.1 ml of trifluoroacetic acid, 2.1 ml of water and 2.1 ml of acetonitrile were added and the mixture was stirred at room temperature for 2 days. The reaction solution was purified by preparative HPLC (RP18 column, mobile phase: acetonitrile/water gradient with addition of 0.1% TFA). The product fractions were concentrated under reduced pressure and the residue was taken up in dichloromethane and washed twice with saturated aqueous sodium bicarbonate solution. The combined aqueous phases were re-extracted with dichloromethane. The combined organic phases were dried over sulphate, filtered and concentrated by evaporation. This gave 168 mg of the target compound (81% of theory, purity 99%).

LC-MS (Method 3): $R_t$=1.98 min; MS (ESIpos): m/z=613 [M+H]$^+$ $^1$H NMR (400 MHz, DMSO-d6) δ[ppm]: 0.008 (2.65), 0.939 (6.29), 0.957 (14.00), 0.975 (6.81), 1.157 (2.65), 1.175 (5.29), 1.193 (2.72), 1.235 (0.88), 1.615 (0.76), 1.632 (1.09), 1.640 (0.98), 1.649 (1.31), 1.658 (1.20), 1.667 (1.11), 1.675 (1.24), 1.694 (0.90), 1.917 (1.16), 1.989 (9.69), 2.329 (0.43), 2.670 (0.50), 2.711 (0.40), 3.473 (15.68), 3.486 (16.00), 4.003 (0.99), 4.021 (2.61), 4.039 (2.63), 4.057 (1.15), 4.133 (0.97), 4.838 (5.71), 4.851 (12.52), 4.864 (5.69), 4.897 (0.77), 7.533 (3.62), 7.555 (6.94), 7.577 (3.68), 7.585 (1.23), 7.964 (5.89), 7.993 (5.83), 8.826 (10.47), 10.373 (4.13), 10.397 (3.99).

Example 172

7-[3,3-Bis(hydroxymethyl)azetidin-1-yl]-6-fluoro-4-oxo-N-[1,1,1,2,2-pentafluoropentan-3-yl]-1-(2,4,6-trifluorophenyl)-1,4-dihydro-1,8-naphthyridine-3-carboxamide (Enantiomer A)

209 mg of 7-[3,3-bis(hydroxymethyl)azetidin-1-yl]-6-fluoro-4-oxo-N-[1,1,1,2,2-pentafluoro-pentan-3-yl]-1-(2,4,6-trifluorophenyl)-1,4-dihydro-1,8-naphthyridine-3-carboxamide (racemate) were separated into the enantiomers by chiral HPLC (preparative HPLC: column Daicel® Chiralpak AD-H, 5 µm, 250×20 mm; mobile phase: 90% n-heptane/10% ethanol; flow rate: 19 ml/min; temperature: 25° C., detection: 240 nm).

Enantiomer A: 84 mg (98.5% ee)

$R_t$=14.72 min [HPLC: column Daicel® Chiralpak AD-H, 1 ml/min; 5 µm, 250×4.6 mm; mobile phase: 90% n-heptane/10% ethanol; detection: 240 nm].

Example 173

7-[3,3-Bis(hydroxymethyl)azetidin-1-yl]-6-fluoro-4-oxo-N-[1,1,1,2,2-pentafluoropentan-3-yl]-1-(2,4,6-trifluorophenyl)-1,4-dihydro-1,8-naphthyridine-3-carboxamide (Enantiomer B)

209 mg of 7-[3,3-bis(hydroxymethyl)azetidin-1-yl]-6-fluoro-4-oxo-N-[1,1,1,2,2-pentafluoro-pentan-3-yl]-1-(2,4,6-trifluorophenyl)-1,4-dihydro-1,8-naphthyridine-3-carboxamide (racemate) was separated into the enantiomers by chiral HPLC (preparative HPLC: column Daicel® Chiralpak AD-H, 5 µm, 250×20 mm; mobile phase: 90% n-heptane/10% ethanol; flow rate: 19 ml/min; temperature: 25° C., detection: 240 nm).

Enantiomer B: 75 mg (96.8% ee)

$R_t$=17.24 min [HPLC: column Daicel® Chiralpak AD-H, 1 ml/min; 5 µm, 250×4.6 mm; mobile phase: 90% n-heptane/10% ethanol; detection: 240 nm].

Example 174

6-Fluoro-7-[3-(hydroxymethyl)piperazin-1-yl]-4-oxo-N-[1,1,1,2,2-pentafluoropentan-3-yl]-1-(2,4,6-trifluorophenyl)-1,4-dihydro-1,8-naphthyridine-3-carboxamide (Diastereomer Mixture)

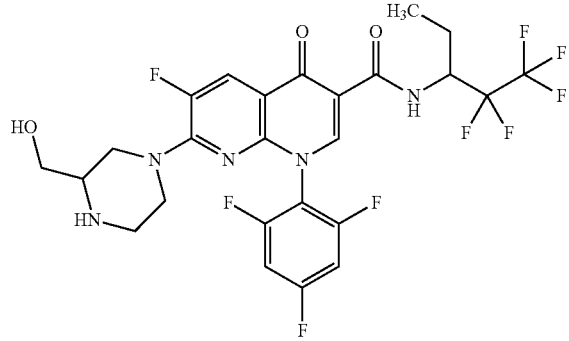 [SMILES: CCC(NC(=O)c1cn(-c2c(F)cc(F)cc2F)c2nc(N3CCNC(CO)C3)c(F)cc2c1=O)C(F)(F)C(F)(F)F]

tert-Butyl 4-[3-fluoro-5-oxo-6-{[1,1,1,2,2-pentafluoropentan-3-yl]carbamoyl}-8-(2,4,6-trifluorophenyl)-5,8-dihydro-1,8-naphthyridin-2-yl]-2-(hydroxymethyl)piperazine-1-carboxylate (diastereomer mixture, 204 mg, 287 µmol) was initially charged in 1.6 ml of dichloromethane, trifluoroacetic acid (780 µl, 10 mmol) was added and the mixture was stirred at room temperature for 1.5 h. The dichloromethane was evaporated and the residue was purified by preparative HPLC (RP18 column, mobile phase: acetonitrile/water gradient with addition of 0.1% TFA). The product fractions were concentrated and the residue was dissolved in dichloromethane/a little methanol and washed twice with saturated aqueous sodium bicarbonate solution. The combined aqueous phases were re-extracted twice with dichloromethane. The combined organic phases were dried over sodium sulfate, filtered and concentrated under reduced pressure. This gave 63 mg of the target compound (48% of theory, purity 96%) as a diastereomer mixture of two diastereomers.

LC-MS (Method 3): $R_t$=1.55 min; MS (ESIpos): m/z=612 [M+H]$^+$ $^1$H NMR (400 MHz, DMSO-d6) δ[ppm]: −0.149 (0.55), −0.008 (4.61), 0.008 (4.48), 0.146 (0.55), 0.943 (7.10), 0.961 (16.00), 0.980 (7.69), 1.142 (0.40), 1.622 (0.93), 1.640 (1.25), 1.647 (1.10), 1.656 (1.48), 1.666 (1.36), 1.675 (1.28), 1.683 (1.48), 1.701 (1.02), 1.924 (1.29), 2.086 (2.96), 2.324 (2.65), 2.368 (0.70), 2.574 (3.33), 2.604 (1.48), 2.637 (2.57), 2.668 (3.19), 2.694 (1.65), 2.711 (0.60), 2.842 (2.77), 2.872 (2.22), 2.971 (1.32), 2.997 (2.27), 3.025 (1.22), 3.145 (1.00), 3.159 (1.89), 3.172 (2.80), 3.186 (3.63), 3.200 (1.94), 3.214 (2.01), 3.228 (3.54), 3.241 (2.90), 3.254 (1.74), 3.268 (1.00), 3.952 (2.22), 3.984 (2.08), 4.040 (2.55), 4.071 (2.43), 4.599 (3.14), 4.612 (6.76), 4.625 (3.03), 4.829 (0.86), 4.856 (1.10), 4.881 (1.12), 4.906 (0.83), 5.755 (1.89), 7.513 (1.39), 7.541 (4.86), 7.564 (4.85), 7.592 (1.36), 8.058 (7.61), 8.092 (7.46), 8.894 (13.63), 10.304 (4.75), 10.329 (4.58).

Example 175

N-[(1S)-1-Cyclopropyl-2,2,2-trifluoroethyl]-7-[(3R,4R)-3,4-dihydroxypyrrolidin-1-yl]-6-fluoro-1-(4-fluoro-2,6-dimethylphenyl)-4-oxo-1,4-dihydro-1,8-naphthyridine-3-carboxamide

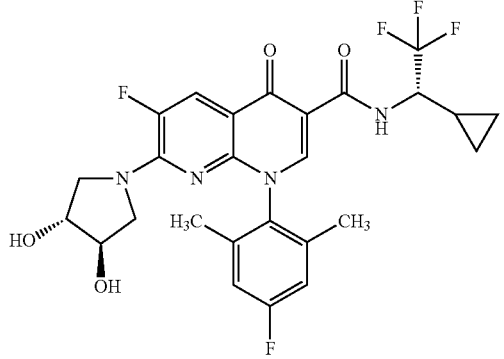 [SMILES: Cc1cc(F)cc(C)c1-n1cc(C(=O)N[C@@H](C2CC2)C(F)(F)F)c(=O)c2cc(F)c(N3C[C@@H](O)[C@H](O)C3)nc21]

7-Chloro-N-[(1S)-1-cyclopropyl-2,2,2-trifluoroethyl]-6-fluoro-1-(4-fluoro-2,6-dimethylphenyl)-4-oxo-1,4-dihydro-1,8-naphthyridine-3-carboxamide (80.0 mg, 165 µmol) was initially charged in 1.6 ml of DMF, (3R,4R)-pyrrolidine-3,4-diol hydrochloride (25.3 mg, 181 µmol) was added followed by N,N-diisopropylethylamine (0.17 ml, 0.99 mmol), and the mixture was stirred at room temperature overnight. Acetonitrile/water/TFA was added to the reaction solution. The precipitate formed was filtered off and dried under high vacuum. This gave 76 mg of the target compound (84% of theory, purity 99%).

LC-MS (Method 3): $R_t$=1.86 min; MS (ESIpos): m/z=553 [M+H]$^+$ $^1$H NMR (400 MHz, DMSO-d6) δ[ppm]: 0.324 (0.76), 0.334 (1.15), 0.347 (1.18), 0.358 (0.93), 0.370 (0.45), 0.503 (0.84), 0.514 (1.21), 0.527 (1.01), 0.537 (0.84), 0.548 (0.87), 0.567 (1.07), 0.578 (1.01), 0.588 (0.93), 0.600 (0.76), 0.612 (0.48), 0.625 (0.56), 0.635 (0.65), 0.646 (1.01), 0.656 (0.98), 0.670 (0.90), 1.174 (0.48), 1.183 (0.70), 1.194 (1.18), 1.203 (0.87), 1.215 (1.12), 1.227 (0.67), 1.235 (0.59), 1.940 (16.00), 1.951 (15.83), 2.328 (0.42), 2.670 (0.45), 3.883 (0.67), 4.342 (0.62), 4.363 (1.04), 4.384 (1.04), 4.404 (0.56), 5.171 (2.64), 7.164 (4.63), 7.188 (4.66), 8.009 (3.34), 8.041 (3.28), 8.429 (7.55), 10.623 (2.41), 10.646 (2.30).

Example 176

N-[(1S)-1-Cyclopropyl-2,2,2-trifluoroethyl]-6-fluoro-7-[2-(hydroxymethyl)-4-methylpiperazin-1-yl]-4-oxo-1-(2,4,6-trifluorophenyl)-1,4-dihydro-1,8-naphthyridine-3-carboxamide (Diastereomer Mixture)

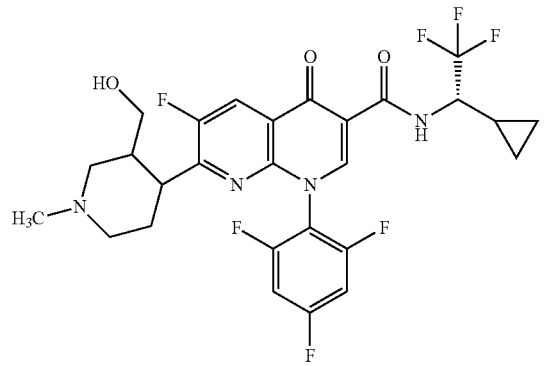 [SMILES: CN1CCC(c2nc3c(cc2F)c(=O)c(C(=O)N[C@@H](C2CC2)C(F)(F)F)cn3-c2c(F)cc(F)cc2F)C(CO)C1]

7-Chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide (100 mg, 203 µmol) was initially charged in 2 ml of DMF, [4-methylpiperazin-2-yl]methanol (30.5 mg, 95% pure, 223 µmol) and N,N-diisopropylethylamine (0.177 ml, 1.01 mmol) were added and the mixture was stirred at room temperature for 3 h. Acetonitrile/water/TFA was added and the reaction solution was purified by preparative HPLC (RP18 column, mobile phase: acetonitrile/water gradient with addition of 0.1% TFA). The product fractions were combined and freed from acetonitrile. The residue was made basic using saturated aqueous sodium bicarbonate solution and extracted three times with dichloromethane. The combined organic phases were washed with saturated aqueous sodium bicarbonate solution. The combined organic phases were dried over sodium sulfate, filtered and concentrated under reduced pressure. The fraction was re-purified by thick-layer chromatography (mobile phase: dichloromethane/methanol=10/1). This gave 48 mg of the target compound (39% of theory, purity 98%) as a diastereomer mixture of two diastereomers.

LC-MS (Method 3): $R_t$=1.38 min; MS (ESIpos): m/z=588 [M+H]$^+$ $^1$H NMR (500 MHz, DMSO-d6) δ[ppm]: −0.007 (1.35), 0.006 (0.98), 0.335 (0.88), 0.340 (0.92), 0.345 (0.84), 0.350 (0.72), 0.519 (0.80), 0.529 (1.19), 0.539 (1.05), 0.547 (0.88), 0.555 (0.82), 0.571 (0.99), 0.579 (0.93), 0.588 (0.79), 0.597 (0.67), 0.633 (0.54), 0.642 (0.71), 0.650 (0.98), 0.654 (0.82), 0.659 (0.97), 0.662 (0.95), 0.670 (0.94), 0.676 (0.47), 0.679 (0.47), 1.188 (0.47), 1.195 (0.69), 1.204 (1.16), 1.211 (0.85), 1.220 (1.14), 1.230 (0.71), 1.236 (0.54), 1.837 (0.54), 1.844 (0.67), 1.861 (1.09), 1.867 (1.10), 1.884 (0.69), 1.891 (0.56), 1.989 (0.93), 1.996 (1.01), 2.012 (1.03), 2.019 (0.90), 2.113 (16.00), 2.516 (1.06), 2.520 (0.93), 2.524 (0.85), 2.697 (1.08), 2.719 (1.00), 2.830 (1.56), 2.853 (1.45), 3.028 (0.41), 3.051 (0.73), 3.076 (0.41), 3.594 (1.65), 3.606 (2.39), 3.618 (1.66), 3.784 (0.85), 3.811 (0.80), 4.261 (0.89), 4.359 (0.58), 4.376 (0.98), 4.393 (0.95), 4.409 (0.52), 4.700 (0.98), 4.710 (1.87), 4.720 (0.93), 7.518 (0.66), 7.541 (1.37), 7.552 (0.92), 7.564 (1.39), 7.586 (0.64), 8.032 (4.28), 8.060 (4.10), 8.869 (7.42), 10.394 (2.60), 10.413 (2.45).

Example 177

N-[(1R)-1-Cyclopropyl-2,2,2-trifluoroethyl]-6-fluoro-1-(4-fluoro-2,6-dimethylphenyl)-7-[(4S)-4-hydroxy-2-oxopyrrolidin-1-yl]-4-oxo-1,4-dihydro-1,8-naphthyridine-3-carboxamide

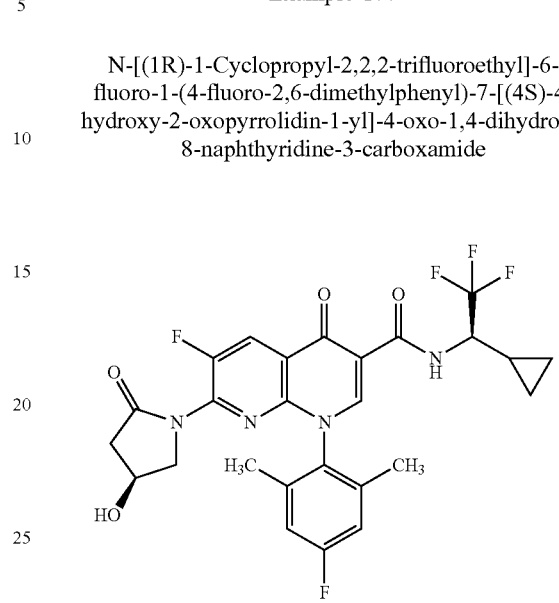

Potassium carbonate (34.1 mg, 0.28 mmol) was initially charged and dried by heating the vessel. Under argon, palladium(II) acetate (4 mg, 0.02 mmol) and 9,9-dimethyl-4,5-bis(diphenylphosphino)xanthene (16 mg, 0.03 mmol) were added, followed by degassed dioxane (1.8 ml). The mixture was stirred at room temperature for 10 min. 7-Chloro-N-[(1R)-1-cyclopropyl-2,2,2-trifluoroethyl]-6-fluoro-1-(4-fluoro-2,6-dimethylphenyl)-4-oxo-1,4-dihydro-1,8-naphthyridine-3-carboxamide (80.0 mg, 165 µmol) and (4S)-4-hydroxypyrrolidin-2-one (20.0 mg, 198 µmol) were added and the mixture was stirred at 80° C. overnight. The reaction solution was filtered and acetonitrile/TFA/water was added, resulting in the precipitation of a solid. The reaction solution was extracted twice with dichloromethane. The residue was purified on a silica gel column (mobile phase: dichloromethane/methanol=30/1). The residue was freed from dichloromethane and re-purified by thick-layer chromatography (mobile phase: dichloromethane/methanol=20/1). This gave a total of 7 mg of the target compound (8% of theory, purity 99%).

LC-MS (Method 3): $R_t$=1.88 min; MS (ESIpos): m/z=551 [M+H]$^+$ $^1$H NMR (400 MHz, DMSO-d6) δ[ppm]: −0.008 (2.34), 0.008 (1.96), 0.348 (1.04), 0.361 (0.95), 0.372 (0.65), 0.383 (0.41), 0.541 (0.62), 0.553 (0.94), 0.569 (1.18), 0.586 (1.28), 0.596 (0.84), 0.607 (0.75), 0.617 (0.61), 0.644 (0.46), 0.653 (0.48), 0.664 (1.03), 0.674 (0.74), 0.681 (0.68), 1.141 (1.13), 1.207 (0.41), 1.216 (0.57), 1.228 (1.04), 1.236 (1.08), 1.248 (1.04), 1.260 (0.64), 1.268 (0.44), 1.948 (15.80), 1.952 (16.00), 2.117 (0.51), 2.278 (1.13), 2.326 (1.59), 2.523 (1.30), 2.808 (1.25), 2.824 (1.27), 2.852 (1.11), 2.868 (1.11), 3.338 (1.55), 3.704 (1.16), 3.717 (1.45), 3.731 (1.26), 3.744 (1.08), 4.358 (1.48), 4.379 (1.07), 4.399 (0.86), 4.420 (0.46), 5.318 (3.02), 5.327 (2.97), 7.181 (2.48), 7.204 (2.52), 8.530 (2.92), 8.554 (2.87), 8.690 (7.03), 10.281 (1.93), 10.304 (1.87).

Example 178

7-[(3S,4S)-3,4-Dihydroxypyrrolidin-1-yl]-6-fluoro-4-oxo-N-[(2S)-1,1,1-trifluorobutan-2-yl]-1-(2,4,6-trifluorophenyl)-1,4-dihydro-1,8-naphthyridine-3-carboxamide

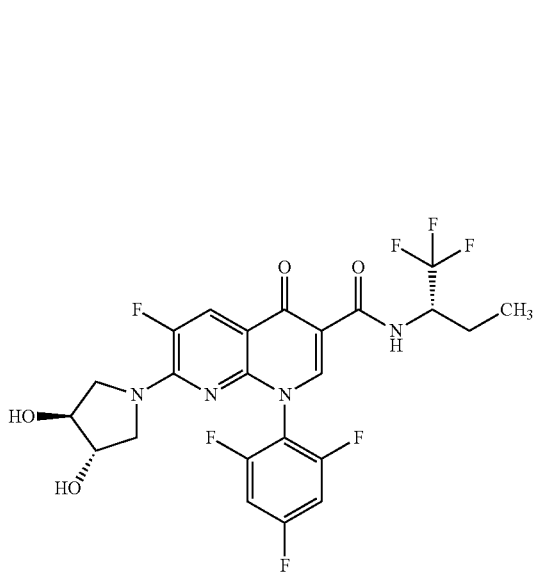 [SMILES: CC[C@H](NC(=O)c1cn(-c2c(F)cc(F)cc2F)c2nc(N3C[C@H](O)[C@@H](O)C3)c(F)cc2c1=O)C(F)(F)F]

7-[(3S,4S)-3,4-Dihydroxypyrrolidin-1-yl]-6-fluoro-4-oxo-1-(2,4,6-trifluorophenyl)-1,4-dihydro-1,8-naphthyridine-3-carboxylic acid (30.0 mg, 68.3 µmol) was dissolved in 0.7 ml of DMF, HATU (31 mg, 0.08 mmol) and DIPEA (42 µl, 0.24 mmol) were added and the mixture was stirred at room temperature for 30 min. (S)-1,1,1-Trifluoro-2-butylamine hydrochloride (13.4 mg, 81.9 µmol) was added and the mixture was stirred at room temperature for 30 min. 0.5 ml of 1 N hydrochloric acid and 1 ml of acetonitrile were added and the mixture was purified by preparative HPLC (RP18 column, mobile phase: acetonitrile/water gradient). This gave 24.3 mg (99% pure, 64% of theory) of the target compound.

LC-MS (Method 3): $R_t$=1.78 min; MS (ESIpos): m/z=549 [M+H]$^+$ $^1$H NMR (400 MHz, DMSO-d6) δ[ppm]: −0.008 (2.33), 0.008 (2.22), 0.950 (7.18), 0.969 (16.00), 0.987 (7.85), 1.604 (1.08), 1.622 (1.42), 1.629 (1.29), 1.639 (1.73), 1.647 (1.54), 1.657 (1.50), 1.664 (1.69), 1.682 (1.29), 1.851 (1.31), 1.861 (1.48), 1.869 (1.52), 1.879 (1.73), 1.886 (1.50), 1.895 (1.33), 1.904 (1.12), 1.914 (0.95), 2.328 (0.76), 2.367 (0.82), 2.524 (3.03), 2.670 (0.85), 2.711 (0.87), 3.073 (0.80), 3.695 (0.85), 3.904 (1.80), 4.014 (1.23), 4.734 (1.42), 4.755 (1.35), 5.201 (4.80), 7.558 (3.87), 7.580 (6.82), 7.601 (3.79), 7.999 (7.53), 8.031 (7.41), 8.841 (12.89), 10.329 (5.19), 10.353 (5.00).

Example 179

N-[(1S)-1-Cyclopropyl-2,2,2-trifluoroethyl]-6-fluoro-7-[3-(hydroxymethyl)-4-methylpiperazin-1-yl]-4-oxo-1-(2,4,6-trifluorophenyl)-1,4-dihydro-1,8-naphthyridine-3-carboxamide (Diastereomer Mixture)

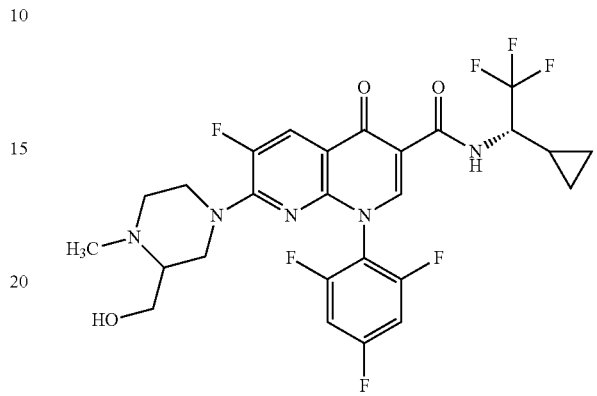

7-Chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide (100 mg, 203 µmol) was initially charged in 2 ml of DMF, [1-methylpiperazin-2-yl] methanol dihydrochloride (47.6 mg, 95% pure, 223 µmol) and N,N-diisopropylethylamine (0.25 ml, 1.42 mmol) were added and the mixture was stirred at room temperature for 3 h. Acetonitrile/water/TFA was added and the reaction solution was purified by preparative HPLC (RP18 column, mobile phase: acetonitrile/water gradient with addition of 0.1% TFA). The product fractions were combined and freed from acetonitrile. The residue was made basic using saturated aqueous sodium bicarbonate solution and extracted three times with dichloromethane. The combined organic phases were washed with saturated aqueous sodium bicarbonate solution. The combined organic phases were dried over sodium sulfate, filtered and concentrated under reduced pressure. The fraction was re-purified by thick-layer chromatography (mobile phase: dichloromethane/methanol=10/1). This gave 80 mg of the target compound (66% of theory, purity 98%).

LC-MS (Method 3): $R_t$=1.37 min; MS (ESIpos): m/z=588 [M+H]$^+$ $^1$H NMR (400 MHz, DMSO-d6) δ[ppm]: −0.008 (2.54), 0.008 (2.44), 0.320 (0.70), 0.330 (1.13), 0.343 (1.11), 0.354 (0.86), 0.366 (0.43), 0.517 (0.75), 0.528 (1.13), 0.541 (1.03), 0.550 (1.17), 0.569 (1.20), 0.579 (0.95), 0.589 (0.86), 0.600 (0.71), 0.614 (0.44), 0.629 (0.61), 0.638 (0.58), 0.649 (1.05), 0.659 (0.90), 0.665 (0.84), 0.671 (0.81), 0.685 (0.41), 1.183 (0.45), 1.191 (0.64), 1.203 (1.10), 1.212 (0.80), 1.223 (1.09), 1.235 (0.67), 1.244 (0.41), 1.932 (0.57), 1.940 (0.71), 1.948 (0.92), 1.957 (0.94), 1.965 (0.73), 1.973 (0.61), 2.079 (0.61), 2.101 (1.15), 2.108 (1.16), 2.130 (0.70), 2.137 (0.62), 2.179 (16.00), 2.524 (0.77), 2.697 (1.34), 2.727 (1.23), 2.849 (0.99), 2.874 (1.10), 2.882 (1.17), 2.907 (0.98), 3.107 (0.61), 3.134 (1.08), 3.162 (0.62), 3.212 (0.61), 3.228 (0.90), 3.241 (1.15), 3.254 (1.03), 3.270 (0.72), 3.481 (0.67), 3.492 (0.98), 3.504 (0.87), 3.520 (0.82), 3.531 (0.54), 3.949 (0.97), 3.978 (0.88), 4.146 (1.17), 4.179 (1.10), 4.355 (0.56), 4.376 (1.00), 4.397 (0.97), 4.417 (0.50), 4.505 (1.26), 4.518 (2.74), 4.531

(1.23), 7.499 (0.64), 7.528 (1.83), 7.540 (0.75), 7.551 (1.81), 7.580 (0.61), 8.071 (3.31), 8.105 (3.22), 8.876 (5.71), 10.386 (2.30), 10.410 (2.21).

Example 180

1-(2-Chloro-4,6-difluorophenyl)-7-(dimethylamino)-6-fluoro-N-(1,1,1,3,3,3-hexafluoropropan-2-yl)-4-oxo-1,4-dihydro-1,8-naphthyridine-3-carboxamide

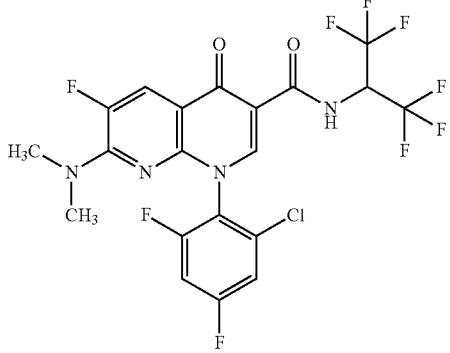

7-Chloro-1-(2-chloro-4,6-difluorophenyl)-6-fluoro-4-oxo-1,4-dihydro-1,8-naphthyridine-3-carboxylic acid (250 mg, 642 µmol), 1,1,1,3,3,3-hexafluoropropan-2-amine (118 mg, 707 µmol) and N,N-diisopropylethylamine (340 µl, 1.9 mmol) were initially charged in 6.5 ml of ethyl acetate, T3P solution (2,4,6-tripropyl-1,3,5,2,4,6-trioxatriphosphinane 2,4,6-trioxide (1.5 ml, 50% pure, 2.6 mmol) was added and the mixture was stirred at 80° C. overnight. More, 1,1,1,3,3,3-hexafluoropropan-2-amine (53.6 mg, 321 µmol), N,N-diisopropylethylamine (57 µl, 0.32 mmol) and T3P solution (2,4,6-tripropyl-1,3,5,2,4,6-trioxatriphosphinane 2,4,6-trioxide) (188 µl, 50% pure, 325 µmol) were added and the mixture was stirred at 80° C. overnight. More, 1,1,1,3,3,3-hexafluoropropan-2-amine (60 mg, 359 µmol) and T3P solution (2,4,6-tripropyl-1,3,5,2,4,6-trioxatriphosphinane 2,4,6-trioxide) (750 µl, 50% purity, 1.3 mmol) were added to the reaction mixture and stirring was continued at 80° C. The mixture was added to water and ethyl acetate and the phases were separated. The aqueous phase was reextracted with ethyl acetate. The combined organic phases were washed with saturated aqueous sodium chloride solution, dried over sodium sulphate, filtered and concentrated on a rotary evaporator. The residue was purified by preparative HPLC (RP18 column, mobile phase: acetonitrile/water+0.1% formic acid gradient).

The product-containing fractions were combined and lyophilized. The crude product was re-purified by prep. HPLC (RP18 column, mobile phase: acetonitrile/water+2% formic acid gradient). This gave 4 mg (100% pure, 1% of theory) of the target compound.

LC-MS (Method 3): $R_t$=1.33 min; MS (ESIpos): m/z=547 [M+H]$^+$ $^1$H NMR (400 MHz, DMSO-d6) δ[ppm]: 0.008 (2.86), 2.328 (0.40), 2.367 (0.43), 3.019 (16.00), 3.023 (15.23), 6.302 (0.75), 6.320 (0.99), 6.345 (1.00), 6.363 (0.65), 7.699 (1.01), 7.706 (1.39), 7.722 (1.62), 7.729 (2.54), 7.745 (2.44), 7.752 (2.62), 7.762 (1.88), 7.773 (1.09), 8.037 (4.69), 8.071 (4.62), 8.948 (8.99), 11.276 (3.01), 11.301 (2.88).

Example 181

7-(3,4-Dihydroxypiperidin-1-yl)-6-fluoro-4-oxo-N-(3,3,4,4,4-pentafluorobutan-2-yl)-1-(2,4,6-trifluorophenyl)-1,4-dihydro-1,8-naphthyridine-3-carboxamide (Diastereomer Mixture)

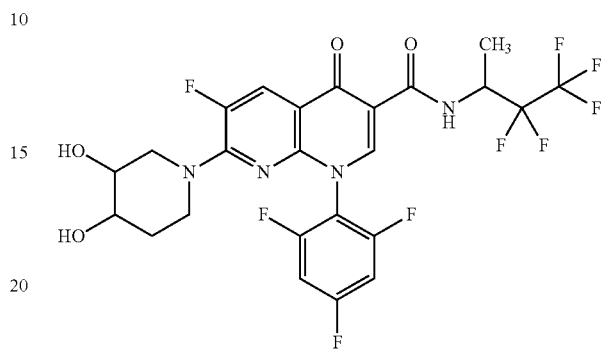

7-Chloro-6-fluoro-4-oxo-N-(3,3,4,4,4-pentafluorobutan-2-yl)-1-(2,4,6-trifluorophenyl)-1,4-dihydro-1,8-naphthyridine-3-carboxamide (150 mg, 290 µmol) (enantiomerically pure) was initially charged in 2.9 ml of N,N-dimethylformamide, and trans-piperidine-3,4-diol hydrochloride (49.0 mg, 319 µmol) and N,N-diisopropylethylamine (230 µl, 1.3 mmol) were added.

The reaction mixture was stirred at 55° C. for 8 h. The reaction mixture was cooled, diluted with acetonitrile and purified by prep. RP-HPLC (column: Reprosil 125×30; 10µ, flow rate: 50 ml/min, acetonitrile/water, 0.1% formic acid). The solvents were concentrated by evaporation under reduced pressure and the residue was dried under high vacuum. This gave 105 mg (61% of theory, 100% pure) of the title compound.

LC-MS (Method 3): $R_t$=1.93 min; MS (ESIpos): m/z=599 [M+H]$^+$ $^1$H NMR (400 MHz, DMSO-d6) δ[ppm]: −0.149 (0.69), −0.008 (6.10), 0.008 (6.04), 0.146 (0.75), 1.230 (1.66), 1.389 (12.14), 1.406 (12.23), 1.771 (1.42), 1.782 (1.57), 1.791 (1.57), 1.814 (1.30), 2.329 (0.82), 2.367 (0.63), 2.671 (0.91), 2.711 (0.63), 3.292 (4.47), 3.350 (2.26), 3.367 (1.51), 3.447 (2.63), 3.530 (1.48), 3.549 (1.69), 3.773 (2.87), 3.806 (2.51), 4.892 (7.52), 4.901 (7.61), 4.970 (0.63), 4.999 (7.34), 5.010 (8.15), 5.034 (1.30), 5.058 (1.12), 7.554 (4.32), 7.576 (7.67), 7.597 (4.26), 8.022 (8.51), 8.057 (8.39), 8.889 (16.00), 10.392 (5.55), 10.416 (5.37).

Example 182

7-(3,4-Dihydroxypiperidin-1-yl)-6-fluoro-4-oxo-N-(3,3,4,4,4-pentafluorobutan-2-yl)-1-(2,4,6-trifluorophenyl)-1,4-dihydro-1,8-naphthyridine-3-carboxamide (Diastereomer 1)

105 mg of 7-(3,4-dihydroxypiperidin-1-yl)-6-fluoro-4-oxo-N-(3,3,4,4,4-pentafluorobutan-2-yl)-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak IF, 5 µm, 250×20 mm; mobile phase: 80% n-heptane/ 20% ethanol; flow rate 15 ml/min; temperature: 25° C., detection: 210 nm).

Diastereomer 1:46.5 mg (>99% de)

$R_t$=1.411 min [HPLC: column Daicel® Chiralpak IF-3, 1 ml/min; 3 µm, 50×4.6 mm; mobile phase: 80% isohexane/ 20% ethanol; detection: 220 nm].

The material obtained was re-purified by prep. HPLC (column: Reprosil 125×30; 10µ, flow rate: 50 ml/min, acetonitrile/water, 0.1% formic acid). The solvents were evaporated under reduced pressure and the residue was dried under high vacuum. This gave 36 mg (21% of theory, 100% pure) of the title compound.

LC-MS (Method 3): $R_t$=1.92 min; MS (ESIpos): m/z=599 [M+H]⁺

¹H NMR (400 MHz, DMSO-d6) δ[ppm]: −0.149 (0.88), −0.008 (7.15), 0.008 (7.01), 0.146 (0.88), 1.205 (1.69), 1.230 (1.76), 1.238 (1.66), 1.389 (13.36), 1.406 (13.46), 1.762 (1.52), 1.771 (1.66), 1.781 (1.80), 1.804 (1.52), 1.814 (1.37), 2.324 (0.74), 2.328 (1.02), 2.666 (0.81), 2.670 (1.13), 2.675 (0.85), 2.711 (0.39), 3.272 (4.09), 3.283 (4.58), 3.351 (2.54), 3.368 (1.73), 3.419 (1.06), 3.445 (3.03), 3.527 (1.62), 3.548 (1.80), 3.571 (1.27), 3.773 (3.07), 3.778 (3.24), 3.805 (2.85), 4.890 (8.88), 4.899 (8.92), 4.969 (0.70), 4.997 (9.23), 5.007 (9.73), 5.033 (1.41), 5.057 (1.16), 5.077 (0.60), 7.555 (4.44), 7.577 (7.72), 7.598 (4.37), 8.023 (9.59), 8.057 (9.41), 8.889 (16.00), 10.392 (6.13), 10.415 (5.89).

Example 183

7-(3,4-Dihydroxypiperidin-1-yl)-6-fluoro-4-oxo-N-(3,3,4,4,4-pentafluorobutan-2-yl)-1-(2,4,6-trifluorophenyl)-1,4-dihydro-1,8-naphthyridine-3-carboxamide (Diastereomer 2)

105 mg of 7-(3,4-dihydroxypiperidin-1-yl)-6-fluoro-4-oxo-N-(3,3,4,4,4-pentafluorobutan-2-yl)-1-(2,4,6-trifluorophenyl)-1,4-dihydro-1,8-naphthyridine-3-carboxamide (diastereomer mixture) were separated into the diastereomers by chiral HPLC (preparative HPLC: column Daicel® Chiralpak IF, 5 µm, 250×20 mm; mobile phase: 80% n-heptane/ 20% ethanol; flow rate 15 ml/min; temperature: 25° C., detection: 210 nm).

Diastereomer 2:46.7 mg (98.6% de)

$R_t$=1.818 min [HPLC: column Daicel® Chiralpak IF-3, 1 ml/min; 3 µm, 50×4.6 mm; mobile phase: 80% isohexane/ 20% ethanol; detection: 220 nm].

The material obtained was re-purified by prep. HPLC (column: Reprosil 125×30; 10µ, flow rate: 50 ml/min, acetonitrile/water, 0.1% formic acid). The solvents were evaporated under reduced pressure and the residue was dried under high vacuum. This gave 38 mg (22% of theory, 100% pure) of the title compound.

LC-MS (Method 1): $R_t$=1.00 min; MS (ESIpos): m/z=599 [M+H]⁺

¹H NMR (400 MHz, DMSO-d6) δ[ppm]: −0.149 (0.53), −0.008 (4.75), 0.008 (4.93), 0.146 (0.53), 1.141 (1.14), 1.205 (1.62), 1.229 (1.72), 1.388 (13.04), 1.405 (13.14), 1.771 (1.42), 1.781 (1.62), 1.791 (1.77), 1.814 (1.42), 1.824 (1.34), 2.117 (0.53), 2.328 (1.19), 2.670 (1.21), 3.270 (3.77), 3.292 (4.95), 3.348 (2.43), 3.365 (1.69), 3.448 (2.91), 3.530 (1.54), 3.552 (1.79), 3.774 (3.24), 3.800 (2.86), 4.891 (8.24), 4.901 (8.32), 4.999 (8.47), 5.009 (9.30), 5.034 (1.34), 5.058 (1.19), 5.077 (0.66), 7.554 (4.73), 7.576 (8.44), 7.598 (4.65), 8.022 (9.48), 8.056 (9.15), 8.889 (16.00), 10.391 (5.79), 10.415 (5.69).

Example 184

6-Fluoro-7-[(2R)-2-(hydroxymethyl)pyrrolidin-1-yl]-4-oxo-N-(3,3,4,4,4-pentafluorobutan-2-yl)-1-(2,4,6-trifluorophenyl)-1,4-dihydro-1,8-naphthyridine-3-carboxamide (Enantiomerically Pure)

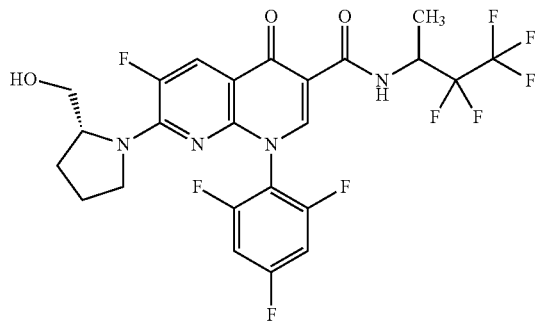 [SMILES: CC(NC(=O)c1cn(-c2c(F)cc(F)cc2F)c2nc(N3CCC[C@@H]3CO)c(F)cc2c1=O)C(F)(F)C(F)(F)F]

7-Chloro-6-fluoro-4-oxo-N-[3,3,4,4,4-pentafluorobutan-2-yl]-1-(2,4,6-trifluorophenyl)-1,4-dihydro-1,8-naphthyridine-3-carboxamide (70.0 mg, 135 µmol) (enantiomerically pure) was initially charged in 1.4 ml of N,N-dimethylformamide, and (2R)-pyrrolidin-2-ylmethanol (15.0 mg, 149 µmol) and N,N-diisopropylethylamine (82 µl, 470 µmol) were added. The reaction mixture was stirred at 55° C. for 8 h. The reaction mixture was cooled, diluted with acetonitrile and purified by prep. RP-HPLC (column: Reprosil 125×30; 10µ, flow rate: 50 ml/min, acetonitrile/water, 0.1% formic acid). The solvents were evaporated under reduced pressure and the residue was dried under high vacuum. This gave 51 mg (65% of theory, 100% pure) of the title compound.

LC-MS (Method 1): $R_t$=1.17 min; MS (ESIpos): m/z=583 [M+H]⁺

¹H NMR (400 MHz, DMSO-d6) δ[ppm]: −0.008 (3.44), 0.008 (3.51), 0.146 (0.41), 1.386 (13.38), 1.403 (13.45), 1.811 (3.37), 1.927 (3.17), 2.329 (0.89), 2.367 (0.93), 2.670 (0.96), 2.711 (0.96), 3.263 (2.00), 3.276 (3.17), 3.290 (3.65), 3.598 (0.62), 4.634 (0.62), 4.966 (0.65), 4.986 (1.17), 5.009 (1.38), 5.029 (1.34), 5.053 (1.17), 5.073 (0.62), 7.500 (1.51), 7.525 (6.09), 7.548 (6.23), 7.573 (1.62), 7.982 (8.77), 8.015 (8.57), 8.846 (16.00), 10.451 (5.85), 10.474 (5.68).

Example 185

6-Fluoro-7-[(2R)-2-(hydroxymethyl)piperidin-1-yl]-4-oxo-N-(3,3,4,4,4-pentafluorobutan-2-yl)-1-(2,4,6-trifluorophenyl)-1,4-dihydro-1,8-naphthyridine-3-carboxamide (Enantiomerically Pure)

Example 186

6-Fluoro-7-[4-hydroxy-4-(hydroxymethyl)piperidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Enantiomerically Pure)

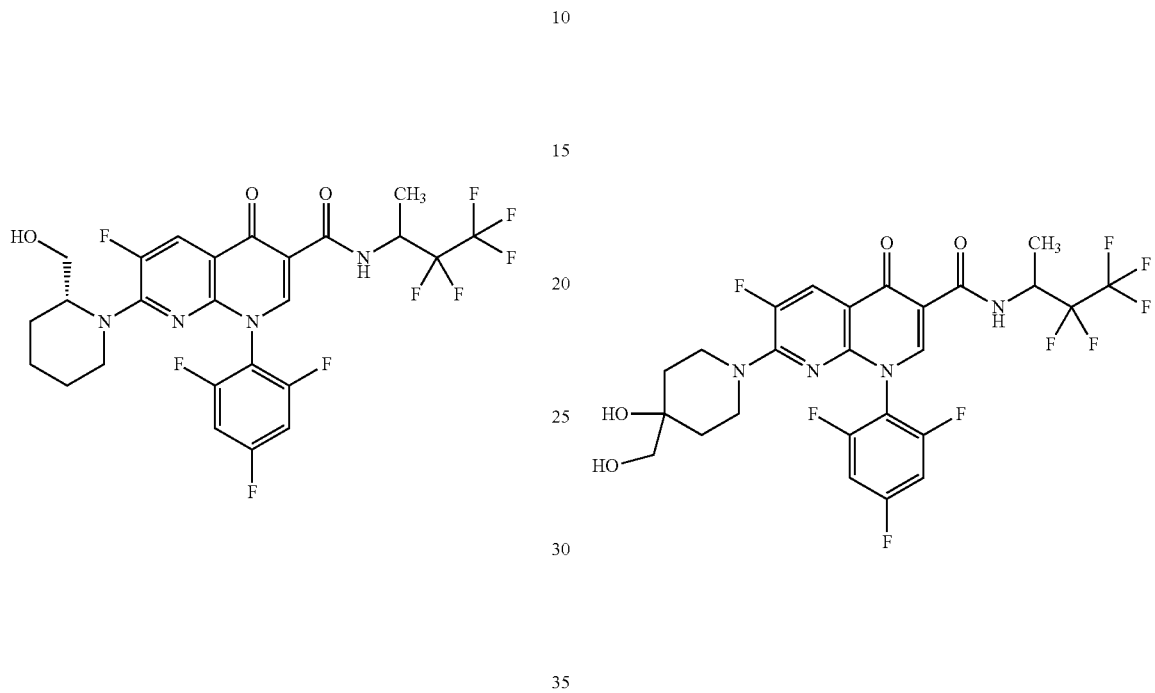

7-Chloro-6-fluoro-4-oxo-N-(3,3,4,4,4-pentafluorobutan-2-yl)-1-(2,4,6-trifluorophenyl)-1,4-dihydro-1,8-naphthyridine-3-carboxamide (70.0 mg, 135 µmol) (enantiomerically pure) was initially charged in 1.4 ml of N,N-dimethylformamide, and (2R)-piperidin-2-ylmethanol (17.1 mg, 149 µmol) and N,N-diisopropylethylamine (82 µl, 470 µmol) were added. The reaction mixture was stirred at 55° C. for 18 h. The reaction mixture was cooled, diluted with acetonitrile and purified by prep. RP-HPLC (column: Reprosil 125×30; 10µ, flow rate: 50 ml/min, acetonitrile/water, 0.1% formic acid). The solvents were evaporated under reduced pressure and the residue was dried under high vacuum. This gave 47 mg (58% of theory, 99% pure) of the title compound.

LC-MS (Method 3): $R_t$=1.22 min; MS (ESIpos): m/z=597 [M+H]$^+$ $^1$H NMR (400 MHz, DMSO-d6) δ[ppm]: −0.149 (0.42), −0.008 (3.95), 0.008 (4.02), 0.146 (0.46), 1.388 (14.45), 1.406 (14.10), 1.470 (2.22), 1.520 (3.70), 1.529 (4.02), 1.549 (6.66), 1.577 (2.64), 1.721 (2.29), 1.741 (2.15), 2.328 (1.06), 2.367 (1.02), 2.671 (1.02), 2.711 (0.99), 2.919 (1.27), 2.949 (2.36), 2.981 (1.27), 3.475 (1.13), 3.492 (1.83), 3.503 (2.85), 3.518 (3.10), 3.533 (2.15), 3.558 (1.37), 3.574 (2.36), 3.587 (2.04), 3.852 (2.15), 3.885 (1.97), 4.287 (2.43), 4.660 (3.42), 4.673 (7.47), 4.687 (3.31), 4.967 (0.63), 4.988 (1.16), 5.010 (1.34), 5.030 (1.37), 5.055 (1.16), 5.076 (0.67), 7.533 (1.73), 7.546 (4.16), 7.553 (4.83), 7.569 (4.83), 7.576 (4.30), 7.589 (1.69), 7.996 (9.37), 8.031 (9.13), 8.870 (16.00), 10.399 (5.92), 10.423 (5.67).

7-Chloro-6-fluoro-4-oxo-N-[3,3,4,4,4-pentafluorobutan-2-yl]-1-(2,4,6-trifluorophenyl)-1,4-dihydro-1,8-naphthyridine-3-carboxamide (70.0 mg, 135 µmol) (enantiomerically pure) was initially charged in 1.4 ml of N,N-dimethylformamide, and 4-(hydroxymethyl)piperidin-4-ol hydrochloride (24.9 mg, 149 µmol) and N,N-diisopropylethylamine (110 µl, 610 µmol) were added. The reaction mixture was stirred at 55° C. for 8 h. The reaction mixture was cooled, diluted with acetonitrile and purified by prep. RP-HPLC (column: Repiosil 125×30; 10µ, flow rate: 50 ml/min, acetonitrile/water, 0.1% formic acid). The solvents were evaporated under reduced pressure and the residue was dried under high vacuum. This gave 55 mg (66% of theory, 100% pure) of the title compound.

LC-MS (Method 3): $R_t$=1.99 min; MS (ESIpos): m/z=613 [M+H]$^+$ $^1$H NMR (400 MHz, DMSO-d6) δ[ppm]: −0.149 (0.92), −0.008 (8.27), 0.008 (7.14), 0.146 (0.92), 1.311 (4.72), 1.345 (6.17), 1.388 (13.79), 1.405 (13.76), 1.504 (2.72), 1.534 (4.37), 1.567 (2.07), 2.328 (1.00), 2.367 (1.00), 2.670 (1.00), 2.711 (0.89), 3.142 (11.28), 3.156 (11.34), 3.249 (2.98), 3.280 (5.93), 3.891 (4.66), 3.923 (4.28), 4.324 (14.08), 4.562 (3.31), 4.576 (7.56), 4.590 (3.25), 4.968 (0.65), 4.989 (1.15), 5.009 (1.39), 5.033 (1.45), 5.055 (1.18), 5.076 (0.65), 7.558 (5.37), 7.580 (10.13), 7.603 (5.34), 8.036 (9.12), 8.070 (8.86), 8.886 (16.00), 10.389 (6.11), 10.413 (5.85).

Example 187

7-[4,4-bis(hydroxymethyl)piperidin-1-yl]-6-fluoro-4-oxo-N-(3,3,4,4,4-pentafluorobutan-2-yl)-1-(2,4,6-trifluorophenyl)-1,4-dihydro-1,8-naphthyridine-3-carboxamide (Enantiomerically Pure)

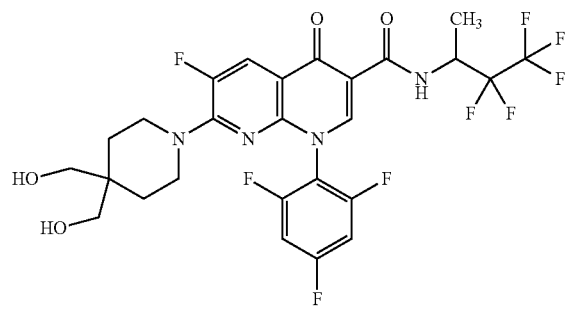 [SMILES: CC(NC(=O)c1cn(-c2c(F)cc(F)cc2F)c2nc(N3CCC(CO)(CO)CC3)c(F)cc2c1=O)C(F)(F)C(F)(F)F]

7-Chloro-6-fluoro-4-oxo-N-(3,3,4,4,4-pentafluorobutan-2-yl)-1-(2,4,6-trifluorophenyl)-1,4-dihydro-1,8-naphthyridine-3-carboxamide (70.0 mg, 135 µmol) (enantiomerically pure) were initially charged in 1.4 ml of N,N-dimethylformamide, and piperidin-4,4-diyldimethanol hydrochloride (27.0 mg, 149 µmol) and N,N-diisopropylethylamine (110 µl, 610 µmol) were added. The reaction mixture was stirred at 55° C. for 8 h. The reaction mixture was cooled, diluted with acetonitrile and purified by prep. RP-HPLC (column: Reprosil 125×30; 10µ, flow rate: 50 ml/min, acetonitrile/water, 0.1% formic acid). The solvents were evaporated under reduced pressure and the residue was dried under high vacuum. This gave 45 mg (53% of theory, 100% pure) of the title compound.

LC-MS (Method 3): $R_t$=2.02 min; MS (ESIpos): m/z=626 [M+H]$^+$ $^1$H NMR (400 MHz, DMSO-d6) δ[ppm]: −0.149 (0.58), 0.008 (4.01), 0.146 (0.58), 1.347 (6.26), 1.361 (7.91), 1.375 (6.74), 1.387 (9.36), 1.404 (8.55), 2.328 (0.61), 2.367 (0.68), 2.671 (0.66), 2.710 (0.68), 3.271 (14.94), 3.285 (16.00), 3.507 (5.81), 3.520 (7.20), 4.405 (4.49), 4.419 (9.86), 4.432 (4.11), 4.967 (0.48), 4.988 (0.76), 5.009 (0.91), 5.031 (0.89), 5.054 (0.76), 7.555 (3.37), 7.577 (6.24), 7.600 (3.27), 8.020 (5.48), 8.055 (5.27), 8.873 (9.38), 10.399 (3.85), 10.424 (3.63).

Example 188

6-Fluoro-N-(1,1,1,3,3,3-hexafluoropropan-2-yl)-7-[(2R)-2-(hydroxymethyl)piperidin-1-yl]-4-oxo-1-(2,4,6-trifluorophenyl)-1,4-dihydro-1,8-naphthyridine-3-carboxamide

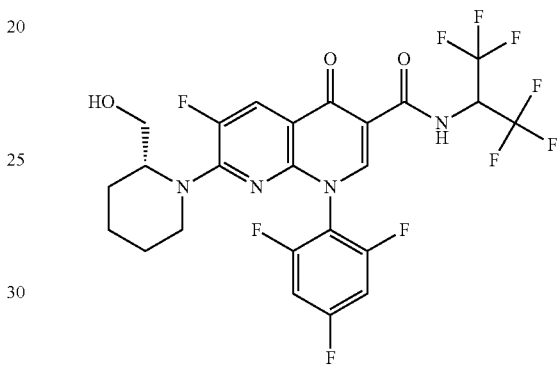

7-Chloro-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide (50.0 mg, 95.8 µmol) was initially charged in 1 ml of DMF, (2R)-piperidin-2-ylmethanol (12.1 mg, 105 µmol) and N,N-diisopropylethylamine (58 µl, 340 µmol) were added and the mixture was stirred at 55° C. for 8 h. The reaction solution was cooled and purified by preparative HPLC (RP18 column, mobile phase: acetonitrile/water gradient with addition of 0.1% formic acid). The product fractions were combined and concentrated by evaporation. This gave 43 mg of the target compound (74% of theory, purity 100%).

LC-MS (Method 3): $R_t$=2.37 min; MS (ESIpos): m/z=601 [M+H]$^+$ $^1$H NMR (400 MHz, DMSO-d6) δ[ppm]: 1.378 (1.60), 1.476 (2.24), 1.534 (3.84), 1.555 (6.73), 1.725 (2.33), 1.743 (2.24), 2.328 (1.90), 2.366 (0.52), 2.670 (2.12), 2.710 (0.80), 2.930 (1.23), 2.960 (2.27), 2.992 (1.32), 3.494 (1.75), 3.506 (2.83), 3.520 (3.01), 3.535 (1.97), 3.578 (2.30), 3.866 (2.09), 3.899 (1.97), 4.298 (2.43), 4.679 (2.73), 4.692 (5.59), 4.705 (2.76), 6.325 (1.75), 6.347 (1.84), 7.547 (1.75), 7.567 (4.82), 7.583 (4.88), 7.604 (1.81), 8.034 (8.97), 8.068 (8.60), 8.541 (0.64), 8.995 (16.00), 11.231 (5.71), 11.256 (5.44).

Example 189

6-Fluoro-N-(1,1,1,3,3,3-hexafluoropropan-2-yl)-7-[4-hydroxy-4-(hydroxymethyl)piperidin-1-yl]-4-oxo-1-(2,4,6-trifluorophenyl)-1,4-dihydro-1,8-naphthyridine-3-carboxamide

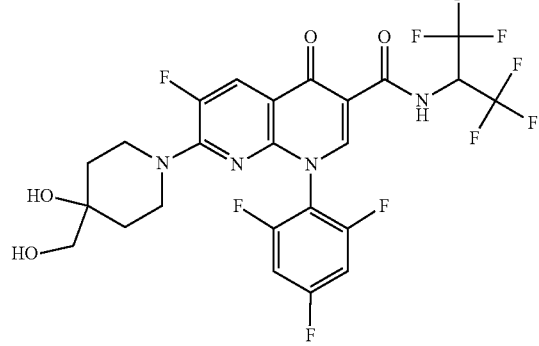

7-Chloro-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide (50.0 mg, 95.8 µmol) was initially charged in 1 ml of DMF, 4-(hydroxymethyl)piperidin-4-ol hydrochloride (18.6 mg, 95% purity, 105 µmol) and N,N-diisopropylethylamine (75 µl, 430 µmol) were added and the mixture was stirred at 55° C. for 8 h. The reaction solution was cooled and purified by preparative HPLC (RP18 column, mobile phase: acetonitrile/water gradient with addition of 0.1% formic acid). The product fractions were combined and concentrated by evaporation. This gave 30 mg of the target compound (50% of theory, purity 100%).

LC-MS (Method 3): $R_t$=2.05 min; MS (ESIpos): m/z=617 [M+H]$^+$ $^1$H NMR (400 MHz, DMSO-d6) δ[ppm]: −0.149 (0.46), −0.008 (5.62), 0.008 (3.80), 0.146 (0.44), 1.320 (4.64), 1.353 (5.97), 1.505 (2.67), 1.515 (3.07), 1.538 (4.37), 1.546 (4.30), 1.570 (2.28), 1.580 (1.92), 2.329 (0.77), 2.671 (0.81), 3.146 (11.34), 3.160 (11.17), 3.262 (3.24), 3.291 (7.90), 3.569 (0.46), 3.907 (4.70), 3.940 (4.16), 4.332 (14.24), 4.565 (3.63), 4.579 (8.00), 4.593 (3.38), 6.307 (1.30), 6.331 (1.78), 6.348 (1.80), 6.367 (1.23), 7.573 (5.26), 7.595 (9.59), 7.617 (5.06), 8.073 (9.13), 8.107 (8.75), 9.009 (16.00), 11.219 (5.76), 11.244 (5.41).

Example 190

1-(3,5-Difluoropyridin-2-yl)-6-fluoro-N-(1,1,1,3,3,3-hexafluoropropan-2-yl)-7-[(2R)-2-(hydroxymethyl)piperidin-1-yl]-4-oxo-1,4-dihydro-1,8-naphthyridine-3-carboxamide

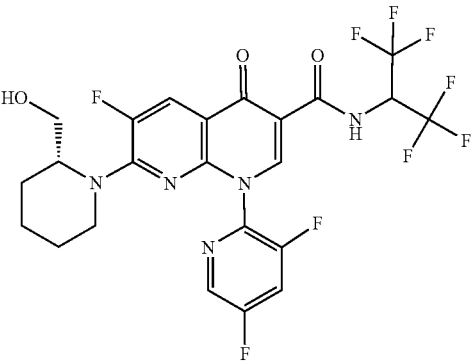 [SMILES: O=C(NC(C(F)(F)F)C(F)(F)F)c1cn(-c2ncc(F)cc2F)c2nc(N3CCCC[C@@H]3CO)c(F)cc2c1=O]

7-Chloro-1-(3,5-difluoropyridin-2-yl)-6-fluoro-N-(1,1,1,3,3,3-hexafluoropropan-2-yl)-4-oxo-1,4-dihydro-1,8-naphthyridine-3-carboxamide (50.0 mg, 99.1 µmol) was initially charged in 1 ml of DMF, (2R)-piperidin-2-ylmethanol (12.6 mg, 109 µmol) and N,N-diisopropylethylamine (8.6 µl, 50 µmol) were added and the mixture was stirred at 55° C. for 8 h. More (2R)-piperidin-2-ylmethanol (5.7 mg, 50 µmol) and N,N-diisopropylethylamine (8.6 µl, 50 µmol) were added and the mixture was stirred at 55° C. The reaction solution was cooled and purified by preparative HPLC (RP18 column, mobile phase: acetonitrile/water gradient with addition of 0.1% formic acid). The product fractions were combined and concentrated by evaporation. This gave 37 mg of the target compound (63% of theory, purity 99%).

LC-MS (Method 3): $R_t$=2.26 min; MS (ESIpos): m/z=584 [M+H]$^+$ $^1$H NMR (400 MHz, DMSO-d6) δ[ppm]: −0.149 (0.99), −0.008 (7.81), 0.008 (7.07), 0.146 (0.93), 1.339 (1.30), 1.525 (9.67), 1.545 (8.81), 1.616 (2.67), 1.647 (2.17), 1.745 (3.97), 2.328 (1.86), 2.367 (0.68), 2.670 (1.98), 2.711 (0.68), 2.921 (2.17), 2.954 (1.61), 3.002 (1.74), 3.031 (0.99), 3.473 (1.74), 3.489 (3.22), 3.500 (6.02), 3.515 (7.75), 3.529 (6.20), 3.581 (2.54), 3.859 (4.59), 3.892 (4.28), 4.286 (3.16), 4.660 (3.10), 4.697 (4.90), 6.300 (1.05), 6.317 (2.67), 6.335 (3.78), 6.360 (3.91), 6.378 (2.60), 6.397 (0.99), 8.037 (9.92), 8.071 (10.23), 8.339 (4.53), 8.357 (4.09), 8.629 (16.00), 8.635 (15.32), 8.956 (9.80), 11.224 (12.84), 11.250 (12.34).

Example 191

7-[4,4-bis(hydroxymethyl)piperidin-1-yl]-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide

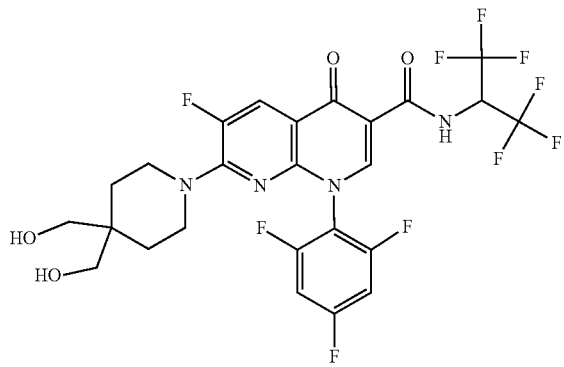 [SMILES: O=C(NC(C(F)(F)F)C(F)(F)F)c1cn(-c2c(F)cc(F)cc2F)c2nc(N3CCC(CO)(CO)CC3)c(F)cc2c1=O]

7-Chloro-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide (50.0 mg, 95.8 µmol) was initially charged in 1 ml of DMF, piperidin-4,4-diyldimethanol hydrochloride (20.2 mg, 95% purity, 105 µmol) and N,N-diisopropylethylamine (75 µl, 430 µmol) were added and the mixture was stirred at 55° C. for 8 h. The reaction solution was cooled and purified by preparative HPLC (RP18 column, mobile phase: acetonitrile/water gradient with addition of 0.1% formic acid). The product fractions were combined and concentrated by evaporation. This gave 52 mg of the target compound (85% of theory, purity 100%).

LC-MS (Method 3): $R_t$=2.07 min; MS (ESIpos): m/z=631 [M+H]$^+$ $^1$H NMR (400 MHz, DMSO-d6) δ[ppm]: 1.354 (7.76), 1.368 (10.28), 1.382 (8.05), 2.328 (1.17), 2.670 (1.30), 3.276 (15.51), 3.285 (16.00), 3.520 (7.34), 3.534 (9.74), 4.423 (5.58), 6.287 (0.42), 6.304 (1.10), 6.329 (1.52), 6.347 (1.61), 6.365 (1.05), 7.571 (4.40), 7.592 (8.22), 7.614 (4.45), 8.058 (7.63), 8.092 (7.49), 8.996 (13.58), 11.232 (5.36), 11.258 (5.09).

Example 192

6-Fluoro-7-[3-hydroxy-3-(hydroxymethyl)piperidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

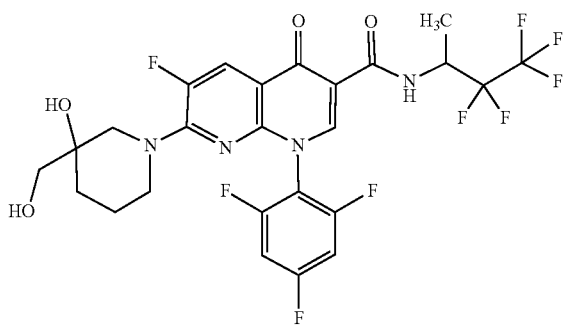 [SMILES: CC(NC(=O)c1cn(-c2c(F)cc(F)cc2F)c2nc(N3CCCC(O)(CO)C3)c(F)cc2c1=O)C(F)(F)C(F)(F)F]

7-Chloro-6-fluoro-4-oxo-N-[3,3,4,4,4-pentafluorobutan-2-yl]-1-(2,4,6-trifluorophenyl)-1,4-dihydro-1,8-naphthyridine-3-carboxamide (100 mg, 94% purity, 182 µmol) (enantiomerically pure) was initially charged in 2 ml of DMF, 3-(hydroxymethyl)piperidin-3-ol (26.2 mg, 200 µmol) and N,N-diisopropylethylamine (110 µl, 640 µmol) were added and the mixture was stirred at room temperature for 18 h. The reaction solution was purified by preparative HPLC (RP18 column, mobile phase: acetonitrile/water gradient with addition of 0.1% formic acid). The product fractions were concentrated by evaporation. This gave 88 mg of the target compound (79% of theory, purity 100%).

LC-MS (Method 3): $R_t$=2.03 min; MS (ESIpos): m/z=613 [M+H]$^+$ $^1$H NMR (400 MHz, DMSO-d6) δ[ppm]: −0.149 (1.00), −0.008 (14.16), 0.008 (7.76), 0.146 (0.94), 1.273 (2.39), 1.387 (15.20), 1.404 (15.48), 1.599 (1.18), 1.628 (4.19), 1.655 (4.40), 2.328 (1.52), 2.670 (1.59), 2.901 (1.97), 3.105 (1.39), 3.132 (4.12), 3.149 (6.34), 3.164 (4.43), 3.177 (1.49), 3.192 (1.28), 3.770 (2.53), 3.803 (2.25), 3.834 (2.81), 3.868 (2.35), 4.241 (10.29), 4.655 (3.15), 4.669 (6.20), 4.683 (2.84), 4.988 (1.25), 5.013 (1.42), 5.032 (1.42), 5.056 (1.18), 7.556 (3.71), 7.566 (4.71), 7.579 (4.68), 7.598 (2.01), 7.971 (7.48), 8.005 (7.34), 8.875 (16.00), 10.424 (5.44), 10.447 (5.23).

Example 193

6-Fluoro-7-[(2S,3S)-3-hydroxy-2-(hydroxymethyl)pyrrolidin-1-yl]-4-oxo-N-(3,3,4,4,4-pentafluoro-2-methylbutan-2-yl)-1-(2,4,6-trifluorophenyl)-1,4-dihydro-1,8-naphthyridine-3-carboxamide

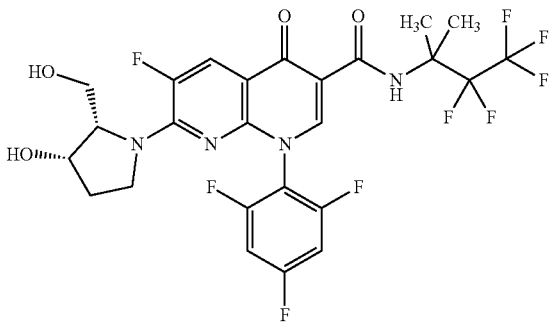 [SMILES: CC(C)(NC(=O)c1cn(-c2c(F)cc(F)cc2F)c2nc(N3CC[C@H](O)[C@@H]3CO)c(F)cc2c1=O)C(F)(F)C(F)(F)F]

7-Chloro-6-fluoro-4-oxo-N-(3,3,4,4,4-pentafluoro-2-methylbutan-2-yl)-1-(2,4,6-trifluoro-phenyl)-1,4-dihydro-1,8-naphthyridine-3-carboxamide (100 mg, 188 µmol) was initially charged in 1.9 ml of DMF, (2S,3S)-2-(hydroxymethyl)pyrrolidin-3-ol hydrochloride (37.6 mg, 244 µmol) and N,N-diisopropylethylamine (150 µl, 850 µmol) were added and the mixture was stirred at 55° C. for 12 h. The reaction solution was cooled and purified by preparative HPLC (RP18 column, mobile phase: acetonitrile/water gradient with addition of 0.1% formic acid). The product fractions were combined and concentrated by evaporation. This gave 93 mg of the target compound (81% of theory, purity 100%).

LC-MS (Method 3): $R_t$=2.08 min; MS (ESIpos): m/z=613 [M+H]$^+$ $^1$H NMR (400 MHz, DMSO-d6) δ[ppm]: −0.008 (3.03), 0.008 (2.80), 1.681 (16.00), 1.953 (1.23), 1.969 (1.25), 2.073 (0.51), 3.478 (1.10), 4.273 (0.92), 5.176 (1.16), 5.185

(1.14), 7.531 (1.06), 7.550 (1.89), 7.570 (1.10), 7.993 (2.68), 8.026 (2.62), 8.783 (5.55), 10.556 (4.22).

Example 194

6-Fluoro-7-[(2S,3S)-3-hydroxy-2-(hydroxymethyl)pyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Enantiomerically Pure)

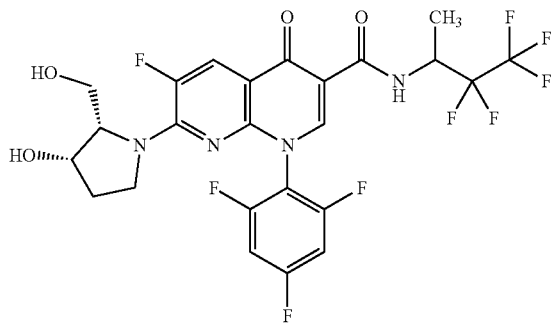 [SMILES: CC(NC(=O)c1cn(-c2c(F)cc(F)cc2F)c2nc(N3CC[C@H](O)[C@@H]3CO)c(F)cc2c1=O)C(F)(F)C(F)(F)F]

7-Chloro-6-fluoro-4-oxo-N-[3,3,4,4,4-pentafluorobutan-2-yl]-1-(2,4,6-trifluorophenyl)-1,4-di-hydro-1,8-naphthyridine-3-carboxamide (80.0 mg, 155 µmol) was initially charged in 1.5 ml of DMF, (2S,3S)-2-(hydroxymethyl)pyrrolidin-3-ol hydrochloride (30.9 mg, 201 µmol) and N,N-diisopropylethylamine (120 µl, 700 µmol) were added and the mixture was stirred at 55° C. for 12 h. The reaction solution was cooled and purified by preparative HPLC (RP18 column, mobile phase: acetonitrile/water gradient with addition of 0.1% formic acid). The combined product fractions were concentrated by evaporation. This gave 75 mg of the target compound (81% of theory, purity 100%).

LC-MS (Method 3): $R_t$=1.98 min; MS (ESIpos): m/z=599 [M+H]$^+$ $^1$H NMR (400 MHz, DMSO-d6) δ[ppm]: −0.149 (1.46), −0.008 (11.75), 0.008 (11.23), 0.146 (1.43), 1.386 (12.95), 1.403 (13.01), 1.953 (3.41), 1.970 (3.44), 2.328 (1.14), 2.367 (0.42), 2.670 (1.17), 2.711 (0.42), 3.481 (3.05), 4.272 (2.50), 4.964 (0.62), 4.986 (1.10), 5.006 (1.33), 5.028 (1.30), 5.051 (1.14), 5.072 (0.58), 5.185 (2.82), 7.531 (2.89), 7.552 (5.16), 7.569 (2.86), 7.976 (7.30), 8.008 (7.08), 8.032 (0.42), 8.848 (16.00), 10.446 (5.71), 10.470 (5.52).

Example 195

7-[4,4-bis(hydroxymethyl)piperidin-1-yl]-1-(3,5-difluoropyridin-2-yl)-6-fluoro-N-(1,1,1,3,3,3-hexafluoropropan-2-yl)-4-oxo-1,4-dihydro-1,8-naphthyridine-3-carboxamide

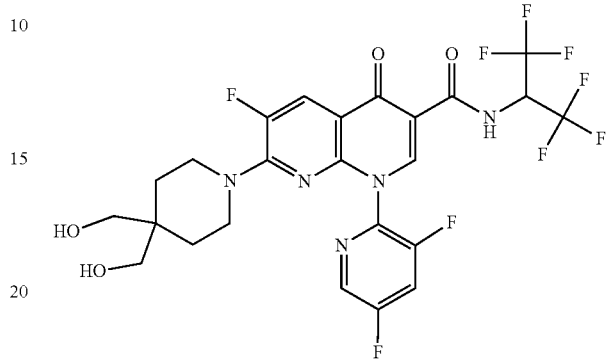

7-Chloro-1-(3,5-difluoropyridin-2-yl)-6-fluoro-N-(1,1,1,3,3,3-hexafluoropropan-2-yl)-4-oxo-1,4-dihydro-1,8-naphthyridine-3-carboxamide (50.0 mg, 99.1 µmol) was initially charged in 1 ml of DMF, piperidin-4,4-diyldimethanol hydrochloride (20.8 mg, 95% purity, 109 µmol) and N,N-diisopropylethylamine (78 µl, 450 µmol) were added and the mixture was stirred at 55° C. overnight. The reaction solution was cooled and purified by preparative HPLC (RP18 column, mobile phase: acetonitrile/water gradient with addition of 0.1% formic acid). The product fractions were combined and concentrated by evaporation. This gave 36 mg of the target compound (59% of theory, purity 99%).

LC-MS (Method 3): $R_t$=1.96 min; MS (ESIpos): m/z=614 [M+H]$^+$ $^1$H NMR (400 MHz, DMSO-d6) δ[ppm]: 1.364 (0.66), 1.378 (1.01), 1.393 (0.69), 3.278 (1.57), 3.291 (1.64), 3.312 (16.00), 3.529 (0.79), 4.413 (0.47), 4.427 (1.05), 4.440 (0.47), 8.061 (0.74), 8.095 (0.72), 8.636 (0.86), 8.642 (0.82), 8.958 (1.64), 11.226 (0.46), 11.251 (0.44).

Example 196

6-Fluoro-N-(1,1,1,3,3,3-hexafluoropropan-2-yl)-7-(2-oxa-6-azaspiro[3.3]hept-6-yl)-4-oxo-1-(2,4,6-trifluorophenyl)-1,4-dihydro-1,8-naphthyridine-3-carboxamide

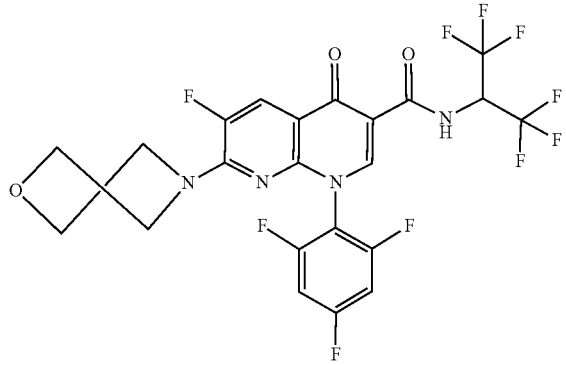 [SMILES: O=C(NC(C(F)(F)F)C(F)(F)F)c1cn(-c2c(F)cc(F)cc2F)c2nc(N3CCOCC3)c(F)cc2c1=O]

7-Chloro-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide (100 mg, 100% purity, 192 μmol) was initially charged in 2.1 ml of DMF, ethanedioic acid 2-oxa-6-azaspiro[3.3]heptane (1:2) (71.8 mg, 249 μmol) and N,N-diisopropylethylamine (120 μl, 670 μmol) were added and the mixture was stirred at 55° C. for 18 h. The reaction solution was allowed to stand at room temperature over the weekend. The mixture was then purified by preparative HPLC (RP18 column, mobile phase: acetonitrile/water gradient with addition of 0.1% formic acid). The product fractions were combined and concentrated by evaporation. This gave 89 mg of the target compound (79% of theory, purity 99%).

LC-MS (Method 3): R$_t$=2.31 min; MS (ESIpos): m/z=585 [M+H]$^+$ $^1$H NMR (400 MHz, DMSO-d6) δ[ppm]: −0.008 (2.33), 0.008 (2.26), 4.656 (16.00), 6.297 (0.41), 6.316 (0.57), 6.339 (0.61), 7.556 (1.64), 7.578 (2.94), 7.600 (1.63), 8.020 (2.85), 8.049 (2.83), 8.965 (4.77), 11.258 (1.92), 11.284 (1.84).

Example 197

1-(3,5-Difluoropyridin-2-yl)-6-fluoro-N-(1,1,1,3,3,3-hexafluoropropan-2-yl)-7-[(2R)-2-(hydroxymethyl)pyrrolidin-1-yl]-4-oxo-1,4-dihydro-1,8-naphthyridine-3-carboxamide

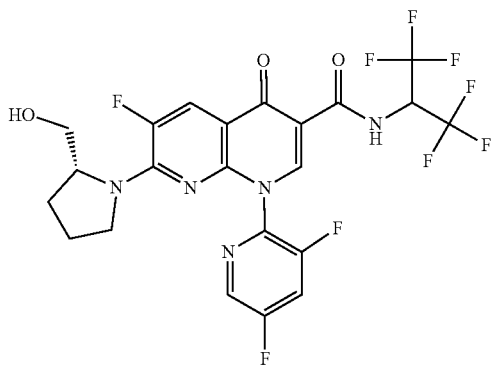 [SMILES: O=C(NC(C(F)(F)F)C(F)(F)F)c1cn(-c2ncc(F)cc2F)c2nc(N3CCC[C@@H]3CO)c(F)cc2c1=O]

7-Chloro-1-(3,5-difluoropyridin-2-yl)-6-fluoro-N-(1,1,1,3,3,3-hexafluoropropan-2-yl)-4-oxo-1,4-dihydro-1,8-naphthyridine-3-carboxamide (50.0 mg, 99.1 μmol) was initially charged in 1 ml of DMF, (2R)-pyrrolidin-2-ylmethanol (11 μl, 99% purity, 110 μmol) and N,N-diisopropylethylamine (60 μl, 350 μmol) were added and the mixture was stirred at 55° C. overnight. The reaction solution was cooled and purified by preparative HPLC (RP18 column, mobile phase: acetonitrile/water gradient with addition of 0.1% formic acid). The product fractions were combined, freed from the solvent and lyophilized. This gave 30 mg (52% of theory, 98% pure) of the title compound.

LC-MS (Method 3): R$_t$=2.17 min; MS (ESIpos): m/z=570 [M+H]$^+$ $^1$H NMR (400 MHz, DMSO-d6) δ[ppm]: −0.149 (1.37), 0.146 (1.76), 1.820 (7.75), 1.934 (7.70), 2.328 (2.31), 2.670 (2.69), 2.711 (0.66), 3.160 (2.09), 3.576 (1.54), 4.710 (1.43), 6.309 (2.91), 6.328 (4.23), 6.352 (4.40), 6.369 (2.97), 8.021 (10.28), 8.054 (10.17), 8.284 (2.97), 8.309 (3.30), 8.335 (3.68), 8.353 (1.87), 8.557 (1.87), 8.612 (16.00), 8.939 (11.22), 8.954 (9.68), 11.287 (12.70), 11.312 (12.10).

Example 198

1-(3,5-Difluoropyridin-2-yl)-6-fluoro-N-(1,1,1,3,3,3-hexafluoropropan-2-yl)-7-[4-hydroxy-4-(hydroxymethyl)piperidin-1-yl]-4-oxo-1,4-dihydro-1,8-naphthyridine-3-carboxamide

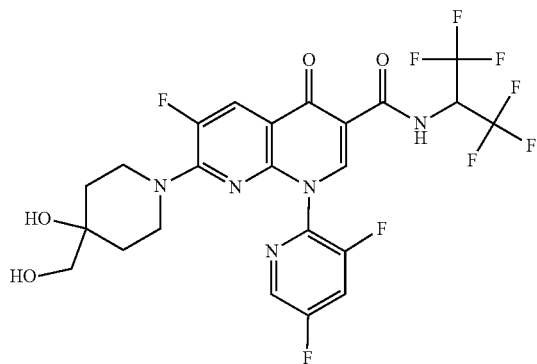 [SMILES: O=C(NC(C(F)(F)F)C(F)(F)F)c1cn(-c2ncc(F)cc2F)c2nc(N3CCC(O)(CO)CC3)c(F)cc2c1=O]

7-Chloro-1-(3,5-difluoropyridin-2-yl)-6-fluoro-N-(1,1,1,3,3,3-hexafluoropropan-2-yl)-4-oxo-1,4-dihydro-1,8-naphthyridine-3-carboxamide (50.0 mg, 99.1 μmol) was initially charged in 1 ml of DMF, 4-(hydroxymethyl)piperidin-4-ol hydrochloride (19.2 mg, 95% purity, 109 μmol) and N,N-diisopropylethylamine (78 μl, 450 μmol) were added and the mixture was stirred at 55° C. overnight. The reaction solution was cooled and purified by preparative HPLC (RP18 column, mobile phase: acetonitrile/water gradient with addition of 0.1% formic acid). The product fractions were combined and freed from the solvent. The residue was purified by silica gel chromatography (mobile phase: dichloro me thane to ethyl acetate). The product-containing fractions were combined, concentrated by evaporation and lyophilized from acetonitrile/water overnight. This gave 22.3 mg (37% of theory, 99% pure) of the title compound.

LC-MS (Method 1): R$_t$=1.02 min; MS (ESIpos): m/z=600 [M+H]$^+$ $^1$H NMR (400 MHz, DMSO-d6) δ[ppm]: −0.149 (0.70), −0.008 (6.17), 0.008 (5.68), 0.146 (0.70), 1.235 (0.55), 1.284 (0.76), 1.298 (1.40), 1.312 (1.56), 1.347 (3.39), 1.383 (2.11), 1.491 (1.10), 1.524 (1.89), 1.543 (1.89), 1.566 (1.92), 1.598 (0.89), 2.041 (1.13), 2.328 (1.01), 2.366 (0.43), 2.670 (1.13), 2.710 (0.52), 3.147 (10.11), 3.162 (10.20), 3.233 (1.01), 3.266 (2.08), 3.912 (2.81), 4.329 (12.64), 4.564 (2.93), 4.578 (6.81), 4.592 (2.96), 6.318 (0.98), 6.343 (1.50), 6.360 (1.59), 6.379 (1.04), 8.076 (7.76), 8.110 (7.60), 8.354 (1.74), 8.360 (2.05), 8.382 (3.11), 8.399 (1.92), 8.405 (2.02), 8.638 (8.98), 8.645 (8.52), 8.969 (16.00), 11.212 (5.31), 11.238 (5.07).

Example 199

6-Fluoro-N-(1,1,1,3,3,3-hexafluoropropan-2-yl)-7-[(2R)-2-(hydroxymethyl)pyrrolidin-1-yl]-4-oxo-1-(2,4,6-trifluorophenyl)-1,4-dihydro-1,8-naphthyridine-3-carboxamide

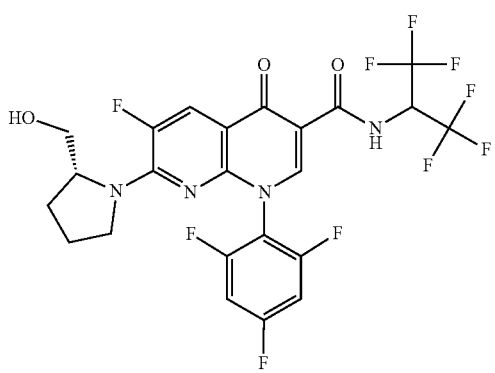 [SMILES: O=C(NC(C(F)(F)F)C(F)(F)F)c1cn(-c2c(F)cc(F)cc2F)c2nc(N3CCC[C@@H]3CO)c(F)cc2c1=O]

7-Chloro-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide (50.0 mg, 95.8 μmol) was initially charged in 1 ml of DMF, (2R)-pyrrolidin-2-ylmethanol (11 μl, 99% purity, 110 μmol) and N,N-diisopropylethylamine (58 μl, 340 μmol) were added and the mixture was stirred at 55° C. for 8 h. The reaction solution was cooled and purified by preparative HPLC (RP18 column, mobile phase: acetonitrile/water gradient with addition of 0.1% formic acid). The product fractions were combined and freed from the solvent. The residue was re-purified by preparative HPLC (RP18 column, mobile phase: acetonitrile/water gradient with addition of 0.1% formic acid). The product fractions were combined and freed from the solvent. The residue was purified by silica gel chromatography (ethyl acetate/cyclohexane gradient). After concentration by evaporation the residue was re-purified by preparative HPLC (RP18 column, mobile phase: acetonitrile/water gradient with addition of 0.1% formic acid). The product-containing fractions were combined, concentrated by evaporation and lyophilized from acetonitrile/water overnight. This gave 14.2 mg (25% of theory, 99% pure) of the title compound.

LC-MS (Method 3): $R_t$=2.27 min; MS (ESIpos): m/z=587 [M+H]$^+$ $^1$H NMR (400 MHz, DMSO-d6) δ[ppm]: −0.149 (0.99), 0.146 (0.93), 1.821 (3.92), 1.933 (3.51), 2.328 (1.13), 2.367 (0.90), 2.670 (1.25), 2.711 (0.87), 3.346 (1.19), 3.603 (0.64), 4.641 (0.64), 6.299 (1.39), 6.317 (2.03), 6.341 (2.15), 6.360 (1.36), 7.518 (1.74), 7.540 (6.68), 7.563 (6.85), 7.587 (1.92), 8.020 (8.68), 8.052 (8.57), 8.974 (16.00), 11.291 (6.45), 11.316 (6.16).

Example 200

6-Fluoro-7-[6-hydroxy-1,4-diazepan-1-yl]-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

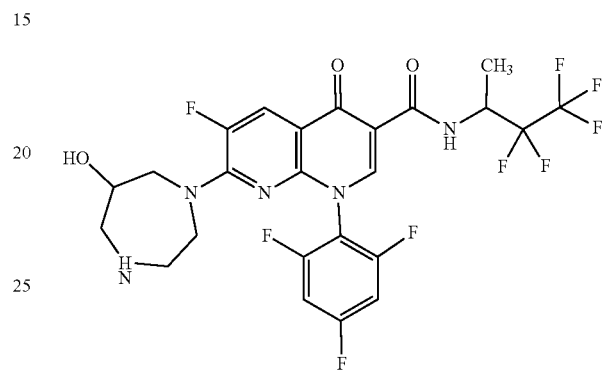

1,4-Diazepan-6-ol dihydrobromide (37.6 mg, 135 μmol) was initially charged in 0.26 ml of DMF and N,N-diisopropylethylamine (170 μl, 970 μmol). 7-Chloro-6-fluoro-4-oxo-N-(3,3,4,4,4-pentafluorobutan-2-yl)-1-(2,4,6-trifluorophenyl)-1,4-dihydro-1,8-naphthyridine-3-carboxamide (enantiomerically pure) (100 mg, 193 μmol) was dissolved in 0.79 ml of DMF and slowly added dropwise to the first mixture and stirred at room temperature overnight. The reaction solution was diluted with acetonitrile, water and TFA and purified by preparative HPLC (RP18 column, mobile phase: acetonitrile/water gradient with addition of 0.1% TFA).

The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 37 mg of the target compound (32% of theory, purity 99%).

LC-MS (Method 3): $R_t$=1.43 min; MS (ESIpos): m/z=598 [M+H]$^+$ $^1$H NMR (400 MHz, DMSO-d6) δ[ppm]: −0.149 (1.01), −0.008 (8.78), 0.008 (8.35), 0.146 (1.01), 0.853 (0.86), 1.234 (1.21), 1.387 (11.18), 1.404 (11.23), 2.156 (0.61), 2.328 (1.59), 2.366 (0.56), 2.570 (3.81), 2.670 (4.29), 2.697 (1.59), 3.627 (1.89), 3.854 (1.84), 3.878 (1.67), 4.729 (1.49), 4.989 (0.98), 5.010 (1.09), 5.033 (1.14), 5.754 (11.43), 7.541 (3.56), 7.547 (3.63), 7.564 (4.21), 7.584 (1.51), 7.993 (7.97), 8.027 (7.80), 8.868 (16.00), 10.414 (4.90), 10.438 (4.79).

Example 201

N-[1-cyclopropyl-2,2,3,3,3-pentafluoropropyl]-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide (Enantiomer 1)

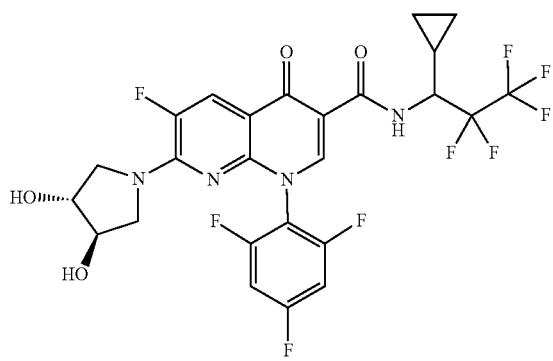 [SMILES: O=C(NC(C1CC1)C(F)(F)C(F)(F)F)c1cn(-c2c(F)cc(F)cc2F)c2nc(N3C[C@@H](O)[C@H](O)C3)c(F)cc2c1=O]

7-Chloro-N-[1-cyclopropyl-2,2,3,3,3-pentafluoropropyl]-6-fluoro-4-oxo-1-(2,4,6-trifluoro-phenyl)-1,4-dihydro-1,8-naphthyridine-3-carboxamide (enantiomer 1) (100 mg, 184 µmol) was initially charged in 1 ml of DMF. (3R,4R)-pyrrolidine-3,4-diol hydrochloride (30.8 mg, 221 µmol) was added, N,N-diisopropylethylamine (160 µl, 920 µmol) was added and the mixture was stirred at room temperature overnight. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave 103 mg of the target compound (90% of theory, purity 98%).

Enantiomer 1: ee>97%, $R_t$=7.703 min [analytical HPLC: column Daicel® Chiralpak IA, 5 µm, 250×4.6 mm; 1 ml/min, 30° C.; mobile phase: 80% isohexane/20% ethanol; detection: 220 nm].

LC-MS (Method 1): $R_t$=1.06 min; MS (ESIpos): m/z=611 [M+H]$^+$ $^1$H NMR (400 MHz, DMSO-d6) δ[ppm]: −0.149 (0.56), −0.008 (4.36), 0.008 (4.16), 0.146 (0.52), 0.308 (0.79), 0.320 (1.84), 0.332 (2.92), 0.345 (3.15), 0.357 (2.45), 0.369 (1.11), 0.486 (0.86), 0.497 (2.37), 0.509 (3.34), 0.521 (2.94), 0.533 (2.22), 0.545 (1.02), 0.566 (1.01), 0.576 (1.14), 0.587 (2.39), 0.599 (2.71), 0.609 (2.26), 0.620 (1.96), 0.633 (1.13), 0.650 (1.29), 0.670 (2.35), 0.683 (2.68), 0.696 (2.09), 0.717 (0.67), 1.207 (0.50), 1.219 (1.14), 1.227 (1.75), 1.240 (2.91), 1.249 (2.16), 1.260 (2.69), 1.272 (1.47), 1.281 (0.95), 2.328 (0.94), 2.367 (0.61), 2.670 (0.98), 2.711 (0.58), 3.066 (1.02), 3.700 (1.05), 3.906 (2.19), 4.022 (1.54), 4.434 (0.67), 4.457 (1.66), 4.479 (2.15), 4.501 (2.09), 4.522 (1.69), 4.545 (0.63), 5.202 (4.77), 7.556 (3.48), 7.577 (6.29), 7.597 (3.48), 8.011 (9.15), 8.043 (8.99), 8.838 (16.00), 10.542 (6.29), 10.566 (6.04).

Example 202

N-[1-cyclopropyl-2,2,3,3,3-pentafluoropropyl]-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide (Enantiomer 2)

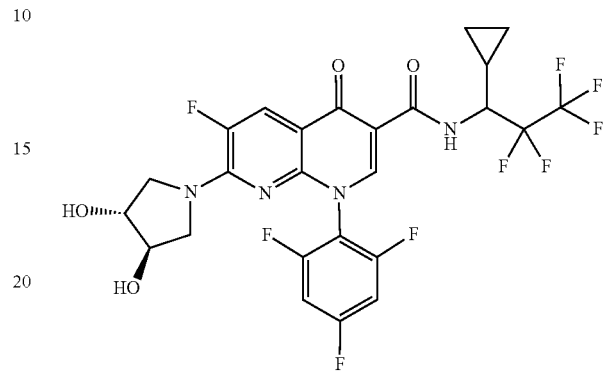

7-Chloro-N-[1-cyclopropyl-2,2,3,3,3-pentafluoropropyl]-6-fluoro-4-oxo-1-(2,4,6-trifluoro-phenyl)-1,4-dihydro-1,8-naphthyridine-3-carboxamide (enantiomer 2) (100 mg, 184 µmol) was initially charged in 1 ml of DMF. (3R,4R)-pyrrolidine-3,4-diol hydrochloride (30.8 mg, 221 µmol) and N,N-diisopropylethylamine (160 µl, 920 µmol) were added and the mixture was stirred at room temperature overnight. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave 105 mg of the target compound (92% of theory, purity 98%).

Enantiomer 2: ee>96.5%. $R_t$=6.54 min [analytical HPLC: column Daicel® Chiralpak IA, 5 µm, 250×4.6 mm; 1 ml/min, 30° C.; mobile phase: 80% isohexane/20% ethanol; detection: 220 nm].

LC-MS (Method 1): $R_t$=1.06 min; MS (ESIpos): m/z=611 [M+H]$^+$ $^1$H NMR (400 MHz, DMSO-d6) δ [ppm]: −0.149 (0.68), 0.146 (0.64), 0.308 (0.75), 0.321 (1.88), 0.333 (2.90), 0.345 (3.19), 0.357 (2.48), 0.369 (1.09), 0.487 (0.83), 0.499 (2.31), 0.511 (3.27), 0.523 (2.86), 0.534 (2.19), 0.547 (1.02), 0.566 (0.95), 0.588 (2.37), 0.600 (2.70), 0.609 (2.25), 0.621 (1.97), 0.634 (1.13), 0.650 (1.24), 0.671 (2.36), 0.684 (2.66), 0.696 (2.08), 0.718 (0.67), 1.206 (0.50), 1.227 (1.70), 1.239 (2.83), 1.249 (2.23), 1.260 (2.64), 1.271 (1.51), 1.293 (0.42), 2.328 (0.94), 2.367 (0.42), 2.671 (0.99), 2.710 (0.41), 3.074 (1.03), 3.691 (1.09), 3.903 (2.19), 4.017 (1.59), 4.432 (0.64), 4.455 (1.67), 4.477 (2.14), 4.498 (2.12), 4.520 (1.69), 4.544 (0.63), 5.203 (5.43), 7.555 (4.56), 7.577 (8.29), 7.598 (4.45), 8.012 (8.76), 8.044 (8.61), 8.838 (16.00), 10.543 (6.02), 10.568 (5.80).

Example 203

N-(1,1-dicyclopropyl-2,2,2-trifluoroethyl)-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide

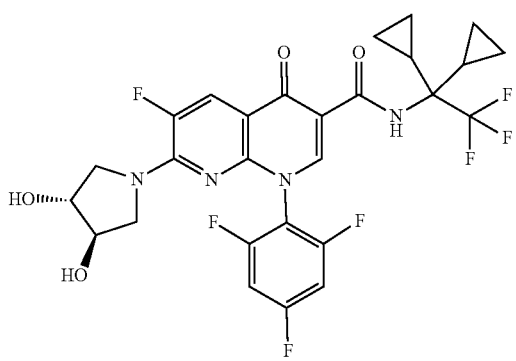 [SMILES: O=C(NC(C1CC1)(C1CC1)C(F)(F)F)c1cn(-c2c(F)cc(F)cc2F)c2nc(N3C[C@@H](O)[C@H](O)C3)c(F)cc2c1=O]

7-Chloro-N-(1,1-dicyclopropyl-2,2,2-trifluoroethyl)-6-fluoro-4-oxo-1-(2,4,6-trifluoro-phenyl)-1,4-dihydro-1,8-naphthyridine-3-carboxamide (70.0 mg, 131 µmol) was initially charged in 0.7 ml of DMF. (3R,4R)-pyrrolidine-3,4-diol hydrochloride (22.0 mg, 157 µmol) and N,N-diisopropylethylamine (110 µl, 660 µmol) were added and the mixture was stirred at room temperature overnight. Water/acetonitrile/TFA were added and the reaction solution was purified by preparative HPLC (RP18 column, mobile phase: acetonitrile/water gradient with addition of 0.1% TFA). The combined product fractions were concentrated by evaporation.

The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave 71 mg of the target compound (88% of theory, purity 98%).

LC-MS (Method 1): $R_t$=1.04 min; MS (ESIpos): m/z=601 [M+H]$^+$ $^1$H NMR (400 MHz, DMSO-d6) δ[ppm]: −0.149 (0.68), −0.008 (5.38), 0.008 (4.77), 0.146 (0.65), 0.458 (1.16), 0.469 (2.08), 0.481 (3.81), 0.493 (4.94), 0.505 (5.07), 0.516 (3.30), 0.527 (2.52), 0.552 (1.70), 0.564 (3.47), 0.578 (4.05), 0.586 (5.38), 0.600 (4.90), 0.608 (3.68), 0.622 (4.87), 0.633 (4.05), 0.645 (5.89), 0.658 (4.94), 0.672 (1.97), 0.685 (2.55), 0.699 (4.87), 0.710 (5.55), 0.723 (4.26), 0.733 (2.72), 0.747 (1.02), 1.175 (0.65), 1.518 (1.60), 1.533 (3.51), 1.540 (3.74), 1.553 (6.26), 1.567 (3.51), 1.574 (3.17), 1.589 (1.36), 1.988 (1.16), 2.086 (5.69), 2.328 (1.09), 2.367 (0.71), 2.670 (1.23), 2.711 (0.78), 3.072 (0.95), 3.684 (1.02), 3.901 (2.04), 4.021 (1.67), 5.198 (4.36), 5.754 (3.34), 7.553 (3.88), 7.575 (6.98), 7.595 (3.91), 8.034 (9.12), 8.066 (8.99), 8.776 (16.00), 9.878 (11.85).

Example 204

N-[1-cyclopropyl-2,2,3,3,3-pentafluoropropyl]-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide (Enantiomer 1)

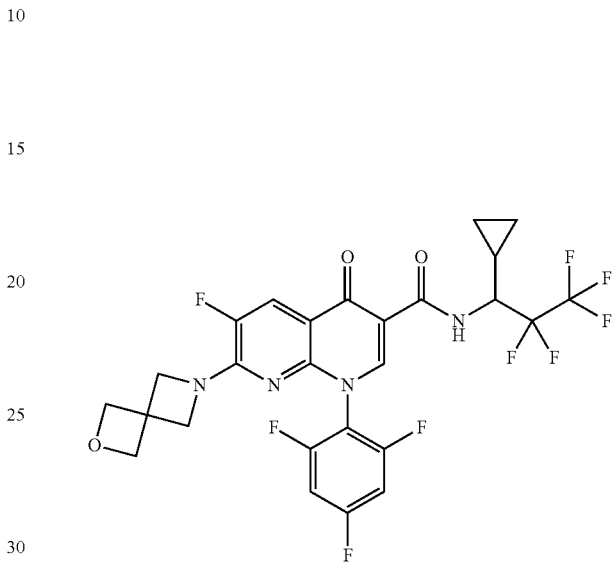

7-Chloro-N-[1-cyclopropyl-2,2,3,3,3-pentafluoropropyl]-6-fluoro-4-oxo-1-(2,4,6-trifluoro-phenyl)-1,4-dihydro-1,8-naphthyridine-3-carboxamide (enantiomer 1) (150 mg, 276 µmol) was initially charged in 1.5 ml of DMF, and N,N-diisopropylethylamine (480 µl, 2.8 mmol) and ethanedioic acid 2-oxa-6-azaspiro[3.3]heptane (1:2) (59.6 mg, 207 µmol) were added at room temperature. The reaction solution was stirred at room temperature overnight. Water/acetonitrile/TFA were added and the reaction solution was purified by preparative HPLC (RP18 column, mobile phase: acetonitrile/water gradient with addition of 0.1% TFA). This gave 160 mg of the target compound (94% of theory, purity 98%).

LC-MS (Method 1): $R_t$=1.21 min; MS (ESIpos): m/z=607 [M+H]$^+$ $^1$H NMR (400 MHz, DMSO-d6) δ[ppm]: −0.149 (0.97), −0.008 (7.80), 0.146 (0.88), 0.310 (0.64), 0.323 (0.97), 0.335 (0.97), 0.346 (0.82), 0.493 (0.74), 0.504 (1.09), 0.517 (0.92), 0.528 (0.70), 0.580 (0.80), 0.593 (0.86), 0.680 (0.88), 1.222 (0.58), 1.234 (1.01), 1.254 (0.88), 2.073 (9.20), 2.327 (1.58), 2.366 (0.74), 2.670 (1.58), 2.710 (0.74), 4.272 (0.43), 4.446 (0.70), 4.468 (0.86), 4.489 (0.82), 4.511 (0.64), 4.655 (16.00), 7.541 (1.70), 7.563 (3.25), 7.585 (1.73), 7.999 (2.88), 8.027 (2.85), 8.833 (5.07), 10.507 (1.95), 10.531 (1.91).

Example 205

7-[3,3-bis(hydroxymethyl)azetidin-1-yl]-N-[1-cyclopropyl-2,2,3,3,3-pentafluoropropyl]-6-fluoro-4-oxo-1-(2,4,6-trifluorophenyl)-1,4-dihydro-1,8-naphthyridine-3-carboxamide (Enantiomer 1)

Example 206

N-[1-cyclopropyl-2,2,3,3,3-pentafluoropropyl]-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide (Enantiomer 2)

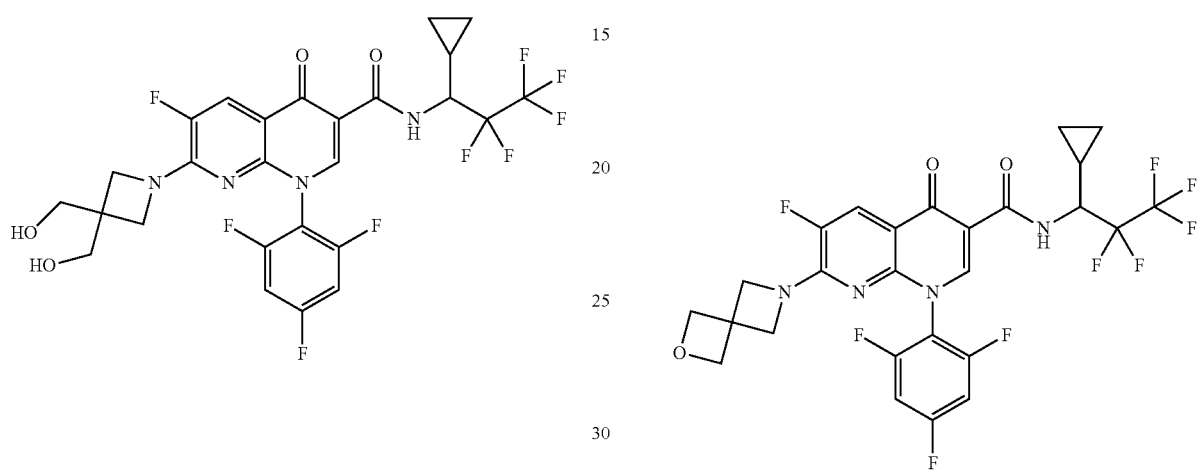

N-[1-cyclopropyl-2,2,3,3,3-pentafluoropropyl]-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide (enantiomer 1) (150 mg, 247 µmol) was initially charged in trifluoroacetic acid (1.5 ml, 20 mmol), 1.5 ml of water and 1.5 ml of acetonitrile were added and the mixture was stirred at room temperature for 2 days. The reaction solution was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave a total of 115 mg of the target compound (73% of theory, purity 98%).

LC-MS (Method 3): $R_t$=1.99 min; MS (ESIpos): m/z=625 [M+H]$^+$ $^1$H NMR (400 MHz, DMSO-d6) δ[ppm]: −0.149 (0.47), 0.146 (0.44), 0.304 (0.53), 0.316 (1.31), 0.328 (2.04), 0.340 (2.20), 0.352 (1.72), 0.365 (0.74), 0.483 (0.59), 0.495 (1.58), 0.507 (2.26), 0.519 (1.97), 0.531 (1.51), 0.542 (0.72), 0.563 (0.67), 0.585 (1.65), 0.597 (1.87), 0.607 (1.59), 0.618 (1.38), 0.630 (0.76), 0.648 (0.85), 0.669 (1.65), 0.682 (1.90), 0.694 (1.43), 0.715 (0.46), 1.223 (1.12), 1.235 (1.99), 1.245 (1.56), 1.256 (1.80), 1.268 (1.01), 2.329 (0.50), 2.671 (0.54), 3.475 (15.57), 3.488 (16.00), 4.131 (1.02), 4.425 (0.49), 4.448 (1.17), 4.470 (1.51), 4.492 (1.47), 4.514 (1.19), 4.537 (0.49), 4.838 (4.89), 4.851 (11.09), 4.864 (4.84), 7.532 (3.57), 7.554 (6.85), 7.576 (3.60), 7.971 (5.68), 8.000 (5.62), 8.814 (10.62), 10.540 (4.12), 10.564 (3.97).

7-Chloro-N-[1-cyclopropyl-2,2,3,3,3-pentafluoropropyl]-6-fluoro-4-oxo-1-(2,4,6-trifluoro-phenyl)-1,4-dihydro-1,8-naphthyridine-3-carboxamide (enantiomer 2) (150 mg, 276 µmol) was initially charged in 1.5 ml of DMF, and N,N-diisopropylethylamine (480 µl, 2.8 mmol) and ethanedioic acid 2-oxa-6-azaspiro[3.3]heptane (1:2) (59.6 mg, 207 µmol) was added at room temperature. The reaction solution was stirred at room temperature overnight. Water/acetonitrile/TFA were added and the reaction solution was purified by preparative HPLC (RP18 column, mobile phase: acetonitrile/water gradient with addition of 0.1% TFA). This gave 155 mg of the target compound (91% of theory, purity 98%).

LC-MS (Method 1): $R_t$=1.21 min; MS (ESIpos): m/z=607 [M+H]$^+$ $^1$H NMR (400 MHz, DMSO-d6) δ[ppm]: 0.311 (0.62), 0.323 (0.97), 0.335 (1.03), 0.347 (0.80), 0.494 (0.75), 0.505 (1.08), 0.517 (0.94), 0.529 (0.72), 0.580 (0.79), 0.592 (0.89), 0.601 (0.73), 0.613 (0.63), 0.646 (0.40), 0.667 (0.77), 0.680 (0.88), 0.692 (0.68), 1.222 (0.54), 1.234 (0.98), 1.245 (0.72), 1.255 (0.87), 1.267 (0.48), 2.073 (6.92), 4.423 (0.41), 4.447 (0.70), 4.468 (0.86), 4.490 (0.81), 4.512 (0.64), 4.656 (16.00), 7.541 (1.69), 7.563 (3.20), 7.585 (1.69), 7.999 (2.70), 8.028 (2.69), 8.833 (4.83), 10.508 (1.95), 10.532 (1.89).

Example 207

7-[3,3-bis(hydroxymethyl)azetidin-1-yl]-N-[1-cyclopropyl-2,2,3,3,3-pentafluoropropyl]-6-fluoro-4-oxo-1-(2,4,6-trifluorophenyl)-1,4-dihydro-1,8-naphthyridine-3-carboxamide (Enantiomer 2)

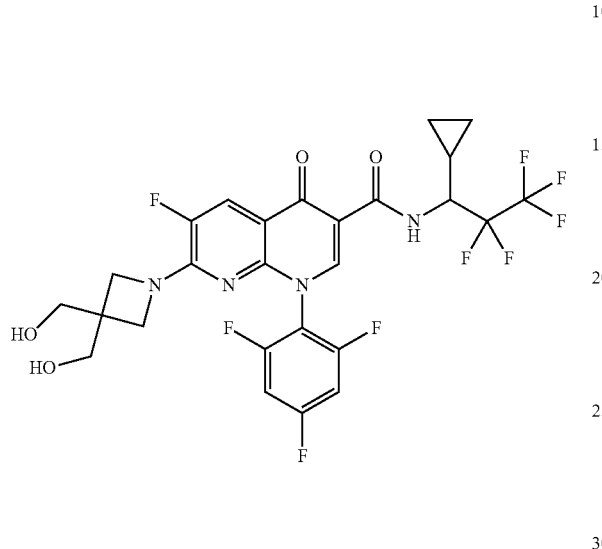

N-[1-cyclopropyl-2,2,3,3,3-pentafluoropropyl]-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide (enantiomer 2) (145 mg, 239 μmol) was initially charged in 1.5 ml of trifluoroacetic acid, 1.5 ml of water and 1.5 ml of acetonitrile were added and the mixture was stirred at room temperature for 2 days. The reaction solution was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave a total of 109 mg of the target compound (72% of theory, purity 98%).

LC-MS (Method 3): $R_t$=1.99 min; MS (ESIpos): m/z=625 [M+H]$^+$ $^1$H NMR (400 MHz, DMSO-d6) δ[ppm]: −0.149 (1.39), −0.008 (10.57), 0.008 (10.54), 0.146 (1.26), 0.315 (1.31), 0.327 (2.02), 0.339 (2.27), 0.351 (1.72), 0.364 (0.76), 0.494 (1.61), 0.506 (2.27), 0.518 (1.97), 0.530 (1.58), 0.562 (0.68), 0.585 (1.64), 0.597 (1.88), 0.606 (1.56), 0.616 (1.37), 0.630 (0.76), 0.648 (0.85), 0.668 (1.64), 0.681 (1.91), 0.693 (1.47), 1.222 (1.17), 1.235 (2.13), 1.244 (1.56), 1.255 (1.86), 1.267 (1.01), 2.328 (1.50), 2.367 (0.98), 2.670 (1.31), 2.710 (0.82), 3.473 (15.78), 3.486 (16.00), 4.138 (1.01), 4.424 (0.46), 4.448 (1.17), 4.470 (1.53), 4.492 (1.50), 4.512 (1.15), 4.536 (0.49), 4.836 (5.16), 4.850 (11.96), 4.863 (5.00), 7.531 (3.88), 7.553 (7.18), 7.575 (3.74), 7.970 (6.53), 7.999 (6.39), 8.813 (11.85), 10.539 (4.31), 10.563 (4.01).

Example 208

N-(1,1-dicyclopropyl-2,2,3,3,3-pentafluoropropyl)-7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxamide

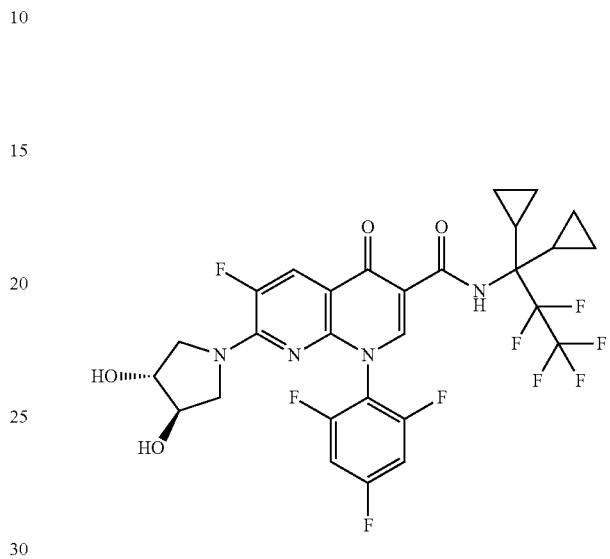

7-Chloro-N-(1,1-dicyclopropyl-2,2,3,3,3-pentafluoropropyl)-6-fluoro-4-oxo-1-(2,4,6-trifluorophenyl)-1,4-dihydro-1,8-naphthyridine-3-carboxamide (65.0 mg, 111 μmol) was initially charged in 0.61 ml of DMF. (3R,4R)-pyrrolidine-3,4-diol hydrochloride (18.6 mg, 134 μmol) and N,N-diisopropylethylamine (97 μl, 560 μmol) were added and the mixture was stirred at room temperature overnight. The reaction solution was diluted with ethyl acetate, extracted twice with water and washed with saturated aqueous sodium chloride solution. The organic phase was dried over sodium sulphate, filtered and concentrated by evaporation. The residue was purified by thick-layer chromatography (mobile phase: dichloromethane/methanol: 30/1). This gave 39 mg of the target compound (52% of theory, purity 97%).

LC-MS (Method 3): $R_t$=2.11 min; MS (ESIpos): m/z=651 [M+H]$^+$ $^1$H NMR (400 MHz, DMSO-d6) δ[ppm]: −0.149 (1.39), −0.008 (11.73), 0.146 (1.28), 0.458 (1.22), 0.481 (3.72), 0.494 (5.46), 0.507 (4.88), 0.516 (3.66), 0.530 (2.18), 0.573 (1.63), 0.585 (3.57), 0.607 (5.78), 0.621 (5.05), 0.642 (5.31), 0.653 (4.70), 0.665 (6.04), 0.678 (4.62), 0.746 (2.09), 0.759 (4.73), 0.771 (5.69), 0.782 (4.94), 0.795 (3.37), 1.236 (0.41), 1.583 (1.57), 1.603 (4.07), 1.618 (6.21), 1.633 (3.80), 1.652 (1.34), 2.328 (1.48), 2.367 (1.02), 2.670 (1.48), 2.711 (0.96), 2.731 (2.90), 2.891 (3.72), 3.069 (1.13), 3.692 (1.13), 3.902 (2.38), 4.017 (1.66), 5.202 (4.79), 7.551 (4.24), 7.573 (7.64), 7.594 (4.18), 7.952 (0.46), 8.036 (9.03), 8.068 (8.94), 8.781 (16.00), 9.849 (11.73).

Example 209

N-(1,1-dicyclopropyl-2,2,2-trifluoroethyl)-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide

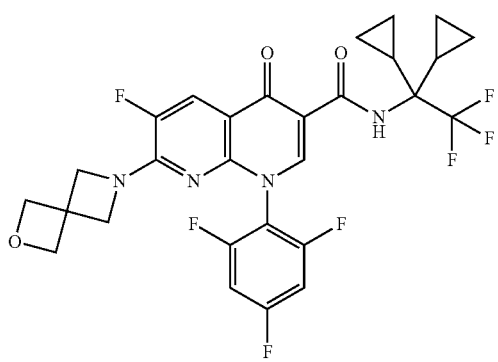 [SMILES: O=C(NC(C1CC1)(C1CC1)C(F)(F)F)c1cn(-c2c(F)cc(F)cc2F)c2nc(N3CC4(COC4)C3)c(F)cc2c1=O]

7-Chloro-N-(1,1-dicyclopropyl-2,2,2-trifluoroethyl)-6-fluoro-4-oxo-1-(2,4,6-trifluoro-phenyl)-1,4-dihydro-1,8-naphthyridine-3-carboxamide (110 mg, 206 µmol) was initially charged in 1.1 ml of DMF, and N,N-diisopropylethylamine (360 µl, 2.1 mmol) and ethanedioic acid 2-oxa-6-azaspiro[3.3]heptane (1:2) (44.6 mg, 155 µmol) were added at room temperature. The reaction solution was stirred at room temperature overnight. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave 103 mg of the target compound (83% of theory, purity 99%).

LC-MS (Method 1): $R_t$=1.24 min; MS (ESIpos): m/z=597 [M+H]$^+$ $^1$H NMR (400 MHz, DMSO-d6) δ[ppm]: 0.008 (1.29), 0.467 (0.73), 0.477 (1.28), 0.489 (1.66), 0.501 (1.73), 0.512 (1.08), 0.523 (0.83), 0.549 (0.55), 0.561 (1.16), 0.575 (1.38), 0.583 (1.83), 0.597 (2.14), 0.612 (1.47), 0.621 (1.72), 0.635 (2.11), 0.648 (1.72), 0.661 (0.65), 0.674 (0.87), 0.688 (1.65), 0.699 (1.84), 0.711 (1.41), 0.723 (0.91), 1.157 (0.53), 1.175 (1.07), 1.193 (0.55), 1.234 (0.46), 1.511 (0.59), 1.526 (1.23), 1.533 (1.33), 1.547 (2.25), 1.561 (1.23), 1.568 (1.10), 1.582 (0.48), 1.989 (1.96), 4.021 (0.56), 4.039 (0.57), 4.653 (16.00), 7.540 (1.63), 7.562 (3.02), 7.584 (1.63), 8.022 (2.63), 8.052 (2.62), 8.774 (4.75), 9.847 (3.87).

Example 210

7-[3,3-bis(hydroxymethyl)azetidin-1-yl]-N-(1,1-dicyclopropyl-2,2,2-trifluoroethyl)-6-fluoro-4-oxo-1-(2,4,6-trifluorophenyl)-1,4-dihydro-1,8-naphthyridine-3-carboxamide

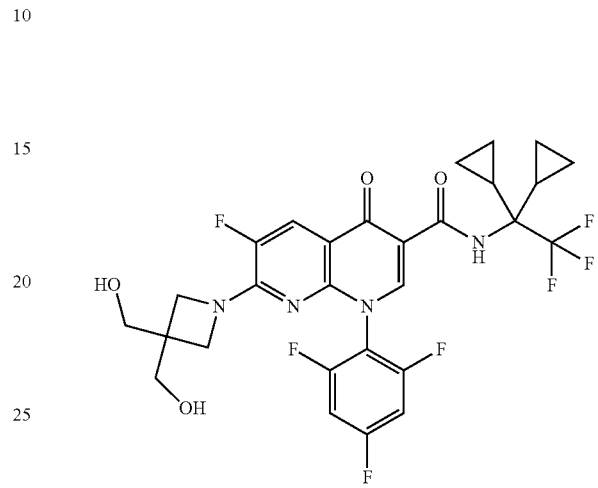

N-(1,1-dicyclopropyl-2,2,2-trifluoroethyl)-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide (101 mg, 169 µmol) was initially charged in 1.1 ml of trifluoroacetic acid, 1.1 ml of water and 1.1 ml of acetonitrile were added and the mixture was stirred at room temperature for 5 days. The reaction solution was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 73 mg of the target compound (69% of theory, purity 98%).

LC-MS (Method 3): $R_t$=2.04 min; MS (ESIpos): m/z=615 [M+H]$^+$ $^1$H NMR (400 MHz, DMSO-d6) δ[ppm]: -0.150 (0.53), -0.008 (5.14), 0.008 (3.74), 0.146 (0.41), 0.477 (2.86), 0.490 (3.72), 0.501 (3.85), 0.523 (2.02), 0.549 (1.30), 0.560 (2.71), 0.575 (3.25), 0.583 (4.07), 0.597 (4.09), 0.617 (3.56), 0.638 (4.71), 0.651 (3.83), 0.664 (1.54), 0.679 (1.91), 0.693 (3.58), 0.704 (4.17), 0.716 (3.19), 0.727 (2.12), 1.233 (0.56), 1.398 (0.74), 1.513 (1.40), 1.528 (3.00), 1.535 (3.25), 1.549 (5.10), 1.563 (2.94), 1.570 (2.49), 1.584 (1.01), 2.073 (0.82), 2.328 (1.36), 2.366 (0.60), 2.670 (1.15), 2.710 (0.43), 3.472 (15.94), 3.485 (16.00), 4.119 (1.05), 4.834 (4.67), 4.847 (11.54), 4.861 (4.71), 7.530 (4.15), 7.551 (7.26), 7.573 (4.17), 7.992 (8.12), 8.021 (7.88), 8.752 (14.09), 9.875 (9.11).

Example 211

N-(1,1-dicyclopropyl-2,2,3,3,3-pentafluoropropyl)-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide

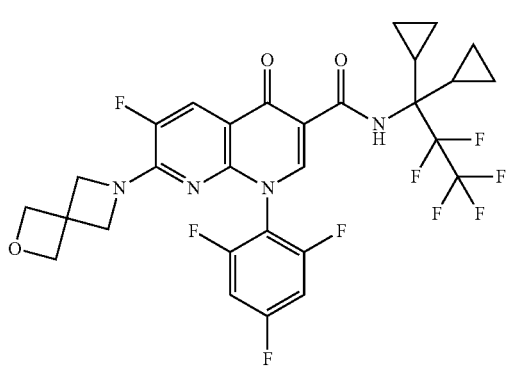 [SMILES: O=C(NC(C1CC1)(C1CC1)C(F)(F)C(F)(F)F)c1cn(-c2c(F)cc(F)cc2F)c2nc(N3CC4(COC4)C3)c(F)cc2c1=O]

7-Chloro-N-(1,1-dicyclopropyl-2,2,3,3,3-pentafluoropropyl)-6-fluoro-4-oxo-1-(2,4,6-trifluorophenyl)-1,4-dihydro-1,8-naphthyridine-3-carboxamide (100 mg, 171 μmol) was initially charged in 0.93 ml of DMF, and N,N-diisopropylethylamine (300 μl, 1.7 mmol) and ethanedioic acid 2-oxa-6-azaspiro[3.3]heptane (1:2) (37.0 mg, 128 μmol) were added at room temperature. The reaction solution was stirred at room temperature overnight. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave 78 mg of the target compound (70% of theory, purity 99%).

LC-MS (Method 1): $R_t$=1.29 min; MS (ESIpos): m/z=647 [M+H]$^+$ $^1$H NMR (400 MHz, DMSO-d6) δ[ppm]: −0.149 (0.66), −0.023 (0.56), −0.008 (5.12), 0.008 (4.77), 0.146 (0.63), 0.476 (1.08), 0.489 (1.56), 0.503 (1.47), 0.524 (0.69), 0.569 (0.47), 0.581 (1.08), 0.603 (1.73), 0.617 (1.90), 0.628 (1.56), 0.640 (1.72), 0.654 (1.83), 0.666 (1.34), 0.733 (0.65), 0.747 (1.38), 0.759 (1.65), 0.769 (1.41), 0.783 (0.97), 1.175 (0.44), 1.234 (0.81), 1.575 (0.48), 1.596 (1.18), 1.611 (1.90), 1.625 (1.10), 1.988 (0.81), 2.328 (0.74), 2.366 (0.55), 2.523 (1.79), 2.665 (0.58), 2.670 (0.79), 2.710 (0.54), 4.653 (16.00), 7.538 (1.67), 7.559 (3.03), 7.581 (1.69), 8.025 (3.04), 8.054 (2.96), 8.777 (5.19), 9.818 (3.56).

Example 212

7-[3,3-bis(hydroxymethyl)azetidin-1-yl]-N-(1,1-dicyclopropyl-2,2,3,3,3-pentafluoropropyl)-6-fluoro-4-oxo-1-(2,4,6-trifluorophenyl)-1,4-dihydro-1,8-naphthyridine-3-carboxamide

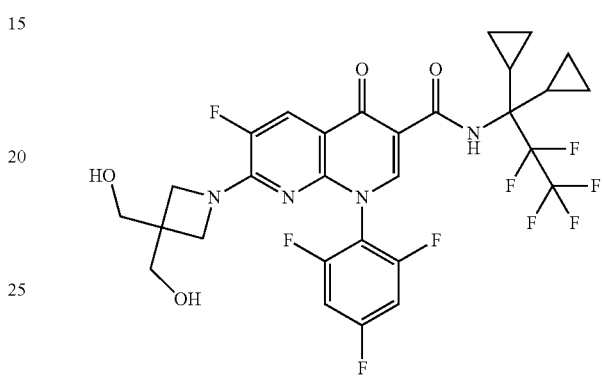

N-(1,1-dicyclopropyl-2,2,3,3,3-pentafluoropropyl)-6-fluoro-7-(2-oxa-6-azaspiro[3.3]hept-6-yl)-4-oxo-1-(2,4,6-trifluorophenyl)-1,4-dihydro-1,8-naphthyridine-3-carboxamide (75.0 mg, 116 μmol) was initially charged in 0.73 ml of trifluoroacetic acid, 0.73 ml of water and 0.73 ml of acetonitrile were added and the mixture was stirred at room temperature for 5 days. The reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave 44 mg of the target compound (56% of theory, purity 98%).

LC-MS (Method 3): $R_t$=2.16 min; MS (ESIpos): m/z=665 [M+H]$^+$ $^1$H NMR (400 MHz, DMSO-d6) δ[ppm]: −0.150 (0.64), −0.008 (5.04), 0.008 (4.74), 0.146 (0.55), 0.491 (3.45), 0.504 (3.22), 0.526 (1.41), 0.582 (2.36), 0.604 (3.62), 0.618 (3.82), 0.645 (3.27), 0.658 (3.89), 0.671 (2.90), 0.752 (2.98), 0.764 (3.70), 0.776 (3.18), 1.235 (0.62), 1.599 (2.63), 1.614 (4.19), 1.627 (2.53), 2.328 (1.31), 2.368 (0.64), 2.670 (1.41), 2.710 (0.52), 3.471 (15.83), 3.484 (16.00), 4.132 (1.04), 4.835 (5.06), 4.849 (12.18), 4.862 (4.99), 7.528 (3.94), 7.551 (6.85), 7.572 (3.84), 7.995 (7.42), 8.024 (7.12), 8.757 (13.07), 9.846 (7.81).

Example 213

6-Fluoro-7-(2-oxa-6-azaspiro[3.3]hept-6-yl)-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 1)

Example 214

7-[3,3-bis(hydroxymethyl)azetidin-1-yl]-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 1)

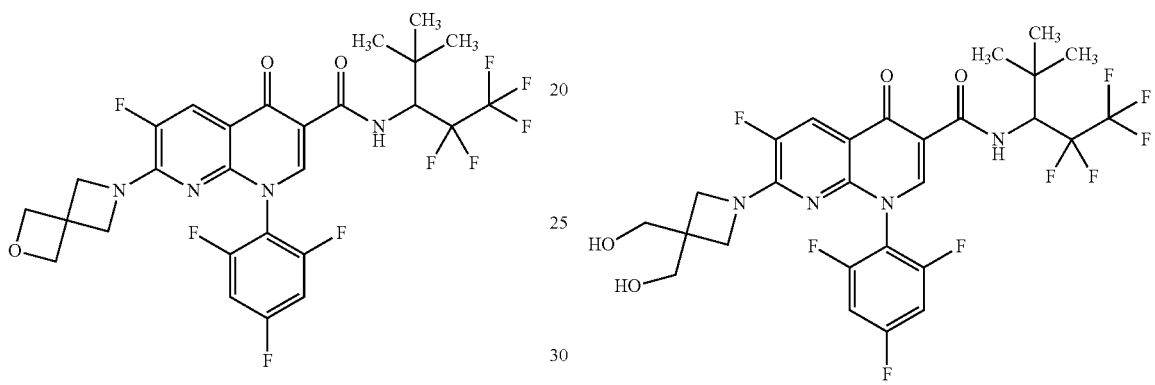

7-Chloro-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (enantiomer 1) (150 mg, 268 µmol) was initially charged in 1.5 ml of DMF, and N,N-diisopropylethylamine (470 µl, 2.7 mmol) and ethanedioic acid 2-oxa-6-azaspiro[3.3]heptane (1:2) (57.9 mg, 201 µmol) were added at room temperature. The reaction solution was stirred at room temperature overnight. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 123 mg of the target compound (72% of theory, purity 98%).

LC-MS (Method 1): $R_t$=1.31 min; MS (ESIpos): m/z=623 [M+H]$^+$ $^1$H NMR (400 MHz, DMSO-d6) δ[ppm]: 1.102 (16.00), 4.657 (10.77), 4.678 (0.51), 4.708 (0.42), 4.753 (0.44), 4.780 (0.42), 7.539 (1.26), 7.561 (2.36), 7.583 (1.24), 8.032 (2.26), 8.061 (2.18), 8.856 (4.05), 10.687 (1.25), 10.713 (1.19).

1.6 ml of acetonitrile, 1.6 ml of water and 1.6 ml of trifluoroacetic acid were added to 6-fluoro-7-(2-oxa-6-azaspiro[3.3]hept-6-yl)-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (enantiomer 1) (120 mg, 98% purity, 189 µmol), and the mixture was stirred at room temperature for 5 days. The reaction solution was purified directly by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave a total of 102 mg of the target compound (83% of theory, purity 98%).

LC-MS (Method 1): $R_t$=1.14 min; MS (ESIpos): m/z=641 [M+H]$^+$ $^1$H NMR (400 MHz, DMSO-d6) δ[ppm]: −0.008 (1.02), 0.008 (0.91), 1.104 (16.00), 2.328 (0.56), 2.670 (0.54), 3.472 (5.03), 3.486 (5.11), 4.680 (0.43), 4.707 (0.43), 4.754 (0.46), 4.780 (0.45), 4.839 (1.68), 4.853 (4.05), 4.866 (1.67), 7.530 (1.27), 7.552 (2.42), 7.574 (1.30), 8.004 (2.43), 8.033 (2.39), 8.837 (4.32), 10.716 (1.34), 10.742 (1.24).

Example 215

6-Fluoro-7-(2-oxa-6-azaspiro[3.3]hept-6-yl)-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 2)

Example 216

7-[3,3-bis(hydroxymethyl)azetidin-1-yl]-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 2)

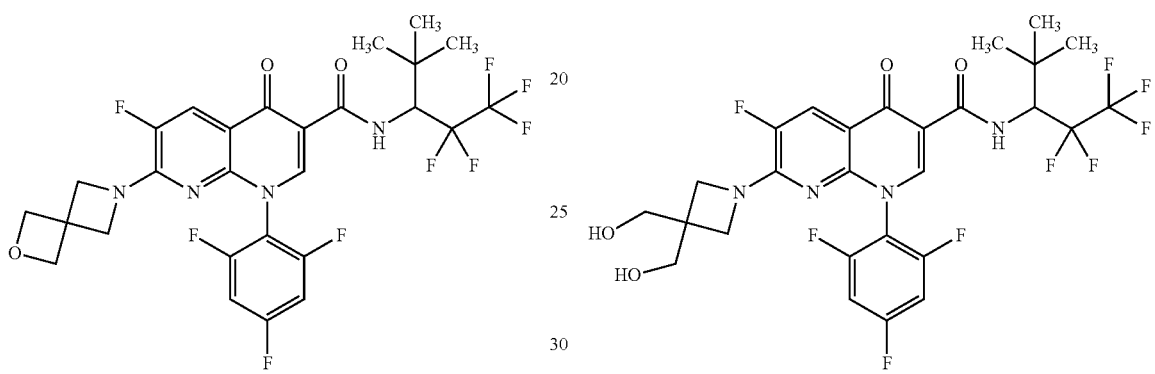

7-Chloro-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (enantiomer 2) (150 mg, 268 μmol) was initially charged in 1.5 ml of DMF, and N,N-diisopropylethylamine (470 μl, 2.7 mmol) and ethanedioic acid 2-oxa-6-azaspiro[3.3]heptane (1:2) (57.9 mg, 201 μmol) were added at room temperature. The reaction solution was stirred at room temperature for 4 h. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave 122 mg of the target compound (72% of theory, purity 98%).

LC-MS (Method 1): $R_t$=1.31 min; MS (ESIpos): m/z=623 [M+H]$^+$ $^1$H NMR (400 MHz, DMSO-d6) δ[ppm]: −0.008 (0.66), 0.008 (0.52), 1.102 (16.00), 2.524 (0.75), 4.656 (10.99), 4.678 (0.52), 4.706 (0.46), 4.752 (0.45), 4.778 (0.43), 7.539 (1.20), 7.561 (2.29), 7.583 (1.22), 8.032 (2.18), 8.061 (2.14), 8.856 (3.81), 10.686 (1.28), 10.713 (1.22).

1.6 ml of acetonitrile, 1.6 ml of water and 1.6 ml of trifluoroacetic acid were added to 6-fluoro-7-(2-oxa-6-azaspiro[3.3]hept-6-yl)-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (enantiomer 2) (120 mg, 98% purity, 189 μmol), and the mixture was stirred at room temperature for 5 days. The reaction solution was purified directly by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. This gave a total of 97 mg of the target compound (79% of theory, purity 98%).

LC-MS (Method 1): $R_t$=1.14 min; MS (ESIpos): m/z=641 [M+H]$^+$ $^1$H NMR (400 MHz, DMSO-d6) δ[ppm]: −0.008 (0.78), 0.008 (0.79), 1.105 (16.00), 3.473 (5.01), 3.486 (5.13), 4.681 (0.40), 4.707 (0.41), 4.754 (0.42), 4.781 (0.42), 4.839 (1.70), 4.853 (4.02), 4.866 (1.66), 7.530 (1.22), 7.552 (2.31), 7.574 (1.21), 8.004 (2.16), 8.033 (2.10), 8.838 (3.89), 10.716 (1.29), 10.742 (1.23).

Example 217

7-[(3R,4R)-3,4-dihydroxypyrrolidin-1-yl]-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 1)

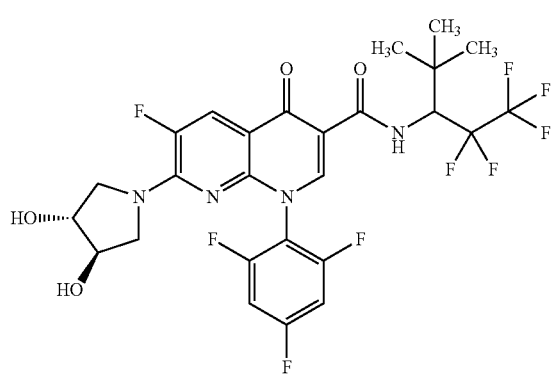 [SMILES: CC(C)(C)C(NC(=O)c1cn(-c2c(F)cc(F)cc2F)c2nc(N3C[C@@H](O)[C@H](O)C3)c(F)cc2c1=O)C(F)(F)C(F)(F)F]

7-Chloro-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (enantiomer 1) (100 mg, 179 µmol) was initially charged in 0.97 ml of DMF. (3R,4R)-pyrrolidine-3,4-diol hydrochloride (29.9 mg, 214 µmol) and N,N-diisopropylethylamine (160 µl, 890 µmol) were added and the mixture was stirred at room temperature for 4 h. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. The residue was purified on silica gel (mobile phase: isocratic: dichloromethane/methanol=50/1). This gave 69 mg of the target compound (60% of theory, purity 98%).

Enantiomer 1: de>88%. $R_t$=5.356 min [analytical HPLC: column Daicel® Chiralpak IA, 5 µm, 250×4.6 mm; 1 ml/min, 70° C.; mobile phase: 80% isohexane/20% ethanol; detection: 220 nm].

LC-MS (Method 1): $R_t$=1.12 min; MS (ESIpos): m/z=627 [M+H]$^+$ $^1$H NMR (400 MHz, DMSO-d6) δ[ppm]: −0.008 (1.17), 0.008 (0.96), 1.109 (16.00), 2.523 (0.73), 3.903 (0.47), 4.761 (0.41), 4.787 (0.41), 5.205 (0.97), 7.554 (0.90), 7.576 (1.58), 7.596 (0.88), 8.044 (2.11), 8.076 (2.07), 8.861 (3.54), 10.720 (1.27), 10.747 (1.22).

Example 218

7-[(3R,4R)-3,4-dihydroxypyrrolidin-1-yl]-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (Enantiomer 2)

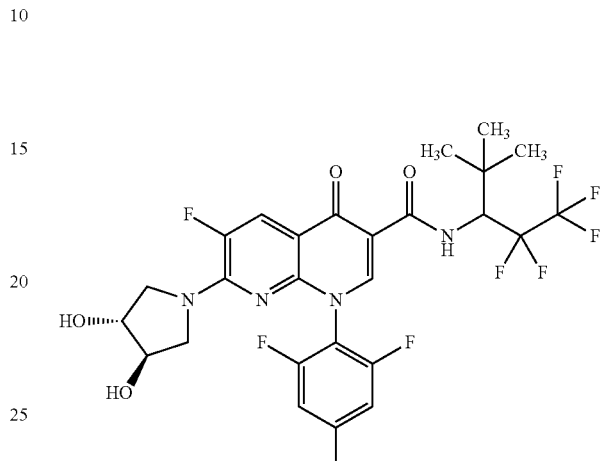

7-Chloro-6-fluoro-4-oxo-N-[1,1,1,2,2-pentafluoro-4,4-dimethylpentan-3-yl]-1-(2,4,6-trifluorophenyl)-1,4-dihydro-1,8-naphthyridine-3-carboxamide (enantiomer 2) (100 mg, 179 µmol) was initially charged in 0.97 ml of DMF. (3R,4R)-pyrrolidine-3,4-diol hydrochloride (29.9 mg, 214 µmol) and N,N-diisopropylethylamine (160 µl, 890 µmol) were added and the mixture was stirred at room temperature for 4 h. Water/acetonitrile/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and a little methanol and washed twice with saturated aqueous sodium bicarbonate solution. The combined aqueous phases were re-extracted twice with dichloromethane. The combined organic phases were dried over sodium sulphate, filtered and concentrated by evaporation. The residue was purified by silica gel (mobile phase: isocratic: dichloromethane/methanol=50/1). This gave 72 mg of the target compound (63% of theory, purity 98%).

Enantiomer 2: de>88.5%. $R_t$=4.677 min [analytical HPLC: column Daicel® Chiralpak IA, 5 µm, 250×4.6 mm; 1 ml/min, 70° C.; mobile phase: 80% isohexane/20% ethanol; detection: 220 nm].

LC-MS (Method 1): $R_t$=1.11 min; MS (ESIpos): m/z=627 [M+H]$^+$ $^1$H NMR (400 MHz, DMSO-d6) δ[ppm]: −0.008 (1.06), 0.008 (0.99), 1.109 (16.00), 2.074 (0.44), 2.523 (0.76), 3.912 (0.47), 4.713 (0.41), 4.760 (0.42), 4.788 (0.41), 5.208 (1.00), 7.554 (0.82), 7.575 (1.47), 7.595 (0.79), 8.044 (2.15), 8.076 (2.10), 8.861 (3.89), 10.720 (1.28), 10.746 (1.21).

Example 219

7-[(3R,4R)-3,4-dihydroxypyrrolidin-1-yl]-6-fluoro-4-oxo-1-(2,4,6-trifluorophenyl)-N-[(2R)-1,1,1-trifluoropropan-2-yl]-1,4-dihydro-1,8-naphthyridine-3-carboxamide

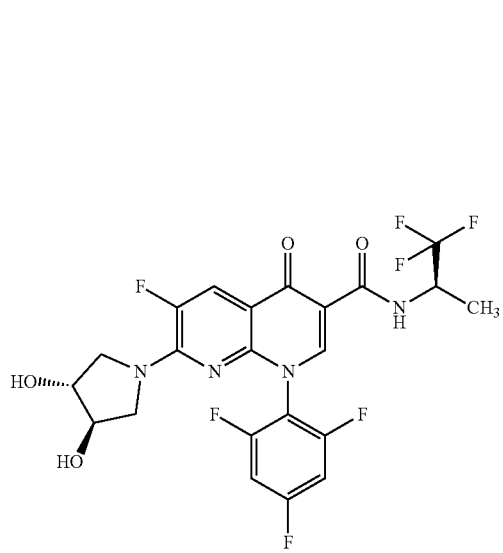 [SMILES: C[C@@H](NC(=O)c1cn(-c2c(F)cc(F)cc2F)c2nc(N3C[C@@H](O)[C@H](O)C3)c(F)cc2c1=O)C(F)(F)F]

7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxylic acid (100 mg, 228 µmol) was initially charged in 1.0 ml of DMF, HATU (95.2 mg, 250 µmol) and N,N-diisopropylethylamine (160 µl, 910 µmol) were added and (2R)-1,1,1-trifluoropropan-2-amine (25 µl, 250 µmol) was added. The reaction solution was stirred at room temperature overnight. Acetonitrile/water/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 74 mg of the target compound (60% of theory, purity 98%).

LC-MS (Method 1): $R_t$=0.89 min; MS (ESIpos): m/z=535 [M+H]$^+$ $^1$H NMR (400 MHz, DMSO-d6) δ[ppm]: −0.008 (3.06), 0.008 (2.77), 1.365 (15.90), 1.383 (16.00), 2.328 (0.77), 2.366 (0.83), 2.670 (0.83), 2.710 (0.77), 3.068 (0.77), 3.690 (0.81), 3.899 (1.79), 4.009 (1.19), 4.861 (1.19), 4.881 (1.83), 4.902 (1.85), 4.921 (1.15), 4.939 (0.42), 5.196 (3.96), 7.556 (3.94), 7.578 (7.04), 7.599 (3.87), 7.988 (7.81), 8.020 (7.73), 8.837 (13.58), 10.382 (5.10), 10.405 (4.90).

Example 220

7-[(3R,4R)-3,4-dihydroxypyrrolidin-1-yl]-6-fluoro-4-oxo-N-(2,2,2-trifluoroethyl)-1-(2,4,6-trifluorophenyl)-1,4-dihydro-1,8-naphthyridine-3-carboxamide

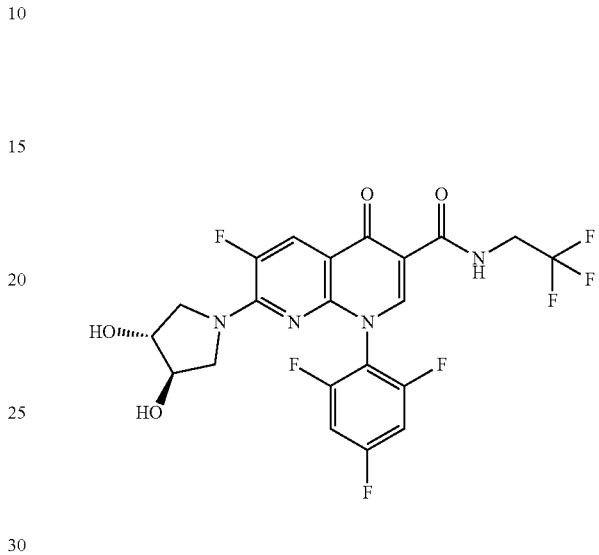

7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxylic acid (80.0 mg, 182 µmol) was initially charged in 1.4 ml of DMF, HATU (83.1 mg, 219 µmol) and N,N-diisopropylethylamine (140 µl, 820 µmol) were added and 2,2,2-trifluorethanamine (21.6 mg, 219 µmol) was added. The reaction mixture was stirred at room temperature for 2 hours. Acetonitrile/water/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. The residue was purified by thick-layer chromatography (mobile phase: dichloromethane/methanol=10/1). This gave 34 mg of the target compound (35% of theory, purity 98%).

LC-MS (Method 1): $R_t$=0.83 min; MS (ESIpos): m/z=521 [M+H]$^+$ $^1$H NMR (400 MHz, DMSO-d6) δ[ppm]: 2.074 (1.03), 2.328 (0.64), 2.367 (0.59), 2.670 (0.55), 2.711 (0.56), 3.058 (0.83), 3.677 (0.89), 3.902 (1.78), 4.192 (1.23), 4.217 (3.82), 4.233 (4.22), 4.241 (3.96), 4.257 (3.78), 4.282 (1.17), 5.196 (5.02), 7.556 (3.74), 7.578 (6.60), 7.599 (3.65), 7.995 (8.81), 8.026 (8.46), 8.838 (16.00), 10.299 (2.67), 10.316 (5.50), 10.332 (2.37).

Example 221

1-(2-Chloro-4,6-difluorophenyl)-7-[(3R,4R)-3,4-dihydroxypyrrolidin-1-yl]-6-fluoro-4-oxo-N-(2,2,2-trifluoroethyl)-1,4-dihydro-1,8-naphthyridine-3-carboxamide (Atropisomer Mixture)

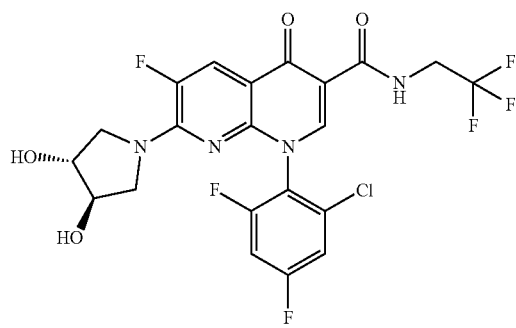 [SMILES: O=C(NCC(F)(F)F)c1cn(-c2c(F)cc(F)cc2Cl)c2nc(N3C[C@@H](O)[C@H](O)C3)c(F)cc2c1=O]

1-(2-Chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic acid (atropisomer mixture) (326 mg, 715 μmol) was initially charged in 3.1 ml of DMF, HATU (299 mg, 787 μmol) and N,N-diisopropylethylamine (500 μl, 2.9 mmol) were added and 2,2,2-trifluorethanamine (62 μl, 790 μmol) was added. The reaction solution was stirred at room temperature for 3 days. Acetonitrile/water/TFA were added and the reaction solution was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 200 mg of the target compound (49% of theory, purity 95%).

LC-MS (Method 3): $R_t$=1.59 min; MS (ESIpos): m/z=537 [M+H]$^+$ $^1$H NMR (400 MHz, DMSO-d6) δ[ppm]: −0.008 (1.90), 0.008 (1.89), 2.073 (6.60), 2.328 (0.43), 2.366 (0.46), 2.670 (0.51), 2.710 (0.49), 3.014 (0.51), 3.228 (0.52), 3.692 (0.57), 3.897 (1.15), 4.011 (0.80), 4.192 (0.87), 4.216 (2.57), 4.233 (2.83), 4.241 (2.64), 4.257 (2.58), 4.282 (0.79), 5.196 (3.43), 5.754 (16.00), 7.685 (0.54), 7.692 (0.86), 7.702 (0.91), 7.708 (0.98), 7.716 (1.72), 7.725 (1.81), 7.731 (1.85), 7.738 (2.30), 7.748 (2.06), 7.762 (1.52), 7.998 (5.32), 8.030 (5.29), 8.788 (10.64), 10.315 (1.72), 10.331 (3.64), 10.347 (1.65).

Example 222

1-(2-Chloro-4,6-difluorophenyl)-7-[(3R,4R)-3,4-dihydroxypyrrolidin-1-yl]-6-fluoro-4-oxo-N-(2,2,2-trifluoroethyl)-1,4-dihydro-1,8-naphthyridine-3-carboxamide (Atropisomer 1)

197 mg of 1-(2-chloro-4,6-difluorophenyl)-7-[(3R,4R)-3,4-dihydroxypyrrolidin-1-yl]-6-fluoro-4-oxo-N-(2,2,2-trifluoroethyl)-1,4-dihydro-1,8-naphthyridine-3-carboxamide (atropisomer mixture) were separated into the atropisomers by chiral HPLC (preparative HPLC: column Daicel® Chiralpak IA, 5 μm, 250×20 mm; mobile phase: 75% n-heptane/25% isopropanol; flow rate 15 ml/min; temperature: 40° C., detection: 220 nm).

Atropisomer 1: 84 mg (stereochemical purity 99%)

$R_t$=10.527 min [analytical HPLC: column Daicel® Chiralpak IA, 1 ml/min; 5 μm, 250×4.6 mm; mobile phase: 80% n-heptane/20% isopropanol+0.2% DEA; detection: 235 nm].

LC-MS (Method 3): $R_t$=1.59 min; MS (ESIpos): m/z=537 [M+H]$^+$ $^1$H NMR (400 MHz, DMSO-d6) δ[ppm]: −0.008 (0.86), 0.008 (0.79), 2.073 (16.00), 2.328 (0.48), 2.670 (0.47), 3.896 (0.71), 4.192 (0.56), 4.216 (1.54), 4.233 (1.68), 4.241 (1.55), 4.257 (1.50), 4.282 (0.44), 5.195 (1.82), 7.685 (0.64), 7.691 (0.96), 7.708 (1.10), 7.715 (1.58), 7.738 (2.03), 7.763 (1.24), 7.999 (3.81), 8.030 (3.71), 8.788 (8.47), 10.315 (1.09), 10.332 (2.20), 10.348 (0.96).

Example 223

1-(2-Chloro-4,6-difluorophenyl)-7-[(3R,4R)-3,4-dihydroxypyrrolidin-1-yl]-6-fluoro-4-oxo-N-(2,2,2-trifluoroethyl)-1,4-dihydro-1,8-naphthyridine-3-carboxamide (Atropisomer 2)

197 mg of 1-(2-chloro-4,6-difluorophenyl)-7-[(3R,4R)-3,4-dihydroxypyrrolidin-1-yl]-6-fluoro-4-oxo-N-(2,2,2-trifluoroethyl)-1,4-dihydro-1,8-naphthyridine-3-carboxamide (atropisomer mixture) were separated into the atropisomers by chiral HPLC (preparative HPLC: column Daicel® Chiralpak IA, 5 μm, 250×20 mm; mobile phase: 75% n-heptane/25% isopropanol; flow rate 15 ml/min; temperature: 40° C., detection: 220 nm).

Atropisomer 2: 84 mg (stereochemical purity 99%)

$R_t$=13.695 min [analytical HPLC: column Daicel® Chiralpak IA, 1 ml/min; 5 μm, 250×4.6 mm; mobile phase: 80% n-heptane/20% isopropanol+0.2% DEA; detection: 235 nm].

LC-MS (Method 3): $R_t$=1.59 min; MS (ESIpos): m/z=537 [M+H]$^+$ $^1$H NMR (400 MHz, DMSO-d6) δ[ppm]: −0.008 (0.69), 2.073 (16.00), 2.328 (0.42), 2.670 (0.40), 3.902 (0.66), 4.192 (0.49), 4.216 (1.51), 4.233 (1.61), 4.241 (1.49), 4.257 (1.48), 4.281 (0.45), 5.196 (2.26), 7.695 (0.64), 7.702 (0.93), 7.717 (0.95), 7.725 (2.09), 7.730 (1.75), 7.740 (1.30), 7.751 (1.78), 7.761 (0.81), 7.998 (3.70), 8.030 (3.57), 8.789 (8.25), 10.315 (1.05), 10.331 (2.13), 10.347 (0.95).

Example 224

1-(2-Chloro-4,6-difluorophenyl)-7-[(3R,4R)-3,4-dihydroxypyrrolidin-1-yl]-6-fluoro-4-oxo-N-[(2S)-1,1,1-trifluoropropan-2-yl]-1,4-dihydro-1,8-naphthyridine-3-carboxamide (Atropisomer Mixture)

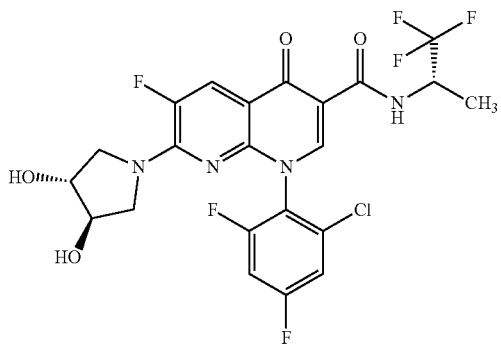 [SMILES: C[C@H](NC(=O)c1cn(-c2c(F)cc(F)cc2Cl)c2nc(N3C[C@@H](O)[C@H](O)C3)c(F)cc2c1=O)C(F)(F)F]

1-(2-Chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic acid (atropisomer mixture) (200 mg, 439 µmol) was initially charged in 1.9 ml of DMF, HATU (184 mg, 483 µmol) and N,N-diisopropylethylamine (310 µl, 1.8 mmol) were added and (2S)-1,1,1-trifluoropropan-2-amine (48 µl, 480 µmol) was added. The reaction solution was stirred at room temperature overnight. Water was added and the reaction solution was stirred briefly. The precipitated solid was filtered off and dried under high vacuum. This gave 240 mg of the target compound (97% of theory, purity 98%).

LC-MS (Method 3): $R_t$=1.72 min; MS (ESIpos): m/z=551 $[M+H]^+$ $^1$H NMR (400 MHz, DMSO-d6) δ[ppm]: 0.936 (16.00), 0.951 (15.00), 1.364 (9.71), 1.370 (9.62), 1.382 (9.80), 2.327 (1.73), 2.366 (1.96), 2.409 (2.10), 2.669 (1.69), 2.690 (5.70), 2.710 (1.60), 2.961 (1.78), 3.889 (1.73), 4.880 (2.05), 5.196 (4.88), 7.715 (2.23), 7.749 (3.69), 7.993 (7.79), 8.025 (7.52), 8.790 (11.94), 10.401 (4.06), 10.425 (4.33).

Example 225

1-(2-Chloro-4,6-difluorophenyl)-7-[(3R,4R)-3,4-dihydroxypyrrolidin-1-yl]-6-fluoro-4-oxo-N-[(2S)-1,1,1-trifluoropropan-2-yl]-1,4-dihydro-1,8-naphthyridine-3-carboxamide (Atropisomer 1)

238 mg of 1-(2-chloro-4,6-difluorophenyl)-7-[(3R,4R)-3,4-dihydroxypyrrolidin-1-yl]-6-fluoro-4-oxo-N-[(2S)-1,1,1-trifluoropropan-2-yl]-1,4-dihydro-1,8-naphthyridine-3-carboxamide (atropisomer mixture) were separated into the atropisomers by chiral HPLC (preparative HPLC: column Daicel® Chiralcel OX-H, 5 µm, 250×20 mm; mobile phase: 75% n-heptane/25% isopropanol; flow rate 15 ml/min; temperature: 45° C., detection: 220 nm).

Atropisomer 1: 82 mg (stereochemical purity>99%)

$R_t$=5.024 min [analytical HPLC: column Daicel® Chiralpak OX-H, 1 ml/min; 5 µm, 250×4.6 mm; mobile phase: 75% isohexane/25% 2-propanol; detection: 220 nm; 30° C.].

LC-MS (Method 3): $R_t$=1.71 min; MS (ESIpos): m/z=551 $[M+H]^+$ $^1$H NMR (400 MHz, DMSO-d6) δ[ppm]: –0.008 (1.60), 0.008 (2.07), 1.365 (15.87), 1.382 (16.00), 2.328 (0.50), 2.670 (0.58), 2.710 (0.44), 3.008 (0.82), 3.226 (0.85), 3.685 (0.85), 3.897 (1.62), 4.007 (1.21), 4.842 (0.45), 4.861 (1.19), 4.880 (1.79), 4.901 (1.84), 4.920 (1.18), 4.939 (0.42), 5.196 (4.26), 7.684 (1.46), 7.691 (2.04), 7.707 (2.51), 7.714 (3.53), 7.730 (1.57), 7.738 (4.02), 7.749 (2.24), 7.765 (2.80), 7.771 (1.97), 7.994 (7.83), 8.026 (7.66), 8.790 (15.94), 10.404 (5.16), 10.427 (4.94).

Example 226

1-(2-Chloro-4,6-difluorophenyl)-7-[(3R,4R)-3,4-dihydroxypyrrolidin-1-yl]-6-fluoro-4-oxo-N-[(2S)-1,1,1-trifluoropropan-2-yl]-1,4-dihydro-1,8-naphthyridine-3-carboxamide (Atropisomer 2)

238 mg of 1-(2-chloro-4,6-difluorophenyl)-7-[(3R,4R)-3,4-dihydroxypyrrolidin-1-yl]-6-fluoro-4-oxo-N-[(2S)-1,1,1-trifluoropropan-2-yl]-1,4-dihydro-1,8-naphthyridine-3-carboxamide (atropisomer mixture) were separated into the atropisomers by chiral HPLC (preparative HPLC: column Daicel® Chiralcel OX-H, 5 µm, 250×20 mm; mobile phase: 75% n-heptane/25% isopropanol; flow rate 15 ml/min; temperature: 45° C., detection: 220 nm).

Atropisomer 2: 97 mg (stereochemical purity>99%)

$R_t$=5.970 min [analytical HPLC: column Daicel® Chiralpak OX-H, 1 ml/min; 5 µm, 250×4.6 mm; mobile phase: 75% isohexane/25% 2-propanol; detection: 220 nm; 30° C.].

LC-MS (Method 3): $R_t$=1.72 min; MS (ESIpos): m/z=551 $[M+H]^+$ $^1$H NMR (400 MHz, DMSO-d6) δ[ppm]: –0.008 (1.15), 0.008 (1.11), 1.371 (15.90), 1.388 (16.00), 3.040 (0.78), 3.214 (0.79), 3.687 (0.79), 3.892 (1.56), 4.007 (1.16), 4.842 (0.43), 4.861 (1.15), 4.881 (1.74), 4.901 (1.80), 4.920 (1.14), 4.938 (0.40), 5.197 (5.26), 7.696 (1.32), 7.703 (2.00), 7.719 (2.02), 7.726 (5.20), 7.740 (2.37), 7.750 (4.75), 7.761 (1.73), 7.993 (7.49), 8.025 (7.38), 8.788 (14.24), 10.401 (5.13), 10.425 (4.92).

Example 227

1-(2-Chloro-4,6-difluorophenyl)-7-[(3R,4R)-3,4-dihydroxypyrrolidin-1-yl]-6-fluoro-4-oxo-N-[(2R)-1,1,1-trifluoropropan-2-yl]-1,4-dihydro-1,8-naphthyridine-3-carboxamide (Atropisomer Mixture)

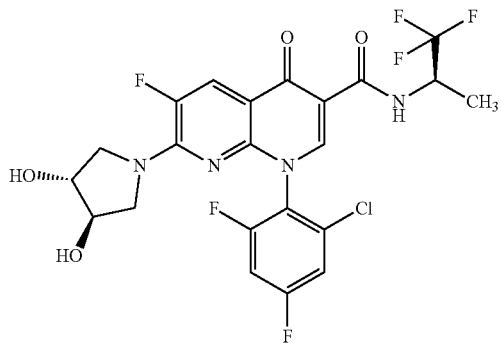 [SMILES: C[C@@H](NC(=O)c1cn(-c2c(F)cc(F)cc2Cl)c2nc(N3C[C@@H](O)[C@H](O)C3)c(F)cc2c1=O)C(F)(F)F]

1-(2-Chloro-4,6-difluorophenyl)-7-[(3R,4R)-3,4-dihydroxypyrrolidin-1-yl]-6-fluoro-4-oxo-1,4-dihydro-1,8-naphthyridine-3-carboxylic acid (atropisomer mixture) (200 mg, 439 µmol) was initially charged in 1.9 ml of DMF, HATU (184 mg, 483 µmol) and N,N-diisopropylethylamine (310 µl, 1.8 mmol) were added and (2R)-1,1,1-trifluoropropan-2-amine (48 µl, 480 µmol) was added. The reaction solution was stirred at room temperature overnight. Water was added and the reaction solution was stirred briefly. The precipitated solid was filtered off and dried under high vacuum. This gave 237 mg of the target compound (96% of theory, purity 98%).

LC-MS (Method 3): $R_t$=1.72 min; MS (ESIpos): m/z=551 [M+H]$^+$ $^1$H NMR (400 MHz, DMSO-d6) δ[ppm]: 0.936 (16.00), 0.951 (14.58), 1.369 (6.83), 1.382 (6.68), 2.327 (0.76), 2.366 (0.73), 2.410 (2.10), 2.427 (2.17), 2.671 (0.62), 2.690 (1.63), 2.709 (0.51), 2.945 (1.23), 2.961 (1.57), 2.978 (1.45), 3.695 (0.70), 3.897 (1.41), 4.861 (0.87), 4.880 (1.32), 4.899 (1.29), 5.194 (3.33), 7.717 (1.99), 7.741 (2.83), 7.992 (3.63), 8.024 (3.64), 8.788 (6.15), 10.401 (2.85), 10.424 (2.73).

Example 228

1-(2-Chloro-4,6-difluorophenyl)-7-[(3R,4R)-3,4-dihydroxypyrrolidin-1-yl]-6-fluoro-4-oxo-N-[(2R)-1,1,1-trifluoropropan-2-yl]-1,4-dihydro-1,8-naphthyridine-3-carboxamide (Atropisomer 1)

235 mg of 1-(2-chloro-4,6-difluorophenyl)-7-[(3R,4R)-3,4-dihydroxypyrrolidin-1-yl]-6-fluoro-4-oxo-N-[(2R)-1,1,1-trifluoropropan-2-yl]-1,4-dihydro-1,8-naphthyridine-3-carboxamide (atropisomer mixture) were separated into the atropisomers by chiral HPLC (preparative HPLC: column Daicel® Chiralpak IE, 5 µm, 250×20 mm; mobile phase: 80% n-heptane/20% ethanol; flow rate 15 ml/min; temperature: 40° C., detection: 220 nm).

Atropisomer 1: 89.4 mg (stereochemical purity>99%)

$R_t$=6.076 min [analytical HPLC: column Daicel® Chiralpak IE, 1 ml/min; 5 µm, 250×4.6 mm; mobile phase: 80% isohexane/20% ethanol; detection: 220 nm; temperature: 30° C.].

LC-MS (Method 3): $R_t$=1.73 min; MS (ESIpos): m/z=551 [M+H]$^+$ $^1$H NMR (400 MHz, DMSO-d6) δ[ppm]: −0.008 (1.70), 0.008 (1.45), 1.364 (14.98), 1.382 (15.05), 2.328 (0.41), 2.367 (0.45), 2.690 (1.41), 2.711 (0.46), 3.032 (0.73), 3.212 (0.75), 3.686 (0.73), 3.899 (1.50), 4.005 (1.04), 4.842 (0.41), 4.861 (1.09), 4.880 (1.66), 4.900 (1.68), 4.920 (1.05), 5.196 (4.33), 7.694 (1.34), 7.701 (2.01), 7.717 (2.15), 7.724 (4.15), 7.731 (3.32), 7.741 (2.73), 7.747 (3.08), 7.753 (3.30), 7.763 (1.74), 7.993 (7.70), 8.024 (7.55), 8.790 (16.00), 10.402 (4.83), 10.425 (4.63).

Example 229

1-(2-Chloro-4,6-difluorophenyl)-7-[(3R,4R)-3,4-dihydroxypyrrolidin-1-yl]-6-fluoro-4-oxo-N-[(2R)-1,1,1-trifluoropropan-2-yl]-1,4-dihydro-1,8-naphthyridine-3-carboxamide (Atropisomer 2)

235 mg of 1-(2-chloro-4,6-difluorophenyl)-7-[(3R,4R)-3,4-dihydroxypyrrolidin-1-yl]-6-fluoro-4-oxo-N-[(2R)-1,1,1-trifluoropropan-2-yl]-1,4-dihydro-1,8-naphthyridine-3-carboxamide (atropisomer mixture) were separated into the atropisomers by chiral HPLC (preparative HPLC: column Daicel® Chiralpak IE, 5 µm, 250×20 mm; mobile phase: 80% n-heptane/20% ethanol; flow rate 15 ml/min; temperature: 40° C., detection: 220 nm).

Atropisomer 2: 95.7 mg (stereochemical purity>99%)

$R_t$=7.196 min [analytical HPLC: column Daicel® Chiralpak IE, 1 ml/min; 5 µm, 250×4.6 mm; mobile phase: 80% isohexane/20% ethanol; detection: 220 nm; temperature: 30° C.].

LC-MS (Method 3): $R_t$=1.73 min; MS (ESIpos): m/z=551 [M+H]$^+$ $^1$H NMR (400 MHz, DMSO-d6) δ[ppm]: −0.008 (1.62), 0.008 (1.41), 1.244 (0.79), 1.258 (0.97), 1.272 (0.54), 1.370 (15.93), 1.388 (16.00), 2.366 (0.45), 2.710 (0.46), 3.012 (0.80), 3.240 (0.83), 3.692 (0.82), 3.892 (1.67), 4.008 (1.18), 4.842 (0.44), 4.861 (1.18), 4.880 (1.76), 4.901 (1.80), 4.920 (1.17), 4.938 (0.42), 5.196 (3.63), 7.686 (1.44), 7.693 (2.00), 7.709 (2.44), 7.716 (3.55), 7.740 (4.63), 7.748 (2.20), 7.758 (2.62), 7.762 (2.72), 7.769 (1.86), 7.993 (7.82), 8.024 (7.71), 8.788 (15.55), 10.401 (5.16), 10.424 (4.94).

Example 230

7-[3,3-bis(hydroxymethyl)azetidin-1-yl]-6-fluoro-N-(1,1,1,3,3,3-hexafluoropropan-2-yl)-4-oxo-1-(2,4,6-trifluorophenyl)-1,4-dihydro-1,8-naphthyridine-3-carboxamide

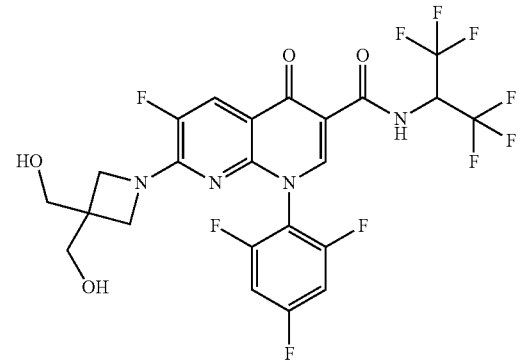 [SMILES: O=C(NC(C(F)(F)F)C(F)(F)F)c1cn(-c2c(F)cc(F)cc2F)c2nc(N3CC(CO)(CO)C3)c(F)cc2c1=O]

6-Fluoro-N-(1,1,1,3,3,3-hexafluoropropan-2-yl)-7-(2-oxa-6-azaspiro[3.3]hept-6-yl)-4-oxo-1-(2,4,6-trifluorophenyl)-1,4-dihydro-1,8-naphthyridine-3-carboxamide (88.0 mg, 99% purity, 149 µmol) was initially charged in 930 µl of acetonitrile, 930 µl of water and 930 µl of trifluoroacetic acid were added and the mixture was stirred at room temperature for 18 h. The mixture was purified by preparative HPLC (column: acetonitrile/water/0.1% formic acid).

The product fractions were concentrated under reduced pressure and the residue was dissolved in a little dichloromethane and washed three times with saturated aqueous sodium bicarbonate solution. The combined organic phases were dried over sodium sulphate, filtered and concentrated under reduced pressure. This gave 56.0 mg of the target compound (62% of theory, purity 100%).

LC-MS (Method 3): $R_t$=1.95 min; MS (ESIpos): m/z=603 [M+H]$^+$ $^1$H NMR (400 MHz, DMSO-d6) δ[ppm]: −0.149 (0.90), −0.008 (7.60), 0.008 (7.41), 0.146 (0.92), 1.157 (0.56), 1.175 (1.07), 1.193 (0.56), 1.989 (1.96), 2.328 (0.67), 2.367 (0.42), 2.671 (0.73), 2.711 (0.44), 3.475 (15.50), 3.489 (16.00), 4.021 (0.69), 4.039 (0.67), 4.142 (1.21), 4.842 (5.05), 4.855 (11.74), 4.868 (4.99), 6.294 (0.86), 6.312 (1.25), 6.336 (1.32), 6.354 (0.84), 7.546 (3.66), 7.568 (6.71), 7.590 (3.68), 7.991 (6.48), 8.020 (6.43), 8.945 (11.99), 11.295 (4.16), 11.320 (4.05).

Example 231

N-[(1S)-1-cyclopropyl-2,2,2-trifluoroethyl]-6-fluoro-4-oxo-7-(pyrrolidin-1-yl)-1-(2,4,6-tri-fluorophenyl)-1,4-dihydro-1,8-naphthyridine-3-carboxamide

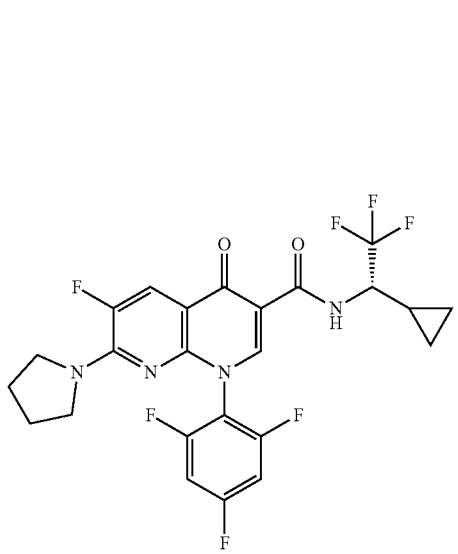 [SMILES: O=C(N[C@@H](C1CC1)C(F)(F)F)c1cn(-c2c(F)cc(F)cc2F)c2nc(N3CCCC3)c(F)cc2c1=O]

According to GP3, 80.0 mg (162 µmol) of 7-chloro-N-[(1S)-1-cyclopropyl-2,2,2-trifluoroethyl]-6-fluoro-4-oxo-1-(2,4,6-trifluorophenyl)-1,4-dihydro-1,8-naphthyridine-3-carboxamide were reacted with 27 µl (320 µmol) of pyrrolidine and 110 µl (650 µmol) of N,N-diisopropylethylamine in 1.0 ml of dimethylformamide. The crude product was diluted with a little acetonitrile and purified by preparative HPLC (column: acetonitrile/water/0.1% formic acid).

This gave 51.1 mg (59% of theory, about 96% pure) of the title compound.

LC-MS (Method 5): $R_t$=1.66 min; MS (ESIpos): m/z=529 [M+H]$^+$ $^1$H NMR (400 MHz, DMSO-d6) δ[ppm]: −0.149 (0.42), 0.146 (0.41), 0.319 (1.90), 0.329 (3.08), 0.342 (3.03), 0.353 (2.43), 0.365 (1.16), 0.500 (0.75), 0.512 (2.08), 0.523 (3.11), 0.536 (2.78), 0.547 (3.13), 0.555 (2.37), 0.566 (3.17), 0.576 (2.59), 0.587 (2.34), 0.597 (1.95), 0.611 (1.18), 0.626 (1.63), 0.636 (1.55), 0.647 (2.81), 0.657 (2.44), 0.663 (2.34), 0.670 (2.33), 0.682 (1.12), 0.691 (0.77), 1.166 (0.55), 1.178 (1.16), 1.187 (1.72), 1.198 (2.98), 1.208 (2.16), 1.219 (2.96), 1.231 (1.96), 1.239 (1.14), 1.252 (0.47), 1.840 (8.25), 2.329 (0.52), 2.671 (0.59), 4.334 (0.42), 4.353 (1.62), 4.374 (2.83), 4.396 (2.79), 4.416 (1.47), 7.536 (5.42), 7.558 (10.40), 7.580 (5.46), 7.975 (7.58), 8.007 (7.54), 8.821 (16.00), 10.476 (6.10), 10.500 (5.89).

Example 232

6-Bromo-7-[(3S)-3-hydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (Enantiomerically Pure)

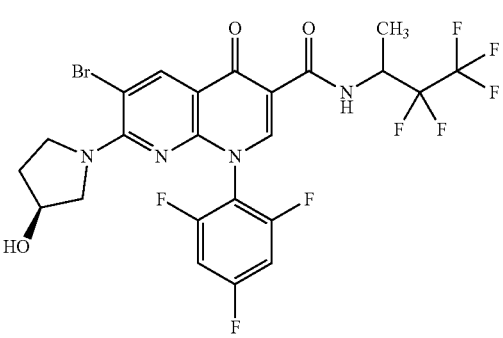 [SMILES: CC(NC(=O)c1cn(-c2c(F)cc(F)cc2F)c2nc(N3CC[C@H](O)C3)c(Br)cc2c1=O)C(F)(F)C(F)(F)F]

At RT, 3.47 g (19.5 mmol) of 1-bromopyrrolidine-2,5-dione (NBS) and 41.0 mg (250 µmol) of 2,2'-(E)-diazene-1,2-diylbis(2-methylpropanenitrile) (AIBN) were added to a solution of 4.99 g (9.07 mmol) of 7-[(3S)-3-hydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (enantiomerically pure) in 120 ml of acetonitrile. The mixture was stirred at 60° C. for 50 min. The reaction mixture was cooled, concentrated to half of its original volume by evaporation and poured onto water and dichloromethane. The phases were separated and the aqueous phase was extracted twice with DCM. The combined organic phases were washed once with sat. sodium chloride solution, dried over sodium sulphate and concentrated. The crude product was purified by normal-phase chromatography (cyclohexane/ethyl acetate gradient). This gave 2.75 g (48% of theory, 100% pure) of the title compound.

LC-MS (Method 1): $R_t$=1.22 min; MS (ESIpos): m/z=629 [M+H]$^+$ $^1$H NMR (400 MHz, DMSO-d6) δ[ppm]: −0.008 (2.11), 0.008 (1.87), 1.386 (9.88), 1.403 (10.35), 1.793 (1.40), 1.849 (1.45), 1.861 (0.98), 1.872 (1.33), 2.074 (0.47), 2.328 (0.74), 2.670 (0.92), 3.461 (1.15), 3.580 (1.46), 4.271 (2.45), 4.980 (3.99), 4.987 (4.14), 5.029 (1.16), 5.052 (0.98), 7.550 (3.37), 7.573 (5.83), 7.594 (3.28), 8.456 (16.00), 8.871 (12.06), 10.322 (4.09), 10.346 (4.07).

Example 233

7-[(3R,4R)-3,4-dihydroxypyrrolidin-1-yl]-6-fluoro-N-[3-methyl-1-(trifluoromethoxy)butan-2-yl]-4-oxo-1-(2,4,6-trifluorophenyl)-1,4-dihydro-1,8-naphthyridine-3-carboxamide (Diastereomer Mixture)

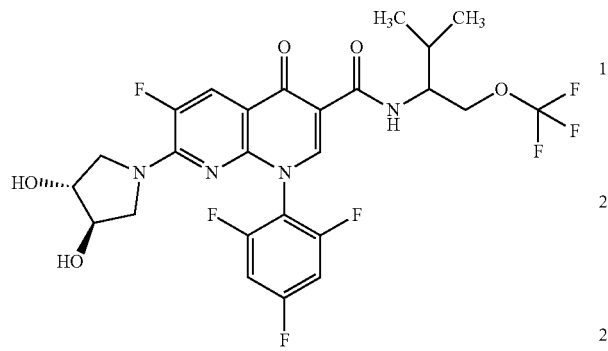

7-[(3R,4R)-3,4-dihydroxypyrrolidin-1-yl]-6-fluoro-4-oxo-1-(2,4,6-trifluorophenyl)-1,4-dihydro-1,8-naphthyridine-3-carboxylic acid (75.0 mg, 171 µmol) was initially charged in 1.3 ml of DMF, HATU (77.9 mg, 205 µmol) and N,N-diisopropylethylamine (130 µl, 770 µmol) were added and 3-methyl-1-(trifluoromethoxy)butan-2-amine hydrochloride (racemic) (42.5 mg, 205 µmol) was added. The reaction mixture was stirred at room temperature overnight. Ethyl acetate was added and the reaction solution was extracted three times with water and the combined aqueous phases were re-extracted twice with ethyl acetate. The combined organic phases were dried over sodium sulphate, filtered and concentrated by evaporation. Acetonitrile/water/TFA were added to the residue and the mixture was purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 68.6 mg of the target compound (66% of theory, purity 97%).

LC-MS (Method 3): $R_t$=1.91 min; MS (ESIpos): m/z=593 [M+H]$^+$ $^1$H NMR (400 MHz, DMSO-d6) δ[ppm]: −0.008 (1.44), 0.008 (1.38), 0.960 (15.75), 0.977 (16.00), 1.939 (0.91), 1.956 (1.47), 1.973 (1.41), 1.989 (0.85), 2.328 (0.46), 2.524 (1.29), 2.670 (0.53), 3.679 (0.42), 3.679 (0.45), 3.915 (0.96), 4.115 (0.89), 4.128 (1.21), 4.146 (2.56), 4.170 (3.20), 4.181 (1.89), 4.200 (2.19), 4.214 (2.11), 4.225 (1.36), 4.239 (0.74), 5.196 (2.32), 7.553 (1.98), 7.575 (3.41), 7.596 (1.90), 8.014 (4.52), 8.045 (4.46), 8.768 (7.51), 10.088 (2.55), 10.109 (2.43).

Example 234

6-Fluoro-7-(3-methyl-2,4-dioxo-1,3,7-triazaspiro[4.4]non-7-yl)-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

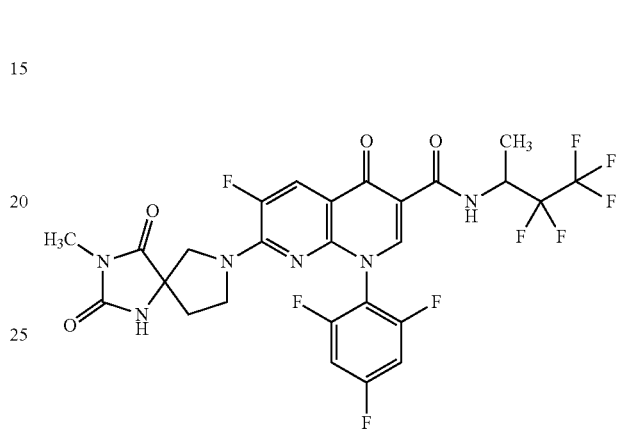

7-Chloro-6-fluoro-4-oxo-N-(3,3,4,4,4-pentafluorobutan-2-yl)-1-(2,4,6-trifluorophenyl)-1,4-dihydro-1,8-naphthyridine-3-carboxamide (enantiomerically pure) (30.0 mg, 57.9 µmol) was initially charged in 0.32 ml of DMF. 3-Methyl-1,3,7-triazaspiro[4.4]nonane-2,4-dione hydrochloride (racemic) (14.3 mg, 69.5 µmol) was added, N,N-diisopropylethylamine (50 µl, 290 µmol) was added and the mixture was stirred at room temperature overnight. The reaction solution was diluted with acetonitrile/water/TFA and purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 35 mg of the target compound (90% of theory, purity 97%).

LC-MS (Method 3): $R_t$=2.01 min; MS (ESIpos): m/z=651 [M+H]$^+$ $^1$H NMR (400 MHz, DMSO-d6) δ[ppm]: −0.149 (0.51), −0.008 (4.35), 0.146 (0.48), 1.387 (4.65), 1.404 (4.66), 2.054 (0.50), 2.247 (0.51), 2.328 (0.89), 2.670 (0.90), 2.839 (16.00), 4.989 (0.42), 5.012 (0.48), 5.030 (0.50), 5.053 (0.42), 5.754 (2.25), 7.540 (1.30), 7.562 (2.34), 7.583 (1.26), 8.057 (2.81), 8.089 (2.79), 8.645 (3.24), 8.862 (4.26), 10.407 (2.00), 10.431 (1.94).

Example 235

7-(2,4-Dioxo-1,3,7-triazaspiro[4.4]non-7-yl)-6-fluoro-4-oxo-N-[3,3,4,4,4-pentafluorobutan-2-yl]-1-(2,4,6-trifluorophenyl)-1,4-dihydro-1,8-naphthyridine-3-carboxamide (Diastereomer Mixture)

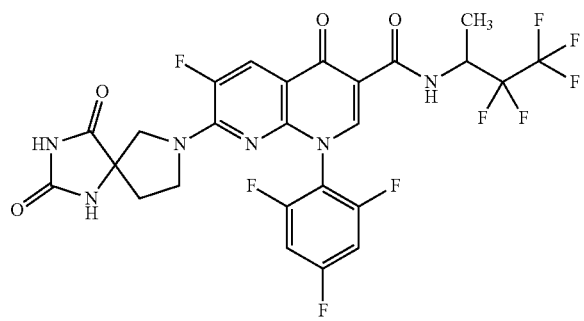 [SMILES: CC(NC(=O)c1cn(-c2c(F)cc(F)cc2F)c2nc(N3CCC4(C3)NC(=O)NC4=O)c(F)cc2c1=O)C(F)(F)C(F)(F)F]

7-Chloro-6-fluoro-4-oxo-N-(3,3,4,4,4-pentafluorobutan-2-yl)-1-(2,4,6-trifluorophenyl)-1,4-dihydro-1,8-naphthyridine-3-carboxamide (enantiomerically pure) (75.0 mg, 145 µmol) was initially charged in 0.79 ml of DMF. 1,3,7-Triazaspiro[4.4]nonane-2,4-dione hydrochloride (racemic) (33.3 mg, 174 µmol) was added, N,N-diisopropylethylamine (130 µl, 720 µmol) was added and the mixture was stirred at room temperature for 2 days. The reaction solution was diluted with acetonitrile/water/TFA and purified by preparative HPLC (RP18 column, mobile phase: acetonitrile/water gradient with addition of 0.1% TFA). The combined product fractions were concentrated by evaporation. The residue was dissolved in dichloromethane and washed twice with saturated aqueous sodium bicarbonate solution. The combined aqueous phases were re-extracted twice with dichloromethane. The combined organic phases were dried over sodium sulphate, filtered and concentrated by evaporation. This gave 81 mg of the target compound (87% of theory, purity 99%).

LC-MS (Method 3): $R_t$=1.88 min; MS (ESIpos): m/z=637 [M+H]$^+$ $^1$H NMR (400 MHz, DMSO-d6) δ[ppm]: −0.064 (0.65), −0.008 (2.78), 0.008 (2.31), 1.235 (0.44), 1.387 (14.93), 1.404 (14.88), 2.063 (1.52), 2.236 (1.54), 2.324 (0.96), 2.328 (1.26), 2.367 (0.89), 2.523 (2.50), 2.670 (1.12), 2.675 (0.84), 2.710 (0.77), 3.589 (0.68), 4.967 (0.72), 4.989 (1.28), 5.012 (1.52), 5.031 (1.56), 5.056 (1.26), 5.075 (0.68), 7.545 (5.71), 7.567 (10.68), 7.589 (5.69), 8.053 (9.66), 8.085 (9.42), 8.390 (11.36), 8.865 (16.00), 10.409 (6.74), 10.433 (6.48), 10.876 (9.42).

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

| Abbreviations and acronyms: | |
|---|---|
| $B_{Max}$ | number of specific binding sites of the radioligand |
| CAFTY | calcium free tyrode |
| CHO | chinese hamster ovary |
| CRE | cAMP-responsive element |
| DMEM | Dulbecco's modified eagle medium |
| DMSO | dimethyl sulfoxide |
| FCS | foetal calf serum |
| FRET | fluorescence resonance energy transfer |
| GIRK1/4 | G-protein-coupled inward rectifier potassium channel, member 1/4 |
| HEPES | hydroxyethylpiperazine-ethanesulfonic acid |
| HTRF | homogeneous time resolved fluorescence |
| $K_d$ | equilibrium dissociation constant |
| $K_i$ | equilibrium inhibitor constant |
| $k_{off}$ | rate of dissociation |
| $k_{on}$ | rate of association |
| nM | nanomolar |
| MEM | minimum essential medium |
| µl | microlitres |
| µM | micromolar |
| ml | millilitres |
| mM | millimolar |
| mtClytin | mitochondrial clytin |
| min | minutes |
| NMS | N-Me-scopolamine |
| PAM | positive allosteric modulator |
| PEI | polyethylenimine |
| Pen/Strep | penicillin/streptomycin |
| sec | seconds |

B-1. Functional M2-GIRK1/4 Activation Test

Both the activation of the M2 receptor by orthosteric agonists alone and the allosteric boosting of orthosterically induced activation by positive allosteric modulators (PAMs) can be determined by means of a cell-based functional GIRK1/4 activity test. The binding of orthosteric agonists (endogenous ligand: acetylcholine) to the M2 receptor leads to receptor activation or a change in conformation of the receptor in the manner of a shift in equilibrium in favour of the active receptor conformation. The binding of the orthosteric agonists to the M2 receptor and hence the activation thereof can be boosted by positive allosteric modulators which bind not to the orthosteric binding site of the agonists but to a separate allosteric binding site.

The agonist-induced change in conformation of the M2 receptor results in a Gαi protein activation. The activation of the Ga subunit leads in turn to dissociation and hence release of the Gβγ subunits from the Gα subunit and the activation of separate downstream signal transduction cascades. The heterodimeric Gβγ complex released binds to the GIRK1/4 potassium channel and induces a ligand-controlled channel activation or opening (Reuveny et al., Nature, July 1994, 370, 143-146). Under physiological conditions, the result is then a selective efflux of potassium from the cell along the electrochemical gradient. The export of positive charge leads to lowering of the transmembrane potential and hence to hyperpolarization of the cell. The extent of hyperpolarization can therefore be regarded as a measure of the activation of the M2 receptor.

The test cell used is a recombinant CHO-DUKX cell line which has been stably transfected with cDNA coding for the human M2 receptor and with cDNA coding for both GIRK1/4 subunits (CHO-DUKX-M2-GIRK). The transmembrane potential, or the relative changes in the transmembrane potential as a function of substance addition or M2 activation, is determined by means of a voltage-sensitive dye (FLIPR Membrane Potential Assay Kit Blue, Molecular Devices #R8034) and the measurement of cell fluorescence using a proprietary fluorescence imaging instrument.

B-1.1. Determination of the Allosteric Potency of the Test Substances ($EC_{50}$ Value)

The test substances are dissolved in dimethyl sulfoxide (DMSO) at a concentration of 10 mM and serially diluted with DMSO in steps of 1:3.16 for a 10-point dose/activity analysis. In accordance with the desired test concentrations, the substances are pie-diluted in loading buffer (composition: 0.6 ml of FLIPR Membrane Potential Assay Kit Blue (10 mg/ml), 0.6 ml of Brilliant Black (10 mg/ml), 2 mM $CaCl_2$ and 2 mM KCl ad 50 ml. sodium gluconate Tyrode (PAA, #T21-155)).

The reporter cells cultivated in MEM alpha medium (supplemented with 10% PCS, 2% Glutamax, 1 mg/ml genticin) were sown with 2000 cells (measurement after 48 h) or 4000 cells (measurement after 24 h) in 30 μl per 384-well in μCLEAR/black Greiner cell culture plates (#781092) and incubated at 37° C. for 24 h or 48 h. The sowing medium consisted of MEM alpha medium (supplemented with 5% PCS, 2% Glutamax, no genticin).

For the particular measurement, the medium was removed and the cells were laden with the volt-age-sensitive dye for at least 6 min at room temperature (30 μl of loading buffer per 384-well). This was followed, in a first measurement, by the determination of the fluorescence for the resting transmembrane potential for a period of 5 sec. Thereafter, 10 μl in each case of the test substances diluted in loading buffer were added, followed by a second measurement to determine the transmembrane potential for a period of 50 sec in 1 sec increments. Finally, the cells were admixed with 10 μl of agonist solution (acetylcholine dissolved in loading buffer). Acetylcholine was used at the concentration corresponding to the $EC_{20}$, which had been determined in a preliminary test. The M2-mediated GIRK1/4 activation or hyperpolarization was then monitored in a third measurement over a period of 60 sec. The $EC_{50}$ value (degree of allosteric potency of test compound) and the efficiency (measure of the boosting of the acetylcholine effect at an $EC_{20}$ acetylcholine concentration) were determined with the aid of a 4-parameter logistic function (Hill function).

B-1.2. Determination of Positive Cooperativity (α Factor)

The test substances were dissolved in DMSO at a concentration of 10 mM and serially diluted with DMSO in steps of 1:3.16 for a 10-point dose/activity analysis. In accordance with the desired test concentrations, the substances were pre-diluted in loading buffer (see above).

The reporter cells cultivated in MEM alpha medium (supplemented with 10% PCS, 2% Glutamax, 1 mg/ml genticin) are sown with 2000 cells (measurement after 48 h) or 4000 cells (measurement after 24 h) in 30 μl per 384-well in μCLEAR/black Greiner cell culture plates (#781092) and incubated at 37° C. for 24 h or 48 h. The sowing medium consisted of MEM alpha medium (supplemented with 5% PCS, 2% Glutamax, no genticin).

For the particular measurement, the medium was removed and the cells were laden with the volt-age-sensitive dye for at least 6 min at room temperature (30 μl of loading buffer per 384-well). This was followed, in a first measurement, by the determination of the resting transmembrane potential for a period of 5 sec in 1 sec increments. Thereafter, 10 μl in each case of the test substances diluted in loading buffer are added, followed by a second measurement to determine the transmembrane potential for a period of 50 sec in 1 sec increments.

Finally, the cells are admixed with 10 μl of agonist solution (acetylcholine dissolved in loading buffer). In contrast to the $EC_{50}$ determination of the test substances (see B-1.1), however, this is not done using one acetylcholine concentration; instead, every concentration of the test substance is combined with an acetylcholine 8-point dose-response curve. For the acetylcholine dilution series, the agonist is serially prediluted in loading buffer in accordance with the desired end concentrations, starting with a maximum end concentration of 3 μM in steps of 1:3.16. The M2-mediated GIRK1/4 activation or hyperpolarization is then monitored in a third measurement over a period of 60 sec in 1 sec increments. The shift in the acetylcholine dose-response curve in the presence of increasing concentrations of the test substance is analysed and quantified by means of GraphPad PRISM (Allosteric $EC_{50}$ shift). The α factor determined is a measure of the strength and direction of the allosteric effect, α values>1 reflect a lowering of the $EC_{50}$ value or an increase in the potency of the agonist (acetylcholine) in the presence of allosterics and mean positive cooperativity between orthosterics (acetylcholine) and allosterics (test substance). Positive cooperativity is the hallmark of a positive allosteric modulator. Conversely, α values<1 are indicative of negative cooperativity between orthosterics and allosterics, and hence characterize negative allosteric modulators, α values=1 mean no cooperativity between orthosteric and allosteric, meaning that the binding affinities of orthosteric and allosteric to the receptor do not affect one another. The greater the magnitude of the α value, the greater the extent of cooperativity between orthosteric and allosteric.

Table 1 below lists, for individual working examples, the $EC_{50}$ and efficiency values thus determined and the α values from this assay (in some cases as mean values from two or more independent individual determinations):

TABLE 1

| Ex. No. | Receptor activity $EC_{50}$ [μmol/L] | Efficiency [%] | Cooperativity (alpha factor) |
| --- | --- | --- | --- |
| 1 | 0.021 | 92 | 35 |
| 2 | 0.0355 | 96 | |
| 3 | 0.038 | 97 | |
| 4 | 0.038 | 89 | |
| 5 | 0.069 | 99 | |
| 6 | 0.00617 | 94 | 58 |
| 7 | 0.00564 | 93 | 57 |
| 8 | 0.0043 | 96 | |
| 9 | 0.00199 | 91 | 39 |
| 10 | 0.00527 | 99 | 70 |
| 11 | 0.0058 | 100 | 60 |
| 12 | 0.02 | 90 | 40 |
| 13 | 0.0062 | 94 | 49 |
| 14 | 0.0055 | 100 | 49 |
| 15 | 0.00915 | 96 | 41 |
| 16 | 0.00845 | 99 | 42 |
| 17 | 0.0795 | 83 | |
| 18 | 0.0205 | 99 | 43 |
| 19 | 0.016 | 98 | |
| 20 | 0.013 | 92 | |
| 21 | 0.003 | 100 | |
| 22 | 0.01 | 95 | 42 |
| 23 | 0.0055 | 100 | 41 |
| 24 | 0.00135 | 100 | 57 |
| 25 | 0.00405 | 95 | 45 |
| 26 | 0.00403 | 100 | |
| 27 | 0.00258 | 92 | |
| 28 | 0.00315 | 100 | |
| 29 | 0.0025 | 100 | |
| 30 | 0.0026 | 100 | |
| 31 | 0.00415 | 100 | 37 |
| 32 | 0.0043 | 100 | 54 |
| 33 | 0.00175 | 100 | 50 |
| 34 | 0.0012 | 100 | 53 |
| 35 | 0.0029 | 100 | |

TABLE 1-continued

| Ex. No. | Receptor activity EC$_{50}$ [µmol/L] | Efficiency [%] | Cooperativity (alpha factor) |
|---|---|---|---|
| 36 | 0.005 | 92 | 51 |
| 37 | 0.006 | 100 | 38 |
| 38 | 0.0101 | 100 | |
| 39 | 0.0205 | 100 | |
| 40 | 0.0023 | 98 | |
| 41 | 0.0033 | 100 | 37 |
| 42 | 0.004 | 100 | |
| 43 | 0.0075 | 100 | |
| 44 | 0.012 | 100 | |
| 45 | 0.00847 | 100 | 62 |
| 46 | 0.051 | 100 | |
| 47 | 0.048 | 81 | |
| 48 | 0.0018 | 78 | 42 |
| 49 | 0.068 | 74 | |
| 50 | 0.0025 | 60 | |
| 51 | 0.036 | 81 | |
| 52 | 0.0013 | 83 | |
| 53 | 0.016 | 100 | 30 |
| 54 | 0.025 | 100 | 30 |
| 55 | 0.025 | 96 | |
| 56 | 0.035 | 100 | |
| 57 | 0.0785 | 89 | |
| 58 | 0.104 | 90 | |
| 59 | 0.0915 | 97 | |
| 60 | 0.0036 | 100 | |
| 61 | 0.0022 | 94 | |
| 62 | 0.0041 | 88 | |
| 63 | 0.0039 | 92 | |
| 64 | 0.012 | 96 | |
| 65 | 0.03 | 89 | 14 |
| 66 | 0.035 | 92 | |
| 67 | 0.01 | 95 | |
| 68 | 0.032 | 92 | |
| 69 | 0.0059 | 100 | |
| 70 | 0.1 | 86 | |
| 71 | 0.0042 | 94 | 26 |
| 72 | 0.011 | 89 | |
| 73 | 0.0027 | 94 | |
| 74 | 0.0039 | 95 | |
| 75 | 0.087 | 100 | |
| 76 | 0.029 | 100 | |
| 77 | 0.0016 | 100 | |
| 78 | 0.0028 | 100 | |
| 79 | 0.0093 | 99 | |
| 80 | 0.024 | 100 | |
| 81 | 0.15 | 87 | |
| 82 | 0.14 | 65 | |
| 83 | 0.044 | 94 | |
| 84 | 0.00835 | 88 | 39 |
| 85 | 0.033 | 100 | |
| 86 | 0.014 | 95 | |
| 87 | 0.0014 | 100 | |
| 88 | 0.0022 | 100 | |
| 89 | 0.00475 | 100 | 44 |
| 90 | 0.0185 | 95 | 30 |
| 91 | 0.0065 | 100 | |
| 92 | 0.0066 | 100 | |
| 93 | 0.012 | 100 | |
| 94 | 0.0047 | 100 | 34 |
| 95 | 0.0155 | 100 | |
| 96 | 0.016 | 96 | |
| 97 | 0.013 | 97 | |
| 98 | 0.0143 | 98 | 50 |
| 99 | 0.0355 | 96 | |
| 100 | 0.0315 | 100 | |
| 101 | 0.0135 | 100 | |
| 102 | 0.295 | 92 | |
| 103 | 0.0081 | 100 | |
| 104 | 0.013 | 97 | |
| 105 | 0.0075 | 97 | |
| 106 | 0.0072 | 100 | |
| 107 | 0.00355 | 92 | |
| 108 | 0.0054 | 96 | 47 |
| 109 | 0.0077 | 100 | |
| 110 | 0.019 | 100 | |
| 111 | 0.0072 | 99 | |
| 112 | 0.00425 | 100 | 33 |
| 113 | 0.002 | 100 | 35 |
| 114 | 0.007 | 94 | |
| 115 | 0.00665 | 98 | 53 |
| 116 | 0.0035 | 97 | |
| 117 | 0.0069 | 99 | |
| 118 | 0.0028 | 100 | |
| 119 | 0.0087 | 100 | |
| 120 | 0.0105 | 96 | |
| 121 | 0.125 | 100 | |
| 122 | 0.00355 | 100 | |
| 123 | 0.0031 | 100 | |
| 124 | 0.018 | 100 | |
| 125 | 0.012 | 97 | |
| 126 | 0.0039 | 97 | |
| 127 | 0.013 | 92 | |
| 128 | 0.0098 | 90 | |
| 129 | 0.066 | 95 | |
| 130 | 0.0023 | 96 | |
| 131 | 0.0046 | 100 | |
| 132 | 0.01 | 99 | |
| 133 | 1.6 | 81 | |
| 134 | 1.83 | 55 | |
| 135 | 2.61 | 75 | |
| 136 | 0.0028 | 84 | |
| 137 | 0.0033 | 91 | |
| 138 | 0.0076 | 84 | |
| 139 | 0.0034 | 100 | |
| 140 | 0.0053 | 95 | |
| 141 | 0.0034 | 97 | |
| 142 | 0.039 | 99 | |
| 143 | 0.0015 | 94 | 40 |
| 144 | 0.0045 | 98 | 67 |
| 145 | 0.0112 | 100 | 86 |
| 146 | 0.012 | 100 | |
| 147 | 0.016 | 94 | |
| 148 | 0.0187 | 96 | |
| 149 | 0.021 | 92 | |
| 150 | 0.024 | 93 | |
| 151 | 0.024 | 100 | |
| 152 | 0.053 | 100 | |
| 153 | 0.048 | 99 | |
| 154 | 0.097 | 100 | |
| 155 | 0.011 | 100 | |
| 156 | 0.011 | 100 | |
| 157 | 0.0026 | 100 | |
| 158 | 0.0037 | 100 | |
| 159 | 0.0071 | 100 | 45 |
| 160 | 0.0073 | 100 | 38 |
| 163 | 0.025 | 93 | |
| 164 | 0.002 | 100 | 45 |
| 165 | 0.0024 | 100 | 48 |
| 166 | 0.0044 | 100 | 31 |
| 167 | 0.0074 | 95 | |
| 168 | 0.004 | 86 | |
| 169 | 0.0038 | 99 | 34 |
| 170 | 0.0081 | 100 | 38 |
| 171 | 0.0013 | 95 | |
| 172 | 0.0033 | 94 | 35 |
| 173 | 0.0025 | 99 | 39 |
| 175 | 0.073 | 83 | |
| 176 | 0.11 | 91 | |
| 177 | 0.53 | 77 | |
| 178 | 0.017 | 99 | |
| 179 | 0.027 | 100 | |
| 180 | 0.0085 | 86 | |
| 181 | 0.0130 | 83 | |
| 182 | 0.0088 | 100 | 27 |
| 183 | 0.0423 | 96 | |
| 184 | 0.0045 | 90 | 24 |
| 185 | 0.0064 | 83 | 13 |
| 186 | 0.0058 | 87 | 20 |
| 187 | 0.0099 | 90 | 25 |
| 188 | 0.026 | 97 | |

TABLE 1-continued

| Ex. No. | Receptor activity EC$_{50}$ [μmol/L] | Efficiency [%] | Cooperativity (alpha factor) |
|---|---|---|---|
| 189 | 0.03 | 100 | |
| 190 | 0.0835 | 100 | |
| 191 | 0.048 | 100 | |
| 192 | 0.1275 | 100 | |
| 193 | 0.0325 | 100 | |
| 194 | 0.0315 | 94 | |
| 195 | 0.058 | 100 | |
| 196 | 0.063 | 100 | |
| 197 | 0.051 | 100 | |
| 198 | 0.033 | 100 | |
| 199 | 0.014 | 100 | |
| 200 | 0.12 | 73 | |
| 201 | 0.0016 | 100 | 39 |
| 202 | 0.001 | 100 | |
| 203 | 0.005 | 100 | 29 |
| 204 | 0.017 | 97 | |
| 205 | 0.0031 | 100 | 25 |
| 206 | 0.01 | 100 | |
| 207 | 0.0033 | 100 | 24 |
| 208 | 0.0018 | 100 | 27 |
| 209 | | | |
| 210 | 0.0021 | 100 | 26 |
| 211 | | | |
| 212 | 0.002 | 100 | 28 |
| 213 | 0.013 | 100 | |
| 214 | 0.0021 | 100 | |
| 215 | 0.0086 | 100 | |
| 216 | 0.0015 | 99 | |
| 217 | 0.0009 | 100 | 39 |
| 218 | 0.0006 | 100 | 39 |
| 219 | 0.0165 | 91 | |
| 220 | 0.080 | 85 | |
| 221 | 0.031 | 85 | |
| 222 | 0.55 | 61 | |
| 223 | 0.026 | 86 | |
| 224 | 0.010 | 96 | |
| 225 | 0.11 | 82 | |
| 226 | 0.0067 | 93 | 31 |
| 227 | 0.011 | 94 | |
| 228 | 0.0064 | 93 | 33 |
| 229 | 0.26 | 67 | |
| 230 | 0.0097 | 97 | 36 |
| 231 | 0.0048 | 82 | |
| 232 | 0.007 | 100 | |
| 233 | 0.0023 | 100 | |
| 234 | 0.0097 | 90 | |
| 235 | 0.004 | 92 | |

B-2. Functional Ca2+ Release Test by Means of M2-Gα16 Reporter Cells

Any potentially agonistic or else potentially allosteric effect of the test substances on the M2 receptor can be determined by a functional Ca$^{2+}$ release test. The activation of the M2 receptor by binding of orthosteric agonists (acetylcholine) or other substances having an agonistic effect leads to a change in conformation of the receptor, which, in the endogenous state, results in God protein activation. However, coupling of the M2 receptor to the exogenously expressed promiscuous Gαq protein Gα16 results in Gα16 protein activation after activation of the M2 receptor, which causes—via a downstream signal transduction cascade—intracellular Ca$^{2+}$ release. The extent of intracellular Ca$^{2+}$ mobilization can therefore be regarded as a measure of the activation of the M2 receptor.

The test cell used is a recombinant CHO cell line which has been stably transfected with cDNA coding for the human M2 receptor and the Gal 6 protein and with cDNA coding for the mitochondrially expressed photoprotein clytin (mtClytin) (CHO mtClytin Gα16 M2). The determination of the intracellular Ca$^{2+}$ release as a function of substance addition or M2 activation is effected by means of a Ca$^{2+}$-sensitive dye (Fluo-8) and the measurement of cell fluorescence using a FLIPR$^{TETRA}$ instrument (Molecular Devices).

B-2.1. Agonism Assay

The test substances are dissolved in DMSO at a concentration of 10 mM and serially diluted with DMSO in steps of 1:3.16 for a 10-point dose/activity analysis. In accordance with the desired test concentrations, the substances are prediluted in Fluo-8 buffer (composition per 100 ml: 500 μl probenecid, 2 ml Brilliant Black (20 mg/ml), 440 μl Fluo-8, 2 mM CaCl$_2$ ad 100 ml CAFTY Tyrode (130 mM NaCl, 5 mM KCl, 20 mM HEPES, 1 mM MgCl$_2$, 5 mM NaHCO$_3$, pH 7.4)).

The reporter cells cultivated in MEM alpha medium (supplemented with 10% PCS, 2% Glutamax) were sown with 3000 cells in 30 μl of sowing medium per 384-well in μCLEAR/black Greiner cell culture plates (#781092) and incubated at 37° C. for 24 h. The sowing medium consists of MEM alpha medium (supplemented with 5% FCS, 2% Glutamax). For the respective measurement, the medium is removed and the cells, after addition of 20 μl in each case of Fluo-8 buffer per 384-well, were incubated in an incubator at 37° C. for 1 h. After addition of 10 μl in each case per 384-well of the prediluted test substances, cell fluorescence was measured for a period of 5 min in 1 sec increments. The relative degree of maximum activation of the M2 receptor by the respective test substances is calculated by normalizing the test signal to the signal corresponding to the EMU concentration of acetylcholine (3 μM).

B-2.2. Determination of the Positive Allosteric Modulator Effect

In order to be able to determine the positive cooperativity of the test substances in relation to the acetylcholine-mediated M2 receptor activation, reference agonist (acetylcholine) is then added for a full dose-response analysis. For this purpose, acetylcholine is serially diluted in Fluo-8 buffer in steps of 1:3.16 beginning with a maximum final concentration of 1 μM. After addition of 10 μl in each case of agonist solution per 384-well, cell fluorescence is again measured for a period of 5 min in 1 sec increments. The same assay plate is used as immediately before for the M2 agonism assay. The shift in the acetylcholine dose-response curve in the presence of increasing concentrations of the test substance is analysed and quantified by means of GraphPad PRISM (Allosteric EC$_{50}$ shift) (see above).

B-3. Selectivity Test with Respect to Human Muscarinic Acetylcholine Receptors

Any potentially agonistic effect, or else positive allosteric effect, of the test substances on other human muscarinic acetylcholine receptors can be determined in a functional Ca$^{2+}$ release test (Eurofins; GPCRProfiler® Services in agonistic and allosteric mode for Mx Receptors; cat #: HTS600GPCR).

The test cells used were the Chem-1 or Chem-4 cell lines transfected with the particular receptor (ChemiScreen™ M1 Calcium-Optimized FLIPR Cell Lines, Eurofins; M1: HTS044C; ChemiScreen™ Calcium-Optimized Stable Cell Line Human Recombinant M2 Muscarininc Acetylcholine Receptor, Eurofins; M2: HTS115C; ChemiScreen™ Human Recombinant M3 Muscarinic Acetylcholine Receptor Calcium-Optimized Stable Cell Line, Eurofins; M3: HTS116C; ChemiScreen™ Human Recombinant M4 Muscarinic Acetylcholine Receptor Calcium-Optimized Stable Cell Line, Eurofins; M4: HTS117C; ChemiScreen™ M5 Calcium-Optimized FLIPR Cell Lines, Eurofins; M5: HTS075C). The substance test is conducted with a FLIPR$^{TETRA}$ instrument (Molecular Devices).

B-3.1. Agonism Assay

In order to determine any potential agonistic effect of the test substances, the respective test substances were added with a final test concentration of 10 μM or 1 μM. $Ca^{2+}$ release or cell fluorescence is measured over a period of 180 sec. The positive control used for normalization of the substance effect to the receptor activation is a concentration of acetylcholine corresponding to the EMU value.

After the agonism assay has ended, the assay plate is incubated at 25° C. for 7 min. After the incubation period, the positive allosteric modulator assay is initialized.

B-3.2. Allosteric Modulator Assay

In order to examine any positive or negative allosteric effect of the test substances on other human muscarinic acetylcholine receptors and the M2 receptor itself, every substance concentration is combined with an acetylcholine 8-point dose-response curve. Addition of agonist solution is again followed in turn by the measurement of cell fluorescence for a period of 180 sec. The shift in the acetylcholine dose-response curve (maximum shift in the $EC_{50}$ of acetylcholine) is analysed and quantified by means of GraphPad PRISM (Sigmoidal dose-response (variable slope)—$EC_{50}$). Finally, quotients of the allosteric shift for the M2 receptor and M4 receptor are formed, which function in turn as a measure of the respective selectivity.

B-4. In Vitro M2 PAM Gi Assay

For the characterization of the test substances on positive allosteric modulation of the human M2 receptor, the carbachol-induced inhibition of the rise in cAMP due to forskolin in recombinant M2 receptor-expressing CHO cells is measured, these additionally expressing a luciferase gene under the control of a cAMP-responsive element (CRE): 3000 cells in 25 μl of full medium (DMEM F12 PAN medium, 10% PCS, 1.35 mM Na pyruvate, 20 mM Hepes, 4 mM Glutamax, 2% sodium bicarbonate, 1% Pen/Strep, 1% 100× non-essential amino acids) are sown per well of a 384 multititre plate (Greiner, TC Platte, black with clear base) and incubated at 37° C., 5% $CO_2$ for 24 hours. Before the measurement, the medium is replaced by 30 μl of test medium (Optimem) and incubated at 37° C., 5% $CO_2$ for 10 minutes. The test substance is prepared in DMSO in various concentrations (starting concentration 10 mM, dilution factor 3.16) as a dose-response curve and pre-diluted 1:50 with calcium-free Tyrode, 2 mM $CaCl_2$, 0.01% BSA. 10 μl of the prediluted substance solution are added to the cells and incubated at 37° C., 5% $CO_2$ for 10 minutes. The M2 receptor is activated by adding 10 μl of carbachol in various concentrations in calcium-free Tyrode, 2 mM $CaCl_2$ and incubated at 37° C., 5% $CO_2$ for 5 minutes. Adenylyl cyclase is activated by adding 10 μl of 1 μM (final concentration) forskolin in calcium-free Tyrode, 2 mM $CaCl_2$ and incubated at 37° C., 5% $CO_2$ for 5 hours. After removing the cell supernatant and adding 20 μl of Luci/Triton buffer (1:1), luminescence is determined in a luminometer for 60 seconds.

Calcium-free Tyrode: 130 mM NaCl, 5 mM KCl, 20 mM HEPES, 1 mM $MgCl_2$, 4.8 mM Na—$HCO_3$, pH 7.4

Luci/Triton buffer (1:1): Luci buffer (20 mM tricine, pH 7.8, 2.67 mM magnesium sulfate, 0.1 mM EDTA, 4 mM DTT, 270 μM coenzyme A, 470 μM D-luciferin, 530 μM ATP) mixed 1:1 with triton buffer (25 mM Tris aqueous hydrochloric acid, pH 7.8, 25 mM $Na_2HPO_4$, 2 mM dithiothreitol, 3% Triton X-100, 10% glycerin).

The $EC_{50}$ value was determined with the aid of a 4-parameter logistic function (Hill function).

B-5. Competitive FRET Binding Test for Human M2 and M4 Receptors

The direct binding of the test substances to the M2 receptor and the boosting of the binding (increasing affinity) of the natural agonist acetylcholine to the M2 receptor in the presence of the test substances (positive allosteric effect) is determined by means of a FRET-based binding assay (HTRF Tag-lite® binding assay, Cisbio). For control of selectivity, the binding of the test substances to the structurally related M4 receptor is examined analogously. The HTRF Tag-lite® assay is a homogeneous binding assay and is based on the competitive binding of a fluorescent ligand (probe) and the unlabeled test substance to the receptor, which is expressed in living cells. The receptor in turn is derivatized with a fluorescent donor dye (terbium cryptate), such that excitation of the donor dye gives rise to a FRET signal between the receptor and probe (acceptor) when the probe is bound to the receptor. The acceptor probe used was a telenzepine derivative conjugated with an HTRF fluorescent dye (red ligand; L0040RED). The probe therefore binds in the conserved orthosteric binding site both of the M2 and of the M4 receptor. The allosteric binding site of the M2 receptor has been characterized by x-ray crystallography and is postulated as being directly above the orthosteric binding pocket (Kruse et al., *Nature*, 2013, 504, 101-106). Both the binding of unlabeled orthosteric agonists (acetylcholine) to the orthosteric binding site and the binding of allosteric modulators (test substances) to the allosteric binding site therefore leads to a concentration-dependent competitive displacement of the probe and hence to a decrease in the FRET-based fluorescence signal.

All binding tests are conducted on white 384 microtitre plates (small volume) in a total volume of 20 μl. The HTRF measurements are undertaken with a PHERAstar instrument (BMG Labtech). For the muscarinic M2 or M4 receptor binding test, SNAPed-M2-expressing cells (C1TT1M2) or SNAPed-M4-expressing cells (C1TT1M4) are used, which have been labelled with a donor fluorophore (Lumi4Tb; CELLCUST). The cells are incubated with the acceptor probe in Tag-lite binding buffer (LABMED) in the presence of test substance or acetylcholine. Subsequently, the fluorescence signal is measured at wavelengths of 665 nm and 620 nm and the HTRF quotient (signal at 665 nm/signal at 620 nm) is determined. The relative specific signal is determined by subtracting the HTRF quotient of negative control (Tag-lite buffer only without probe).

B-5.1. Binding of the Test Substances

In order to determine the binding of the test substances to the M2 or M4 receptor in the absence of orthosteric agonist, a dose-response analysis of the test substances is undertaken in the competitive format of the M2-Tag-lite® or M4-Tag-lite® binding assay. The test substances are dissolved in DMSO at a concentration of 10 mM and serially diluted with DMSO in steps of 1:3.16 for a dose-response analysis. The maximum test concentration corresponds to 10 μM. The molar concentration of the test substance that brought about a half-maximum reduction in the HTRF signal in relation to the maximum and remaining HTRF signal at the highest substance concentration ($EC_{50}$ of the binding) is determined by means of GraphPad PRISM (Sigmoidal dose response). At the same time, the strength of the competition effect is determined by calculating the maximum decrease in the specific HTRF signal at the highest substance concentration (% max. competition).

B-5.2. Binding of the Test Substances in Allosteric Mode

To examine the allosteric modulation of the M2 receptor by the test compounds, firstly, a dose-response analysis of the test substances in the competitive format of the M2-Tag-lite® or M4-Tag-lite® binding assay in the presence of a concentration of acetylcholine corresponding to the $EC_{20}$ value is undertaken, the latter being determined in a separate 11-point acetylcholine dose-response analysis (3 µM). The test substances are dissolved in DMSO at a concentration of 10 mM and serially diluted with DMSO in steps of 1:3.16 for a 10-point dose/activity analysis. The maximum test concentration corresponds to 10 µM. The molar concentration of the test substance that brought about a half-maximum reduction in the HTRF signal in relation to the maximum and remaining HTRF signal at the highest substance concentration in the presence of an acetylcholine concentration corresponding to the $EC_{20}$ value ($EC_{50}$ of the binding) is determined by means of GraphPad PRISM (Sigmoidal dose response). At the same time, the strength of the competition effect is determined by calculating the maximum decrease in the specific HTRF signal at the highest substance concentration (% max. competition).

In order to examine the boosting of the binding of acetylcholine to the M2 or M4 receptor, in addition, secondly, an 11-point dose-response analysis of acetylcholine in the competitive format of the M2-Tag-lite® or M4-Tag-lite® binding assay was undertaken in the absence or in the presence of 1 µM or 10 µM test substance. The shift in the acetylcholine dose-response curve (maximum shift in the $EC_{50}$ value of acetylcholine) was analysed and quantified by means of GraphPad PRISM (Sigmoidal dose-response).

B-6. Radioligand Binding Assay for Human M2 Receptors

The allosteric mechanism of action of the test substances can be further investigated in detail and be quantified by various radioligand binding assays. The binding of the allostere to the allosteric binding site of the M2 receptor results in an increase in the binding affinity of the orthosteric ligand for the M2 receptor in the case of positive cooperativity. The increase in the binding affinity of the orthosteric ligand by the allostere in the ternary complex consisting of orthostere, allostere and M2 receptor is in turn due to modulation of the binding kinetics of the orthostere. The allostere can alter the association and/or dissociation rate of the orthostere at the M2 receptor. A lowering of the dissociation rate reflects in this case a stabilization of the ternary complex and accompanies therefore a lowering of the dissociation constant of the orthosteric ligand under equilibrium conditions (Lazareno, Determination of Allosteric Interactions Using Radioligand-Binding Techniques in *Methods in Molecular Biology*, vol. 259, Receptor Signal Transduction Protocols, 2nd ed.; Kostenis and Mohr, *Trends Pharmacol. Sci.* 1996, 17(8), 280-283).

B-6.1. $^3$H-Oxotremorine M Radioligand Binding Assay Under Equilibrium Conditions In order to check and to quantify the influence of the test substances on the binding affinity of orthosteric agonists for the M2 receptor, a radioligand binding assay under equilibrium conditions can be conducted. In this case, the binding of the radiolabelled M2 receptor agonist $^3$H-oxotremorine M to the M2 receptor is investigated at different concentrations of $^3$H-oxotremorine M in the binding equilibrium (Croy et al., *Mol. Pharmacol.* 2014, 86, 106-115). Based on the amount of radioactive agonist specifically bound to the M2 receptor as a function of the agonist concentration (graphically represented as the so-called Langmuir isotherm), firstly the equilibrium dissociation constant $K_d$ of the agonist can be calculated as a quantitative measure of its binding affinity for the M2 receptor and secondly the concentration or number of specific binding sites of the radioligand (agonist) $B_{max}$ in the absence or presence of different concentrations of the test substances (positive allosteric modulators) (Hulme and Trevethick, *Brit. J. Pharmacol.* 2010, 161, 1219-1237).

The radioligand binding assay for the M2 receptor (Euroscreen, FAST-0261B) is carried out by means of $^3$H-labelled oxotremorine M (NET671) as agonist. The agonist binding to the M2 receptor is carried out in triplicate on 96-well microtitre plates (Master Block, Greiner, 786201) in binding buffer (sodium/potassium phosphate buffer, pH 7.4). For this purpose, each assay of M2 membrane extracts (20 µg of protein/96 well) are incubated with various concentrations of radiolabelled agonists (0.2-100 nM) alone or in the presence of 1 µM or 10 µM test substance or binding buffer alone in a total volume of 0.1 mL at 37° C. for 60 min. The non-specific binding of $^3$H-labelled oxotremorine M to the membrane is determined by co-incubating with N-methylscopolamine (NMS), an orthosteric antagonist of the M2 receptor, in a 200-fold excess. In order to stop the binding reaction, the samples are then filtered via GF/C filter (Perkin Elmer, 6005174), which had previously been wetted with 0.5% polyethylenimine (PEI) solution, for 2 h at room temperature. The filters are washed six times each with 0.5 mL of ice-cold wash buffer (10 mM sodium/potassium phosphate buffer, pH 7.4) and 50 µL of Microscint 20 scintillation solution (Packard) is added per assay. The samples are then incubated for 15 min on an orbital shaker before the radioactivity is measured by means of a Top-Count™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $K_d$ and $B_{max}$ of $^3$H-oxotremorine M for the M2 receptor are determined with the aid of a "one-site" specific binding model (Cray et al., *Mol. Pharmacol.* 2014, 86, 106-115).

B-6.2. $^3$H-NMS Competitive Radioligand Binding Assay Under Equilibrium Conditions In order to check and to quantify further the influence of the test substances on the binding affinity of orthosteric agonists for the M2 receptor, a competitive radioligand binding assay under equilibrium conditions is also conducted. In this case, the binding of the antagonistic radioligand $^3$H—N-methylscopolamine ($^3$H-NMS) to the M2 receptor is determined in the absence or presence of various concentrations of non-radiolabelled agonist oxotremorine M (Cray et al., *Mol. Pharmacol.* 2014, 86, 106-115; Schober et al., *Mol. Pharmacol.* 2014, 86, 116-123). The radiolabelled probe (antagonist) and the non-labelled agonist compete for the binding to the orthosteric binding site of the M2 receptor. The ability to displace the radiolabelled probe therefore serves as a measure of the binding affinity of the agonist for the receptor and can be quantified in accordance with the Cheng-Prusoff equation as an equilibrium inhibition constant ($K_i$) (Cheng and Rrusoff, *Biochem. Pharmacol.* 1973, 22(23), 3099-3108). In order to further investigate the allosteric effect of the test substances, the influence of the test substances on the $K_i$ of oxotremorine M is determined.

The antagonist inhibition binding assay for the M2 receptor (Euroscreen, FAST-0261B) is carried out on 96-well microtitre plates (Master Block, Greiner, 786201) in binding buffer (50 mM Tris buffer pH 7.4, 1 mM EDTA, 10 µg/ml saponin) using $^3$H-NMS as M2 receptor antagonist. To adjust the binding equilibrium, each assay of M2 membrane extracts (20 µg of protein/96 well) are incubated with a defined concentration of radiolabelled antagonist (0.5 nM) alone or in the presence of various concentrations of non-labelled agonists (oxotremorine M; 0.001 nM to 1 mM) with or without 1 μM or 10 μM test substance or binding buffer alone in a total volume of 0.1 mL at 25° C. for 2 h. The non-specific binding of $^3$H-labelled NMS to the membrane is determined by co-incubating with non-radiolabelled acetylcholine in a 200-fold excess. In order to stop the binding reaction, the samples are then filtered over GF/C filters (Perkin Elmer, 6005174), which had previously been wetted with 0.5% PEI solution, for 2 h at room temperature. The filters are washed six times each with 0.5 mL of ice-cold wash buffer (10 mM sodium/potassium phosphate buffer, pH 7.4) and 50 μL of Microscint 20 scintillation solution (Packard) is added per assay. The samples were then incubated for 15 min on an orbital shaker before the radioactivity is measured by means of a TopCount™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $K_i$ values in the presence or absence of test substance are quantified with the aid of the Cheng-Prusoff equation (Cheng and Prusoff, *Biochem. Pharmacol.* 1973, 22(23), 3099-3108). In this case, the $IC_{50}$ values of the substances are determined according to a four parameter logistic equation and the $K_d$ of NMS determined in a radioligand binding assay under equilibrium conditions (Schober et al., *Mol. Pharmacol.* 2014, 86, 116-123).

B-6.3. $^3$H-Oxotremorine M dissociation kinetics test

By means of a kinetic radioligand binding assay, the kinetics of the dissociation of the radiolabelled agonist $^3$H-oxotremorine M for the M2 receptor in the presence or absence of test substance can be investigated. By these means, the influence of the allosteric activity of the test substances on the dissociation constant ($k_{off}$ rate) of the M2 agonist can be determined and thus the allosteric mechanism of the test substances can be further characterized (Lazareno, Determination of Allosteric Interactions Using Radioligand-Binding Techniques in *Methods in Molecular Biology*, vol. 259, Receptor Signal Transduction Protocols, 2nd ed.; Schrage et al., *Biochem. Pharmacol.*, 2014, 90, 307-319).

The radioligand dissociation binding assay for the M2 receptor (Euroscreen, FAST-0261B) is carried out with $^3$H-labelled oxotremorine M (NET671) as agonist. The binding reaction is carried out in binding buffer (sodium/potassium phosphate buffer, pH 7.4) on 96-well microtitre plates (Master Block, Greiner, 786201). For this purpose, each assay of M2 membrane extracts (20 μg of protein/96 well) are pre-incubated with a defined concentration of radiolabelled agonist (9.65 nM) alone or in the presence of 1 μM or 10 μM test substance or binding buffer alone at 37° C. for 60 min. NMS is then added in 200-fold excess at various time points (one time point per assay) and the mixtures incubated in a total volume of 0.1 mL at 37° C. In order to stop the binding reaction, the samples are then filtered over GF/C filters (Perkin Elmer, 6005174), which had previously been wetted with 0.5% PEI solution, for 2 h at room temperature. The filters are washed six times each with 0.5 mL of ice-cold wash buffer (10 mM sodium/potassium phosphate buffer, pH 7.4) and 50 μL of Microscint 20 scintillation solution (Packard) is added per assay. The samples are then incubated for 15 min on an orbital shaker before the radioactivity is measured by means of a Top-Count™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $k_{off}$ was determined with the aid of a "one phase" exponential decay model of the dissociation (Hulme and Trevethick, *Brit. J. Pharmacol.* 2010, 161, 1219-1237; Kostenis and Mohr, *Trends Pharmacol. Sci.* 1996, 17(8), 280-283).

B-6.4. $^3$H-M2-PAM Binding Test

Binding affinity of the test substances for the human M2 receptor can be determined directly using a radiolabelled test substance as probe. To this end, a positive allosteric test substance was radiolabelled by tritiation ($^3$H-M2-PAM).

Using a radioligand binding test under equilibrium conditions, it is possible, firstly, to determine the equilibrium dissociation constant $K_d$ of the positive allosteric test substance ($^3$H-M2-PAM) as a quantitative measure of its binding affinity for the M2 receptor and, secondly, to determine the number of specific binding sites of the radioligand $B_{max}$ in the absence or presence of an orthosteric agonist (acetylcholine) (Hulme and Trevethick, *Brit. J. Pharmacol.* 2010, 161, 1219-1237; Schober et al., *Mol. Pharmacol.* 2014, 86, 116-123). For the $^3$H-M2-PAM equilibrium binding test, M2 receptor cell membrane preparations (CHO—S/hM2, 200 μg) in incubation buffer (10 mM Tris/HCl pH 7.4.2 mM MgCl2, 120 mM NaCl, protease inhibitors, 0.3% BSA) were incubated together with different concentrations of the allosteric radioligand $^3$H-M2-PAM (0.5-4000 nM) in the absence or presence of acetylcholine (100 μM) at 4° C. for 1 h. Unspecific binding is determined by addition of an excess of non-radiolabelled allosteric ligand (M2-PAM) (10 μM). To terminate the binding reaction, the samples are filtered through a Brandel filter system and washed with stop buffer (50 mM Tris/HCl pH 7.4, 500 mM NaCl, 0.3% BSA). Beforehand, the filters were wetted with 0.3% strength PEI solution. Kd and Bmax value of the allosteric radioligand are determined based on a "one-site" specific binding model (GraphPad Prism).

Using a competitive $^3$H-M2-PAM binding test, it is possible to determine the affinity of unlabeled allosteric test substances for the binding site of the radioligand $^3$H-M2-PAM at the M2 receptor. (Croy et al., *Mol. Pharmacol.* 2014, 86, 106-115; Schober et al., *Mol. Pharmacol.* 2014, 86, 116-123). The radiolabelled probe $^3$H-M2-PAM) and the non-labelled allosteric test substance compete for binding to the allosteric binding site of the M2 receptor. The ability to displace the radiolabelled probe therefore serves as a measure of the allosteric binding affinity of the test substances for the receptor and can be quantified in accordance with the Cheng-Prusoff equation as an equilibrium inhibition constant ($K_i$) (Cheng and Prusoff, *Biochem. Pharmacol.* 1973, 22(23), 3099-3108). Here, displacement of the radiolabelled allosteric probe is determined in the presence or absence of orthosteric agonists (acetylcholine). Analogously to the above-described $^3$H-M2-PAM binding test, the $^3$H-M2-PAM competition binding test is carried out under equilibrium conditions. Here, the membrane preparations comprising M2 receptor are incubated with 1 nM $^3$H-M2-PAM and various concentrations of unlabeled test substance in the absence or presence of acetylcholine (100 μM). The $K_i$ values in the presence or absence of acetylcholine are determined with the aid of the Cheng-Prusoff equation (Cheng and Prusoff, *Biochem. Pharmacol.* 1973, 22(23), 3099-3108).

B-7. Effects of the Test Substances on Acetylcholine-Mediated GIRK1/4 Channel Currents in Primary Atrial Rat Cardiomyocytes The substance testing is carried out in accordance with a patch clamp protocol described in the literature for the electrophysiological measurement of acetylcholine-induced GIRK1/4 membrane currents in native rat atrial myocytes (Cheng and Prusoff, *Biochem. Pharmacol.* 1973, 22(23), 3099-3108, see e.g. Beckmann and Rinne et al., *Cell. Physiol. Biochem.* 2008, 21, 259-268).

An acetylcholine dose-response curve for GIRK1/4 activity is initially determined in the absence of test substance (DMSO control) by perfusing test solutions with increasing acetylcholine concentration and measuring the resulting membrane currents. The membrane currents or change in the membrane currents are measured for a given ACh concentration for approx. 10 to 20 seconds. After application of the maximum ACh concentration within a DRC series, a solution of atropine (10 µM) is perfused followed by washing out of the substance solutions in order to ensure the M2 selectivity and reversibility of M2 activation. Changes of the membrane currents are appropriately recorded. Here, each acetylcholine concentration of the membrane current measured is in each case normalized to the maximum acetylcholine-induced membrane current (I/IMax). An acetylcholine dose-response curve comprises in this case five different concentrations (1 nM, 10 nM, 100 nM, 1 µM, 10 µM). The $EC_{50}$ value is determined with the aid of a 4-parameter logistic function (Hill function).

In order to determine the allosteric effect of the test substances on the M2 receptor, the acetylcholine dose-response curve is determined for the GIRK1/4 membrane current in the presence of a constant concentration of the respective test substance (e.g. 1 µM). For this purpose, after pre-incubation of the cell with the test substance for approx. 20 seconds and measurement of the membrane currents, a test solution comprising the same substance concentration and a defined ACh concentration is perfused for approx. 10 to 20 seconds and the membrane currents are measured. After application of the maximum acetylcholine concentration within a measurement series, the perfusion of a solution with atropine (10 µM) is in turn carried out in order to check the M2 selectivity of the substance effect. The $EC_{50}$ value in the presence of test substance is determined analogously with the aid of a 4-parameter logistic function (Hill function) (see above).

The shift in the acetylcholine dose-response curve is determined and quantified by the change in the $EC_{50}$ value for acetylcholine in the absence or presence of the test substance.

B-8. Effects of the Test Substances on Isolated Perfused Rat Heart

Male Wistar rats (strain: HsdCpb:WU) with a body weight of 200-250 g are anaesthetized with Narcoren (100 mg/kg). The thorax is opened and the heart is then exposed, excised and connected to a Langendorff apparatus by placing a cannula into the aorta. The heart is perfused retrogradely at 9 ml/min at constant flow with a Krebs-Henseleit buffer solution (gassed with 95% $O_2$ and 5% $CO_2$, pH 7.4, 35° C.; with the following composition in mmol/l: NaCl 118; KCl 3; NaHCO$_3$ 22; $KH_2PO_4$ 1.2; magnesium sulfate 1.2; $CaCl_2$ 1.8; glucose 10; Na pyruvate 2). To measure the contractility of the heart, a balloon, made of thin plastic film, which is attached to a PE tube and filled with water is introduced via an opening in the left auricle of the heart into the left ventricle. The balloon is connected to a pressure transducer. The end-diastolic pressure is adjusted to 5-10 mmHg via the balloon volume. The data are enhanced by a bridge amplifier and registered on a computer using the LabChart software (ADInstruments).

To investigate the allosteric effect of the test substances, the hearts are perfused with addition of 300 nmol/l of the test substance. After 15 min, carbachol is added cumulatively to the perfusion solution in increasing concentrations. Lowering of the heart rate resulting therefrom is compared, as dose-response curve, with effects on hearts which had been treated with solvent in place of test substance. The shift in the carbachol dose-response curve is analysed and quantified by GraphPad PRISM (sigmoidal dose-response).

B-9. Effects of the Test Substances on the Heart Rate in Anaesthetized Rats

Male rats of the strain (WI) WU Br from the breeder Charles River are anaesthetized initially with a 4-5% isoflurane inhalation for approx. 3 min. Subsequently, anaesthesia is maintained using a 1.5% isoflurane inhalation. For this purpose, the anaesthetized animals are fixed on a heated operating plate. By means of visual inspection and between toe reflex, the depth of anaesthesia is checked.

For the application of the test substance, an i.v. route into the jugular vein is used. A caudal to cranial skin incision is then made longitudinally and both the cervical musculature and the salivary glands are severed. The right common carotid artery is exposed and blood supply is arrested to both proximally and distally. Using micro instrumentation, a TIP catheter (1.2F) is introduced into the vessel in order to measure the arterial pressure and the heart rate.

Initially, both parameters are monitored for 10 min in the basal state without substance addition. The substances to be investigated are dissolved in suitable solvent mixtures and subsequently administered at various dosages to a group of animals in each case via the jugular vein by an infusion pump over 5 min. A solvent-treated group is used as control under the same experimental conditions. The arterial blood pressure and heart rate with substance addition is determined for 20 min. The data are registered with the PowerLab system (ADinstruments) and evaluated using the LabChart program (ADinstruments).

B-10. Radiotelemetric Measurement of Blood Pressure and Heart Rate of Conscious Rats A commercially available telemetry system from Data Sciences International DSI, USA, is employed for the measurements on conscious rats described below. The system consists of 3 main components: (1) implantable transmitters (Physiotel® telemetry transmitter), (2) receivers (Physiotel® receiver), which are linked via a multiplexer (DSI Data Exchange Matrix) to a (3) data acquisition computer. The telemetry system makes it possible to continuously record blood pressure, heart rate and body motion of conscious animals in their usual habitat.

The studies are conducted on adult female rats (Wistar Unitever/WU or Spontaneous Hypertensive Rat/SHR) with a body weight of >200 g. After transmitter implantation, the experimental animals are housed singly in type III Makrolon® cages. They have free access to standard feed and water. The day/night rhythm in the test laboratory is set by changing the illumination of the room.

Transmitter Implantation:

The telemetry transmitters used (e.g. PA-C40 HD-S10, DSI) are surgically implanted under aseptic conditions in the experimental animals at least 14 days before the first experimental use. For the implantation, the fasted animals are anaesthetized with isoflurane (IsoFlo®, Abbott, initiation 5%, maintenance 2%) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vetbond™, 3M). The transmitter housing is fixed intraperitoneally to the abdominal wall muscle, and the wound is closed layer by layer. Post-operatively, an antibiotic (Ursocyclin® 10%, 60 mg/kg s.c., 0.06 ml/100 g body weight, Serumwerk Bemburg AG, Germany) for infection prophylaxis and an analgesic (Rimadyl®, 4 mg/kg s.c., Pfizer, Germany) are administered.

Substances and Solutions:

Unless stated otherwise, the substances to be studied are administered orally to a group of animals in each case (M=6). In accordance with an administration volume of 2 ml/kg of body weight, the test substances are dissolved in suitable solvent mixtures. A solvent-treated group of animals is used as control.

Experimental Outline:

The telemetry measuring system is configured for 24 animals. Each of the instrumented rats living in the system is assigned a separate receiving antenna (RPC-1 Receiver, DSI). The implanted senders can be activated externally via an installed magnetic switch and are switched to transmission during the pre-run of the experiment. The signals emitted can be detected online by a data acquisition system (Dataquest™ A.R.T. for Windows, DSI or Ponemah, DSI) and processed accordingly. In the standard procedure, the following are measured for 10-second periods in each case: (1) systolic blood pressure (SBP), (2) diastolic blood pressure (DBP), (3) mean arterial pressure (MAP), (4) heart rate (HR) and (5) activity (ACT). These parameters are measured over 24 hours after administration. The acquisition of measurements is repeated under computer control at 5-minute intervals. The source data obtained as absolute values are corrected in the diagram with the currently measured barometric pressure (Ambient Pressure Reference Monitor, APR-1, DSI).

Evaluation:

After the end of the experiment, the acquired individual data are sorted using the analysis software (Dataquest™ A.R.T. 4.1 Analysis or Ponemah, DSI). The 2 hour time point before substance application is assumed as the blank value. The data are smoothed over a presettable period by determination of the means (30 minute mean).

B-11. Effects of the Test Substances on the Heart Rate in Anaesthetized Dogs

Male or female cross-breeds (Mongrels, Marshall BioResources, USA) with a body weight between 20 and 30 kg are anaesthetized with pentobarbital (30 mg/kg iv, Narcoren®, Merial, Germany). Pancuronium chloride (Pancuronium-Actavis®, Actavis, Germany, 1 mg/animal iv) serves here additionally as muscle relaxant. The dogs are intubated and ventilated with an oxygen-air mixture (40/60%) (approximately 5-6 L/min). The ventilation is conducted using a ventilation device from GE Healthcare (Avance), which also serves as anaesthesia monitor (CO2 analyser). The anaesthesia is maintained by a constant infusion of pentobarbital (50 µg/kg/min); fentanyl (10 µg/kg/h) serves as analgesic. An alternative to pentobarbital consists of using isoflurane (1-2% by volume).

The dog is provided with the following:
bladder catheter for bladder emptying or measurement of urine flow
ECG leads to the extremities (for ECG measurement)
insertion of a NaCl-filled Fluidmedic-PE-300 loop into the *A. femoralis*. This is linked to a pressure sensor (Braun Melsungen, Melsungen, Germany) for measuring the systemic blood pressure
insertion of a NaCl-filled venous catheter (Vygon, Germany) into the *V. femoralis* for infusing test substances or withdrawing blood.
insertion of a Millar Tip catheter (Typ 350 PC, Millar Instruments, Houston, USA) via the left atrium or via a sluice for measuring the heart haemodynamics incorporated into the *A. carotis*
insertion of a Swan-Ganz catheter (CCOmbo 7.5F, Edwards, Irvine, USA) via the *V. jugularis* into the *A. pulmonalis* for measuring cardiac output, oxygen saturation, pulmonary arterial pressures and central venous pressure.
provision of an ultrasound flowmeter probe (Transsonic Systems, Ithaka, USA) to the Aorta descendens for measuring aorta flow
provision of an ultrasound flowmeter probe (Transsonic Systems, Ithaka, USA) to the left Aorta coronaria for measuring coronary flow
placement of a Braunule into the Venae cephalicae for infusing pentobarbital, liquid substitution and for withdrawing blood (determination of the substance plasma levels or other clinical blood values)
placement of a Braunule into the Venae saphenae for infusing fentanyl and substance application The primary signals are possibly amplified (Gould Amplifier, Gould Instrument Systems, Valley View, USA) or Edwards Vigilance Monitor (Edwards, Irvine, USA) and subsequently fed into the Ponemah system (DataSciences Inc, Minneapolis, USA) for evaluation. The signals are recorded continuously over the whole experimental time course, further processed digitally by this software and averaged over 30 s.

B-12, Effects of the Test Substances on the Heart Rate and Heart Rate Variability in Healthy, Conscious does To characterize test substances with regard to their effect on heart rate, heart rate variability (HRV) and blood pressure, telemetric measurements are conducted in healthy, male Beagle dogs. Under isoflurane anaesthesia, a telemetry transmitter (model L21, from Data Sciences International, USA) is firstly implanted in the animals. After left-sided thoracotomy, pressure sensors are then placed in the aorta and in the left ventricle. To record an electrocardiogram (ECG), further electrodes are placed on the heart. For wound healing, the animals are then placed back in the pen under antibiotic (clindamycin, Zoetis, Germany) and analgesic (fentanyl, Janssen, Germany) aftercare. By means of the antennae installed in the animal pen, the blood pressure and ECG signals are forwarded to a data acquisition computer and evaluated by analysis software (Ponemah, Data Sciences International, USA). The telemetry system makes it possible to continuously monitor blood pressures and ECG signals in conscious animals. Technical details can be found in the documentation from the manufacturing company (Data Sciences International, USA).

The substances to be investigated are administered orally to the healthy dogs in suitable solvent mixtures by means of a gelatine capsule. A vehicle-treated group of animals is employed as control. The telemetry measurement is started before substance administration and recorded for a time period of several hours. The time course is displayed graphically by means of data smoothed by determination of means with the aid of the GraphPadPrism software (GraphPad, USA). To analyse the HRV, the ECG data are subjected to a frequency-domain heart rate variability analysis. For this purpose, the R-R intervals of the recorded ECGs are used.

Data outside the previously defined range of 0.2 s-1.5 s are excluded from the analysis. The excluded data are replaced by values which had been obtained by linear interpolation. These data are converted by spline interpolation into equally-spaced supporting points. To analyse the heart rate variability, the data are further subdivided in 30 s steps to packets of 300 s length. For each data packet, a Fourier transformation is calculated. The power is further calculated in three frequency bands (vlf=0.0033-0.04 1/s; lf=0.04-0.15 1/s; hf=0.15-0.5 1/s). To characterize the test substance, the total power (sum total of all three frequency bands) of the HRV analysis is used.

The invention claimed is:

1. A compound of formula (II)

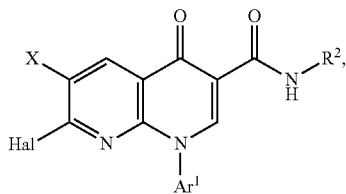

(II)

wherein
X is halogen;
$R^2$ is a group of the formula

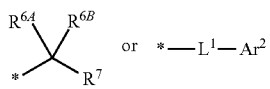

wherein
* marks the point of attachment to the nitrogen atom of the amide moiety,
$R^{6A}$ is hydrogen or $(C_1-C_4)$-alkyl,
$R^{6B}$ is hydrogen, $(C_1-C_4)$-alkyl, cyclopropyl, monofluoromethyl, difluoromethyl, trifluoromethyl, methoxymethyl or trifluoromethoxymethyl,
$R^7$ is $(C_1-C_6)$-alkyl or $(C_3-C_5)$-cycloalkyl which is up to tetrasubstituted by fluorine,
wherein $(C_1-C_6)$-alkyl is optionally substituted by amino, hydroxy, or $(C_1-C_6)$-alkoxy and up to pentasubstituted by fluorine,
wherein $(C_1-C_6)$-alkoxy may be up to pentasubstituted by fluorine;
$L^1$ is a bond or a group of the formula —C($R^{8A}R^{8B}$)—(C($R^{9A}R^{9B}$))$_m$—,
wherein
m is 0 or 1,
$R^{8A}$ is hydrogen or methyl,
$R^{8B}$ is hydrogen, methyl, trifluoromethyl, pentafluoroethyl or trifluoromethoxymethyl,
$R^{9A}$ and $R^{9B}$ are independently hydrogen or methyl,
$Ar^1$ is a group of formula

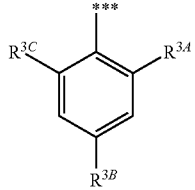

wherein
* * * marks the point of attachment to the nitrogen atom,
$R^{3A}$ is fluorine, chlorine, trifluoromethyl or methyl,
$R^{3B}$ is hydrogen or fluorine,
and
$R^{3C}$ is hydrogen, fluorine, chlorine or methyl;
or
$Ar^1$ is a pyridine ring which is attached via a ring carbon atom,
wherein the pyridine ring is optionally mono- or disubstituted by fluorine, chlorine, cyano, methyl or trifluoromethyl,
$Ar^2$ is phenyl,
wherein phenyl is optionally mono- to trisubstituted, identically or differently, by fluorine, chlorine, $(C_1-C_3)$-alkyl, difluoromethoxymethyl, trifluoromethoxymethyl or trifluoromethyl,
or
$Ar^2$ is a 5- to 10-membered monocyclic, bicyclic or tricyclic carbocycle or heterocycle which optionally contains one or two further identical or different heteroatoms from the group consisting of N and O as ring members,
wherein the 5- to 10-membered monocyclic, bicyclic or tricyclic carbocycle or heterocycle is optionally up to trisubstituted by identical or different substituents from the group consisting of $(C_1-C_3)$-alkyl, trifluoromethyl and $(C_1-C_4)$-alkoxycarbonyl and furthermore up to tetrasubstituted by fluorine,
and
Hal is fluorine, chlorine, bromine or iodine.

2. A compound of formula (IV)

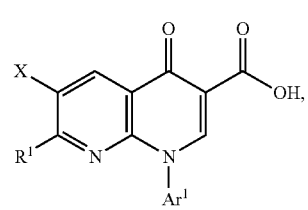

(IV)

wherein
X is halogen;
$R^1$ is hydrogen,
or
is —$NR^4R^5$,
wherein
$R^4$ is hydrogen, methyl, $(C_2-C_4)$-alkyl or $(C_3-C_6)$-cycloalkyl,
wherein $(C_2-C_4)$-alkyl is optionally substituted by hydroxyl or up to trisubstituted by fluorine;
and
$R^5$ is $(C_1-C_6)$-alkyl, $(C_3-C_6)$-cycloalkyl, 3- to 6-membered saturated heterocyclyl or $(C_1-C_4)$-alkylsulfonyl,
wherein $(C_1-C_6)$-alkyl, $(C_3-C_6)$-cycloalkyl and 3- to 6-membered saturated heterocyclyl are optionally up to trisubstituted, identically or differently, by methyl, difluoromethyl, trifluoromethyl, hydroxyl, hydroxycarbonyl, oxo, methoxy, difluoromethoxy, trifluoromethoxy or cyano, and additionally up to tetrasubstituted by fluorine, or R⁴ and R⁵ together with the nitrogen atom to which they are bonded form a saturated or partially unsaturated, 3- to 6-membered monocyclic or 6- to 10-membered bicyclic heterocycle which optionally contains one or two further, identical or different heteroatoms selected from the group of N, O, S, SO and SO$_2$ as ring members, wherein the 3- to 6-membered monocyclic and the 6- to 10-membered bicyclic heterocycle are optionally substituted by 1 to 5 substituents independently selected from the group consisting of (C$_1$-C$_4$)-alkyl, difluoromethyl, trifluoromethyl, hydroxy, hydroxycarbonyl, oxo, (C$_1$-C$_3$)-alkoxy, difluoromethoxy, trifluoromethoxy, cyano, (C$_1$-C$_3$)-alkoxycarbonyl, aminocarbonyl, mono-(C$_1$-C$_3$)-alkylaminocarbonyloxy, —NHC(=O)R$^{14A}$, —CH$_2$NHC(=O)R$^{14B}$, —OC(=O)R$^{15}$, and additionally up to tetrasubstituted by fluorine, wherein (C$_1$-C$_4$)-alkyl is optionally mono- or disubstituted, identically or differently, by hydroxyl and (C$_1$-C$_3$)-alkoxy, and up to tetrasubstituted by fluorine, R$^{14A}$ and R$^{14B}$ are independently (C$_1$-C$_3$)-alkyl or cyclopropyl, and wherein R$^{15}$ is (C$_1$-C$_4$)-alkyl, Ar$^1$ is selected from the group consisting of

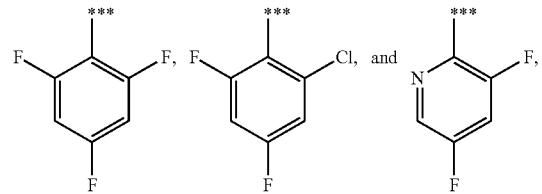

wherein

*** marks the point of attachment to the nitrogen atom.

3. The compound of claim 1, wherein Hal is chlorine.

* * * * *